(12) United States Patent  
Vandyck et al.

(10) Patent No.: US 12,180,192 B2
(45) Date of Patent: *Dec. 31, 2024

(54) MODULATORS OF THR-β AND METHODS OF USE THEREOF

(71) Applicant: ALIGOS THERAPEUTICS, INC., South San Francisco, CA (US)

(72) Inventors: Koen Vandyck, Beringen (BE); Pierre Jean-Marie Bernard Raboisson, Wavre (BE); David McGowan, Brussels (BE); Jerome Deval, El Granada, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 58 days.

This patent is subject to a terminal disclaimer.

(21) Appl. No.: 17/330,232

(22) Filed: May 25, 2021

(65) Prior Publication Data
US 2021/0355112 A1 Nov. 18, 2021

Related U.S. Application Data

(63) Continuation of application No. 16/869,211, filed on May 7, 2020, now Pat. No. 11,091,467.

(Continued)

(51) Int. Cl.
C07D 403/10 (2006.01)
C07D 401/10 (2006.01)
(Continued)

(52) U.S. Cl.
CPC ......... C07D 403/14 (2013.01); C07D 401/10 (2013.01); C07D 401/14 (2013.01);
(Continued)

(58) Field of Classification Search
CPC .............................. C07D 403/10; A61K 31/53
(Continued)

(56) References Cited

U.S. PATENT DOCUMENTS 7,230,031 B2 6/2007 Shiohara et al.
8,791,266 B2 7/2014 Kawata et al.
(Continued)

FOREIGN PATENT DOCUMENTS

CN 108727344 A 11/2018
CN 109574995 A 4/2019
(Continued)

OTHER PUBLICATIONS

Alkhouri, Naim, From Expert Opinion on Investigational Drugs, 2020, 29(2):99-101.

(Continued)

Primary Examiner — Jeffrey H Murray
(74) Attorney, Agent, or Firm — Foley & Lardner LLP

(57) ABSTRACT

Disclosed herein are compounds of Formula I:

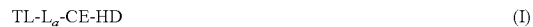

or a pharmaceutically acceptable salt, prodrug, amide or ester thereof, where i) TL is a moiety of Formula IIa, IIb, IIIa, IIIb, IIIc, or IIId; ii) CE is a moiety of Formula IV; iii) HD is a moiety of Formula V or VI; where the substituents are as defined herein. Disclosed are also pharmaceutical compositions comprising the above compounds, and methods of treating disease by administering or contact a patient with one or more of the above compounds.

(Continued)

-continued

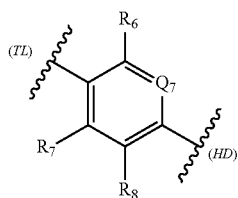
(IV)

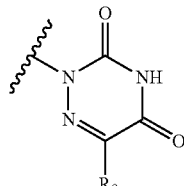

(V)

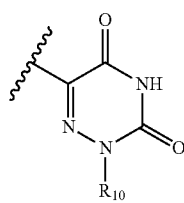

(VI)

23 Claims, 2 Drawing Sheets

Related U.S. Application Data

(60) Provisional application No. 63/005,661, filed on Apr. 6, 2020, provisional application No. 62/944,052, filed on Dec. 5, 2019, provisional application No. 62/845,252, filed on May 8, 2019.

(51) Int. Cl.
    *C07D 401/14*    (2006.01)
    *C07D 403/12*    (2006.01)
    *C07D 403/14*    (2006.01)
    *C07D 405/14*    (2006.01)
    *C07D 409/14*    (2006.01)
    *C07D 471/04*    (2006.01)
    *C07D 487/04*    (2006.01)

(52) U.S. Cl.
    CPC ......... *C07D 403/12* (2013.01); *C07D 405/14* (2013.01); *C07D 409/14* (2013.01); *C07D 471/04* (2013.01); *C07D 487/04* (2013.01)

(58) Field of Classification Search
    USPC .......................................... 544/182; 514/242
    See application file for complete search history.

(56) References Cited

U.S. PATENT DOCUMENTS

| | | | |
|---|---|---|---|
| 10,800,767 B2 | 10/2020 | Kirschberg et al. | |
| 11,091,467 B2 * | 8/2021 | Vandyck ............. | C07D 409/14 |
| 11,548,892 B1 | 1/2023 | Campbell et al. | |
| 2015/0182482 A1 | 7/2015 | Soeberdt et al. | |
| 2019/0262328 A1 | 8/2019 | Srinivasan et al. | |
| 2020/0115362 A1 | 4/2020 | Kirschberg et al. | |
| 2020/0190064 A1 | 6/2020 | Yu et al. | |
| 2020/0354345 A1 | 11/2020 | Vandyck et al. | |
| 2020/0399249 A1 | 12/2020 | Yu et al. | |
| 2021/0163480 A1 | 6/2021 | Campbell et al. | |
| 2023/0183245 A1 | 6/2023 | Von Deyn et al. | |

FOREIGN PATENT DOCUMENTS

| | | |
|---|---|---|
| EP | 1 088 819 A2 | 4/2001 |
| EP | 1 262 177 A2 | 12/2002 |
| EP | 2 695 611 A1 | 2/2014 |
| JP | 2012-106996 A | 6/2012 |
| WO | WO-01/98256 A1 | 12/2001 |
| WO | WO-03/064369 A1 | 8/2003 |
| WO | WO-2004/047827 A1 | 6/2004 |
| WO | WO-2007/009913 A1 | 1/2007 |
| WO | WO-2009/037172 A1 | 3/2009 |
| WO | WO-2010/122980 A1 | 10/2010 |
| WO | WO-2014/023698 A1 | 2/2014 |
| WO | WO-2014/043706 A1 | 3/2014 |
| WO | WO-2015/059465 A1 | 4/2015 |
| WO | WO-2016/112305 A1 | 7/2016 |
| WO | WO-2017/210526 A1 | 12/2017 |
| WO | WO-2018/075650 A1 | 4/2018 |
| WO | WO-2018/167103 A1 | 9/2018 |
| WO | WO-2018/193006 A1 | 10/2018 |
| WO | WO-2019/018610 A1 | 1/2019 |
| WO | WO-2019/099457 A1 | 5/2019 |
| WO | WO-2019/111048 A1 | 6/2019 |
| WO | WO-2019/144835 A1 | 8/2019 |
| WO | WO-2019/178023 A1 | 9/2019 |
| WO | WO-2019/213611 A1 | 11/2019 |
| WO | WO-2019/218797 A1 | 11/2019 |
| WO | WO-2019/239436 A1 | 12/2019 |
| WO | WO-2019/240938 A1 | 12/2019 |
| WO | WO-2019/242766 A1 | 12/2019 |
| WO | WO-2020/010068 A1 | 1/2020 |
| WO | WO-2020/041741 | 2/2020 |
| WO | WO-2020/073974 A1 | 4/2020 |
| WO | WO-2020/077123 | 4/2020 |
| WO | WO-2020/123827 | 6/2020 |
| WO | WO-2020/169069 | 8/2020 |
| WO | WO-2020/228577 | 11/2020 |
| WO | WO-2020/229014 | 11/2020 |
| WO | WO-2020/239076 A1 | 12/2020 |
| WO | WO-2021/018226 | 2/2021 |
| WO | WO-2021/032161 | 2/2021 |
| WO | WO-2021/032218 | 2/2021 |
| WO | WO-2021/041237 | 3/2021 |
| WO | WO-2021/043185 | 3/2021 |
| WO | WO-2021/050945 | 3/2021 |
| WO | WO-2021/057791 | 4/2021 |
| WO | WO-2021/078274 A1 | 4/2021 |
| WO | WO-2021/104288 A1 | 6/2021 |
| WO | WO-2021/143706 A1 | 7/2021 |

OTHER PUBLICATIONS

Azimi et al., "A QSAR study for modeling of thyroid receptors β1 selective ligands by application of adaptive neuro-fuzzy inference system and radial basis function," Journal of Chemometrics, 2012, 26(5):135-142.
Banker et al., Modern Pharmaceutics, 3rd Ed., Marcel Dekker, New York, 1996, 451, 596.
Bennet et al., Eds., Cecil Textbook of Medicine, 20th Ed., 1996, 1:1004-1010.
Danzi et al., "Cardiac specific effects of thyroid hormone analogues," Hormone and Metabolic Research, 2011, 43(11):737-742.
Dermer et al., Bio/Technology, 1994, 12:320.
Dow et al., "Discovery of a novel series of 6-azauracil-based thyroid hormone receptor ligands: potent, TRβ subtype-selective thyromimetics," Bioorganic & Medicinal Chemistry Letters, 2003, 13(3):379-382.
Freshney et al., Culture of Animal Cells, A Manual of Basic Technique, Alan R. Liss, Inc., 1983, New York, p. 4.
Girschick et al., "Similarity Boosted Quantitative Structure-Activity Relationship—A Systematic Study of Enhancing Structural Descriptors by Molecular Similarity," Journal of Chemical Information and Modeling, 2013, 53(5):1017-1025.

(56) References Cited

OTHER PUBLICATIONS

Harrison et al., "Resmetirom (MGL-3196) for the treatment of non-alcoholic steatohepatitis: a multicenter, randomized, double-blind, placebo-controlled, phase 2 trial," Lancet, Nov. 30, 2019, 394(10213):2012-2024.

Jakobsson et al., "Potential Role of Thyroid Receptor β Agonists in the Treatment of Hyperlipidemia," Drugs, 2017, 77(15):1613-1621.

Joharapurkar et al., "Selective Thyromimetics Using Receptor and Tissue Selectivity Approaches: Prospects for Dyslipidemia," Journal of Medicinal Chemistry, 2012, 55(12):5649-5675.

Kelly et al., "Discovery of 2-[3,5-Dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor β Agonist in Clinical Trials for the Treatment of Dyslipidemia", Journal of Medicinal Chemistry, Apr. 8, 2014, pp. 3912-3923, vol. 57, No. 10, American Chemical Society.

Kelly et al., "Discovery of 2-[3,5-Dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor b Agonist in Clinical Trials for the Treatment of Dyslipidemia," Journal of Medicinal Chemistry, 2014, 57(10):3912-3923.

Kowalik et al., Frontiers in Endocrinology, 2018, 9(382):1-11.

Li et al., "Thyroid receptor agonists for the treatment of androgenetic alopecia," Bioorganic & Medicinal Chemistry Letters, 2010, 20(1):306-308.

Liu et al., "QSAR study of selective ligands for the thyroid hormone receptor β," Bioorganic & Medicinal Chemistry, 2007, 15(15):5251-5261.

Park et al., "Improved docking, screening and selectivity prediction for small molecule nuclear receptor modulators using conformational ensembles," Journal of Computer-Aided Molecular Design, 2010, 24(5):459-471.

Ren et al., "Prediction of binding affinities to B1 isoform of human thyroid hormone receptor by genetic algorithm and projection pursuit regression," Bioorganic & Medicinal Chemistry Letters, 2007, 17(9):2474-2482.

Shiohara et al., "Design, synthesis, and structure-activity relationship (SAR) of N-[7-(4-hydroxyphenoxy)-6-methylindan-4-yl]malonamic acids as thyroid hormone receptor b (TRb) selective agonists," Bioorganic & Medicinal Chemistry, 2013, 21(3):592-607.

Taub et al., "Lipid lowering in healthy volunteers treated with multiple doses of MGL-3196, a liver-targeted thyroid hormone receptor-β agonist," Atherosclerosis (Amsterdam, Netherlands), 2013, 230(2):373-380.

Wolff, Manfred E., Burger's Medicinal Chemistry, 5th Ed., Part 1, John Wiley & Sons, 1995, 975-977.

\* cited by examiner

MODULATORS OF THR-β AND METHODS OF USE THEREOF

CROSS-REFERENCE TO RELATED APPLICATIONS

This application is a continuation of U.S. patent application Ser. No. 16/869,211, filed on May 7, 2020, which claims the benefit of priority to U.S. Provisional Patent Application Ser. No. 63/005,661, filed on Apr. 6, 2020, U.S. Provisional Patent Application Ser. No. 62/944,052, filed on Dec. 5, 2019, and U.S. Provisional Patent Application Ser. No. 62/845,252, filed on May 8, 2019, the entire disclosure of each of which is hereby incorporated by reference herein.

FIELD OF THE INVENTION

The present invention is in the field of pharmaceutical compounds and preparations and method of their use in the treatment of disease. In particular, the present invention is in the field of THR-β modulators and their use.

BACKGROUND OF THE DISCLOSURE

In parallel with the global increase in obesity, nonalcoholic fatty liver disease (NAFLD) is becoming the leading cause of chronic liver disease and liver transplantation worldwide [1,2]. NAFLD is believed to affect 30% of the adult population and 70-80% of individuals who are obese and diabetic. NAFLD is defined as excess liver fat accumulation greater than 5% induced by causes other than alcohol intake. NAFLD progresses to liver inflammation (nonalcoholic steatohepatitis, NASH) and fibrosis in a variable proportion of individuals, ultimately leading to liver failure and hepatocellular carcinoma (HCC) in susceptible individuals [3].

In the United States alone, NASH is the third most common indication for liver transplantation and is on a trajectory to become the most common [4]. The most important medical need in patients with NAFLD and NASH is an effective treatment to halt the progression and possibly reverse fibrosis, which is the main predictor of liver disease evolution [5,6].

Thyroid hormone (TH) is essential for normal development, growth and metabolism of all vertebrates. Its effects are mediated principally through triiodothyronine (T3), which acts as a ligand for the TH receptors (TRs, or THRs) β1, β2 and α1 [7]. In the absence of ligand, TR first binds as a heterodimer or homodimer on TH response elements (TRE) located in the promoter regions of target genes, where it interacts with corepressors. Upon ligand binding, the TR homodimers are dissociated in favor of heterodimer formation with the retinoid-X receptor (RXR), resulting in release of the corepressors and recruitment of coactivators. This new complex attracts a large number of proteins which engage the RNA polymerase II in the transcription of the targeted genes.

Two different genetic loci, denoted THRA and THRB, are responsible for encoding multiple interrelated TR isoforms that have distinct tissue distributions and biological functions. The two major isoforms with the broadest level of tissue expression are TRα1 and TRβ1 [8]. While TRα1 is expressed first during fetal development and is widely expressed in adult tissues, TRβ1 appears later in development and displays highest expression in the adult liver, kidney, and lung [9]. TRα1 is a key regulator of cardiac output, whereas TRβ1 helps in the control of metabolism in the liver. Importantly, the natural thyroid hormone T3 activates both TRα1 and TRβ1 without any significant selectivity.

Design of thyromimetic small molecule agents led to the identification of TR (or THR) agonists with varying levels of TRβ selectivity despite high structural similarity between the ligand-binding domains for TRβ and TRα. TRβ selectivity achieved by some of these compounds resulted in an improved therapeutic index for lipid lowering relative to cardiac effects such as heart rate, cardiac hypertrophy, and contractility [10-12].

Another strategy to avoid activation of TRα in cardiac tissue is to design prodrugs of phosphonate-containing TR agonists that are specifically converted to the active agonist in the liver but remain stable as an inactive prodrug in blood and extrahepatic tissues, including the heart [13]. TRα and TRβ agonists are also used in indications other than liver-related disorders, as has been known in the art.

SUMMARY

Disclosed herein are compounds of Formula I':

TL-L$_a$-CE-HD  (I')

or a pharmaceutically acceptable salt, prodrug, amide or ester thereof, where i) TL is a moiety of Formula IIa, IIb, IIIa, IIIb, IIIc, or IIId; ii) L$_a$ is independently a bond; —(C(R$_a$)$_2$)$_n$—; oxygen; sulfur; —NR$_a$— iii) CE is a moiety of Formula IV; iv) HD is a moiety of Formula V or VI; where the substituents are as defined herein. Disclosed are also pharmaceutical compositions comprising the above compounds, and methods of treating disease by administering or contact a patient with one or more of the above compounds.

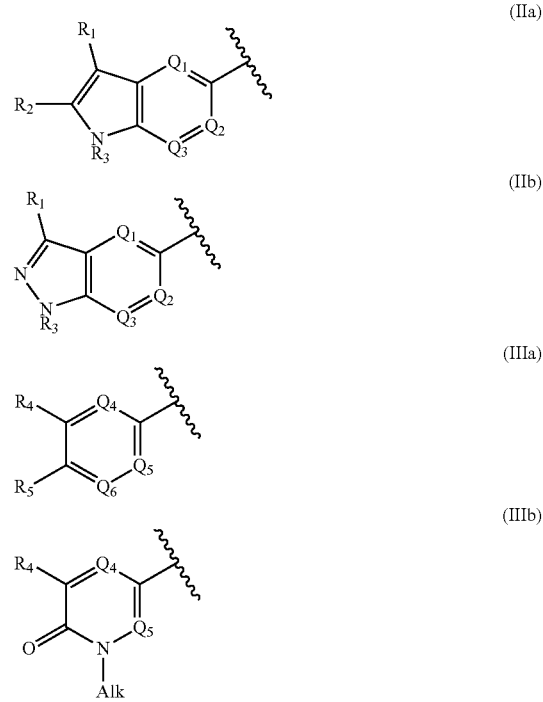

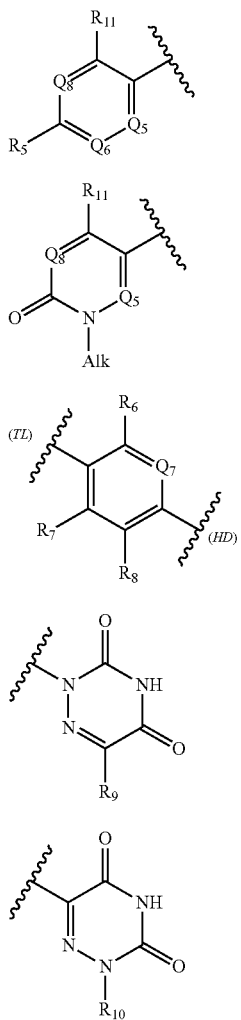

(IIIc)

(IIId)

(IV)

(V)

(VI)

DETAILED DESCRIPTION OF THE EMBODIMENTS

Figure 1:
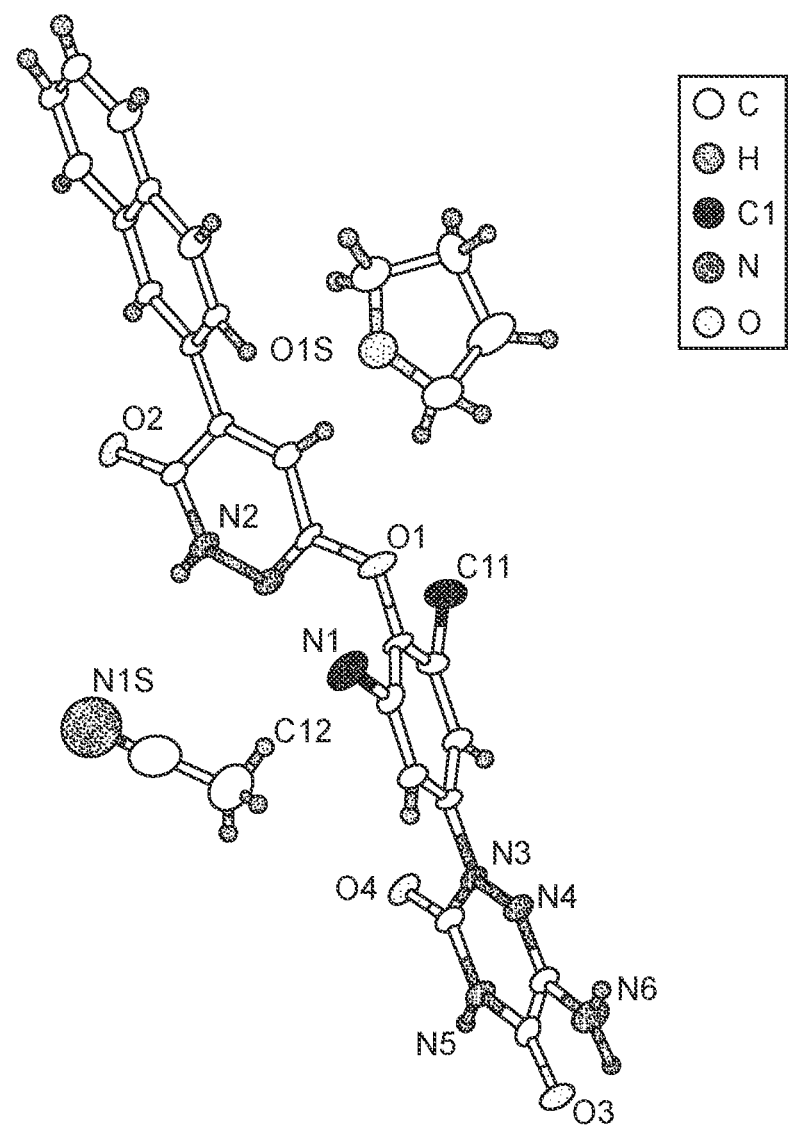
FIG. 1 depicts the chemical structure of Compound 67 as confirmed by x-ray crystallography.
Figure 2:
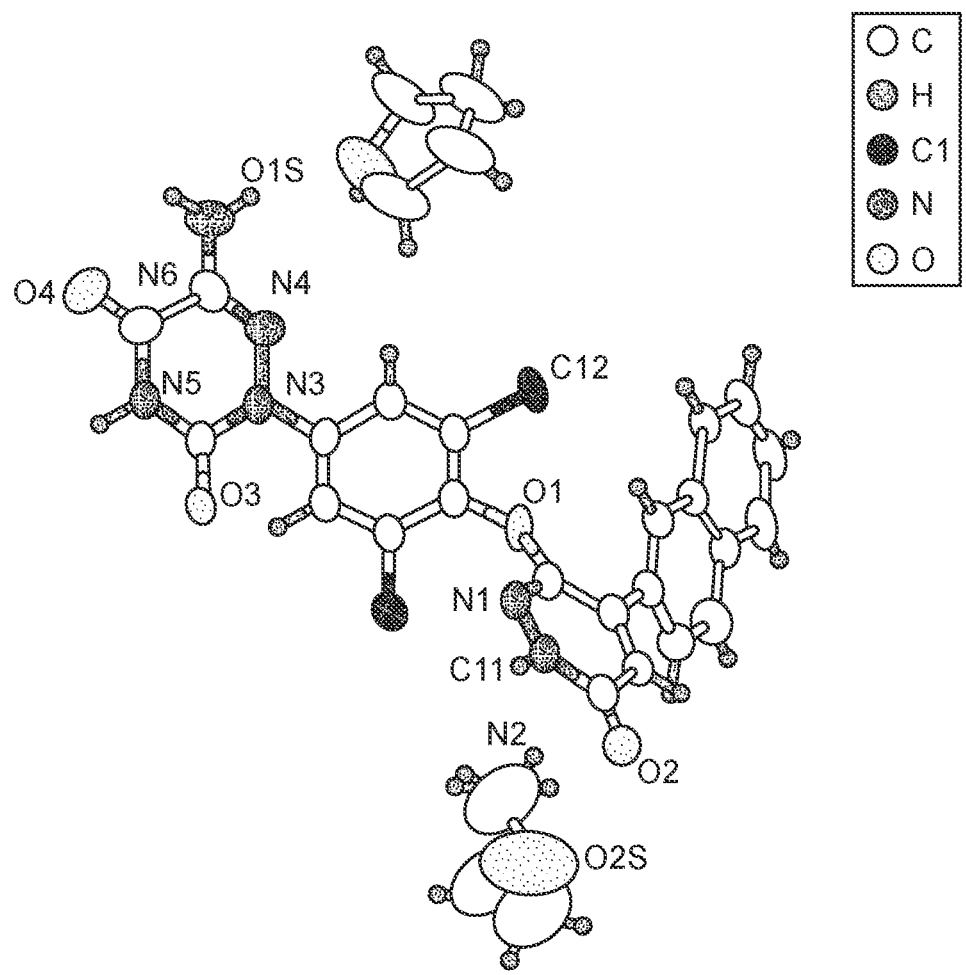
FIG. 2 depicts the chemical structure of Compound 67-A as confirmed by x-ray crystallography.

Disclosed herein are novel compounds that are effective modulators of THR-β activity that can be used for the treatment of various THR-β related disorders. The compounds and the methods of their use are discussed in detail below. Certain of the compounds disclosed herein are agonists, while others are antagonists, of TRα and/or TRβ receptors and are used to treat liver-related disorders and other indications known in the art that are mediated by TRα and/or TRβ receptors.

Definitions

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In the definition of chemical substituents, each of $R_x$ and $R_y$ is independently hydrogen, alkyl, carbocyclic ring, heterocyclic ring, aryl, or heteroaryl, all of which, except hydrogen, are optionally substituted.

Unless otherwise indicated, the abbreviations "TR" and "THR" refer to thyroid hormone receptors.

As used herein, "pharmaceutically acceptable salt" refers to a salt of a compound that does not cause significant irritation to a patient to which it is administered and does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, N-methyl-D-glucamine, tris(hydroxymethyl)methylamine; and salts with the amino group of amino acids such as, without limitation, arginine and lysine. Useful acid-based salts include, without limitation, hydrochlorides, hydrobromides, sulfates, nitrates, phosphates, methane-sulfonates, ethanesulfonates, p-toluenesulfonates and salicylates.

As used herein, "pharmaceutically acceptable ester" refers to an ester of a compound that does not cause significant irritation to a patient to which it is administered. The ester is metabolized in the body to result in the parent compound, e.g., the claimed compound. Accordingly, the ester does not abrogate the biological activity and properties of the compound. Pharmaceutical esters can be obtained by reaction of a compound disclosed herein with an alcohol. Methyl, ethyl, and isopropyl esters are some of the common esters to be prepared. Other esters suitable are well-known to those skilled in the art (see, for example Wuts, P.G.M., Greene's Protective Groups in Organic Synthesis, 5$^{th}$ Ed., John Wiley & Sons, New York, N.Y., 2014, which is incorporated herein by reference in its entirety).

Where the compounds disclosed herein have at least one chiral center, they may exist as a racemate or as individual enantiomers. It should be noted that all such isomers and mixtures thereof are included in the scope of the present disclosure. Thus, the illustration of a chiral center without a designation of R or S signifies that the scope of the disclosure includes the R isomer, the S isomer, the racemic mixture of the isomers, or mixtures where one isomer is present in greater abundance than the other.

Where the processes for the preparation of the compounds disclosed herein give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The compounds may also be resolved by formation of diastereomeric esters or amides followed by chromatographic separation and removal of the chiral auxiliary.

Unless otherwise indicated, when a substituent is deemed to be "optionally substituted" it is meant that the substituent is a group that may be substituted with one or more group(s) individually and independently selected, without limitation, from alkyl, alkenyl, alkynyl, cycloalkyl, aryl, heteroaryl, heteroalicyclic, hydroxy, alkoxy, aryloxy, mercapto, alkylthio, arylthio, cyano, halo, carbonyl, thiocarbonyl, O-carbamoyl, N-carbamoyl, O-thiocarbamoyl, N-thiocarbamoyl, C-amido, N-amido, S-sulfonamido, N-sulfonamido, C-carboxy, O-carboxy, is O-cyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Wuts, above.

As used herein, a "carbocyclic ring" is a ring structure in which all the atoms in the ring are carbon atoms. If any of the atoms in the ring is anything other than a carbon atom, then the ring is a "heterocyclic ring." Examples of atoms that are within a ring include sulfur, oxygen, and nitrogen. A carbocyclic ring or a heterocyclic ring may be polycyclic, e.g., a fused ring system, a spirocyclic ring system, or a bridged ring system. These polycyclic rings include, for example, adamantyl, norbornyl (i.e., bicyclo[2.2.1]heptanyl), norbornenyl, decalinyl, 7,7-dimethyl-bicyclo[2.2.1]heptanyl, and the like. Additional non-limiting examples include:

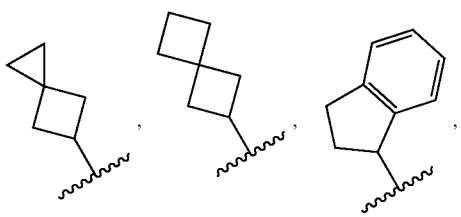

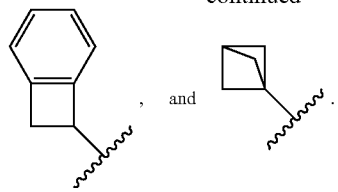

As used herein, "aryl" refers to a carbocyclic (all carbon) ring that has a fully delocalized pi-electron system. The "aryl" group can be made up of two or more fused rings (rings that share two adjacent carbon atoms). When the aryl is a fused ring system, then the ring that is connected to the rest of the molecule has a fully delocalized pi-electron system. The other ring(s) in the fused ring system may or may not have a fully delocalized pi-electron system. Examples of aryl groups include, without limitation, the radicals of benzene, naphthalene and azulene. Additional non-limiting examples include:

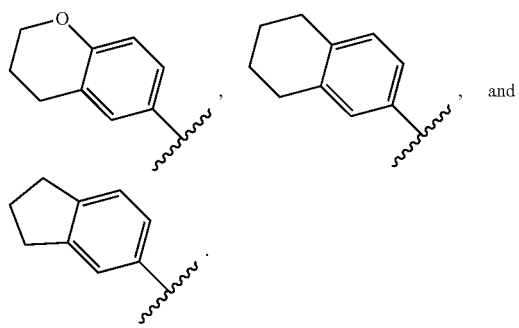

As used herein, "heteroaryl" refers to a ring that has a fully delocalized pi-electron system and contains one or more heteroatoms selected from the group consisting of nitrogen, oxygen, and sulfur in the ring. The "heteroaryl" group can be made up of two or more fused rings (rings that share two adjacent carbon atoms). When the heteroaryl is a fused ring system, then the ring that is connected to the rest of the molecule has a fully delocalized pi-electron system. The other ring(s) in the fused ring system may or may not have a fully delocalized pi-electron system. Examples of heteroaryl rings include, without limitation, furan, thiophene, phthalazinone, pyrrole, oxazole, thiazole, imidazole, pyrazole, isoxazole, isothiazole, triazole, thiadiazole, pyridine, pyridazine, pyrimidine, pyrazine and triazine.

Wherever "hetero" is used it is intended to mean a group as specified, such as an alkyl or an aryl group, where at least one carbon atom has been replaced with a heteroatom selected from nitrogen, oxygen and sulfur.

As used herein, "alkyl" refers to a straight or branched chain fully saturated (no double or triple bonds) hydrocarbon group. An alkyl group of the presently disclosed compounds may comprise from 1 to 20 carbon atoms. An alkyl group herein may also be of medium size having 1 to 10 carbon atoms. An alkyl group herein may also be a lower alkyl having 1 to 5 carbon atoms. Examples of alkyl groups include, without limitation, methyl, ethyl, n-propyl, isopropyl, n-butyl, i-butyl, sec-butyl, t-butyl, amyl, t-amyl, hexyl, heptyl, octyl, nonyl, decyl, undecyl and dodecyl.

An alkyl group of the presently disclosed compounds may be substituted or unsubstituted. When substituted, the substituent group(s) can be one or more group(s) independently selected from cycloalkyl, aryl, heteroaryl, heteroalicyclyl, hydroxy, protected hydroxy, alkoxy, aryloxy, mercapto, alkylthio, arylthio, cyano, halogen, carbonyl, thiocarbonyl, O-carbamoyl, N-carbamoyl, O-thiocarbamoyl, N-thiocarbamoyl, C-amido, N-amido, S-sulfonamido, N-sulfonamido, C-carboxy, protected C-carboxy, O-carboxy, isocyanato, thiocyanato, isothiocyanato, nitro, silyl, trihalomethanesulfonyl, —$NR_xR_y$, and protected amino.

As used herein, "alkenyl" refers to an alkyl group that contains in the straight or branched hydrocarbon chain one or more double bonds. An alkenyl group of the presently disclosed compounds may be unsubstituted or substituted. When substituted, the substituent(s) may be selected from the same groups disclosed above regarding alkyl group substitution, or with regard to optional substitution.

As used herein, "alkynyl" refers to an alkyl group that contains in the straight or branched hydrocarbon chain one or more triple bonds. An alkynyl group of the presently disclosed compounds may be unsubstituted or substituted. When substituted, the substituent(s) may be selected from the same groups disclosed above regarding alkyl group substitution, or with regard to optional substitution.

As used herein, "acyl" refers to an "$R_xC(=O)$—" group.

As used herein, "cycloalkyl" refers to a completely saturated (no double bonds) hydrocarbon ring. Cycloalkyl groups of the presently disclosed compounds may range from $C_3$ to $C_8$. A cycloalkyl group may be unsubstituted or substituted. If substituted, the substituent(s) may be selected from those indicated above regarding substitution of an alkyl group. The "cycloalkyl" group can be made up of two or more fused rings (rings that share two adjacent carbon atoms). When the cycloalkyl is a fused ring system, then the ring that is connected to the rest of the molecule is a cycloalkyl as defined above. The other ring(s) in the fused ring system may be a cycloalkyl, a cycloalkenyl, an aryl, a heteroaryl, or a heteroalicyclic.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). A cycloalkenyl group of the presently disclosed compounds may unsubstituted or substituted. When substituted, the substituent(s) may be selected from the same groups disclosed above regarding alkyl group substitution. The "cycloalkenyl" group can be made up of two or more fused rings (rings that share two adjacent carbon atoms). When the cycloalkenyl is a fused ring system, then the ring that is connected to the rest of the molecule is a cycloalkenyl as defined above. The other ring(s) in the fused ring system may be a cycloalkyl, a cycloalkenyl, an aryl, a heteroaryl, or a heteroalicyclic.

The term "alkylene" refers to an alkyl group, as defined herein, which is a biradical and is connected to two other moieties. Thus, methylene (—$CH_2$—), ethylene (—$CH_2CH_2$—), propylene (—$CH_2CH_2CH_2$—), isopropylene (IUPAC: (methyl)ethylene) (—$CH_2$—$CH(CH_3)$—), and isobutylene (IUPAC: 2-(methyl)propylene) (—$CH_2$—CH($CH_3$)—$CH_2$—) are examples, without limitation, of an alkylene group. Similarly, the term "cycloalkylene" refers to a cycloalkyl group, as defined here, which binds in an analogous way to two other moieties. If the alkyl and cycloalkyl groups contain unsaturated carbons, the terms "alkenylene" and "cycloalkenylene" are used.

As used herein, "heterocycloalkyl," "heteroalicyclic," or "heteroali-cyclyl" refers to a ring having in the ring system one or more heteroatoms independently selected from nitrogen, oxygen and sulfur. The ring may also contain one or more double bonds provided that they do not form a fully delocalized pi-electron system in the rings. The ring defined herein can be a stable 3- to 18-membered ring that consists of carbon atoms and from one to five heteroatoms selected from the group consisting of nitrogen, oxygen, and sulfur. Heteroalicyclyl groups of the presently disclosed compounds may be unsubstituted or substituted. When substituted, the substituent(s) may be one or more groups independently selected from the group consisting of halogen, hydroxy, protected hydroxy, cyano, nitro, alkyl, alkoxy, acyl, acyloxy, carboxy, protected carboxy, amino, protected amino, carboxamide, protected carboxamide, alkylsulfonamido and trifluoromethane-sulfonamido. The "heterocycloalkyl" group can be made up of two or more fused rings (rings that share two adjacent carbon atoms). When the heterocycloalkyl is a fused ring system, then the ring that is connected to the rest of the molecule is a heterocycloalkyl as defined above. The other ring(s) in the fused ring system may be a cycloalkyl, a cycloalkenyl, an aryl, a heteroaryl, or a heteroalicyclic.

As used herein, "aralkyl" refers to an alkylene substituted with an aryl group.

As used herein, "carbocyclic alkyl" or "(carbocyclic) alkyl" refers to an alkylene substituted with a carbocyclic group.

As used herein, "heterocyclicalkyl" or (heterocyclic)alkyl" refers to an alkylene substituted with a heterocyclic group. Similarly, "(heterocycloalkyl)alkyl" refers to an alkylene substituted with a heterocycloalkyl group.

As used herein, "heteroarylalkyl" or "(heteroaryl)alkyl" refers to an alkylene substituted with a heteroaryl group.

An "O-carboxy" group refers to a "$R_xC(=O)O$—" group.
A "C-carboxy" group refers to a "—$C(=O)R$" group.
An "acetyl" group refers to a $CH_3C(=O)$— group.
A "C-amido" group refers to a "—$C(=O)NR_xR_y$" group.
An "N-amido" group refers to a "$RC(=O)NR_x$—" group.

The term "perhaloalkyl" refers to an alkyl group in which all the hydrogen atoms are replaced by halogen atoms.

Any unsubstituted or monosubstituted amine group on a compound herein can be converted to an amide, any hydroxy group can be converted to an ester and any carboxyl group can be converted to either an amide or ester using techniques well-known to those skilled in the art (see, for example Wuts, above).

It is understood that, in any compound of the presently disclosed compounds having one or more chiral centers, if an absolute stereochemistry is not expressly indicated, then each center may independently be R or S or a mixture thereof. In addition, it is understood that, in any compound of the presently disclosed compounds having one or more double bond(s) generating geometrical isomers that can be defined as E or Z each double bond may independently be E or Z, or a mixture thereof.

It is understood that the disclosure of a compound herein inherently includes the disclosure of a tautomer thereof, if applicable. For instance, the disclosure of:

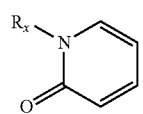

also includes the disclosure of:

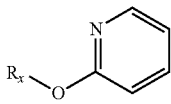

and vice versa, even if only one of the two structures is disclosed.

Throughout the present disclosure, when a compound is illustrated or named, it is understood that the isotopically enriched analogs of the compound are also contemplated. For example, a compound may have a deuterium incorporated instead of a hydrogen, or a carbon-13 instead of carbon with natural isotopic distribution. The isotopic enrichment may be in one location on the compound, i.e., only one hydrogen is replaced by a deuterium, or in more than one location. The present disclosure also encompasses compounds where all the similar atoms are replaced by their less common isotope, for example, a perdeutero compound where all the hydrogen atoms are replaced by a deuterium. The isotopically enriched compounds are useful when obtaining NMR spectra or when making use of an isotope effect in managing the kinetics of the reaction the compound undergoing.

The term "pharmaceutical composition" refers to a mixture of one or more compounds disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

In certain embodiments, the same substance can act as a carrier, diluent, or excipient, or have any of the two roles, or have all three roles. Thus, a single additive to the pharmaceutical composition can have multiple functions.

The term "physiologically acceptable" defines a carrier or diluent that does not abrogate the biological activity and properties of the compound.

Compounds

In one aspect, disclosed herein are compounds of Formula I:

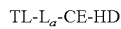 (I)

or a pharmaceutically acceptable salt, prodrug, amide or ester thereof, where:

i) TL is a moiety of Formula IIa, IIb, IIIa, IIIb, IIIc, or IId:

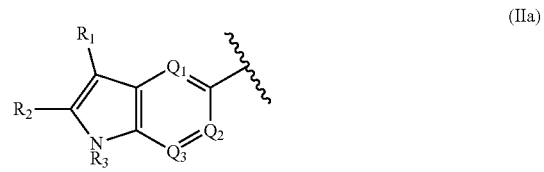 (IIa)

 (IIb)

 (IIIa)

 (IIIb)

 (IIIc)

 (IIId)

where:
each of $Q_1$, $Q_2$, $Q_3$, $Q_4$, $Q_5$, $Q_6$ and $Q_8$, is independently nitrogen or —$CR_b$—, wherein each $R_b$ is independently hydrogen, halogen, or lower alkyl;
$R_1$ is hydrogen, an optionally substituted alkyl, an optionally substituted carbocyclic group, an optionally substituted aryl group, an optionally substituted heterocyclic group, an optionally substituted heteroaryl group, an optionally substituted carbocyclic alkyl group, an optionally substituted aralkyl group, an optionally substituted heterocyclicalkyl group, an optionally substituted heteroarylalkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;
$R_2$ is hydrogen, halogen, optionally substituted alkyl, optionally substituted cycloalkyl, or —CN;
$R_3$ is hydrogen or lower alkyl;
$R_4$ is an optionally substituted alkyl, an optionally substituted carbocyclic group, an optionally substituted aryl group, an optionally substituted heterocyclic group, an optionally substituted heteroaryl group, an optionally substituted carbocyclic alkyl group, an optionally substituted aralkyl group, an optionally substituted heterocyclicalkyl group, an optionally substituted heteroarylalkyl group, an optionally substituted amino group, an optionally substituted sulfamoyl group, an optionally substituted carbamoyl group, or an optionally substituted carbamoyl alkyl group, where the nitrogen of the carbamoyl or carbamoyl alkyl group is optionally a heteroatom in a ring structure; and $R_5$ is hydroxy, $NH_2$, alkylamino, alkanoylamino, or alkylsulfonylamino;

or $R_4$ and $R_5$ taken together along with the carbon atoms to which they are attached form a five- or six-membered optionally substituted carbocyclic group, optionally substituted aryl group, optionally substituted heterocyclic group, or optionally substituted heteroaryl group;

or $R_4$ and $R_5$ taken together along with the carbon atoms to which they are attached form a seven to eleven membered, optionally substituted spirocyclic ring or a seven to eleven membered, optionally substituted spiro-heterocyclic ring; and Alk is hydrogen or an optionally substituted alkyl;

ii) CE is a moiety of Formula IV

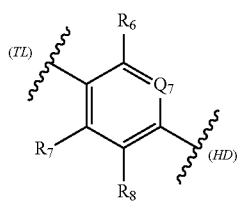

(IV)

wherein:
each of $R_6$ and $R_7$ is independently selected from halogen, —CN, optionally substituted lower alkyl, optionally substituted lower alkoxy, optionally substituted lower alkenyl, or cyclopropyl;

$R_8$ is selected from hydrogen, optionally substituted lower alkyl, optionally substituted lower alkoxy, cyano, or halogen;

optionally $R_7$ and $R_8$ taken together, along with the carbon atoms to which they are attached, form a 4, 5- or 6-membered carbocyclic, heterocyclic, aryl, or heteroaryl ring $Q_7$ is nitrogen or —$CR_c$—, wherein $R_c$ is hydrogen, halogen, or lower alkyl;

(TL) denotes the point where the moiety of Formula IV connects to TL-$L_a$-; and (HD) denotes the point where the moiety of Formula IV connects to —HD;

iii) HD is a moiety of Formula V or VI:

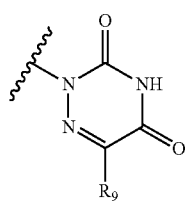

(V)

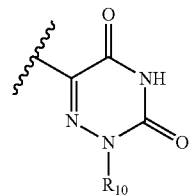

(VI)

wherein:
$R_9$ is selected from hydrogen, —$(C(R_d)_2)_n$—$C(R_d)_3$, —$(C(R_d)_2)_n$—$OR_d$, —$(C(R_d)_2)_n$—$N(R_a)_2$, —$(C(R_d)_2)_n$—$S(=O)_qR_d$, —$(C(R_d)_2)_n$—CN, —$(C(R_d)_2)_n$—C≡C—$R_d$, —$(C(R_d)_2)_n$—C(=O)—$OR_d$, —$(C(R_d)_2)_n$—HeAr, or —$(C(R_d)_2)_n$—C(=O)—$N(R_a)_2$; wherein each $R_d$ is independently hydrogen or optionally substituted lower alkyl;

each q is independently selected from 0, 1, or 2;

each n is independently selected from 0, 1, 2, 3, 4, or 5; and

HeAr is a 5- or 6-membered heteroaryl.

$R_{10}$ is hydrogen, —$C(R_e)_3$, wherein each $R_e$ is independently hydrogen, halogen, or optionally substituted lower alkyl; and $R_{11}$ is an aryl group, optionally substituted with lower alkyl, halogen, cycloalkyl; or a bicyclic ring system containing either aromatic or saturated rings; or a bicyclic heterocyclic containing either aromatic or saturated ring systems iv) $L_a$ is independently a bond; —$(C(R_a)_2)_n$—; oxygen; sulfur; —$NR_a$—; wherein:

each $R_a$ is independently a hydrogen or lower alkyl; and n is 0, 1, 2, 3, 4 or 5.

In some embodiments, $R_1$ is an optionally substituted alkyl, an optionally substituted carbocyclic group, an optionally substituted aryl group, and an optionally substituted C-carboxy or O-carboxy group. In some of these embodiments, the alkyl is selected from the group consisting of methyl, ethyl, n-propyl, i-propyl, n-butyl, i-butyl, and t-butyl. In certain embodiments, the carbocyclic group is cyclohexane or cyclopentane. In various embodiments, the aryl group is phenyl. In some embodiments, the C-carboxy group is a moiety of formula —C(=O)—O—R and the O-carboxy group a moiety of formula —O—C(=O)—R, where R is selected from the group consisting of methyl, ethyl, n-propyl, i-propyl, n-butyl, i-butyl, and t-butyl.

In some embodiments, $R_2$ is selected from the group consisting of hydrogen, methyl, ethyl, n-propyl, i-propyl, n-butyl, i-butyl, and t-butyl.

In some embodiments, $Q_1$, $Q_2$, $Q_3$, and $Q_4$ are —$CR_b$—, where each $R_b$ is independently selected from the group consisting of hydrogen, methyl, ethyl, n-propyl, i-propyl, n-butyl, i-butyl, and t-butyl.

In some embodiments, $R_4$ is selected from the group consisting of methyl, ethyl, n-propyl, i-propyl, n-butyl, i-butyl, and t-butyl.

In some embodiments, $R_5$ is hydroxy.

In some embodiments, TL is a moiety selected from:
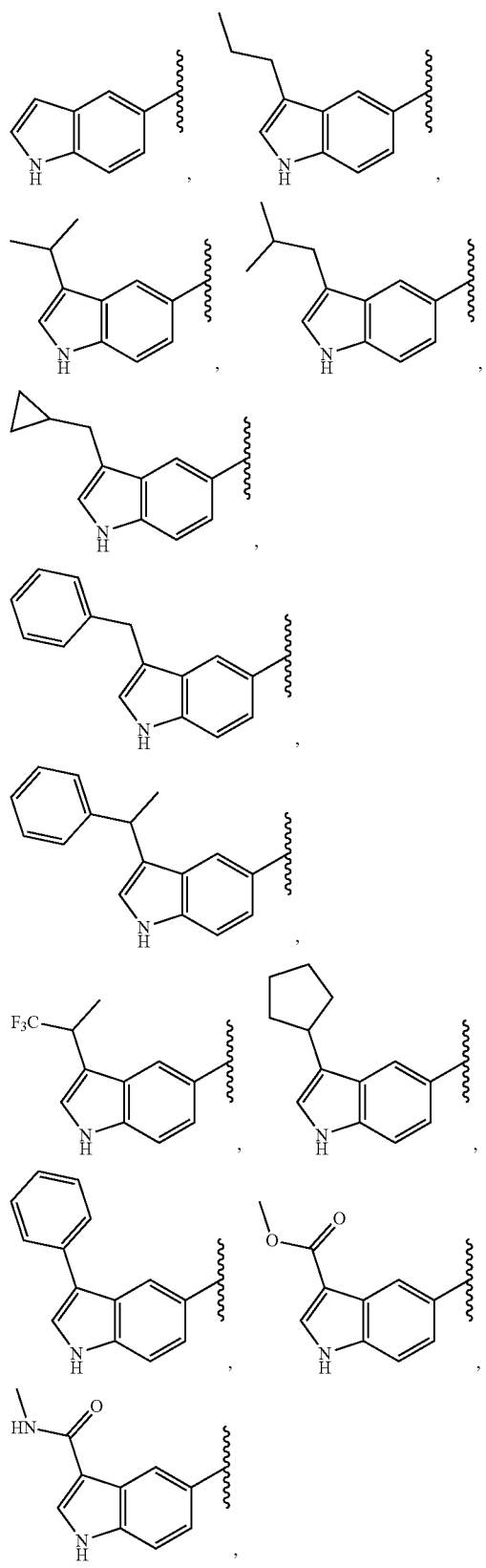
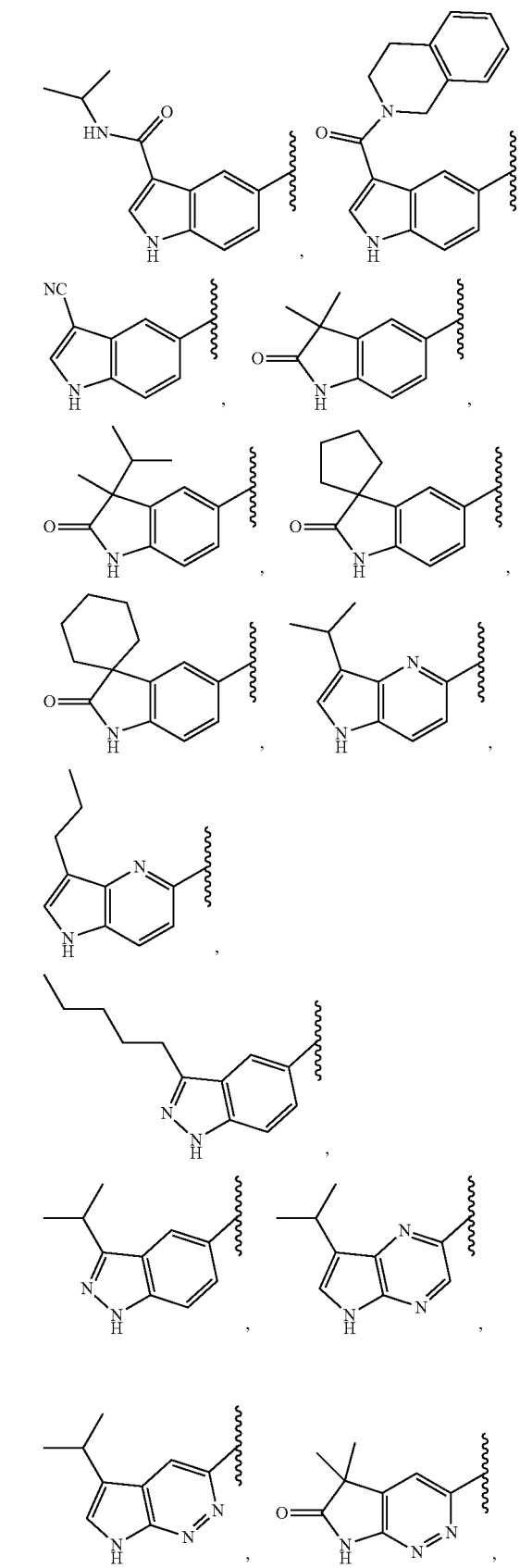

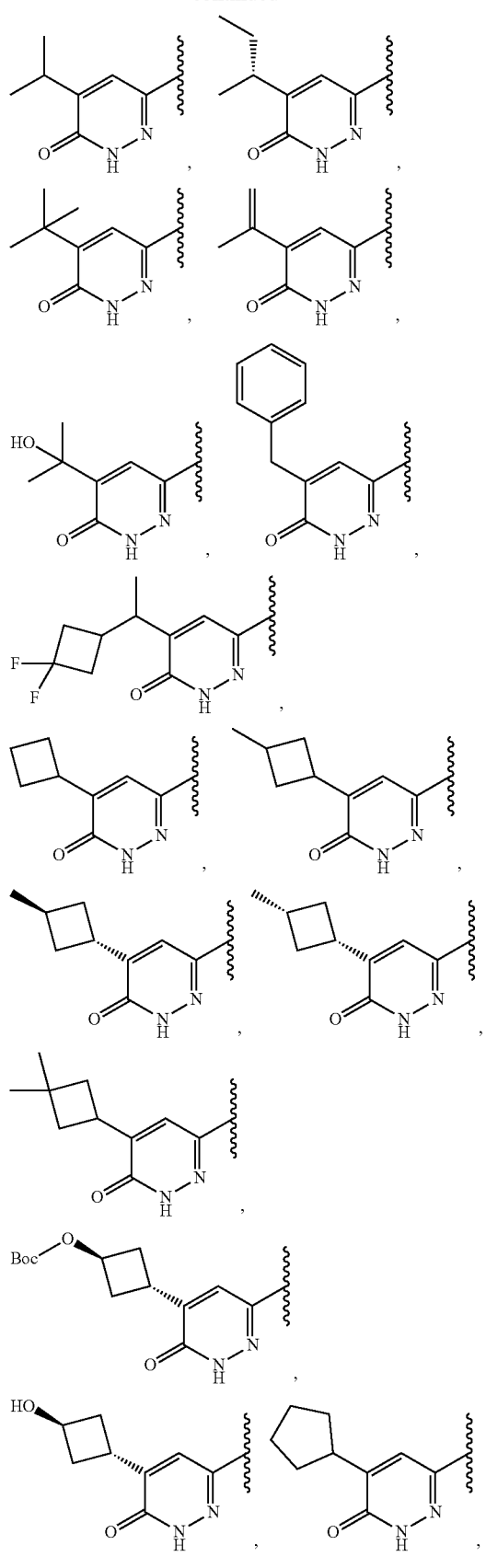
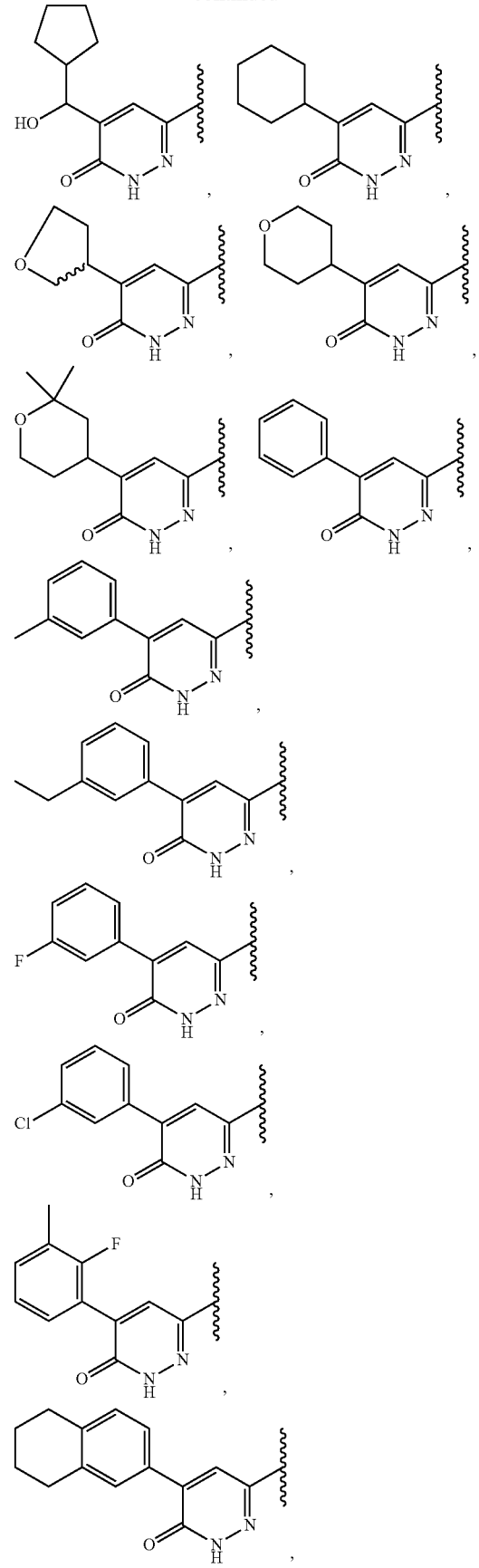

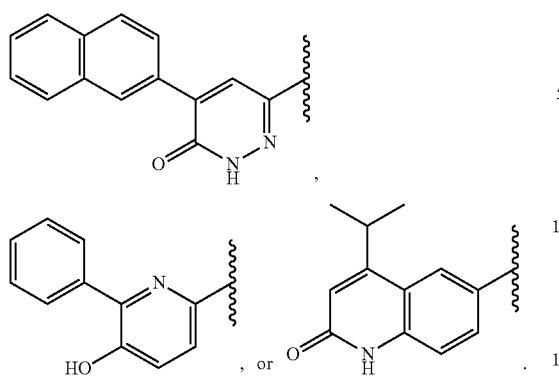
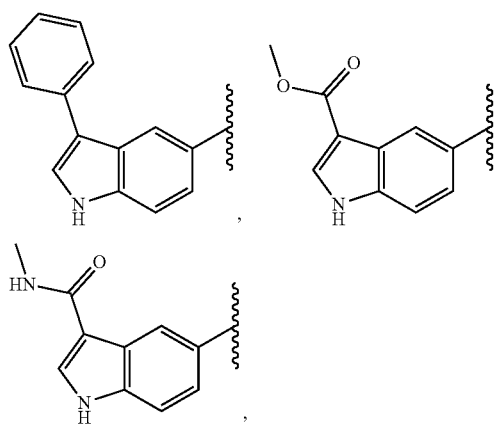
In some embodiments, TL is a moiety selected from:
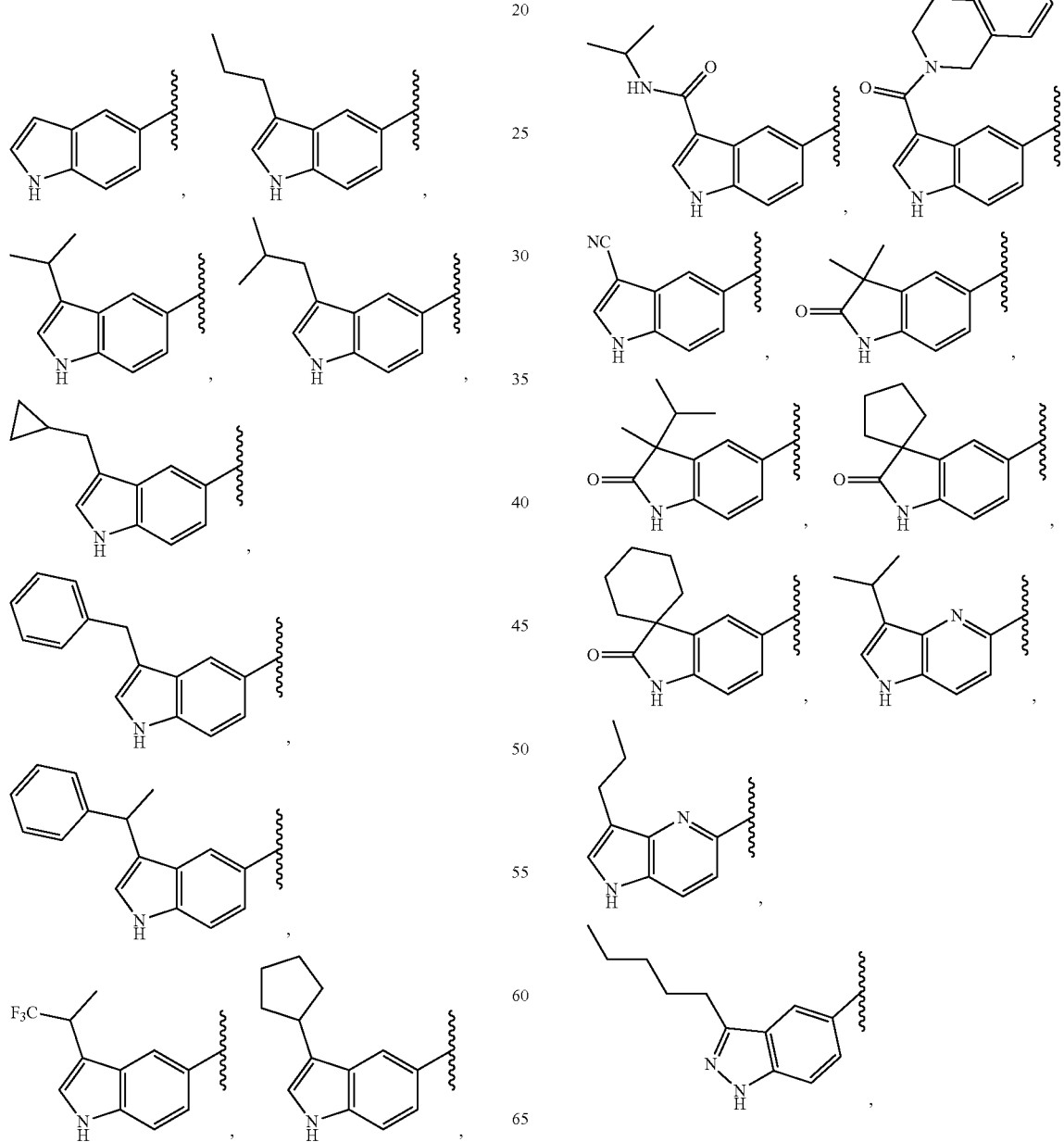

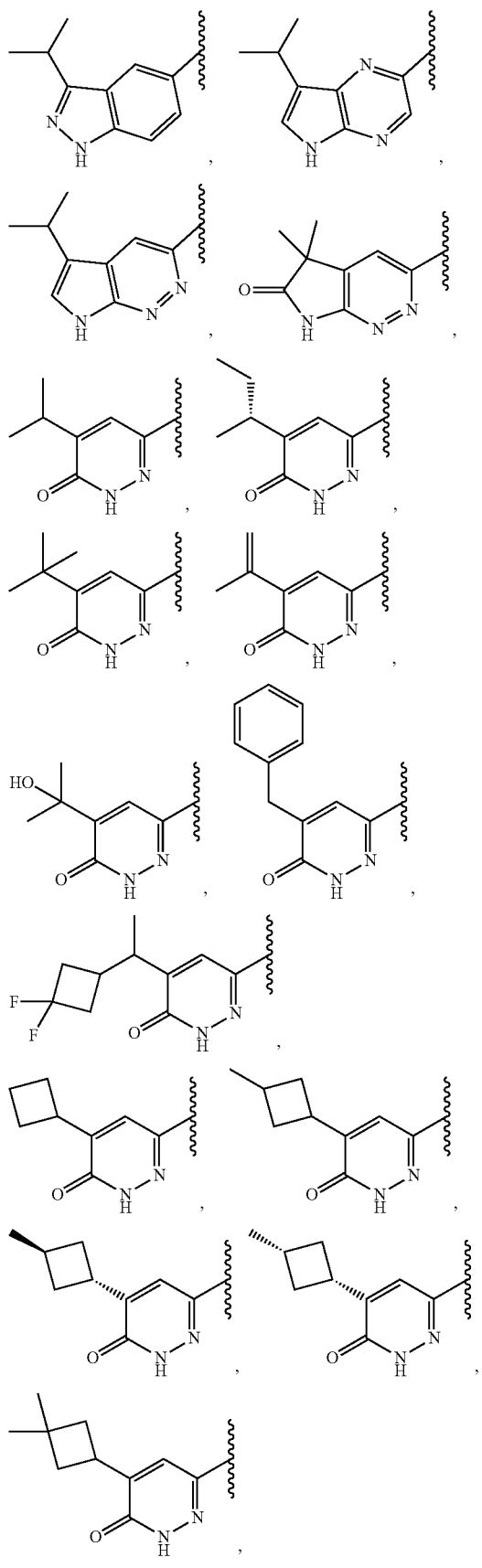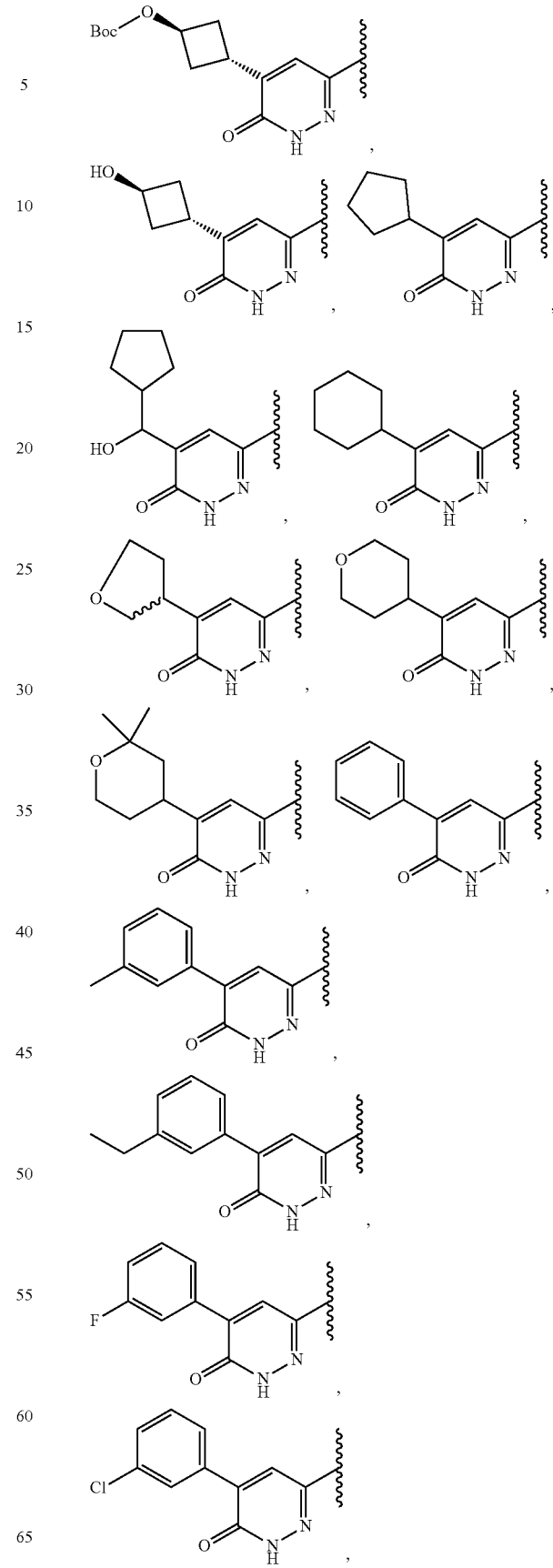

21
-continued

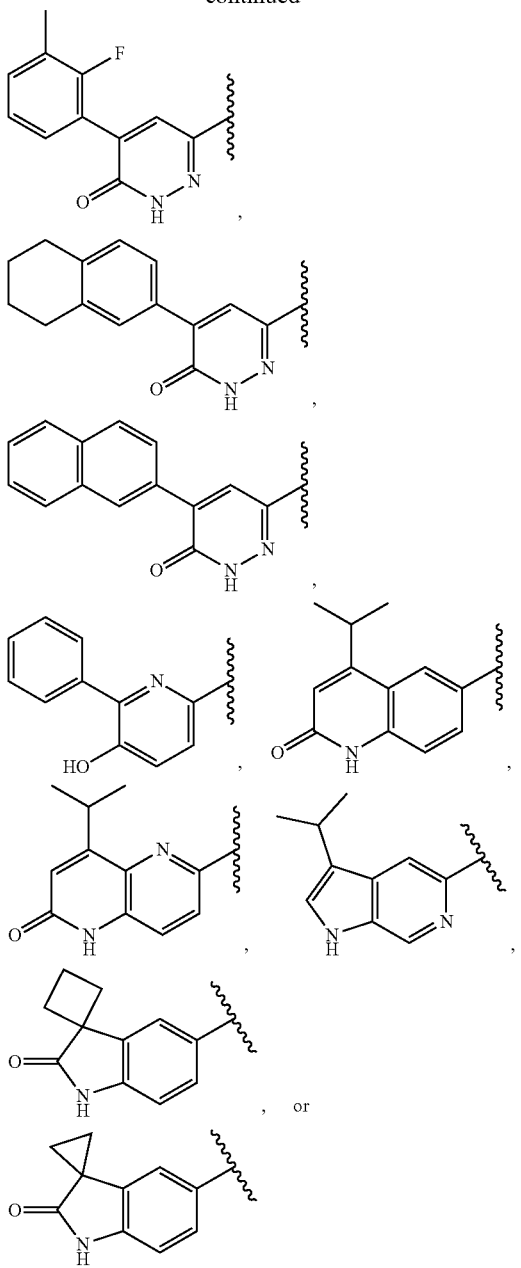

In some embodiments of the compound of Formula I, each of $R_6$ and $R_7$ is independently chlorine, bromine, and iodine. In other embodiments, each of $R_6$ and $R_7$ is independently —CN, an optionally substituted lower alkyl or an optionally substituted lower alkoxy, where the lower alkyl and the alkyl group of the lower alkoxy is each independently selected from methyl, ethyl, n-propyl, i-propyl, n-butyl, s-butyl, and t-butyl. In some embodiments, $R_6$ and $R_7$ are the same. In certain embodiments, each of $R_6$ and $R_7$ is independently chlorine or methyl.

In some embodiments of the compound of Formula I, $R_8$ is hydrogen.

In some embodiments, $R_c$ is hydrogen or methyl.

In some embodiments, disclosed herein are compounds of Formula I, where:

22

TL is a moiety of Formula IIa, IIb, IIIa, IIIb, IIIc, or IIId;

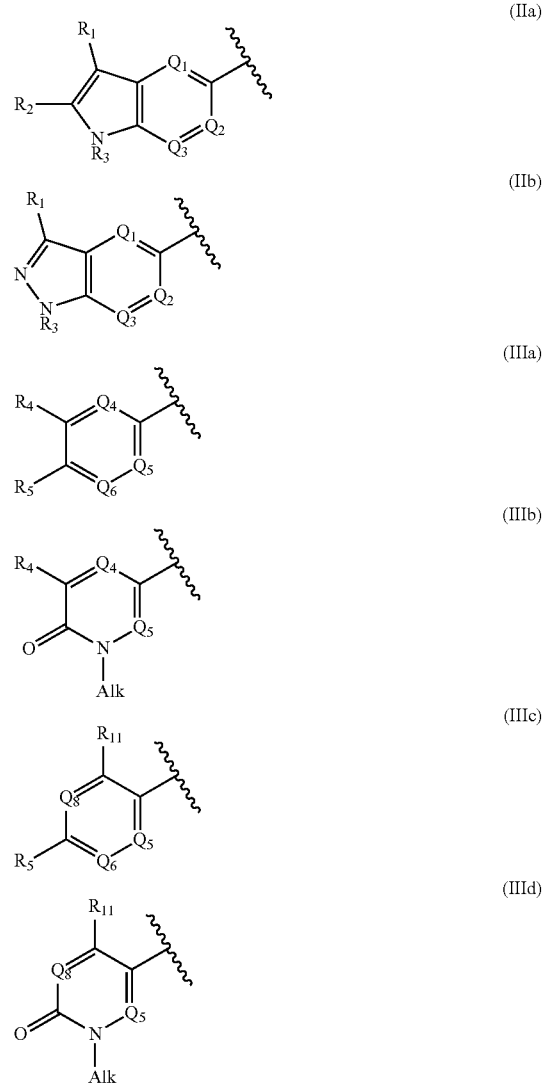

where:
each of $Q_1$, $Q_2$, $Q_3$, $Q_4$, $Q_5$, $Q_6$ and $Q_8$, is independently nitrogen or —$CR_b$—, wherein each $R_b$ is independently hydrogen, halogen, or lower alkyl;

$R_1$ is an optionally substituted alkyl, an optionally substituted carbocyclic group, an optionally substituted aryl group, an optionally substituted heterocyclic group, an optionally substituted heteroaryl group, an optionally substituted carbocyclic alkyl group, an optionally substituted aralkyl group, an optionally substituted heterocyclicalkyl group, an optionally substituted heteroarylalkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;

$R_2$ is halogen, optionally substituted alkyl, optionally substituted cycloalkyl, or —CN;

$R_3$ is hydrogen $R_4$ is an optionally substituted alkyl, an optionally substituted carbocyclic group, an optionally substituted aryl group, an optionally substituted heterocyclic group, an optionally substituted heteroaryl group, an optionally substituted carbocyclic alkyl group, an optionally substituted aralkyl group, an optionally substituted heterocyclicalkyl group, an optionally substituted heteroarylalkyl group, an optionally substituted amino group, an optionally substituted sulfamoyl group, an optionally substituted carbamoyl group, or an optionally substituted carbamoyl alkyl group, where the nitrogen of the carbamoyl or carbamoyl alkyl group is optionally a heteroatom in a ring structure; and $R_5$ is hydroxy, $NH_2$, alkylamino, alkanoylamino, or alkylsulfonylamino;

or $R_4$ and $R_5$ taken together along with the carbon atoms to which they are attached form a five- or six-membered optionally substituted carbocyclic group, optionally substituted aryl group, optionally substituted heterocyclic group, or optionally substituted heteroaryl group;

or $R_4$ and $R_5$ taken together along with the carbon atoms to which they are attached form a seven to eleven membered, optionally substituted spirocyclic ring or a seven to eleven membered, optionally substituted spiro-heterocyclic ring;

or when $Q_6$ is nitrogen and $R_5$ is hydroxy, then the tautomer of the moiety of Formula III; and Alk is hydrogen or an optionally substituted alkyl;

CE is a moiety of Formula IV

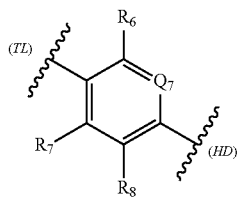

(IV)

where:
each of $R_6$ and $R_7$ is independently selected from halogen, —CN, optionally substituted lower alkyl, optionally substituted lower alkoxy, optionally substituted lower alkenyl, or cyclopropyl;

$R_8$ is selected from hydrogen, optionally substituted lower alkyl, optionally substituted lower alkoxy, cyano, or halogen;

$Q_7$ is nitrogen or —$CR_c$—, where $R_c$ is hydrogen, halogen, or lower alkyl;

(TL) denotes the point where the moiety of Formula IV connects to TL-$L_a$-; and (HD) denotes the point where the moiety of Formula IV connects to —HD;

HD is a moiety of Formula V or VI:

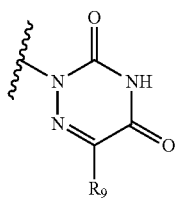

(V)

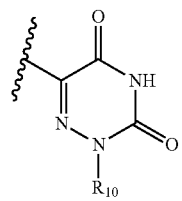

(VI)

where
$R_9$ is —$NH_2$ and $R_{10}$ is —$CH_3$; and
$L_a$ is oxygen.

In other embodiments, disclosed herein are compounds of Formula I, where:
TL is a moiety of Formula II:

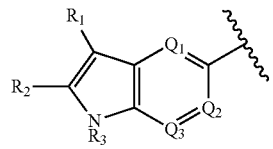

(II)

where:
each of $Q_1$, $Q_2$, and $Q_3$ is independently nitrogen or —$CR_b$—, where each $R_b$ is independently hydrogen, halogen, or lower alkyl;

$R_1$ is an optionally substituted alkyl, an optionally substituted carbocyclic group, an optionally substituted aryl group, an optionally substituted heterocyclic group, an optionally substituted heteroaryl group, an optionally substituted carbocyclic alkyl group, an optionally substituted aralkyl group, an optionally substituted heterocyclicalkyl group, an optionally substituted heteroarylalkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;

$R_2$ is halogen, optionally substituted alkyl, optionally substituted cycloalkyl, or —CN;

$R_3$ is hydrogen;

CE is a moiety of Formula IV

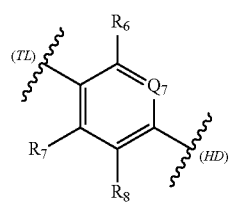

(IV)

where:
each of $R_6$ and $R_7$ is independently selected from halogen, —CN, optionally substituted lower alkyl, optionally substituted lower alkoxy, optionally substituted lower alkenyl, or cyclopropyl;

$R_8$ is selected from hydrogen, optionally substituted lower alkyl, optionally substituted lower alkoxy, cyano, or halogen;

$Q_7$ is nitrogen or —$CR_c$—, where $R_c$ is hydrogen, halogen, or lower alkyl;

(TL) denotes the point where the moiety of Formula IV connects to TL-$L_a$-; and (HD) denotes the point where the moiety of Formula IV connects to —HD;

HD is a moiety of Formula V:

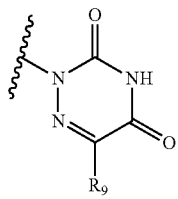

(V)

where $R_9$ is hydrogen, —CN or —C≡C—$R_d$, where $R_d$ is hydrogen or lower alkyl; and $L_a$ is oxygen.

In some embodiments, La is a combination of two or more of a bond; —$(C(R_a)_2)_n$—; oxygen; sulfur; or —$NR_a$—.

In another aspect, disclosed herein are compounds of Formula I':

TL-$L_a$-CE-HD          (I')

or a stereoisomer or a tautomer thereof, or a pharmaceutically acceptable salt, prodrug, amide or ester thereof, wherein:

i) TL is a moiety of Formula IIa, IIb, IIIa, IIIb, IIIc, or IIId:

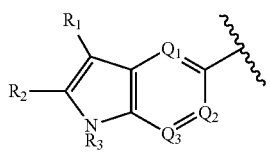

(IIa)

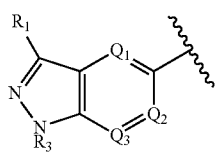

(IIb)

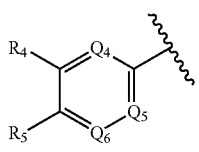

(IIIa)

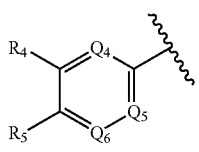

(IIIb)

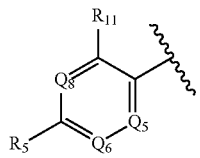

(IIIc)

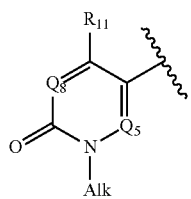

(IIId)

wherein:
each of $Q_1$, $Q_2$, $Q_3$, $Q_4$, $Q_5$, $Q_6$, and $Q_8$, is independently nitrogen or —$CR_b$—, wherein each $R_b$ is independently hydrogen, halogen, or lower alkyl;

$R_1$ is hydrogen, an optionally substituted alkyl, an optionally substituted non-aromatic carbocyclic group, an optionally substituted aryl group, an optionally substituted heterocycloalkyl group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;

$R_2$ is hydrogen, halogen, optionally substituted alkyl, optionally substituted cycloalkyl, or —CN;

$R_3$ is hydrogen or lower alkyl;

$R_4$ is an optionally substituted alkyl, an optionally substituted alkenyl, an optionally substituted non-aromatic carbocyclic group, an optionally substituted aryl group, an optionally substituted heterocyclic group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted sulfamoyl group, an optionally substituted carbamoyl group, or an optionally substituted carbamoyl alkyl group, where the nitrogen of the carbamoyl or carbamoyl alkyl group is optionally a heteroatom in a ring structure; and $R_5$ is hydroxy, $NH_2$, alkylamino, alkanoylamino, or alkylsulfonylamino;

or $R_4$ and $R_5$ taken together along with the carbon atoms to which they are attached form a five- or six-membered optionally substituted non-aromatic carbocyclic group, optionally substituted aryl group, optionally substituted heterocyclic group, or optionally substituted heteroaryl group;

or $R_4$ and $R_5$ taken together along with the carbon atoms to which they are attached form a seven to eleven membered, optionally substituted spirocyclic ring or a seven to eleven membered, optionally substituted spiro-heterocyclic ring;

Alk is hydrogen or an optionally substituted alkyl; and $R_{11}$ is an aryl group optionally substituted with one to five substituents independently selected from lower alkyl, alkoxy, haloalkoxy, halogen, and cycloalkyl; or a heteroaryl group optionally substituted with one to five substituents independently selected from lower alkyl, alkoxy, haloalkoxy, halogen, and cycloalkyl; or a bicyclic ring system; or a bicyclic heterocyclic ring system;

ii) CE is a moiety of Formula IV

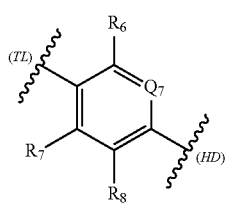

(IV)

wherein:
each of $R_6$ and $R_7$ is independently selected from halogen, —CN, optionally substituted lower alkyl, optionally substituted lower alkoxy, optionally substituted lower alkenyl, or cyclopropyl;

$R_8$ is selected from hydrogen, optionally substituted lower alkyl, optionally substituted lower alkoxy, cyano, or halogen;

optionally $R_7$ and $R_8$ taken together, along with the carbon atoms to which they are attached, form a 4-, 5- or 6-membered non-aromatic carbocyclic, heterocycloalkyl, aryl, or heteroaryl ring $Q_7$ is nitrogen or —$CR_c$—, wherein $R_c$ is hydrogen, halogen, or lower alkyl;

(TL) denotes the point where the moiety of Formula IV connects to TL-$L_a$-; and (HD) denotes the point where the moiety of Formula IV connects to —HD;

iii) HD is a moiety of Formula V or VI:

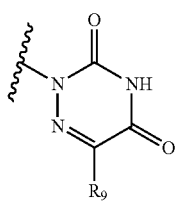

(V)

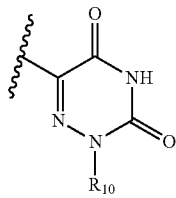

(VI)

wherein:
$R_9$ is selected from hydrogen, —$(C(R_a)_2)_n$—$C(R_d)_3$, —$(C(R_a)_2)_n$—$OR_d$, —$(C(R_a)_2)_n$—$N(R_d)_2$, —$(C(R_a)_2)_n$—$S(=O)_qR_d$, —$(C(R_a)_2)_n$—CN, —$(C(R_a)_2)_n$—C≡C—$R_d$, —$(C(R_a)_2)_n$—C(=O)—$OR_d$, —$(C(R_a)_2)_n$—HeAr, or —$(C(R_a)_2)_n$—C(=O)—$N(R_d)_2$; wherein
each $R_d$ is independently hydrogen or optionally substituted lower alkyl;

each q is independently selected from 0, 1, or 2;
each n is independently selected from 0, 1, 2, 3, 4, or 5;
HeAr is a 5- or 6-membered heteroaryl; and
$R_{10}$ is hydrogen or —$C(R_e)_3$, wherein each $R_e$ is independently hydrogen, halogen, or optionally substituted lower alkyl; and $L_a$ is independently a bond; —$(C(R_a)_2)_z$—; oxygen; sulfur; or —$NR_a$—; wherein:
each $R_a$ is independently a hydrogen or lower alkyl; and
z is 0, 1, 2, 3, 4 or 5;

provided that:
(1) when TL is a moiety of Formula IIIa, wherein $Q_4$, $Q_5$, and $Q_6$ are —CH—, and $R_4$ is an optionally substituted $C_1$-$C_3$alkyl group, an optionally substituted sulfamoyl group, or an optionally substituted carbamoyl group; HD is a moiety of Formula V, wherein $R_9$ is H or —CN; and $Q_7$ is —CH—, then $R_5$ cannot be hydroxy;

(2) when TL is a moiety of Formula IIa, wherein $Q_1$, $Q_2$, and $Q_3$ are —CH—, $R_1$ is —$CH_3$, and $R_2$ is hydrogen; HD is a moiety of Formula V, wherein $R_9$ is hydrogen; $Q_7$ is —CH—; $R_6$ is halogen or methyl; and $R_7$ and $R_8$ taken together, along with the carbon atoms to which they are attached, form a 5-membered non-aromatic carbocyclic ring, then $R_4$ and $R_5$ taken together along with the carbon atoms to which they are attached cannot form a five-membered heteroaryl group;

(3) when TL is a moiety of Formula IIIa, wherein $Q_4$ is nitrogen, $Q_5$ and $Q_6$ are —CH—, and $R_5$ is —OH; HD is a moiety of Formula V, wherein $R_9$ is —CN; $Q_7$ is —CH—; $L_a$ is —$CH_2$—, then $R_4$ cannot be cyclohexyl, cycloheptyl, isopropyl, or optionally substituted benzene;

(4) when TL is a moiety of Formula IIIb, wherein $Q_4$ is —CH— and $Q_5$ is nitrogen; HD is a moiety of Formula V, wherein $R_9$ is hydrogen, —CN, or —$CO_2H$; $Q_7$ is —CH—; and $R_6$ and $R_7$ are independently halogen or methyl, or $R_7$ and $R_8$ taken together, along with the carbon atoms to which they are attached, form a 5-membered non-aromatic carbocyclic ring, then $R_4$ cannot be isopropyl or 2-hydroxy-1-methyl-ethyl;

(5) when TL is a moiety of Formula IIIb, wherein $Q_4$ is —$CR_c$— and $Q_5$ is nitrogen; HD is a moiety of Formula V, wherein $R_9$ is —CN; $Q_7$ is —CH—; and $L_a$ is —O—, then
(a) none of $R_6$, $R_7$, and $R_8$ can be deuterium;
(b) $Q_4$ cannot be —CD-, wherein D is deuterium; and
(c) $R_4$ cannot be a three- to five-membered cycloalkyl ring optionally substituted with one or more halogens; non-aromatic (carbocyclic)alkyl optionally substituted with methyl or hydroxy; (1H-pyrazol-4-yl)methyl; (3-methylisoxazol-5-yl)methyl; phenyl; benzyl optionally substituted with methyl, halogen, hydroxy, or methoxy; phenethyl optionally substituted with halogen; $C_1$-$C_4$ alkyl optionally substituted with one to six substituents selected from halogen, hydroxyl, and deuterium; (tetrahydro-2H-pyran-4-yl)methyl; or a three- to five-membered heterocycloalkyl optionally substituted with benzyl;

(6) when TL is a moiety of Formula IIIb, wherein (i) $Q_4$ and $Q_5$ are nitrogen, (ii) $Q_4$ and $Q_5$ are —$CR_b$—, or (iii) $Q_4$ is nitrogen and $Q_5$ is —$CR_c$—; HD is a moiety of Formula V, wherein $R_9$ is —CN; and $Q_7$ is —CH—; then $R_4$ cannot be —$CH(CH_3)_2$ or —$CH(CD_3)_2$;

(7) when TL is a moiety of Formula IIIa, wherein $Q_4$ is —CH—, $Q_5$ and $Q_6$ are nitrogen, and $R_4$ is isopropyl; HD is a moiety of Formula V, wherein $R_9$ is —CN; and $Q_7$ is —CH—; then $R_5$ cannot be —$NH_2$ or —$NHCH_3$;

(8) when TL is a moiety of Formula IIIb, wherein $Q_4$ is —CH— and $Q_5$ is nitrogen; $L_a$ is —O—; $Q_7$ is —CH—; and HD is a moiety of Formula V, then $R_9$ cannot be methyl;
(9) when TL is a moiety of Formula IIIb, wherein $Q_4$ is —CH—, $Q_5$ is nitrogen, and $R_4$ is isopropyl; $L_a$ is —O—; $Q_7$ is —CH—; and HD is a moiety of Formula V, then $R_9$ cannot be isopropyl;
(10) when TL is a moiety of Formula IIa, wherein $Q_1$, $Q_2$, and $Q_3$ are —CH—; $L_a$ is —O—; $Q_7$ is —CH—; $R_6$ and $R_7$ are independently chlorine or trifluoromethyl; and HD is a moiety of Formula V, wherein $R_9$ is —CN or methyl, then $R_1$ cannot be isopropyl, 4-tetrahydropyranyl, or —C(O)NH$_2$;
(11) when TL is a moiety of Formula IIa, wherein $Q_1$ and $Q_2$ are —CH—, and $Q_3$ is nitrogen; $L_a$ is —O—; $Q_7$ is —CH—; $R_6$ and $R_7$ are chlorine; and HD is a moiety of Formula V, wherein $R_9$ is —CN, then $R_1$ cannot be isopropyl;
(12) when TL is a moiety of Formula IIb, wherein $Q_1$, $Q_2$, and $Q_3$ are —CH—; $L_a$ is —O—; $Q_7$ is —CH—; $R_6$ and $R_7$ are chlorine; and HD is a moiety of Formula V, wherein $R_9$ is —CN, then $R_1$ cannot be isopropyl;
(13) when TL is a moiety of Formula IIIb, wherein $Q_4$ is —CH— and $Q_5$ is nitrogen; $L_a$ is —O—; $Q_7$ is —CH—; $R_6$ and $R_7$ are chlorine; and HD is a moiety of Formula VI, wherein $R_{10}$ is H, Me, Et, isopropyl, —CH$_2$CF$_3$, or —CH$_2$CHF$_2$, then $R_4$ cannot be $C_2$-$C_5$ alkyl or $C_1$-$C_3$ hydroxyalkyl;
(14) when TL is a moiety of Formula IIIb, wherein $Q_4$ is —CH— and $Q_5$ is nitrogen; $L_a$ is —O—; $Q_7$ is —CH—; $R_6$ and $R_7$ are chlorine; and HD is a moiety of Formula VI, wherein $R_{10}$ is H or Me, then $R_4$ cannot be cyclopropyl; and
(15) when TL is a moiety of Formula IIIb, wherein $Q_4$ is —CH— and $Q_5$ is nitrogen; $L_a$ is —CH$_2$—; $Q_7$ is —CH—; $R_6$ and $R_7$ are both chlorine or both methyl; and HD is a moiety of Formula VI, wherein $R_{10}$ is H or Me, then $R_4$ cannot be isopropyl.

In some embodiments, when TL is a moiety of Formula IIIb, wherein $Q_4$ is —CH— and $Q_5$ is nitrogen; HD is a moiety of Formula V, wherein $R_9$ is —CH$_2$CN or —C≡CH; $Q_7$ is —CH—; and $R_6$ and $R_7$ are chlorine, then $R_4$ cannot be isopropyl.

In another aspect, disclosed herein are compounds of Formula I':

TL-L$_a$-CE-HD               (I')

or a stereoisomer or a tautomer thereof, or a pharmaceutically acceptable salt, prodrug, amide or ester thereof, wherein:

i) TL is a moiety of Formula IIa, IIb, IIIa, IIIb, IIIc, or IId:

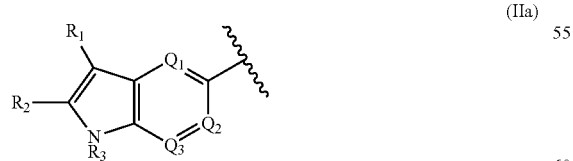

(IIa)

(IIb)

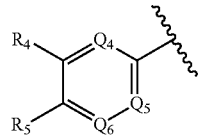

(IIIa)

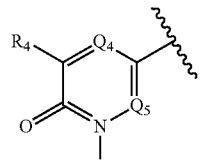

(IIIb)

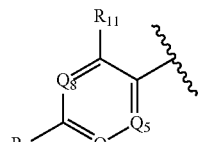

(IIIc)

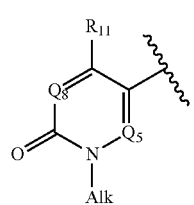

(IIId)

wherein:
each of $Q_1$, $Q_2$, $Q_3$, $Q_4$, $Q_5$, $Q_6$, and $Q_8$, is independently nitrogen or —CR$_b$—, wherein each R$_b$ is independently hydrogen, halogen, or lower alkyl;
$R_1$ is hydrogen, an optionally substituted alkyl, an optionally substituted non-aromatic carbocyclic group, an optionally substituted aryl group, an optionally substituted heterocycloalkyl group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;
$R_2$ is hydrogen, halogen, optionally substituted alkyl, optionally substituted cycloalkyl, or —CN;
$R_3$ is hydrogen or lower alkyl;
$R_4$ is an optionally substituted alkyl, an optionally substituted alkenyl, an optionally substituted non-aromatic carbocyclic group, an optionally substituted aryl group, an optionally substituted heterocyclic group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted sulfamoyl group, an optionally substituted carbamoyl group, or an optionally substituted carbamoyl alkyl group, where the nitrogen of the carbamoyl or carbamoyl alkyl group is optionally a heteroatom in a ring structure; and $R_5$ is hydroxy, $NH_2$, alkylamino, alkanoylamino, or alkylsulfonylamino;

or $R_4$ and $R_5$ taken together along with the carbon atoms to which they are attached form a five- or six-membered optionally substituted non-aromatic carbocyclic group, optionally substituted aryl group, optionally substituted heterocyclic group, or optionally substituted heteroaryl group;

or $R_4$ and $R_5$ taken together along with the carbon atoms to which they are attached form a seven to eleven membered, optionally substituted spirocyclic ring or a seven to eleven membered, optionally substituted spiro-heterocyclic ring;

Alk is hydrogen or an optionally substituted alkyl; and $R_{11}$ is an aryl group optionally substituted with one to five substituents independently selected from lower alkyl, alkoxy, haloalkoxy, halogen, and cycloalkyl; or a heteroaryl group optionally substituted with one to five substituents independently selected from lower alkyl, alkoxy, haloalkoxy, halogen, and cycloalkyl; or a bicyclic ring system; or a bicyclic heterocyclic ring system;

ii) CE is a moiety of Formula IV

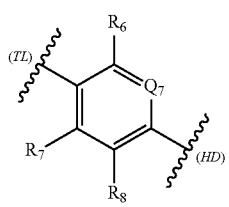
(IV)

wherein:

each of $R_6$ and $R_7$ is independently selected from halogen, —CN, optionally substituted lower alkyl, optionally substituted lower alkoxy, optionally substituted lower alkenyl, or cyclopropyl;

$R_8$ is selected from hydrogen, optionally substituted lower alkyl, optionally substituted lower alkoxy, cyano, or halogen;

optionally $R_7$ and $R_8$ taken together, along with the carbon atoms to which they are attached, form a 4-, 5- or 6-membered non-aromatic carbocyclic, heterocycloalkyl, aryl, or heteroaryl ring $Q_7$ is nitrogen or —$CR_c$—, wherein $R_c$ is hydrogen, halogen, or lower alkyl;

(TL) denotes the point where the moiety of Formula IV connects to TL-$L_a$-; and (HD) denotes the point where the moiety of Formula IV connects to —HD;

iii) HD is a moiety of Formula V or VI:

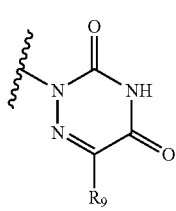
(V)

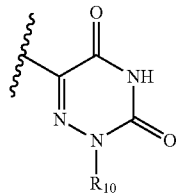
(VI)

wherein:

$R_9$ is selected from hydrogen, —$(C(R_d)_2)_n$—$C(R_d)_3$, —$(C(R_a)_2)_n$—$OR_d$, —$(C(R_a)_2)_n$—$N(R_d)_2$, —$(C(R_d)_2)_n$—$S(=O)_q R_d$, —$(C(R_d)_2)_n$—CN, —$(C(R_d)_2)_n$—C≡C—$R_d$, —$(C(R_d)_2)_n$—C(=O)—$OR_d$, —$(C(R_a)_2)_n$—HeAr, or —$(C(R_a)_2)_n$—C(=O)—$N(R_d)_2$; wherein each $R_d$ is independently hydrogen or optionally substituted lower alkyl;

each q is independently selected from 0, 1, or 2;

each n is independently selected from 0, 1, 2, 3, 4, or 5;

HeAr is a 5- or 6-membered heteroaryl; and $R_{10}$ is hydrogen or —$C(R_e)_3$, wherein each $R_e$ is independently hydrogen, halogen, or optionally substituted lower alkyl; and (iv) $L_a$ is independently a bond; —$(C(R_a)_2)_z$—; oxygen; sulfur; or —$NR_a$—; wherein:

each $R_a$ is independently a hydrogen or lower alkyl; and z is 0, 1, 2, 3, 4 or 5;

provided that:

(1) when TL is a moiety of Formula IIIa, wherein $Q_4$, $Q_5$, and $Q_6$ are —CH—, and $R_4$ is an optionally substituted $C_1$-$C_3$alkyl group, an optionally substituted sulfamoyl group, or an optionally substituted carbamoyl group; HD is a moiety of Formula V, wherein $R_9$ is H or —CN; and $Q_7$ is —CH—, then $R_5$ cannot be hydroxy;

(2) when TL is a moiety of Formula IIa, wherein $Q_1$, $Q_2$, and $Q_3$ are —CH—, $R_1$ is —$CH_3$, and $R_2$ is hydrogen; HD is a moiety of Formula V, wherein $R_9$ is hydrogen; $Q_7$ is —CH—; $R_6$ is halogen or methyl; and $R_7$ and $R_8$ taken together, along with the carbon atoms to which they are attached, form a 5-membered non-aromatic carbocyclic ring, then $R_4$ and $R_5$ taken together along with the carbon atoms to which they are attached cannot form a five-membered heteroaryl group;

(3) when TL is a moiety of Formula IIIa, wherein $Q_4$ is nitrogen, $Q_5$ and $Q_6$ are —CH—, and $R_5$ is —OH; HD is a moiety of Formula V, wherein $R_9$ is —CN; $Q_7$ is —CH—; $L_a$ is —$CH_2$—, then $R_4$ cannot be cyclohexyl, cycloheptyl, isopropyl, or optionally substituted benzene;

(4) when TL is a moiety of Formula IIIb, wherein $Q_4$ is —CH— and $Q_5$ is nitrogen; HD is a moiety of Formula V, wherein $R_9$ is hydrogen, —CN, or —$CO_2H$; $Q_7$ is —CH—; and $R_6$ and $R_7$ are independently halogen or methyl, or $R_7$ and $R_8$ taken together, along with the carbon atoms to which they are attached, form a 5-membered non-aromatic carbocyclic ring, then $R_4$ cannot be isopropyl or 2-hydroxy-1-methyl-ethyl;

(5) when TL is a moiety of Formula IIIb, wherein $Q_4$ is —$CR_c$— and $Q_5$ is nitrogen; HD is a moiety of Formula V, wherein $R_9$ is —CN; $Q_7$ is —CH—; and $L_a$ is —O—, then (a) none of $R_6$, $R_7$, and $R_8$ can be deuterium;

(b) $Q_4$ cannot be —CD-, wherein D is deuterium; and (c) $R_4$ cannot be a three- to five-membered cycloalkyl ring optionally substituted with one or more halogens; non-aromatic (carbocyclic)alkyl optionally substituted with methyl or hydroxy; (1H-pyrazol-4-yl)methyl; (3-methylisoxazol-5-yl)methyl; phenyl; benzyl optionally substituted with methyl, halogen, hydroxy, or methoxy; phenethyl optionally substituted with halogen; $C_1$-$C_4$ alkyl optionally substituted with one to six substituents selected from halogen, hydroxyl, and deuterium; (tetrahydro-2H-pyran-4-yl)methyl; or a three- to five-membered heterocycloalkyl optionally substituted with benzyl;

(6) when TL is a moiety of Formula IIIb, wherein (i) $Q_4$ and $Q_5$ are nitrogen, (ii) $Q_4$ and $Q_5$ are —$CR_b$—, or (iii) $Q_4$ is nitrogen and $Q_5$ is —$CR_c$—; HD is a moiety of Formula V, wherein $R_9$ is —CN; and $Q_7$ is —CH—; then $R_4$ cannot be —CH(CH$_3$)$_2$ or —CH(CD$_3$)$_2$;

(7) when TL is a moiety of Formula IIIa, wherein $Q_4$ is —CH—, $Q_5$ and $Q_6$ are nitrogen, and $R_4$ is isopropyl; HD is a moiety of Formula V, wherein $R_9$ is —CN; and $Q_7$ is —CH—; then $R_5$ cannot be —NH$_2$ or —NHCH$_3$;

(8) when TL is a moiety of Formula IIIb, wherein $Q_4$ is —CH— and $Q_5$ is nitrogen; $L_a$ is —O—; $Q_7$ is —CH—; and HD is a moiety of Formula V, then $R_9$ cannot be methyl;

(9) when TL is a moiety of Formula IIIb, wherein $Q_4$ is —CH—, $Q_5$ is nitrogen, and $R_4$ is isopropyl; $L_a$ is —O—; $Q_7$ is —CH—; and HD is a moiety of Formula V, then $R_9$ cannot be isopropyl;

(10) when TL is a moiety of Formula IIa, wherein $Q_1$, $Q_2$, and $Q_3$ are —CH—; $L_a$ is —O—; $Q_7$ is —CH—; $R_6$ and $R_7$ are independently chlorine or trifluoromethyl; and HD is a moiety of Formula V, wherein $R_9$ is —CN or methyl, then $R_1$ cannot be isopropyl, 4-tetrahydropyranyl, or —C(O)NH$_2$;

(11) when TL is a moiety of Formula IIa, wherein $Q_1$ and $Q_2$ are —CH—, and $Q_3$ is nitrogen; $L_a$ is —O—; $Q_7$ is —CH—; $R_6$ and $R_7$ are chlorine; and HD is a moiety of Formula V, wherein $R_9$ is —CN, then $R_1$ cannot be isopropyl;

(12) when TL is a moiety of Formula IIb, wherein $Q_1$, $Q_2$, and $Q_3$ are —CH—; $L_a$ is —O—; $Q_7$ is —CH—; $R_6$ and $R_7$ are chlorine; and HD is a moiety of Formula V, wherein $R_9$ is —CN, then $R_1$ cannot be isopropyl;

(13) when TL is a moiety of Formula IIIb, wherein $Q_4$ is —CH— and $Q_5$ is nitrogen; $L_a$ is —O—; $Q_7$ is —CH—; $R_6$ and $R_7$ are chlorine; and HD is a moiety of Formula VI, wherein $R_{10}$ is H, Me, Et, isopropyl, —CH$_2$CF$_3$, or —CH$_2$CHF$_2$, then $R_4$ cannot be $C_2$-$C_5$ alkyl or $C_1$-$C_3$ hydroxyalkyl;

(14) when TL is a moiety of Formula IIIb, wherein $Q_4$ is —CH— and $Q_5$ is nitrogen; $L_a$ is —O—; $Q_7$ is —CH—; $R_6$ and $R_7$ are chlorine; and HD is a moiety of Formula VI, wherein $R_{10}$ is H or Me, then $R_4$ cannot be cyclopropyl;

(15) when TL is a moiety of Formula IIIb, wherein $Q_4$ is —CH— and $Q_5$ is nitrogen; $L_a$ is —CH$_2$—; $Q_7$ is —CH—; $R_6$ and $R_7$ are both chlorine or both methyl; and HD is a moiety of Formula VI, wherein $R_{10}$ is H or Me, then $R_4$ cannot be isopropyl; and

(16) when TL is a moiety of Formula IIIb, wherein $Q_4$ is —CH— and $Q_5$ is nitrogen; HD is a moiety of Formula V, wherein $R_9$ is —CH$_2$CN or —C≡CH; $Q_7$ is —CH—; and $R_6$ and $R_7$ are chlorine, then $R_4$ cannot be isopropyl.

In another aspect, disclosed herein are compounds of Formula I':

TL-$L_a$-CE-HD  (I')

or a stereoisomer or a tautomer thereof, or a pharmaceutically acceptable salt, prodrug, amide or ester thereof, wherein:

i) TL is a moiety of Formula IIa, IIb, IIIa, IIIb, IIIc, or IId:

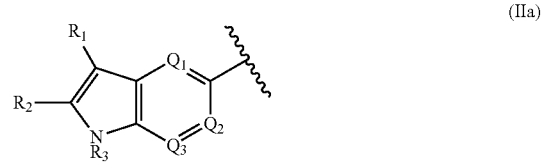
(IIa)

(IIb)

(IIIa)

(IIIb)

(IIIc)

(IIId)

wherein:
each of $Q_1$, $Q_2$, $Q_3$, $Q_4$, $Q_5$, $Q_6$, and $Q_8$, is independently nitrogen or —$CR_b$—, wherein each $R_b$ is independently hydrogen, halogen, or lower alkyl;

$R_1$ is hydrogen, an optionally substituted alkyl, an optionally substituted non-aromatic carbocyclic group, an optionally substituted aryl group, an optionally substituted heterocycloalkyl group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;

$R_2$ is hydrogen, halogen, optionally substituted alkyl, optionally substituted cycloalkyl, or —CN;

$R_3$ is hydrogen or lower alkyl;

$R_4$ is an optionally substituted alkyl, an optionally substituted alkenyl, an optionally substituted non-aromatic carbocyclic group, an optionally substituted aryl group, an optionally substituted heterocyclic group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted sulfamoyl group, an optionally substituted carbamoyl group, or an optionally substituted carbamoyl alkyl group, where the nitrogen of the carbamoyl or carbamoyl alkyl group is optionally a heteroatom in a ring structure; and $R_5$ is hydroxy, $NH_2$, alkylamino, alkanoylamino, or alkylsulfonylamino;

or $R_4$ and $R_5$ taken together along with the carbon atoms to which they are attached form a five- or six-membered optionally substituted non-aromatic carbocyclic group, optionally substituted aryl group, optionally substituted heterocyclic group, or optionally substituted heteroaryl group;

or $R_4$ and $R_5$ taken together along with the carbon atoms to which they are attached form a seven to eleven membered, optionally substituted spirocyclic ring or a seven to eleven membered, optionally substituted spiro-heterocyclic ring;

Alk is hydrogen or an optionally substituted alkyl; and $R_{11}$ is an aryl group optionally substituted with one to five substituents independently selected from lower alkyl, halogen, and cycloalkyl; or a bicyclic ring system containing either aromatic or saturated rings; or a bicyclic heterocyclic containing either aromatic or saturated ring systems;

ii) CE is a moiety of Formula IV

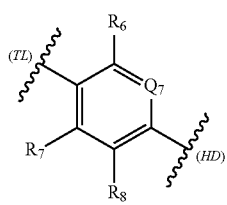

(IV)

wherein:
each of $R_6$ and $R_7$ is independently selected from halogen, —CN, optionally substituted lower alkyl, optionally substituted lower alkoxy, optionally substituted lower alkenyl, or cyclopropyl;

$R_8$ is selected from hydrogen, optionally substituted lower alkyl, optionally substituted lower alkoxy, cyano, or halogen;

optionally $R_7$ and $R_8$ taken together, along with the carbon atoms to which they are attached, form a 4-, 5- or 6-membered non-aromatic carbocyclic, heterocycloalkyl, aryl, or heteroaryl ring $Q_7$ is nitrogen or —$CR_c$—, wherein $R_e$ is hydrogen, halogen, or lower alkyl;

(TL) denotes the point where the moiety of Formula IV connects to TL-$L_a$-; and (HD) denotes the point where the moiety of Formula IV connects to —HD;

iii) HD is a moiety of Formula V or VI:

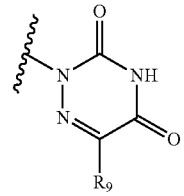

(V)

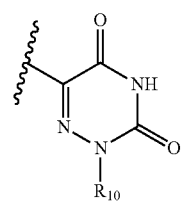

(VI)

wherein:
$R_9$ is selected from hydrogen, —$(C(R_d)_2)_n$—$C(R_a)_3$, —$(C(R_a)_2)_n$—$OR_d$, —$(C(R_a)_2)_n$—$N(R_a)_2$, —$(C(R_a)_2)_n$—$S(=O)_qR_a$, —$(C(R_a)_2)_n$—CN, —$(C(R_a)_2)_n$—C≡C—$R_d$, —$(C(R_d)_2)_n$—C(=O)—$OR_d$, —$(C(R_a)_2)_n$—HeAr, or —$(C(R_a)_2)_n$—C(=O)—$N(R_a)_2$; wherein each $R_d$ is independently hydrogen or optionally substituted lower alkyl;

each q is independently selected from 0, 1, or 2;

each n is independently selected from 0, 1, 2, 3, 4, or 5;

HeAr is a 5- or 6-membered heteroaryl; and $R_{10}$ is hydrogen or —$C(R_e)_3$, wherein each $R_e$ is independently hydrogen, halogen, or optionally substituted lower alkyl; and $L_a$ is independently a bond; —$(C(R_a)_2)_z$—; oxygen; sulfur; or —$NR_a$—; wherein:

each $R_a$ is independently a hydrogen or lower alkyl; and z is 0, 1, 2, 3, 4 or 5;

provided that:

(1) when TL is a moiety of Formula IIIa, wherein $Q_4$, $Q_5$, and $Q_6$ are —CH—, and $R_4$ is an optionally substituted $C_1$-$C_3$alkyl group, an optionally substituted sulfamoyl group, or an optionally substituted carbamoyl group; HD is a moiety of Formula V, wherein $R_9$ is H or —CN; and $Q_7$ is —CH—, then $R_5$ cannot be hydroxy;

(2) when TL is a moiety of Formula IIa, wherein $Q_1$, $Q_2$, and $Q_3$ are —CH—, $R_1$ is —$CH_3$, and $R_2$ is hydrogen; HD is a moiety of Formula V, wherein $R_9$ is hydrogen; $Q_7$ is —CH—; $R_6$ is halogen or methyl; and $R_7$ and $R_8$ taken together, along with the carbon atoms to which they are attached, form a 5-membered non-aromatic carbocyclic ring, then $R_4$ and $R_5$ taken together along with the carbon atoms to which they are attached cannot form a five-membered heteroaryl group;

(3) when TL is a moiety of Formula IIIa, wherein $Q_4$ is nitrogen, $Q_5$ and $Q_6$ are —CH—, and $R_5$ is —OH; HD is a moiety of Formula V, wherein $R_9$ is —CN; $Q_7$ is —CH—; $L_a$ is —$CH_2$—, then $R_4$ cannot be cyclohexyl, cycloheptyl, isopropyl, or optionally substituted benzene;

(4) when TL is a moiety of Formula IIIb, wherein $Q_4$ is —CH— and $Q_5$ is nitrogen; HD is a moiety of Formula V, wherein $R_9$ is hydrogen, —CN, or —$CO_2H$; $Q_7$ is —CH—; and $R_6$ and $R_7$ are independently halogen or methyl, or $R_7$ and $R_8$ taken together, along with the carbon atoms to which they are attached, form a 5-membered non-aromatic carbocyclic ring, then $R_4$ cannot be isopropyl or 2-hydroxy-1-methyl-ethyl;

(5) when TL is a moiety of Formula IIIb, wherein $Q_4$ is —$CR_c$— and $Q_5$ is nitrogen; HD is a moiety of Formula V, wherein $R_9$ is —CN; $Q_7$ is —CH—; and $L_a$ is —O—, then
 (a) none of $R_6$, $R_7$, and $R_8$ can be deuterium;
 (b) $Q_4$ cannot be —CD-, wherein D is deuterium; and
 (c) $R_4$ cannot be a three- to five-membered cycloalkyl ring optionally substituted with one or more halogens; $C_1$-$C_4$ alkyl optionally substituted with one to six substituents selected from halogen, hydroxyl, and deuterium; or a three- to five-membered heterocycloalkyl;

(6) when TL is a moiety of Formula IIIb, wherein (i) $Q_4$ and $Q_5$ are nitrogen, (ii) $Q_4$ and $Q_5$ are —$CR_b$—, or (iii) $Q_4$ is nitrogen and $Q_5$ is —$CR_c$—; HD is a moiety of Formula V, wherein $R_9$ is —CN; and $Q_7$ is —CH—; then $R_4$ cannot be —CH(CH$_3$)$_2$ or —CH(CD$_3$)$_2$; and (7) when TL is a moiety of Formula IIIa, wherein $Q_4$ is —CH—, $Q_5$ and $Q_6$ are nitrogen, and $R_4$ is isopropyl; HD is a moiety of Formula V, wherein $R_9$ is —CN; and $Q_7$ is —CH—; then $R_5$ cannot be —NH$_2$ or —NHCH$_3$.

In some embodiments, when TL is a moiety of Formula IIIb, wherein $Q_4$ is —CH— and $Q_5$ is nitrogen; HD is a moiety of Formula V, wherein $R_9$ is —CH$_2$CN or —C≡CH; $Q_7$ is —CH—; and $R_6$ and $R_7$ are chlorine, then $R_4$ cannot be isopropyl.

In another aspect, disclosed herein are compounds of Formula I':

TL-$L_a$-CE-HD (I')

or a stereoisomer or a tautomer thereof, or a pharmaceutically acceptable salt, prodrug, amide or ester thereof, wherein:
i) TL is a moiety of Formula IIa, IIb, IIIa, IIIb, IIIc, or IIId:

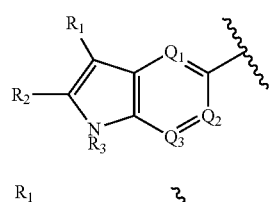
(IIa)

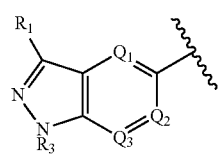
(IIb)

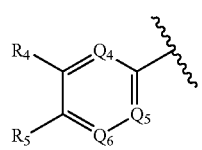
(IIIa)

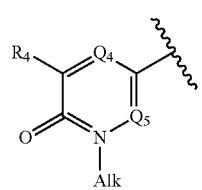
(IIIb)

-continued

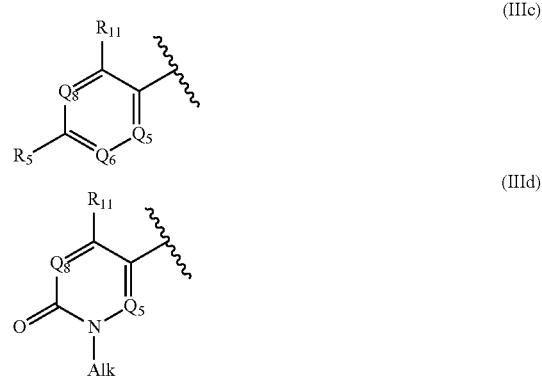
(IIIc)

(IIId)

wherein:
each of $Q_1$, $Q_2$, $Q_3$, $Q_4$, $Q_5$, $Q_6$, and $Q_8$, is independently nitrogen or —$CR_b$—, wherein each $R_b$ is independently hydrogen, halogen, or lower alkyl;

$R_1$ is hydrogen, an optionally substituted alkyl, an optionally substituted non-aromatic carbocyclic group, an optionally substituted aryl group, an optionally substituted heterocycloalkyl group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;

$R_2$ is hydrogen, halogen, optionally substituted alkyl, optionally substituted cycloalkyl, or —CN;

$R_3$ is hydrogen or lower alkyl;

$R_4$ is an optionally substituted alkyl, an optionally substituted alkenyl, an optionally substituted non-aromatic carbocyclic group, an optionally substituted aryl group, an optionally substituted heterocyclic group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted sulfamoyl group, an optionally substituted carbamoyl group, or an optionally substituted carbamoyl alkyl group, where the nitrogen of the carbamoyl or carbamoyl alkyl group is optionally a heteroatom in a ring structure; and $R_5$ is hydroxy, NH$_2$, alkylamino, alkanoylamino, or alkylsulfonylamino;

or $R_4$ and $R_5$ taken together along with the carbon atoms to which they are attached form a five- or six-membered optionally substituted non-aromatic carbocyclic group, optionally substituted aryl group, optionally substituted heterocyclic group, or optionally substituted heteroaryl group;

or $R_4$ and $R_5$ taken together along with the carbon atoms to which they are attached form a seven to eleven membered, optionally substituted spirocyclic ring or a seven to eleven membered, optionally substituted spiro-heterocyclic ring;

Alk is hydrogen or an optionally substituted alkyl; and $R_{11}$ is an aryl group optionally substituted with one to five substituents independently selected from lower alkyl, halogen, and cycloalkyl; or a bicyclic ring system containing either aromatic or saturated rings; or a bicyclic heterocyclic containing either aromatic or saturated ring systems;

ii) CE is a moiety of Formula IV

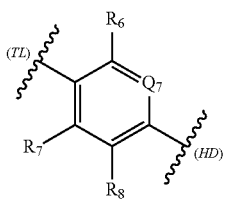

(IV)

wherein:

each of $R_6$ and $R_7$ is independently selected from halogen, —CN, optionally substituted lower alkyl, optionally substituted lower alkoxy, optionally substituted lower alkenyl, or cyclopropyl;

$R_8$ is selected from hydrogen, optionally substituted lower alkyl, optionally substituted lower alkoxy, cyano, or halogen;

optionally $R_7$ and $R_8$ taken together, along with the carbon atoms to which they are attached, form a 4-, 5- or 6-membered non-aromatic carbocyclic, heterocycloalkyl, aryl, or heteroaryl ring $Q_7$ is nitrogen or —$CR_c$—, wherein $R_c$ is hydrogen, halogen, or lower alkyl;

(TL) denotes the point where the moiety of Formula IV connects to TL-$L_a$-; and (HD) denotes the point where the moiety of Formula IV connects to —HD;

iii) HD is a moiety of Formula V or VI:

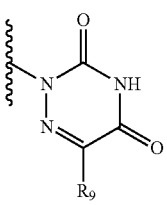

(V)

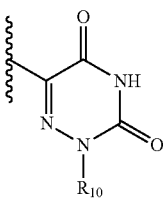

(VI)

wherein:

$R_9$ is selected from hydrogen, —$(C(R_d)_2)_n$—$C(R_a)_3$, —$(C(R_a)_2)_n$—$OR_d$, —$(C(R_a)_2)_n$—$N(R_a)_2$, —$(C(R_a)_2)_n$—$S(=O)_qR_a$, —$(C(R_d)_2)_n$—CN, —$(C(R_d)_2)_n$—C≡C—$R_d$, —$(C(R_d)_2)_n$—C(=O)—$OR_d$, —$(C(R_a)_2)_n$—HeAr, or —$(C(R_a)_2)_n$—C(=O)—$N(R_a)_2$; wherein each $R_d$ is independently hydrogen or optionally substituted lower alkyl;

each q is independently selected from 0, 1, or 2;

each n is independently selected from 0, 1, 2, 3, 4, or 5;

HeAr is a 5- or 6-membered heteroaryl; and $R_{10}$ is hydrogen or —$C(R_e)_3$, wherein each $R_e$ is independently hydrogen, halogen, or optionally substituted lower alkyl; and (iv) $L_a$ is independently a bond; —$(C(R_a)_2)_z$—; oxygen; sulfur; or —$NR_a$—; wherein:

each $R_a$ is independently a hydrogen or lower alkyl; and z is 0, 1, 2, 3, 4 or 5;

provided that:

(1) when TL is a moiety of Formula IIIa, wherein $Q_4$, $Q_5$, and $Q_6$ are —CH—, and $R_4$ is an optionally substituted $C_1$-$C_3$alkyl group, an optionally substituted sulfamoyl group, or an optionally substituted carbamoyl group; HD is a moiety of Formula V, wherein $R_9$ is H or —CN; and $Q_7$ is —CH—, then $R_5$ cannot be hydroxy;

(2) when TL is a moiety of Formula IIa, wherein $Q_1$, $Q_2$, and $Q_3$ are —CH—, $R_1$ is —$CH_3$, and $R_2$ is hydrogen; HD is a moiety of Formula V, wherein $R_9$ is hydrogen; $Q_7$ is —CH—; $R_6$ is halogen or methyl; and $R_7$ and $R_8$ taken together, along with the carbon atoms to which they are attached, form a 5-membered non-aromatic carbocyclic ring, then $R_4$ and $R_5$ taken together along with the carbon atoms to which they are attached cannot form a five-membered heteroaryl group;

(3) when TL is a moiety of Formula IIIa, wherein $Q_4$ is nitrogen, $Q_5$ and $Q_6$ are —CH—, and $R_5$ is —OH; HD is a moiety of Formula V, wherein $R_9$ is —CN; $Q_7$ is —CH—; $L_a$ is —$CH_2$—, then $R_4$ cannot be cyclohexyl, cycloheptyl, isopropyl, or optionally substituted benzene;

(4) when TL is a moiety of Formula IIIb, wherein $Q_4$ is —CH— and $Q_5$ is nitrogen; HD is a moiety of Formula V, wherein $R_9$ is hydrogen, —CN, —$CH_2CN$, —C≡CH, or —$CO_2H$; $Q_7$ is —CH—; and $R_6$ and $R_7$ are independently halogen or methyl, or $R_7$ and $R_8$ taken together, along with the carbon atoms to which they are attached, form a 5-membered non-aromatic carbocyclic ring, then $R_4$ cannot be isopropyl or 2-hydroxy-1-methyl-ethyl;

(5) when TL is a moiety of Formula IIIb, wherein $Q_4$ is —$CR_c$— and $Q_5$ is nitrogen; HD is a moiety of Formula V, wherein $R_9$ is —CN; $Q_7$ is —CH—; and $L_a$ is —O—, then (a) none of $R_6$, $R_7$, and $R_8$ can be deuterium;

(b) $Q_4$ cannot be —CD-, wherein D is deuterium; and (c) $R_4$ cannot be a three- to five-membered cycloalkyl ring optionally substituted with one or more halogens; $C_1$-$C_4$ alkyl optionally substituted with one to six substituents selected from halogen, hydroxyl, and deuterium; or a three- to five-membered heterocycloalkyl;

(6) when TL is a moiety of Formula IIIb, wherein (i) $Q_4$ and $Q_5$ are nitrogen, (ii) $Q_4$ and $Q_5$ are —$CR_b$—, or (iii) $Q_4$ is nitrogen and $Q_5$ is —$CR_c$—; HD is a moiety of Formula V, wherein $R_9$ is —CN; and $Q_7$ is —CH—; then $R_4$ cannot be —$CH(CH_3)_2$ or —$CH(CD_3)_2$; and (7) when TL is a moiety of Formula IIIa, wherein $Q_4$ is —CH—, $Q_5$ and $Q_6$ are nitrogen, and $R_4$ is isopropyl; HD is a moiety of Formula V, wherein $R_9$ is —CN; and $Q_7$ is —CH—; then $R_5$ cannot be —$NH_2$ or —$NHCH_3$.

In some embodiments of the compound of Formula I', TL is a moiety of Formula IIa, IIb, IIIa, IIIb, IIIc, or IIId;

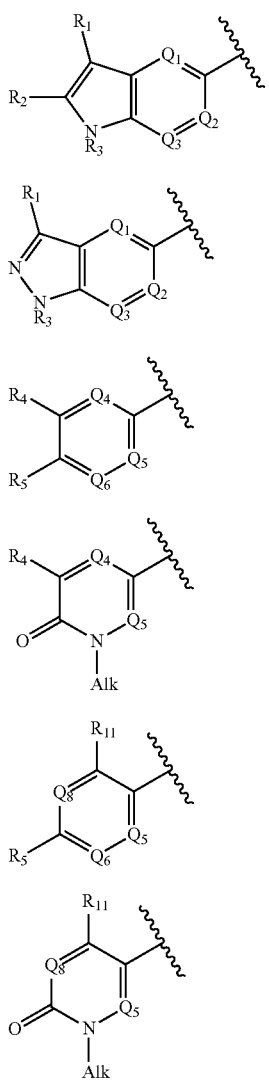

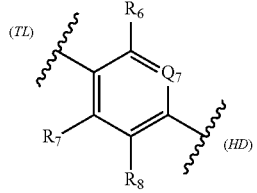

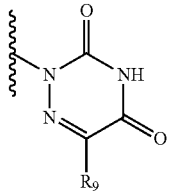

wherein:

each of $Q_1$, $Q_2$, $Q_3$, $Q_4$, $Q_5$, $Q_6$ and $Q_8$, is independently nitrogen or —$CR_b$—, wherein each $R_b$ is independently hydrogen, halogen, or lower alkyl;

$R_1$ is an optionally substituted alkyl, an optionally substituted non-aromatic carbocyclic group, an optionally substituted aryl group, an optionally substituted heterocycloalkyl group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;

$R_2$ is halogen, optionally substituted alkyl, optionally substituted cycloalkyl, or —CN;

$R_3$ is hydrogen;

$R_4$ is an optionally substituted alkyl, an optionally substituted non-aromatic carbocyclic group, an optionally substituted aryl group, an optionally substituted heterocycloalkyl group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted sulfamoyl group, an optionally substituted carbamoyl group, or an optionally substituted carbamoyl alkyl group, where the nitrogen of the carbamoyl or carbamoyl alkyl group is optionally a heteroatom in a ring structure; and $R_5$ is hydroxy, $NH_2$, alkylamino, alkanoylamino, or alkylsulfonylamino;

or $R_4$ and $R_5$ taken together along with the carbon atoms to which they are attached form a five- or six-membered optionally substituted non-aromatic carbocyclic group, optionally substituted aryl group, optionally substituted heterocycloalkyl group, or optionally substituted heteroaryl group;

or $R_4$ and $R_5$ taken together along with the carbon atoms to which they are attached form a seven to eleven membered, optionally substituted spirocyclic ring or a seven to eleven membered, optionally substituted spiro-heterocyclic ring; and Alk is hydrogen or an optionally substituted alkyl;

CE is a moiety of Formula IV wherein:

each of $R_6$ and $R_7$ is independently selected from halogen, —CN, optionally substituted lower alkyl, optionally substituted lower alkoxy, optionally substituted lower alkenyl, or cyclopropyl;

$R_8$ is selected from hydrogen, optionally substituted lower alkyl, optionally substituted lower alkoxy, cyano, or halogen;

$Q_7$ is nitrogen or —$CR_c$—, wherein $R_c$ is hydrogen, halogen, or lower alkyl;

(TL) denotes the point where the moiety of Formula IV connects to TL-$L_a$-; and (HD) denotes the point where the moiety of Formula IV connects to —HD;

HD is a moiety of Formula V or VI:

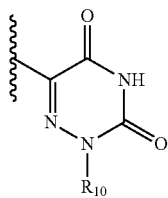

(VI)

wherein:
$R_9$ is selected from —$NH_2$, —CN, —$CH_2$—S—$CH_3$, or —$CH_2$—S(=O)$_2$—$CH_3$;
$R_{10}$ is —$CH_3$; and
$L_a$ is oxygen or —$CH_2$—.

In some embodiments of the compound of Formula I',
TL is a moiety of Formula IIa:

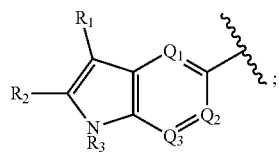

(IIa)

and
HD is a moiety of Formula V:

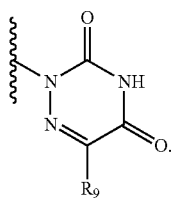

(V)

In some embodiments of the compound of Formula I':
TL is a moiety of Formula IIa:

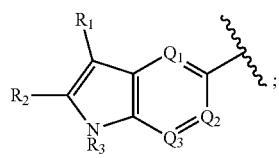

(IIa)

and
HD is a moiety of Formula VI:

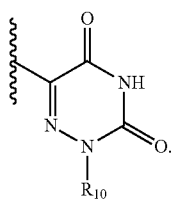

(VI)

In some embodiments of the compound of Formula I':
TL is a moiety of Formula IIb:

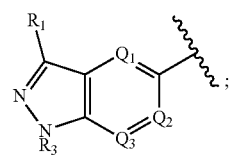

(IIb)

and
HD is a moiety of Formula V:

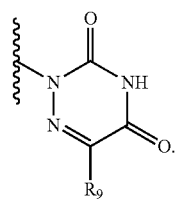

(V)

In some embodiments of the compound of Formula I':
TL is a moiety of Formula IIb:

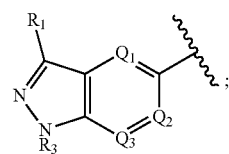

(IIb)

and
HD is a moiety of Formula VI:

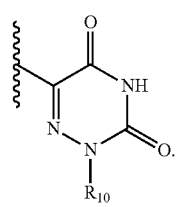

(VI)

In some embodiments of the compound of Formula I',
TL is a moiety of Formula IIIa:

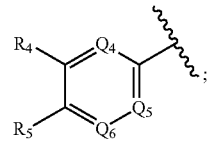

(IIIa)

and
HD is a moiety of Formula V:

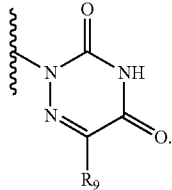
(V)

In some embodiments of the compound of Formula I', TL is a moiety of Formula IIIa:

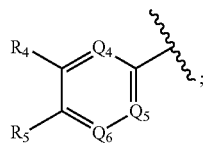
(IIIa)

and
HD is a moiety of Formula VI:

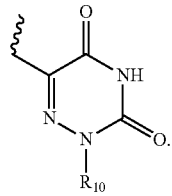
(VI)

In some embodiments of the compound of Formula I', TL is a moiety of Formula IIIb:

(IIIb)

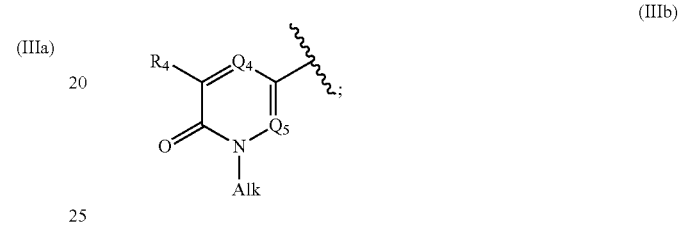

and
HD is a moiety of Formula V:

(V)

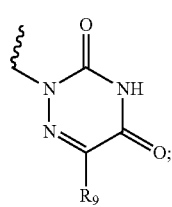

wherein:
R$_9$ is selected from hydrogen, —(C(R$_d$)$_2$)$_n$—OR$_d$, —(C(R$_d$)$_2$)$_n$—N(R$_d$)$_2$, —(C(R$_d$)$_2$)$_n$—S(═O)$_q$R$_d$, —(C(R$_d$)$_2$)$_n$—C≡C—R$_d$, —(C(R$_d$)$_2$)$_n$—C(═O)—OR$_d$, —(C(R$_d$)$_2$)$_n$—HeAr, or —(C(R$_d$)$_2$)$_n$—C(═O)—N(R$_d$)$_2$;

wherein
each R$_d$ is independently hydrogen or optionally substituted C$_1$-C$_5$ alkyl;
each q is independently 0 or 2; and
each n is independently 0 or 1.

In some embodiments of the compound of Formula I', TL is a moiety of Formula IIIb:

(IIIb)

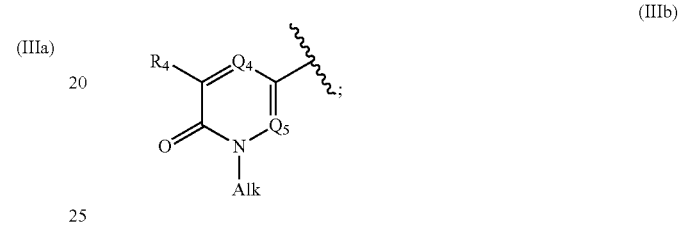

and
HD is a moiety of Formula VI:

(VI)

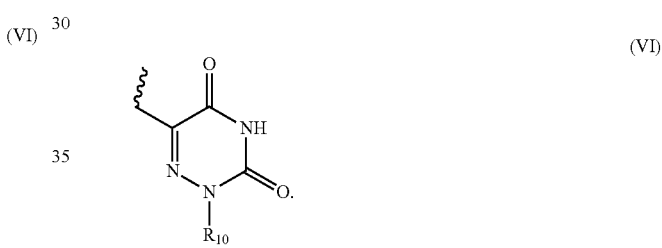

In some embodiments of the compound of Formula I', TL is a moiety of Formula IIIc:

(IIIc)

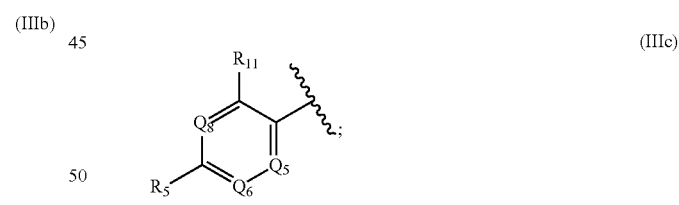

and
HD is a moiety of Formula V:

(V)

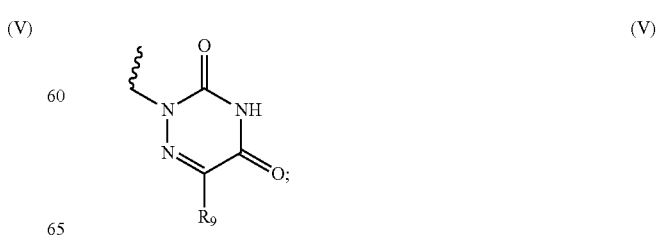

In some embodiments of the compound of Formula I', TL is a moiety of Formula IIIc:

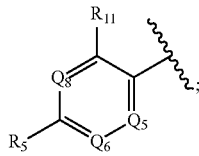
(IIIc)

and
HD is a moiety of Formula VI:

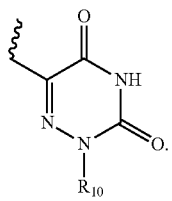
(VI)

In some embodiments of the compound of Formula I', TL is a moiety of Formula IIId:

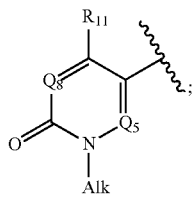
(IIId)

and
HD is a moiety of Formula V:

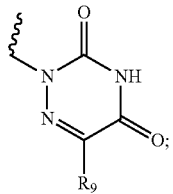
(V)

In some embodiments of the compound of Formula I', TL is a moiety of Formula IIId:

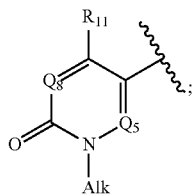
(IIId)

and
HD is a moiety of Formula VI:

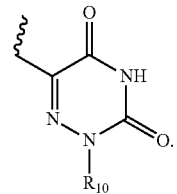
(VI)

In some embodiments of the compound of Formula I', TL is a moiety of Formula II:

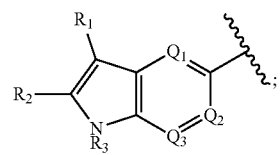
(II)

wherein:
each of $Q_1$, $Q_2$, and $Q_3$ is independently nitrogen or —$CR_b$—, wherein each $R_b$ is independently hydrogen, halogen, or lower alkyl;
$R_1$ is an optionally substituted alkyl, an optionally substituted non-aromatic carbocyclic group, an optionally substituted aryl group, an optionally substituted heterocycloalkyl group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;
$R_2$ is halogen, optionally substituted alkyl, optionally substituted cycloalkyl, or —CN;
$R_3$ is hydrogen;
CE is a moiety of Formula IV

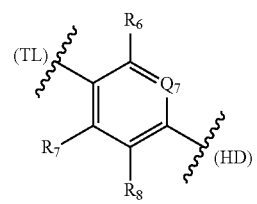
(IV)

wherein:
each of $R_6$ and $R_7$ is independently selected from halogen, —CN, optionally substituted lower alkyl, optionally substituted lower alkoxy, optionally substituted lower alkenyl, or cyclopropyl;
$R_8$ is selected from hydrogen, optionally substituted lower alkyl, optionally substituted lower alkoxy, cyano, or halogen;

$Q_7$ is nitrogen or —$CR_c$—, wherein $R_c$ is hydrogen, halogen, or lower alkyl;

(TL) denotes the point where the moiety of Formula IV connects to TL-$L_a$-; and (HD) denotes the point where the moiety of Formula IV connects to —HD;

HD is a moiety of Formula V:

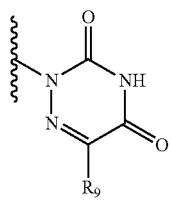

(V)

wherein $R_9$ is hydrogen, —CN, —$NH_2$, —$C(R_d)_2$—S—$R_d$, —$C(R_d)_2$—S(=O)$_2R_d$, or —C≡C—$R_d$, wherein each $R_d$ is independently hydrogen or lower alkyl; and $L_a$ is oxygen or —$CH_2$—.

In some embodiments of the compound of Formula I', $Q_1$, $Q_2$, $Q_3$, and $Q_4$ are —$CR_b$—, where each $R_b$ is independently selected from the group consisting of hydrogen, methyl, ethyl, n-propyl, i-propyl, n-butyl, i-butyl, and t-butyl. In some embodiments of the compound of Formula I', $Q_1$, $Q_2$, and $Q_3$ are —CH—.

In some embodiments of the compound of Formula I', $Q_1$ is —CH—, and $Q_2$ and $Q_3$ are nitrogen. In some embodiments of the compound of Formula I', $Q_2$ is —CH—, and $Q_1$ and $Q_3$ are nitrogen. In some embodiments of the compound of Formula I', $Q_3$ is —CH—, and $Q_1$ and $Q_2$ are nitrogen.

In some embodiments of the compound of Formula I', $Q_1$ is nitrogen, and $Q_2$ and $Q_3$ are —CH—. In some embodiments of the compound of Formula I', $Q_2$ is nitrogen, and $Q_1$ and $Q_3$ are —CH—. In some embodiments of the compound of Formula I', $Q_3$ is nitrogen, and $Q_1$ and $Q_2$ are —CH—.

In some embodiments of the compound of Formula I', $Q_4$, $Q_5$, and $Q_6$ are —$CR_b$—, where each $R_b$ is independently selected from the group consisting of hydrogen, methyl, ethyl, n-propyl, i-propyl, n-butyl, i-butyl, and t-butyl. In some embodiments of the compound of Formula I', $Q_4$, $Q_5$, and $Q_6$ are —CH—.

In some embodiments of the compound of Formula I', $Q_4$ is —CH—, and $Q_5$ and $Q_6$ are nitrogen. In some embodiments of the compound of Formula I', $Q_5$ is —CH—, and $Q_4$ and $Q_6$ are nitrogen. In some embodiments of the compound of Formula I', $Q_6$ is —CH—, and $Q_4$ and $Q_5$ are nitrogen.

In some embodiments of the compound of Formula I', $Q_4$ is nitrogen, and $Q_5$ and $Q_6$ are —CH—. In some embodiments of the compound of Formula I', $Q_5$ is nitrogen, and $Q_4$ and $Q_6$ are —CH—. In some embodiments of the compound of Formula I', $Q_6$ is nitrogen, and $Q_4$ and $Qs$ are —CH—.

In some embodiments of the compound of Formula I', $Q_4$ is —CH— and $Q_5$ is nitrogen In some embodiments of the compound of Formula I', $Q_5$ and $Q_6$ are nitrogen.

In some embodiments of the compound of Formula I', $Q_5$ is nitrogen and $Q_8$ is —CH—.

In some embodiments of the compound of Formula I', $Q_5$, $Q_6$, and $Q_8$ are —$CR_b$—, where each $R_b$ is independently selected from the group consisting of hydrogen, methyl, ethyl, n-propyl, i-propyl, n-butyl, i-butyl, and t-butyl. In some embodiments of the compound of Formula I', $Q_5$, $Q_6$, and $Q_8$ are —CH—.

In some embodiments of the compound of Formula I', $Q_5$ is —CH—, and $Q_6$ and $Q_8$ are nitrogen. In some embodiments of the compound of Formula I', $Q_6$ is —CH—, and $Q_5$ and $Q_8$ are nitrogen. In some embodiments of the compound of Formula I', $Q_5$ is —CH—, and $Q_5$ and $Q_6$ are nitrogen.

In some embodiments of the compound of Formula I', $R_1$ is hydrogen, an optionally substituted alkyl, an optionally substituted non-aromatic carbocyclic group, an optionally substituted aryl group, and an optionally substituted C-carboxy group. In some embodiments of the compound of Formula I', the alkyl is selected from the group consisting of methyl, ethyl, n-propyl, i-propyl, n-butyl, i-butyl, and t-butyl. In some embodiments of the compound of Formula I', at least one carbon atom of the listed alkyl moieties is perfluorinated. In some embodiments of the compound of Formula I', the alkyl is substituted with cycloalkyl or aryl. In some embodiments of the compound of Formula I', the cycloalkyl is selected from the group consisting of cyclopropyl, cyclopentyl, and cyclohexyl. In some embodiments of the compound of Formula I', the aryl is optionally substituted phenyl. In some embodiments of the compound of Formula I', the carbocyclic group is cyclohexane or cyclopentane. In some embodiments of the compound of Formula I', the aryl group is phenyl. In some embodiments of the compound of Formula I', the C-carboxy group is a moiety of formula —C(=O)—O—R, where R is selected from the group consisting of methyl, ethyl, n-propyl, i-propyl, n-butyl, i-butyl, and t-butyl.

In some embodiments of the compound of Formula I', $R_1$ is hydrogen, $C_1$-$C_6$ alkyl, a non-aromatic $C_3$-$C_{12}$ carbocyclic group, a $C_6$-$C_{10}$ aryl group, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, a (carbocyclic)alkyl group, an aralkyl group, a (heterocycloalkyl)alkyl group, a (heteroaryl)alkyl group, an amino group, a C-carboxy or O-carboxy group, —CN, or a carbamoyl group; and $R_1$ is optionally substituted with one to five $R_k$ independently selected from the group consisting of hydroxy, halogen, —CN, amino, oxo, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is hydrogen. In some embodiments of the compound of Formula I', $R_1$ is —CN.

In some embodiments of the compound of Formula I', $R_1$ is an optionally substituted $C_1$-$C_6$ alkyl. In some embodiments of the compound of Formula I', $R_1$ is $C_1$-$C_6$ alkyl optionally substituted with one to five $R_k$ independently selected from the group consisting of hydroxy, halogen, —CN, amino, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_1$ is $C_1$-$C_6$ alkyl.

In some embodiments of the compound of Formula I', $R_1$ is an optionally substituted non-aromatic carbocyclic group. In some embodiments of the compound of Formula I', $R_1$ is a non-aromatic $C_3$-$C_{12}$ carbocyclic group optionally substituted with one to five $R_k$ independently selected from the group consisting of hydroxy, oxo, halogen, amino, O-carboxy, C-carboxy, C-amido, N-amido, $C_1$-$C_6$ alkyl, $C_1$-$C_6$ haloalkyl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is an optionally substituted aryl group. In some embodiments of the compound of Formula I', $R_1$ is a $C_6$-$C_{10}$ aryl group optionally substituted with one to five $R_k$ independently selected from the group consisting of hydroxy, halogen, —CN, O-carboxy, C-carboxy, C-amido, N-amido, amino, $C_1$-$C_6$ alkyl, $C_1$-$C_6$ haloalkyl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is an optionally substituted heterocycloalkyl group. In some embodiments of the compound of Formula I', $R_1$ is a 3- to 6-membered heterocycloalkyl ring containing one to four ring heteroatoms independently selected from oxygen, sulfur, or nitrogen, wherein the heterocycloalkyl ring is optionally substituted with one to five $R_k$ independently selected from the group consisting of hydroxy, oxo, halogen, amino, O-carboxy, C-carboxy, C-amido, N-amido, $C_1$-$C_6$ alkyl, $C_1$-$C_6$ haloalkyl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is an optionally substituted heteroaryl group. In some embodiments of the compound of Formula I', $R_1$ is a five- to ten-membered heteroaryl group containing one to four ring heteroatoms independently selected from oxygen, sulfur, or nitrogen, wherein the heteroaryl group is optionally substituted with one to five $R_k$ independently selected from the group consisting of hydroxy, halogen, —CN, amino, O-carboxy, C-carboxy, C-amido, N-amido, $C_1$-$C_6$ alkyl, $C_1$-$C_6$ haloalkyl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is an optionally substituted (carbocyclic)alkyl group. In some embodiments of the compound of Formula I', $R_1$ is (cyclopentyl)$C_1$-$C_6$ alkyl, (cyclobutyl)$C_1$-$C_6$ alkyl, (cyclopentyl)$C_1$-$C_6$ alkyl, (cyclohexyl)$C_1$-$C_6$ alkyl, (cycloheptyl)$C_1$-$C_6$ alkyl, (cyclooctyl)$C_1$-$C_6$ alkyl, or (cyclononyl)$C_1$-$C_6$ alkyl, and $R_1$ is optionally substituted with one to five $R_k$ independently selected from the group consisting of hydroxy, halogen, —CN, amino, O-carboxy, C-carboxy, C-amido, N-amido, oxo, $C_1$-$C_6$ alkyl, $C_1$-$C_6$ haloalkyl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is an optionally substituted aralkyl group. In some embodiments of the compound of Formula I', $R_1$ is a benzyl group optionally substituted with one to five $R_k$ independently selected from the group consisting of hydroxy, halogen, —CN, amino, O-carboxy, C-carboxy, C-amido, N-amido, $C_1$-$C_6$ alkyl, $C_1$-$C_6$ haloalkyl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is an optionally substituted (heterocycloalkyl)alkyl group. In some embodiments of the compound of Formula I, $R_1$ is a (heterocycloalkyl)alkyl group optionally substituted with one to five $R_k$ independently selected from the group consisting of hydroxy, oxo, halogen, amino, O-carboxy, C-carboxy, C-amido, N-amido, $C_1$-$C_6$ alkyl, $C_1$-$C_6$ haloalkyl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is an optionally substituted (heteroaryl)alkyl group. In some embodiments of the compound of Formula I', $R_1$ is a (heteroaryl)alkyl group optionally substituted with one to five $R_k$ independently selected from the group consisting of hydroxy, halogen, —CN, amino, O-carboxy, C-carboxy, C-amido, N-amido, $C_1$-$C_6$ alkyl, $C_1$-$C_6$ haloalkyl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is an optionally substituted amino group. In some embodiments of the compound of Formula I', $R_1$ is an amino group optionally substituted with one or two substituents independently selected from the group consisting of $C_1$-$C_6$ alkyl, $C_1$-$C_6$ haloalkyl, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, $C_6$-$C_{10}$ aryl, C-carboxy, C-amido, —(SO$_2$)($C_1$-$C_6$ alkyl), —C(O)O($C_1$-$C_6$ alkyl), —C(O)O($C_1$-$C_6$ haloalkyl), —C(O)O($C_3$-$C_9$ cycloalkyl), —C(O)O(3- to 6-membered heterocycloalkyl), —C(O)O (five- to ten-membered heteroaryl), and —C(O)O($C_6$-$C_{10}$ aryl). In some embodiments of the compound of Formula I', $R_1$ is —NR$_m$R$_n$, wherein R$_m$ and R$_n$ are independently selected from the group consisting of hydrogen, $C_1$-$C_6$ alkyl, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, $C_6$-$C_{10}$ aryl, C-carboxy, C-amido, —(SO$_2$)($C_1$-$C_6$ alkyl), —C(O)O($C_1$-$C_6$ alkyl), —C(O)O($C_3$-$C_9$ cycloalkyl), —C(O)O(3- to 6-membered heterocycloalkyl), —C(O)O (five- to ten-membered heteroaryl), and —C(O)O($C_6$-$C_{10}$ aryl); or $R_m$ and $R_n$ together with the nitrogen to which they are attached form a 3- to 18-membered heterocycloalkyl ring; and $R_1$ is optionally substituted with one to five $R_k$ independently selected from the group consisting of hydroxy, halogen, —CN, amino, $C_1$-$C_6$ alkyl, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is an optionally substituted C-carboxy group. In some embodiments of the compound of Formula I', $R_1$ is —C(O)($C_1$-$C_6$ alkyl), —C(O)($C_3$-$C_9$ cycloalkyl), —C(O)(3- to 6-membered heterocycloalkyl), —C(O)(five- to ten-membered heteroaryl), and —C(O)($C_6$-$C_{10}$ aryl); and $R_1$ is optionally substituted with one to five $R_k$ independently selected from the group consisting of hydroxy, halogen, —CN, amino, $C_1$-$C_6$ alkyl, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is an optionally substituted O-carboxy group. In some embodiments of the compound of Formula I', $R_1$ is —OC(O)($C_1$-$C_6$ alkyl), —OC(O)($C_3$-$C_9$ cycloalkyl), —OC(O)(3- to 6-membered heterocycloalkyl), —OC(O)(five- to ten-membered heteroaryl), and —OC(O)($C_6$-$C_{10}$ aryl); and $R_1$ is optionally substituted with one to five $R_k$ independently selected from the group consisting of hydroxy, halogen, —CN, amino, $C_1$-$C_6$ alkyl, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is an optionally substituted carbamoyl group. In some embodiments of the compound of Formula I', $R_1$ is —C(O)NR$_m$R$_n$, wherein $R_m$ and $R_n$ are independently selected from the group consisting of hydrogen, $C_1$-$C_6$ alkyl, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl; or $R_m$ and $R_n$ together with the nitrogen to which they are attached form a 3- to 18-membered heterocycloalkyl ring; and $R_1$ is optionally substituted with one to five $R_k$ independently selected from the group consisting of hydroxy, halogen, —CN, amino, $C_1$-$C_6$ alkyl, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_1$ is hydrogen, an optionally substituted $C_1$-$C_6$ alkyl, an optionally substituted non-aromatic $C_3$-$C_{12}$ carbocyclic group, an optionally substituted $C_6$-$C_{10}$ aryl group, and an optionally substituted C-carboxy group.

In some embodiments of the compound of Formula I', $R_1$ is hydrogen, an optionally substituted $C_1$-$C_6$ alkyl, an optionally substituted non-aromatic $C_3$-$C_{12}$ carbocyclic group, an optionally substituted $C_6$-$C_{10}$ aryl group, an optionally substituted C-carboxy group, and an optionally substituted carbamoyl group.

In some embodiments of the compound of Formula I', $R_1$ is hydrogen; —CN; $C_1$-$C_6$ alkyl; a non-aromatic $C_3$-$C_{12}$ carbocyclic ring; a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic)alkyl group; an aralkyl group; a (heterocycloalkyl)alkyl group; or —C(O)—$R_j$; wherein $R_j$ is —NR$_m$R$_n$ or —OR$_m$; $R_m$ is hydrogen or $C_1$-$C_6$ alkyl; $R_n$ is $C_1$-$C_6$ alkyl; or $R_m$ and $R_n$, together with the nitrogen to which they are attached, form a ring structure; and $R_1$ is optionally substituted with one to five $R_k$ independently selected from hydroxy, halogen, $C_1$-$C_6$ alkyl, $C_1$-$C_6$ haloalkyl, $C_1$-$C_6$ alkoxy, and $C_6$-$C_{10}$ aralkoxy.

In some embodiments of the compound of Formula I', $R_1$ is hydrogen, —CN, $C_1$-$C_6$ alkyl; a non-aromatic $C_3$-$C_{12}$ carbocyclic ring; a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic)alkyl group; an aralkyl group; a (heterocycloalkyl)alkyl group; or —C(O)—$R_j$; wherein $R_j$ is —NR$_m$R$_n$ or —OR$_m$; $R_m$ is hydrogen or $C_1$-$C_6$ alkyl; $R_n$ is $C_1$-$C_6$ alkyl; or $R_m$ and $R_n$, together with the nitrogen to which they are attached, form a ring structure; and $R_1$ is optionally substituted with one to three $R_k$ independently selected from phenyl and haloalkyl.

In some embodiments of the compound of Formula I', $R_1$ is hydrogen, —CN, $C_1$-$C_6$ alkyl, cyclopentyl, phenyl, (cyclopropyl)alkyl, benzyl, or —C(O)—$R_j$; wherein $R_j$ is —NR$_m$R$_n$ or —OR$_m$; $R_m$ is hydrogen or $C_1$-$C_6$ alkyl; $R_n$ is $C_1$-$C_6$ alkyl; or $R_m$ and $R_n$, together with the nitrogen to which they are attached, form 1,2,3,4-tetrahydroisoquinoline; and $R_1$ is optionally substituted with one to three $R_k$ independently selected from phenyl and haloalkyl.

In some embodiments of the compound of Formula I', $R_1$ is hydrogen, —CN, $C_1$-$C_6$ alkyl, cyclopentyl, phenyl, (cyclopropyl)alkyl, benzyl, isopropylamino, or —C(O)—$R_j$; wherein $R_j$ is —NR$_m$R$_n$ or —OR$_m$; $R_m$ is hydrogen or $C_1$-$C_6$ alkyl; $R_n$ is $C_1$-$C_6$ alkyl; or $R_m$ and $R_n$, together with the nitrogen to which they are attached, form 1,2,3,4-tetrahydroisoquinoline; and $R_1$ is optionally substituted with one to three $R_k$ independently selected from phenyl and haloalkyl.

In some embodiments of the compound of Formula I', $R_2$ is hydrogen, halogen, $C_1$-$C_6$ alkyl, $C_3$-$C_9$ cycloalkyl, or —CN; and $R_2$ is optionally substituted with one to five substituents independently selected from the group consisting of hydroxy, halogen, —CN, amino, $C_1$-$C_6$ alkyl, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_2$ is hydrogen. In some embodiments of the compound of Formula I', $R_2$ is halogen. In some embodiments of the compound of Formula I', $R_2$ is —CN.

In some embodiments of the compound of Formula I', $R_2$ is optionally substituted $C_1$-$C_6$ alkyl. In some embodiments of the compound of Formula I', $R_2$ is $C_1$-$C_6$ alkyl optionally substituted with one to five substituents independently selected from the group consisting of hydroxy, halogen, —CN, amino, O-carboxy, C-carboxy, C-amido, N-amido, $C_1$-$C_6$ alkoxy, $C_6$-$C_{10}$ aralkoxy, $C_3$-$C_8$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_2$ is optionally substituted $C_3$-$C_9$ cycloalkyl. In some embodiments of the compound of Formula I', $R_2$ is $C_3$-$C_8$ cycloalkyl optionally substituted with one to five substituents independently selected from the group consisting of hydroxy, halogen, —CN, amino, $C_1$-$C_6$ alkyl, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_2$ is $C_3$-$C_9$ cycloalkyl optionally substituted with one to ten substituents independently selected from the group consisting of hydroxy, halogen, and $C_1$-$C_6$ alkoxy.

In some embodiments of the compound of Formula I', $R_2$ is hydrogen or optionally substituted $C_1$-$C_6$ alkyl. In some embodiments of the compound of Formula I', $R_2$ is selected from the group consisting of hydrogen, methyl, ethyl, n-propyl, i-propyl, n-butyl, i-butyl, and t-butyl.

In some embodiments of the compound of Formula I', $R_2$ is hydrogen; halogen; $C_1$-$C_6$ alkyl optionally substituted with one to five substituents independently selected from the group consisting of hydroxy, halogen, and $C_1$-$C_6$ alkoxy; $C_3$-$C_9$ cycloalkyl optionally substituted with one to ten substituents independently selected from the group consisting of hydroxy, halogen, and $C_1$-$C_6$ alkoxy; or —CN.

In some embodiments of the compound of Formula I', $R_3$ is hydrogen. In some embodiments of the compound of Formula I', $R_3$ is lower alkyl.

In some embodiments of the compound of Formula I', $R_4$ is an optionally substituted alkyl, an optionally substituted alkenyl, an optionally substituted non-aromatic carbocyclic group, an optionally substituted aryl group, an optionally substituted heterocycloalkyl group, an optionally substituted heteroaryl group, an optionally substituted (carbocyclic) alkyl group, an optionally substituted aralkyl group, or an optionally substituted (heterocycloalkyl)alkyl group.

In some embodiments of the compound of Formula I', $R_4$ is $C_1$-$C_6$ alkyl; $C_2$-$C_{10}$ alkenyl; a non-aromatic $C_3$-$C_{12}$ carbocyclic ring; a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic)alkyl group; an aralkyl group; or a (heterocycloalkyl)alkyl group; and $R_4$ is optionally substituted with one to five $R_g$ independently selected from the group consisting of hydroxy, halogen, CN, $C_1$-$C_6$ alkyl, $C_6$-$C_{10}$ aryl, $C_1$-$C_6$ alkoxy, $C_1$-$C_6$ haloalkoxy, and $C_6$-$C_{10}$ aralkoxy, or two $R_g$ together with the atoms to which they are attached form an aromatic or non-aromatic 3- to 6-membered ring, optionally containing one or two ring heteroatoms independently selected from oxygen, sulfur, or nitrogen.

In some embodiments of the compound of Formula I', $R_4$ is $C_1$-$C_6$ alkyl; $C_2$-$C_{10}$ alkenyl; a non-aromatic $C_3$-$C_{12}$ carbocyclic ring; a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic)alkyl group; an aralkyl group; or a (heterocycloalkyl)alkyl group; and $R_4$ is optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy, or two $R_g$ together with the atoms to which they are attached form a ring.

In some embodiments of the compound of Formula I', $R_4$ is $C_1$-$C_6$ alkyl; $C_2$-$C_{10}$ alkenyl; a non-aromatic $C_3$-$C_{12}$ carbocyclic ring; a 3- to 6-membered heterocycloalkyl ring containing one to four ring heteroatoms independently selected from oxygen, sulfur, or nitrogen; a (carbocyclic) alkyl group; an aralkyl group; or a (heterocycloalkyl)alkyl group; and $R_4$ is optionally substituted with one to five $R_g$ independently selected from the group consisting of hydroxy, halogen, CN, $C_1$-$C_6$ alkyl, $C_6$-$C_{10}$ aryl, $C_1$-$C_6$ alkoxy, $C_1$-$C_6$ haloalkoxy, and $C_6$-$C_{10}$ aralkoxy, or two $R_g$ together with the atoms to which they are attached form an aromatic or non-aromatic 3- to 6-membered ring, optionally containing one or two ring heteroatoms independently selected from oxygen, sulfur, or nitrogen.

In some embodiments of the compound of Formula I', $R_4$ is $C_1$-$C_6$ alkyl, $C_2$-$C_{10}$ alkenyl, a non-aromatic $C_3$-$C_{12}$ carbocyclic ring, a 3- to 6-membered heterocycloalkyl ring containing one to four ring heteroatoms independently selected from oxygen, sulfur, or nitrogen, a (carbocyclic) alkyl group, an aralkyl group, or a (heterocycloalkyl)alkyl group; and $R_4$ is optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy.

In some embodiments of the compound of Formula I', $R_4$ is $C_1$-$C_6$ alkyl, $C_2$-$C_{10}$ alkenyl, cyclopropyl, cyclobutyl, cyclopentyl, cyclohexyl, tetrahydrofuranyl, tetrahydropyranyl, azetidinyl, pyridazin-3(2H)-one, phenyl, naphthyl, pyridinyl, cinnolinyl, isoquinolinyl, quinolinyl, pyrazolo[1,5-a]pyridinyl, imidazo[1,5-a]pyridinyl, benzo[b]thiophenyl, a (cyclobutyl)alkyl group, a (cyclopentyl)alkyl group, a benzyl group, a (tetrahydrofuranyl)alkyl group, or a (tetrahydropyranyl)alkyl group; and $R_4$ is optionally substituted with one to five $R_g$ independently selected from the group consisting of hydroxy, halogen, CN, $C_1$-$C_6$ alkyl, $C_6$-$C_{10}$ aryl, $C_1$-$C_6$ alkoxy, $C_1$-$C_6$ haloalkoxy, and $C_6$-$C_{10}$ aralkoxy, or two $R_g$ together with the atoms to which they are attached form an aromatic or non-aromatic 3- to 6-membered ring, optionally containing one or two ring heteroatoms independently selected from oxygen, sulfur, or nitrogen.

In some embodiments of the compound of Formula I', $R_4$ is $C_1$-$C_6$ alkyl, $C_2$-$C_{10}$ alkenyl, cyclopropyl, cyclobutyl, cyclopentyl, cyclohexyl, tetrahydrofuranyl, tetrahydropyranyl, a (cyclobutyl)alkyl group, a (cyclopentyl)alkyl group, a benzyl group, a (tetrahydrofuranyl)alkyl group, or a (tetrahydropyranyl)alkyl group; and $R_4$ is optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy.

In some embodiments of the compound of Formula I', $R_4$ is an optionally substituted alkyl. In some embodiments of the compound of Formula I', $R_4$ is an optionally substituted $C_1$-$C_6$ alkyl. In some embodiments of the compound of Formula I', $R_4$ is $C_1$-$C_6$ alkyl optionally substituted with one to five $R_g$ independently selected from the group consisting of hydroxy, halogen, —CN, amino, O-carboxy, C-carboxy, C-amido, N-amido, $C_6$-$C_{10}$ aryl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_4$ is $C_1$-$C_6$ alkyl optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy. In some embodiments of the compound of Formula I', $R_4$ is selected from the group consisting of methyl, ethyl, n-propyl, i-propyl, n-butyl, i-butyl, and t-butyl. In some embodiments of the compound of Formula I', $R_4$ is $C_1$-$C_6$ alkyl. In some embodiments of the compound of Formula I', $R_4$ is $C_1$-$C_3$ alkyl. In some embodiments of the compound of Formula I', $R_4$ is $C_5$-$C_6$ alkyl.

In some embodiments of the compound of Formula I', $R_4$ is an optionally substituted alkenyl. In some embodiments of the compound of Formula I', $R_4$ is an optionally substituted $C_2$-$C_{10}$ alkenyl. In some embodiments of the compound of Formula I', $R_4$ is $C_2$-$C_{10}$ alkenyl optionally substituted with one to five $R_g$ independently selected from the group consisting of hydroxy, halogen, —CN, amino, O-carboxy, C-carboxy, C-amido, N-amido, $C_6$-$C_{10}$ aryl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_4$ is $C_2$-$C_{10}$ alkenyl optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy.

In some embodiments of the compound of Formula I', $R_4$ is an optionally substituted non-aromatic carbocyclic group. In some embodiments of the compound of Formula I', $R_4$ is an optionally substituted non-aromatic $C_3$-$C_{12}$ carbocyclic group. In some embodiments of the compound of Formula I', $R_4$ is a non-aromatic $C_3$-$C_{12}$ carbocyclic group optionally substituted with one to five $R_g$ independently selected from the group consisting of hydroxy, oxo, halogen, CN, amino, O-carboxy, C-carboxy, C-amido, N-amido, $C_1$-$C_6$ alkyl, $C_1$-$C_6$ haloalkyl, $C_6$-$C_{10}$ aryl, $C_1$-$C_6$ alkoxy, $C_1$-$C_6$ haloalkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl, or two $R_g$ together with the atoms to which they are attached form an aromatic or non-aromatic 3- to 6-membered ring, optionally containing one or two ring heteroatoms independently selected from oxygen, sulfur, or nitrogen. In some embodiments of the compound of Formula I', $R_4$ is a non-aromatic $C_3$-$C_{12}$ carbocyclic group optionally substituted with one to five $R_g$ independently selected from the group consisting of hydroxy, oxo, halogen, amino, O-carboxy, C-carboxy, C-amido, N-amido, $C_1$-$C_6$ alkyl, $C_1$-$C_6$ haloalkyl, $C_6$-$C_{10}$ aryl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_4$ is a non-aromatic $C_3$-$C_{12}$ carbocyclic group optionally substituted with one to five $R_g$ independently selected from the group consisting of hydroxy, halogen, CN, $C_1$-$C_6$ alkyl, $C_6$-$C_{10}$ aryl, $C_1$-$C_6$ alkoxy, $C_1$-$C_6$ haloalkoxy, and $C_6$-$C_{10}$ aralkoxy, or two $R_g$ together with the atoms to which they are attached form an aromatic or non-aromatic 3- to 6-membered ring, optionally containing one or two ring heteroatoms independently selected from oxygen, sulfur, or nitrogen. In some embodiments of the compound of Formula I', $R_4$ is a non-aromatic $C_3$-$C_{12}$ carbocyclic group optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy.

In some embodiments of the compound of Formula I', $R_4$ is an optionally substituted heterocycloalkyl group. In some embodiments of the compound of Formula I', $R_4$ is an optionally substituted 3- to 6-membered heterocycloalkyl ring containing one to four ring heteroatoms independently selected from oxygen, sulfur, or nitrogen; wherein the heterocycloalkyl ring is optionally substituted with one to five $R_g$ independently selected from the group consisting of hydroxy, oxo, halogen, CN, amino, O-carboxy, C-carboxy, C-amido, N-amido, $C_1$-$C_6$ alkyl, $C_1$-$C_6$ haloalkyl, $C_6$-$C_{10}$ aryl, $C_1$-$C_6$ alkoxy, $C_1$-$C_6$ haloalkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl, or two $R_g$ together with the atoms to which they are attached form an aromatic or non-aromatic 3- to 6-membered ring, optionally containing one or two ring heteroatoms independently selected from oxygen, sulfur, or nitrogen. In some embodiments of the compound of Formula I', $R_4$ is an optionally substituted 3- to 6-membered heterocycloalkyl ring containing one to four ring heteroatoms independently selected from oxygen, sulfur, or nitrogen; wherein the heterocycloalkyl ring is optionally substituted with one to five $R_g$ independently selected from the group consisting of hydroxy, oxo, halogen, amino, O-carboxy, C-carboxy, C-amido, N-amido, $C_1$-$C_6$ alkyl, $C_1$-$C_6$ haloalkyl, $C_6$-$C_{10}$ aryl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_4$ is an optionally substituted 3- to 6-membered heterocycloalkyl ring containing one to four ring heteroatoms independently selected from oxygen, sulfur, or nitrogen; wherein the heterocycloalkyl ring is optionally substituted with one to five $R_g$ independently selected from the group consisting of hydroxy, halogen, CN, oxo, $C_1$-$C_6$ alkyl, $C_6$-$C_{10}$ aryl, $C_1$-$C_6$ alkoxy, $C_1$-$C_6$ haloalkoxy, and $C_6$-$C_{10}$ aralkoxy. In some embodiments of the compound of Formula I', $R_4$ is an optionally substituted 3- to 6-membered heterocycloalkyl ring containing one to four ring heteroatoms independently selected from oxygen, sulfur, or nitrogen; wherein the heterocycloalkyl ring is optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy.

In some embodiments of the compound of Formula I', $R_4$ is an optionally substituted (carbocyclic)alkyl group. In some embodiments of the compound of Formula I', $R_4$ is (cyclopropyl)$C_1$-$C_6$ alkyl, (cyclobutyl)$C_1$-$C_6$ alkyl, (cyclopentyl)$C_1$-$C_6$ alkyl, (cyclohexyl)$C_1$-$C_6$ alkyl, (cycloheptyl)$C_1$-$C_6$ alkyl, (cyclooctyl)$C_1$-$C_6$ alkyl, or (cyclononyl)$C_1$-$C_6$ alkyl, and $R_4$ is optionally substituted with one to five $R_g$ independently selected from the group consisting of hydroxy, halogen, —CN, amino, O-carboxy, C-carboxy, C-amido, N-amido, oxo, $C_1$-$C_6$ alkyl, $C_1$-$C_6$ haloalkyl, $C_6$-$C_{10}$ aryl, $C_1$-$C_6$ alkoxy, $C_1$-$C_6$ haloalkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl, or two $R_g$ together with the atoms to which they are attached form an aromatic or non-aromatic 3- to 6-membered ring, optionally containing one or two ring heteroatoms independently selected from oxygen, sulfur, or nitrogen. In some embodiments of the compound of Formula I', $R_4$ is (cyclopropyl)$C_1$-$C_6$ alkyl, (cyclobutyl)$C_1$-$C_6$ alkyl, (cyclopentyl)$C_1$-$C_6$ alkyl, (cyclohexyl)$C_1$-$C_6$ alkyl, (cycloheptyl)$C_1$-$C_6$ alkyl, (cyclooctyl)$C_1$-$C_6$ alkyl, or (cyclononyl)$C_1$-$C_6$ alkyl, and $R_4$ is optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy.

In some embodiments of the compound of Formula I', $R_4$ is an optionally substituted aralkyl group. In some embodiments of the compound of Formula I', $R_4$ is a benzyl group optionally substituted with one to five $R_g$ independently selected from the group consisting of hydroxy, halogen, —CN, amino, O-carboxy, C-carboxy, C-amido, N-amido, $C_1$-$C_6$ alkyl, $C_1$-$C_6$ haloalkyl, $C_6$-$C_{10}$ aryl, $C_1$-$C_6$ alkoxy, $C_1$-$C_6$ haloalkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl, or two $R_g$ together with the atoms to which they are attached form an aromatic or non-aromatic 3- to 6-membered ring, optionally containing one or two ring heteroatoms independently selected from oxygen, sulfur, or nitrogen. In some embodiments of the compound of Formula I', $R_4$ is a benzyl group optionally substituted with one to five $R_g$ independently selected from the group consisting of hydroxy, halogen, —CN, amino, O-carboxy, C-carboxy, C-amido, N-amido, $C_1$-$C_6$ alkyl, $C_1$-$C_6$ haloalkyl, $C_6$-$C_{10}$ aryl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_4$ is a benzyl group optionally substituted with one to five $R_g$ independently selected from the group consisting of hydroxy, halogen, CN, $C_1$-$C_6$ alkyl, $C_6$-$C_{10}$ aryl, $C_1$-$C_6$ alkoxy, $C_1$-$C_6$ haloalkoxy, and $C_6$-$C_{10}$ aralkoxy. In some embodiments of the compound of Formula I', $R_4$ is a benzyl group optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy.

In some embodiments of the compound of Formula I', $R_4$ is an optionally substituted (heterocycloalkyl)alkyl group. In some embodiments of the compound of Formula I', $R_4$ is a (heterocycloalkyl)alkyl group optionally substituted with one to five $R_g$ independently selected from the group consisting of hydroxy, oxo, halogen, amino, CN, O-carboxy, C-carboxy, C-amido, N-amido, $C_1$-$C_6$ alkyl, $C_1$-$C_6$ haloalkyl, $C_6$-$C_{10}$ aryl, $C_1$-$C_6$ alkoxy, $C_1$-$C_6$ haloalkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl, or two $R_g$ together with the atoms to which they are attached form an aromatic or non-aromatic 3- to 6-membered ring, optionally containing one or two ring heteroatoms independently selected from oxygen, sulfur, or nitrogen. In some embodiments of the compound of Formula I', $R_4$ is a (heterocycloalkyl)alkyl group optionally substituted with one to five $R_g$ independently selected from the group consisting of hydroxy, oxo, halogen, amino, O-carboxy, C-carboxy, C-amido, N-amido, $C_1$-$C_6$ alkyl, $C_1$-$C_6$ haloalkyl, $C_6$-$C_{10}$ aryl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_4$ is a (heterocycloalkyl)alkyl group optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy.

In some embodiments of the compound of Formula I', $R_4$ is an optionally substituted (heteroaryl)alkyl group. In some embodiments of the compound of Formula I', $R_4$ is a (heteroaryl)alkyl group optionally substituted with one to five $R_g$ independently selected from the group consisting of hydroxy, halogen, —CN, amino, O-carboxy, C-carboxy, C-amido, N-amido, $C_1$-$C_6$ alkyl, $C_1$-$C_6$ haloalkyl, $C_6$-$C_{10}$ aryl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl, or two $R_g$ together with the atoms to which they are attached form an aromatic or non-aromatic 3- to 6-membered ring, optionally containing one or two ring heteroatoms independently selected from oxygen, sulfur, or nitrogen. In some embodiments of the compound of Formula I', $R_4$ is a (heteroaryl)alkyl group optionally substituted with one to five $R_g$ independently selected from the group consisting of hydroxy, halogen, —CN, amino, O-carboxy, C-carboxy, C-amido, N-amido, $C_1$-$C_6$ alkyl, $C_1$-$C_6$ haloalkyl, $C_6$-$C_{10}$ aryl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_4$ is a (heteroaryl)alkyl group optionally substituted with one to five $R_g$ independently selected from the group consisting of hydroxy, halogen, CN, $C_1$-$C_6$ alkyl, $C_6$-$C_{10}$ aryl, $C_1$-$C_6$ alkoxy, $C_1$-$C_6$ haloalkoxy, and $C_6$-$C_{10}$ aralkoxy. In some embodiments of the compound of Formula I', $R_4$ is a (heteroaryl)alkyl group optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy.

In some embodiments of the compound of Formula I', $R_4$ is a $C_6$-$C_{10}$ aryl group or a five- to ten-membered heteroaryl ring containing one to four ring heteroatoms independently selected from oxygen, sulfur, or nitrogen; and $R_4$ is optionally substituted with one to five $R_g$ independently selected from the group consisting of hydroxy, halogen, CN, $C_1$-$C_6$ alkyl, $C_6$-$C_{10}$ aryl, $C_1$-$C_6$ alkoxy, $C_1$-$C_6$ haloalkoxy, and $C_6$-$C_{10}$ aralkoxy, or two $R_g$ together with the atoms to which they are attached form an aromatic or non-aromatic 3- to 6-membered ring, optionally containing one or two ring heteroatoms independently selected from oxygen, sulfur, or nitrogen. In some embodiments of the compound of Formula I', $R_4$ is a $C_6$-$C_{10}$ aryl group or a five- to ten-membered heteroaryl ring containing one to four ring heteroatoms independently selected from oxygen, sulfur, or nitrogen; and $R_4$ is optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy.

In some embodiments of the compound of Formula I', $R_4$ is an optionally substituted $C_6$-$C_{10}$ aryl group. In some embodiments of the compound of Formula I', $R_4$ is a $C_6$-$C_{10}$ aryl group optionally substituted with one to five $R_g$ independently selected from the group consisting of hydroxy, halogen, —CN, O-carboxy, C-carboxy, C-amido, N-amido, amino, $C_1$-$C_6$ alkyl, $C_1$-$C_6$ haloalkyl, $C_6$-$C_{10}$ aryl, $C_1$-$C_6$ alkoxy, $C_1$-$C_6$ haloalkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl, or two $R_g$ together with the atoms to which they are attached form an aromatic or non-aromatic 3- to 6-membered ring, optionally containing one or two ring heteroatoms independently selected from oxygen, sulfur, or nitrogen. In some embodiments of the compound of Formula I', $R_4$ is a $C_6$-$C_{10}$ aryl group optionally substituted with one to five $R_g$ independently selected from the group consisting of hydroxy, halogen, —CN, O-carboxy, C-carboxy, C-amido, N-amido, amino, $C_1$-$C_6$ alkyl, $C_1$-$C_6$ haloalkyl, $C_6$-$C_{10}$ aryl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_4$ is a $C_6$-$C_{10}$ aryl group optionally substituted with one to five $R_g$ independently selected from the group consisting of hydroxy, halogen, CN, $C_1$-$C_6$ alkyl, $C_6$-$C_{10}$ aryl, $C_1$-$C_6$ alkoxy, $C_1$-$C_6$ haloalkoxy, and $C_6$-$C_{10}$ aralkoxy, or two $R_g$ together with the atoms to which they are attached form an aromatic or non-aromatic 3- to 6-membered ring, optionally containing one or two ring heteroatoms independently selected from oxygen, sulfur, or nitrogen. In some embodiments of the compound of Formula I', $R_4$ is a $C_6$-$C_{10}$ aryl group optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy.

In some embodiments of the compound of Formula I', $R_4$ is benzene optionally substituted with one to five $R_g$ independently selected from the group consisting of hydroxy, halogen, CN, $C_1$-$C_6$ alkyl, $C_1$-$C_6$ alkoxy, and $C_1$-$C_6$ haloalkoxy, or two $R_g$ together with the atoms to which they are attached form an aromatic or non-aromatic 3- to 6-membered ring, optionally containing one or two ring heteroatoms independently selected from oxygen, sulfur, or nitrogen. In some embodiments of the compound of Formula I', $R_4$ is benzene optionally substituted with one to five $R_g$ independently selected from the group consisting of hydroxy, halogen, $C_1$-$C_6$ alkyl, and $C_1$-$C_6$ alkoxy, or two $R_g$ together with the atoms to which they are attached form a ring.

In some embodiments of the compound of Formula I', $R_4$ is naphthalene optionally substituted with one to five $R_g$ independently selected from the group consisting of hydroxy, halogen, $C_1$-$C_6$ alkyl, and $C_1$-$C_6$ alkoxy.

In some embodiments of the compound of Formula I', $R_4$ is an optionally substituted heteroaryl group. In some embodiments of the compound of Formula I', $R_4$ is five- to ten-membered heteroaryl ring containing one to four ring heteroatoms independently selected from oxygen, sulfur, or nitrogen, wherein the heteroaryl ring is optionally substituted with one to five $R_g$ independently selected from the group consisting of hydroxy, halogen, —CN, amino, O-carboxy, C-carboxy, C-amido, N-amido, $C_1$-$C_6$ alkyl, $C_1$-$C_6$ haloalkyl, $C_6$-$C_{10}$ aryl, $C_1$-$C_6$ alkoxy, $C_1$-$C_6$ haloalkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl, or two $R_g$ together with the atoms to which they are attached form an aromatic or non-aromatic 3- to 6-membered ring, optionally containing one or two ring heteroatoms independently selected from oxygen, sulfur, or nitrogen. In some embodiments of the compound of Formula I', $R_4$ is five- to ten-membered heteroaryl ring containing one to four ring heteroatoms independently selected from oxygen, sulfur, or nitrogen, wherein the heteroaryl ring is optionally substituted with one to five $R_g$ independently selected from the group consisting of hydroxy, halogen, —CN, amino, O-carboxy, C-carboxy, C-amido, N-amido, $C_1$-$C_6$ alkyl, $C_1$-$C_6$ haloalkyl, $C_6$-$C_{10}$ aryl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_4$ is five- to ten-membered heteroaryl ring containing one to four ring heteroatoms independently selected from oxygen, sulfur, or nitrogen, wherein the heteroaryl ring is optionally substituted with one to five $R_g$ independently selected from the group consisting of hydroxy, halogen, CN, $C_1$-$C_6$ alkyl, $C_6$-$C_{10}$ aryl, $C_1$-$C_6$ alkoxy, $C_1$-$C_6$ haloalkoxy, and $C_6$-$C_{10}$ aralkoxy. In some embodiments of the compound of Formula I', $R_4$ is five- to ten-membered heteroaryl ring containing one to four ring heteroatoms independently selected from oxygen, sulfur, or nitrogen, wherein the heteroaryl ring is optionally substituted with one to five $R_g$ independently selected from the group consisting of hydroxy, halogen, $C_1$-$C_6$ alkyl, $C_6$-$C_{10}$ aryl, $C_1$-$C_6$ alkoxy, and $C_6$-$C_{10}$ aralkoxy.

In some embodiments of the compound of Formula I', $R_4$ is an optionally substituted amino group. In some embodiments of the compound of Formula I', $R_4$ is an amino group optionally substituted with one or two substituents independently selected from the group consisting of $C_1$-$C_6$ alkyl, $C_1$-$C_6$ haloalkyl, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, $C_6$-$C_{10}$ aryl, C-carboxy, C-amido, —($SO_2$)($C_1$-$C_6$ alkyl), —C(O)O($C_1$-$C_6$ alkyl), —C(O)O($C_1$-$C_6$ haloalkyl), —C(O)O($C_3$-$C_9$ cycloalkyl), —C(O)O(3- to 6-membered heterocycloalkyl), —C(O)O (five- to ten-membered heteroaryl), and —C(O)O($C_6$-$C_{10}$ aryl). In some embodiments of the compound of Formula I', $R_4$ is —$NR_mR_n$, wherein $R_m$ and $R_n$ are independently selected from the group consisting of hydrogen, $C_1$-$C_6$ alkyl, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, $C_6$-$C_{10}$ aryl, C-carboxy, C-amido, —($SO_2$)($C_1$-$C_6$ alkyl), —C(O)O($C_1$-$C_6$ alkyl), —C(O)O($C_3$-$C_9$ cycloalkyl), —C(O)O(3- to 6-membered heterocycloalkyl), —C(O)O (five- to ten-membered heteroaryl), and —C(O)O($C_6$-$C_{10}$ aryl); or $R_m$ and $R_n$ together with the nitrogen to which they are attached form a 3- to 18-membered heterocycloalkyl ring; and $R_1$ is optionally substituted with one to five $R_g$ independently selected from the group consisting of hydroxy, halogen, —CN, amino, $C_1$-$C_6$ alkyl, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_4$ is an optionally substituted sulfamoyl group. In some embodiments of the compound of Formula I', $R_4$ is —$SO_2NR_mR_n$, wherein $R_m$ and $R_a$ are independently selected from the group consisting of hydrogen, $C_1$-$C_6$ alkyl, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl; or $R_m$ and $R_n$ together with the nitrogen to which they are attached form a 3- to 18-membered heterocycloalkyl ring; and $R_1$ is optionally substituted with one to five $R_g$ independently selected from the group consisting of hydroxy, halogen, —CN, amino, $C_1$-$C_6$ alkyl, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_4$ is an optionally substituted carbamoyl group. In some embodiments of the compound of Formula I', $R_4$ is —C(O)$NR_mR_n$, wherein $R_m$ and $R_n$ are independently selected from the group consisting of hydrogen, $C_1$-$C_6$ alkyl, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl; or $R_m$ and $R_n$ together with the nitrogen to which they are attached form a 3- to 18-membered heterocycloalkyl ring; and $R_1$ is optionally substituted with one to five $R_g$ independently selected from the group consisting of hydroxy, halogen, —CN, amino, $C_1$-$C_6$ alkyl, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_5$ is hydroxy. In some embodiments of the compound of Formula I', $R_5$ is $NH_2$.

In some embodiments of the compound of Formula I', $R_5$ is alkylamino. In some embodiments of the compound of Formula I', $R_5$ is —$NR_uR_v$, wherein $R_u$ is hydrogen or $C_1$-$C_6$ alkyl and $R_v$ is $C_1$-$C_{12}$ alkyl optionally substituted with one to five substituents independently selected from the group consisting of hydroxy, halogen, —CN, amino, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_5$ is alkanoylamino. In some embodiments of the compound of Formula I', $R_5$ is —$NR_uC(O)R_v$, wherein $R_u$ is hydrogen or $C_1$-$C_6$ alkyl and $R_v$ is $C_1$-$C_{12}$ alkyl optionally substituted with one to five substituents independently selected from the group consisting of hydroxy, halogen, —CN, amino, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_5$ is alkylsulfonylamino. In some embodiments of the compound of Formula I', $R_5$ is —$NR_uSO_2R_v$, wherein $R_u$ is hydrogen or $C_1$-$C_6$ alkyl and $R_v$ is $C_1$-$C_{12}$ alkyl optionally substituted with one to five substituents independently selected from the group consisting of hydroxy, halogen, —CN, amino, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_5$ is hydroxy or $NH_2$. In some embodiments of the compound of Formula I', $R_5$ is hydroxy, $NH_2$, $C_1$-$C_6$ alkylamino, $C_1$-$C_6$ alkanoylamino, or $C_1$-$C_6$ alkylsulfonylamino.

In some embodiments of the compound of Formula I', $R_4$ and $R_5$ taken together along with the carbon atoms to which they are attached form a five- or six-membered optionally substituted non-aromatic $C_3$-$C_{12}$ carbocyclic group, optionally substituted $C_6$-$C_{10}$ aryl group, optionally substituted heterocyclic group, or optionally substituted heteroaryl group. In some embodiments of the compound of Formula I', $R_4$ and $R_5$ taken together along with the carbon atoms to which they are attached form a five- or six-membered non-aromatic $C_3$-$C_{12}$ carbocyclic group, $C_6$-$C_{10}$ aryl group, 4- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, wherein the carbocyclic group, the aryl group, the heterocycloalkyl group, and the heteroaryl group are optionally substituted with one to five substituents independently selected from the group consisting of hydroxy, halogen, —CN, amino, O-carboxy, C-carboxy, C-amido, N-amido, $C_1$-$C_6$ alkyl, $C_1$-$C_6$ haloalkyl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_4$ and $R_5$ taken together along with the carbon atoms to which they are attached form a seven to eleven membered, optionally substituted spirocyclic ring or a seven to eleven membered, optionally substituted spiro-heterocyclic ring. In some embodiments of the compound of Formula I', $R_4$ and $R_5$ taken together along with the carbon atoms to which they are attached form a seven to eleven membered, spirocyclic ring or a seven to eleven membered spiro-heterocyclic ring; and the spirocyclic ring and spiro-heterocyclic ring are optionally substituted with one to five substituents independently selected from the group consisting of hydroxy, halogen, —CN, amino, O-carboxy, C-carboxy, C-amido, N-amido, $C_1$-$C_6$ alkyl, $C_1$-$C_6$ haloalkyl, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', $R_4$ and $R_5$ taken together along with the carbon atoms to which they are attached form a five- or six-membered optionally substituted non-aromatic carbocyclic group, optionally substituted aryl group, optionally substituted heterocycloalkyl group, or optionally substituted heteroaryl group.

In some embodiments of the compound of Formula I', $R_4$ and $R_5$ taken together along with the carbon atoms to which they are attached form a five- or six-membered non-aromatic carbocyclic group; a $C_6$-$C_{10}$ aryl group; a 3- to 6-membered heterocycloalkyl ring containing one to four ring heteroatoms independently selected from oxygen, sulfur, or nitrogen; or a five- to ten-membered heteroaryl ring containing one to four ring heteroatoms independently selected from oxygen, sulfur, or nitrogen; and wherein the carbocyclic group, the aryl group, the heterocycloalkyl ring, and the heteroaryl ring are optionally substituted with one to five $R_g$ independently selected from the group consisting of hydroxy, halogen, $C_1$-$C_6$ alkyl, $C_1$-$C_6$ alkoxy, and oxo, and/or optionally two $R_g$ together with the atom(s) to which they are attached form a 3- to 6-membered carbocyclic group.

In some embodiments of the compound of Formula I', $R_4$ and $R_5$ taken together along with the carbon atoms to which they are attached form a 3- to 6-membered heterocycloalkyl ring containing one to four ring heteroatoms independently selected from oxygen, sulfur, or nitrogen; and wherein the heterocycloalkyl ring is optionally substituted with one to five $R_g$ independently selected from the group consisting of $C_1$-$C_6$ alkyl and oxo, and/or optionally two $R_g$ together with the atom(s) to which they are attached form a 3- to 6-membered non-aromatic carbocyclic group.

In some embodiments of the compound of Formula I', $R_4$ and $R_5$ taken together along with the carbon atoms to which they are attached form a pyrrolidine optionally substituted with one to five $R_g$ independently selected from the group consisting of $C_1$-$C_6$ alkyl and oxo, and/or optionally two $R_g$ together with the atom(s) to which they are attached form a 3- to 6-membered non-aromatic carbocyclic group.

In some embodiments of the compound of Formula I', TL is a moiety of Formula IIIaa:

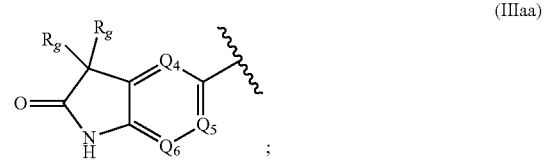

(IIIaa)

wherein each $R_g$ is independently $C_1$-$C_6$ alkyl; or the two $R_g$ together with the atom to which they are attached form an alkene optionally substituted with $C_1$-$C_6$ alkyl; or the two $R_g$ together with the atom to which they are attached form a 3- to 6-membered non-aromatic carbocyclic group. In some embodiments of the compound of Formula I', the two $R_g$ together with the atom to which they are attached form a cyclopropyl group, a cyclobutyl group, a cyclopentyl group, or a cyclohexyl group.

In some embodiments of the compound of Formula I', TL is a moiety of Formula IIIaa:

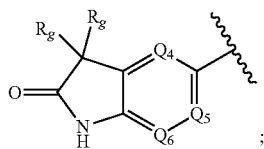

(IIIaa)

wherein each $R_g$ is independently $C_1$-$C_6$ alkyl or the two $R_g$ together with the atom(s) to which they are attached form a 3- to 6-membered non-aromatic carbocyclic group. In some embodiments of the compound of Formula I', the two $R_g$ together with the atom to which they are attached form a cyclopentyl group or a cyclohexyl group.

In some embodiments of the compound of Formula I', TL is a moiety of Formula IIIab:

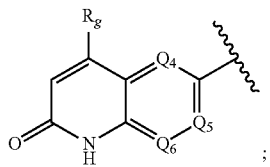

(IIIab)

wherein $R_g$ is $C_1$-$C_6$ alkyl. In some embodiments of the compound of Formula I', $R_g$ is isopropyl.

In some embodiments of the compound of Formula I', TL is a moiety of Formula IIIac:

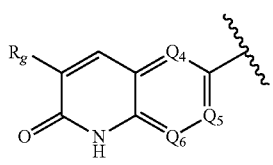

(IIIac)

wherein $R_g$ is $C_1$-$C_6$ alkyl. In some embodiments of the compound of Formula I', $R_g$ is methyl.

In some embodiments of the compound of Formula I', TL is a moiety of Formula IIIad:

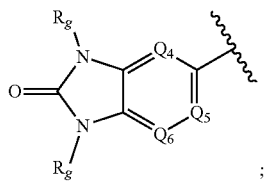

(IIIad)

wherein each $R_g$ is independently hydrogen or $C_1$-$C_6$ alkyl.

In some embodiments of the compound of Formula I', $R_4$ is an optionally substituted alkyl, an optionally substituted alkenyl, an optionally substituted non-aromatic carbocyclic group, an optionally substituted aryl group, an optionally substituted heterocycloalkyl group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, or an optionally substituted carbamoyl group; and $R_5$ is hydroxy, $NH_2$, alkylamino, alkanoylamino, or alkylsulfonylamino.

In some embodiments of the compound of Formula I', $R_4$ is $C_1$-$C_6$ alkyl; $C_2$-$C_{10}$ alkenyl; a non-aromatic $C_3$-$C_{12}$ carbocyclic ring, a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic)alkyl group; an aralkyl group; a (heterocycloalkyl)alkyl group; a (heteroaryl)alkyl group; or —C(O)$NR_mR_n$;

$R_m$ and $R_n$ are independently selected from the group consisting of hydrogen, $C_1$-$C_6$ alkyl, $C_1$-$C_6$ haloalkyl, $C_2$-$C_6$ alkoxy, a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic)alkyl group; an aralkyl group; a (heterocycloalkyl)alkyl group; or a (heteroaryl)alkyl group; or $R_m$ and $R_n$ together with the nitrogen to which they are attached form a 3- to 18-membered heterocycloalkyl ring;

and $R_4$ is optionally substituted with one to five $R_g$ independently selected from the group consisting of hydroxy, halogen, $C_1$-$C_6$ alkyl, $C_1$-$C_6$ haloalkyl, $C_6$-$C_{10}$ aryl, $C_1$-$C_6$ alkoxy, and $C_6$-$C_{10}$ aralkoxy; and $R_5$ is hydroxy, $NH_2$, alkylamino, alkanoylamino, or alkylsulfonylamino.

In some embodiments of the compound of Formula I', $R_4$ is $C_1$-$C_6$ alkyl; $C_2$-$C_{10}$ alkenyl; a non-aromatic $C_3$-$C_{12}$ carbocyclic ring, a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic)alkyl group; an aralkyl group; a (heterocycloalkyl)alkyl group; a (heteroaryl)alkyl group; or —C(O)$NR_mR_n$;

$R_m$ and $R_n$ are independently selected from the group consisting of hydrogen, $C_1$-$C_6$ alkyl, $C_1$-$C_6$ haloalkyl, $C_2$-$C_6$ alkoxy, a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic)alkyl group; an aralkyl group; a (heterocycloalkyl)alkyl group; or a (heteroaryl)alkyl group; or $R_m$ and $R_n$ together with the nitrogen to which they are attached form a 3- to 18-membered heterocycloalkyl ring;

and $R_4$ is optionally substituted with one to five $R_g$ independently selected from the group consisting of hydroxy, halogen, $C_1$-$C_6$ alkyl, $C_1$-$C_6$ haloalkyl, $C_6$-$C_{10}$ aryl, $C_1$-$C_6$ alkoxy, and $C_6$-$C_{10}$ aralkoxy; and $R_5$ is hydroxy.

In some embodiments of the compound of Formula I', Alk is hydrogen or optionally substituted $C_1$-$C_6$ alkyl. In some embodiments of the compound of Formula I', Alk is hydrogen or $C_1$-$C_6$ alkyl optionally substituted with one to five substituents independently selected from the group consisting of hydroxy, halogen, —CN, amino, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', Alk is hydrogen. In some embodiments of the compound of Formula I', Alk is $C_1$-$C_6$ alkyl optionally substituted with one to five substituents independently selected from the group consisting of hydroxy, halogen, —CN, amino, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', Alk is $C_1$-$C_6$ alkyl optionally substituted with one to five substituents independently selected from the group consisting of hydroxy, halogen, and $C_1$-$C_6$ alkoxy.

In some embodiments of the compound of Formula I', $R_{11}$ is an aryl group optionally substituted with one to five substituents independently selected from lower alkyl, alkoxy, haloalkoxy, halogen, and $C_3$-$C_9$ cycloalkyl; or a heteroaryl group optionally substituted with one to five substituents independently selected from lower alkyl, alkoxy, haloalkoxy, halogen, and cycloalkyl; or a bicyclic ring system containing either aromatic or saturated rings; or a bicyclic heterocyclic containing either aromatic or saturated ring systems. In some embodiments of the compound of Formula I', $R_{11}$ is an aryl group optionally substituted with one to five substituents independently selected from lower alkyl, halogen, and $C_3$-$C_9$ cycloalkyl; or a bicyclic ring system containing either aromatic or saturated rings; or a bicyclic heterocyclic containing either aromatic or saturated ring systems. In some embodiments of the compound of Formula I', $R_{11}$ is a $C_6$-$C_{10}$ aryl group optionally substituted with one to five substituents independently selected from lower alkyl, alkoxy, haloalkoxy, halogen, and $C_3$-$C_9$ cycloalkyl; or a five- to ten-membered heteroaryl group containing one to four ring heteroatoms independently selected from oxygen, sulfur, or nitrogen, wherein the heteroaryl group is optionally substituted with one to five substituents independently selected from lower alkyl, alkoxy, haloalkoxy, halogen, and $C_3$-$C_9$ cycloalkyl; or a 7- to 12-membered bicyclic ring system containing either aromatic or saturated rings; or a 7- to 12-membered bicyclic heterocyclic containing either aromatic or saturated ring systems. In some embodiments of the compound of Formula I', $R_1$ is a $C_6$-$C_{10}$ aryl group optionally substituted with one to five substituents independently selected from lower alkyl, halogen, and $C_3$-$C_9$ cycloalkyl; or a 7- to 12-membered bicyclic ring system containing either aromatic or saturated rings; or a 7- to 12-membered bicyclic heterocyclic containing either aromatic or saturated ring systems. In some embodiments of the compound of Formula I', $R_{11}$ is a $C_6$-$C_{10}$ aryl group optionally substituted with one to five substituents independently selected from lower alkyl, alkoxy, haloalkoxy, halogen, and $C_3$-$C_9$ cycloalkyl. In some embodiments of the compound of Formula I', $R_{11}$ is a $C_6$-$C_{10}$ aryl group optionally substituted with one to five substituents independently selected from lower alkyl, halogen, and $C_3$-$C_9$ cycloalkyl. In some embodiments of the compound of Formula I', $R_{11}$ a five- to ten-membered heteroaryl group containing one to four ring heteroatoms independently selected from oxygen, sulfur, or nitrogen, wherein the heteroaryl group is optionally substituted with one to five substituents independently selected from lower alkyl, alkoxy, haloalkoxy, halogen, and $C_3$-$C_9$ cycloalkyl. In some embodiments of the compound of Formula I', $R_{11}$ is a 7- to 12-membered bicyclic ring system containing either aromatic or saturated rings. In some embodiments of the compound of Formula I', $R_{11}$ is a 7- to 12-membered bicyclic heterocyclic containing either aromatic or saturated ring systems. In some embodiments of the compound of Formula I', $R_{11}$ is a benzene optionally substituted with one to five substituents independently selected from $C_1$-$C_5$ alkyl, $C_1$-$C_5$ alkoxy, $C_1$-$C_5$ haloalkoxy, halogen, and $C_3$-$C_9$ cycloalkyl; pyridine optionally substituted with $C_1$-$C_5$ alkyl; cinnoline; isoquinoline; quinoline; pyrazolo[1,5-a]pyridine; imidazo[1,5-a]pyridine; benzo[b]thiophene; chromane; 1,2,3,4-tetrahydronaphthalene; or naphthalene. In some embodiments of the compound of Formula I', $R_{11}$ is a benzene optionally substituted with one to five substituents independently selected from $C_1$-$C_5$ alkyl, halogen, and $C_3$-$C_9$ cycloalkyl; 1,2,3,4-tetrahydronaphthalene; or naphthalene.

In some embodiments of the compound of Formula I', each of $R_6$ and $R_7$ is independently halogen or $C_1$-$C_5$ alkyl optionally substituted with one to five substituents independently selected from hydroxy, halogen, and $C_1$-$C_6$ alkoxy; and $R_8$ is hydrogen; or $R_6$ is halogen or $C_1$-$C_5$ alkyl optionally substituted with one to five substituents independently selected from hydroxy, halogen, and $C_1$-$C_6$ alkoxy; and $R_7$ and $R_8$ taken together, along with the carbon atoms to which they are attached, form a 4-, 5- or 6-membered carbocyclic ring.

In some embodiments of the compound of Formula I', each of $R_6$ and $R_7$ is independently chlorine, bromine, and iodine. In some embodiments of the compound of Formula I', each of $R_6$ and $R_7$ is independently —CN, an optionally substituted lower alkyl or an optionally substituted lower alkoxy, where the lower alkyl and the alkyl group of the lower alkoxy is each independently selected from methyl, ethyl, n-propyl, i-propyl, n-butyl, s-butyl, and t-butyl. In some embodiments of the compound of Formula I', $R_6$ and $R_7$ are the same. In some embodiments of the compound of Formula I', each of $R_6$ and $R_7$ is independently chlorine or methyl. In some embodiments of the compound of Formula I', $R_6$ is Cl, $R_7$ is Cl, and $R_8$ is hydrogen. In some embodiments of the compound of Formula I', $R_6$ is Cl, $R_7$ is Cl, and $R_8$ is methyl. In some embodiments of the compound of Formula I', $R_6$ is halogen and $R_7$ and $R_8$ taken together, along with the carbon atoms to which they are attached, form a 4-membered carbocyclic ring.

In some embodiments of the compound of Formula I', $R_8$ is hydrogen. In some embodiments of the compound of Formula I', $R_8$ is optionally substituted lower alkyl. In some embodiments of the compound of Formula I', $R_8$ is lower alkyl optionally substituted with one to five substituents selected from the group consisting of hydroxy, halogen, amino, —CN, O-carboxy, C-carboxy, C-amido, N-amido, $C_1$-$C_6$ alkoxy, $C_3$-$C_5$ cycloalkyl, a 3- to 5-membered heterocycloalkyl group containing one heteroatom independently selected from oxygen, sulfur, or nitrogen. In some embodiments of the compound of Formula I', $R_8$ is optionally substituted lower alkoxy. In some embodiments of the compound of Formula I', $R_8$ is lower alkoxy optionally substituted with one to five substituents selected from the group consisting of hydroxy, halogen, amino, —CN, O-carboxy, C-carboxy, C-amido, N-amido, $C_1$-$C_6$ alkoxy, $C_3$-$C_5$ cycloalkyl, a 3- to 5-membered heterocycloalkyl group containing one heteroatom independently selected from oxygen, sulfur, or nitrogen. In some embodiments of the compound of Formula I', $R_8$ is cyano. In some embodiments of the compound of Formula I', $R_8$ is halogen.

In some embodiments of the compound of Formula I', $R_7$ and $R_8$ taken together, along with the carbon atoms to which they are attached, form a 4-, 5- or 6-membered non-aromatic carbocyclic, a 3- to 5-membered heterocycloalkyl, a $C_6$-$C_{10}$ aryl, or a five- to ten-membered heteroaryl ring.

In some embodiments of the compound of Formula I', $Q_7$ is nitrogen. In some embodiments of the compound of Formula I', $Q_7$ is —$CR_c$—. In some embodiments of the compound of Formula I', $R_c$ is hydrogen. In some embodiments of the compound of Formula I', $R_e$ is halogen. In some embodiments of the compound of Formula I', $R_c$ is lower alkyl. In some embodiments of the compound of Formula I', $R_e$ is hydrogen or methyl. In some embodiments of the compound of Formula I', $Q_7$ is —CH—.

In some embodiments of the compound of Formula I', $R_9$ is hydrogen, —$(C(R_a)_2)_n$—$N(R_a)_2$, —$(C(R_a)_2)_n$—CN, or —$(C(R_a)_2)_n$—C≡C—$R_a$. In some embodiments of the compound of Formula I', $R_9$ is hydrogen, —$(CH_2)_n$—$N(R_a)_2$, —$(CH_2)_n$—CN, or —$(CH_2)_n$—C≡C—$R_d$. In some embodiments of the compound of Formula I', $R_9$ is selected from hydrogen, —$N(R_d)_2$, —CN, or —C≡C—$R_d$. In some embodiments of the compound of Formula I', $R_9$ is selected from hydrogen, —$NH_2$, —CN, or —C≡CH.

In some embodiments of the compound of Formula I', $R_9$ is hydrogen. In some embodiments of the compound of Formula I', $R_9$ is —$(C(R_a)_2)_n$—$C(R_a)_3$. In some embodiments of the compound of Formula I', $R_9$ is —$(C(R_d)_2)_n$—$OR_d$. In some embodiments of the compound of Formula I', $R_9$ is —$(C(R_d)_2)_n$—$N(R_d)_2$. In some embodiments of the compound of Formula I', $R_9$ is —$NH_2$. In some embodiments of the compound of Formula I', $R_9$ is —$(C(R_a)_2)_n$—$S(=O)_qR_a$. In some embodiments of the compound of Formula I', $R_9$ is —$(C(R_a)_2)_n$—CN. In some embodiments of the compound of Formula I', $R_9$ is —CN. In some embodiments of the compound of Formula I', $R_9$ is —$(C(R_d)_2)_n$—C≡C—$R_d$. In some embodiments of the compound of Formula I', $R_9$ is —C≡CH. In some embodiments of the compound of Formula I', $R_9$ is —$(C(R_a)_2)_n$—$C(=O)$—$OR_d$. In some embodiments of the compound of Formula I', $R_9$ is —$(C(R_a)_2)_n$—HeAr. In some embodiments of the compound of Formula I', $R_9$ is —$(C(R_d)_2)_n$—$C(=O)$—$N(R_d)_2$.

In some embodiments of the compound of Formula I', each $R_d$ is independently hydrogen or lower alkyl optionally substituted with one to five substituents independently selected from the group consisting of hydroxy, halogen, —CN, amino, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', each $R_d$ is hydrogen. In some embodiments of the compound of Formula I', each $R_d$ is independently lower alkyl optionally substituted with one to five substituents independently selected from the group consisting of hydroxy, halogen, —CN, amino, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl.

In some embodiments of the compound of Formula I', q is 0. In some embodiments of the compound of Formula I', q is 1. In some embodiments of the compound of Formula I', q is 2.

In some embodiments of the compound of Formula I', n is 0. In some embodiments of the compound of Formula I', n is 1. In some embodiments of the compound of Formula I', n is 2. In some embodiments of the compound of Formula I', n is 3. In some embodiments of the compound of Formula I', n is 4. In some embodiments of the compound of Formula I', n is 5.

In some embodiments of the compound of Formula I', HeAr is a 5- or 6-membered heteroaryl group containing one to three ring heteroatoms independently selected from oxygen, sulfur, or nitrogen.

In some embodiments of the compound of Formula I', $R_{10}$ is hydrogen or —$C(R_e)_3$, wherein each $R_e$ is independently hydrogen, halogen, or lower alkyl optionally substituted with one to five substituents independently selected from the group consisting of hydroxy, halogen, —CN, amino, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_{10}$ is hydrogen. In some embodiments of the compound of Formula I', $R_{10}$ is —$C(R_e)_3$, wherein each $R_e$ is independently hydrogen, halogen, or lower alkyl optionally substituted with one to five substituents independently selected from the group consisting of hydroxy, halogen, —CN, amino, O-carboxy, C-carboxy, C-amido, N-amido, $C_1$-$C_6$ alkoxy, $C_6$-$C_{10}$ aralkoxy, $C_3$-$C_9$ cycloalkyl, a 3- to 6-membered heterocycloalkyl group containing one to four ring heteroatoms independently selected from oxygen, sulfur, or nitrogen, a five- to ten-membered heteroaryl group containing one to four ring heteroatoms independently selected from oxygen, sulfur, or nitrogen, and $C_6$-$C_{10}$ aryl. In some embodiments of the compound of Formula I', $R_{10}$ is —$C(R_e)_3$, wherein each $R_e$ is independently hydrogen, halogen, or lower alkyl. In some embodiments of the compound of Formula I', $R_{10}$ is hydrogen, —$CHF_2$, —$CH_3$, or ethyl.

In some embodiments of the compound of Formula I', $L_a$ is a bond; —$(C(R_a)_2)_z$—; oxygen; sulfur; or —$NR_a$—. In some embodiments of the compound of Formula I', $L_a$ is a bond. In some embodiments of the compound of Formula I', $L_a$ is —$(C(R_a)_2)_z$—. In some embodiments of the compound of Formula I', $L_a$ is —$CH_2$—. In some embodiments of the compound of Formula I', $L_a$ is oxygen. In some embodiments of the compound of Formula I', $L_a$ is sulfur. In some embodiments of the compound of Formula I', $L_a$ is —$NR_a$—. In some embodiments of the compound of Formula I', each $R_a$ is hydrogen. In some embodiments of the compound of Formula I', each $R_a$ is independently lower alkyl. In some embodiments of the compound of Formula I', each $R_a$ is independently a hydrogen or lower alkyl.

In some embodiments of the compound of Formula I', z is 0. In some embodiments of the compound of Formula I', z is 1. In some embodiments of the compound of Formula I', z is 2. In some embodiments of the compound of Formula I', z is 3. In some embodiments of the compound of Formula I', z is 4. In some embodiments of the compound of Formula I', z is 5.

In another aspect, disclosed herein is a compound selected from the group consisting of:

11 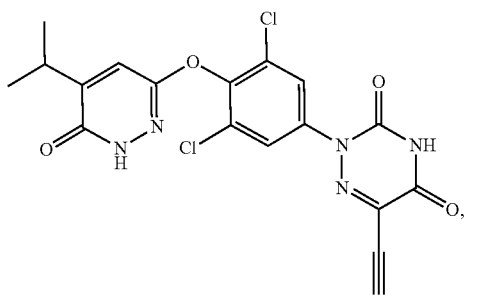
12 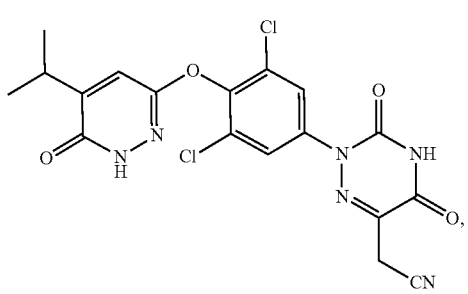
13 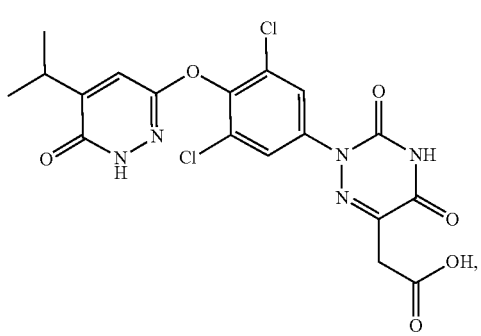
14 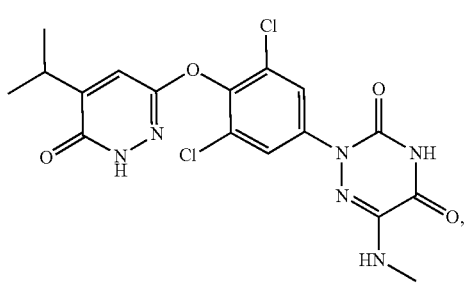
15 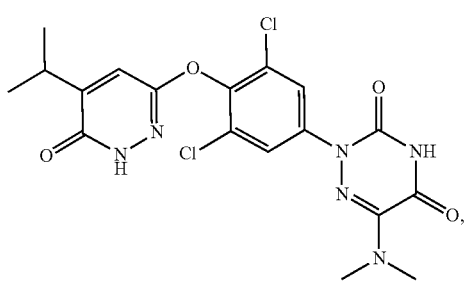
16 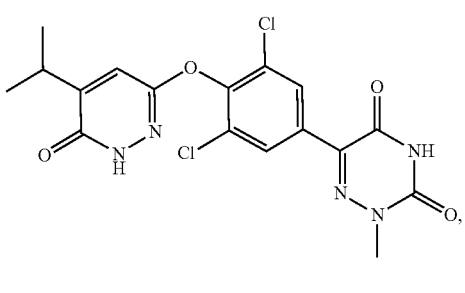
17 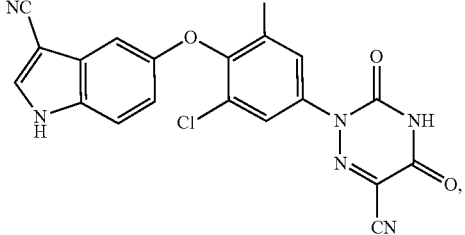
18 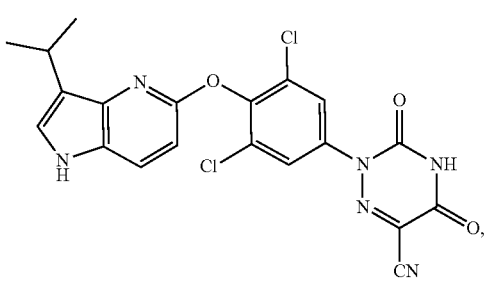
19 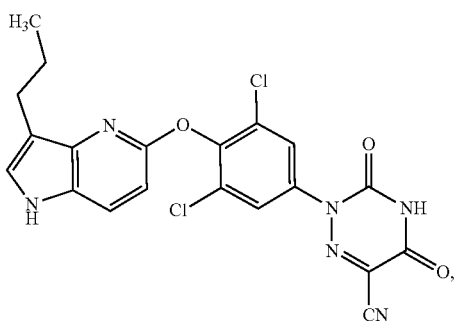
20 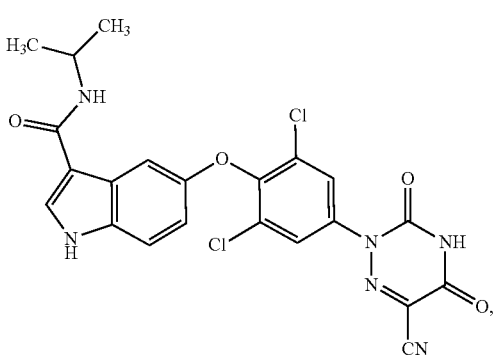

77
-continued
21
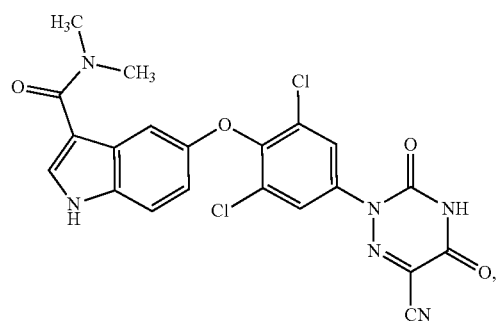
22
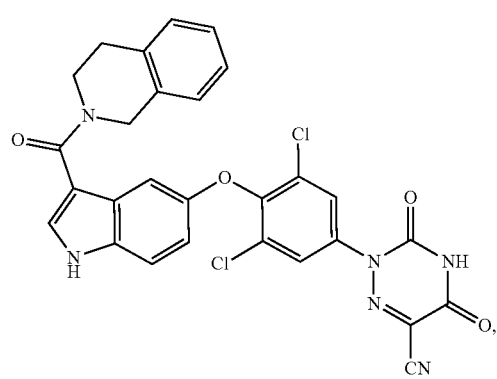
23
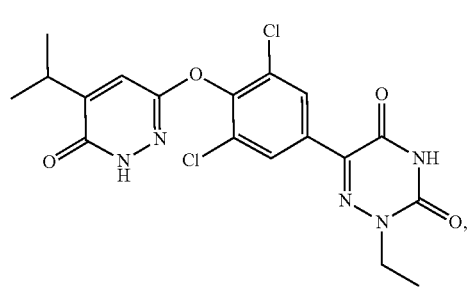
24
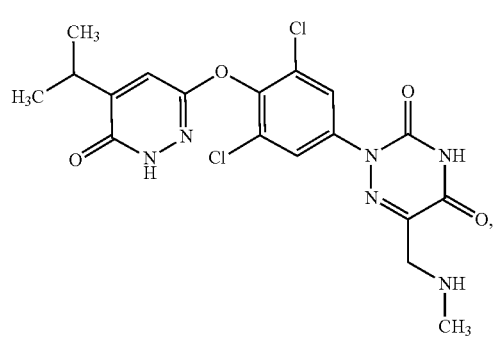
25
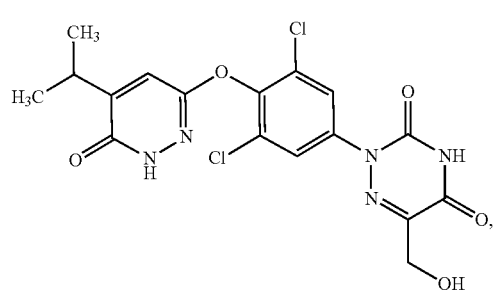
78
-continued
26
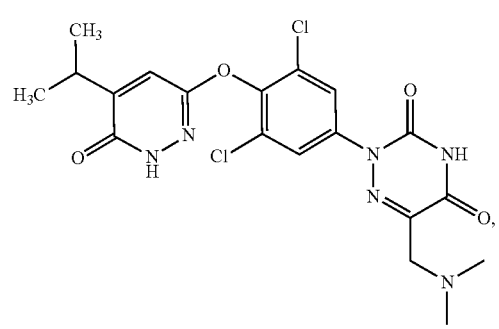
27
28
29
30
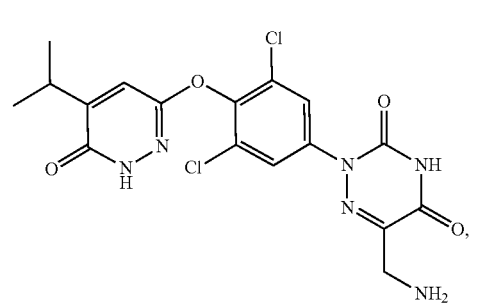

-continued
31
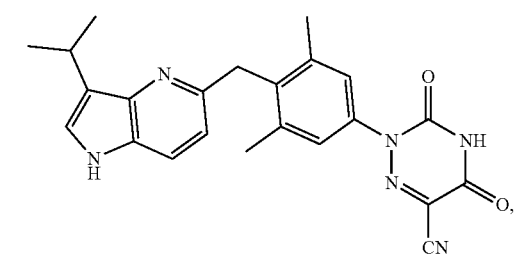
32
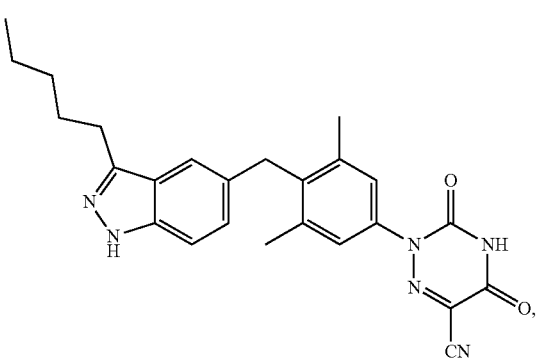
33
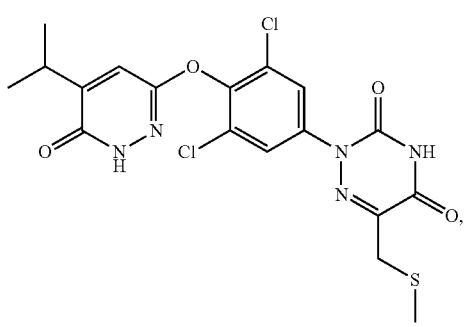
34
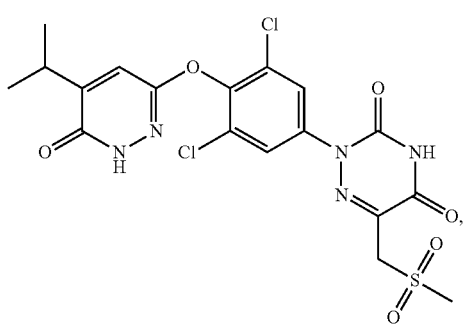
35
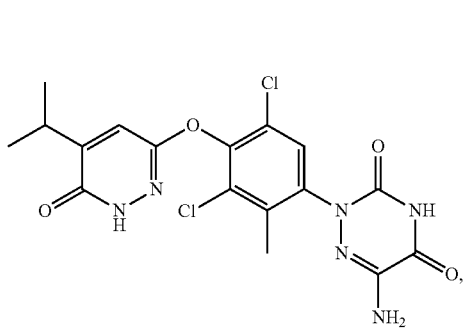
-continued
35-A
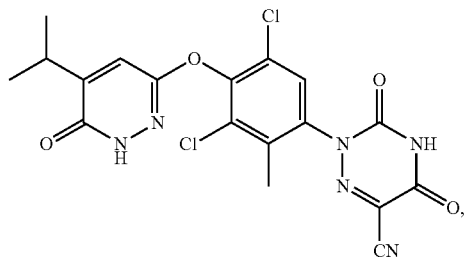
36
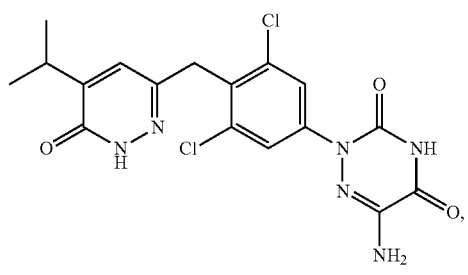
37
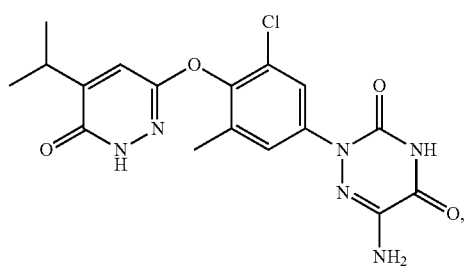
38
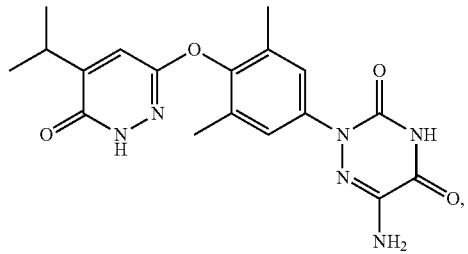
39
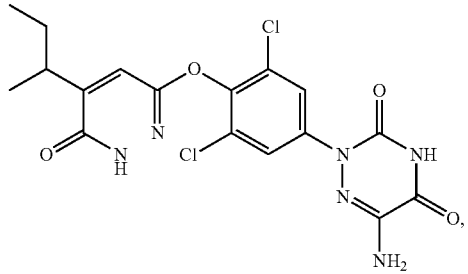
39-A or 39-B
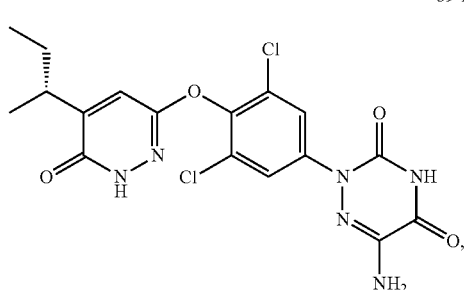

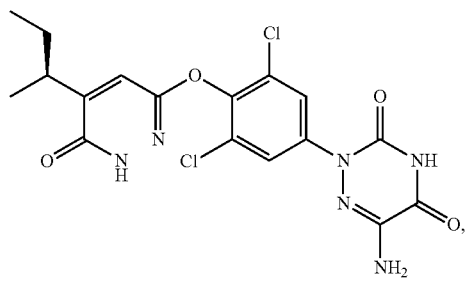
39-A or 39-B
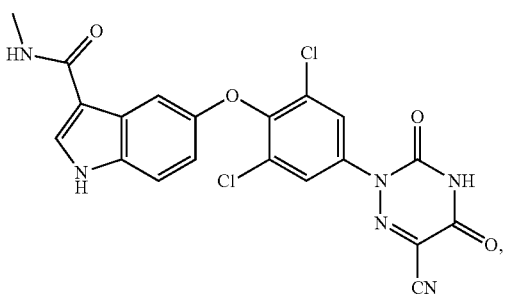
44
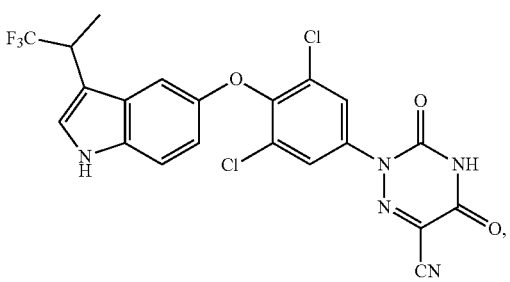
45
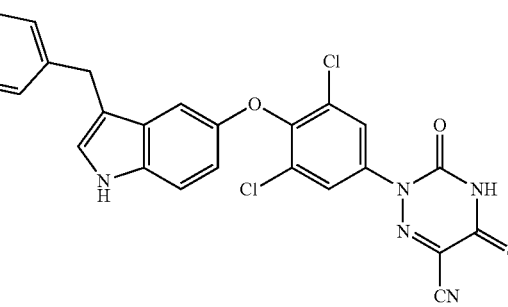
46
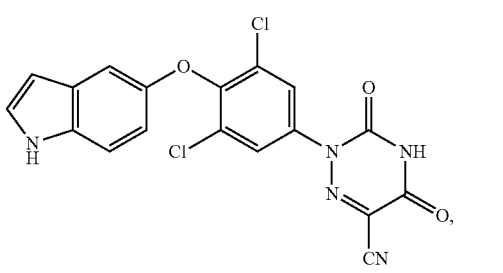
47
40
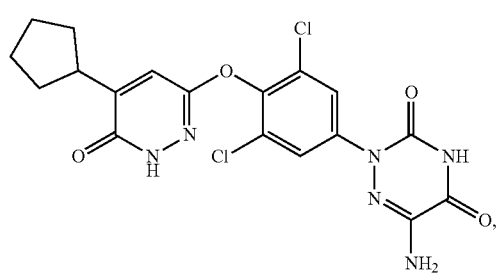
41
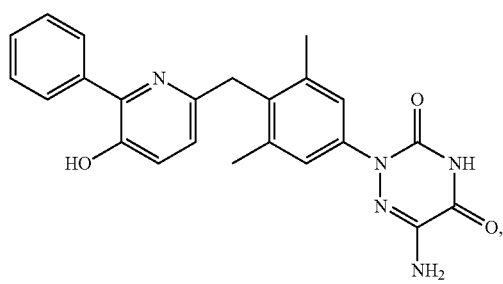
42
43
48

49
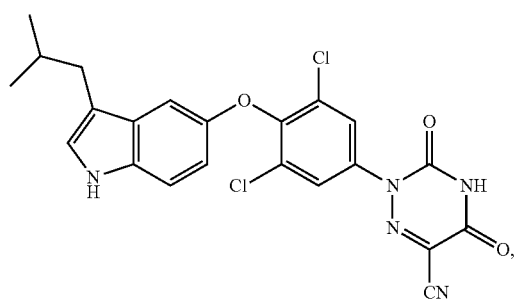
50
51
52
53
54
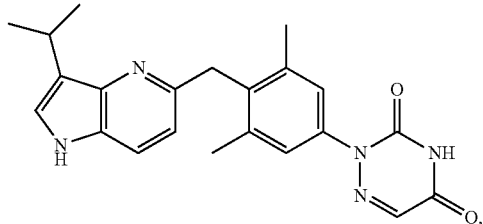
55
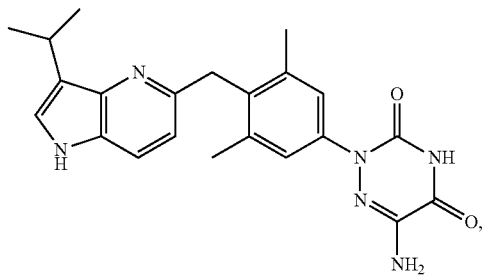
56
57
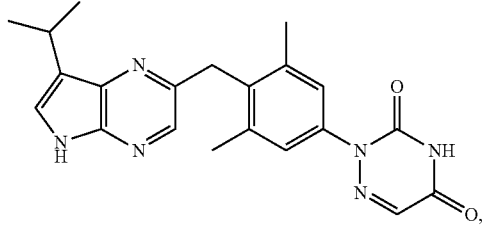
58
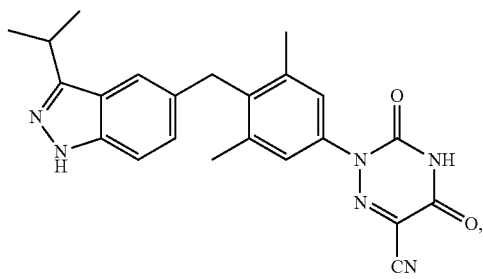
59
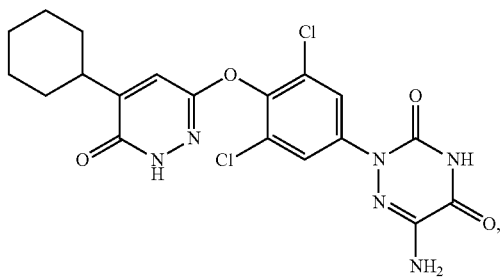
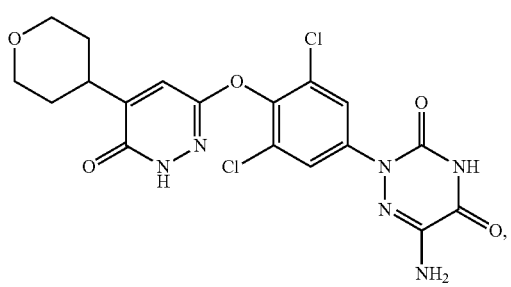

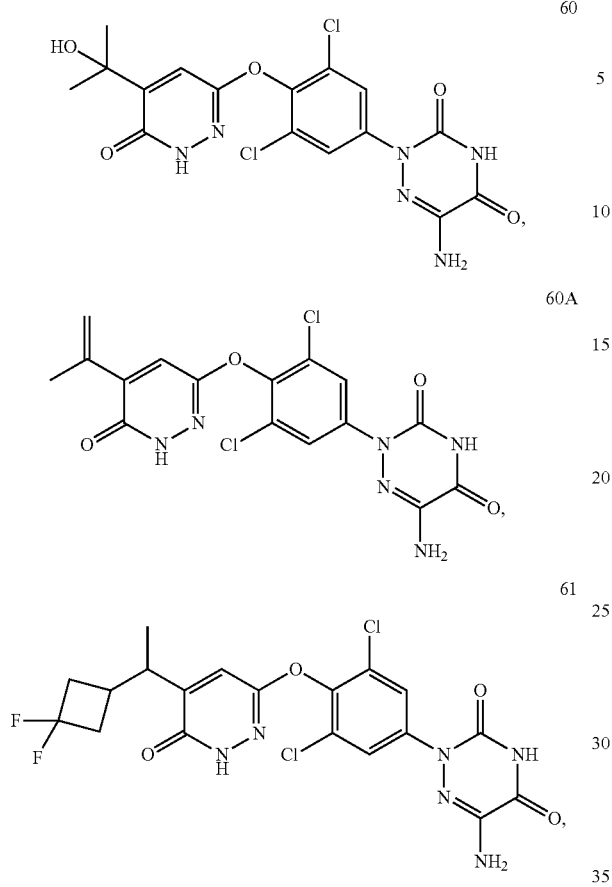
60
60A
61
61A or 61-B
61-A or 61-B
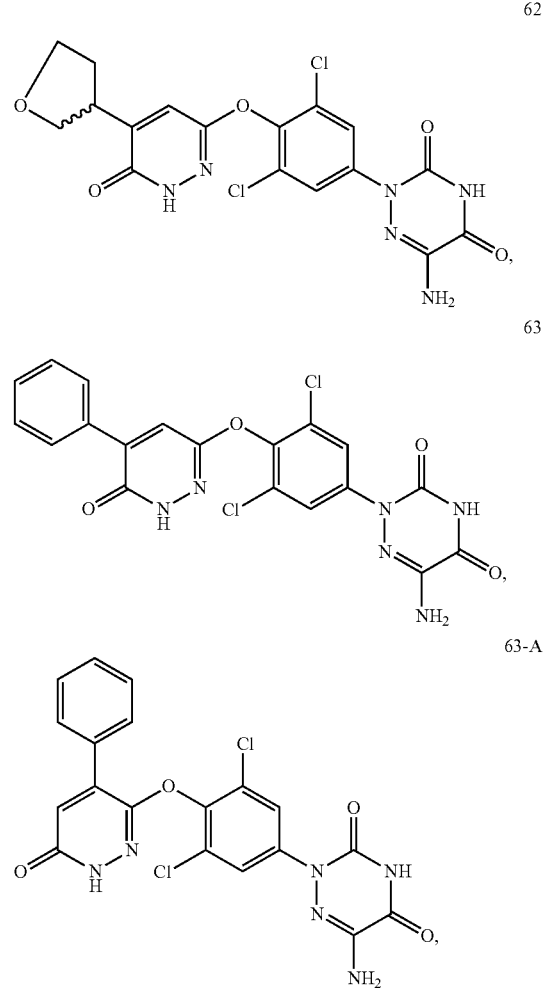
62
63
63-A
64
65

66
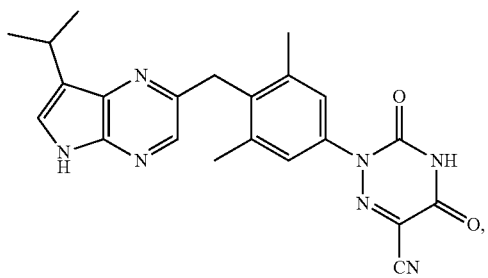
67
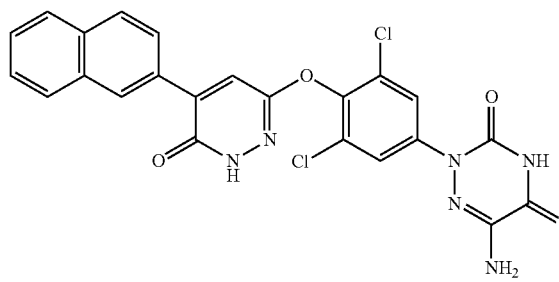
67-A
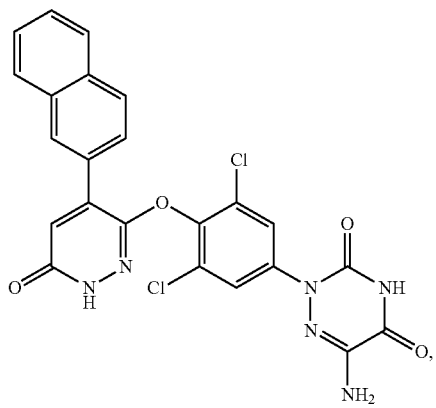
68
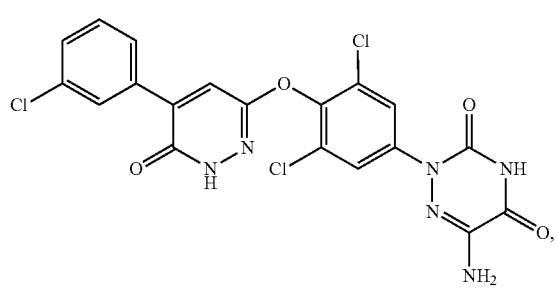
68-A
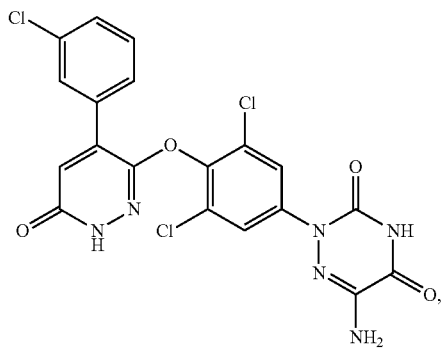
69
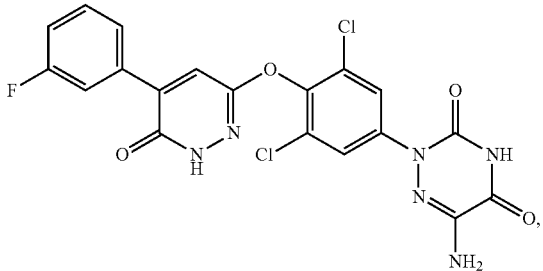
69-A
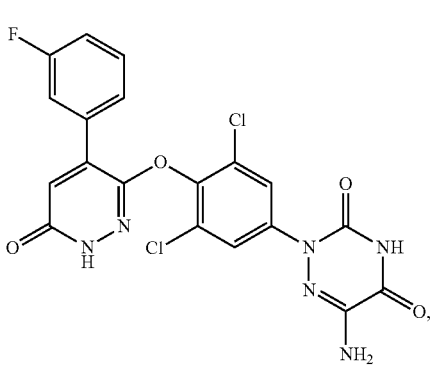
70
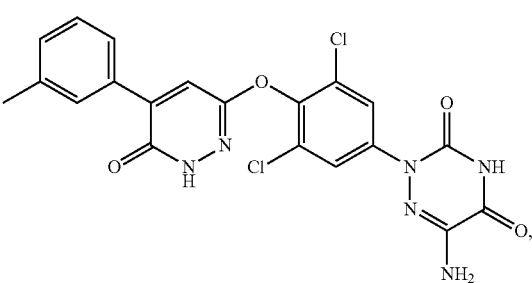
70-A
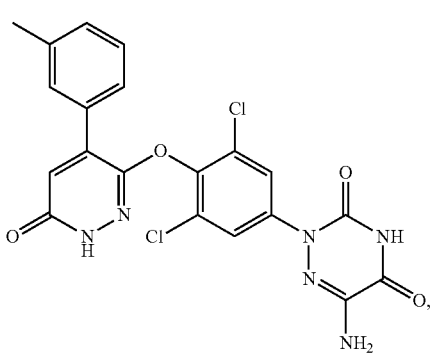
71
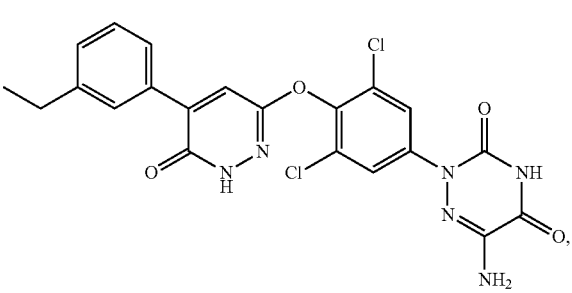

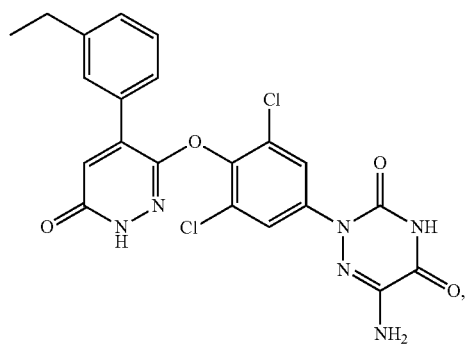
71-A
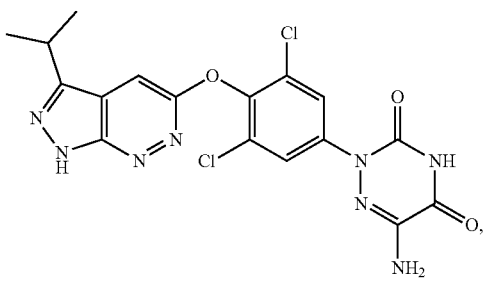
75
72
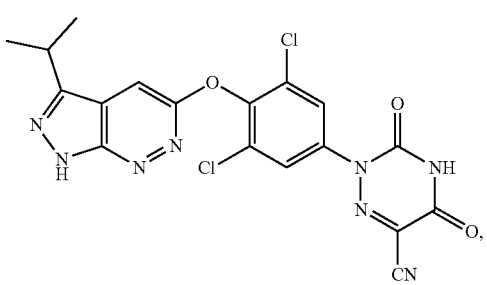
75-A
72-A
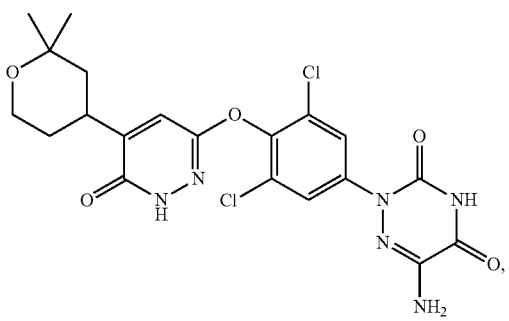
76
73
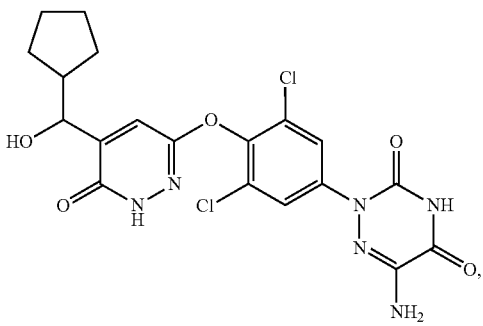
77
74
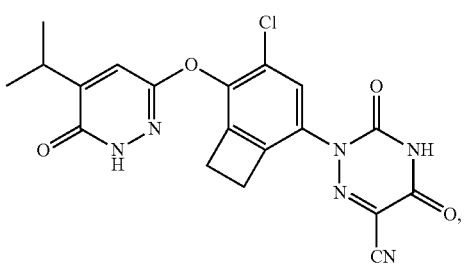
78

79
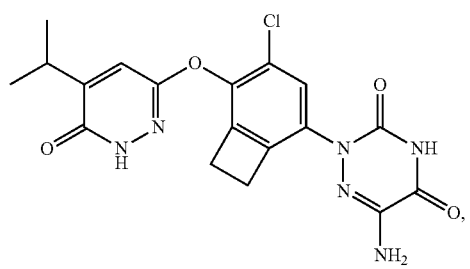
80
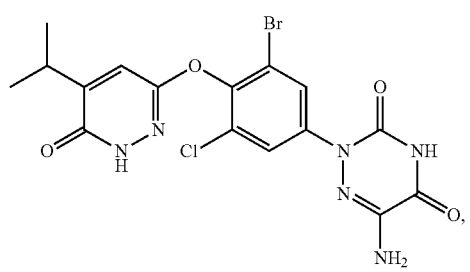
81
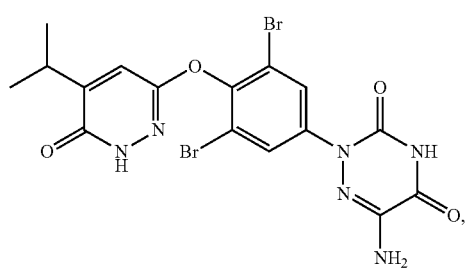
82
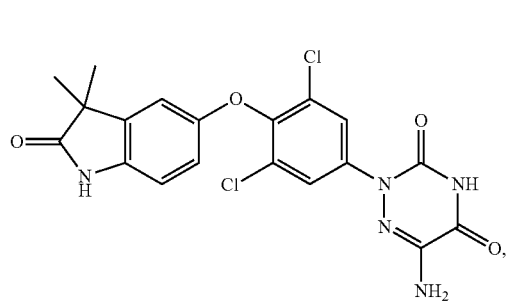
83
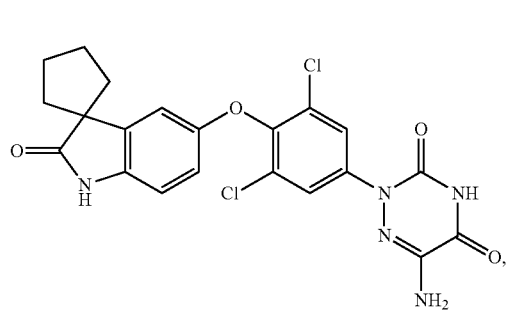
84
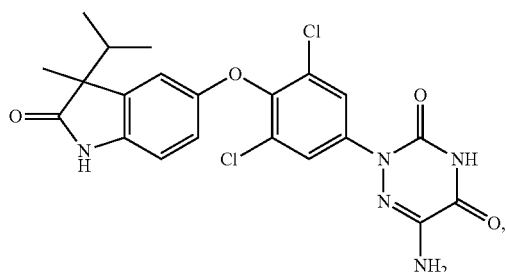
85
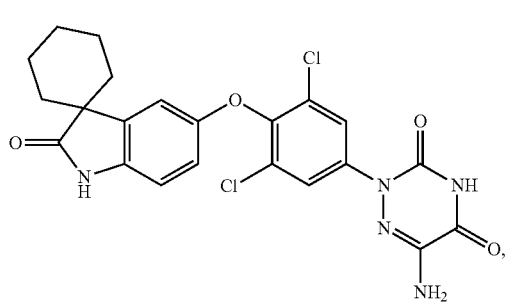
86
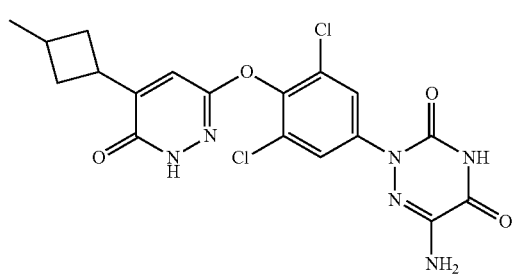
86-A
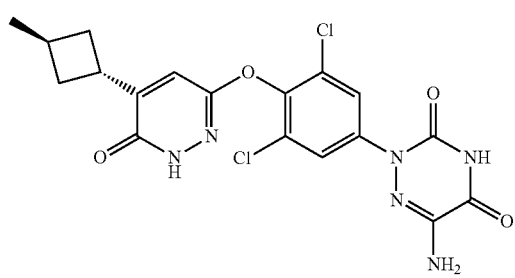
86-B
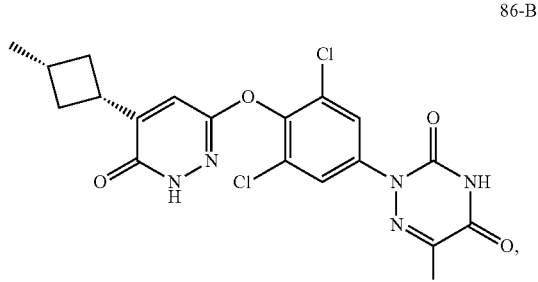

87-A
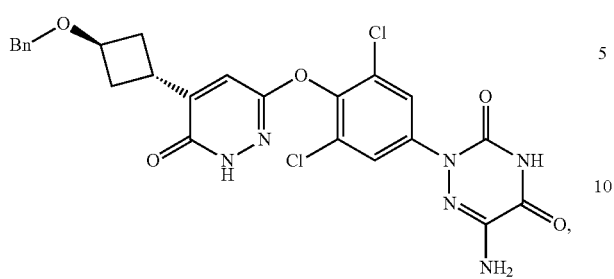
87-B
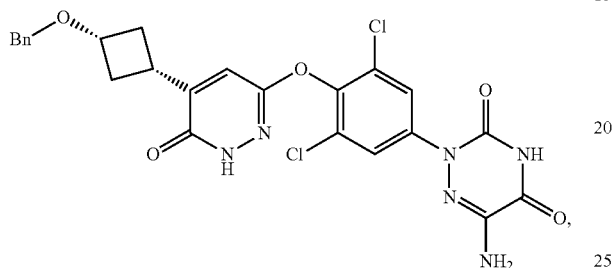
88
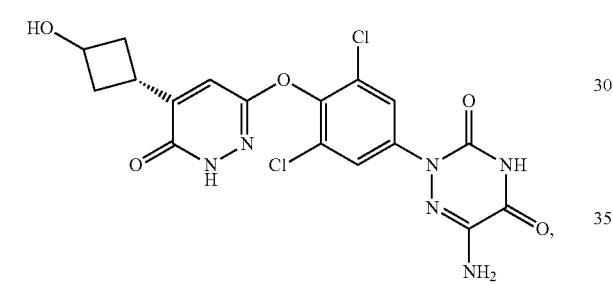
88-A
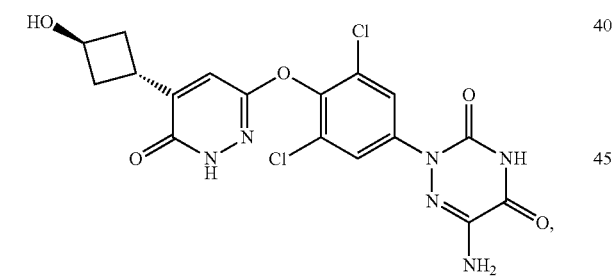
88-B
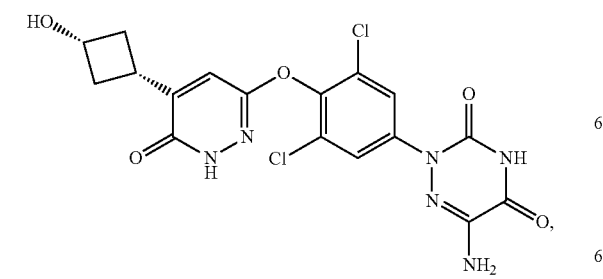
89
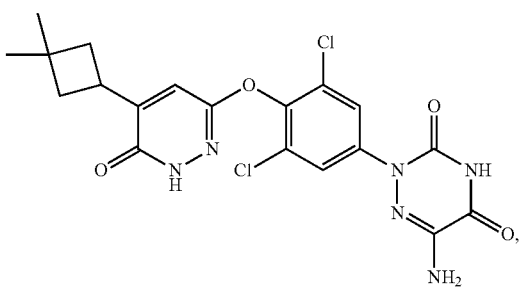
90
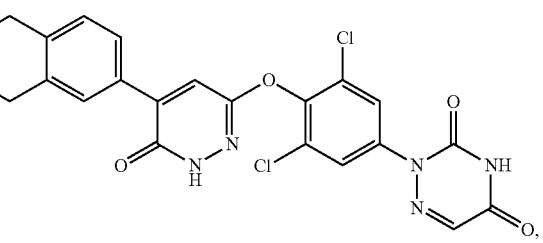
91
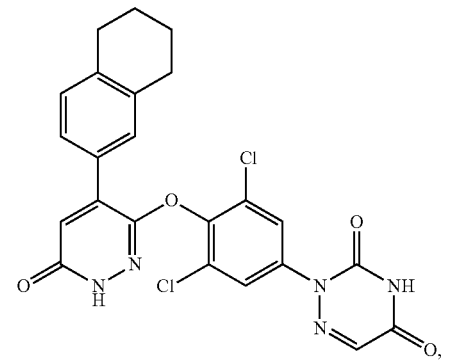
91-A
92
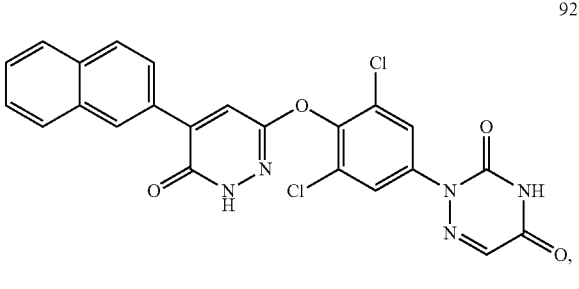

92-A
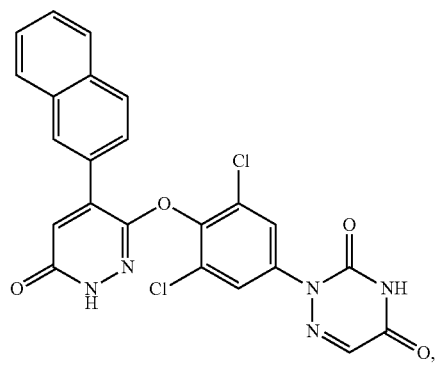
93
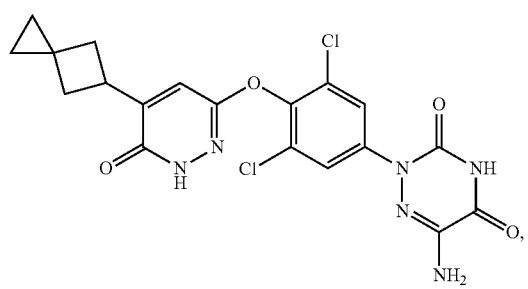
94
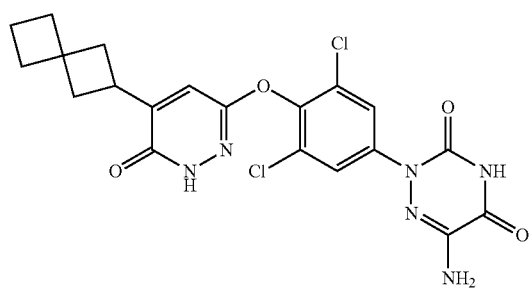
95
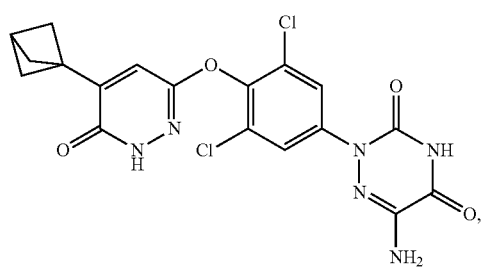
96
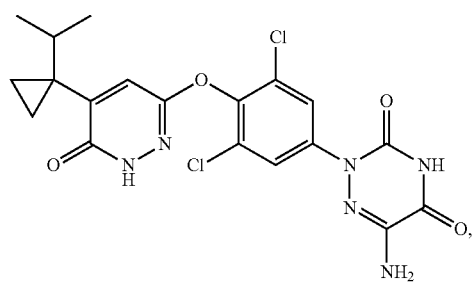
97
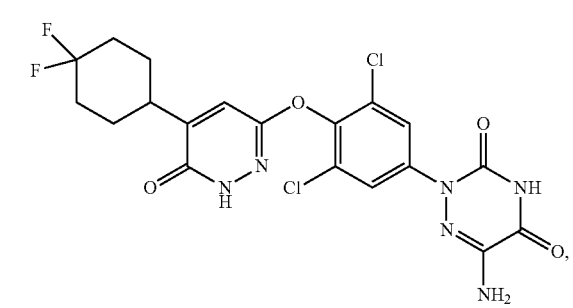
98
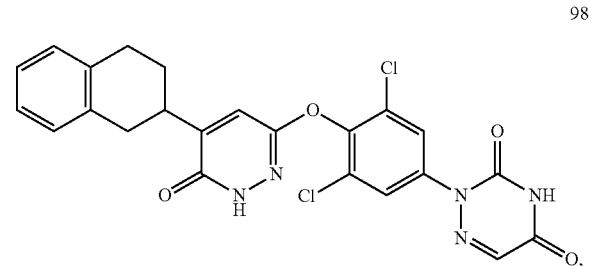
99
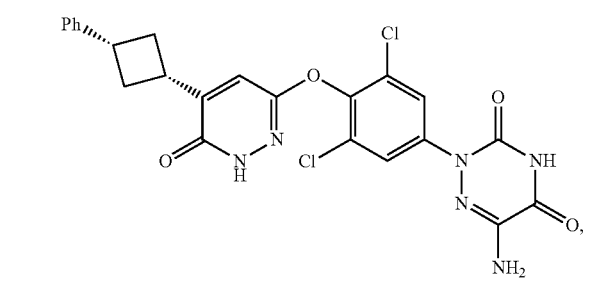
100
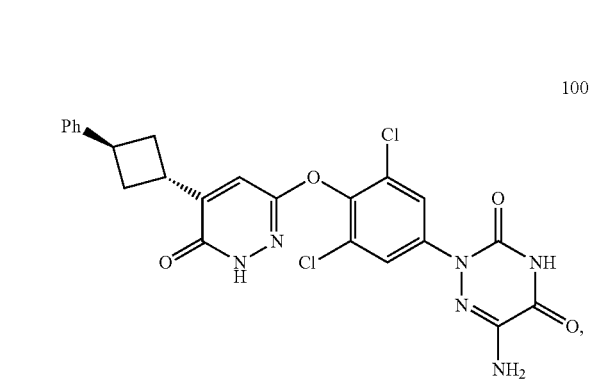
101
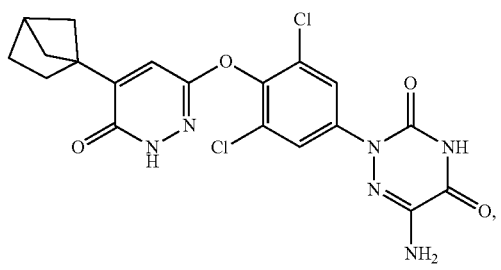

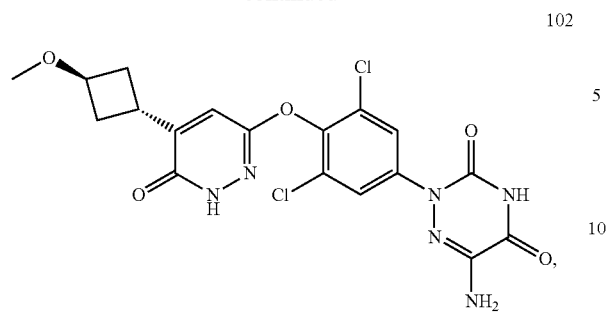
102
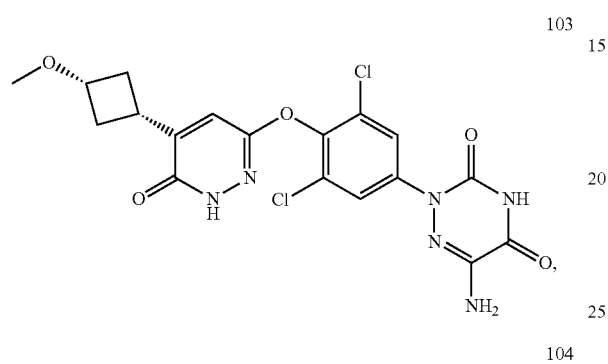
103
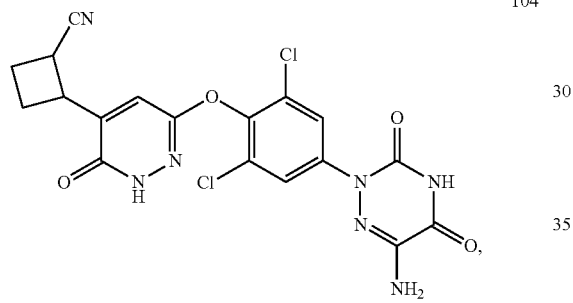
104
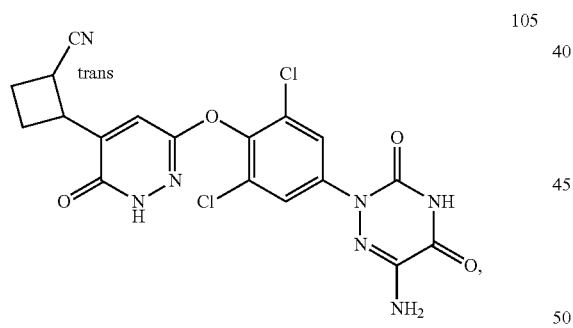
105
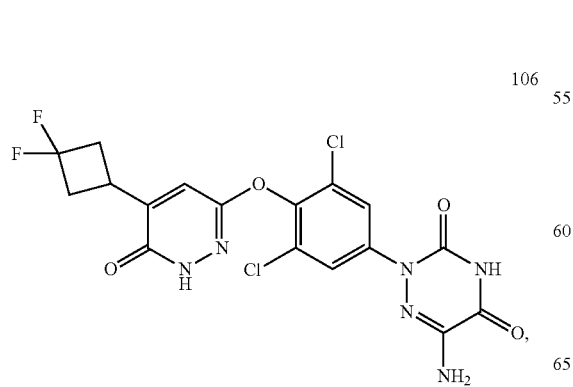
106
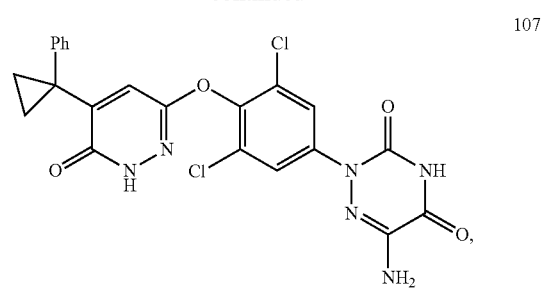
107
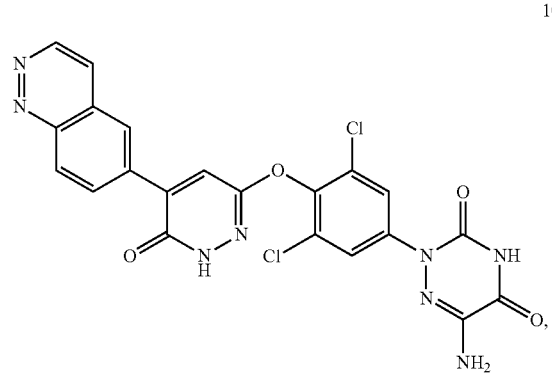
108
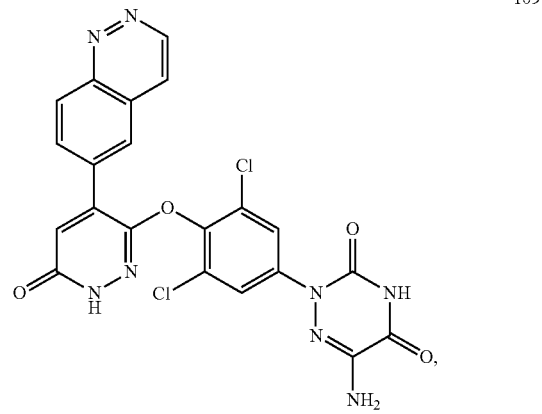
109
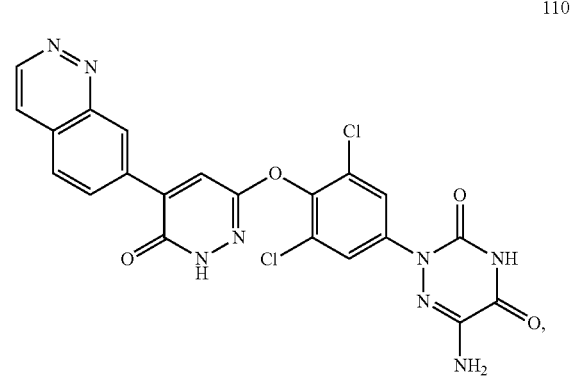
110

111
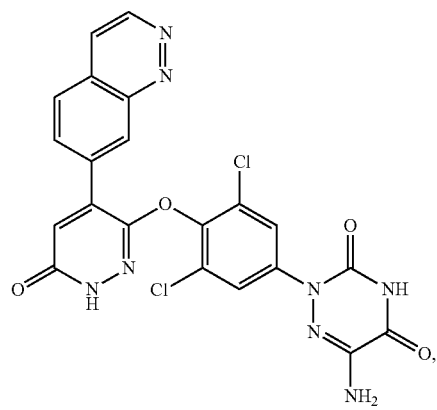
112
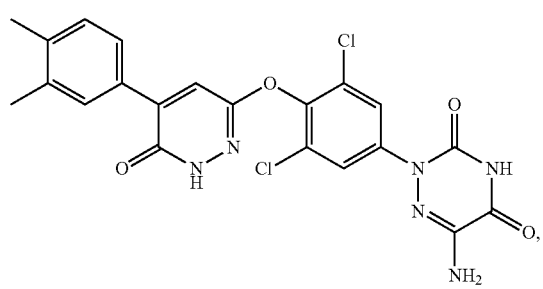
113
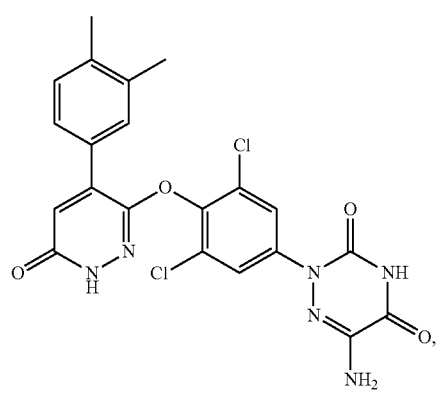
114
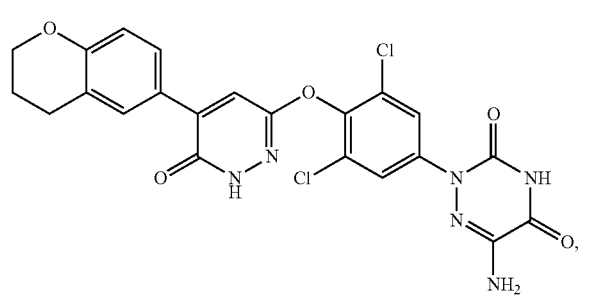
115
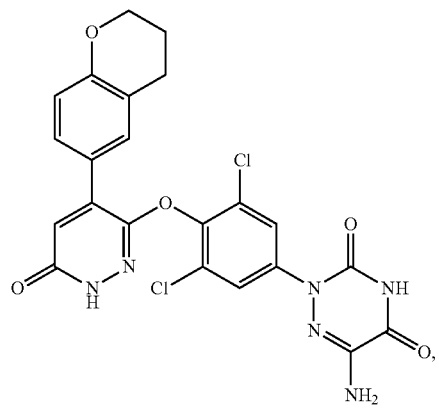
116
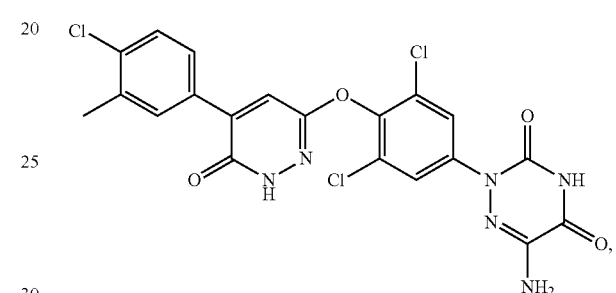
117
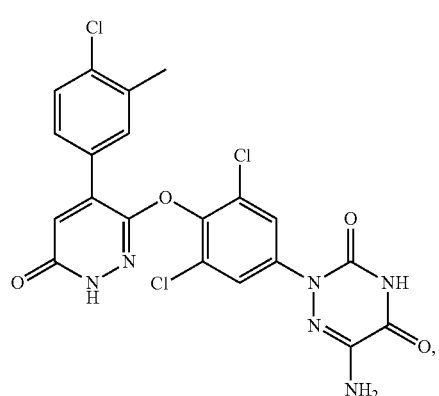
118
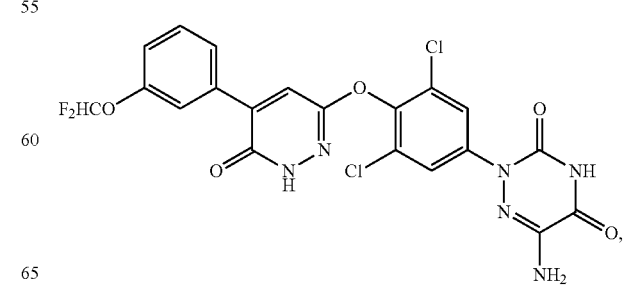

119
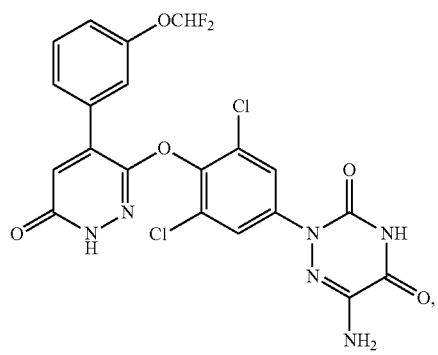
120
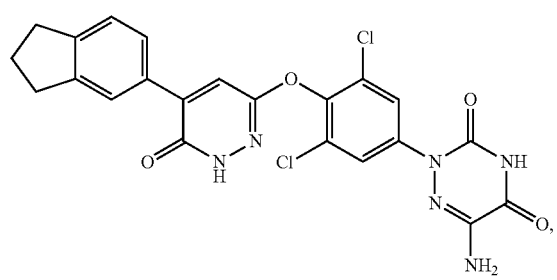
121
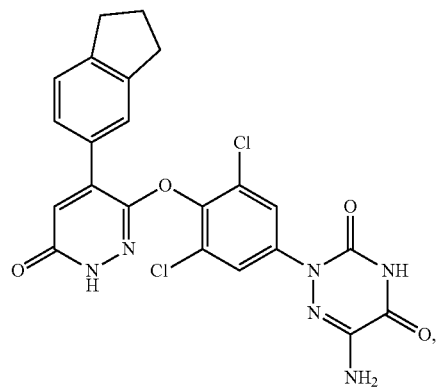
122
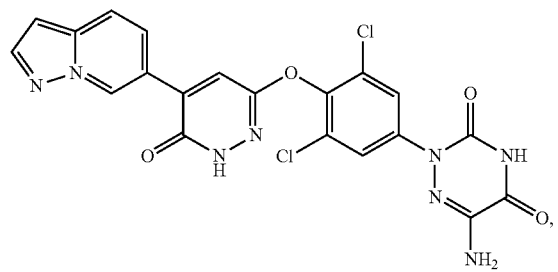
123
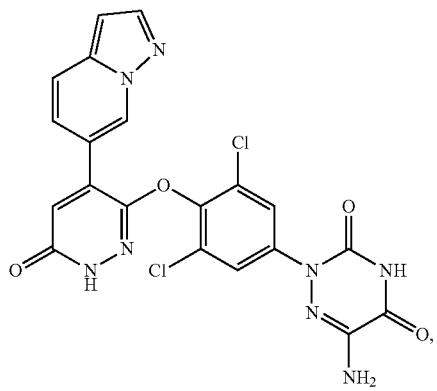
124
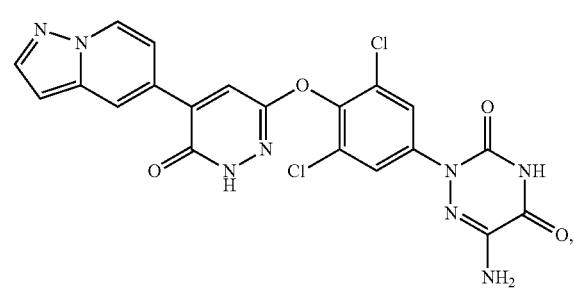
125
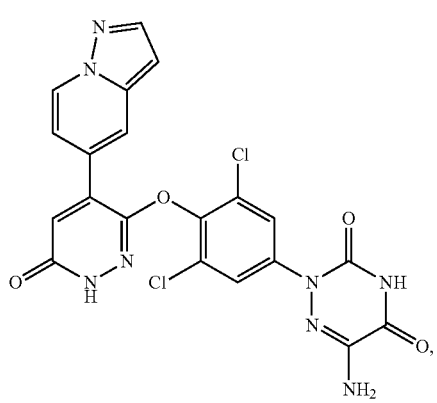
126
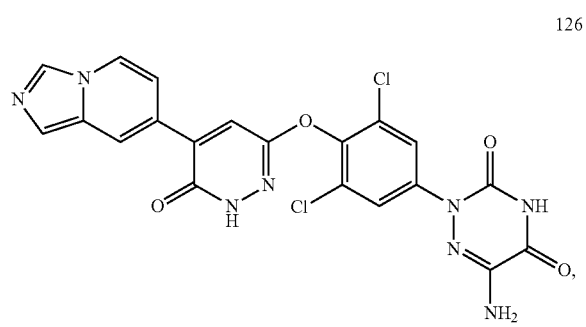

127
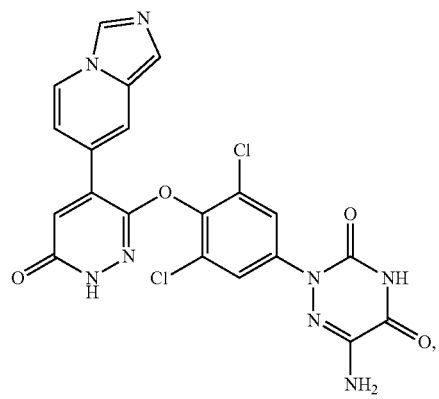
128
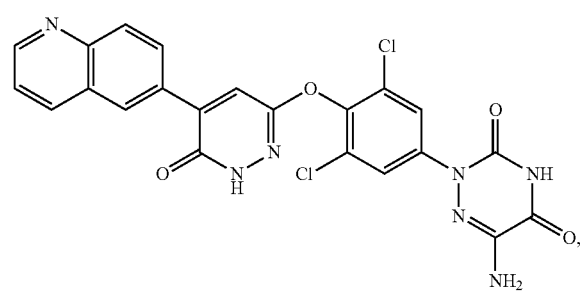
129
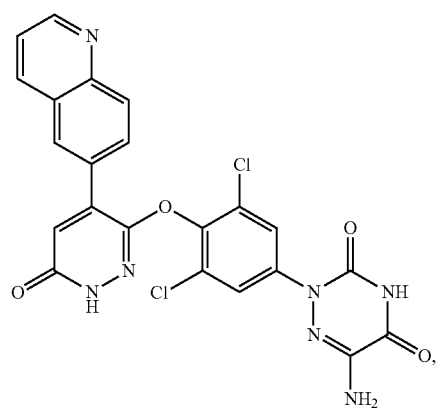
130
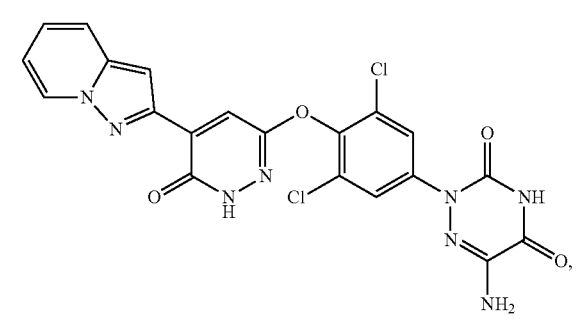
131
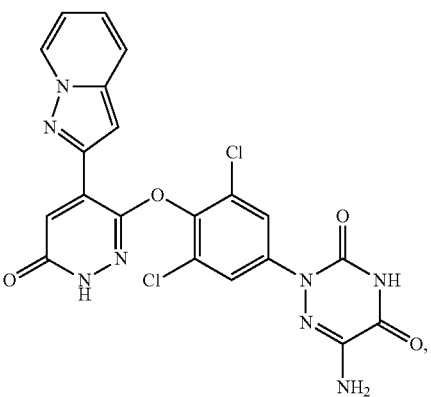
132
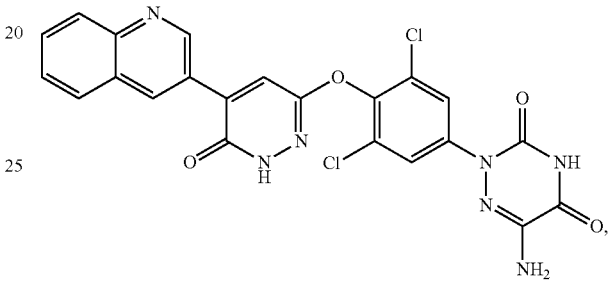
133
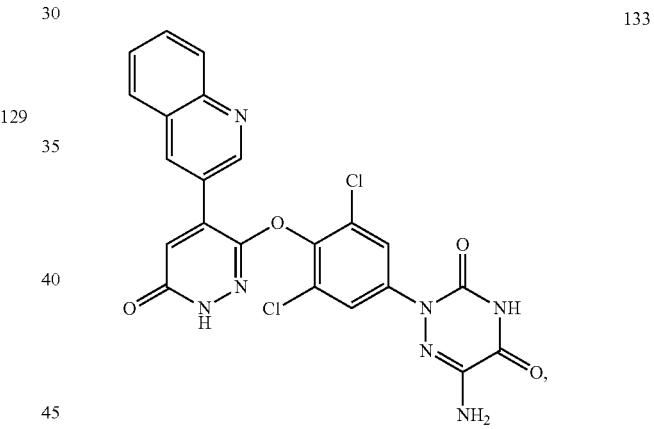
134
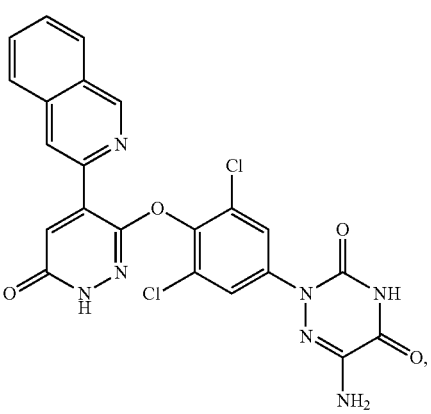

135
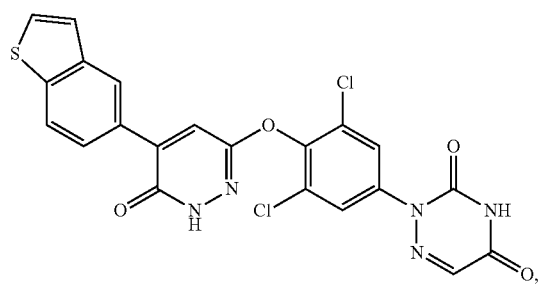
136
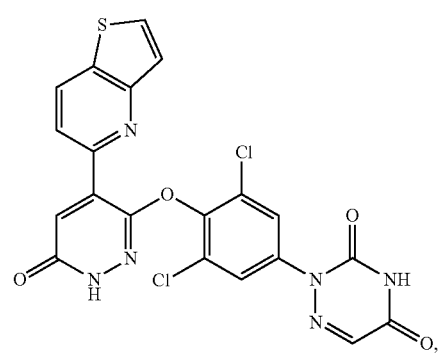
137
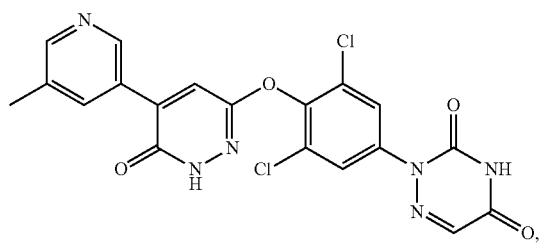
138
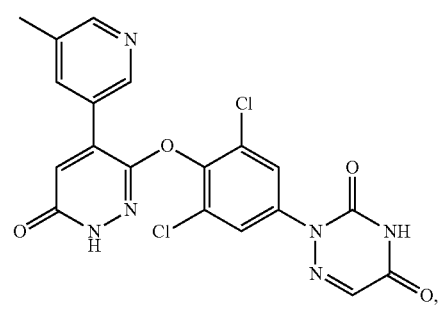
139
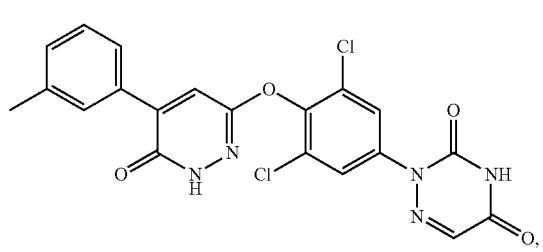
140
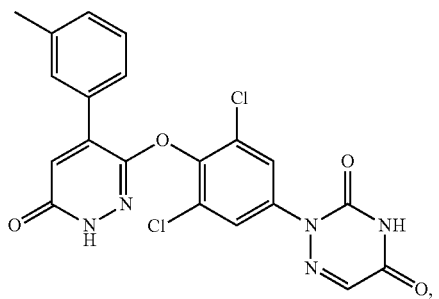
141
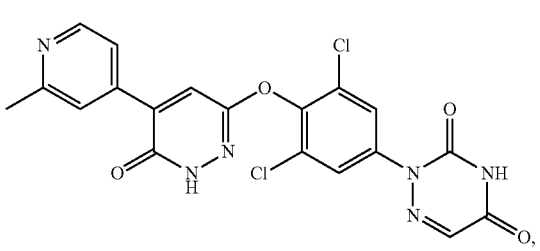
142
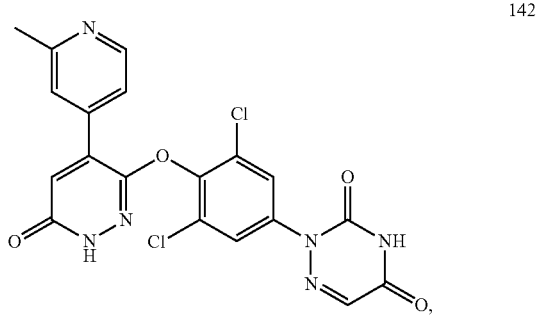
143
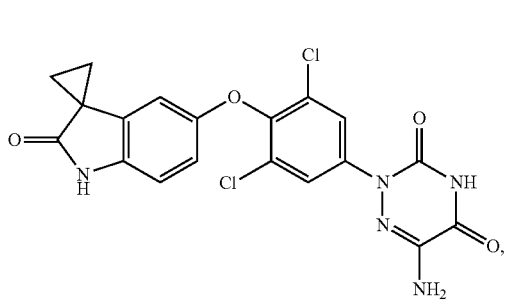
144

145
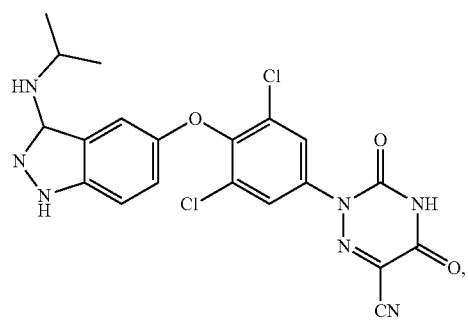
146
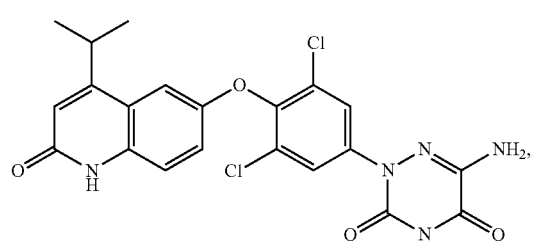
147
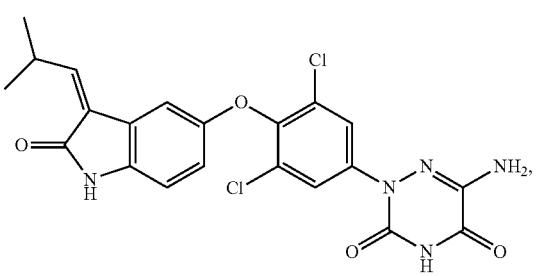
148
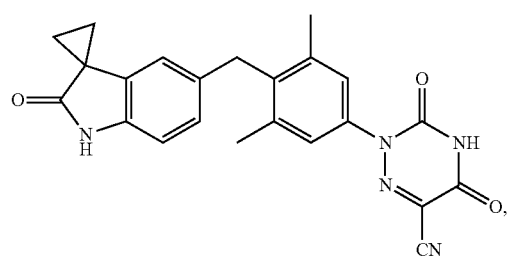
149
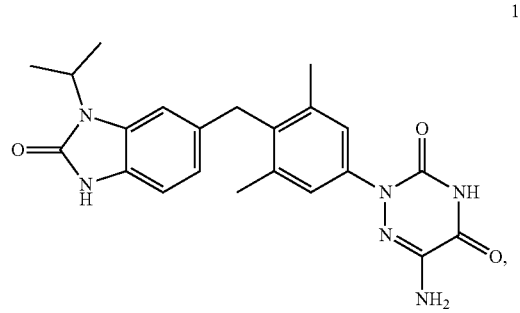
150
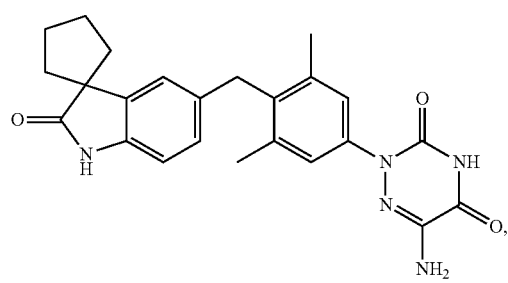
151
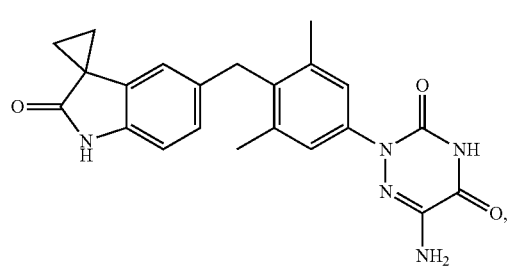
152
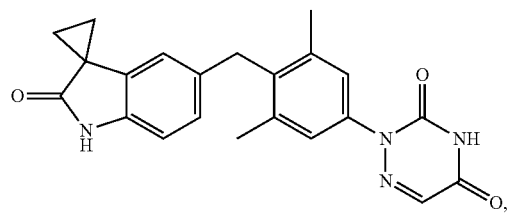
153
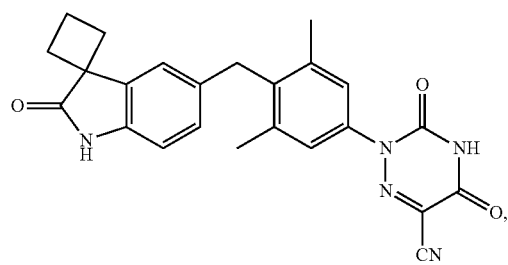
154
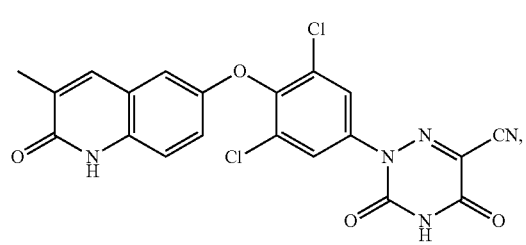

155
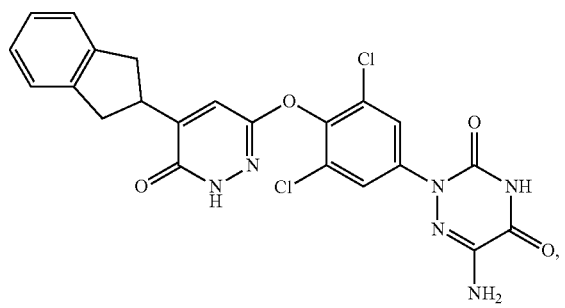
156
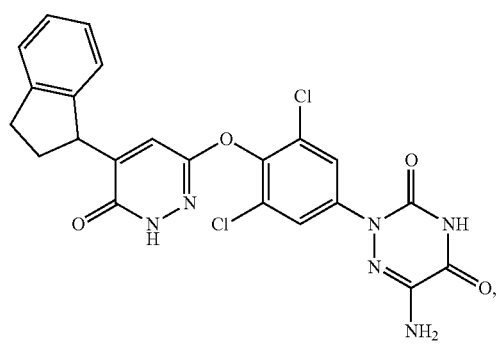
157
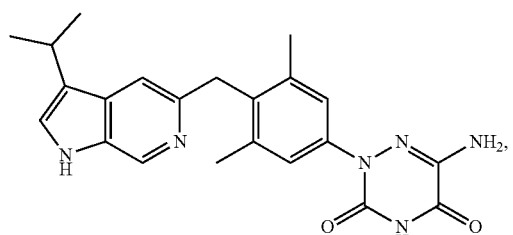
158
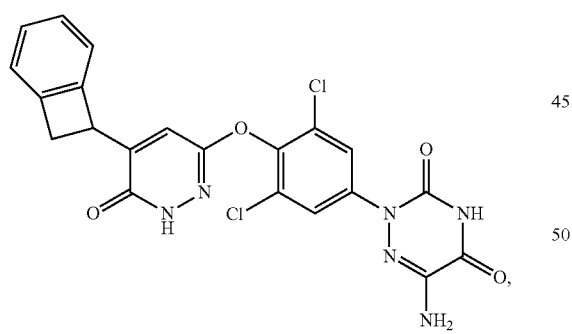
159
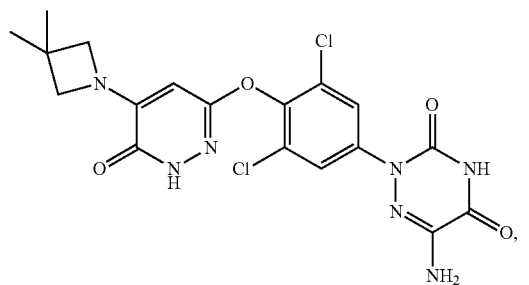
160
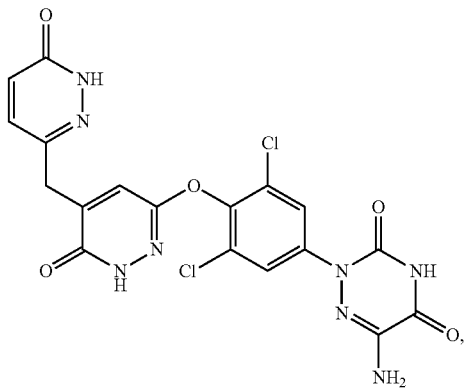
161
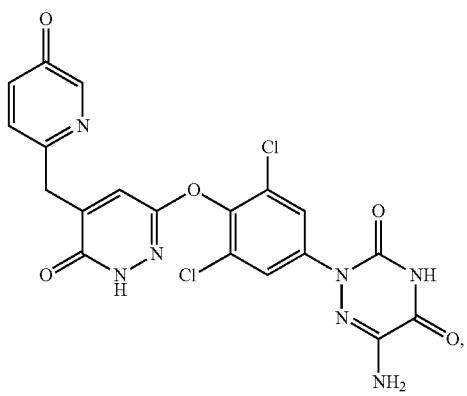
162
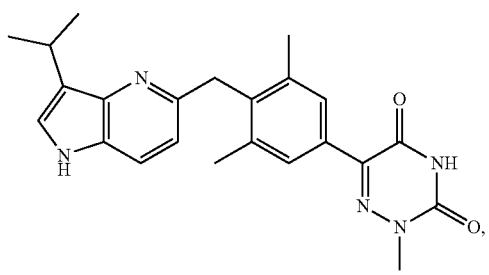
163 or 164
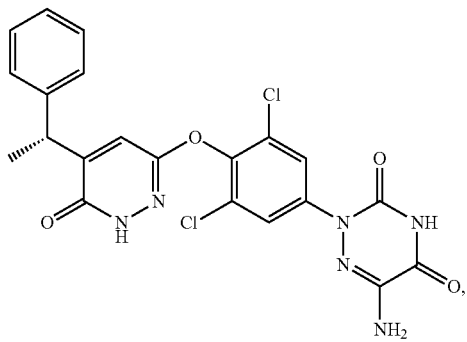

-continued
163 or 164
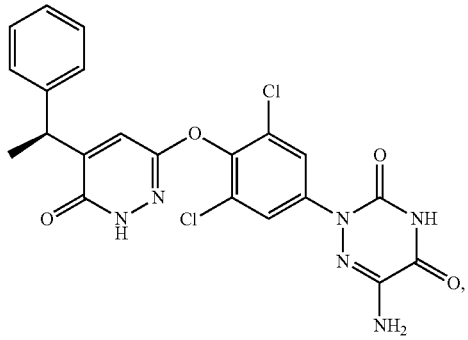
165 or 166
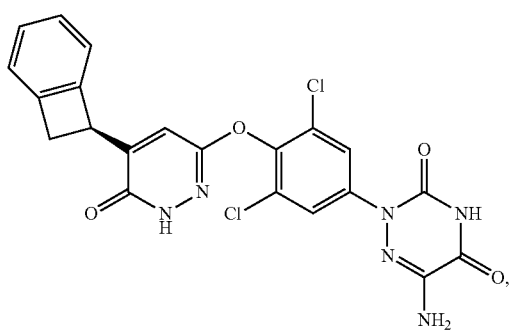
165 or 166
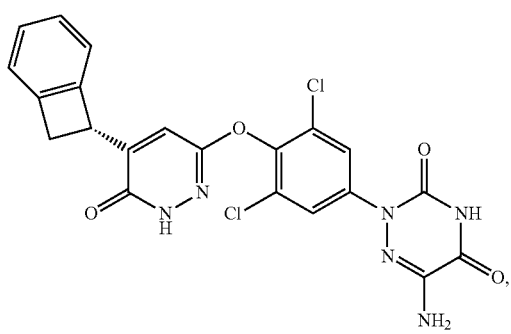
167 or 168
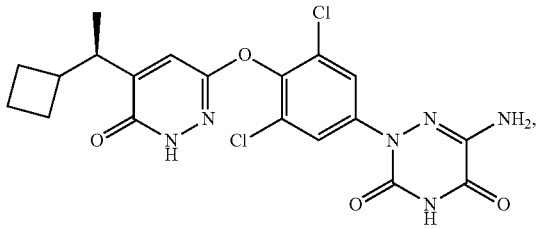
167 or 168
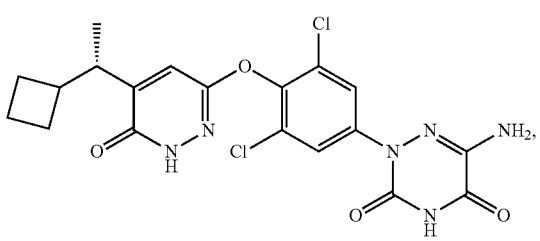
-continued
169 or 170
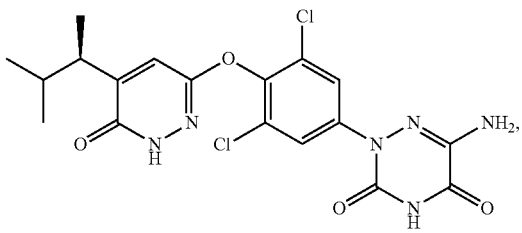
169 or 170
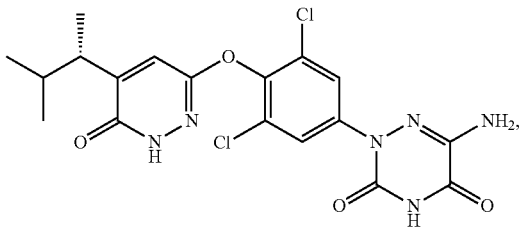
171
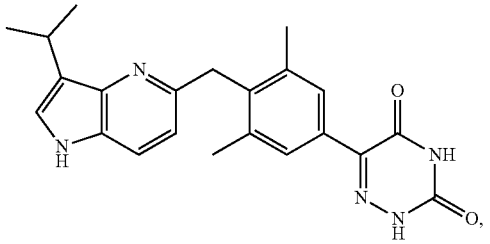
172
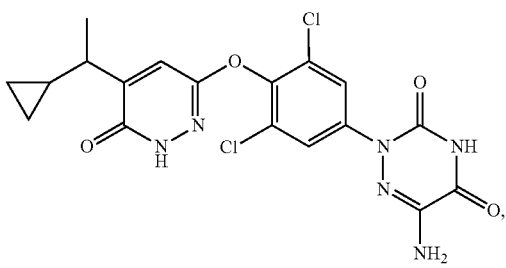
173
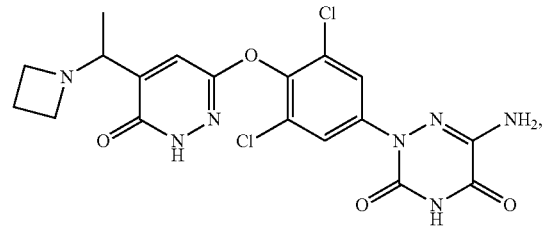
174
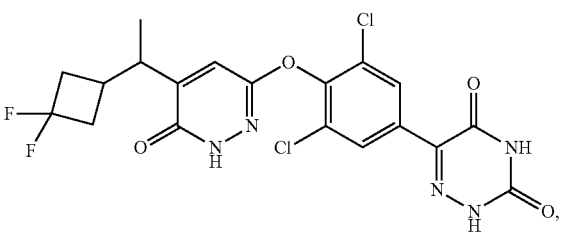

175

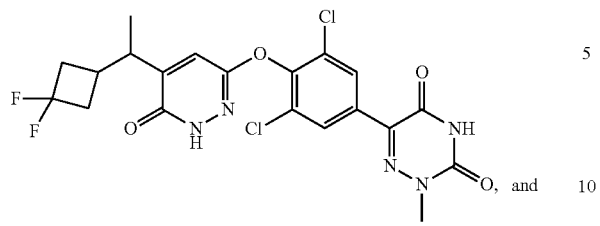

, and

176

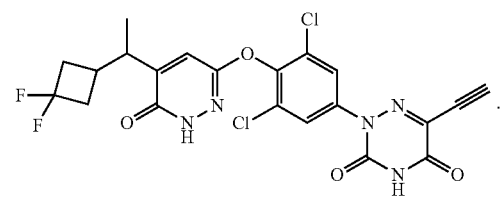

Synthesis of the Compounds

The presently disclosed compounds were synthesized using the general synthetic procedures set forth in Schemes 1-10 below. The carrying out of each individual illustrated step is within the skill of an ordinary artisan, who also knows how to modify the synthetic procedures of the below schemes to synthesize the full scope of the compounds disclosed herein. The synthetic procedure for individual compounds is provided in the Examples section, below.

As described in Scheme 1, an aromatic amine compound of Formula S-II is transformed to an aza-uracil compound of Formula S-III, first by generating the corresponding diazonium salt, followed by reaction with an N-(2-cyanoacetyl)-carbamate, and finally cyclization, resulting in the formation of a compound of Formula S-III. Next the nitrile of Formula S-III is hydrolyzed to a carboxylic acid compound of Formula S-IV. The compound of Formula S-IV is then reacted with diphenylphosphoryl azide (DPPA), resulting in the formation of a compound of Formula S-V. Finally, the compound of Formula S-V is deprotected.

Scheme 1

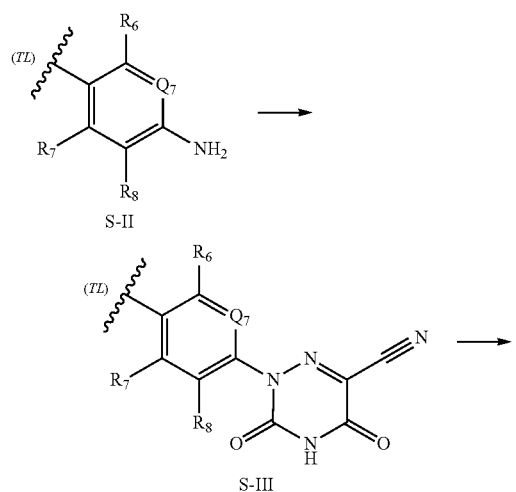

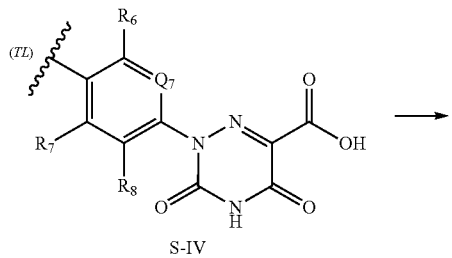

As described in Scheme 2, the aromatic amine compound of Formula S-II can be converted to a boronic acid compound of Formula S-VII, first by generation of the diazonium salt, followed by reaction with tetrahydroxydiborane. The corresponding boronic acid is then coupled with a suitably protected (with protecting group 'PG') bromo-azauracil compound of Formula Int-I. The resulting bromide compound of Formula S-VIII is then further transformed, either by a substitution reaction, or by transition metal catalyzed transformations as exemplified in the Examples section, below. Removal of the protecting group 'PG' results in a compound of Formula S-X.

Scheme 2

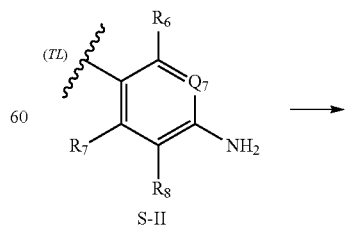

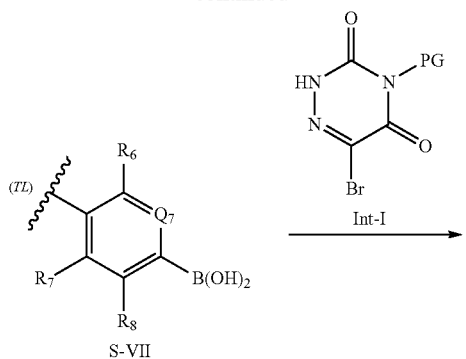

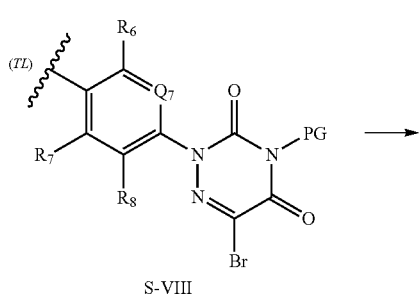

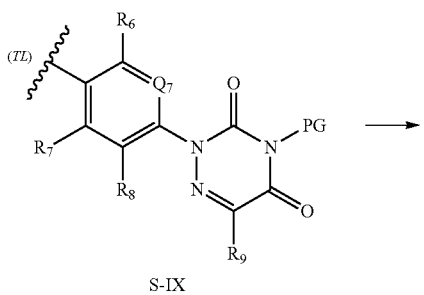

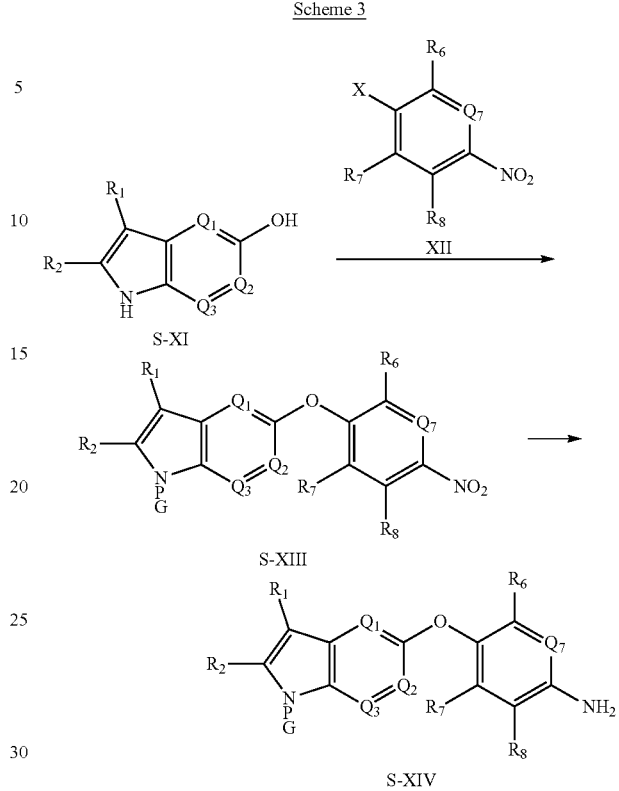

The synthesis of an aromatic amine compound of Formula S-XIV is described in Scheme 3. A compound of Formula S-XI is reacted with a compound of Formula S-XII, ('X' represents a halogen like F or Cl), followed by protection with a protecting group 'PG', resulting in a compound of Formula S-XIII. Reduction of the nitro functionality of the compound of Formula S-XIII results in the formation of an aromatic amine compound of Formula S-XIV.

Scheme 4 describes the synthesis of a compound of Formula S-XIX. A transmetalation reaction of a compound of Formula S-XVI ('X' in the structure represents a halogen, e.g., Br or I) is followed by an addition to the aldehyde of general Formula S-XV affording the alcohol compound of Formula S-XVII, which is then reduced to a compound of Formula S-XVIII. Deprotection of PG2 of the compound of Formula S-XVIII results in the formation of a compound of Formula S-XIX.

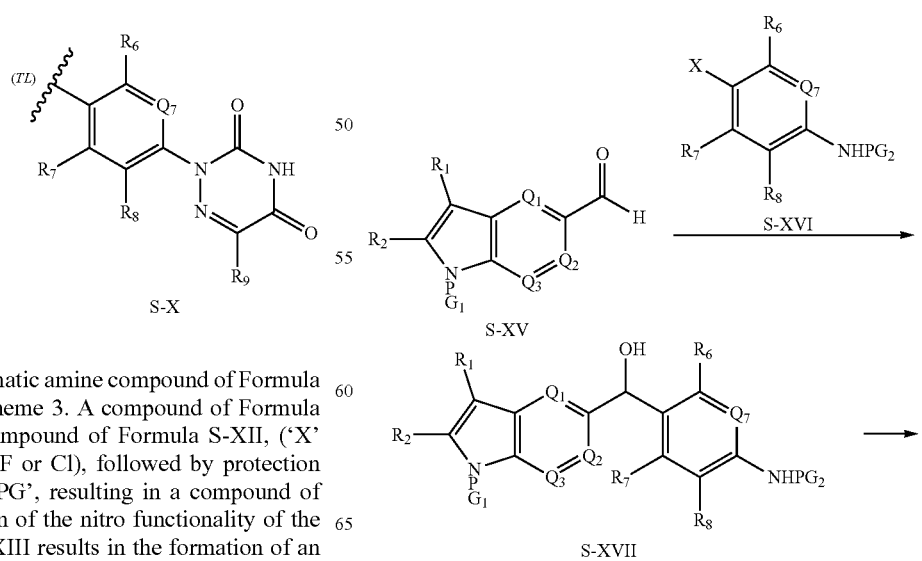

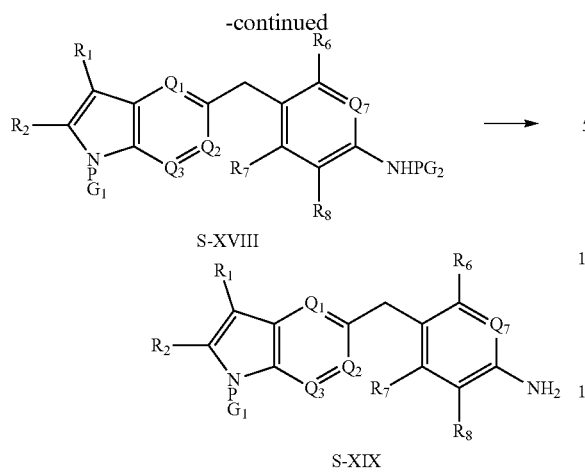

S-XVIII

S-XIX

As described in Scheme 5, a compound of Formula S-XX is obtained by coupling a compound of Formula S-VII with a bromide compound of Formula Int-II.

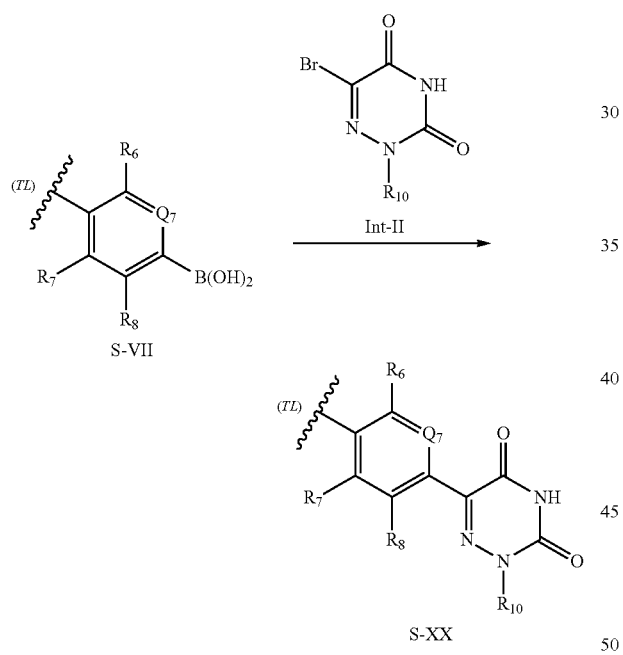

Scheme 5

S-VII

Int-II

S-XX used as the starting material instead of S-XXI. Alternatively, the indazole halogenide may undergo lithium-halogen exchange. The resulting aryl lithium species could react with an aldehyde of type S-XXVIII to form compounds of formula S-XXIX. Further elaboration of structures of formula S—XXIX are described in Scheme 7.

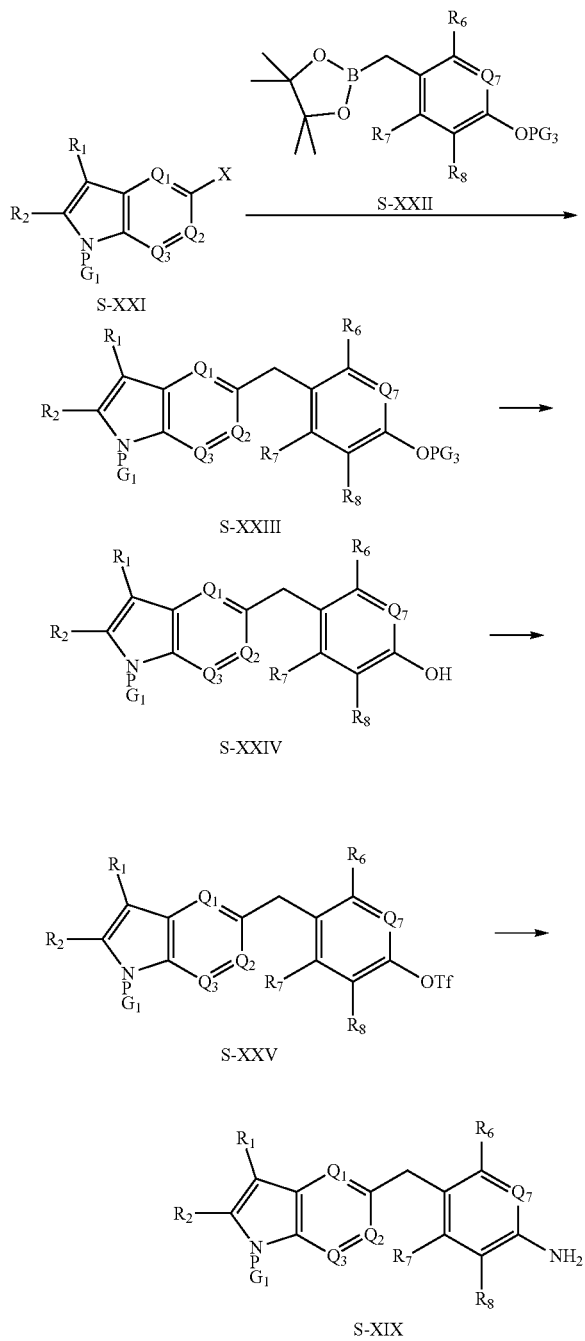

Scheme 6a

S-XXI

S-XXII

S-XXIII

S-XXIV

S-XXV

S-XIX

Scheme 6a depicts an alternative synthesis of the compounds of the general Formula S-XIX. A compound of Formula S-XXI (wherein the structure represents a halogen, e.g., $C_1$, Br or I) is coupled with a compound of Formula S-XXII in a Suzuki type coupling, resulting in the formation of a compound of Formula S-XXIII. The protecting group PG3, for example a benzyl moiety, can then be removed resulting in a compound of Formula S-XXIV. The resulting phenol functionality can then be replaced with a triflate group, resulting in a compound of general Formula S-XXV. The —OTf group can then be replaced with a —NH₂ moiety via a transition metal catalyzed reaction, such as a Buchwald coupling, for example with t-Butyl carbamate or benzophenone imine, followed by deprotection, resulting in a compound of general Formula S-XIX. The method described in Scheme 6a could also apply when an indazole halogenide is Scheme 6b depicts the synthesis of a compound of formula S—XXII from a compound of formula S-XXVI in a Suzuki reaction with 4,4,5,5-tetramethyl-2-[(4,4,5,5-tetramethyl-1,3,2-dioxaborolan-2-yl)methyl]-1,3,2-dioxaborolane.

Scheme 6b

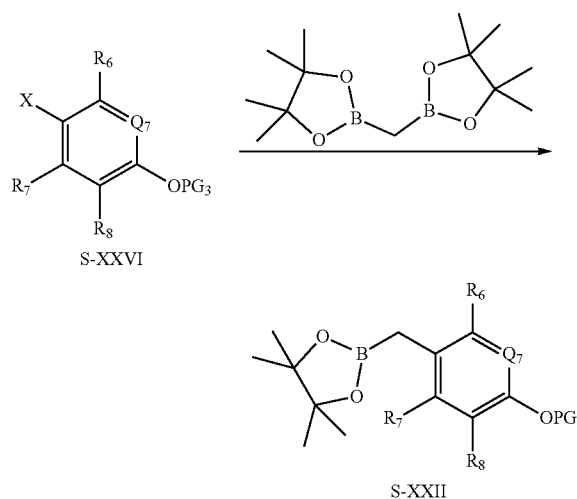

Scheme 7 describes the synthesis of a compound of Formula S-XXXI. A transmetalation reaction of a compound of Formula S-XXVII ('X' in the structure represents a halogen, e.g., Br or I) is followed by an addition to the aldehyde of general formula S-XXVIII affording the alcohol compound of Formula S-XXIX, which is then reduced to a compound of Formula S-XXX. Deprotection of PG2 of the compound of Formula S-XXX results in the formation of a compound of Formula S-XXXI.

Scheme 7

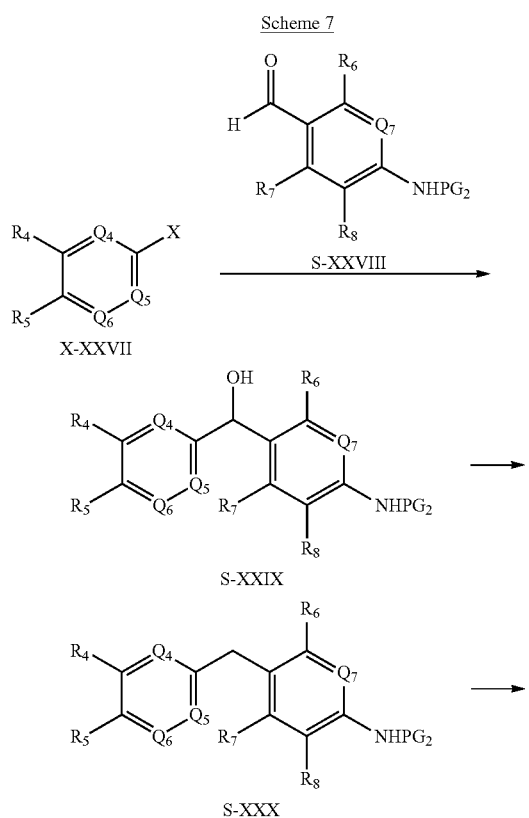

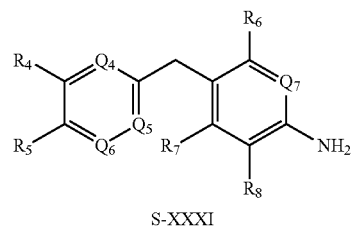

Scheme 8 describes the general synthesis of compounds of Formula S-XXI and products thereof. When $R_1$, for example, is hydrogen, and Y is hydrogen, then $R_1$ can be transformed to the corresponding acyl group via the acid chloride and a Lewis acid (e.g. $InBr_3$) in a non-polar, aprotic solvent (e.g. dichloroethane). The newly formed ketone group can be partially reduced to the alcohol or fully reduced to the corresponding alkane. Further transformations of a ketone group are evident to those skilled in the art. In a second example, where $R_1$ is hydrogen, and Y is an appropriate protecting group (e.g. tosyl) then $R_1$ can be converted to iodide via an iodinating agent (e.g. NIS) using available literature procedures.

Scheme 8

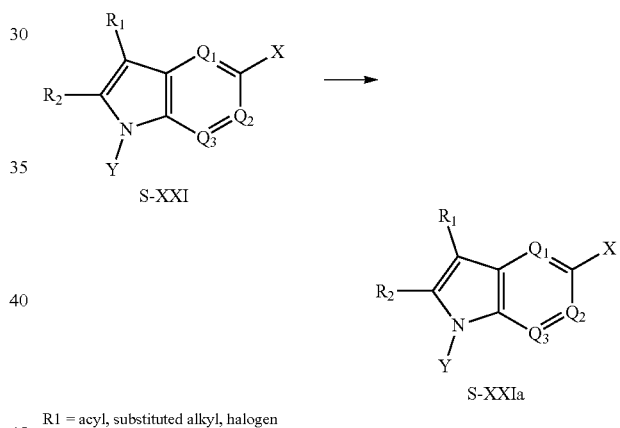

R1 = acyl, substituted alkyl, halogen

Scheme 9 describes the general synthesis of compounds of Formula S-XXXIII. 4-bromo-6-chloropyridazin-3-amine can be converted to the corresponding 4-aryl-6-chloro-pyridazin-3-amine (S-XXXII) using, for example, an ArB(OH)$_2$ (e.g. phenylboronic acid) and a palladium catalyst (e.g. $PdCl_2(PPh_3)_2$) in typical Suzuki-Miyaura conditions. Subsequent transformation of the amino group to a Cl via typical Sandmeyer reaction conditions (e.g. $CuCl_2$, t-Bu-ONO, acetonitrile, heat) affords compounds of type S-XXXIII.

Scheme 9

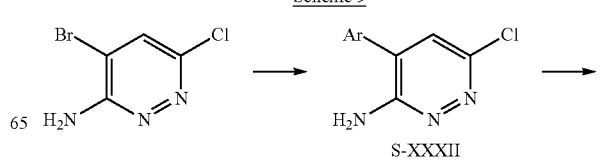

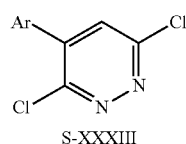

S-XXXIII

Scheme 10 describes the general synthesis of compounds of Formula S-XXXVI. Compounds of formula S-XXXIV may be coupled with the phenol HO-CE-HD under a Cu(I) mediated coupling reaction in DMSO with base (e.g. $K_2CO_3$) at elevated temperature to afford intermediates of type S-XXXV. Subsequent hydrolysis of the chloropyridazine via acetic acid and an acetate salt (e.g. NaOAc) affords products of formula S-XXXVI where the desired regioisomer can be isolated. In the context of scheme 10, the group HD may contain a general protecting group that can be cleaved at the stage of the intermediates S-XXXV or at the end of the synthesis to afford compounds of formula S-XXXVI.

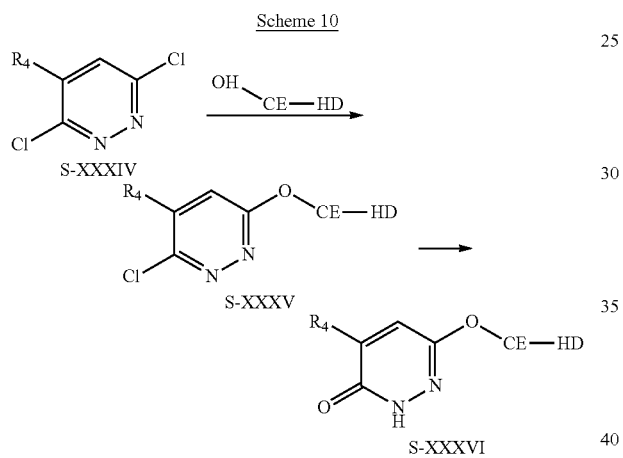

The synthesis of compounds of formula S-XXXVII can be performed using literature procedures. For example, an alkynylester can be combined with a protected aniline using a Ru catalyst under the conditions described in Org. Lett. 2014, 16, 3568-3571 to afford 6-bromoquinolones. Alternatively, the compounds of formula S-XXXVII can be formed by other procedures reported in the literature, including but not limited to the following examples: (a) Kadnikov, D. V.; et al. J. Org. Chem. 2004, 69, 6772. (b) Manley, P. J.; et al. Org. Lett. 2004, 6, 2433. (c) Jia, C.; Piao, D.; et al. J. Org. Chem. 2000, 65, 7516. (d) Inamoto, K.; et al. J. Org. Chem. 2010, 75, 3900. (e) Ferguson, J.; et al. Org. Lett. 2013, 15, 1998. (f) Fan, H; Org. Lett. 2018, 20, 7929-7932.

Alternatively, Scheme 11 depicts the synthesis of compounds of formula S-XXXVII that can be made starting from a dihalogenated aminoaryl (S-XXXVII-a). The amine is then protected (e.g. trimethylacetamide) to afford an amide intermediate (S-XXXVII-b). Under strongly basic conditions (e.g. n-buLi, TIF) S-XXXVII-b reacts with an aldehyde containing the desired Rg substitution to afford the alcohol product S-XXXVI-c, which is oxidized (via a common oxidizing agent; e.g. Dess-Martin reagent) in a subsequent step to afford the ketone S-XXXVII-d. The ketone undergoes an aldol type reaction with a protected ester (e.g. t-butyl) to afford intermediate S-XXXVII-e. In the final step, an intramolecular cyclization can occur to afford the compounds of formula S-XXXVII.

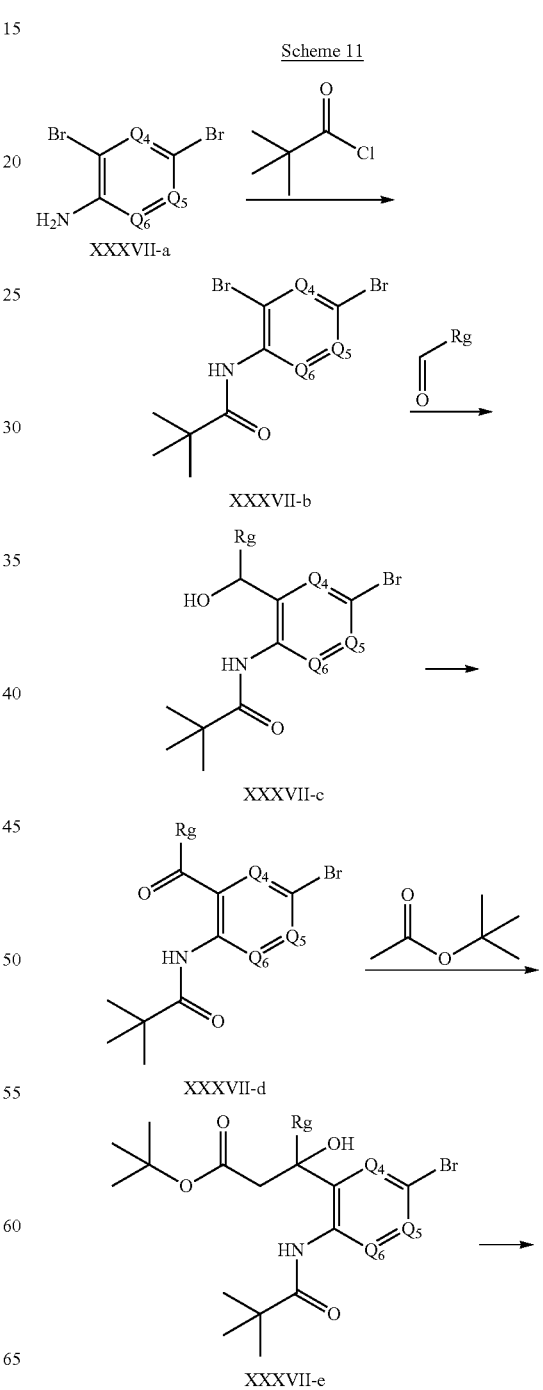

-continued

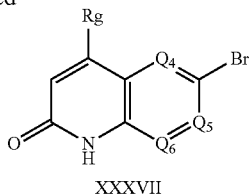

XXXVII

Incorporation of the compounds of formula S-XXXVII to form final products can occur using analogous methods as described in Schemes 6a and 6b.

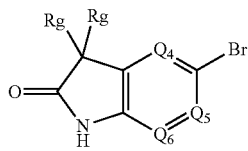

S-XXXVIII

Several methods exist to access compounds of formula XXXVIII and they include but are not limited to the methods found in the following references or referenced therein: (a) Hajra, S; et al. Org. Lett. 2018, 20, 4540-4544. (b) Zaytsev, S. et al. Journal of Organic Chemistry (2018), 83(15), 8695-8709. (c) Wu, C; et al. Organic Letters (2014), 16(7), 1960-1963. (d) Ye, N; et al. ACS Infect Dis. 2016, 2(6), 382-392. Incorporation of the compounds of formula S—XXXVIII to form final products can occur using analogous methods as described in Schemes 6a and 6b.

As described in Scheme 12, a compound of Formula S-XXXIX is obtained by coupling a compound of Formula S-VII with an azauracil compound of Formula Int-A. The benzyloxymethyl acetal can then be deprotected using a variety of methods described in the literature.

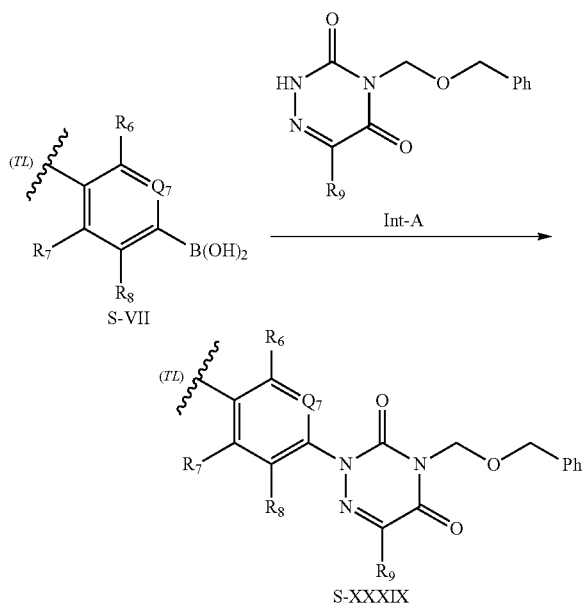

Scheme 12

Pharmaceutical Compositions

In another aspect, disclosed herein are pharmaceutical compositions comprising, consisting essentially of, or consisting of a compound as described herein, and at least one pharmaceutically acceptable excipient.

In another aspect, disclosed herein are pharmaceutical compositions comprising a compound of Formula I, as described herein, and a pharmaceutically acceptable diluent, excipient, or carrier. In some embodiments, disclosed herein are pharmaceutical compositions comprising, consisting essentially of, or consisting of a compound of Formula I, as described herein, and at least one pharmaceutically acceptable diluent, excipient, or carrier.

In another aspect, disclosed herein are pharmaceutical compositions comprising, consisting essentially of, or consisting of a compound of Formula I', as described herein, and at least one pharmaceutically acceptable excipient.

The pharmaceutical composition disclosed herein may comprise a pharmaceutically acceptable carrier, such as diluents, disintegrants, sweetening agents, glidants, or flavoring agents and may be formulated into an oral dosage form such as tablets, capsules, powders, granules, suspensions, emulsions, or syrups; or a parenteral dosage form such as liquids for external use, suspensions for external use, emulsions for external use, gels (ointments or the like), inhaling agents, spraying agents, injections, etc. Said dosage forms may be formulated in various forms, e.g., a dosage form for single administration or for multiple administrations.

The pharmaceutical composition disclosed herein may include excipients such as lactose, corn starch, or the like, glidants such as magnesium stearate, etc., emulsifying agents, suspending agents, stabilizers, and isotonic agents, etc. If desired, a sweetening agent and/or a flavoring agent may be added. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Inorganic salt or buffers include, but are not limited to, citric acid, sodium chloride, potassium chloride, sodium sulfate, potassium nitrate, sodium phosphate monobasic, sodium phosphate dibasic, and combinations thereof.

Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition disclosed herein may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, transdermal, rectal, transmucosal, or intestinal administration; parenteral delivery, including intramuscular, subcutaneous, intravenous, intramedullary injections, as well as inhalation, intrathecal, direct intraventricular, intraperitoneal, intranasal, or intraocular injections.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. These pharmaceutical compositions, then, may be formulated in a conventional manner using one or more known physiologically acceptable carriers comprising excipients and/or auxiliaries, which facilitate processing of the active compounds into preparations that can be used pharmaceutically. Any of the well-known techniques, carriers, and excipients may be used as suitable and as understood in the art; e.g., in Remington's Pharmaceutical Sciences, above.

Pharmaceutical compositions suitable for use in the presently disclosed formulations include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. In some embodiments, a therapeutically effective amount means an amount of compound effective to alleviate or ameliorate symptoms of disease or prolong the survival of the subject being treated.

Although the exact dosage can be determined on a drug-by-drug basis, in most cases, some generalizations regarding the dosage can be made. The daily dosage regimen for an adult human patient may be, for example, an oral dose of between 0.001 mg and 1000 mg of each ingredient, preferably between 0.01 mg and 500 mg, for example 1 to 200 mg or each active ingredient of the pharmaceutical compositions disclosed herein or a pharmaceutically acceptable salt thereof calculated as the free base or free acid, the composition being administered 1 to 4 times per day or per week. Alternatively, the compositions disclosed herein may be administered by continuous such as sustained, delayed, or extended release, preferably at a dose of each ingredient up to 500 mg per day. Thus, the total daily dosage by oral administration of each ingredient will typically be in the range 0.1 mg to 2000 mg.

Methods of Treatment

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a compound as described herein.

In another aspect, disclosed herein are methods of treating a thyroid hormone receptor related disorder in a patient, the method comprising the steps of identifying a patient in need of treatment for the thyroid hormone receptor related disorder, and administering to the patient, or contacting the patient with, a compound of Formula I, as described herein. In some embodiments, the method of treating a thyroid hormone receptor related disorder in a patient consists essentially of or consists of the steps of identifying a patient in need of treatment for the thyroid hormone receptor related disorder, and administering to the patient, or contacting the patient with, a compound of Formula I, as described herein.

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a compound of Formula I', as described herein.

In some embodiments, a health care professional, such as a physician, physician's assistant, nurse practitioner, or the like, identifies an individual as being in need of treatment for the thyroid hormone receptor related disorder, and/or a candidate for treatment with a compound disclosed herein. The identification may be based on medical test results, non-responsiveness to other, first-line therapies, the specific nature of the particular liver disorder, or the like.

In some embodiments, the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are methods of treating a disorder or disease in a subject in need thereof, the method comprising, consisting essentially of, or consisting of administering to the subject a therapeutically effective amount of a compound or composition disclosed herein, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are methods of treating NASH in a subject in need thereof, the method comprising, consisting essentially of, or consisting of administering to the subject a therapeutically effective amount of a compound or composition disclosed herein.

In another aspect, disclosed herein are methods of treating obesity in a subject in need thereof, the method comprising, consisting essentially of, or consisting of administering to the subject a therapeutically effective amount of a compound or composition disclosed herein.

In another aspect, disclosed herein are methods of treating hyperlipidemia in a subject in need thereof, the method comprising, consisting essentially of, or consisting of administering to the subject a therapeutically effective amount of a compound or composition disclosed herein.

In another aspect, disclosed herein are methods of treating hypercholesterolemia in a subject in need thereof, the method comprising, consisting essentially of, or consisting of administering to the subject a therapeutically effective amount of a compound or composition disclosed herein.

In another aspect, disclosed herein are methods of treating diabetes in a subject in need thereof, the method comprising, consisting essentially of, or consisting of administering to the subject a therapeutically effective amount of a compound or composition disclosed herein.

In another aspect, disclosed herein are methods of treating liver steatosis in a subject in need thereof, the method comprising, consisting essentially of, or consisting of administering to the subject a therapeutically effective amount of a compound or composition disclosed herein.

In another aspect, disclosed herein are methods of selectively modulating the activity of a thyroid hormone receptor beta (THR-β) comprising, consisting essentially of, or consisting of contacting a compound as described herein, with a thyroid hormone receptor. In some embodiments, the contacting is in vitro or ex vivo, whereas in other embodiments, the contacting is in vivo.

In another aspect, disclosed herein are methods of selectively modulating the activity of a thyroid hormone receptor beta (THR-β) comprising contacting a compound of Formula I, as described herein, with a thyroid hormone receptor. In some embodiments, the contacting is in vitro or ex vivo, whereas in other embodiments, the contacting is in vivo. In some embodiments, the method of selectively modulating the activity of a thyroid hormone receptor beta (THR-β) consists essentially of or consists of contacting a compound of Formula I, as described herein, with a thyroid hormone receptor.

In another aspect, disclosed herein are methods of selectively modulating the activity of a thyroid hormone receptor beta (THR-β) comprising, consisting essentially of, or consisting of contacting a compound of Formula I', as described herein, with a thyroid hormone receptor. In some embodiments, the contacting is in vitro or ex vivo, whereas in other embodiments, the contacting is in vivo.

In another aspect, disclosed herein are methods of selectively modulating the activity of a thyroid hormone receptor beta (THR-β) comprising, consisting essentially of, or consisting of contacting a composition described herein, with a thyroid hormone receptor. In some embodiments, the contacting is in vitro or ex vivo, whereas in other embodiments, the contacting is in vivo.

EXAMPLES

The following exemplify aspects of the present invention and is not limiting of its scope. Conditions for the preparation of several of the compounds disclosed herein are presented. Procedures for the synthesis of common intermediates are provided only once. The chemical names were generated using Marvin 17.28.0 or Chemdraw 18.1.

The following abbreviations are used in the present disclosure:

| Table of Abbreviations: | |
|---|---|
| Ac | Acetate |
| ACN | Acetonitrile |
| anhyd. | Anhydrous |
| aq. | Aqueous |
| Bu | Butyl |
| CAN | Ceric ammonium nitrate |
| conc. | Concentrated |
| DCM | Dichloromethane |
| DIPEA | N,N-Diisopropylethylamine |
| DMA | N,N-dimethylacetamide |
| DMF | N,N-Dimethylformamide |
| DMSO | Dimethyl sulfoxide |
| DPPA | Diphenylphosphoryl azide |
| dppf | 1,1'-Bis(diphenylphosphino)ferrocene |
| EA = EtOAc | Ethyl acetate |
| ECF | Ethyl chloroformate |
| Et | Ethyl |
| EtOH | Ethanol |
| FA | Formic acid |
| g | Gram(s) |
| h | Hour(s) |
| Me | Methyl |
| MeOH | Methanol |
| min | Minute(s) |
| NIS | N-Iodosuccinimide |
| PE | Petroleum ether |
| rt | Room temperature |
| sat. | Saturated |
| Selectfluor ™ | 1-Chloromethyl-4-fluoro-1,4-diazoniabicyclo[2.2.2]octane bis(tetrafluoroborate) |
| TBAF | Tetra-n-butylammonium fluoride |
| TBSCL | t-Butyldimethylsilyl chloride |
| TFA | Trifluoroacetic acid |
| THF | Tetrahydrofuran |

Synthesis of Building Blocks

1. Synthesis of 3-isopropyl-1H-indol-5-ol

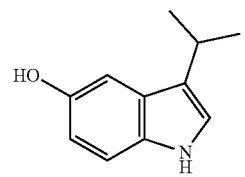

To a stirred mixture of (4-methoxyphenyl)hydrazine (10.00 g, 72.375 mmol, 1.0 eq) in 100 mL of AcOH was added isovaleraldehyde (6.23 g, 0.072 mmol, 1 eq) dropwise at 80° C. The resulting mixture was stirred for 2 h at 120° C. The resulting mixture was concentrated under vacuum. The resulting mixture was extracted with EA (3×100 mL). The combined organic layers were washed with brine (1×100 mL), dried over anhydr. Na$_2$SO$_4$. After filtration, the filtrate was concentrated under reduced pressure. The residue was purified by silica gel column chromatography to afford 3-isopropyl-5-methoxy-1H-indole (2.6 g, 19%) as a brown solid.

To a solution of 3-isopropyl-5-methoxy-1H-indole (9.03 g, 47.713 mmol, 1.0 eq) in DCM (100.00 mL) was added boron tribromide (35.88 g, 143.217 mmol, 3 eq) dropwise for 1 h at −78° C. The resulting mixture was stirred for additional 3 h at rt. The reaction was quenched by the addition of H₂O at 0° C. The resulting mixture was extracted with EA. The combined organic layers were washed with brine, dried over anhydrous Na₂SO₄. After filtration, the filtrate was concentrated under reduced pressure. The residue was purified by silica gel column chromatography to afford 3-isopropyl-1H-indol-5-ol (5.86 g, 56%) as a black oil.

2a. Synthesis of 5-bromo-3-isopropyl-1H-indole

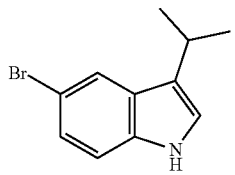

To a stirred solution of 4-bromophenyl-hydrazine (50.00 g, 267.32 mmol, 1.00 eq) in AcOH (500 mL) was added isovaleraldehyde (23.03 g, 267.37 mmol, 1.00 eq) dropwise at 80° C. The resulting mixture was stirred for 3 h at 120° C. The resulting mixture was concentrated under vacuum. The resulting mixture was extracted with EA (3×500 mL). The combined organic layers were washed with brine (1×300 mL), dried over anhydrous Na₂SO₄. After filtration, the filtrate was concentrated under reduced pressure. The residue was purified by silica gel column chromatography to afford 5-bromo-3-isopropyl-1H-indole (28 g, 44%) as a brown solid.

2b. Synthesis of 5-bromo-3-isopropyl-1-(p-tolylsulfonyl)pyrrolo[3,2-b]pyridine

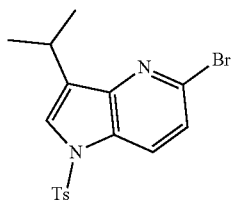 [SMILES: Cc1ccc(S(=O)(=O)n2cc(C(C)C)c3nc(Br)ccc32)cc1]

To a stirred solution of 5-bromo-3-isopropyl-1H-pyrrolo[3,2-b]pyridine (2.0 g, 8.36 mmol, 1 eq), DMAP (20.44 mg, 167.29 μmol, 0.02 eq) and DIPEA (2.38 g, 18.40 mmol, 2.2 eq) in DCM (60 mL) was added TosCl (1.91 g, 10.04 mmol, 1.2 eq) at 20° C. Then the resulting mixture was stirred at 20° C. for 12 h. TLC (Petroleum ether/Ethyl acetate=5/1, UV) showed the starting material was consumed completely. The mixture was diluted with H₂O (100 mL) and extracted with DCM (100 mL×3). The combined organic layers were washed with brine (200 mL), dried over anhydrous Na₂SO₄, filtered and concentrated to give a residue. The residue was purified by flash silica gel chromatography (Ethyl acetate in Petroleum ether=0~10%) to give 5-bromo-3-isopropyl-1-(p-tolylsulfonyl)pyrrolo[3,2-b]pyridine (2.6 g, 5.61 mmol, 67.0% yield) as an off-white solid.

2c. Synthesis of 5-bromo-3-pentyl-1H-indazole

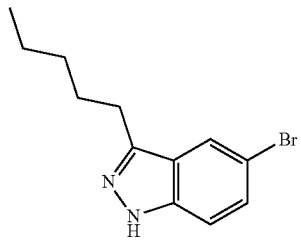

To a solution of 5-bromo-2-fluoro-benzaldehyde (25 g, 123.15 mmol, 1 eq) in THF (100 mL) was added bromo (pentyl)magnesium (1 M, 184.73 mL, 1.5 eq) at 0° C. The mixture was stirred at 20° C. for 1 hr. The reaction mixture was quenched by addition sat. aq. NH₄C₁ (50 mL) at 0° C., and then diluted with H₂O (50 mL) and extracted with EA (100 mL*2). The combined organic layers were washed with brine (50 mL), dried over anhydrous Na₂SO₄, filtered and concentrated under reduced pressure to give a residue, which was purified by flash silica gel chromatography (Eluent of 0-30% Ethyl acetate/Petroleum ether) to give 1-(5-bromo-2-fluoro-phenyl)hexan-1-ol (9.5 g, 34.53 mmol, 28% yield) as colorless oil.

To a solution of 1-(5-bromo-2-fluoro-phenyl)hexan-1-ol (9.5 g, 34.53 mmol, 1 eq) in DCM (100 mL) was added 4A MS (10 g) and PDC (25.98 g, 69.05 mmol, 2 eq) at 20° C. The mixture was stirred at 20° C. for 12 h. The mixture was filtered and concentrated under reduced pressure to give a residue, which was purified by flash silica gel chromatography (Eluent of 0~30% Ethyl acetate/Petroleum ether) to give 1-(5-bromo-2-fluoro-phenyl)hexan-1-one (8.2 g, 30.02 mmol, 87% yield) as a pale yellow solid.

To a solution of 1-(5-bromo-2-fluoro-phenyl)hexan-1-one (5 g, 18.31 mmol, 1 eq) in NMP (2 mL) was added hydrazine hydrate (2.16 g, 36.61 mmol, 2.09 mL, 85% purity, 2 eq) at 20° C. The mixture was stirred at 100° C. for 12 h. The reaction mixture was added to ice water (50 mL) and extracted with EA (50 mL*2). The combined organic layers were washed with brine (10 mL), dried over anhydrous Na₂SO₄, filtered and concentrated under reduced pressure to give a residue, which was purified by flash silica gel chromatography (Eluent of 0~20% Ethyl acetate/Petroleum ether) to give 5-bromo-3-pentyl-1H-indazole (2 g, 7.49 mmol, 41% yield) as a white solid.

3. Synthesis of 3-isopropyl-1-(4-methylbenzenesulfonyl)indole-5-carbaldehyde

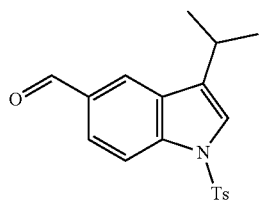 [SMILES: Cc1ccc(S(=O)(=O)n2cc(C(C)C)c3cc(C=O)ccc32)cc1]

To a stirred solution of 5-bromo-3-isopropyl-1H-indole (3.0 g, 12.6 mmol, 1.00 eq) in toluene (50 mL) was added Bu₄NHSO₄ (0.43 g, 1.27 mmol, 0.10 eq) in portions at 0° C. TsCl (2.90 g, 15.26 mmol, 1.2 eq) was added dropwise at 0°

C. The resulting mixture was stirred overnight at rt. The resulting mixture was concentrated under vacuum. The resulting mixture was extracted with EA (3×100 mL). The combined organic layers were washed with brine (1×200 mL), dried over anhydrous Na$_2$SO$_4$. After filtration, the filtrate was concentrated under reduced pressure. The residue was purified by silica gel column chromatography to afford 5-bromo-3-isopropyl-1-(4-methylbenzenesulfonyl) indole (4.0 g, 67%) as a light yellow solid.

To a stirred solution of 5-bromo-3-isopropyl-1-(4-methylbenzene-sulfonyl)indole (4 g, 10.2 mmol, 1.00 eq) in THF were added n-BuLi (31.2 ml, 51.0 mmol, 5.0 eq, 1.6 M in hexane) dropwise at −78° C. under nitrogen atmosphere. The resulting mixture was stirred for 40 min at −78° C. under nitrogen atmosphere. DMF (3.70 g, 0.051 mmol, 5.0 eq) was added at −78° C. under nitrogen atmosphere. The resulting mixture was stirred for 1.5 h at −78° C. under nitrogen atmosphere. The reaction was quenched with water (50 mL). The resulting mixture was extracted with EA (3×100 mL). The combined organic layers were washed with brine (1×200 mL), dried over anhydrous Na$_2$SO$_4$. After filtration, the filtrate was concentrated under reduced pressure. The residue was purified by silica gel column chromatography to afford 3-isopropyl-1-(4-methylbenzenesulfonyl)indole-5-carbaldehyde (1.1 g, 31%) as a light yellow oil.

4. Synthesis of 4-[(benzyloxy)methyl]-6-bromo-2H-1,2,4-triazine-3,5-dione

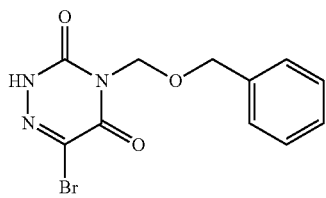 [SMILES: O=c1[nH]nc(Br)c(=O)n1COCc1ccccc1]

6-bromo-2,4-dihydro-1,2,4-triazine-3,5-dione (10.00 g, 52.091 mmol, 1.00 eq) was placed in acetic anhydride (50 mL) under reflux (140° C.) for 5 h. After dry concentration of the reaction medium, a precipitate is isolated and then recrystallized from ether to get the desired product. The desired product was isolated as a light yellow solid (11.6 g, 95% pure, 90% yield). NaH (2.19 g, 54.755 mmol, 1.10 eq, 60%) was placed in DMF (50 mL) under nitrogen. A solution of 2-acetyl-6-bromo-4H-1,2,4-triazine-3,5-dione (11.60 g, 49.571 mmol, 1.0 eq) in DMF (150 mL) was poured dropwise. The reaction medium was stirred for 1 h at rt and then [(chloromethoxy)methyl]benzene (8.54 g, 54.53 mmol, 1.1 eq) was added and stirred then continues for 18 h at rt. After dry concentration the obtained residue was taken up with H$_2$O (200 mL) and extracted with ethyl acetate (EA) (3×500 mL). After drying on Na$_2$SO$_4$, the organic phase are evaporated and the obtained clear oil was purified and 15 g of crystals were isolated. Crystals were placed in EtOH (400 mL) in the presence of TsOH (100.0 mg, 0.581 mmol, 0.01 eq). This mixture was heated with reflux for 4 h and then dry concentrated. The residue was taken up with H$_2$O and then extracted with EA. After drying and evaporation of the organic phases, the desired product was obtained as a yellow oil (9.5 g, yellow oil, 90% pure, 61% yield).

5a. Synthesis of 6-bromo-2-methyl-4H-1,2,4-triazine-3,5-dione

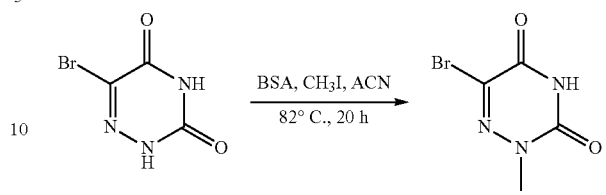

To a stirred solution of 6-bromo-2,4-dihydro-1,2,4-triazine-3,5-dione (200.0 mg, 1.04 mmol, 1.0 eq) in ACN (5 mL) were added BSA (529.8 mg, 2.61 mmol, 2.5 eq) dropwise at 0° C. under argon atmosphere. The resulting mixture was stirred for 3 h at 82° C. under argon atmosphere, and then added CH$_3$I (251.4 mg, 1.77 mmol, 1.7 eq) dropwise at 82° C., continued stirred 20 h at 82° C. The mixture was allowed to cool down to rt, concentrated under reduced pressure, and then dissolved in DCM, washed with water and brine, dried over anhydrous Na$_2$SO$_4$. After filtration, the filtrate was concentrated under reduced pressure. The residue was purified by silica gel column chromatography to afford 6-bromo-2-methyl-4H-1,2,4-triazine-3,5-dione (870 mg, 69%) as a yellow solid.

5b. Synthesis of 6-bromo-2-ethyl-4H-1,2,4-triazine-3,5-dione 6-bromo-2-ethyl-4H-1,2,4-triazine-3,5-dione was prepared similarly as described for 6-bromo-2-methyl-4H-1,2,4-triazine-3,5-dione using 2.5 eq of iodoethane instead of 1.7 eq CH$_3$I.

6. Synthesis of 5-(2,6-dichloro-4-nitrophenoxy)-3-isopropyl-1H-indole

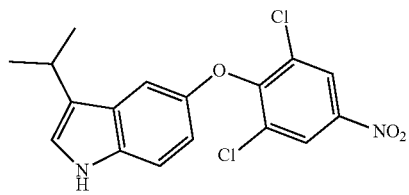 [SMILES: CC(C)c1c[nH]c2ccc(Oc3c(Cl)cc([N+](=O)[O-])cc3Cl)cc12]

To a stirred solution of 3-isopropyl-1H-indol-5-ol (1.00 g, 5.71 mmol, 1.00 eq) in THF was added tert-butoxypotassium (0.64 g, 5.70 mmol, 1.0 eq) dropwise at 0° C. The resulting mixture was stirred for 30 min at rt. After completion of reaction, the resulting mixture was concentrated under vacuum and re-dissolved by DMF. The second reaction flask: To a stirred solution of 1,2,3-trichloro-5-nitrobenzene (1.29 g, 5.70 mmol, 1.0 eq) in DMF was added the first reaction flask at 0° C. The resulting mixture was stirred for 5 min at 0° C., and then warmed to 100° C. and stirred for 1 h. The resulting mixture was extracted with EA. The combined organic layers were washed with brine and dried over anhydrous Na$_2$SO$_4$. The residue was purified by silica gel column chromatography to afford 5-(2,6-dichloro-4-nitrophenoxy)-3-isopropyl-1H-indole (1.3 g, 55%) as a yellow solid.

7. Synthesis of 5-(2,6-dimethyl-4-nitrophenoxy)-3-isopropyl-1H-indole

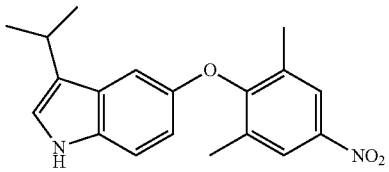 [SMILES: Cc1cc([N+](=O)[O-])cc(C)c1Oc1ccc2[nH]cc(C(C)C)c2c1]

To a stirred mixture of 3-isopropyl-1H-indol-5-ol (5.10 g, 29.10 mmol, 1.0 eq) in 50 mL of DMSO were added $K_2CO_3$ (4.42 g, 32.0 mmol, 1.1 eq) and 2-fluoro-1,3-dimethyl-5-nitrobenzene (4.92 g, 29.1 mmol, 1.0 eq) in portions at rt. The resulting mixture was stirred for 2 h at 100° C. The resulting mixture was extracted with EA (3×100 mL). The combined organic layers were washed with brine (3×50 mL), dried over anhydrous $Na_2SO_4$. After filtration, the filtrate was concentrated under reduced pressure. The residue was purified by silica gel column chromatography to afford 5-(2,6-dimethyl-4-nitrophenoxy)-3-isopropyl-1H-indole (6 g, 64%) as a light yellow solid.

8. Synthesis of 5-(2,6-dichloro-4-nitrophenoxy)-1H-indole

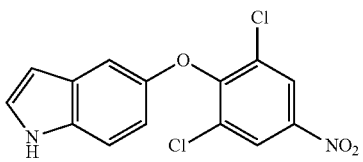 [SMILES: O=[N+]([O-])c1cc(Cl)c(Oc2ccc3[nH]ccc3c2)c(Cl)c1]

To a solution of 5-hydroxyindol (16.0 g, 120.2 mmol, 1.0 eq) in acetonitrile (320 mL) was added potassium tert-butoxide (13.48 g, 120.2 mmol, 1.0 eq) at 0° C. After 20 mins, the mixture was concentrated to remove acetonitrile and dissolved in N,N-dimethylformamide (320 mL). Then 1,2,3-trichloro-5-nitrobenzene (27.21 g, 120.2 mmol, 1.00 eq) was added at 0° C. The resulting solution was stirred at 100° C. overnight and then quenched with water (300 mL). The resulting solution was extracted with ethyl acetate (3×500 mL) and the organic layers were combined, washed with brine (2×300 mL), dried over anhydrous sodium sulfate, filtered and concentrated under reduced pressure. The residue was purified to provide 28 g (68% yield) of 5-(2,6-dichloro-4-nitrophenoxy)-1H-indole as yellow solid.

9. Synthesis of 5-dichloro-4-[[3-isopropyl-1-(4-methy-lbenzenesu-lfonyl)indol-5-yl]oxy]aniline

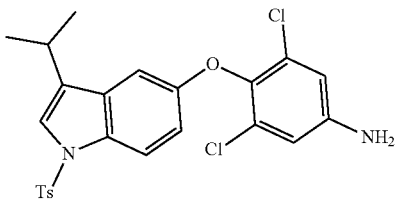 [SMILES: Cc1ccc(S(=O)(=O)n2cc(C(C)C)c3cc(Oc4c(Cl)cc(N)cc4Cl)ccc32)cc1]

To a stirred solution of 5-(2,6-dichloro-4-nitrophenoxy)-3-isopropyl-1H-indole (1.29 g, 3.532 mmol, 1.0 eq) in toluene (50.00 mL) was added TsCl (0.81 g, 4.239 mmol, 1.2 eq) in toluene (10 mL), KOH (50%) (21.4 mL), $Bu_4NHSO_4$ (0.12 g, 0.353 mmol, 0.1 eq) dropwise at 0° C. The resulting mixture was stirred for 6 h at rt. After completion of reaction, the resulting mixture was extracted with EA (3×50 mL). The combined organic layers were washed with brine, dried over anhydrous $Na_2SO_4$. After filtration, the filtrate was concentrated under reduced pressure. The residue was purified by silica gel column chromatography to afford 5-(2,6-dichloro-4-nitrophenoxy)-3-isopropyl-1-(4-methyl-benzenesulfonyl)indole (1.40 g, 75%) as a yellow solid.

To a stirred solution of 5-(2,6-dichloro-4-nitrophenoxy)-3-isopropyl-1-(4-methylben-zenesul-fonyl)indole (1.40 g, 2.73 mmol, 1.0 eq) and $NH_4Cl$ (1.16 g, 21.62 mmol, 8.0 eq) in EtOH (50 mL) and $H_2O$ (25 mL) was added Fe powder (0.75 g, 13.514 mmol, 5.00 eq) in portions at rt under nitrogen atmosphere. The resulting mixture was stirred for 2 h at 50° C. under nitrogen atmosphere. The resulting mixture was filtered, the filter cake was washed with EA. The filtrate was concentrated under reduced pressure. The aqueous layer was extracted with EA, dried over anhydrous $Na_2SO_4$. After filtration, the filtrate was concentrated under reduced pressure. The residue was purified by silica gel column chromatography to afford 3,5-dichloro-4-[[3-isopropyl-1-(4-methy-lbenzenesulfonyl)-indol-5-yl]oxy]aniline (1.11 g, 78%) as a white solid.

10. Synthesis of 4-[[3-isopropyl-1-(4-methylbenzene-sulfonyl)indol-5-yl]oxy]-3,5-dimethylaniline

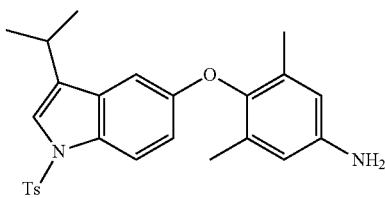 [SMILES: Cc1ccc(S(=O)(=O)n2cc(C(C)C)c3cc(Oc4c(C)cc(N)cc4C)ccc32)cc1]

To a stirred mixture of 5-(2,6-dimethyl-4-nitrophenoxy)-3-isopropyl-1H-indole (5.00 g, 15.414 mmol, 1.00 eq) in 50 mL of toluene were added TsCl (3.53 g, 0.018 mmol, 1.2 eq), $Bu_4NHSO_4$ (0.52 g, 0.002 mmol, 0.1 eq), KOH (50 mL) (50 mmol, 0.1 eq) dropwise at 0° C. The mixture was stirred overnight at rt and quenched with water (50 mL). The resulting mixture was extracted with EA (3×200 mL). The combined organic layers were washed with brine (1×100 mL), dried over anhydrous $Na_2SO_4$. After filtration, the filtrate was concentrated under reduced pressure. The residue was purified by silica gel column chromatography in hexane to afford 5-(2,6-dimethyl-4-nitrophenoxy)-3-isopropyl-1-(4-methylbenzenesulfonyl)indole (5.8 g, 79%) as a light yellow solid.

To a stirred mixture of 5-(2,6-dimethyl-4-nitrophenoxy)-3-isopropyl-1-(4-methylbenzene-sulfonyl)indole (5.80 g, 12.120 mmol, 1.0 eq) in MeOH (70 mL) were added Pd/C (1.74 g) in portions. The resulting mixture was stirred overnight at rt under hydrogen atmosphere. The resulting mixture was filtered, the filter cake was washed with MeOH (1×500 mL). The filtrate was concentrated under reduced pressure to get a residue, which was purified by silica gel column chromatography to afford 4-[[3-isopropyl-1-(4- methylbenzene-sulfonyl)indol-5-yl]oxy]-3,5-dimethyl-aniline (3.2 g, 59%) as a light yellow solid.

11. Synthesis of 4-[[3-isopropyl-1-(4-methyl-benzenesulfonyl)indol-5-yl]methyl]-3,5-dimethylaniline

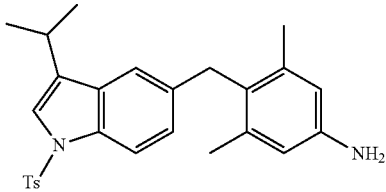

To a stirred solution of N-(4-bromo-3,5-dimethylphenyl)-2,2,2-trifluoro-acetamide (260.16 mg, 0.879 mmol, 1.0 eq) in THF (5 mL) under nitrogen was added MeLi—LiBr (1.7 mL, 1.76 mmol, 2.0 eq, 1 M in ether) at −78° C. Then t-BuLi (1.6 mL, 2.64 mmol, 3.00 eq, 1.6M in hexane) was added dropwise at −78° C. The mixture was stirred for 20 min at −78° C. 3-isopropyl-1-(4-methylbenzene-sulfonyl)indole-5-carbaldehyde (300 mg, 0.879 mmol, 1.0 eq) was added at −78° C. The resulting mixture was stirred for 1 h at rt. The reaction was quenched with water (10 mL) at rt. The resulting mixture was extracted with EA (3×50 mL). The combined organic layers were washed with brine (2×100 mL), dried over anhydrous $Na_2SO_4$. After filtration, the filtrate was concentrated under reduced pressure. The residue was purified to afford 2,2,2-trifluoro-N-(4-[hydroxy[3-isopropyl-1-(4-methyl-benzenesulfonyl)indol-5-yl]methyl]-3,5-dimethylphenyl)acetamide (300 mg, 61%) as a white solid.

A solution of 2,2,2-trifluoro-N-(4-[hydroxy[3-isopropyl-1-(4-methyl-benzenesulfonyl)indol-5-yl]methyl]-3,5-dimethylphenyl)acetamide (300.0 mg, 0.537 mmol, 1.00 eq) in DCM (5 mL) was stirred under nitrogen at 0° C. Then a solution of $Et_3SiH$ (374.7 mg, 3.22 mmol, 6.0 eq) in DCM (15 mL) and TMSOTf (7.16 mg, 0.032 mmol, 0.06 eq) in DCM (5 mL) was added dropwise to the reaction mixture. The reaction mixture was stirred for 30 min at 0° C. and 1.5 h at rt. The reaction mixture was quenched with saturated $NaHCO_3$ solution (20 mL). The resulting solution was extracted with dichloromethane (3×50 mL) and the organic layers were combined, washed with brine (2×30 mL), dried over anhydrous sodium sulfate, filtered and concentrated under reduced pressure to afford crude product. The crude product containing 2,2,2-trifluoro-N-(4-[[3-isopropyl-1-(4-methylbenzene-sulfonyl)indol-5-yl]methyl]-3,5-dimethylphenyl)acetamide was isolated as a yellow solid (260 mg, 85% pure, 76% yield).

To a solution of 2,2,2-trifluoro-N-(4-[[3-isopropyl-1-(4-methyl-benzenesulfonyl)indol-5-yl]methyl]-3,5-dimethylphenyl)acetamide (260.0 mg, 0.479 mmol, 1.0 eq) in MeOH (10 mL) and $H_2O$ (2 mL) stirred under nitrogen at rt was added NaOH (76.66 mg, 1.917 mmol, 4.0 eq). The reaction mixture was stirred at 60° C. overnight. The reaction mixture was quenched with water (20 mL). The resulting solution was extracted with dichloromethane (3×50 mL) and the organic layers were combined, washed with brine (2×30 mL), dried over anhydrous sodium sulfate, filtered and concentrated under reduced pressure to afford crude product. The crude product was isolated as a yellow solid containing 4-[[3-isopropyl-1-(4-methyl-benzenesulfonyl)indol-5-yl]methyl]-3,5-dimethylaniline (230 mg, 90% pure, 97% yield).

12. Synthesis of 3,5-dichloro-4-[[1-(4-methylbenzenesulfonyl)indol-5-yl]oxy]aniline

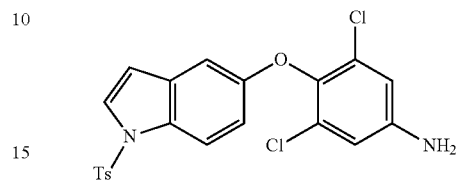

To a solution of 5-(2,6-dichloro-4-nitrophenoxy)-1H-indole (28.0 g, 86.65 mmol, 1.0 eq) in toluene (720 mL) was added tetrabutylammonium hydrogen sulfate (2.94 g, 8.665 mmol, 0.10 eq) and potassium hydroxide (120.00 g, 2138.8 mmol, 25.0 eq) in water (120 mL) at 0° C. 4-Toluene sulfonyl chloride (19.82 g, 103.98 mmol, 1.20 eq) in toluene (720 mL) was added dropwise at 0° C. Then the reaction was stirred at rt for 3 h and quenched with water (200 mL). The mixture was extracted with ethyl acetate (3×500 mL) and the organic layers were combined, concentrated under reduced pressure. The residue was purified to provide 5-(2,6-dichloro-4-nitrophenoxy)-1-(4-methylbenzenesulfonyl)indole (34 g, 78% yield) as yellow solid.

To a solution of 5-(2,6-dichloro-4-nitrophenoxy)-1-(4-methylbenzene-sulfonyl)-indole (26.00 g, 54.47 mmol, 1.0 eq) in ethanol (500 mL) and water (250 mL) was added iron dust (15.21 g, 272.36 mmol, 5.0 eq) and ammonium chloride (23.31 g, 435.78 mmol, 8.0 eq). The resulting solution was stirred for 2 h at 50° C. The resulting mixture was filtered, the filter cake was washed with dichloromethane (6×100 mL). The filtrate was extracted with dichloromethane (3×500 mL). The combined organic layers were combined, washed with brine (300 mL), dried over anhydrous sodium sulfate and concentrated under reduced pressure to provide 3,5-dichloro-4-[[1-(4-methylbenzenesulfonyl)indol-5-yl]oxy]aniline (23 g, 88% yield) of as a light yellow solid.

13a. Synthesis of 6-(4-amino-2,6-dichlorophenoxy)-4-isopropyl-2H-pyridazin-3-one

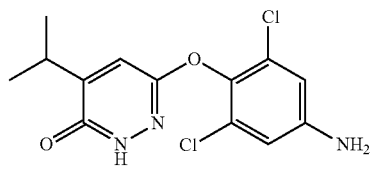

To a solution of 3,6-dichloropyridazine (50.00 g, 335.64 mmol, 1.0 eq) in $H_2O$ (1.20 L) was added $AgNO_3$ (57.02 g, 335.64 mmol, 1.0 eq), isobutyric acid (29.57 g, 335.64 mmol, 1.0 eq) in portions at rt under air atmosphere and then stirred at 50° C. under nitrogen atmosphere. $H_2SO_4$ (98.76 g, 1006.9 mmol, 3.0 eq) was added in portions at 50° C. and stirred at 60° C. Then $(NH_4)_2S_2O_8$ (229.78 g, 1006.914 mmol, 3.0 eq) was added and stirred for 30 min at 70° C. under nitrogen atmosphere. The mixture was neutralized to pH 9 with NaOH solution. The resulting mixture was extracted with EA (3×1 L). The combined organic layers were washed with brine (2×1 L), dried over anhydrous Na$_2$SO$_4$. After filtration, the filtrate was concentrated. The residue was purified by silica gel column chromatography to afford 3,6-dichloro-4-isopropylpyridazine (30 g, 47%) as a light yellow oil.

To a solution of 3,6-dichloro-4-isopropylpyridazine (20.00 g, 104.679 mmol, 1.0 eq) in DMSO (200 mL) were added phenol, 4-amino-2,6-dichloro- (18.63 g, 104.68 mmol, 1.0 eq), K$_2$CO$_3$ (58.16 g, 420.81 mmol, 4.02 eq) and CuI (11.96 g, 62.81 mmol, 0.60 eq) in portions. The resulting mixture was stirred overnight at 90° C. under nitrogen atmosphere. The mixture was acidified to pH 8 with conc. HCl. The resulting mixture was extracted with EA (3×500 mL). The combined organic layers were washed with brine (3×300 mL), dried over anhydrous Na$_2$SO$_4$. After filtration, the filtrate was concentrated. The residue was purified by silica gel column chromatography to afford 3,5-dichloro-4-[(6-chloro-5-isopropyl-pyridazin-3-yl)oxy]-aniline (17 g, 49%) as a green solid.

To a solution of 3,5-dichloro-4-[(6-chloro-5-isopropylpyridazin-3-yl)oxy]aniline (17.00 g, 51.111 mmol, 1.0 eq) in HOAc (200 mL) was added NaOAc (24.33 g, 178.89 mmol, 3.50 eq) in portions. The mixture was stirred overnight at 100° C. under nitrogen atmosphere. The mixture was added NaOH (12.27 g, 306.77 mmol, 6.0 eq), and MeOH (200 mL) in portions. The resulting mixture was stirred overnight at 120° C. under nitrogen atmosphere. The resulting mixture was extracted with EA (3×500 mL). The combined organic layers were washed with brine (2×200 mL), dried over anhydrous Na$_2$SO$_4$. After filtration, the filtrate was concentrated. The residue was purified by silica gel column chromatography to afford 6-(4-amino-2,6-dichlorophenoxy)-4-isopropyl-2H-pyridazin-3-one (11 g, 69%) as a off-white solid.

13b. Synthesis of 3,5-dichloro-4-[(5-isopropyl-6-methoxypyridazin-3-yl)oxy]aniline

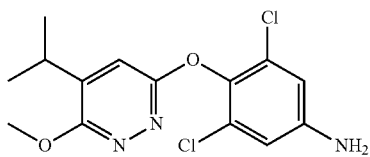 [SMILES: COc1nnc(Oc2c(Cl)cc(N)cc2Cl)cc1C(C)C]

A mixture of 3,6-dichloro-4-isopropylpyridazine (80.0 g, 419 mmol, 1.00 eq), 4-amino-2,6-dichlorophenol (74.5 g, 419 mmol, 1.0 eq), K$_2$CO$_3$ (232 g, 1675 mmol, 4.0 eq) and CuI (47.9 g, 251 mmol, 0.6 eq) in DMSO (800 mL) was stirred overnight at 60° C. After cooled down to 25° C., the solution was then poured onto ice water (3 L) and the pH of the mixture was adjusted to 8 with hydrochloric acid (3 N). The resulting mixture was extracted with EA (3×1 L). The combined organic layers were washed with brine (3×1 L), dried over anhydrous Na$_2$SO$_4$. After filtration, the filtrate was concentrated under reduced pressure. The residue was purified by silica gel column chromatography (eluting with petroleum ether to ethyl acetate ratio (PE:EA) of 5:1) to afford 3,5-dichloro-4-[(6-chloro-5-isopropylpyridazin-3-yl)oxy]aniline (35.0 g, 24% yield) as an off-white solid. LCMS (ESI, m/z): 332 [M+H]$^+$.

A mixture of 3,5-dichloro-4-[(6-chloro-5-isopropylpyridazin-3-yl)oxy]-aniline (10.0 g, 30.1 mmol, 1.00 eq) and potassium methoxide (21.1 g, 301 mmol, 10.0 eq) in MeOH (50 mL) was stirred for 48 h at 65° C. After cooled down to 25° C., the PH value of the mixture was adjusted to 6-7 with hydrochloric acid (1 N). The resulting mixture was extracted with EA (3×500 mL). The combined organic layers were dried over anhydrous Na$_2$SO$_4$, filtered and concentrated under reduced pressure. The residue was purified by silica gel column chromatography (eluting with PE:EA of 5:1) to afford 3,5-dichloro-4-[(5-isopropyl-6-methoxypyridazin-3-yl)oxy]aniline (6.80 g, 65% yield) as a white solid.

LCMS (ESI, m/z): 328 [M+H]$^+$.

14a. Synthesis of 3,5-dichloro-4-[(5-isopropyl-6-oxo-1H-pyridazin-3-yl)oxy]phenylboronic Acid

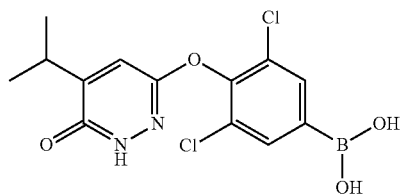

A 1000 mL round-bottom flask was charged with 6-(4-amino-2,6-dichlorophenoxy)-4-isopropyl-2H-pyridazin-3-one (14.13 g, 44.98 mmol, 1.0 eq) in MeOH (200 mL). HCl (4.10 mL, 112.439 mmol, 3 eq) was added dropwise at 0° C. H$_2$O (100 mL) was added at 0° C. The mixture was stirred for 10 min, then NaNO$_2$ (3.72 g, 53.971 mmol, 1.20 eq) was added, and was stirred for an additional 30 min at 0° C. Tetrahydroxydiborane (40.32 g, 449.749 mmol, 10.0 eq) was added. The reaction was stirred for 1 h at 60° C. The resulting solution was quenched with water (50 mL). The resulting solution was extracted with dichloromethane (3×400 mL) and the organic layers were combined, dried over anhydrous sodium sulfate, filtered and concentrated under reduced pressure. Purification resulted in 3,5-dichloro-4-[(5-isopropyl-6-oxo-1H-pyridazin-3-yl)oxy]phenylboronic acid (6.3 g, 37%) as a white solid.

14b. Synthesis of 3,5-dichloro-4-[(5-isopropyl-6-methoxypyridazin-3-yl)oxy]phenylboronic acid

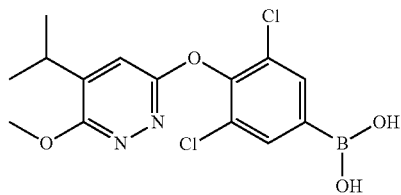 [SMILES: COc1nnc(Oc2c(Cl)cc(B(O)O)cc2Cl)cc1C(C)C]

To a stirred mixture of 3,5-dichloro-4-[(5-isopropyl-6-methoxy-pyridazin-3-yl)oxy]aniline (5.80 g, 17.7 mmol, 1.00 eq) and CuBr$_2$ (7.89 g, 35.3 mmol, 2.00 eq) in ACN (40 mL) were added tert-butyl nitrite (4.24 mL, 35.4 mmol, 2.0 eq) dropwise at 0° C. The resulting mixture was then warmed up to room temperature and stirred for an additional 3 h. The resulting mixture was concentrated under reduced pressure. The residue was purified by silica gel column chromatography (eluting with PE:EA of 10:1) to afford 6-(4-bromo-2,6-dichlorophenoxy)-4-isopropyl-3-methoxy-pyridazine (3.50 g, 48% yield) as a yellow solid.

LCMS (ESI, m/z): 391[M+H]$^+$.

A mixture of 6-(4-bromo-2,6-dichlorophenoxy)-4-isopropyl-3-methoxypyridazine (1.00 g, 2.55 mmol, 1.00 eq), bis(pinacolato)diboron (972 mg, 3.83 mmol, 1.50 eq), Pd(dppf)Cl$_2$ (187 mg, 0.256 mmol, 0.10 eq) and KOAc (750 mg, 7.64 mmol, 3.00 eq) in 1,4-dioxane (10 mL) was stirred for 2 h at 90° C. After cooled down to 25° C., the solids were filtered out and the filter cake was washed with EA (3×20 mL). The filtrate was concentrated under reduced pressure. The residue was purified by reverse phase chromatography (Column: C18 silica gel; Mobile phase, A: water (containing 0.5% TFA) and B: ACN (20% to 95% over 20 min) to afford 3,5-dichloro-4-[(5-isopropyl-6-methoxypyridazin-3-yl)oxy]phenylboronic acid (610 mg, 64% yield) as a brown solid.

LCMS (ESI, m/z): 359 [M+H]$^+$.

15. Synthesis of 2-(3,5-dichloro-4-[[3-iodo-1-(4-methylbenzenesulfonyl)-indol-5-yl]oxy]phenyl)-3,5-dioxo-4H-1,2,4-triazine-6-carbonitrile

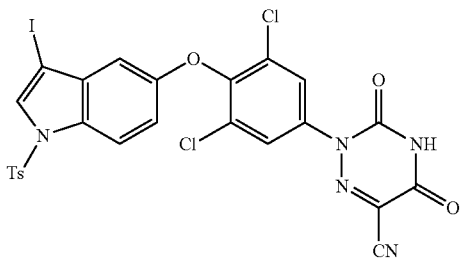 [SMILES: Cc1ccc(S(=O)(=O)n2cc(I)c3cc(Oc4c(Cl)cc(-n5nc(C#N)c(=O)[nH]c5=O)cc4Cl)ccc32)cc1]

To a solution of 3,5-dichloro-4-[[1-(4-methylbenzenesulfonyl)indol-5-yl]oxy]aniline (15.00 g, 33.532 mmol, 1.0 eq) in water (700 mL), concentrated hydrochloric acid (336 mL) and acetic acid (942 mL) was added sodium nitrite (4.86 g, 70.418 mmol, 2.1 eq) in water (50 mL) dropwise at 0° C. After the addition, the reaction was stirred at 0° C. for 45 min. Then the reaction mixture was poured into a solution of ethyl N-(2-cyanoacetyl)carbamate (7.85 g, 50.30 mmol, 1.5 eq) in water (600 mL) and pyridine (336 mL) at 0° C. quickly. The resulting mixture was stirred at 0° C. for 30 min and filtered. The filter cake was washed with water (100 mL) and petroleum ether (200 mL), dried under reduced pressure to provide ethyl (Z)-(2-cyano-2-(2-(3,5-dichloro-4-((1-tosyl-1H-indol-5-yl)oxy)phenyl)-hydrazineylidene)-acetyl)carbamate (18.4 g, 80% yield) as red solid.

To a solution of ethyl (Z)-(2-cyano-2-(2-(3,5-dichloro-4-((1-tosyl-1H-indol-5-yl)oxy)phenyl)hydrazineylidene)acetyl)carbamate (18.40 g, 29.95 mmol, 1.0 eq) in N,N-dimethylacetamide (300 mL) was added potassium acetate (11.76 g, 119.782 mmol, 4.0 eq). The reaction was stirred at 120° C. for 2 h and quenched with water (100 mL). The mixture was extracted with ethyl acetate (3×100 mL) and the organic layers were combined, washed with brine (100 mL), dried over anhydrous sodium sulfate and concentrated under reduced pressure. The residue was purified to provide 2-(3,5-dichloro-4-[[1-(4-methylbenzenesulfonyl)indol-5-yl]oxy]phenyl)-3,5-dioxo-4H-1,2,4-triazine-6-carbonitrile (14 g, 80% yield) as brown solid.

To a stirred solution of 2-(3,5-dichloro-4-[[1-(4-methylbenzene-sulfonyl)indol-5-yl]oxy]phenyl)-3,5-dioxo-4H-1,2,4-triazine-6-carbonitrile (7.0 g, 12.32 mmol, 1.0 eq) and p-toluenesulfonic acid (0.210 g, 1.232 mmol, 0.1 eq) in dichloromethane (300 mL) was added N-iodosuccinimide (4.16 g, 18.47 mmol, 1.5 eq) at 0° C. under nitrogen atmosphere. The reaction mixture was stirred for 6 h at 0° C. and quenched with water (200 mL). The resulting mixture was extracted with dichloromethane (3×200 mL) and the combined organic layers were combined, washed with saturated sodium thiosulfate solution (2×500 mL), dried over anhydrous sodium sulfate and concentrated under reduced pressure. The residue was purified to provide 2-(3,5-dichloro-4-[[3-iodo-1-(4-methylbenzene-sulfonyl)indol-5-yl]oxy]phenyl)-3,5-dioxo-4H-1,2,4-triazine-6-carbonitrile (5.30 g, 43% yield) as a brown solid.

16. Synthesis of 2-[3,5-dichloro-4-[(5-isopropyl-6-oxo-1H-pyridazin-3-yl)oxy]phenyl]-3,5-dioxo-4H-1,2,4-triazine-6-carbonitrile

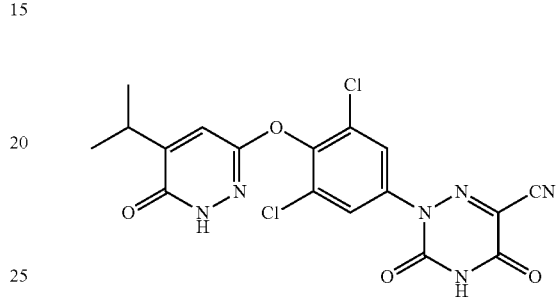

To a solution of 6-(4-amino-2,6-dichlorophenoxy)-4-isopropyl-2H-pyridazin-3-one (500 mg, 1.591 mmol, 1.0 eq) in HOAc (43.8 mL, 764.03 mmol) and HCl (15.3 mL, 503.55 mmol) were added NaNO$_2$ (230.59 mg, 3.34 mmol, 2.1 eq) in H$_2$O (33.4 mL) dropwise at 0° C. The resulting mixture was stirred for 30 min at 0° C. under nitrogen atmosphere. The above solution was quickly poured into the second reaction flask which was placed ethyl N-(2-cyanoacetyl)carbamate (372.75 mg, 2.387 mmol, 1.5 eq) and H$_2$O (40.9 mL) in pyridine (20 mL) at 0° C. The resulting mixture was for 30 min at 0° C. The precipitated solids were collected by filtration and washed with PE and H$_2$O (3×300 mL). to afford ethyl N—[(Z)-cyano(2-[3,5-dichloro-4-[(5-isopropyl-6-oxo-1H-pyridazin-3-yl)oxy]phenyl]hydrazin-1-ylidene)-carbonyl]-carbamate, which can also be named ethyl (Z)-(2-cyano-2-(2-(3,5-dichloro-4-((5-isopropyl-6-oxo-1,6-dihydropyridazin-3-yl)oxy)phenyl)-hydrazineylidene)acetyl)-carbamate (name generated by Chemdraw) (640 mg, 84%) as an orange solid.

To a solution of ethyl N—[(Z)-cyano(2-[3,5-dichloro-4-[(5-isopropyl-6-oxo-1H-pyridazin-3-yl)oxy]phenyl]hydrazin-1-ylidene)carbonyl]carbamate, which can also be named ethyl (Z)-(2-cyano-2-(2-(3,5-dichloro-4-((5-isopropyl-6-oxo-1,6-dihydropyridazin-3-yl)oxy)phenyl)hydrazineylidene)acetyl)carbamate (640.00 mg, 1.330 mmol, 1.00 eq) in DMA (13.36 mL) was added KOAc (261.01 mg, 2.660 mmol, 2.00 eq) in portions at rt. The mixture was stirred for 3 h at 120° C. under nitrogen atmosphere. The reaction was quenched with Water. The resulting mixture was extracted with EA (3×100 mL). The combined organic layers were washed with brine (4×100 mL), dried over anhydrous Na$_2$SO$_4$. After filtration, the filtrate was concentrated. This resulted in 2-[3,5-dichloro-4-[(5-isopropyl-6-oxo-1H-pyridazin-3-yl)oxy]phenyl]-3,5-dioxo-4H-1,2,4-triazine-6-carbonitrile (590 mg, 102%) as a dark orange solid.

17. Synthesis of 4-[(benzyloxy)methyl]-6-bromo-2-[3,5-dichloro-4-[(5-isopropyl-6-oxo-1H-pyridazin-3-yl)oxy]-phenyl]-1,2,4-triazine-3,5-dione

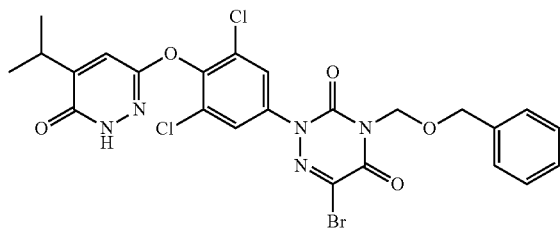 [SMILES: CC(C)c1cc(Oc2c(Cl)cc(-n3nc(Br)c(=O)n(COCc4ccccc4)c3=O)cc2Cl)n[nH]c1=O]

To a solution of 3,5-dichloro-4-[(5-isopropyl-6-oxo-1H-pyridazin-3-yl)oxy]phenylboronic acid (5.00 g, 11.663 mmol, 1.0 eq) in DCM (200 ml) stirred at rt was added 4-[(benzyloxy)methyl]-6-bromo-2H-1,2,4-triazine-3,5-dione (4.37 g, 13.995 mmol, 1.2 eq), Cu(OAc)$_2$ (4.24 g, 23.326 mmol, 2 eq) and pyridine (1.85 g, 23.326 mmol, 2 eq). The reaction mixture was stirred for 2 days at rt under oxygen, and was then concentrated under reduced pressure to afford the crude product. Purification resulted in 4-[(benzyloxy)methyl]-6-bromo-2-[3,5-dichloro-4-[(5-isopropyl-6-oxo-1H-pyridazin-3-yl)oxy]-phenyl]-1,2,4-triazine-3,5-dione (2.2 g, yield 28%) as an off-white solid.

18. Synthesis of (E)-N'-[3,5-dichloro-4-([3-iodo-1H-pyrrolo[3,2-b]pyridin-5-yl]oxy)phenyl]-N,N-dimethylmethanimidamide

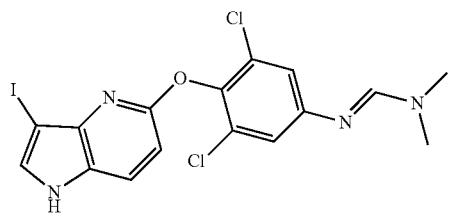 [SMILES: CN(C)/C=N/c1cc(Cl)c(Oc2ccc3[nH]cc(I)c3n2)c(Cl)c1]

A 8 mL vial was charged with 6-chloro-2-methyl-3-nitropyridine (20.00 g, 115.895 mmol, 1.0 eq), phenol, 4-amino-2,6-dichloro- (24.76 g, 139.07 mmol, 1.2 eq), K$_2$CO$_3$ (48.05 g, 347.69 mmol, 3.0 eq) and DMF (200 mL). The resulting mixture was stirred overnight at 60° C. The reaction mixture was quenched with water (400 mL). The resulting mixture was extracted with EA (3×500 mL) and the organic layers were combined, washed with brine (2×400 mL), dried over anhydrous sodium sulfate, filtered and concentrated under reduced pressure to afford crude product. The crude product was purified by silica gel column chromatography and eluted with EA:PE (0%~40% over 30 min) to provide the desired product 3,5-dichloro-4-[(6-methyl-5-nitropyridin-2-yl)oxy]aniline (36.4 g, 91%) as a yellow solid.

LCMS (ESI, m/z): 314 [M+H]$^+$.

To a solution of 3,5-dichloro-4-[(6-methyl-5-nitropyridin-2-yl)oxy]-aniline (36.40 g, 115.88 mmol, 1.0 eq) and (dimethoxymethyl)dimethylamine (33.14 g, 278.1 mmol, 2.4 eq) in dimethylformamide (400 mL) was added TEA (11.73 g, 115.9 mmol, 1.0 eq). The resulting mixture was stirred for 4 h at 100° C. The mixture was cooled to 60° C. and concentrated under reduced pressure to remove half of DMF. The resulting solution was passed to the next step without further treatment.

A solution of (E)-N'-(3,5-dichloro-4-((6-((E)-2-(dimethylamino)vinyl)-5-nitropyridin-2-yl)oxy)phenyl)-N,N-dimethylformimidamide (49.17 g, 115.89 mmol, 1.0 eq) in DMF (200 mL) and MeOH (400 mL) was added Pd/C (10.0 g, 93.967 mmol, 0.81 eq) and NaOAc (9.51 g, 115.89 mmol, 1.0 eq) under hydrogen. The resulting mixture was stirred overnight at room temperature. The mixture was filtered through a celite pad and washed with MeOH (50 mL). The filtrate was concentrated under reduced pressure to afford crude product. The crude product was purified by silica gel column chromatography and eluted with EA:PE (0%~70% over 30 min) to provide the desired product (E)-N'-(3,5-dichloro-4-[1H-pyrrolo[3,2-b]pyridin-5-yloxy]phenyl)-N,N-dimethylmethanimidamide (21.5 g, 45%) as a brown solid.

LCMS (ESI, m/z): 349 [M+H]$^+$.

A solution of (E)-N'-(3,5-dichloro-4-[1H-pyrrolo[3,2-b]pyridin-5-yloxy]phenyl)-N,N-dimethylmethanimidamide (5.00 g, 14.32 mmol, 1.0 eq) and I$_2$ (4.00 g, 15.75 mmol, 1.1 eq) in dimethylformamide (50 mL) was added KOH (3.21 g, 57.27 mmol, 4.0 eq). The resulting mixture was stirred overnight at room temperature and quenched with water (80 mL). The resulting mixture was extracted with EA (3×100 mL) and the organic layers were combined, washed with brine (2×80 mL), dried over anhydrous sodium sulfate, filtered and concentrated under reduced pressure to afford crude product. The crude product was triturated with PE:EA of 5:1 to provide the desired product (E)-N'-[3,5-dichloro-4-([3-iodo-1H-pyrrolo[3,2-b]pyridin-5-yl]oxy)phenyl]-N,N-dimethylmethanimidamide (5.9 g, 78%) as a yellow solid.

LCMS (ESI, m/z): 475 [M+H]$^+$.

19. Synthesis of 3,5-dichloro-4-([3-isopropyl-1H-pyrrolo[3,2-b]pyridin-5-yl]oxy)aniline

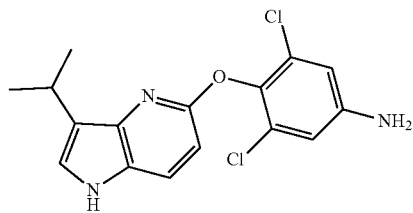 [SMILES: CC(C)c1c[nH]c2ccc(Oc3c(Cl)cc(N)cc3Cl)nc12]

To a solution of (E)-N'-[3,5-dichloro-4-([3-iodo-1H-pyrrolo[3,2-b]pyridin-5-yl]oxy)phenyl]-N,N-dimethylmethanimidamide (3.0 g, 6.31 mmol, 1.0 eq), K$_3$PO$_4$ (2.01 g, 9.471 mmol, 1.5 eq) and 1,1'-Bis (di-t-butylphosphino)ferrocene palladium dichloride (0.410 g, 0.631 mmol, 0.10 eq) in dioxane (75 mL) and H$_2$O (15 mL) was added 4,4,5,5-tetramethyl-2-(prop-1-en-2-yl)-1,3,2-dioxaborolane (4.24 g, 25.26 mmol, 4.0 eq) under nitrogen. The resulting mixture was stirred overnight at 60° C. and quenched with water (100 mL). The resulting mixture was extracted with EA (3×150 mL) and the organic layers were combined, washed with brine (2×100 mL), dried over anhydrous sodium sulfate, filtered and concentrated under reduced pressure to afford crude product. The crude product was purified by column and eluted with EA:PE (0% 50% over 30 min) to provide the desired product (E)-N'-(3,5-dichloro-4-

[[3-(prop-1-en-2-yl)-1H-pyrrolo[3,2-b]pyridin-5-yl]oxy]phenyl)-N,N-dimethylmethanimidamide (430 mg, 14%) as a yellow solid.

LCMS (ESI, m/z): 389 [M+H]⁺.

To a solution of (E)-N'-(3,5-dichloro-4-[[3-(prop-1-en-2-yl)-1H-pyrrolo[3,2-b]pyridin-5-yl]oxy]phenyl)-N,N-dimethylmethanimidamide (400.0 mg, 1.028 mmol, 1.0 eq) in MeOH (25 mL) was added Pd/C (250.0 mg, 2.349 mmol, 2.3 eq). The resulting mixture was stirred for 1 h at room temperature under hydrogen atmosphere. The mixture was filtered through a celite pad and washed with MeOH (20 mL). The combined organic layers were concentrated under reduced pressure to afford crude product (E)-N'-[3,5-dichloro-4-([3-isopropyl-1H-pyrrolo[3,2-b]pyridin-5-yl]-oxy)phenyl]-N,N-dimethylmethanimidamide (380 mg, crude) as a yellow solid.

LCMS (ESI, m/z): 391 [M+H]⁺.

To a solution of (E)-N'-[3,5-dichloro-4-([3-isopropyl-1H-pyrrolo[3,2-b]pyridin-5-yl]oxy)phenyl]-N,N-dimethylmethanimidamide (380.0 mg, 0.97 mmol, 1.0 eq) in ethyl alcohol (25 mL) was added ethylenediamine (262.6 mg, 4.37 mmol, 4.5 eq). The resulting mixture was stirred refluxed overnight. The reaction mixture was concentrated under reduced pressure to afford the crude product 3,5-dichloro-4-([3-isopropyl-1H-pyrrolo[3,2-b]pyridin-5-yl]oxy)aniline (350 mg, crude) as a yellow-semi solid.

LCMS (ESI, m/z): 336 [M+H]⁺.

20. Synthesis of 4-[(benzyloxy)methyl]-6-[3,5-dichloro-4-[(5-isopropyl-6-methoxypyridazin-3-yl)oxy]phenyl]-2H-1,2,4-triazine-3,5-dione

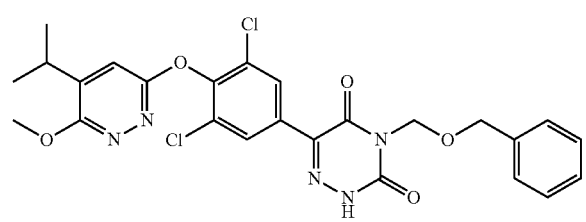 [SMILES: COc1nnc(Oc2c(Cl)cc(-c3n[nH]c(=O)n(COCc4ccccc4)c3=O)cc2Cl)cc1C(C)C]

A mixture of 3,5-dichloro-4-[(5-isopropyl-6-methoxypyridazin-3-yl)oxy]phenylboronic acid (400 mg, 1.12 mmol, 1.0 eq), 4-[(benzyloxy)methyl]-6-bromo-2H-1,2,4-triazine-3,5-dione (398 mg, 1.28 mmol, 1.15 eq), PdAmphos (Cl)₂ (79.3 mg, 0.112 mmol, 0.1 eq) and K₃PO₄ (713 mg, 3.36 mmol, 3.0 eq) in 1,4-dioxane (8 mL)/water (0.8 mL) was stirred for 2 h at 90° C. After cooled down to 25° C., the solids were filtered out and the filter cake was washed with EA (3×15 mL). The filtrate was concentrated under reduced pressure. The residue was purified by silica gel column chromatography (eluting with PE:EA of 1:1) to afford 4-[(benzyl-oxy)methyl]-6-[3,5-dichloro-4-[(5-isopropyl-6-methoxypyridazin-3-yl)oxy]-phenyl]-2H-1,2,4-triazine-3,5-dione (190 mg, 30% yield) as a light yellow solid.

LCMS (ESI, m/z): 544 [M+H]⁺.

21. Procedures for the synthesis of 2-(4-(benzyloxy)-2,6-dimethylbenzyl)-4,4,5,5-tetramethyl-1,3,2-dioxaborolane

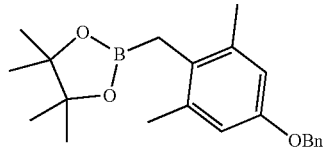 [SMILES: Cc1cc(OCc2ccccc2)cc(C)c1CB1OC(C)(C)C(C)(C)O1]

To a solution of 5-benzyloxy-2-bromo-1,3-dimethyl-benzene (1 g, 3.43 mmol) and 4,4,5,5-tetramethyl-2-[(4,4,5,5-tetramethyl-1,3,2-dioxaborolan-2-yl)meth-yl]-1,3,2-dioxaborolane (1.84 g, 6.87 mmol) in dioxane (10 mL) was added 8 N aq. KOH (858.57 μL, 6.86 mmol), followed by addition of Pd[P(t-Bu)₃]₂ (87.75 mg, 171.71 μmol) at rt (~15° C.) under N₂ protection. Then the mixture was stirred at 30° C. for 18 h. TLC (PE:EA of 10:1, stained by 12) showed the bromide was consumed completely and two new spots formed. The mixture was diluted with water (40 mL), extracted with ethyl acetate (50×2 mL). The combined organic phases were dried over anhydrous Na₂SO₄, filtered and concentrated in vacuo to give crude product, which was purified by flash silica gel chromatography (Eluent of 0~2% Ethyl acetate/Petroleum ether) to give desired 2-(4-(benzyloxy)-2,6-dimethylbenzyl)-4,4,5,5-tetramethyl-1,3,2-dioxaborolane (870 mg, 72% yield) as a white solid.

22. Synthesis of [4-[[3-isopropyl-1-(p-tolylsulfonyl)pyrrolo[3,2-b]pyridin-5-yl]methyl]-3,5-dimethyl-phenyl] trifluoromethanesulfonate

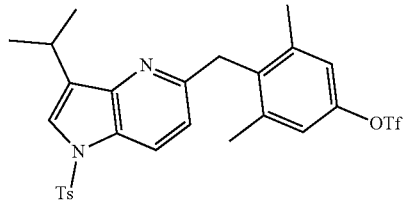

To a solution of 5-bromo-3-isopropyl-1-(p-tolylsulfonyl)pyrrolo[3,2-b]pyridine (1.0 g, 2.54 mmol, 1 eq) and 2-[(4-benzyloxy-2,6-dimethyl-phenyl)methyl]-4,4,5,5-tetramethyl-1,3,2-dioxaborolane (1.79 g, 5.09 mmol, 2 eq) in dioxane (30 mL) and H₂O (6 mL) was added dichloropalladium; tris-o-tolylphosphane (299.79 mg, 381.39 μmol, 0.15 eq) and K₃PO₄ (1.62 g, 7.63 mmol, 3 eq) at 20° C. under N₂ protection. Then the resulting mixture was stirred at 100° C. for 15 h under N₂ atmosphere. The combined mixture (combined with 300 mg batch) was diluted with H₂O (100 mL) and extracted with EA (100 mL×3). The combined organic layers were washed with brine (100 mL), dried over anhydrous Na₂SO₄, filtered and concentrated under reduced pressure to give a residue, which was purified by flash silica gel chromatography (Ethyl acetate in Petroleum ether=0~10%) to give 5-[(4-benzyloxy-2,6-dimethyl-phenyl)methyl]-3-isopropyl-1-(p-tolylsulfonyl)pyrrolo[3,2-b]pyridine (1.36 g, 2.44 mmol, 74% yield, 96.5% purity) as a yellow solid.

To a solution of 5-[(4-benzyloxy-2,6-dimethyl-phenyl)methyl]-3-isopropyl-1-(p-tolylsulfonyl)pyrrolo[3,2-b]pyridine (1.36 g, 2.52 mmol, 1 eq) in MeOH (20 mL) and THF (10 mL) was added Pd—C(10%, 1.07 g) under N$_2$. The suspension was degassed under vacuum and purged with H$_2$ several times. The mixture was stirred under H$_2$ (50 psi) at 35° C. for 18 hours. The mixture was filtered and the filtrate was concentrated, purified by flash silica gel chromatography (0~100% Ethyl acetate in Petroleum ether) to give 4-[[3-isopropyl-1-(p-tolylsulfonyl)pyrrolo[3,2-b]pyridin-5-yl]methyl]-3,5-dimethyl-phenol (1 g, 2.23 mmol, 88% yield) as a white solid.

To a solution of 4-[[3-isopropyl-1-(p-tolylsulfonyl)pyrrolo[3,2-b]pyridin-5-yl]methyl]-3,5-dimethyl-phenol (1 g, 2.23 mmol, 1 eq) and pyridine (440.84 mg, 5.57 mmol, 2.5 eq) in DCM (25 mL) at 0° C. was added dropwise Tf$_2$O (754.76 mg, 2.68 mmol, 441.38 µL, 1.2 eq) slowly. After the addition, the mixture was stirred at 0° C. for 1 h. The reaction mixture was partitioned between H$_2$O (30 mL) and DCM (30 mL). The organic phase was separated, washed with brine (10 mL*3), dried over anhydrous MgSO$_4$, filtered and concentrated to give crude product, which was purified by flash silica gel chromatography (0~10% Ethyl acetate in Petroleum ether) to give [4-[[3-isopropyl-1-(p-tolylsulfonyl)pyrrolo[3,2-b]pyridin-5-yl]methyl]-3,5-dimethyl-phenyl] trifluoromethanesulfonate (1.25 g, 2.15 mmol, 97% yield) as a colorless gum.

23. Synthesis of 4-[[3-isopropyl-1-(p-tolylsulfonyl)pyrrolo[3,2-b]pyridin-5-yl]methyl]-3,5-dimethyl-aniline

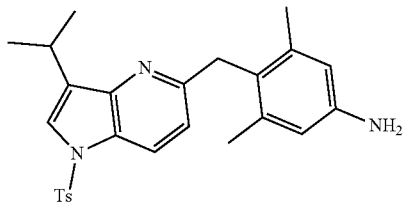 [SMILES: Cc1ccc(S(=O)(=O)n2cc(C(C)C)c3nc(Cc4c(C)cc(OS(=O)(=O)C(F)(F)F)cc4C)ccc32)cc1]

To a solution of [4-[[3-isopropyl-1-(p-tolylsulfonyl)pyrrolo[3,2-b]pyridin-5-yl]methyl]-3,5-dimethyl-phenyl] trifluoromethanesulfonate (300 mg, 516.67 µmol, 1 eq) and tert-butyl carbamate (121.05 mg, 1.03 mmol, 2 eq) in dioxane (8 mL) was added Pd$_2$(dba)$_3$ (47.31 mg, 51.67 µmol, 0.1 eq), (5-diphenylphosphanyl-9,9-dimethyl-xanthen-4-yl)-diphenyl-phosphane (59.79 mg, 103.33 µmol, 0.2 eq) and Cs$_2$CO$_3$ (505.03 mg, 1.55 mmol, 3 eq) at 20° C. under N$_2$ protection. Then the resulting mixture was stirred at 100° C. for 15 h under N$_2$. LCMS showed the reaction was complete. The mixture was diluted with H$_2$O (50 mL) and extracted with EA (50×3 mL). The combined organic layers were washed with brine (100 mL), dried over anhydrous Na$_2$SO$_4$, filtered and concentrated under reduced pressure to give a residue. The residue was purified by flash silica gel chromatography (Ethyl acetate in Petroleum ether=0~10%) to give tert-butyl N-[4-[[3-isopropyl-1-(p-tolylsulfonyl)pyrrolo[3,2-b]pyridin-5-yl]methyl]-3,5-dimethyl-phenyl] carbamate (200 mg, 350.19 µmol, 68% yield, 95.9% purity) as a light yellow solid.

To a solution of tert-butyl N-[4-[[3-isopropyl-1-(p-tolylsulfonyl)-pyrrolo[3,2-b]pyridin-5-yl]methyl]-3,5-dimethyl-phenyl] carbamate (170 mg, 310.39 µmol, 1 eq) in MeOH (3 mL) was added 4 M HCl gas in MeOH (8 mL) at 20° C. Then the resulting mixture was stirred at 20° C. for 12 h. MeOH was removed under reduced pressure and the residue was partitioned between EA (50 mL) and H$_2$O (50 mL). The EA phase was washed with H$_2$O (50 mL) again. The combined aqueous layers were adjusted to pH 7~8 with sat. aq. NaHCO$_3$, then extracted with EA (50 mL×2). The combined organic layers were washed with brine (50 mL), dried over anhydrous Na$_2$SO$_4$, filtered and concentrated to give 4-[[3-isopropyl-1-(p-tolylsulfonyl)-pyrrolo[3,2-b]pyridin-5-yl]methyl]-3,5-dimethyl-aniline (120 mg, 261.40 µmol, 84% yield, 97.5% purity) as a light yellow solid.

24. Synthesis of 2,2,2-trifluoro-N-(4-formyl-3,5-dimethylphenyl)acetamide

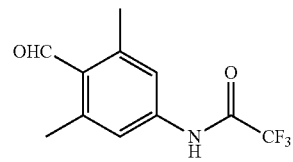 [SMILES: Cc1cc(NC(=O)C(F)(F)F)cc(C)c1C=O]

Trifluoroacetic anhydride (2 eq, 5.63 mL) was added to a solution of 4-iodo-3,5-dimethylaniline (1 eq, 5 g, 20.24 mmol) in anhydrous DCM (150 mL) under N$_2$ at 0° C. Then, the reaction mixture was stirred at 25° C. for 2.5 hours. To the reaction mixture was added water (200 mL), the layers were separated, and the aqueous layer was extracted with DCM (2×150 mL). The combined organic layers were dried over MgSO$_4$, filtered and evaporated to dryness. The crude mixture was purified by flash chromatography on silica gel (DCM) to give 2,2,2-trifluoro-N-(4-iodo-3,5-dimethylphenyl)acetamide (6.35 g, 91%) as a white solid.

Anhydrous THF (35 mL) was added to a mixture of 2,2,2-trifluoro-N-(4-iodo-3,5-dimethylphenyl)acetamide (1 eq, 2.40 g, 7 mmol) and NaH 60% (1.5 eq, 420 mg) under N$_2$ at 0° C. The reaction mixture was stirred at 25° C. for 1.5 h, then cooled to −78° C. and t-BuLi (2.4 eq, 9.88 mL) was added dropwise. The reaction mixture was stirred at −78° C. for 40 min. Then, anhydrous DMF (5 eq, 2.71 mL) was added and the reaction was further stirred at −78° C. for 1 h. The reaction mixture was hydrolyzed with sat. aq. NH$_4$Cl (5 mL), poured in DCM (250 mL) and washed 4 times with brine. The combined organic layers were dried over MgSO$_4$, filtered and evaporated to dryness. The crude mixture was recrystallized from hot EtOH to give 2,2,2-trifluoro-N-(4-formyl-3,5-dimethylphenyl)acetamide (317 mg, 19%) as a yellow solid. The supernatant was recrystallized from hot toluene to give more 2,2,2-trifluoro-N-(4-formyl-3,5-dimethylphenyl)acetamide (909 mg, 53%) as a light yellow solid.

25. Synthesis of 3,5-dimethyl-4-((3-pentyl-1H-indazol-5-yl)methyl)aniline

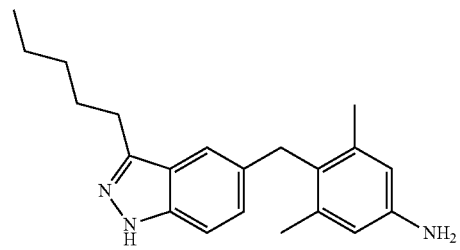 [SMILES: CCCCCc1n[nH]c2ccc(Cc3c(C)cc(N)cc3C)cc12]

Anhydrous THF (8.3 mL) was added to a mixture of 5-bromo-3-pentyl-1H-indazole (1 eq, 668 mg, 2.5 mmol) and NaH 60% (1.5 eq, 150 mg) at 0° C., under $N_2$. The resulting reaction mixture was stirred at 25° C. for 1 h. Then, the mixture was cooled to −78° C. and n-BuLi (1.5 eq, 2.34 mL) was added dropwise and the reaction mixture was stirred at −78° C. for 2 h. Then, a solution of 2,2,2-trifluoro-N-(4-formyl-3,5-dimethylphenyl)acetamide (1 eq, 613 mg) in anhydrous THF (8.3 mL) was added dropwise to the reaction mixture at −78° C. The reaction was further stirred at this temperature for 1.75 h and finally hydrolyzed with sat. aq. $NH_4C_1$ (5 mL), poured in DCM (100 mL) and washed 3 times with water. The organic phase was dried over $MgSO_4$, filtered and evaporated to dryness. The crude mixture was purified by flash chromatography on silica gel (20% to 40% EA in Cyclohexane) to give 2,2,2-trifluoro-N-(4-(hydroxy(3-pentyl-1H-indazol-5-yl)methyl)-3,5-dimethylphenyl)acetamide (317 mg, 29%) as a white solid.

A solution of $Et_3SiH$ (6 eq, 0.71 mL) in anhydrous DCM (20 mL) followed by a solution of TMSOTf (0.075 eq, 0.01 mL) in anhydrous DCM (7 mL) were added dropwise to a solution of 2,2,2-trifluoro-N-(4-(hydroxy(3-pentyl-1H-indazol-5-yl)methyl)-3,5-dimethylphenyl)acetamide (1 eq, 317 mg, 0.73 mmol) in anhydrous DCM (7 mL) at 0° C. under $N_2$. The reaction was stirred at 0° C. for 1 h, at which point the ice bath was removed and the reaction was stirred at 25° C. After 19 h, extra $Et_3SiH$ (6 eq, 0.71 mL) and TMSOTf (0.075 eq, 0.01 mL) were added and the reaction mixture was further stirred at 25° C. for 5 h. Then, the reaction was quenched with sat. aq. $NaHCO_3$ (20 mL) and the aqueous phase was extracted 3 times with DCM (3×50 mL). The combined organic layers were washed with brine (150 mL), dried over $MgSO_4$, filtered and evaporated to dryness. The crude mixture was purified by flash chromatography on silica gel (0% to 30% EA in Cyclohexane) to give N-(3,5-dimethyl-4-((3-pentyl-1H-indazol-5-yl)methyl)phenyl)-2,2,2-trifluoroacetamide (144 mg, 47%) as a white solid.

NaOH (4 eq, 54 mg) was added to a solution of N-(3,5-di-methyl-4-((3-pentyl-1H-indazol-5-yl)methyl)phenyl)-2,2,2-trifluoroacetamide (1 eq, 141 mg, 0.34 mmol) in MeOH (7 mL) and water (1.4 mL) under $N_2$. The reaction mixture was stirred at 60° C. for 90 h. Then, the reaction mixture was quenched with water (30 mL). The resulting solution was extracted with DCM (3×20 mL) and the combined organic layers were washed with brine (2×20 mL), dried over $MgSO_4$, filtered and evaporated to dryness to give 3,5-dimethyl-4-((3-pentyl-1H-indazol-5-yl)methyl)aniline (105 mg, 97%) as a white solid, which was used without further purification.

Example 1: Synthesis of Compound 1

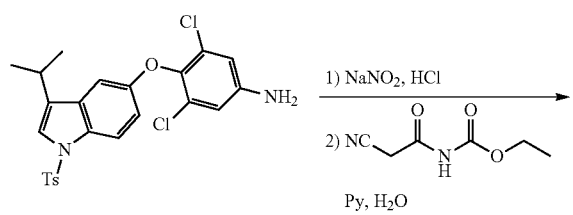

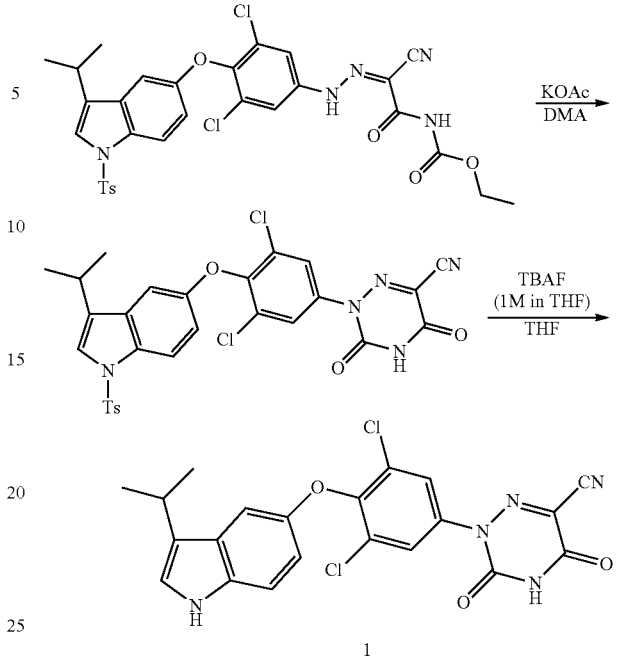

To a stirred solution of 3,5-dichloro-4-[[3-isopropyl-1-(4-methylbenzene-sulfonyl)indol-5-yl]methyl]aniline (1.11 g, 2.277 mmol, 1.00 eq) in HCl (21.90 mL), HOAc (62.50 mL) and $H_2O$ (47.68 mL) was added $NaNO_2$ (0.32 g, 4.566 mmol, 2 eq) in $H_2O$ (4.2 mL) dropwise for 1 h at 0° C. The second reaction flask was placed ethyl N-(2-cyanoacetyl)carbamate (0.53 g, 3.424 mmol, 1.5 eq) in $H_2O$ (58.41 mL) and Pyridine (22.35 mL) for 10 min at 0° C. The above solution was quickly poured into the second reaction flask for 30 min at 0° C. The precipitated solids were collected by filtration and washed with water and PE. The resulting mixture was concentrated under vacuum. This resulted in ethyl N—[(Z)-cyano[2-(3,5-dichloro-4-[[3-isopropyl-1-(4-methylbenzene-sulfonyl)indol-5-yl]methyl]phenyl)-hydrazin-1-ylidene]carbonyl]carbamate, which can also be named ethyl (Z)-(2-cyano-2-(2-(3,5-dichloro-4-((3-isopropyl-1-tosyl-1H-indol-5-yl)oxy)phenyl)hydrazineylidene)acetyl)carbamate as a red solid.

To a stirred solution of ethyl N—[(Z)-cyano[2-(3,5-dichloro-4-[[3-isopropyl-1-(4-methylbenzenesulfonyl)indol-5-yl]-oxy]phenyl)hydrazin-1-ylidene]-carbonyl]carbamate, which can also be named ethyl (Z)-(2-cyano-2-(2-(3,5-dichloro-4-((3-isopropyl-1-tosyl-1H-indol-5-yl)oxy)phenyl)hydrazineylidene)acetyl)carbamate (1.16 g, 1.773 mmol, 1.00 eq) in DMA (20.00 mL) was added KOAc (0.35 g, 3.546 mmol, 2 eq) in portions at rt. The resulting mixture was stirred for 2 h at 120° C. under nitrogen atmosphere. The reaction was quenched by the addition of water (10 mL) at rt. The precipitated solids were collected by filtration and washed with water (3×10 mL). The solid was dried overnight at rt to afford 2-(3,5-dichloro-4-[[3-isopropyl-1-(4-methylbenzenesulfonyl)indol-5-yl]oxy]-phenyl)-3,5-dioxo-4H-1,2,4-triazine-6-carbonitrile (521.2 mg, 45%) as a red solid.

To a stirred solution of 2-(3,5-dichloro-4-[[3-isopropyl-1-(4-methyl-benzenesulfonyl)indol-5-yl]oxy]phenyl)-3,5-dioxo-4H-1,2,4-triazine-6-carbonitrile (521.20 mg, 0.854 mmol, 1.00 eq) in THF (20.00 mL) was added TBAF (20 mL) in portions at rt under nitrogen atmosphere. The resulting mixture was stirred for 20 h at 65° C. under nitrogen atmosphere. The reaction was quenched with H₂O. The resulting mixture was extracted with EA, washed with brine, dried over anhydrous Na₂SO₄. After filtration, the filtrate was concentrated under reduced pressure. The residue was purified by Prep-TLC (DCM:MeOH 16:1) to afford the crude product (200 mg). The crude product (200 mg) was purified by prep-HPLC to afford 2-[3,5-dichloro-4-[(3-isopropyl-1H-indol-5-yl)oxy]-phenyl]-3,5-dioxo-4H-1,2,4-triazine-6-carbonitrile (11.5 mg, 3%, compound 1) as a yellow solid.

¹H-NMR: (300 MHz, DMSO-d₆) δ ppm: 10.67-10.60 (m, 1H), 7.77 (s, 2H), 7.30 (d, J=8.7 Hz, 1H), 7.07 (s, 1H), 6.82 (d, J=2.5 Hz, 1H), 6.67 (dd, J=8.9, 2.5 Hz, 1H), 2.94 (p, J=7.0 Hz, 1H), 1.18 (d, J=6.8 Hz, 6H).

Example 2: Synthesis of Compound 2

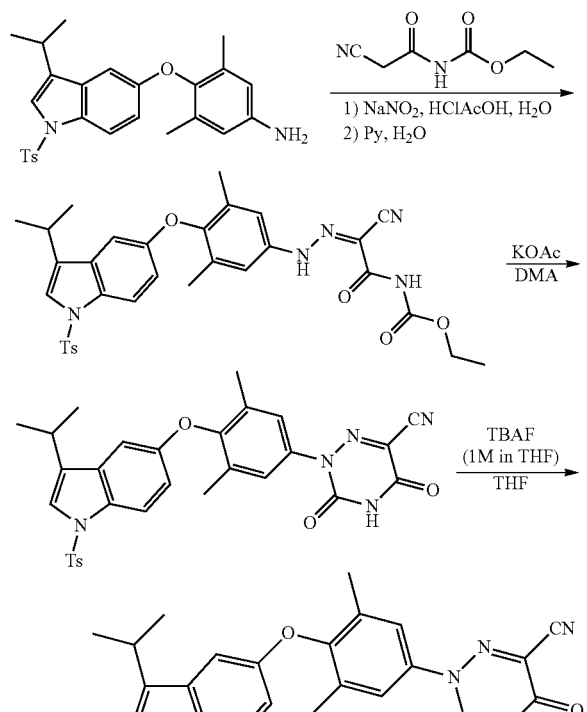

A 100 mL 3-necked round-bottom flask, maintained with an inert atmosphere of nitrogen, was charged with 4-[[3-isopropyl-1-(4-methylbenzene-sulfonyl)indol-5-yl]oxy]-3,5-dimethyl-aniline (450.00 mg, 1.003 mmol, 1.00 eq) in con. HCl (9.60 mL), AcOH (27.40 mL) and H₂O (20.9 mL). To a stirred solution was added NaNO₂ (145.35 mg, 2.107 mmol, 2.1 eq) in H₂O (1.8 mL) and dropwise for 45 min at 0° C. The second reaction flask was placed methyl N-(2-cyanoacetyl)carbamate (213.85 mg, 1.505 mmol, 1.50 eq) in H₂O (25.6 mL) and pyridine (9.80 mL) for 10 min at 0° C. The above solution was quickly poured into the second reaction flask for 30 min at 0° c. The precipitated solids were collected by filtration and washed with water and PE. The resulting mixture was concentrated under vacuum. This resulted in ethyl N—[(Z)-cyano[2-(4-[[3-isopropyl-1-(4-methylbenzenesulfonyl)indol-5-yl]oxy]-3,5-dimethylphenyl)hydrazin-1-ylidene]-carbonyl]carbamate, which can also be named ethyl (Z)-(2-cyano-2-(2-(4-((3-isopropyl-1-tosyl-1H-indol-5-yl)oxy)-3,5-dimethylphenyl)hydraziney-lidene)acetyl)carbamate as a red solid.

To a stirred solution of ethyl N—[(Z)-cyano[2-(4-[[3-isopropyl-1-(4-methyl-benzenesulfonyl)indol-5-yl]oxy]-3,5-dimethylphenyl)hydrazin-1-ylidene]-carbonyl]carbamate, which can also be named ethyl (Z)-(2-cyano-2-(2-(4-((3-isopropyl-1-tosyl-1H-indol-5-yl)oxy)-3,5-dimethylphenyl) hydrazineylidene)acetyl)carbamate (name generated by Chemdraw) (560.0 mg, 0.910 mmol, 1.00 eq) in DMA (10.00 mL) was added KOAc (178.52 mg, 1.819 mmol, 2.0 eq) in portions at rt. The resulting mixture was stirred for 2 h at 120° C. under nitrogen atmosphere. The reaction was quenched by the addition of water (10 mL) at rt. The resulting mixture was extracted with EA (3×100 mL). The combined organic layers were washed with brine (100 mL), dried over anhydrous Na₂SO₄. After filtration, the filtrate was concentrated under reduced pressure. The residue was purified by silica gel column chromatography to afford 2-(4-[[3-isopropyl-1-(4-methylbenzene-sulfonyl)indol-5-yl]oxy]-3,5-dimethylphenyl)-3,5-dioxo-4H-1,2,4-triazine-6-carbonitrile (350 mg, 56%) as a red solid.

To a stirred solution of 2-(4-[[3-isopropyl-1-(4-methyl-benzene-sulfonyl)-indol-5-yl]oxy]-3,5-dimethylphenyl)-3,5-dioxo-4H-1,2,4-tri-azine-6-carbo-nitrile (330.00 mg, 1 eq) in THF was added TBAF (1 M in THF) (8.00 mL) at rt. The resulting mixture was stirred for 48 h at 65° C. The resulting mixture was diluted with water (100 mL). The resulting mixture was extracted with EA (3×100 mL). The combined organic layers were washed with brine (100 mL), dried over anhydrous Na₂SO₄. After filtration, the filtrate was concentrated under reduced pressure. Purification afforded 2-[4-[(3-isopropyl-1H-indol-5-yl)oxy]-3,5-dimethyl-phenyl]-3,5-dioxo-4H-1,2,4-triazine-6-carbonitrile (132.3 mg, 54%) as a yellow solid.

¹H-NMR: (300 MHz, DMSO-d₆) δ ppm: 10.66 (s, 1H), 7.29-7.20 (m, 3H), 7.04 (d, J=2.2 Hz, 1H), 6.77 (d, J=2.4 Hz, 1H), 6.60 (dd, J=8.8, 2.5 Hz, 1H), 2.94 (p, J=6.9 Hz, 1H), 2.10 (s, 6H), 1.19 (d, J=6.8 Hz, 6H).

Example 3: Synthesis of Compound 3

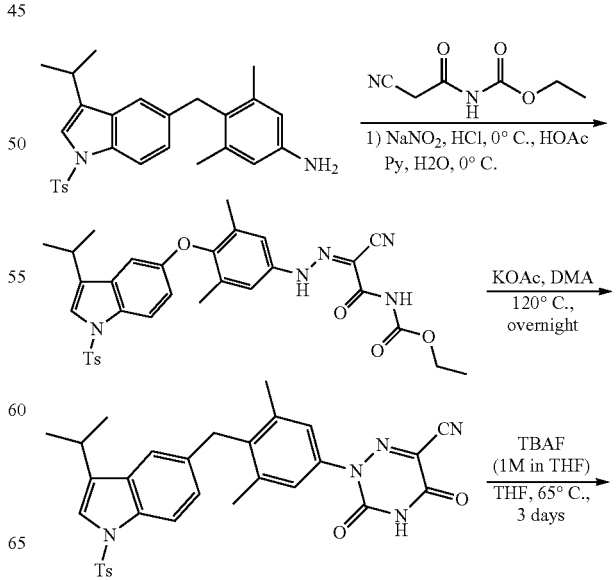

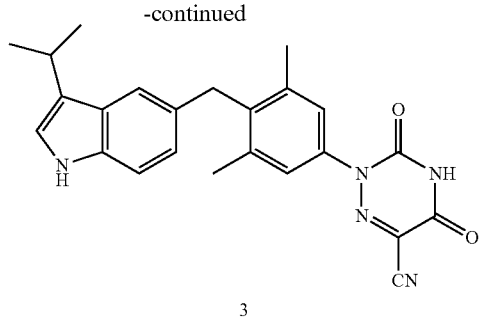

3

The first reaction flask, to a solution of 4-[[3-isopropyl-1-(4-methyl-benzenesulfonyl)indol-5-yl]methyl]-3,5-dimethylaniline (480.00 mg, 1.075 mmol, 1.00 eq) in concentrated HCl (9.60 mL), HOAc (28.80 mL) and H₂O (22.4 mL) stirred under nitrogen at 0° C. was added NaNO₂ (155.72 mg, 2.257 mmol, 2.1 eq) in H₂O (22.4 mL). The reaction mixture was stirred for 45 min at 0° C. The second reaction flask, a solution of ethyl N-(2-cyanoacetyl)carbamate (251.72 mg, 1.612 mmol, 1.50 eq) in H₂O (27.2 mL) and pyridine (9.60 mL) was stirred at 0° C. for 10 min. The first reaction flask was quickly poured into the second reaction flask, the reaction mixture stirred at 0° C. for 30 min. The precipitated solids were collected by filtration and washed with water (3×50 mL) and PE (3×50 mL). The resulting mixture was concentrated under vacuum. The crude product was isolated as a yellow solid, 520 mg, 80% pure, 63% yield.

To a solution of ethyl N—[(Z)-cyano[2-(4-[[3-isopropyl-1-(4-methyl-benzenesulfonyl)indol-5-yl]methyl]-3,5-dimethylphenyl)hydrazin-1-ylidene]-carbon-yl]carbamate, which can also be named ethyl (Z)-(2-cyano-2-(2-(4-((3-isopropyl-1-tosyl-1H-indol-5-yl)methyl)-3,5-dimethylphenyl)hydrazineylidene)acetyl)carbamate (350.00 mg, 0.570 mmol, 1.0 eq) in DMA (8.0 mL) stirred at rt was added KOAc (111.94 mg, 1.141 mmol, 2.0 eq). The reaction mixture was stirred at 120° C. for 3 h. The reaction was quenched by addition of water (10 mL) at rt. The precipitation solids were collected by filtration and washed with water (3×10 mL). the solids were dried in a vacuum over 2 h at 60° C. to afford 2-(4-[[3-isopropyl-1-(4-methylbenzenesulfonyl)indol-5-yl]methyl]-3,5-dimethylphenyl)-3,5-dioxo-4H-1,2,4-triazine-6-carbonitrile. The desired product was isolated as a dark orange solid, 250 mg, 80% pure, 62% yield.

To a solution of 2-(4-[[3-isopropyl-1-(4-methylbenzenesulfonyl)indol-5-yl]methyl]-3,5-dimethylphenyl)-3,5-dioxo-4H-1,2,4-triazine-6-carbonitrile (200.00 mg, 0.352 mmol, 1.00 eq) in THF (5.00 mL) stirred under nitrogen at 0° C. was added TBAF (10.57 mL, 10.570 mmol, 30.00 eq, 1 M in THF). The reaction mixture was stirred at 65° C. for 3 days. The reaction mixture was concentrated under reduced pressure to afford the crude product. The sample was purified to afford 2-(4-((3-isopropyl-1H-indol-5-yl)methyl)-3,5-dimethylphenyl)-3,5-dioxo-2,3,4,5-tetrahydro-1,2,4-triazine-6-carbo-nitrile. as a yellow solid (compound 3, 29.7 mg, 99% pure, 20% yield).

¹H NMR (400 MHz, DMSO-d₆) δ ppm: 13.00 (br, 1H), 10.63 (s, 1H), 7.19-7.22 (m, 2H), 7.14 (s, 2H), 7.01 (d, J=2.0 Hz, 1H), 6.68-6.71 (m, 1H), 4.11 (s, 2H), 3.00-3.04 (m, 1H), 2.27 (s, 6H), 1.24-1.25 (m, 6H).

Example 4: Synthesis of Compound 4

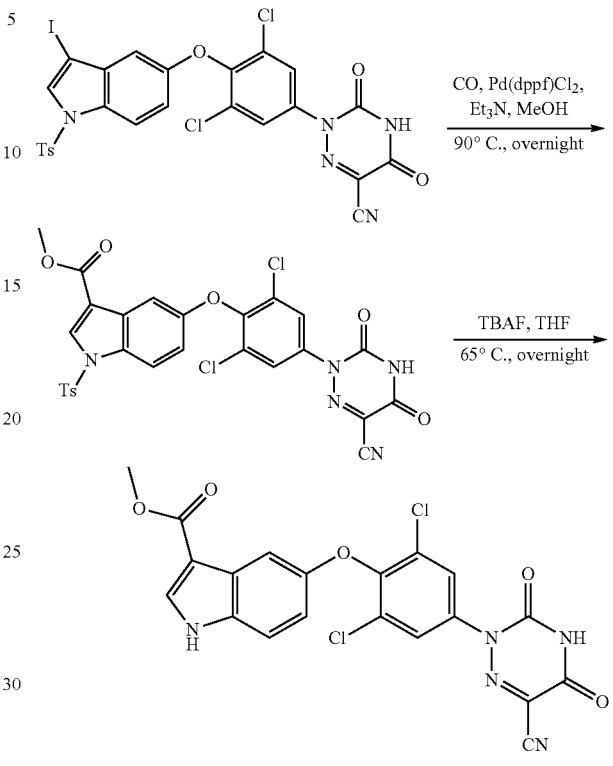

4

A 50 mL autoclave was charged with 2-(3,5-dichloro-4-[[3-iodo-1-(4-methylbenzenesulfonyl)indol-5-yl]oxy]phenyl)-3,5-dioxo-4H-1,2,4-triazine-6-carbo-nitrile (1.00 g, 1.44 mmol, 1.00 eq), dichloro[1,1'-bis(diphenylphosphino)-ferrocene]-palladium(II) (0.11 g, 0.144 mmol, 0.10 eq), triethylamine (0.44 g, 4.32 mmol, 3.00 eq), methanol (10 mL). The contents of the autoclave were placed under an atmosphere of carbon monoxide (30 atm). The reaction was stirred overnight at 90° C. The catalysts were filtered out. The filtrate was concentrated under reduced pressure. The residue was purified to provide 500 mg (yield 67%) of methyl 5-[2,6-dichloro-4-(6-cyano-3,5-dioxo-4H-1,2,4-triazin-2-yl)phenoxy]-1-(4-methylbenzene-sulfonyl)-indole-3-carboxylate as a brown solid.

A 40 mL vial was charged with methyl 5-[2,6-dichloro-4-(6-cyano-3,5-dioxo-4H-1,2,4-triazin-2-yl)phenoxy]-1-(4-methylbenzenesulfonyl)indole-3-carboxyl-ate (400 mg, 0.639 mmol, 1.00 eq), tetrahydrofuran (5 mL), tetrabutylammonium fluoride (6.39 mL, 1 M in tetrahydrofuran, 6.39 mmol, 10.0 eq). The reaction was stirred overnight at 65° C. and quenched with water (10 mL). The resulting solution was extracted with dichloromethane (3×20 mL) and the organic layers were combined, washed with brine (2×10 mL), dried over anhydrous sodium sulfate, filtered and concentrated under reduced pressure. The residue was purified to provide 30.4 mg (yield 15%) of methyl 5-[2,6-dichloro-4-(6-cyano-3,5-dioxo-4H-1,2,4-triazin-2-yl)phenoxy]-1H-indole-3-carboxylate as a yellow solid.

¹H NMR (300 MHz, Methanol-d₄) δ ppm: 7.97 (s, 1H), 7.80 (s, 2H), 7.41-7.44 (m, 2H), 6.88-6.92 (m, 1H), 3.84 (s, 3H).

Example 5: Synthesis of Compound 5

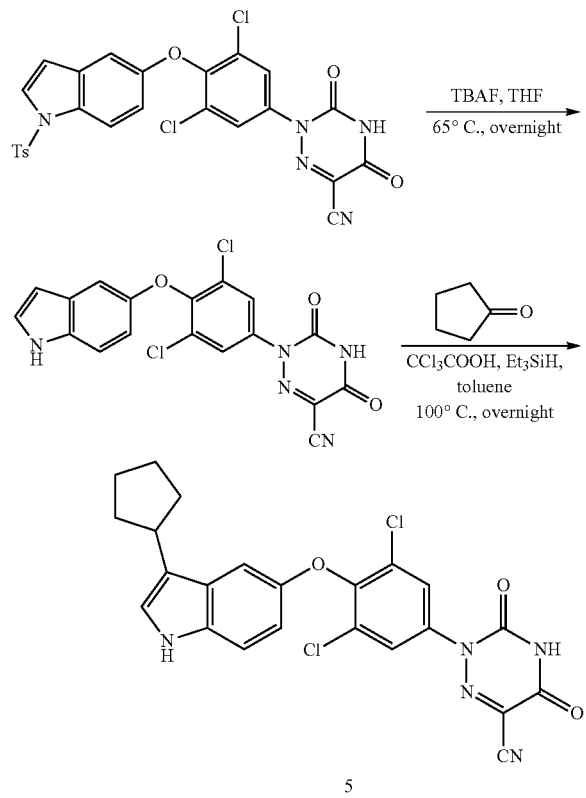

A 250 mL round-bottom was charged with 2-(3,5-dichloro-4-[[1-(4-methylbenzenesulfonyl)indol-5-yl]oxy]phenyl)-3,5-dioxo-4H-1,2,4-triazine-6-carbo-nitrile (1.00 g, 1.759 mmol, 1.00 eq), tetrahydrofuran (20 mL), tetrabutylammonium fluoride (52.78 mL, 1 M in tetrahydrofuran, 52.78 mmol, 30.00 eq). The resulting solution stirred overnight at 65° C. and then quenched with water (150 mL). The resulting mixture was extracted with ethyl acetate (3×200 mL) and the organic layers were combined, washed with brine (3×200 mL), dried over anhydrous sodium sulfate, filtered and concentrated under reduced pressure. The residue was purified to provide 500 mg (69% yield) of 2-[3,5-dichloro-4-(1H-indol-5-yloxy)phenyl]-3,5-dioxo-4H-1,2,4-triazine-6-carbonitrile as a yellow solid.

To a solution of 2-[3,5-dichloro-4-(1H-indol-5-yloxy)phenyl]-3,5-dioxo-4H-1,2,4-triazine-6-carbonitrile (300 mg, 0.724 mmol, 1.00 eq), trichloroacetic acid (355 mg, 2.17 mmol, 3.00 eq) and triethylsilane (337 mg, 2.90 mmol, 4.0 eq) in toluene (10 mL) stirred under nitrogen at 100° C. was added cyclopentanone (366 mg, 4.35 mmol, 6.00 eq). The reaction mixture stirred overnight at 100° C. and concentrated under reduced pressure. Purification resulting in 20.2 mg (6% yield) of 2-[3,5-dichloro-4-[(3-cyclopentyl-1H-indol-5-yl)oxy]phenyl]-3,5-dioxo-4H-1,2,4-tri-azine-6-carbonitrile as a yellow solid.

$^1$H NMR (300 MHz, DMSO-d$_6$) δ ppm: 10.77 (s, 1H), 7.81 (s, 2H), 7.30-7.34 (m, 1H), 7.13 (d, J=1.8 Hz, 1H), 6.90 (d, J=2.4 Hz, 1H), 6.64-6.68 (m, 1H), 3.06-3.14 (m, 1H), 1.99-2.03 (m, 2H), 1.60-1.78 (m, 6H).

Example 6: Synthesis of Compound 6

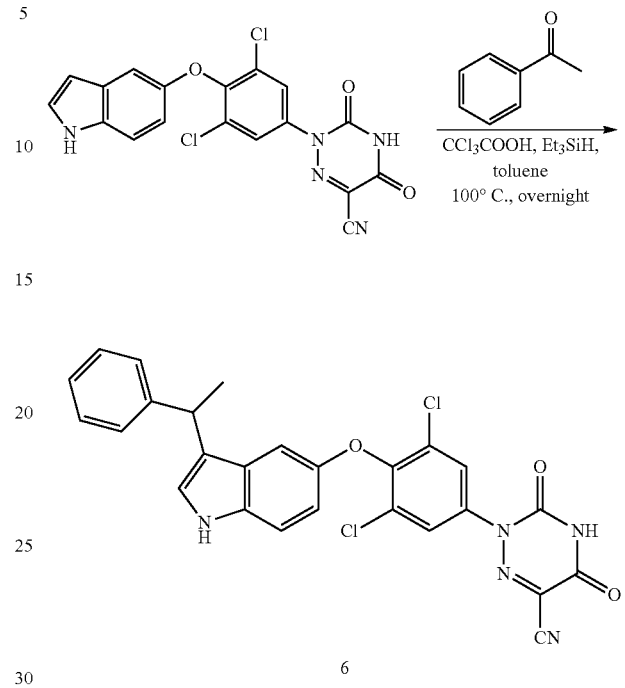

A 50 mL round-bottom flask was charged with 2-[3,5-dichloro-4-(1H-indol-5-yloxy)phenyl]-3,5-dioxo-4H-1,2,4-triazine-6-carbonitrile (300 mg, 0.724 mmol, 1.00 eq), trichloroacetic acid (355 mg, 2.17 mmol, 3.00 eq), toluene (10.00 mL), triethylsilane (504.10 mg, 4.35 mmol, 6.00 eq) under nitrogen. acetophenone (261 mg, 2.17 mmol, 3.00 eq) was added at 100° C. The resulting solution was stirred overnight at 100° C. and concentrated under reduced pressure. The residue was dissolved in water (20 mL) and extracted with dichloromethane (3×50 mL). The organic layers were combined, washed with brine (2×10 mL), dried over anhydrous sodium sulfate, filtered and concentrated under reduced pressure. Purification resulted in 63.2 mg (17% yield) of 2-(3,5-dichloro-4-[[3-(1-phenylethyl)-1H-indol-5-yl]oxy]phenyl)-3,5-dioxo-4H-1,2,4-triazine-6-carbonitrile as a yellow solid.

$^1$H NMR (300 MHz, DMSO-d$_6$) δ ppm: 10.88 (s, 1H), 7.75 (s, 2H), 7.21-7.29 (m, 2H), 7.13-7.21 (m, 4H), 7.06-7.11 (m, 1H), 6.63-6.67 (m, 1H), 6.38-6.39 (m, 1H), 4.11-4.18 (m, 1H), 1.56-1.59 (m, 3H).

Example 7: Synthesis of Compound 7

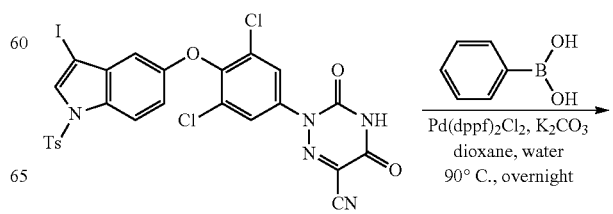

-continued

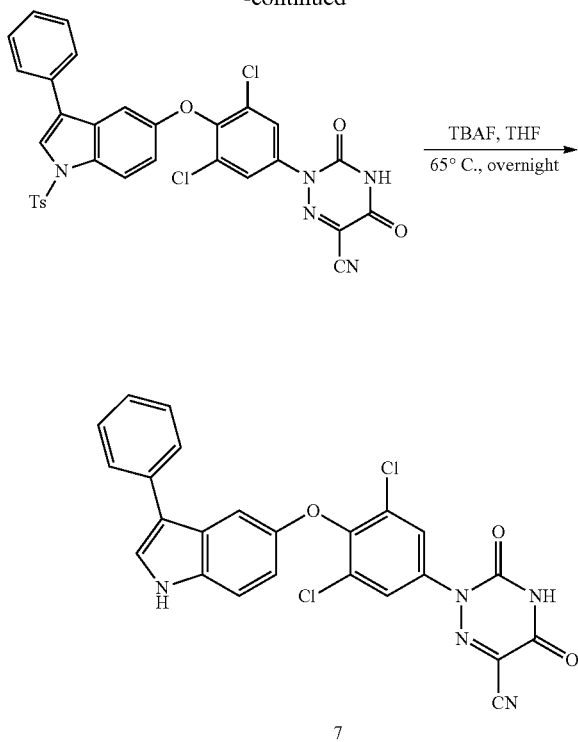

To a stirred solution of 2-(3,5-dichloro-4-[[3-iodo-1-(4-methylbenzene-sulfonyl)indol-5-yl]oxy]phenyl)-3,5-dioxo-4H-1,2,4-triazine-6-carbo-nitrile (400 mg, 0.576 mmol, 1.00 eq) and phenyl boronic acid (91.3 mg, 0.749 mmol, 1.30 eq) in dioxane (4 mL) and water (0.8 mL) was added dichloro[1,1'-bis(diphenylphosphino)-ferrocene]palladium(II) (42.2 mg, 0.0580 mmol, 0.10 eq) and potassium carbonate (238.88 mg, 1.728 mmol, 3.00 eq) at rt under nitrogen atmosphere. The reaction mixture was stirred overnight at 90° C. and concentrated under reduced pressure. The residue was purified to provide 170 mg (42% yield) of 2-(3,5-dichloro-4-[[1-(4-methyl-benzene-sulfonyl)-3-phenylindol-5-yl]oxy]phenyl)-3,5-dioxo-4H-1,2,4-triazine-6-carbonitrile as a light brown solid.

To a stirred solution of 2-(3,5-dichloro-4-[[1-(4-methyl-benzenesulfon-yl)-3-phenylindol-5-yl]oxy]phenyl)-3,5-di-oxo-4H-1,2,4-triazine-6-carbonitrile (160 mg, 0.248 mmol, 1.00 eq) in tetrahydrofuran (4 mL) was added t-butyl-ammonium fluoride (4.96 mL, 1 M in tetrahydrofuran, 4.96 mmol, 20.00 eq) at rt under nitrogen atmosphere. Then the reaction mixture was stirred overnight at 65° C. and quenched with water (10 mL). The resulting mixture was extracted with ethyl acetate (3×10 mL) and the combined organic layers were combined, washed with brine (3×20 mL), dried over anhydrous sodium sulfate and concentrated under reduced pressure. Purification resulted in of 2-[3,5-dichloro-4-[(3-phenyl-1H-indol-5-yl)oxy]phenyl]-3,5-di-oxo-4H-1,2,4-triazine-6-carbonitrile (compound 7, 39 mg, 32%) as a light orange solid.

$^1$H NMR (300 MHz, Methanol-d$_4$) δ ppm: 7.78 (s, 2H), 7.50-7.56 (m, 2H), 7.49 (s, 1H), 7.35-7.41 (m, 3H), 7.18-7.23 (m, 2H), 681-6.84 (m, 1H).

Example 8: Synthesis of Compound 8

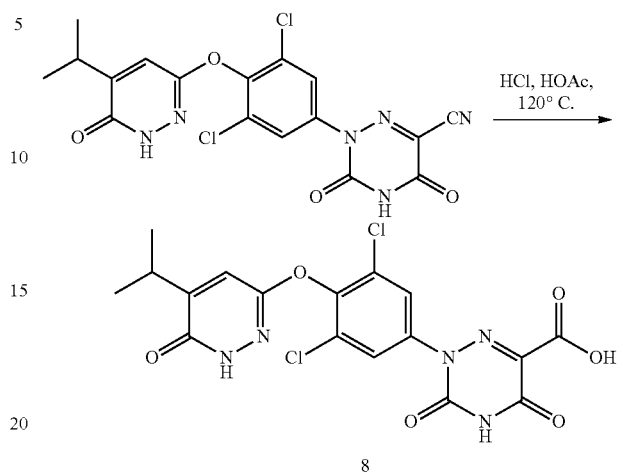

To a solution of 2-[3,5-dichloro-4-[(5-isopropyl-6-oxo-1H-pyridazin-3-yl)oxy]phenyl]-3,5-dioxo-4H-1,2,4-triaz-ine-6-carbonitrile (200.00 mg, 0.460 mmol, 1.00 eq) in HOAc (4.43 mL, 0.074 mmol, 0.16 eq) was added HCl (2.00 mL, 0.055 mmol, 0.12 eq) in portions at rt. The resulting mixture was stirred overnight at 120° C. under nitrogen atmosphere. The crude product (160 mg) was purified to afford 2-[3,5-dichloro-4-[(5-isopropyl-6-oxo-1H-pyridazin-3-yl)oxy]phenyl]-3,5-dioxo-4H-1,2,4-triazine-6-carboxylic acid (78.3 mg, 38%) as an off-white solid.

$^1$H NMR (400 MHz, DMSO-d$_6$): δ ppm: 13.82 (s, 1H), 12.70 (s, 1H), 12.19 (s, 1H), 7.82 (s, 2H), 7.44 (s, 1H), 3.05 (p, J=6.8 Hz, 1H), 1.20 (d, J=6.9 Hz, 6H).

Example 9: Synthesis of Compound 9

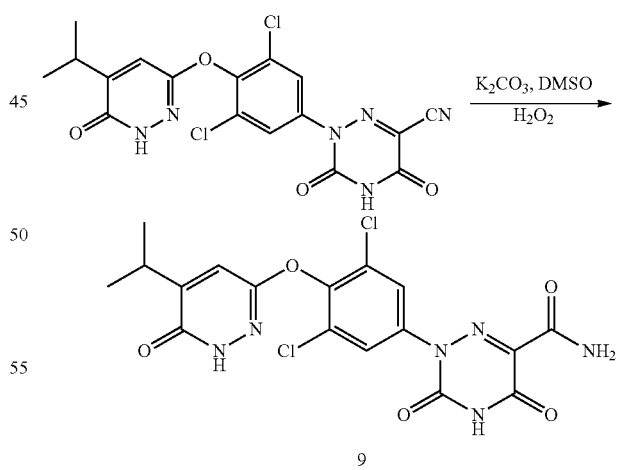

To a solution of 2-[3,5-dichloro-4-[(5-isopropyl-6-oxo-1H-pyridazin-3-yl)oxy]phenyl]-3,5-dioxo-4H-1,2,4-triaz-ine-6-carbonitrile (200.00 mg, 0.460 mmol, 1.00 eq) in DMSO (5 mL) was added K$_2$CO$_3$ (190.53 mg, 1.379 mmol, 3.00 eq) and H$_2$O$_2$ (2 mL, 30% in water) in portions at 0° C. The resulting mixture was stirred for 5 h at rt. The reaction was quenched with saturated Na$_2$S$_2$O$_3$ solution at rt and concentrated under reduced pressure. The residue was purified by reverse flash chromatography with the following conditions (column, C18; mobile phase, ACN in water, 10% to 80% gradient in 30 min) to provide the crude product (150 mg), which was then purified by Prep-HPLC (Column: XBridge Prep OBD C18 Column, Mobile Phase A: Water (10 mM $NH_4HCO_3$), Mobile Phase B: ACN; Flow rate: 60 mL/min; Gradient: 20% B to 33% B in 9 min) to afford 2-[3,5-dichloro-4-[(5-isopropyl-6-oxo-1H-pyridazin-3-yl)oxy]phenyl]-3,5-dioxo-4H-1,2,4-triazine-6-carboxamide (112.1 mg, 54%) as a white solid.

$^1$H NMR (400 MHz, DMSO-$d_6$) δ ppm: 12.76 (s, 1H), 12.20 (s, 1H), 8.14 (br, 1H), 7.85-7.90 (m, 3H), 7.44 (s, 1H), 3.05 (p, J=6.8 Hz, 1H), 1.20 (d, J=6.8 Hz, 6H).

Example 10: Synthesis of Compound 10

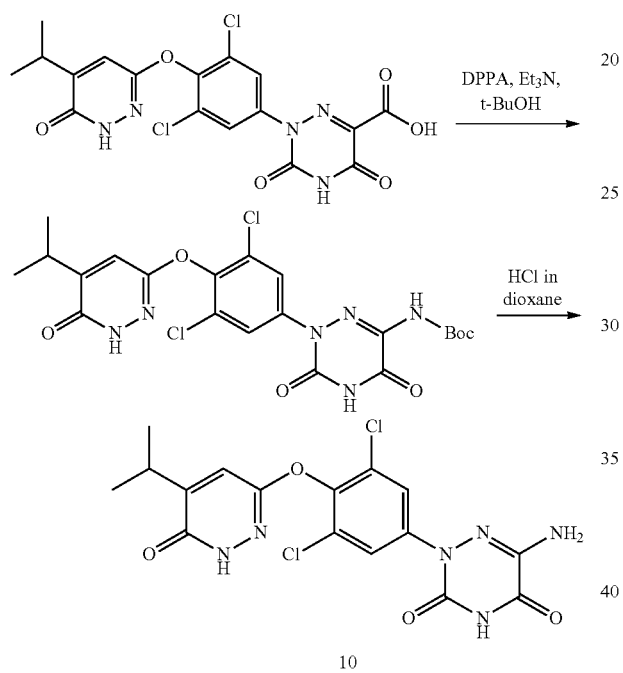

To a solution of 2-[3,5-dichloro-4-[(5-isopropyl-6-oxo-1H-pyridazin-3-yl)oxy]phenyl]-3,5-dioxo-4H-1,2,4-triazine-6-carboxylic acid (200.00 mg, 0.440 mmol, 1.00 eq) in t-BuOH (20.00 mL, 210.465 mmol) were added DPPA (375.64 mg, 1.365 mmol, 3.10 eq) and $Et_3N$ (138.12 mg, 1.365 mmol, 3.10 eq) in portions at rt. The resulting mixture was stirred for 24 h at 85° C. under nitrogen atmosphere. The resulting mixture was concentrated. The residue was dissolved in $CH_2Cl_2$ (100 mL), and was then washed with $NH_4Cl_1$ (4×200 mL), $NaHCO_3$ and brine. The combined organic layers were dried over anhydrous $Na_2SO_4$. After filtration, the filtrate was concentrated. The residue was purified by silica gel column chromatography, eluted with $CH_2Cl_2$:MeOH (50:1), to afford tert-butyl N-(2-[3,5-dichloro-4-[(5-isopropyl-6-oxo-1H-pyridazin-3-yl)oxy]phenyl]-3,5-dioxo-4H-1,2,4-triazin-6-yl)-carbamate (110 mg, 48%) as a white solid.

LCMS (ESI, m/z): 525 [M+H]$^+$.

A solution of t-butyl N-(2-[3,5-dichloro-4-[(5-isopropyl-6-oxo-1H-pyridazin-3-yl)oxy]phenyl]-3,5-dioxo-4H-1,2,4-triazin-6-yl)carbamate (90.0 mg, 1 eq) in 4 N HCl in 1,4-dioxane (5.00 mL) was stirred overnight at rt. The resulting mixture was concentrated. The crude product (70 mg) was purified by Prep-HPLC (Column: XBridge Prep OBD C18, Mobile Phase A: Water (10 mmol/L $NH_4HCO_3$+ 0.1% $NH_3 \cdot H_2O$), Mobile Phase B: ACN; Flow rate: 60 mL/min; Gradient: 10 B to 40 B in 8 min) to afford 6-amino-2-[3,5-dichloro-4-[(5-isopropyl-6-oxo-1H-pyridazin-3-yl)oxy]phenyl]-4H-1,2,4-tri-azine-3,5-dione (18.8 mg, 26%) as a white solid.

$^1$H NMR (400 MHz, DMSO-$d_6$) δ ppm: 12.26 (s, 1H), 12.18 (s, 1H), 7.85 (s, 2H), 7.41 (s, 1H), 6.45 (s, 2H), 2.95-3.10 (m, 1H), 1.19 (d, J=6.9 Hz, 6H).

Example 11: Synthesis of Compound 11

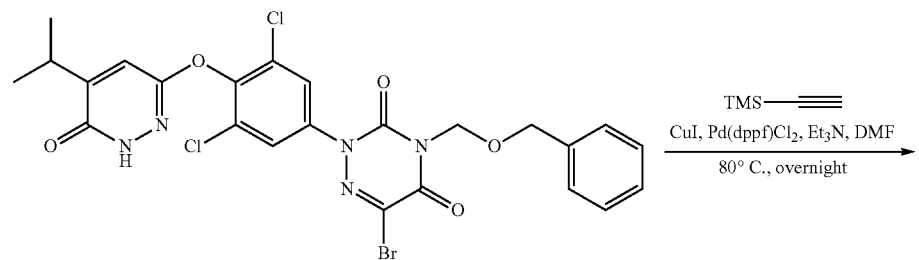

-continued

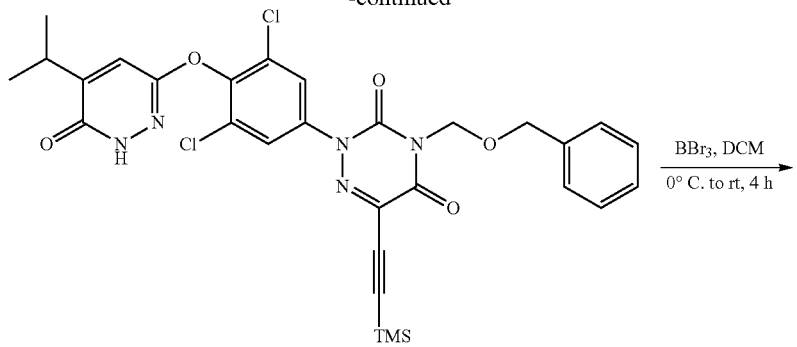

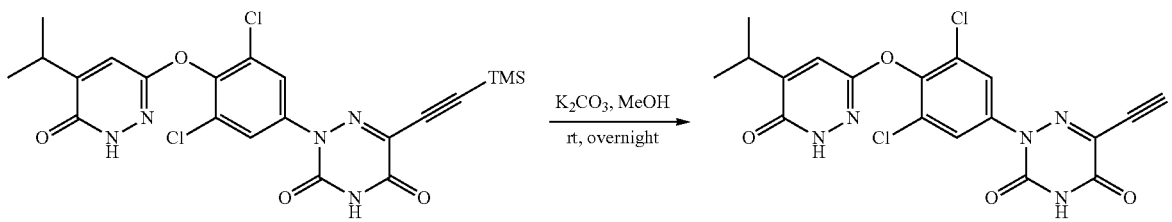

To a stirred solution of 4-[(benzyloxy)methyl]-6-bromo-2-[3,5-dichloro-4-[(5-isopropyl-6-oxo-1H-pyridazin-3-yl)oxy]phenyl]-1,2,4-triazine-3,5-di-one (430.00 mg, 0.706 mmol, 1.00 eq) and trimethylsilylacetylene (207.96 mg, 2.117 mmol, 3.0 eq) in DMF (10 mL) were added CuI (26.88 mg, 0.141 mmol, 0.20 eq), Et$_3$N (214.25 mg, 2.117 mmol, 3.00 eq) and Pd(dppf)Cl$_2$ (103.28 mg, 0.141 mmol, 0.20 eq) in portions at rt under nitrogen atmosphere. The reaction mixture was stirred overnight at 80° C. and quenched with water (10 mL). The resulting mixture was extracted with EA (3×40 mL). The combined organic layers were washed with water (1×100 mL), dried over anhydrous Na$_2$SO$_4$. After filtration, the filtrate was concentrated under reduced pressure. The residue was purified by silica gel column chromatography to afford 4-[(benzyloxy)methyl]-2-[3,5-dichloro-4-[(5-isopropyl-6-oxo-1H-pyridazin-3-yl)oxy]phenyl]-6-[2-(trimethylsilyl)ethynyl]-1,2,4-triazine-3,5-dione (260 mg, 52%) as a off-white solid.

To a stirred solution of 4-[(benzyloxy)methyl]-2-[3,5-dichloro-4-[(5-isopropyl-6-oxo-1H-pyridazin-3-yl)oxy]phenyl]-6-[2-(trimethylsilyl)ethynyl]-1,2,4-triazine-3,5-dione (240.00 mg, 0.383 mmol, 1.00 eq) in DCM (5 mL) was added BBr3 (383.84 mg, 1.532 mmol, 4.00 eq) dropwise at 0° C. under nitrogen atmosphere. The reaction was stirred for 4 h at rt and quenched with MeOH (5 mL). The resulting mixture was concentrated under reduced pressure to provide 100 mg (crude) of 2-[3,5-dichloro-4-[(5-isopropyl-6-oxo-1H-pyridazin-3-yl)oxy]phenyl]-6-[2-(trimethylsilyl)-ethynyl]-4H-1,2,4-triazine-3,5-dione as light brown solid.

To a solution of 2-[3,5-dichloro-4-[(5-isopropyl-1H-pyridazin-3-yl)oxy]phenyl]-6-[2-(trimethylsilyl)ethynyl]-4H-1,2,4-triazine-3,5-dione (100.00 mg, 0.197 mmol, 1.00 eq) in MeOH (10 mL) was added K$_2$CO$_3$ (109.16 mg, 0.790 mmol, 4.00 eq) stirred at rt. The reaction mixture was stirred overnight at rt and concentrated under reduced pressure to afford the residue. Purification resulted in 19.4 mg (yield 22%) of 2-[3,5-dichloro-4-[(5-isopropyl-6-oxo-1H-pyridazin-3-yl)oxy]phenyl]-6-ethynyl-4H-1,2,4-triazine-3,5-dione as a white solid.

$^1$H NMR (400 MHz, DMSO-d$_6$) δ ppm: 12.75 (s, 1H), 12.23 (s, 1H), 7.77 (s, 2H), 7.44 (s, 1H), 4.70 (s, 1H), 3.03-3.10 (m, 1H), 1.20 (d, J=6.8 Hz, 6H)

Example 12: Synthesis of Compound 12

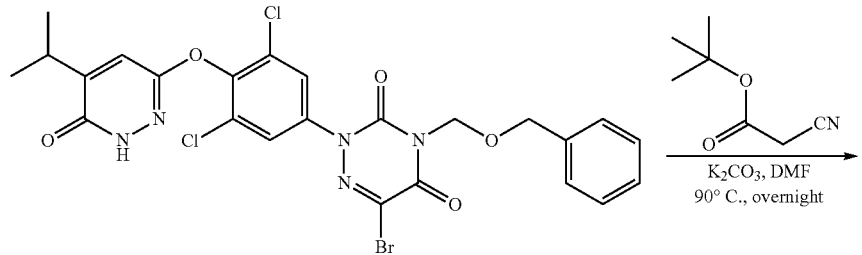

-continued

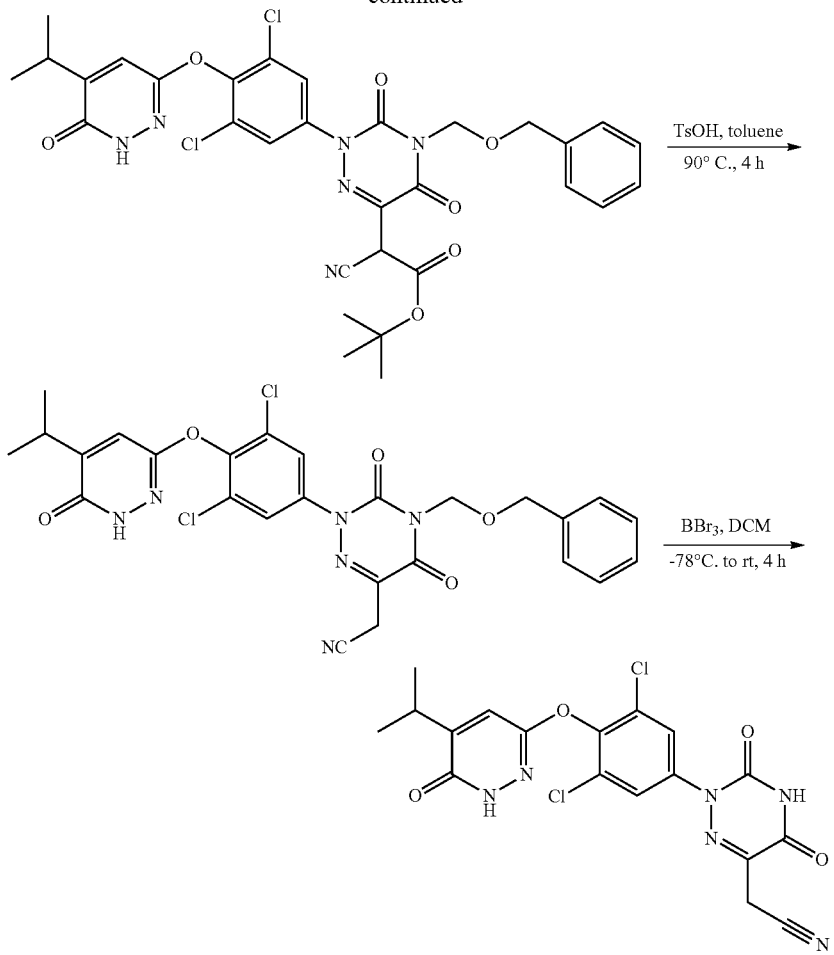

12

To a solution of 4-[(benzyloxy)methyl]-6-bromo-2-[3,5-dichloro-4-[(5-isopropyl-6-oxo-1H-pyridazin-3-yl)oxy]phenyl]-1,2,4-triazine-3,5-dione (300.00 mg, 0.492 mmol, 1.00 eq) and tert-butyl 2-cyanoacetate (208.54 mg, 1.477 mmol, 3.0 eq) in DMF (5.00 mg) stirred at rt was added $K_2CO_3$ (272.21 mg, 1.970 mmol, 4.0 eq). The reaction mixture was stirred overnight at 90° C. The reaction mixture was quenched with water (30 mL). The resulting mixture was extracted with dichloromethane (3×50 mL) and the organic layers were combined, washed with brine (2×50 mL), dried over anhydrous sodium sulfate, filtered and concentrated under reduced pressure. The residue was purified to provide 190 mg (95% pure) tert-butyl 2-[4-[(benzyloxy)methyl]-2-[3,5-dichloro-4-[(5-isopropyl-6-oxo-1H-pyridazin-3-yl)oxy]phenyl]-3,5-dioxo-1,2,4-triazin-6-yl]-2-cyanoacetate (190 mg, 58%) as a yellow solid.

A 50 mL round-bottom flask was charged with tert-butyl 2-[4-[(benzyloxy)methyl]-2-[3,5-dichloro-4-[(5-isopropyl-6-oxo-1H-pyridazin-3-yl)oxy]-phenyl]-3,5-dioxo-1,2,4-triazin-6-yl]-2-cyanoacetate (190.00 mg, 0.284 mmol, 1.00 eq), TsOH (24.43 mg, 0.142 mmol, 0.5 eq) and toluene (5 mL). The resulting solution was stirred for 4 h at 90° C. and quenched with water (10 mL). The resulting mixture was extracted with dichloromethane (3×50 mL) and the organic layers were combined, washed with brine (2×30 mL), dried over anhydrous sodium sulfate, filtered and concentrated under reduced pressure to provide 190 mg of crude (70% pure) 2-[4-[(benzyloxy)methyl]-2-[3,5-dichloro-4-[(5-isopropyl-6-oxo-1H-pyridazin-3-yl)oxy]-phenyl]-3,5-dioxo-1,2,4-triazin-6-yl]acetonitrile (190 mg, 82% yield) as a yellow oil.

To a solution of 2-[4-[(benzyloxy)methyl]-2-[3,5-dichloro-4-[(5-isopropyl-6-oxo-1H-pyridazin-3-yl)oxy]phenyl]-3,5-dioxo-1,2,4-triazin-6-yl]aceto-nitrile (190.00 mg, 0.334 mmol, 1.00 eq) in DCM (3 mL) stirred under nitrogen at −78° C. was added $BBr_3$ (501.57 mg, 2.002 mmol, 6.0 eq). The reaction mixture was stirred at rt for 4 h. The reaction mixture was quenched with water (10 mL). The resulting solution was extracted with dichloromethane (3×20 mL) and the organic layers were combined, washed with brine (2×10 mL), dried over anhydrous sodium sulfate, filtered and concentrated under reduced pressure to afford the crude product. Purification resulted in 24.9 mg (16% yield) of 2-(2-[3,5-dichloro-4-[(5-isopropyl-6-oxo-1H-pyridazin-3-yl)oxy]phenyl]-3,5-dioxo-4H-1,2,4-triazin-6-yl)acetonitrile as a white solid.

$^1$H NMR (400 MHz, DMSO-$d_6$) δ ppm: 12.71 (s, 1H), 12.20 (s, 1H), 7.81 (s, 2H), 7.46 (s, 1H), 4.05 (s, 2H), 3.03-3.07 (m, 1H), 1.11-1.31 (m, 6H).

Example 13: Synthesis of Compound 13

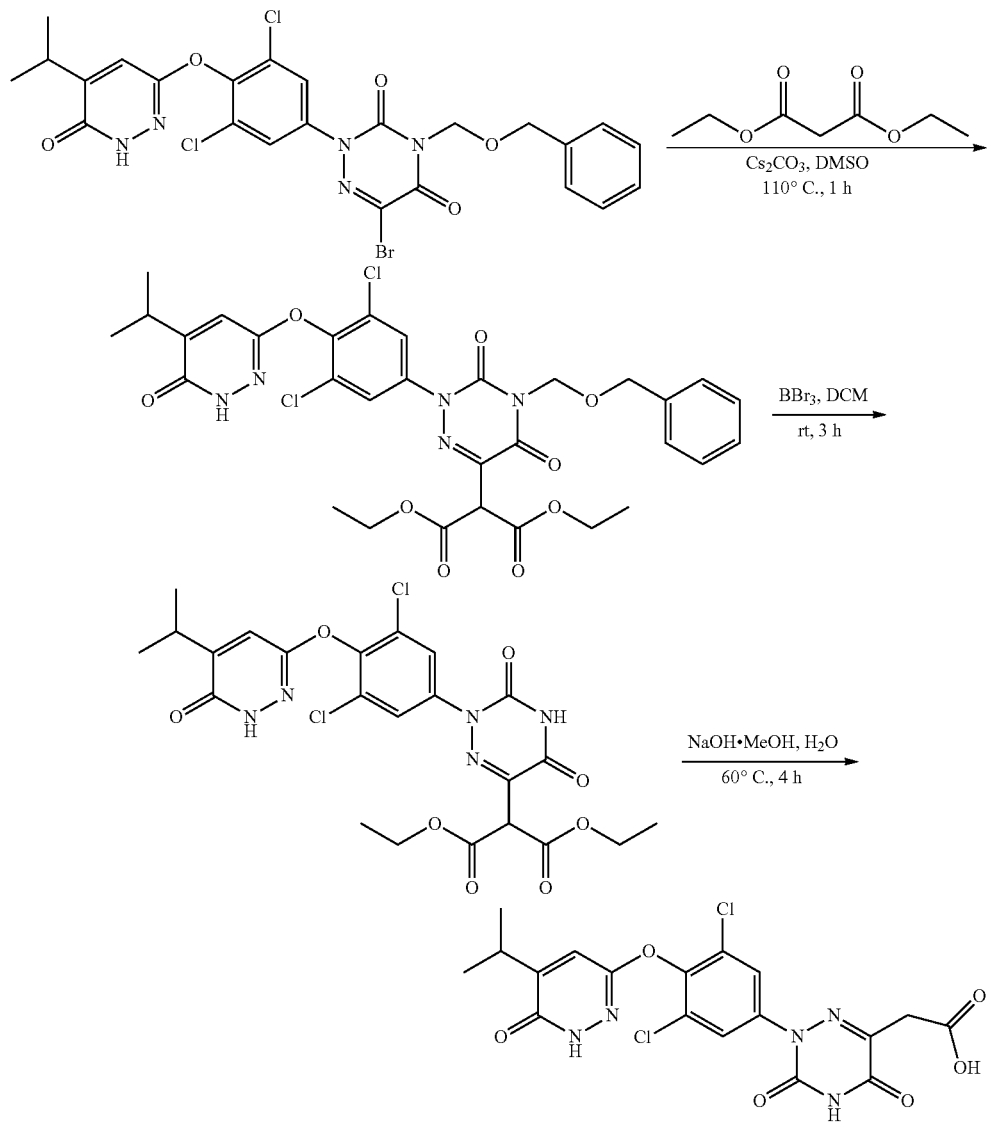

To a solution of 4-[(benzyloxy)methyl]-6-bromo-2-[3,5-dichloro-4-[(5-isopropyl-6-oxo-1H-pyridazin-3-yl)oxy]phenyl]-1,2,4-triazine-3,5-dione (350.00 mg, 0.574 mmol, 1.00 eq) and diethyl malonate (184.02 mg, 1.149 mmol, 2.00 eq) in DMSO (5 mL) stirred under nitrogen at rt was added Cs₂CO₃ (561.52 mg, 1.723 mmol, 3.0 eq). The reaction mixture was stirred at 110° C. for 1 h. The reaction mixture was quenched with water (20 mL). The resulting solution was extracted with dichloromethane (3×50 mL) and the organic layers were combined, washed with brine (2×30 mL), dried over anhydrous sodium sulfate, filtered and concentrated under reduced pressure to afford crude product. The crude product was diluted with dichloromethane (50 mL) and made the slurry with 100~200 silica gel mesh (2 g). The sample was purified and the desired product was isolated as a yellow oil. 270 mg, 90% pure, 61% yield.

To a solution of 1,3-diethyl 2-[4-[(benzyloxy)methyl]-2-[3,5-dichloro-4-[(5-isopropyl-6-oxo-1H-pyridazin-3-yl)oxy]phenyl]-3,5-dioxo-1,2,4-triazin-6-yl]-propanedioate (250.00 mg, 0.363 mmol, 1.00 eq) in DCM (5.00 mL) stirred under nitrogen at 0° C. was added BBr₃ (363.86 mg, 1.452 mmol, 4.00 eq). The reaction mixture was stirred at rt for 3 h. The reaction mixture was quenched with water (15 mL). The resulting solution was extracted with dichloromethane (3×30 mL) and the organic layers were combined, washed with brine (2×15 mL), dried over anhydrous sodium sulfate, filtered and concentrated under reduced pressure to afford crude product. No further purification was carried out on this material. The crude product was isolated as a yellow solid, 210 mg, 70% pure, 71% yield.

To a solution of 1,3-diethyl 2-(2-[3,5-dichloro-4-[(5-isopropyl-6-oxo-1H-pyridazin-3-yl)oxy]phenyl]-3,5-dioxo-4H-1,2,4-triazin-6-yl)propanedioate (210.00 mg, 0.369 mmol, 1.00 eq) in MeOH (5.00 mL) and H₂O (1.00 mL) stirred at rt was added NaOH (147.78 mg, 3.695 mmol, 10.00 eq). The reaction mixture was stirred at 60° C. for 4 h. The pH value of the mixture was adjusted to ~5-6 with hydrochloric acid (1 M). The resulting solution was extracted with dichloromethane (3×30 mL) and the organic layers were combined, washed with brine (2×10 mL) dried over anhydrous sodium sulfate, filtered and concentrated under reduced pressure to afford crude product. The crude product was purified to provide 2-(2-(3,5-dichloro-4-((5-isopropyl-6-oxo-1,6-dihydropyridazin-3-yl)oxy)phenyl)-3,5-dioxo-2,3,4,5-tetra-hydro-1,2,4-triazin-6-yl)acetic acid. The desired product was isolated as a white solid (54.0 mg, 99.5% pure, 31% yield)

$^1$H NMR (300 MHz, DMSO-d$_6$) δ ppm: 7.82 (s, 1H), 7.44 (s, 1H), 3.44 (s, 2H), 3.01-3.10 (m, 1H), 1.19-1.24 (m, 6H).

Example 14: Synthesis of Compound 14

(3.3 mL, 6.565 mmol, 10.00 eq, 2 M in THF) at rt. The reaction mixture was stirred overnight at 110° C. The reaction mixture was concentrated under reduced pressure to afford the residue. The residue was purified to provide 220 mg (yield 53%) of 4-[(benzyloxy)methyl]-2-[3,5-dichloro-4-[(5-isopropyl-6-oxo-1H-pyridazin-3-yl)oxy]-phenyl]-6-(dimethylamino)-1,2,4-triazine-3,5-dione as a light yield solid.

To a stirred solution of 4-[(benzyloxy)methyl]-2-[3,5-dichloro-4-[(5-isopropyl-6-oxo-1H-pyridazin-3-yl)oxy]phenyl]-6-(methylamino)-1,2,4-triazine-3,5-dione (400.00 mg, 0.715 mmol, 1.00 eq) in DCM was added BBr$_3$ (716.55 mg, 2.860 mmol, 4.00 eq) at −78° C. The resulting solution was stirred for 4 h at rt. The reaction mixture was concentrated under reduced pressure to afford the crude product. Purification resulted in 86.9 mg (yield 54%) 2-[3,5-dichloro-4-[(5-isopropyl-6-oxo-1H-pyridazin-3-yl)oxy]phenyl]-6-(methylamino)-4H-1,2,4-triazine-3,5-dione as a white solid.

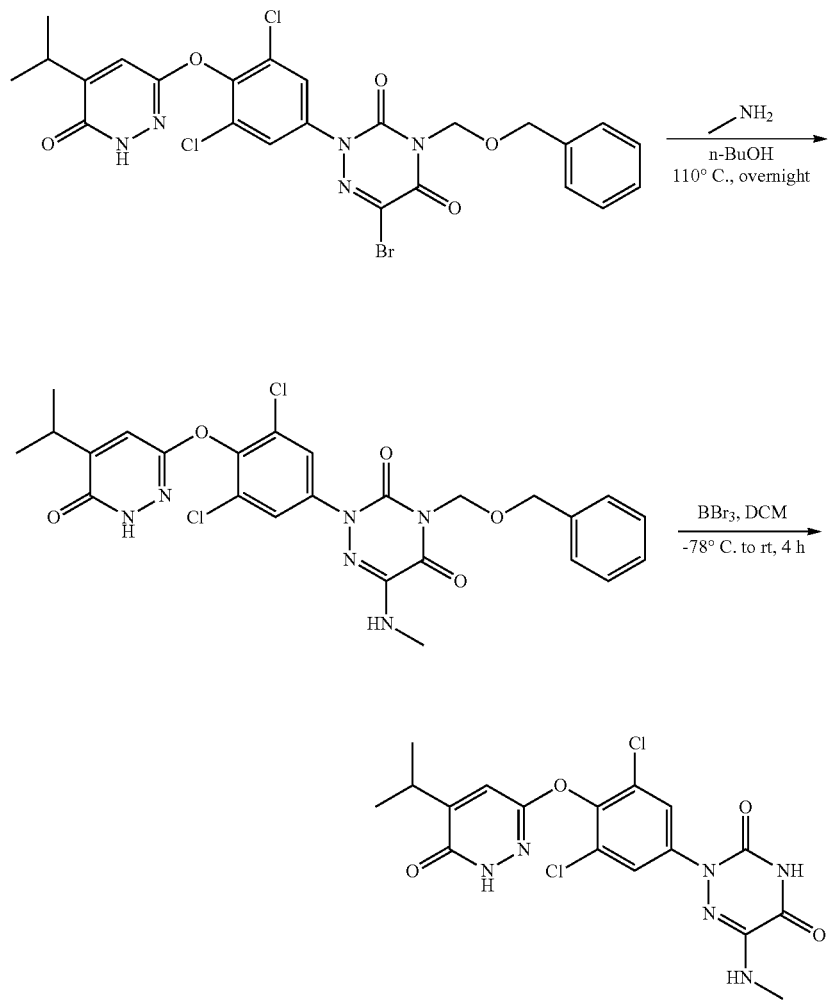

14

To a stirred solution of 4-[(benzyloxy)methyl]-6-bromo-2-[3,5-dichloro-4-[(5-isopropyl-6-oxo-1H-pyridazin-3-yl)oxy]phenyl]-1,2,4-triazine-3,5-di-one (400.00 mg, 0.657 mmol, 1.00 eq) in n-BuOH (5 mL) was added methylamine $^1$H NMR (300 MHz, DMSO-d$_6$) δ ppm: 12.99 (s, 1H), 12.23 (s, 1H), 8.82 (d, J=4.8 Hz, 1H), 8.16 (s, 2H), 7.42 (s, 1H), 3.03-3.08 (m, 1H), 2.79 (d, J=4.8 Hz, 3H), 1.20 (d, J=6.9 Hz, 6H).

Example 15: Synthesis Compound 15

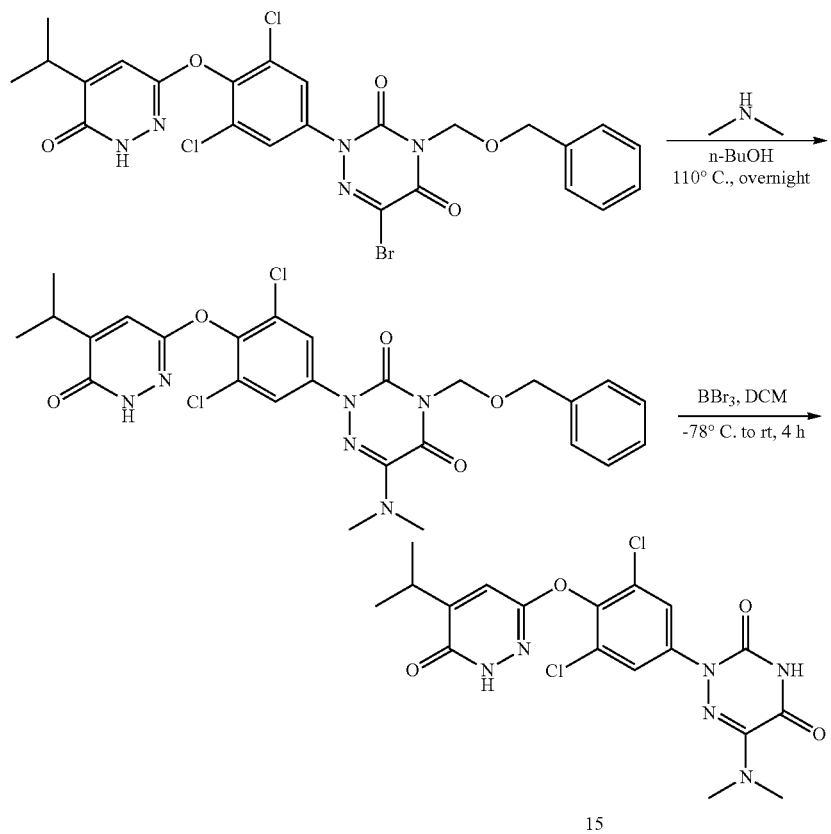

To a 50 mL round-bottom flask were added 4-[(benzyloxy)methyl]-6-bromo-2-[3,5-dichloro-4-[(5-isopropyl-6-oxo-1H-pyridazin-3-yl)oxy]phenyl]-1,2,4-triazine-3,5-dione (400.00 mg, 0.657 mmol, 1.00 eq) in n-BuOH (8 mL) and dimethylamine (3.3 mL, 6.565 mmol, 10.00 eq, 2 M in THF) at rt. The reaction mixture was stirred overnight at 110° C. The reaction mixture was concentrated under reduced pressure to afford the residue. The residue was purified to provide 170 mg (yield 41%) of 4-[(benzyloxy)methyl]-2-[3,5-dichloro-4-[(5-isopropyl-6-oxo-1H-pyridazin-3-yl)-oxy]phenyl]-6-(dimethylamino)-1,2,4-triazine-3,5-dione as a light pink solid.

A 50 mL round bottom flask was charged with 4-[(benzyloxy)methyl]-2-[3,5-dichloro-4-[(5-isopropyl-6-oxo-1H-pyridazin-3-yl)oxy]phenyl]-6-(dimethyl-amino)-1,2,4-triazine-3,5-dione (160.00 mg, 0.279 mmol, 1.00 eq), DCM (10.00 mL). BBr3 (279.61 mg, 1.116 mmol, 4.00 eq) was added at −78° C. The resulting solution was stirred 4 h at rt. The reaction mixture was concentrated under reduced pressure to afford the crude product. Purification resulted in 54.3 mg (yield 42%) of 2-[3,5-dichloro-4-[(5-isopropyl-6-oxo-1H-pyridazin-3-yl)oxy]phenyl]-6-(dimethylamino)-4H-1,2,4-triazine-3,5-dione.

$^1$HNMR (300 MHz, DMSO-$d_6$) δ ppm: 7.91 (s, 2H), 7.43 (s, 1H), 3.03-3.10 (m, 1H), 2.99 (d, J=8.1 Hz, 6H), 1.20 (d, J=6.9 Hz, 6H).

Example 16: Synthesis of Compounds 16 and 23

Compound 16

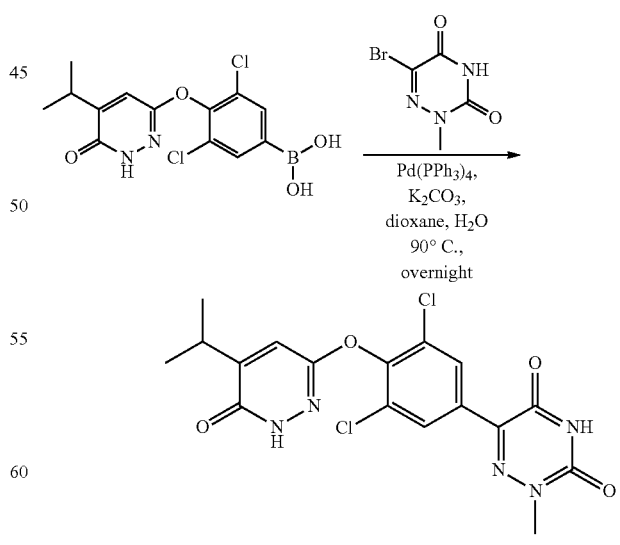

To a stirred mixture of 3,5-dichloro-4-[(5-isopropyl-6-oxo-1H-pyridazin-3-yl)oxy]phenylboronic acid (250.00 mg, 0.729 mmol, 1.00 eq), 6-bromo-2-methyl-4H-1,2,4-triazine-3,5-dione (180.19 mg, 0.875 mmol, 1.20 eq), K₂CO₃ (201.48 mg, 1.458 mmol, 2.00 eq) in dioxane (10 mL) and H₂O (1 mL) was added Pd(PPh₃)₄ (168.46 mg, 0.146 mmol, 0.20 eq) under nitrogen atmosphere. The resulting mixture was stirred overnight at 90° C. under nitrogen atmosphere. The reaction was quenched with water (15 mL) and extracted with EA (3×15 mL). The combined organic layers were washed with brine (2×15 mL), dried over anhydrous sodium sulfate filtered and concentrated under reduced pressure. The crude product was triturated with EA:PE of 1:5 and MeCN (5 mL), washed with ether (5 mL) to provide the desired product 6-[3,5-dichloro-4-[(5-isopropyl-6-oxo-1H-pyridazin-3-yl)oxy]phenyl]-2-methyl-4H-1,2,4-triazine-3,5-dione (103.8 mg, 34%) as a white solid.

¹H NMR (300 MHz, DMSO-d₆) δ ppm: 12.45 (br, 1H), 12.21 (s, 1H), 8.10 (s, 2H), 7.43 (s, 1H), 3.58 (s, 3H), 3.11-2.97 (m, 1H), 1.20 (d, J=6.9 Hz, 6H).

Compound 23

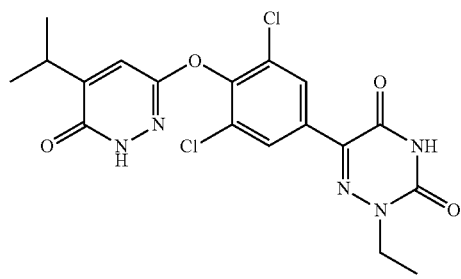

23

Compound 23 was prepared similarly as described for compound 16, using 6-bromo-2-ethyl-4H-1,2,4-triazine-3,5-dione instead of 6-bromo-2-methyl-4H-1,2,4-triazine-3,5-dione.

¹H NMR (300 MHz, DMSO-d₆) δ: 12.39 (s, 1H), 12.18 (s, 1H), 8.09 (s, 2H), 7.40-7.41 (m, 1H), 3.95-4.03 (m, 2H), 3.00-3.07 (m, 1H), 1.28 (t, J=7.0 Hz, 3H), 1.28 (t, J=6.9 Hz, 6H). LCMS (ESI, m/z): 438 [M+H]⁺.

Example 17: Synthesis of Compound 17

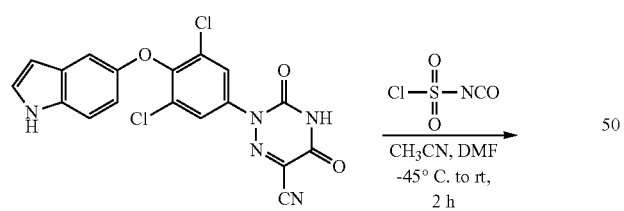

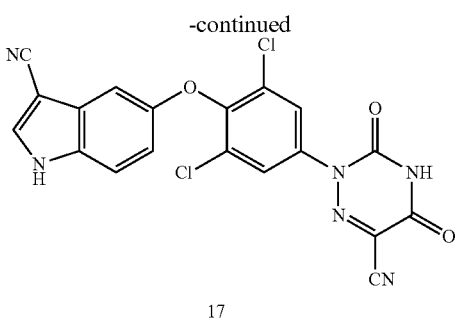

17

To a solution of 2-[3,5-dichloro-4-(1H-indol-5-yloxy)phenyl]-3,5-dioxo-4H-1,2,4-triazine-6-carbonitrile (250.0 mg, 0.604 mmol, 1.00 eq) in acetonitrile (4 mL) was added dropwise chlorosulfonyl isocyanate (102.5 mg, 0.724 mmol, 1.2 eq) in acetonitrile (0.4 mL) at −45° C. under nitrogen. Over the course of the addition a fine precipitate formed. The mixture was stirred at −45° C. under nitrogen for 10 min. N,N-dimethylformamide (4 mL) was then slowly added, and the mixture was allowed to warm to rt and stirred for 2 h. The reaction was quenched by the addition of water/ice (10 mL) at 0° C. The resulting mixture was extracted with ethyl acetate (3×15 mL). The combined organic layers were washed with water (3×10 mL), saturated NaHCO₃, and brine, dried anhydrous sodium sulfate, filtered and evaporated. The residue was purified by Prep-TLC with dichloromethane:methanol (12:1) to afford crude product (160 mg). The crude product (160 mg) was purified by Prep-HPLC with the following conditions (Column: Kinetex EVO C 18 Column, 30*150, 5 μm; Mobile Phase A: Water (0.05% TFA), Mobile Phase B: ACN; Flow rate: 60 mL/min; Gradient: 50% B to 50% B in 8 min) to provide 5-[2,6-dichloro-4-(6-cyano-3,5-dioxo-4H-1,2,4-triazin-2-yl)phenoxy]-1H-indole-3-carbonitrile (75.9 mg, 29% yield) of as a light yellow solid.

¹H NMR (300 MHz, DMSO-d₆) δ 13.30 (s, 1H), 12.28 (s, 1H), 8.28 (d, J=3.0 Hz, 1H), 7.84 (s, 2H), 7.58 (d, J=9.0 Hz, 1H), 6.97-7.01 (m, 1H), 6.86 (d, J=2.4 Hz, 1H).

Example 18: Synthesis of Compounds 18 and 19

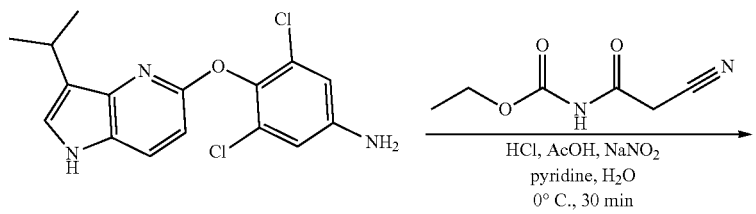

-continued

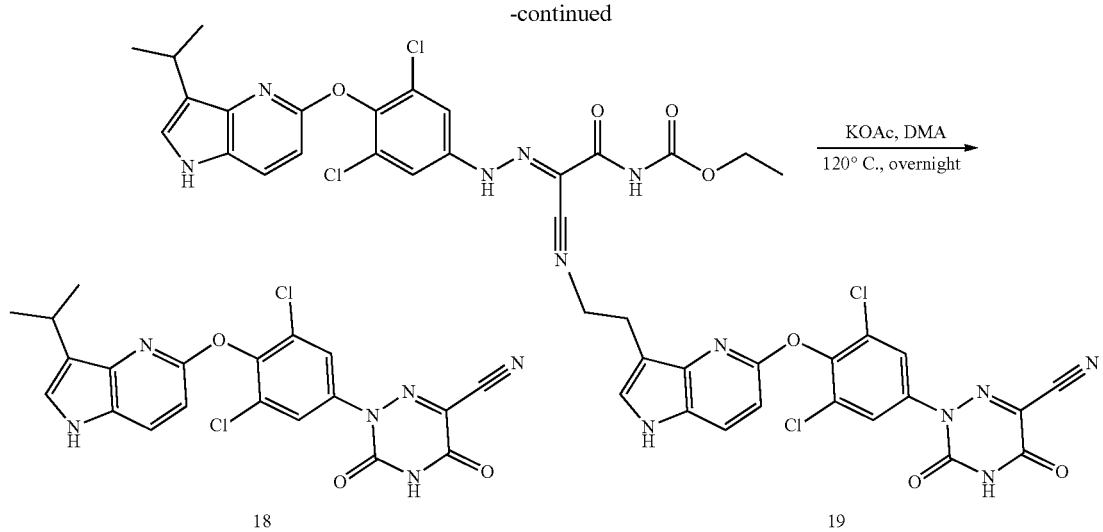

NaNO₂ (150.8 mg, 2.19 mmol, 2.1 eq) in H₂ (12 mL) was added dropwise to a solution of 3,5-dichloro-4-([3-isopropyl-1H-pyrrolo[3,2-b]pyridin-5-yl]oxy)aniline (350.0 mg, 1.04 mmol, 1.0 eq) in HCl (5.5 mL, conc.), AOH (16 mL) and H₂a (12 mL). The mixture was stirred for 30 min at 0° C. Then the reaction mixture was poured into a solution of ethyl N-(2-cyanoacetyl)carbamate (243.8 mg, 1.56 mmol, 1.5 eq) in H₂O (16 mL) and pyridine (5.5 mL) at 0° C. quickly. The resulting mixture was stirred at 0° C. for 30 min and filtered. The filter cake was washed with water (2×15 mL) and petroleum ether (2×15 mL) dried under reduced pressure to provide (350 mg, crude) ethyl N—[(E)-cyano ([2-[3,5-dichloro-4-([3-isopropyl-1H-pyrrolo[3,2-b]pyridin-5-yl]oxy)phenyl]hydrazin-1-ylidene])carbonyl]carbamate as a yellow solid.

LCMS (ESI, m/z): 503 [M+H]⁺.

To a solution of ethyl N—[(E)-cyano([2-[3,5-dichloro-4-([3-isopropyl-1H-pyrrolo[3,2-b]pyridin-5-yl]oxy)phenyl]hydrazin-1-ylidene])carbonyl]carbamate (350.00 mg, 0.695 mmol, 1.00 eq) in DMA (20 mL) was added KOAc (341.22 mg, 3.477 mmol, 5.00 eq). The resulting mixture was stirred overnight at 120° C. and quenched with water (30 mL). The resulting mixture was extracted with EA (3×40 mL) and the organic layers were combined, washed with brine (2×30 mL), dried over anhydrous sodium sulfate, filtered and concentrated under reduced pressure to afford crude product. The crude product was purified by TLC (Mobile phase: MeOH/DCM=1:7; Rf=0.4; detection: UV) to provide the crude product (180 mg). The product was separated by Prep-Chiral-HPLC Column: CHIRALPAK IE, 2*25 cm, 5 m; Mobile Phase A: Hex (0.1% FA)—HPLC, Mobile Phase B: EtOH—HPLC; Flow rate: 20 mL/min; Gradient: 10% B to 10% B in 21 min. Purification resulted in desired product 2-[3,5-dichloro-4-([3-isopropyl-1H-pyrrolo[3,2-b]pyridin-5-yl]oxy)phenyl]-3,5-dioxo-4H-1,2,4-triazine-6-carbonitrile (86.3 mg, 26%) as a yellow solid.

¹H NMR (300 MHz, DMSO-d₆) δ 13.25 (br, 1H), 11.00 (s, 1H), 7.82 (d, J=8.7 Hz, 1H), 7.76 (s, 2H), 7.28 (d, J=2.4 Hz, 1H), 6.89 (d, J=8.7 Hz, 1H), 2.78-2.95 (m, 1H), 1.13 (d, J=6.6 Hz, 6H).

LCMS (ESI, m/z): 457.0 [M+H]⁺.

The reaction also produces the by-product compound 2-[3,5-dichloro-4-([3-propyl-1H-pyrrolo[3,2-b]-pyridin-5-yl]oxy)phenyl]-3,5-dioxo-4H-1,2,4-triazine-6-carbonitrile (20.8 mg, 6%) as a yellow solid.

¹H NMR (300 MHz, DMSO-d₆) δ 13.26 (br, 1H), 11.03 (s, 1H), 7.82 (d, J=8.4 Hz, 1H), 7.76 (s, 2H), 7.33 (d, J=2.4 Hz, 1H), 6.87 (d, J=8.7 Hz, 1H), 2.42 (t, J=7.5 Hz, 2H), 1.45-1.58 (m, 2H), 0.77 (t, J=7.5 Hz, 3H). LCMS (ESI, m/z): 457.0 [M+H]⁺.

Example 19: Synthesis of Compounds 20, 21 and 22

Compound 21

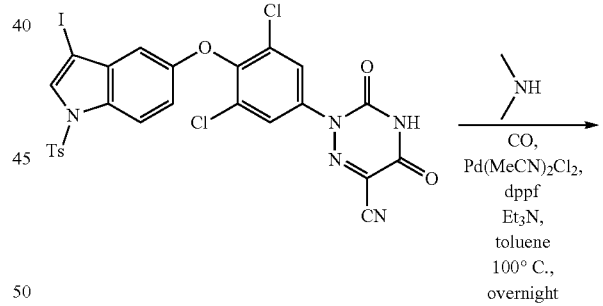

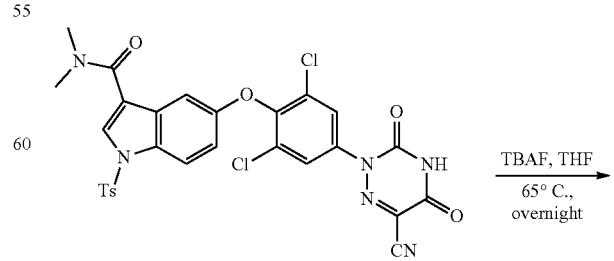

-continued

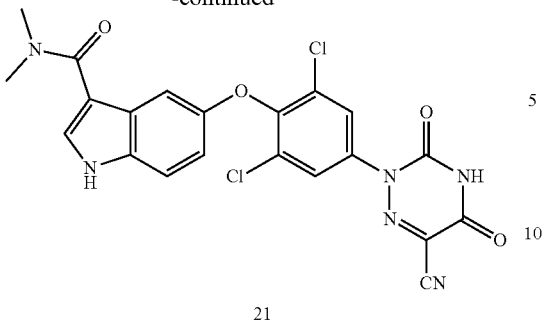

21

A 20 mL autoclave was charged with 2-(3,5-dichloro-4-[[3-iodo-1-(4-methylbenzenesulfonyl)indol-5-yl]oxy]phenyl)-3,5-dioxo-4H-1,2,4-triazine-6-carbo-nitrile (600.00 mg, 0.864 mmol, 1.00 eq), dimethylamine (2.59 mL, 2 M in tetrahydrofuran, 5.185 mmol, 6.00 eq), 1,1'-bis(diphenylphosphino)ferrocene (95.47 mg, 0.173 mmol, 0.20 eq), bis(acetonitrile)palladium(II) chloride (22.42 mg, 0.0864 mmol, 0.10 eq), triethylamine (262.35 mg, 2.593 mmol, 3.00 eq), toluene (15 mL). The contents of the autoclave were placed under an atmosphere of carbon monoxide (20 atm). The reaction was stirred overnight at 100° C. and quenched with water (10 mL). The resulting mixture was extracted with ethyl acetate (3×15 mL) and the organic layers were combined, washed with brine (3×15 mL), dried over anhydrous sodium sulfate. After filtration, the filtrate was concentrated under reduced pressure. The residue was chromatographed on a C18 column chromatography with $CH_3CN$:Water (3:2) to provide 300 mg (49% yield) of 5-[2,6-dichloro-4-(6-cyano-3,5-dioxo-4H-1,2,4-triazin-2-yl)phenoxy]-N,N-dimethyl-1-(4-methylbenzenesulfonyl)indole-3-carboxamide as a light brown solid.

LCMS (ESI, m/z): 637 [M−H]⁻.

To a stirred solution of 5-[2,6-dichloro-4-(6-cyano-3,5-dioxo-4H-1,2,4-triazin-2-yl)phenoxy]-N,N-dimethyl-1-(4-methylbenzenesulfonyl)indole-3-carbox-amide (200.00 mg, 0.313 mmol, 1.00 eq) in tetrahydrofuran (10 mL) was added tetrabutylammonium fluoride (1.25 mL, 1 M in tetrahydrofuran, 1.251 mmol, 4.00 eq) at room temperature under nitrogen atmosphere. The reaction mixture was stirred for overnight at 65° C. and quenched with water (5 mL). The resulting mixture was extracted with dichloromethane (3×20 mL) and the organic layers were combined, washed with brine (5×10 mL) and hydrochloric acid (1 M), dried over anhydrous sodium sulfate. After filtration, the filtrate was concentrated under reduced pressure. The crude product (150 mg) was purified by Prep-HPLC with the following conditions (Column: XBridge Shield RP18 OBD Column, 19*250 mm, 10 μm; Mobile Phase A: Water (10 mM $NH_4HCO_3$), Mobile Phase B: ACN; Flow rate: 25 mL/min; Gradient: 27% B to 47% B in 7 min) to provide 52 mg (34% yield) of 5-[2,6-dichloro-4-(6-cyano-3,5-dioxo-4H-1,2,4-triazin-2-yl)phenoxy]-N,N-dimethyl-1H-indole-3-carboxamide as a light yellow solid.

$^1$H NMR (300 MHz, Methanol-$d_4$) δ 7.76 (s, 1H), 7.68 (s, 2H), 7.41 (d, J=9.0 Hz, 1H), 7.08 (d, J=2.1 Hz, 1H), 6.90-6.94 (m, 1H), 3.13 (s, 6H).

LCMS (ESI, m/z): 485 [M+H]⁺.

Compound 20

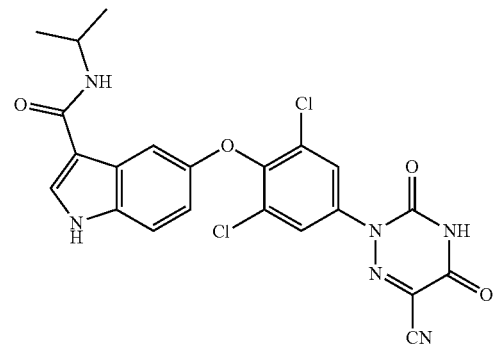

Compound 20 was prepared similarly as described for compound 21, using 2 eq of isopropylamine instead of 6 eq dimethylamine and reacting overnight at 80° C.

$^1$H NMR (300 MHz, Methanol-$d_4$) δ 7.89 (s, 1H), 7.77 (s, 2H), 7.50 (d, J=2.4 Hz, 1H), 7.38 (d, J=9.3 Hz, 1H), 6.87-6.91 (m, 1H), 4.12-4.16 (m, 1H), 1.21 (d, J=6.6 Hz, 6H).

LCMS (ESI, m/z): 499 [M+H]⁺.

Compound 22

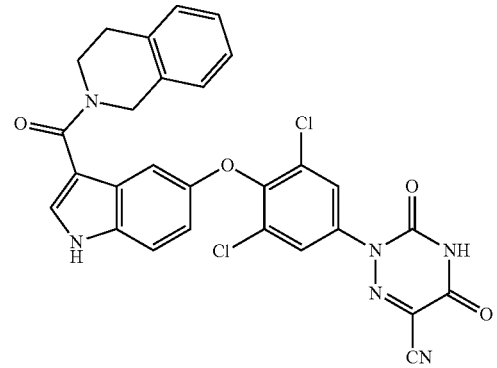

Compound 22 was prepared similarly as described for compound 21, using 1.5 eq tetrahydroisoquinoline instead of 6 eq dimethylamine.

$^1$H NMR (400 MHz, Methanol-$d_4$) δ 7.70 (d, J=8.4 Hz, 3H), 7.45 (d, J=8.8 Hz, 1H), 7.15-7.17 (m, 3H), 7.07 (br, 1H), 6.93-6.99 (m, 1H), 6.91-6.92 (m, 1H), 4.78 (s, 2H), 3.86 (t, J=6.0 Hz, 2H), 2.87 (t, J=5.8 Hz, 2H).

LCMS: 573 [M+H]⁺.

Example 20: Synthesis of Compounds 24, 25 and 26

Compound 25

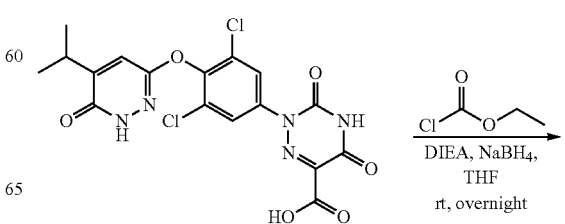

-continued

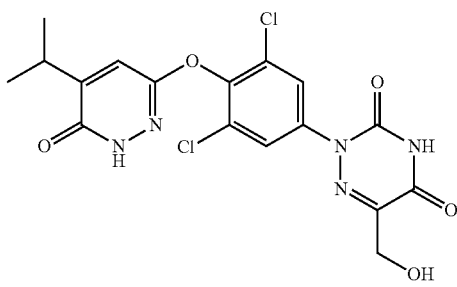

25

To a solution of 2-[3,5-dichloro-4-[(5-isopropyl-6-oxo-1H-pyridazin-3-yl)oxy]phenyl]-3,5-dioxo-4H-1,2,4-triazine-6-carboxylic acid (500 mg, 1.101 mmol, 1.00 eq) and N,N-diisopropylethylamine (298.77 mg, 2.312 mmol, 2.10 eq) in tetrahydrofuran (30 mL) at 0° C. under nitrogen was added ethyl chloroformate (126.62 mg, 1.167 mmol, 1.06 eq) dropwise. The mixture was stirred for 1 h at room temperature and treated dropwise with a solution of sodium borohydride (124.94 mg, 3.302 mmol, 3.00 eq) in water (2 mL) at 0° C. The resulting solution was stirred overnight at room temperature and then quenched slowly with saturated NaHCO₃ solution (10 mL). The resulting mixture was extracted with chloroform/isopropanol (3/1) (5×30 mL) and the organic layers were combined, dried over anhydrous sodium sulfate, filtered and concentrated under reduced pressure to provide the crude product. The crude product (400 mg) was purified by preparative HPLC using the following gradient conditions: Column: XSelect CSH Prep C18 OBD Column, 5 m, 19*150 mm; Mobile Phase A: Water (10 mM $NH_4HCO_3$+0.1% $NH_3·H_2O$), Mobile Phase B: ACN; Flow rate: 25 mL/min; Gradient: 19% B to 31% B in 8 min), resulting in of 2-[3,5-dichloro-4-[(5-isopropyl-6-oxo-1H-pyridazin-3-yl)oxy]phenyl]-6-(hydroxymeth-yl)-4H-1,2,4-triazine-3,5-dione (100.6 mg, 21% yield) as a white solid.

¹H NMR (300 MHz, DMSO-d₆) δ 12.48 (br, 1H), 12.22 (br, 1H), 7.86 (s, 2H), 7.44 (s, 1H), 5.30 (t, J=6.0 Hz, 1H), 4.40 (d, J=6.0 Hz, 2H), 3.02-3.11 (m, 1H), 1.20 (d, J=6.9 Hz, 6H).

LCMS (ESI, m/z): 440 [M+H]⁺.

Compound 24

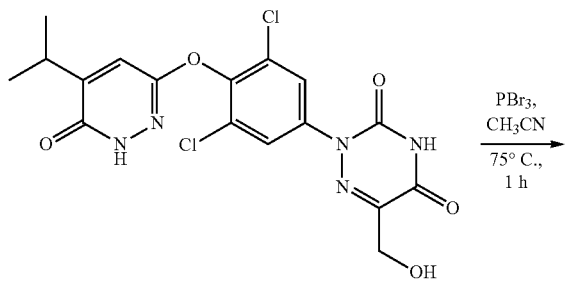

-continued

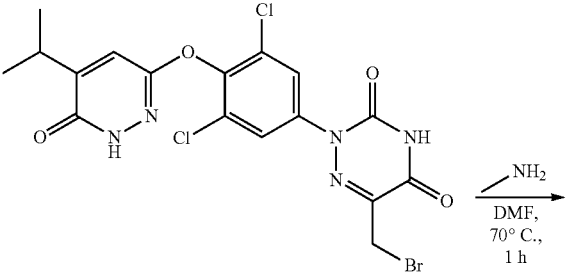

25

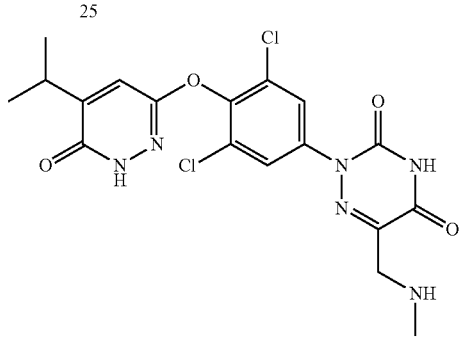

24

A 50-mL round-bottom flask was charged with 2-[3,5-dichloro-4-[(5-isopropyl-6-oxo-1H-pyridazin-3-yl)oxy]phenyl]-6-(hydroxymethyl)-4H-1,2,4-triazine-3,5-dione (1.60 g, 3.634 mmol, 1.00 eq), acetonitrile (15 mL). Phosphorus tribromide (0.3 mL) was added at 0° C. under nitrogen. The resulting solution was stirred for 1 h at 75° C. The mixture was cooled to room temperature and then quenched with saturated NaHCO₃ aqueous (10 mL). The resulting mixture was extracted with ethyl acetate (3×15 mL) and the organic layers were combined, washed with brine (1×30 mL), dried over anhydrous sodium sulfate, filtered and concentrated under reduced pressure to provide 1.1 g (39% yield) of 6-(bromomethyl)-2-[3,5-dichloro-4-[(5-isopropyl-6-oxo-1H-pyridazin-3-yl)oxy]phenyl]-4H-1,2,4-triazine-3,5-dione as a yellow solid.

LCMS (ESI, m/z): 502 [M+H]⁺.

A 50-mL round-bottom flask was charged with 6-(bromomethyl)-2-[3,5-dichloro-4-[(5-isopropyl-6-oxo-1H-pyridazin-3-yl)oxy]phenyl]-4H-1,2,4-tri-azine-3,5-dione (400 mg, 0.795 mmol, 1.00 eq), methylamine (1.2 mL, 2 M in tetrahydrofuran, 2.385 mmol, 3.00 eq) and N,N-dimethylformamide (8 mL). The mixture was stirred for 1 h at 70° C. The mixture was cooled to room temperature and diluted with water (5 mL). At this time, it was acidified by the addition of 1 N hydrochloric acid (5 mL) and was extracted with ethyl acetate (3×10 mL). The organic layer was discarded. The aqueous layer was made basic by the addition saturated NaHCO₃ solution (15 mL) and extracted with a mixture solution of chloroform:isopropanol of 3:1 (5×30 mL) and the organic layers were combined, dried over anhydrous sodium sulfate, filtered and concentrated under reduced pressure to provide the crude product. The crude product (300 mg) was purified by preparative HPLC using the following gradient conditions: Column: XBridge Prep OBD C18 Column, 30×150 mm 5 μm; Mobile Phase A: Water (10 mM $NH_4HCO_3$+0.1% $NH_3·H_2O$), Mobile Phase B: ACN; Flow rate: 60 mL/min; Gradient: 17% B to 35% B in 8 min. Purification resulted in of 2-[3,5-dichloro-4-[(5-isopropyl-6-oxo-1H-pyridazin-3-yl)oxy]phenyl]-6-[(methylamino)methyl]-4H-1,2,4-triazine-3,5-dione (64.8 mg, 18% yield) as a white solid. $^1$H NMR (300 MHz, DMSO-$d_6$) δ 12.23 (br, 1H), 7.88 (s, 2H), 7.43 (s, 1H), 3.83 (s, 2H), 3.01-3.19 (m, 1H), 2.51 (s, 3H), 1.20 (d, J=6.9 Hz, 6H). LCMS (ESI, m/z): 453 [M+H]$^+$.

Compound 26

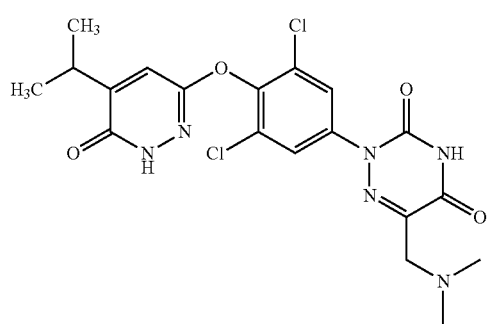

Compound 26 was prepared similarly as described for compound 24, using dimethylamine instead methylamine and reacting at 60° C. for 1 h. $^1$H NMR (300 MHz, DMSO-$d_6$) δ 12.21 (br, 1H), 7.80 (s, 2H), 7.45 (s, 1H), 3.37 (br, 2H), 3.03-3.08 (m, 1H), 2.25 (s, 6H), 1.20 (d, J=6.9 Hz, 6H). LCMS (ESI, m/z): 467 [M+H]$^+$.

Example 21: Synthesis of Compound 27

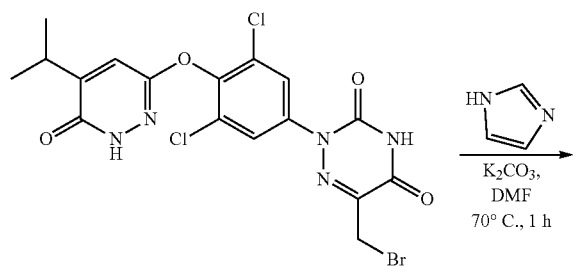

-continued

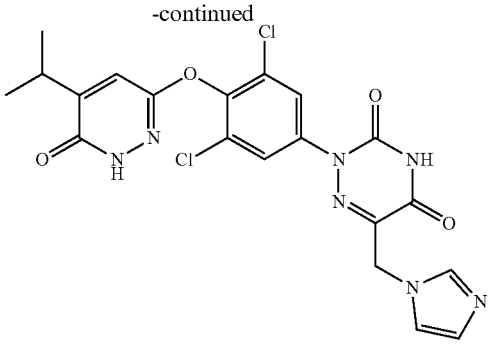

A 100-mL round-bottom flask was charged with 6-(bromomethyl)-2-[3,5-dichloro-4-[(5-isopropyl-6-oxo-1H-pyridazin-3-yl)oxy]phenyl]-4H-1,2,4-triazine-3,5-dione (400.00 mg, 0.795 mmol, 1.00 eq), imidazole (64.95 mg, 0.954 mmol, 1.20 eq), potassium carbonate (219.75 mg, 1.590 mmol, 2.00 eq) and N,N-dimethylformamide (8 mL). The mixture was stirred for 1 h at 70° C. and was subsequently cooled to room temperature and diluted with water (5 mL). At this time, it was acidified by the addition of 1 N hydrochloric acid (5 mL) and was extracted with ethyl acetate (3×10 mL). The organic layer was discarded. The aqueous layer was made basic by the addition saturated NaHCO$_3$ solution (15 mL) and extracted with a mixture of chloroform:isopropanol of 3:1 (5×30 mL) and the organic layers were combined, dried over anhydrous sodium sulfate, filtered and concentrated under reduced pressure to provide the crude product. The crude product (150 mg) was purified by preparative HPLC using the following gradient conditions: Column: XBridge Prep OBD C18 Column, 30×150 mm, 5 m; Mobile Phase A: Water (10 mM NH$_4$HCO$_3$+0.1% NH$_3$·H$_2$O), Mobile Phase B: ACN; Flow rate: 60 mL/min; Gradient: 19% B to 37% B in 8 min; Purification resulted in of 2-[3,5-dichloro-4-[(5-isopropyl-6-oxo-1H-pyridazin-3-yl)oxy]phenyl]-6-(imidazol-1-ylmethyl)-4H-1,2,4-triazine-3,5-dione (14.5 mg, 4% yield) as a white solid.

$^1$H NMR (300 MHz, DMSO-$d_6$) δ 12.19 (s, 1H), 7.74 (s, 2H), 7.69 (s, 1H), 7.43 (s, 1H), 7.21 (s, 1H), 6.90 (s, 1H), 5.15 (s, 2H), 3.02-3.09 (m, 1H), 1.19 (d, J=6.9 Hz, 6H). LCMS (ESI, m/z): 490 [M+H]$^+$.

Example 22. Synthesis of Compound 28

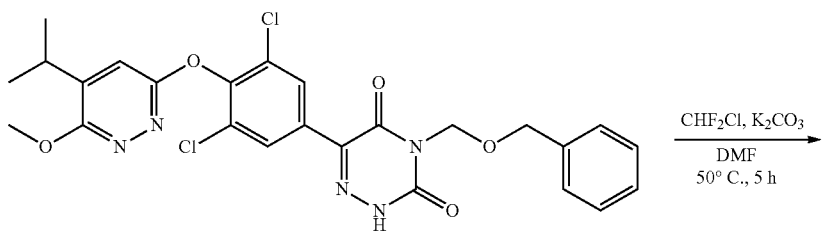

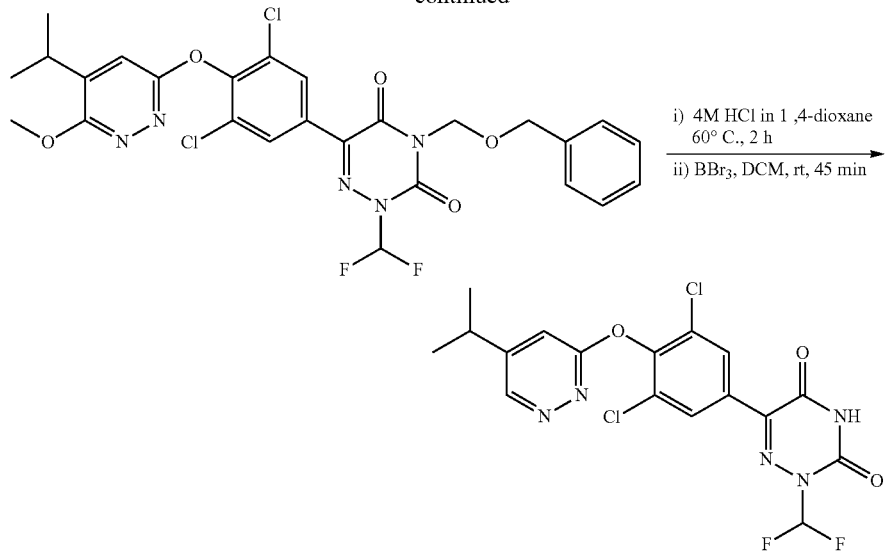

To a stirred mixture of 4-[(benzyloxy)methyl]-6-[3,5-dichloro-4-[(5-isopropyl-6-methoxypyridazin-3-yl)oxy]phenyl]-2H-1,2,4-triazine-3,5-dione (310 mg, 0.569 mmol, 1.00 eq) and $K_2CO_3$ (630 mg, 4.56 mmol, 8.00 eq) in DMF (20 mL) was bubbled with difluorochloromethane for 4 h and the mixture was stirred for 5 h at 50° C. The reaction was quenched by the addition of water (50 mL). The resulting mixture was extracted with EA (3×30 mL). The combined organic layers were washed with water (150 mL), dried over anhydrous $Na_2SO_4$, filtered and concentrated under reduced pressure. The residue was purified by silica gel column chromatography (eluting with PE:EA of 2:1) to afford 230 mg (65% yield) of 4-[(benzyloxy)methyl]-6-[3,5-dichloro-4-[(5-isopropyl-6-methoxypyridazin-3-yl)oxy]phenyl]-2-(difluoromethyl)-1,2,4-triazine-3,5-dione as a light yellow solid.

LCMS (ESI, m/z): 594 [M+H]$^+$.

4-[(Benzyloxy)methyl]-6-[3,5-dichloro-4-[(5-isopropyl-6-methoxy-pyridazin-3-yl)oxy]phenyl]-2-(difluoromethyl)-1,2,4-triazine-3,5-dione (230 mg, 0.387 mmol, 1.00 eq) in a solution of hydrogen chloride (4 mL, 4M in 1,4-dioxane) was stirred for 2 h at 60° C. After cooled down to 25° C., the resulting mixture was concentrated under vacuum. The residue was then diluted with DCM (5 mL) and added a solution of $BBr_3$ (1.5 mL, 1 M in DCM) dropwise at 25° C. The final reaction mixture was stirred for 45 min at 25° C. The reaction was quenched by the addition of water (1 mL). The resulting mixture was concentrated under reduced pressure. The residue was purified by reverse phase chromatography (column: $C_{18}$ silica gel; Mobile phase, A: water (containing 10 mM $NH_4HCO_3$) and B: ACN (0% to 50% over 15 min); Detector: UV 220/254 nm). The product fractions were lyophilized to afford 113.4 mg (63% yield) of 6-[3,5-dichloro-4-[(5-isopropyl-6-oxo-1H-pyridazin-3-yl)oxy]phenyl]-2-(difluoromethyl)-4H-1,2,4-triazine-3,5-dione as a white solid.

$^1$H NMR (400 MHz, DMSO-d$_6$) δ ppm: 12.78 (br s, 1H), 12.22 (br s, 1H), 7.99 (s, 2H), 7.83 (t, J=57.2 Hz, 1H), 7.45 (s, 1H), 3.13-2.98 (m, 1H), 1.20 (d, J=7.2 Hz, 6H). LCMS (ESI, m/z): 460 [M+H]$^+$.

Example 23 Synthesis of Compound 29

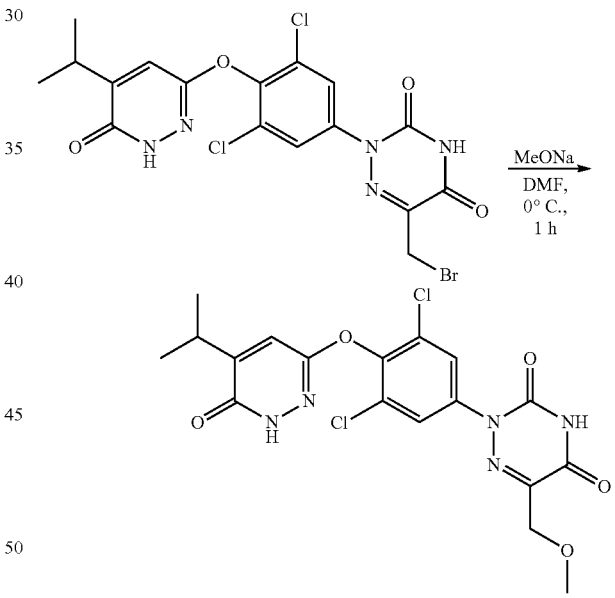

A 50-mL round-bottom flask was charged with 6-(bromomethyl)-2-[3,5-dichloro-4-[(5-isopropyl-6-oxo-1H-pyridazin-3-yl)oxy]phenyl]-4H-1,2,4-triazine-3,5-dione (400 mg, 0.795 mmol, 1.00 eq), N,N-dimethylformamide (8 mL) under nitrogen. Sodium methylate (0.50 mL, 30% w/w in methanol) was added at 0° C. The mixture was stirred for 1 h at 0° C. The mixture was acidified by the addition of 1 N hydrochloric acid (5 mL) and was extracted with ethyl acetate (3×15 mL). The organic layer was washed with brine (2×30 mL), dried over anhydrous sodium sulfate, filtered and concentrated under reduced pressure. The residue was chromatographed on a silica gel column with dichloromethane/methanol (10/1) to provide the crude product (150 mg)

and then was purified by preparative HPLC using the following gradient conditions: Column: XSelect CSH Prep C18 OBD Column, 5 μm, 19*150 mm; Mobile Phase A: Water (0.1% FA), Mobile Phase B: ACN; Flow rate: 25 mL/min; Gradient: 31% B to 51% B in 8 min; Purification resulted in 2-[3,5-dichloro-4-[(5-isopropyl-6-oxo-1H-pyridazin-3-yl)oxy]phenyl]-6-(methoxymethyl)-4H-1,2,4-triazine-3,5-dione (26.2 mg, 7% yield) of as a white solid.

$^1$H NMR (300 MHz, DMSO-d$_6$) δ 12.53 (s, 1H), 12.22 (s, 1H), 7.80 (s, 2H), 7.45 (s, 1H), 4.32 (s, 2H), 3.03-3.07 (m, 1H), 2.48 (s, 3H), 1.20 (d, J=6.9 Hz, 6H).

LCMS (ESI, m/z): 454 [M+H]$^+$.

Example 24 Synthesis of Compound 30

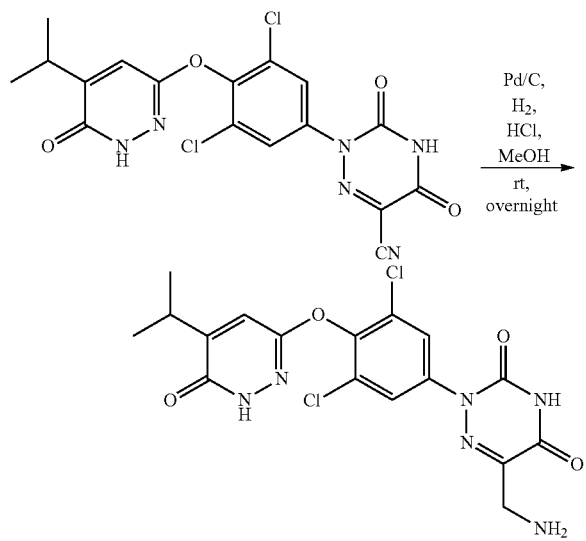

30

A 100-mL round-bottom flask was charged with 2-[3,5-dichloro-4-[(5-isopropyl-6-oxo-1H-pyridazin-3-yl)oxy]phenyl]-3,5-dioxo-4H-1,2,4-triazine-6-carbo-nitrile (300.00 mg, 0.689 mmol, 1.00 eq), concentrated hydrochloric acid (2 mL), Pd/C (30.00 mg, 0.282 mmol, 0.41 eq), methanol (30.00 mL, 0.936 mmol, 1.36 eq) under hydrogen. The resulting solution was stirred overnight at room temperature and then filtered through celite. The celite pad was washed with methanol (5×30 mL), the filtrate was collected and concentrated under reduced pressure. The residue was diluted with saturated NaHCO$_3$ solution (10 ml) and extracted with chloroform:isopropanol (3:1) (5×15 mL) and the organic layers were combined, dried over anhydrous sodium sulfate, filtered and concentrated under reduced pressure. The crude product (300 mg) was purified by preparative HPLC using the following gradient conditions: Column: Kinetex EVO C18 Column, 30*150, 5 m; Mobile Phase A: Water (10 mM NH$_4$HCO$_3$+0.1% NH$_3$·H$_2$O), Mobile Phase B: ACN; Flow rate: 25 mL/min; Gradient: 5% B to 30% B in 9 min. Purification resulted in 6-(aminomethyl)-2-[3,5-dichloro-4-[(5-isopropyl-6-oxo-1H-pyridazin-3-yl)oxy]phenyl]-4H-1,2,4-triazine-3,5-dione (29.6 mg, 10% yield) of a white solid. $^1$H NMR (300 MHz, DMSO-d$_6$) δ 7.93 (s, 2H), 7.42 (s, 1H), 3.84 (br, 2H), 3.02-3.07 (m, 1H), 1.20 (d, J=6.9 Hz, 6H). LCMS (ESI, m/z): 439 [M+H]$^+$.

Example 25. Synthesis of Compound 31

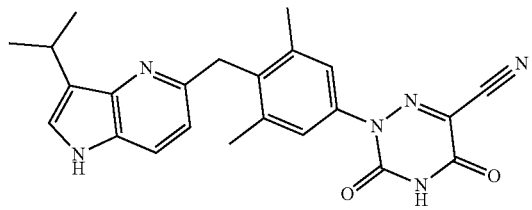

31

To a mixture of 4-[[3-isopropyl-1-(p-tolylsulfonyl)pyrrolo[3,2-b]pyridin-5-yl]methyl]-3,5-dimethyl-aniline (70 mg, 156.39 μmol, 1 eq), con. HCl (87.97 μL, 6.75 eq) in H$_2$O (1 mL) was added dropwise a solution of sodium nitrite (14.84 mg, 215.04 μmol, 1.38 eq) in H$_2$O (1 mL) while maintaining the temperature below 0° C. After the completion of addition, the reaction mixture was stirred for 0.5 h. A mixture of ethyl N-(2-cyanoacetyl)carbamate (27.47 mg, 175.94 μmol, 1.13 eq) and NaOAc (43.30 mg, 527.83 μmol, 3.38 eq) in EtOH (3 mL) was added drop-wise to the resulting diazonium salt solution below 0° C. and stirred for a further 2 h. The reaction mixture (combined with another 50 mg batch) was diluted with H$_2$O (10 mL), adjusted to pH 7~8 by sat. aq. NaHCO$_3$, then extracted with EA (50 mL×3). The combined organic layers were washed with brine (100 mL), dried over anhydrous Na$_2$SO$_4$, filtered and concentrated to give a residue The residue was purified by flash silica gel chromatography (Ethyl acetate in Petroleum ether=0~35%) to give ethyl N-[(2E)-2-cyano-2-[[4-[[3-isopropyl-1-(p-tolylsulfonyl)pyrrolo[3,2-b]pyridin-5-yl]methyl]-3,5-dimethyl-phenyl]hydrazono]acetyl]carbamate (75 mg, 31% yield) as a yellow solid.

A mixture of ethyl N-[(2E)-2-cyano-2-[[4-[[3-isopropyl-1-(p-tolylsulfonyl)pyrrolo[3,2-b]pyridin-5-yl]methyl]-3,5-dimethyl-phenyl]hydrazono]-acetyl]carbamate (55 mg, 89.47 μmol, 1 eq) and NaOAc (36.70 mg, 447.36 μmol, 5 eq) in AcOH (5 mL) was stirred at 130° C. for 5 h. AcOH was removed under reduced pressure, the residue was diluted with H$_2$O (50 mL), adjusted to pH 7~8 by sat. aq. NaHCO$_3$, then extracted with EA (50 mL×3). The combined organic layers were washed with brine (50 mL), dried over anhydrous Na$_2$SO$_4$, filtered and concentrated under reduced pressure to give 2-[4-[[3-isopropyl-1-(p-tolylsulfonyl)pyrrolo[3,2-b]pyridin-5-yl]methyl]-3,5-dimethyl-phenyl]-3,5-dioxo-1,2,4-triazine-6-carbonitrile (65 mg) as a yellow solid, which was directly used in the next step without further purification.

To a solution of 2-[4-[[3-isopropyl-1-(p-tolylsulfonyl)pyrrolo[3,2-b]pyridin-5-yl]methyl]-3,5-dimethyl-phenyl]-3,5-dioxo-1,2,4-triazine-6-carbonitrile (60 mg, 105.51 μmol, 1 eq) in THF (5 mL) was added TBAF (1 M in THF, 2.53 mL, 24 eq) in one portion at 20° C. Then the resulting mixture was stirred at 65° C. for 8 h under N$_2$. LCMS showed the reaction was complete. The mixture was diluted with H$_2$O (100 mL) and extracted with EA (50 mL×3). The combined organic layers were washed with sat. aq. NH$_4$Cl (100 mL×3), dried over anhydrous Na$_2$SO$_4$, filtered and concentrated under reduced pressure to give crude product, which was purified by prep. HPLC [Column: Welch Xtimate C18 150*30 mm, 5 μm; Mobile phase: from 15% ACN in water (0.225% FA) to 45% ACN in water (0.225% FA)] to give 2-[4-[(3-isopropyl-1H-pyrrolo[3,2-b]pyridin-5-yl)methyl]-

3,5-dimethyl-phenyl]-3,5-dioxo-1,2,4-triazine-6-carbonitrile (25 mg, 56% yield, 98.3% purity) as a light yellow solid.

¹H NMR (400 MHz, DMSO-d₆) δ 13.11-12.66 (m, 1H), 10.83 (br s, 1H), 7.57 (d, J=8.4 Hz, 1H), 7.30 (d, J=2.1 Hz, 1H), 7.15 (s, 2H), 6.70 (d, J=8.4 Hz, 1H), 4.24 (s, 2H), 3.20 (td, J=6.8, 13.7 Hz, 1H), 2.39 (s, 6H), 1.33 (d, J=6.9 Hz, 6H).

Example 26. Synthesis of Compound 32

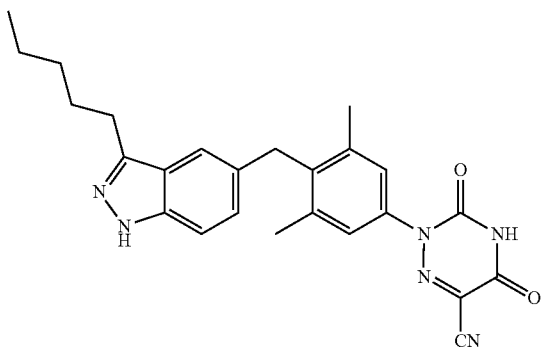

A solution of NaNO₂ (2.1 eq, 45 mg) in water (6.5 mL) was added to a solution of 3,5-dimethyl-4-((3-pentyl-1H-indazol-5-yl)methyl)aniline (1 eq, 100 mg, 0.31 mmol) in HCl 37% (106 eq, 2.7 mL), acetic acid (8.3 mL) and water (6.5 mL) at 0° C. under N₂. The reaction mixture was stirred at 0° C. for 1 h. In parallel, a solution of ethyl N-(2-cyanoacetyl)carbamate (1.5 eq, 73 mg) in water (7.8 mL) and pyridine (2.7 mL) was stirred at 0° C. for 15 min. The first reaction mixture was quickly added to the second one. The resulting reaction mixture was stirred at 0° C. for 2 h.

The precipitate was filtered and washed with water and petroleum ether to give ethyl-(2-cyano-2-(2-(3,5-dimethyl-4-((3-pentyl-1H-indazol-5-yl)methyl)-phenyl)hydrazineylidene)acetyl)carbamate (13 mg) as a yellow solid. The filtrate was extracted with DCM (3×50 mL) and the combined organic phases were dried over MgSO₄, filtered and evaporated to dryness to give ethyl-(2-cyano-2-(2-(3,5-dimethyl-4-((3-pentyl-1H-indazol-5-yl)methyl)phenyl)hydrazineylidene)acetyl)-carbamate (225 mg) as a yellow solid. The crude was used as such in the next step.

Sodium acetate (4 eq, 102 mg) was added to a solution of ethyl-(2-cyano-2-(2-(3,5-dimethyl-4-((3-pentyl-1H-indazol-5-yl)methyl)phenyl)hydrazineylid-ene)acetyl)carbamate (1 eq, 152 mg, 0.31 mmol) in acetic acid (5 mL) under N₂. The reaction mixture was heated to reflux for 4 h and then cooled to 0° C., water (10 mL) was added and the mixture was stirred for 30 min. Then, the precipitate was filtered, washed with water and petroleum ether and purified by flash chromatography on silica gel (0 to 10% MeOH in DCM) to give 40 mg of a red solid which was further triturated in Et₂O and iPr₂O to give compound 32 (20 mg, 15%) as an orange solid. ¹H-NMR (DMSO, 400 MHz): 0.83 (t, J=2.5 Hz, 3H); 1.27 (br, s, 4H); 1.63-1.70 (quint, J=7.7 Hz, 2H); 2.28 (s, 6H); 2.80 (t, J=7.2 Hz, 2H); 4.15 (s, 2H); 7.00 (d, J=8.8 Hz, 1H); 7.18 (s, 2H); 7.27 (s, 1H); 7.35 (d, J=8.8 Hz, 1H); 12.51 (s, 1H); 12.99 (s, 1H)

Example 27. Synthesis of Compound 33

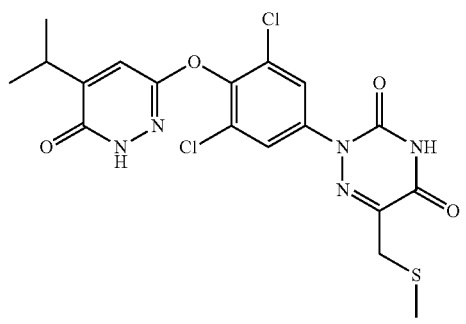

A 50 mL round-bottom flask was charged with 2-[3,5-dichloro-4-[(5-iso-propyl-6-oxo-1H-pyridazin-3-yl)oxy]phenyl]-6-(hydroxymethyl)-4H-1,2,4-triazine-3,5-dione (1.60 g, 3.63 mmol), CH₃CN (15 mL). PBr₃ (0.3 mL) was added at 0° C. under N₂. The resulting solution was stirred for 1 h at 75° C. The mixture was cooled to rt and then quenched with NaHCO₃ (sat., aq., 10 mL). The resulting mixture was extracted with EA (3×15 mL) and the organic layers were combined, washed with brine (1×30 mL), dried over anhyd. Na₂SO₄, filtered and concentrated under reduced pressure to provide 6-(bromomethyl)-2-[3,5-dichloro-4-[(5-isopropyl-6-oxo-1H-pyridazin-3-yl)oxy]phenyl]-4H-1,2,4-triazine-3,5-dione as a yellow solid (1.1 g, 39%).

A 50 mL round-bottom flask was charged with 6-(bromomethyl)-2-[3,5-dichloro-4-[(5-isopropyl-6-oxo-1H-pyridazin-3-yl)oxy]phenyl]-4H-1,2,4-triazine-3,5-dione (300 mg, 0.60 mmol), DMF (8 mL). NaSCH₃ (125 mg, 1.79 mmol) was added at 0° C. The mixture was acidified by the addition of 1 N aq. HCl (5 mL) and was extracted with EA (3×15 mL). The organic layers were combined, washed with brine (2×50 mL), dried over anhyd. Na₂SO₄, filtered and concentrated under reduced pressure. The residue was purified on a silica gel column with PE:EA (1:3) to provide the crude product (150 mg) and then was purified by preparative HPLC. Purification resulted in 2-[3,5-dichloro-4-[(5-isopropyl-6-oxo-1H-pyridazin-3-yl)oxy]phenyl]-6-[(methylsulfanyl)-methyl]-4H-1,2,4-triazine-3,5-dione as an off-white solid (32.9 mg, 12%). ¹H NMR (300 MHz, DMSO-d₆) δ 12.55 (br, 1H), 12.21 (s, 1H), 7.81 (s, 2H), 7.45 (s, 1H), 3.54 (s, 2H), 3.01-3.10 (m, 1H), 2.11 (s, 3H), 1.20 (d, J=6.6 Hz, 6H). LCMS (ESI, m/z): 470 [M+H]⁺.

Example 28. Synthesis of Compound 34

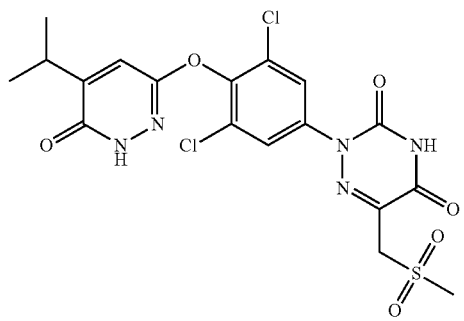

A 50 mL round-bottom flask was charged with 6-(bromomethyl)-2-[3,5-dichloro-4-[(5-isopropyl-6-oxo-1H-pyridazin-3-yl)oxy]phenyl]-4H-1,2,4-triazine-3,5-dione (480 mg, 0.954 mmol), DMF (8 mL), CH$_3$SO$_2$Na (292 mg, 2.86 mmol). The mixture was stirred for 1 h at 60° C. The mixture was acidified by the addition of HCl (aq., 1N, 5 mL) and was extracted with EA (3×15 mL). The organic layers were combined, washed with brine (2×50 mL), dried over anhyd. Na$_2$SO$_4$, filtered and concentrated under reduced pressure. The residue was purified on a silica gel column with DCM:MeOH (10:1) to provide the crude product and then was purified by preparative HPLC to afford 2-[3,5-dichloro-4-[(5-isopropyl-6-oxo-1H-pyridazin-3-yl)oxy]-phenyl]-6-(methanesulfonylmethyl)-4H-1,2,4-triazine-3,5-dione as a white solid (70.8 mg, 15%).

$^1$H NMR (300 MHz, DMSO-d$_6$) δ 12.74 (br, 1H), 12.22 (s, 1H), 7.84 (s, 2H), 7.45 (s, 1H), 4.48 (s, 2H), 3.01-3.11 (m, 4H), 1.20 (d, J=6.9 Hz, 6H). LCMS (ESI, m/z): 502 [M+H]$^+$.

Example 29. Synthesis of Compound 35

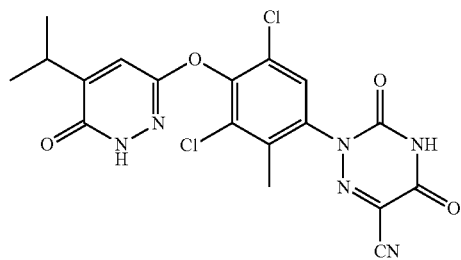

35-A

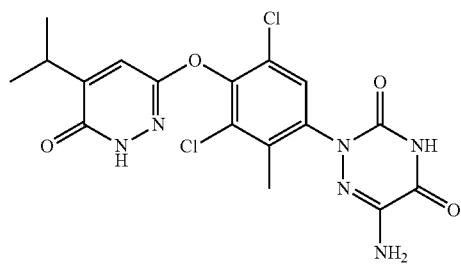

35

A 500 mL round-bottom was charged with 3-methyl-4-nitrophenol (4.50 g, 29.4 mmol), benzyltrimethylammonium tetrachloroiodate (24.6 g, 58.8 mmol), AcOH (600 mL). The reaction was stirred 18 h at 70° C. The solids were removed by filtration and washed with AcOH (300 mL). The organic layers were concentrated under reduced pressure. The residue was dissolved in EA:water (500 mL:250 mL). The organic layer was separated, washed with brine (2×200 mL), dried over anhyd. Na$_2$SO$_4$, filtered and concentrated under reduced pressure. The crude product was purified on a silica gel column with EA:PE (4:94) to provide 2,6-dichloro-3-methyl-4-nitrophenol as a brown solid (4.9 g, 64%).

A 250 mL vial was charged with 2,6-dichloro-3-methyl-4-nitrophenol (5.00 g, 22.5 mmol), Fe powder (6.29 g, 113 mmol), NH$_4$C$_1$ (9.64 g, 180 mmol), EtOH (50 mL), and water (25 mL). The reaction was stirred overnight at 50° C. The solids were removed by filtration, and the filtrate was concentrated under reduced pressure. The residue was purified on a silica gel with EA:PE (2:5) to provide 4-amino-2,6-dichloro-3-methylphenol as a light brown solid (3.45 g, 59%).

3,5-Dichloro-4-[(6-chloro-5-isopropylpyridazin-3-yl)oxy]-2-methylaniline was prepared similarly as described for 3,5-dichloro-4-[(6-chloro-5-isopropyl-pyridazin-3-yl)oxy]-aniline to afford a brown solid (3.9 g, 73%), starting from 4-amino-2,6-dichloro-3-methylphenol.

6-(4-Amino-2,6-dichloro-3-methylphenoxy)-4-isopropyl-2H-pyridazin-3-one was prepared similarly as described for 6-(4-amino-2,6-dichlorophenoxy)-4-isopropyl-2H-pyridazin-3-one, starting from 4-amino-2,6-dichloro-3-methylphenol, to afford an off-white solid (2.5 g, 56%).

Ethyl (E)-(2-cyano-2-(2-(3,5-dichloro-4-((5-isopropyl-6-oxo-1,6-dihydropyridazin-3-yl)oxy)phenyl)hydrazineylidene)acetyl)carbamate was prepared similarly as described for ethyl (E)-(2-cyano-2-(2-(3,5-dichloro-4-((3-isopropyl-1H-pyrrolo[3,2-b]pyridin-5-yl)oxy)phenyl)hydrazineylidene)acetyl)carbamate to afford an orange solid (140 mg, 72%).

2-[3,5-Dichloro-4-[(5-isopropyl-6-oxo-1H-pyridazin-3-yl)oxy]-2-methyl-phenyl]-3,5-dioxo-4H-1,2,4-triazine-6-carbonitrile (compound 35-A) was prepared similarly as described for 2-[4-[[3-isopropyl-1-(p-tolylsulfonyl)pyrrolo[3,2-b]pyridin-5-yl]methyl]-3,5-dimethyl-phenyl]-3,5-dioxo-1,2,4-triazine-6-carbonitrile, to afford a brown solid (2.1 g, 64%).

2-[3,5-Dichloro-4-[(5-isopropyl-6-oxo-1H-pyridazin-3-yl)oxy]-2-methylphenyl]-3,5-dioxo-4H-1,2,4-triazine-6-carboxylic acid was prepared similarly as described for 2-[3,5-dichloro-4-[(5-isopropyl-6-oxo-1H-pyridazin-3-yl)oxy]-phenyl]-3,5-dioxo-4H-1,2,4-triazine-6-carboxylic acid to afford a brown solid (1.0 g, 52%).

t-Butyl-N-(2-[3,5-dichloro-4-[(5-isopropyl-6-oxo-1H-pyridazin-3-yl)oxy]-2-methylphenyl]-3,5-dioxo-4H-1,2,4-triazin-6-yl)carbamate was prepared similarly as described for t-butyl N-(2-[3,5-dichloro-4-[(5-isopropyl-6-oxo-1H-pyridazin-3-yl)oxy]phenyl]-3,5-dioxo-4H-1,2,4-triazin-6-yl)-carbamate to afford a brown solid (600 mg, 71%).

A 100 mL round-bottom flask was charged with t-butyl-N-(2-[3,5-dichloro-4-[(5-isopropyl-6-oxo-1H-pyridazin-3-yl)oxy]-2-methylphenyl]-3,5-dioxo-4H-1,2,4-triazin-6-yl) carbamate (600 mg, 1.11 mmol), DCM (15.0 mL). TFA (5 mL) was added dropwise at 0° C. The reaction was stirred overnight at rt and concentrated under reduced pressure. The residue was dissolved with EA (50 mL). The pH of the solution was adjusted to 8 with NaHCO$_3$ (sat., aq.), then extracted with EA (3×20 mL), the organic layers were combined, washed with brine (2×10 mL), dried over anhyd. Na$_2$SO$_4$, the solids were removed by filtration and the filtrate was concentrated under reduced pressure. The crude product was purified by preparative HPLC to provide 6-amino-2-[3,5-dichloro-4-[(5-isopropyl-6-oxo-1H-pyridazin-3-yl)oxy]-2-methyl-phenyl]-4H-1,2,4-triazine-3,5-dione (compound 35) as a white solid (105 mg, 39%). $^1$H NMR (300 MHz, DMSO-d$_6$) δ 12.18 (br, 2H), 7.72 (s, 1H), 7.45 (s, 1H), 6.39 (br, 2H), 3.01-3.10 (m, 1H), 2.20 (s, 3H), 1.20 (d, J=6.9 Hz, 6H). LCMS (ESI, m/z): 439 [M+H]$^+$.

Example 30. Synthesis of Compound 36

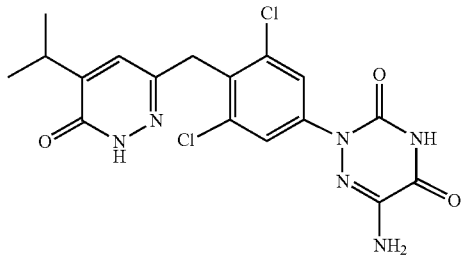

6-[(4-Amino-2,6-dichlorophenyl)methyl]-4-isopropyl-2H-pyridazin-3-one was prepared according to the literature procedure (*J. Med. Chem.* 2014, 57, 3912-3923) to afford a yellow solid (1.9 g, 50%).

Ethyl (2-cyano-2-(2-(3,5-dichloro-4-((5-isopropyl-6-oxo-1,6-dihydropyridazin-3-yl)methyl)phenyl)hydrazineylidene)acetyl)carbamate was prepared similarly as described for ethyl (2-cyano-2-(2-(4-((3-isopropyl-1-tosyl-1H-indol-5-yl)methyl)-3,5-dimethylphenyl)hydrazineylidene)acetyl) carbamate to afford a yellow solid (659 mg, 86%).

2-[3,5-Dichloro-4-[(5-isopropyl-6-oxo-1H-pyridazin-3-yl)methyl]phenyl]-3,5-dioxo-4H-1,2,4-triazine-6-carbonitrile was prepared similarly as described for 2-(4-[[3-isopropyl-1-(4-methylbenzene-sulfonyl)indol-5-yl]oxy]-3,5-dimethylphenyl)-3,5-dioxo-4H-1,2,4-triazine-6-carbonitrile to afford off-white solid (1.3 g, 86%).

2-[3,5-Dichloro-4-[(5-isopropyl-6-oxo-1H-pyridazin-3-yl)methyl]phenyl]-3,5-dioxo-4H-1,2,4-triazine-6-carboxylic acid was prepared similarly as described for 2-[3,5-dichloro-4-[(5-isopropyl-6-oxo-1H-pyridazin-3-yl)oxy]phenyl]-3,5-dioxo-4H-1,2,4-triazine-6-carboxylic acid to afford a yellow oil (800 mg, 48%).

t-Butyl-N-(2-[3,5-dichloro-4-[(5-isopropyl-6-oxo-1H-pyridazin-3-yl)methyl]phenyl]-3,5-dioxo-4H-1,2,4-triazin-6-yl)-carbamate was prepared similarly as described for t-butyl N-(2-[3,5-dichloro-4-[(5-isopropyl-6-oxo-1H-pyridazin-3-yl)oxy]phenyl]-3,5-dioxo-4H-1,2,4-triazin-6-yl)-carbamate to afford a yellow solid (600 mg, 65%).

6-Amino-2-[3,5-dichloro-4-[(5-isopropyl-6-oxo-1H-pyridazin-3-yl)methyl]-phenyl]-4H-1,2,4-triazine-3,5-dione was prepared similarly as described for 6-amino-2-[3,5-dichloro-4-[(5-isopropyl-6-oxo-1H-pyridazin-3-yl)oxy]-2-methylphenyl]-4H-1,2,4-triazine-3,5-dione to afford a white solid (227 mg, 49%). $^1$H NMR (300 MHz, DMSO-$d_6$) δ 7.76 (s, 2H), 7.30 (s, 1H), 6.52 (br, 2H), 4.24 (s, 2H), 2.98-3.02 (m, 1H), 1.15 (d, J=6.9 Hz, 6H). LCMS (ESI, m/z): 423 [M+H]$^+$.

Example 31. Synthesis of Compound 37

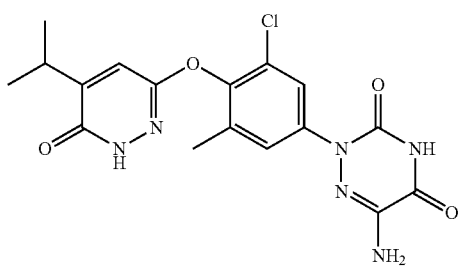

4-Amino-2-chloro-6-methylphenol was prepared similarly as described in WO2004014382 to afford a brown solid (10.8 g, 88%).

3-Chloro-4-[(6-chloro-5-isopropylpyridazin-3-yl)oxy]-5-methylaniline was prepared similarly as described for 3,5-dichloro-4-[(6-chloro-5-isopropyl-pyridazin-3-yl)oxy]-aniline to afford a brown semi-solid (9.5 g, 68%).

6-(4-Amino-2-chloro-6-methylphenoxy)-4-isopropyl-2H-pyridazin-3-one was prepared similarly as described for 6-(4-amino-2,6-dichlorophenoxy)-4-isopropyl-2H-pyridazin-3-one to afford a pink solid (6.5 g, 68%).

Ethyl (2-(2-(3-chloro-4-((5-isopropyl-6-oxo-1,6-dihydropyridazin-3-yl)oxy)-5-methylphenyl)hydrazineylidene)-2-cyanoacetyl)carbamate was prepared similarly as described for ethyl (2-cyano-2-(2-(4-((3-isopropyl-1-tosyl-1H-indol-5-yl)methyl)-3,5-dimethylphenyl)hydrazineylidene)acetyl) carbamate to afford a yellow solid (4.56 g, 75%).

2-[3-Chloro-4-[(5-isopropyl-6-oxo-1H-pyridazin-3-yl)oxy]-5-methylphenyl]-3,5-dioxo-4H-1,2,4-triazine-6-carbonitrile was prepared similarly as described for 2-[3,5-dichloro-4-[(5-isopropyl-6-oxo-1H-pyridazin-3-yl)oxy]phenyl]-3,5-dioxo-4H-1,2,4-triazine-6-carbonitrile to afford a light yellow solid (2.3 g, 53%).

2-[3-Chloro-4-[(5-isopropyl-6-oxo-1H-pyridazin-3-yl)oxy]-5-methylphenyl]-3,5-dioxo-4H-1,2,4-triazine-6-carboxylic acid was prepared similarly as described for 2-[3,5-dichloro-4-[(5-isopropyl-6-oxo-1H-pyridazin-3-yl)oxy]phenyl]-3,5-dioxo-4H-1,2,4-triazine-6-carboxylic acid to afford a white solid (880 mg, 75%).

t-Butyl-N-(2-[3-chloro-4-[(5-isopropyl-6-oxo-1H-pyridazin-3-yl)oxy]-5-methylphenyl]-3,5-dioxo-4H-1,2,4-triazin-6-yl)-carbamate was prepared similarly as described for t-butyl N-(2-[3,5-dichloro-4-[(5-isopropyl-6-oxo-1H-pyridazin-3-yl)oxy]phenyl]-3,5-dioxo-4H-1,2,4-triazin-6-yl)-carbamate to afford a white solid (790 mg, 70%).

6-Amino-2-[3-chloro-4-[(5-isopropyl-6-oxo-1H-pyridazin-3-yl)oxy]-5-methyl-phenyl]-4H-1,2,4-triazine-3,5-dione was prepared similarly as described for 6-amino-2-[3,5-dichloro-4-[(5-isopropyl-6-oxo-1H-pyridazin-3-yl)oxy]-2-methylphenyl]-4H-1,2,4-triazine-3,5-dione to afford a white solid (100 mg, 50%). $^1$H NMR (400 MHz, DMSO-$d_6$) δ 12.18 (br, 1H), 12.10 (s, 1H), 7.58-7.61 (m, 1H), 7.51-7.48 (m, 1H), 7.34-7.37 (m, 1H), 6.41 (s, 2H), 3.08-2.99 (m, 1H), 2.18 (s, 3H), 1.19 (d, J=6.8 Hz, 6H). LCMS (ESI, m/z): 405.0 [M+H]$^+$.

Example 32. Synthesis of Compound 38

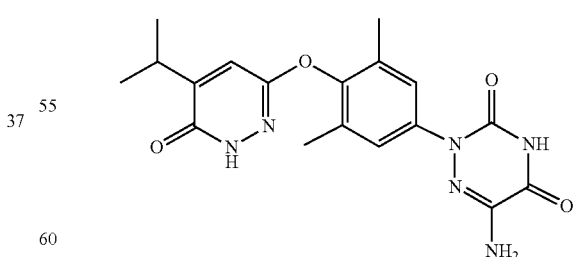

6-Amino-2-[4-[(5-isopropyl-6-oxo-1H-pyridazin-3-yl)oxy]-3,5-dimethylphenyl]-4H-1,2,4-triazine-3,5-dione was prepared similarly as described for 6-amino-2-(3,5-dichloro-4-((5-isopropyl-6-oxo-1,6-dihydropyridazin-3-yl)oxy)phenyl)-1,2,4-triazine-3,5(2H,4H)-dione to afford a white solid (238 mg, 54%). $^1$H NMR (300 MHz, DMSO-d$_6$) δ 12.10 (br, 1H), 12.00 (br, 1H), 7.30 (s, 1H), 7.25 (s, 2H), 6.32 (br, 2H), 3.01-3.09 (m, 1H), 2.10 (s, 6H), 1.20 (d, J=6.6 Hz, 6H). LCMS (ESI, m/z): 385 [M+H]$^+$.

Example 33. Synthesis of Compounds 39-A, and 39-B

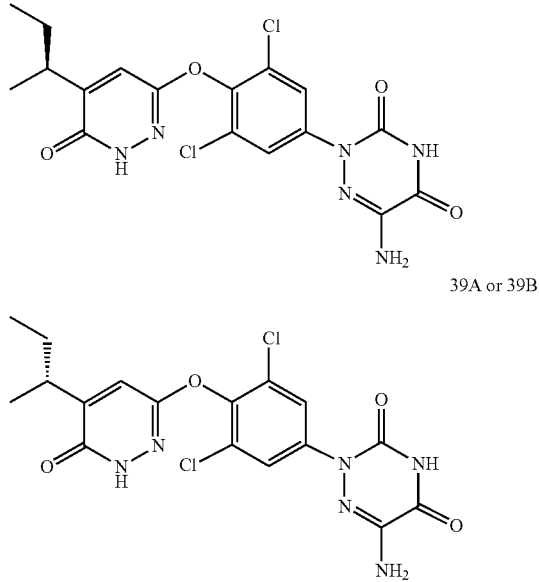

3,6-Dichloro-4-(sec-butyl)pyridazine was prepared similarly as described for 3,6-dichloro-4-isopropylpyridazine (see also Samaritoni, J. G. Homolytic alkylation of 3,6-dichloropyridazine. *Org. Prep. Proced. Int.* 1988, 20, 117-121) to afford a yellow oil (23.3 g, 79%).

To a mixture of 3,6-dichloro-4-(sec-butyl)pyridazine (7.00 g, 34.1 mmol) and 4-amino-2,6-dichlorophenol (6.68 g, 37.6 mmol) in DMSO (70 mL) was added K$_2$CO$_3$ (14.2 g, 103 mmol) and CuI (1.95 g, 10.2 mmol). The resulting mixture was stirred overnight at 90° C. under N$_2$. The solids were removed by filtration and the filtrate was quenched with NH$_4$Cl$_1$ (sat. aq., 150 mL). The resulting mixture was extracted with EA (3×200 mL) and the organic layers were combined, washed with brine (2×150 mL), dried over anhyd. Na$_2$SO$_4$, the solids were removed by filtration and the filtrate was concentrated under reduced pressure to afford crude product. The sample was purified by silica column chromatography, eluted with EA:PE (0~40% over 20 min). Fractions were collected, combined, and concentrated under reduced pressure to provide 3,5-dichloro-4-[[6-chloro-5-(sec-butyl)pyridazin-3-yl]oxy]aniline as a brown semi-solid (10 g, 72%).

A mixture of 3,5-dichloro-4-[[6-chloro-5-(sec-butyl) pyridazin-3-yl]oxy]-aniline (10 g, 28.9 mmol) and NaOAc (8.28 g, 101 mmol) in AcOH (100 mL) was stirred overnight at 100° C. The mixture was concentrated under reduced pressure to remove AcOH. The residue was diluted with water (100 mL) and the pH was adjusted to 8 with NaOH (aq., 1 M). The mixture was extracted with EA (3×150 mL) and the organic layers were combined, dried over anhyd. Na$_2$SO$_4$, filtered and concentrated under reduced pressure. The residue was dissolved in MeOH (100 mL) and NaOH (100 mL, 1 M aq.) and the resulting mixture was stirred overnight at 100° C. The mixture was concentrated under reduced pressure to remove MeOH. The resulting mixture was extracted with EA (3×150 mL) and the organic layers were combined, washed with brine (2×100 mL), dried over anhyd. Na$_2$SO$_4$, filtered and concentrated under reduced pressure to afford crude product. The sample was purified by silica column chromatography (EA:PE=0~70% over 20 min). Fractions were collected, combined, and concentrated under reduced pressure to provide 6-(4-amino-2,6-dichlorophenoxy)-4-(sec-butyl)-2H-pyridazin-3-one as a light yellow solid (5.95 g, 60%).

Ethyl (2-(2-(4-((5-(sec-butyl)-6-oxo-1,6-dihydropyridazin-3-yl)oxy)-3,5-dichlorophenyl)hydrazineylidene)-2-cyanoacetyl)carbamate, a yellow solid (4.63 g, 77%), was prepared similarly as described for ethyl (2-cyano-2-(2-(3,5-dichloro-4-((1-tosyl-1H-indol-5-yl)oxy)phenyl)-hydrazineylidene)-acetyl) carbamate.

A mixture of ethyl (2-(2-(4-((5-(sec-butyl)-6-oxo-1,6-dihydropyridazin-3-yl)oxy)-3,5-dichlorophenyl)hydrazineylidene)-2-cyanoacetyl)carbamate (4.40 g, 8.88 mmol) and NaOAc (3.64 g, 44.4 mmol) in AcOH (50 mL) was stirred for 2 h at 120° C. The mixture was poured into water (100 mL) and the crude product was obtained by filtration. The sample was purified by column chromatography (CH$_3$OH:DCM=0~15% over 20 min). Fractions were collected, combined, and concentrated under reduced pressure to provide 2-(3,5-dichloro-4-[[6-oxo-5-(sec-butyl)-1H-pyridazin-3-yl]oxy]phenyl)-3,5-dioxo-4H-1,2,4-triazine-6-carbonitrile as a yellow solid (2.27 g, 52%).

A mixture of 2-(3,5-dichloro-4-[[6-oxo-5-(sec-butyl)-1H-pyridazin-3-yl]oxy]phenyl)-3,5-dioxo-4H-1,2,4-triazine-6-carbonitrile (1.00 g, 2.23 mmol) in conc. HCl (5 mL) and AcOH (10 mL) was stirred for 2 h at 120° C. The mixture was poured into water (20 mL) and the desired product 2-(3,5-dichloro-4-[[6-oxo-5-(sec-butyl)-1H-pyridazin-3-yl]oxy]phenyl)-3,5-dioxo-4H-1,2,4-triazine-6-carboxylic acid was obtained by filtration as a white solid (860 mg, 78%).

To a mixture of 2-(3,5-dichloro-4-[[6-oxo-5-(sec-butyl)-1H-pyridazin-3-yl]oxy]phenyl)-3,5-dioxo-4H-1,2,4-triazine-6-carboxylic acid (860 mg, 1.84 mmol) in tBuOH (15.0 mL) was added DPPA (1.52 g, 5.52 mmol) and NEt$_3$ (743 mg, 7.35 mmol). The resulting mixture was stirred overnight at 85° C. under N$_2$, then concentrated under reduced pressure. The residue was diluted with DCM (50 mL), washed with brine (30 mL), dried over anhyd. Na$_2$SO$_4$, the solids were removed by filtration and the filtrate was concentrated under reduced pressure to afford crude product that was purified by column chromatography and eluted with MeOH:DCM (0~7% over 20 min). Fractions were concentrated under reduced pressure to provide racemic t-butyl-N-[2-(3,5-dichloro-4-[[6-oxo-5-(sec-butyl)-1H-pyridazin-3-yl]oxy]-phenyl)-3,5-dioxo-4H-1,2,4-triazin-6-yl]carbamate as a white solid (700 mg, 67%).

t-Butyl-N-[2-(3,5-dichloro-4-[[6-oxo-5-(sec-butyl)-1H-pyridazin-3-yl]-oxy]phenyl)-3,5-dioxo-4H-1,2,4-triazin-6-yl]carbamate (500 mg, 0.927 mmol) was further purified by preparatory SFC-HPLC (Column: Reg-AD, 30×250 mm, 5 μm; Mobile Phase A: CO$_2$, Mobile Phase B: EtOH (8 mmol/L NH$_3$.MeOH)-HPLC; Flow rate: 50 mL/min; Gradient: 50% B; 220 nm; Injection Volume: 4 mL; Number Of Runs: 11). Purification resulted in enantiomer 1 as white solid (130 mg, 26%, Rt: 5.79 min), and enantiomer 2 as a white solid (Rt: 6.97 min, 190 mg, 37%).

The boc group of each enantiomer was separately deprotected in DCM (10 mL) and TFA (3 mL). The resulting mixtures were stirred for 4 h at rt and concentrated under reduced pressure. The solvent was removed under reduced pressure, the mixtures were diluted with EA (30 mL), washed with NaHCO$_3$ (sat., aq., 20 mL), dried over anhyd. Na$_2$SO$_4$, the solids were removed by filtration and the filtrate was concentrated under reduced pressure to afford the crude product.

Compound 39-A (corresponding to enantiomer 1) was purified by preparative HPLC (Column: Xselect CSH OBD Column 30×150 mm 5 µm; Mobile Phase A: Water (10 mmol/L NH$_4$HCO$_3$+0.1% NH$_3$·H$_2$O), Mobile Phase B: ACN; Flow rate: 60 mL/min; Gradient: 23 B to 43 B in 7 min; 220 nm; RT: 5.32 min) to afford a white solid (49.6 mg, 46%). $^1$H NMR (300 MHz, DMSO-d$_6$) δ 11.95-12.52 (m, 2H), 7.86 (s, 2H), 7.42 (s, 1H), 6.52 (s, 2H), 2.86-2.94 (m, 1H), 1.64-1.74 (m, 1H), 1.45-1.56 (m, 1H), 1.17 (d, J=6.9 Hz, 3H), 0.86 (t, J=7.5 Hz, 3H). LCMS (ESI, m/z): 439.0 [M+H]$^+$.

Compound 39-B (corresponding to enantiomer 2) was triturated with EA:MeOH (5 mL:1 mL) to provide the desired product as an off-white solid (67.5 mg, 42%). $^1$H NMR (300 MHz, DMSO-d$_6$) δ 12.19-12.28 (m, 2H), 7.86 (s, 2H), 7.42 (s, 1H), 6.53 (s, 2H), 2.83-2.94 (m, 1H), 1.61-1.77 (m, 1H), 1.43-1.58 (m, 1H), 1.18 (d, J=6.9 Hz, 3H), 0.86 (t, J=7.4 Hz, 3H). LCMS (ESI, m/z): 439.0 [M+H]$^+$.

SFC Analysis on compounds 39-A, and 39-B: Column name: Enantiocel C3-3, 4.6×100 mm, 3 µm. Co-Solvent: 20% EtOH (0.1% DEA). Flow (mL/min): 4. Temperature: 35° C. Detector: 220 nm. 39-A: Rt=2.947 min. 39-B: Rt=3.269 min.

Example 34. Synthesis of Compounds 40-A and 40

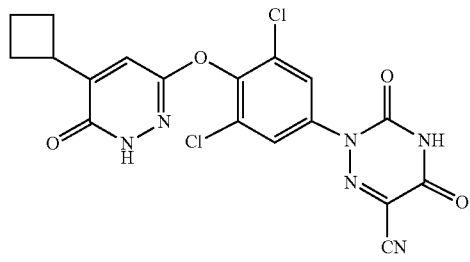

40-A

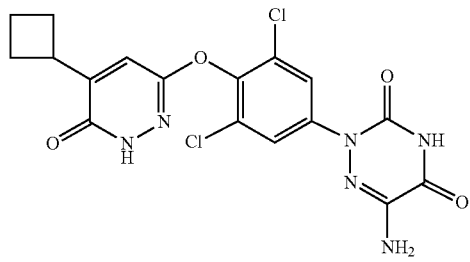

40

3,6-dichloro-4-cyclobutylpyridazine was prepared similarly as described for 3,6-dichloro-4-isopropylpyridazine to afford a colorless oil (12 g, 38%).

3,5-dichloro-4-[(6-chloro-5-cyclobutylpyridazin-3-yl) oxy]aniline was prepared similarly as described for 3,5-dichloro-4-[[6-chloro-5-(sec-butyl)pyridazin-3-yl]oxy]aniline to afford a yellow solid (3.07 g, 34%).

A stirred mixture of 3,5-dichloro-4-[(6-chloro-5-cyclobutylpyridazin-3-yl)oxy]aniline (2.52 g, 7.31 mmol), NaOAc (2.10 g, 25.6 mmol) in AcOH (25 mL) was stirred overnight at 100° C. The resulting mixture was concentrated under reduced pressure to remove AcOH. The residue was diluted with water (30 mL) and the pH was adjusted to 8 with NaOH (aq., 1 M). The mixture was extracted with EA (3×60 mL) and the organic layers were combined, dried over anhyd. Na$_2$SO$_4$, the solids were removed by filtration and the filtrate was concentrated under reduced pressure. The residue was dissolved in MeOH (25 mL) and NaOH solution (25 mL, 1 M aq.) and the resulting mixture was stirred overnight at 120° C. The mixture was concentrated under reduced pressure. The resulting mixture was extracted with EA (3×60 mL), the organic layers were combined, washed with brine (2×40 mL), dried over anhyd. Na$_2$SO$_4$, the solids were removed by filtration and the filtrate was concentrated under reduced pressure to afford 6-(4-amino-2,6-dichlorophenoxy)-4-cyclobutyl-2H-pyridazin-3-one (2.27 g, crude) as a brown solid.

Ethyl (2-cyano-2-(2-(3,5-dichloro-4-((5-cyclobutyl-6-oxo-1,6-dihydro-pyridazin-3-yl)oxy)phenyl)hydrazineylidene)acetyl)carbamate (2.61 g, crude yellow solid) was prepared similarly as described for ethyl (2-cyano-2-(2-(3,5-dichloro-4-((1-tosyl-1H-indol-5-yl)oxy)phenyl)-hydrazineylidene)-acetyl) carbamate.

To a stirred mixture of ethyl (2-cyano-2-(2-(3,5-dichloro-4-((5-cyclobutyl-6-oxo-1,6-dihydropyridazin-3-yl)oxy)phenyl)hydrazineylidene)acetyl)carbamate (2.50 g, 5.07 mmol) in DMA (25 mL) was added KOAc (1.99 g, 20.3 mmol) in portions at rt. The resulting mixture was stirred for 5 h at 120° C. under N$_2$. The reaction was quenched with water (200 mL) and extracted with EA (3×150 mL), and the organic layers were combined, dried over anhyd. Na$_2$SO$_4$, the solids were removed by filtration and the filtrate was concentrated under reduced pressure. The crude product was purified by silica gel column chromatography, eluted with DCM:MeOH (9:1) to afford 2-[3,5-dichloro-4-[(5-cyclobutyl-6-oxo-1H-pyridazin-3-yl)oxy]phenyl]-3,5-dioxo-4H-1,2,4-triazine-6-carbonitrile as a brown solid (compound 40-A, 2.1 g, 84%). $^1$H NMR (300 MHz, DMSO-d$_6$) δ 13.27 (br, 1H), 12.19 (s, 1H), 7.79 (s, 2H), 7.49-7.51 (m, 1H), 3.50-3.62 (m, 1H), 1.93-2.34 (m, 5H), 1.75-1.88 (m, 1H).

To a stirred mixture of 2-[3,5-dichloro-4-[(5-cyclobutyl-6-oxo-1H-pyridazin-3-yl)oxy]phenyl]-3,5-dioxo-4H-1,2,4-triazine-6-carbonitrile (1.30 g, 2.91 mmol) in AcOH (12 mL) was added HCl (6 mL) dropwise at rt. The resulting mixture was stirred for 2 h at 120° C. The resulting mixture was concentrated under reduced pressure to remove AcOH. The pH of the mixture was adjusted to 8 with Na$_2$CO$_3$ (sat., aq.). The resulting mixture was extracted with EA (3×50 mL). The pH of the mixture was adjusted to 5 with HCl (1 M). The resulting mixture was extracted with EA (3×50 mL) and the organic layers were combined, dried over anhyd. Na$_2$SO$_4$, the solids were removed by filtration and the filtrate was concentrated under reduced pressure to afford 2-[3,5-dichloro-4-[(5-cyclobutyl-6-oxo-1H-pyridazin-3-yl)oxy]-phenyl]-3,5-dioxo-4H-1,2,4-triazine-6-carboxylic acid (1.0 g, crude) as a yellow solid. The crude product was used in the next step without further purification.

To a stirred solution of 2-[3,5-dichloro-4-[(5-cyclobutyl-6-oxo-1H-pyridazin-3-yl)oxy]phenyl]-3,5-dioxo-4H-1,2,4-triazine-6-carboxylic acid (800 mg, 1.72 mmol) in t-BuOH (30 mL) was added DPPA (1.42 g, 5.15 mmol) and NEt$_3$ (694 mg, 6.86 mmol) dropwise at rt. The resulting mixture was stirred overnight at 85° C. and concentrated under reduced pressure. The residue was diluted with EA (50 mL) and washed with brine (40 mL). The organic layers were combined was dried over anhyd. Na$_2$SO$_4$, filtered and concentrated under reduced pressure. The residue was purified by silica gel column chromatography with PE:EA (4:1) to afford t-butyl-N-(2-[3,5-dichloro-4-[(5-cyclobutyl-6-oxo-1H-pyridazin-3-yl)oxy]phenyl]-3,5-dioxo-4H-1,2,4-triazin-6-yl)-carbamate as a yellow solid (518 mg, 53%).

To a stirred solution of t-butyl-N-(2-[3,5-dichloro-4-[(5-cyclobutyl-6-oxo-1H-pyridazin-3-yl)oxy]phenyl]-3,5-dioxo-4H-1,2,4-triazin-6-yl)carbamate (450 mg, 0.837 mmol) in DCM (5 mL) was added TFA (2.50 mL) dropwise at 0° C. The resulting mixture was stirred for 3 h at rt and concentrated under reduced pressure. The residue was diluted with DCM (30 mL), washed with NaHCO₃ (sat., aq., 40 mL), dried over anhyd. Na₂SO₄, the solids were removed by filtration and the filtrate was concentrated under reduced pressure. The crude product was purified by preparative HPLC to afford 6-amino-2-[3,5-dichloro-4-[(5-cyclobutyl-6-oxo-1H-pyridazin-3-yl)oxy]phenyl]-4H-1,2,4-triazine-3,5-dione as a white solid (89.4 mg, 24%). $^1$H NMR (300 MHz, DMSO-d₆) δ 12.27 (s, 1H), 12.15 (s, 1H), 7.85 (s, 2H), 7.46-7.47 (m, 1H), 6.52 (s, 2H), 3.50-3.62 (m, 1H), 1.96-2.34 (m, 5H), 1.80-1.87 (m, 1H). LCMS (ESI, m/z): 459 [M+Na]⁺.

Example 35. Synthesis of Compound 41

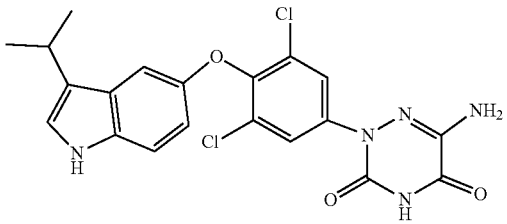

2-[3,5-dichloro-4-[(3-isopropyl-1H-indol-5-yl)oxy]-phenyl]-3,5-dioxo-4H-1,2,4-triazine-6-carboxylic acid was prepared similarly as described for 2-[3,5-dichloro-4-[(5-isopropyl-6-oxo-1H-pyridazin-3-yl)oxy]phenyl]-3,5-dioxo-4H-1,2,4-triazine-6-carboxylic acid, with the exception that mixture was stirred for 2 h at 100° C. to afford a brown solid (200 mg, crude).

t-butyl-N-(2-[3,5-dichloro-4-[(3-isopropyl-1H-indol-5-yl)oxy]phenyl]-3,5-dioxo-4H-1,2,4-triazin-6-yl)carbamate was prepared, from 2-(3,5-dichloro-4-((3-isopropyl-1H-indol-5-yl)oxy)phenyl)-3,5-dioxo-2,3,4,5-tetrahydro-1,2,4-triazine-6-carboxylic acid, similarly as described for t-butyl N-(2-[3,5-dichloro-4-[(5-isopropyl-6-oxo-1H-pyridazin-3-yl)oxy]phenyl]-3,5-dioxo-4H-1,2,4-triazin-6-yl)-carbamate (from 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carboxylic acid) to afford a yellow solid (117 mg, crude).

6-amino-2-[3,5-dichloro-4-[(3-isopropyl-1H-indol-5-yl)oxy]phenyl]-4H-1,2,4-triazine-3,5-dione (compound 41) was prepared similarly as described for 6-amino-2-[3,5-dichloro-4-[(5-isopropyl-6-oxo-1H-pyridazin-3-yl)oxy]-2-methylphenyl]-4H-1,2,4-triazine-3,5-dione to afford a white solid (13 mg, 17%). $^1$H NMR (300 MHz, MeOH-d₄) 7.88 (s, 2H), 7.25-7.29 (m, 1H), 7.01 (s, 1H), 6.85-6.86 (m, 1H), 6.73-6.77 (m, 1H), 2.98-3.08 (m, 1H), 1.28-1.36 (m, 6H).

Example 36. Synthesis of Compound 42

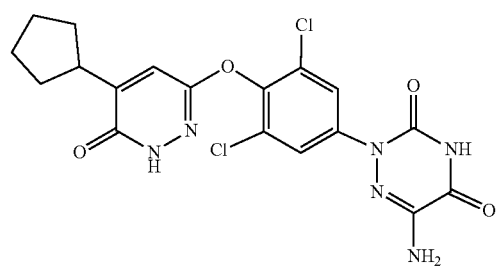

6-amino-2-(3,5-dichloro-4-((5-cyclopentyl-6-oxo-1,6-dihydropyridazin-3-yl)oxy)phenyl)-1,2,4-triazine-3,5(2H, 4H)-dione was prepared similarly as described for 6-amino-2-(3,5-dichloro-4-((5-cyclobutyl-6-oxo-1,6-dihydropyridazin-3-yl)oxy)-phenyl)-1,2,4-triazine-3,5(2H, 4H)-dione to afford a white solid (101 mg, 51%).

$^1$H NMR (300 MHz, DMSO-d₆) δ 12.21 (br, 1H), 12.17 (br, 1H), 7.85 (s, 2H), 7.44 (s, 1H), 6.52 (br, 2H), 3.03-3.33 (m, 1H), 1.90-1.98 (m, 2H), 1.50-1.78 (m, 6H). LCMS (ESI, m/z): 451 [M+H]⁺.

Example 37. Synthesis of Compound 43

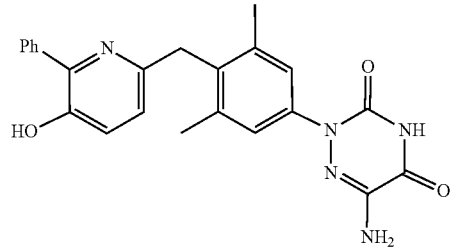

6-(4-amino-2,6-dimethylbenzyl)-2-phenylpyridin-3-ol was prepared similarly as described in WO 2010122980, and JP 2012106996.

6-amino-2-[4-[(5-hydroxy-6-phenylpyridin-2-yl)-methyl]-3,5-dimethylphenyl]-4H-1,2,4-triazine-3,5-dione was prepared from 6-(4-amino-2,6-dimethylbenzyl)-2-phenylpyridin-3-ol similarly as described in the conversion of 6-(4-amino-2,6-dichlorophenoxy)-4-isopropylpyridazin-3 (2H)-one to prepare 6-amino-2-(3,5-dichloro-4-((5-isopropyl-6-oxo-1,6-dihydropyridazin-3-yl)oxy)phenyl)-1,2,4-triazine-3,5(2H,4H)-dione to afford a white solid (43.8 mg, 49%). $^1$H NMR (300 MHz, DMSO-d₆) δ 9.32-9.89 (m, 2H), 7.99 (d, J=7.2 Hz, 2H), 7.31-7.43 (m, 3H), 7.19-7.24 (m, 3H), 6.76 (d, J=8.1 Hz, 1H), 6.21 (s, 2H), 4.09 (s, 2H), 2.11 (s, 6H). LCMS (ESI, m/z): 416 [M+H]⁺.

Example 38. Synthesis of Compound 44

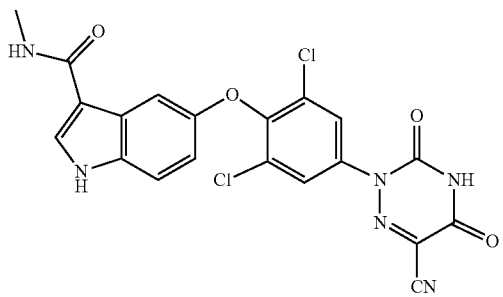

5-[2,6-dichloro-4-(6-cyano-3,5-dioxo-4H-1,2,4-triazin-2-yl)phenoxy]-N-methyl-1-(4-methylbenzenesulfonyl)indole-3-carboxamide was prepared similarly as described for 5-[2,6-dichloro-4-(6-cyano-3,5-dioxo-4H-1,2,4-triazin-2-yl)phenoxy]-N,N-dimethyl-1-(4-methylbenzenesulfonyl)indole-3-carboxamide to afford a light brown solid (200 mg, 50%).

Subsequent tosyl group deprotection was performed similarly as described for the formation of 5-[2,6-dichloro-4-(6-cyano-3,5-dioxo-4H-1,2,4-triazin-2-yl)phenoxy]-N,N-dimethyl-1H-indole-3-carboxamide to afford 5-[2,6-dichloro-4-(6-cyano-3,5-dioxo-4H-1,2,4-triazin-2-yl)phenoxy]-N-methyl-1H-indole-3-carboxamide as a yellow solid (21.5 mg, 14%). $^1$H NMR (300 MHz, MeOH-$d_4$) δ 7.85 (s, 1H), 7.78 (s, 2H), 7.52 (d, J=2.4 Hz, 1H), 7.41 (d, J=8.7 Hz, 1H), 6.91-6.94 (m, 1H), 2.87 (s, 3H). LCMS (ESI, m/z): 471 [M+H]$^+$.

Example 39. Synthesis of Compound 45

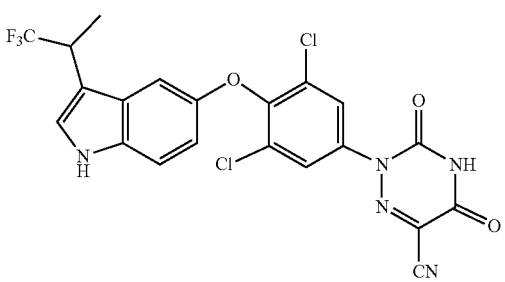

A 50 mL round-bottom flask was charged with 5-(2,6-dichloro-4-nitrophenoxy)-1-(4-methylbenzenesulfonyl)indole (1.00 g, 2.10 mmol), NIS (0.71 g, 3.14 mmol), p-toluenesulfonic acid (0.05 g, 0.314 mmol), DCM (30 mL). The reaction stirred for 5 h at rt and then quenched with water (150 mL). The resulting mixture was extracted with DCM (3×200 mL) and the organic layers were combined, washed with brine (1×200 mL), dried over anhyd. Na$_2$SO$_4$, filtered and concentrated under reduced pressure. The residue was purified on a silica gel column with EA:PE (1:4) to provide 5-(2,6-dichloro-4-nitrophenoxy)-3-iodo-1-(4-methylbenzenesulfonyl)indole as a yellow solid (580 mg, 41%).

A 50 mL round-bottom was charged with 5-(2,6-dichloro-4-nitrophenoxy)-3-iodo-1-(4-methylbenzenesulfonyl)indole (350 mg, 0.580 mmol), 4,4,6-trimethyl-2-(3,3,3-trifluoroprop-1-en-2-yl)-1,3,2-dioxaborinane (155 mg, 0.696 mmol), PdCl$_2$(dppf) (42.5 mg, 0.058 mmol), K$_2$CO$_3$ (241 mg, 1.74 mmol), ethylene glycol dimethyl ether (10 mL), and water (2 mL). The resulting solution stirred overnight under N$_2$ at 80° C. and was quenched with water (10 mL), then extracted with EA (3×30 mL) and the organic layers were combined, washed with brine (2×10 mL), dried over anhyd. Na$_2$SO$_4$, the solids were removed by filtration and the filtrate was concentrated under reduced pressure. The residue was purified on a silica gel column with EA:PE (1:4) to provide of 5-(2,6-dichloro-4-nitrophenoxy)-1-(4-methylbenzene-sulfonyl)-3-(3,3,3-trifluoroprop-1-en-2-yl)indole as a white solid (220 mg, 53%).

A 100 mL round-bottom flask was charged with 5-(2,6-dichloro-4-nitrophenoxy)-1-(4-methylbenzenesulfonyl)-3-(3,3,3-trifluoroprop-1-en-2-yl)indole (210 mg, 0.368 mmol), Pd/C (200 mg), and EA (20 mL) under hydrogen. The mixture was stirred for 3 h at rt. The reaction mixture was diluted with EA (60 mL) and filtered through celite, the celite pad was washed with EA (2×10 mL), the filtrate was concentrated under reduced pressure to afford the 3,5-dichloro-4-[[1-(4-methylbenzene-sulfonyl)-3-(1,1,1-trifluoropropan-2-yl)indol-5-yl]oxy]aniline as a yellow solid (155 mg crude).

Ethyl (2-cyano-2-(2-(3,5-dichloro-4-((1-tosyl-3-(1,1,1-trifluoropropan-2-yl)-1H-indol-5-yl)oxy)phenyl)hydrazineylidene)acetyl)carbamate, an orange solid (110 mg, 54%) was prepared similarly as described for ethyl (2-cyano-2-(2-(3,5-dichloro-4-((1-tosyl-1H-indol-5-yl)oxy)phenyl)-hydrazineylidene)-acetyl) carbamate.

2-(3,5-dichloro-4-[[1-(4-methylbenzenesulfonyl)-3-(1,1,1-trifluoropropan-2-yl)indol-5-yl]oxy]phenyl)-3,5-dioxo-4H-1,2,4-triazine-6-carbonitrile, a yellow solid (80 mg, 54%) was prepared similarly as described for 2-(4-[[3-isopropyl-1-(4-methylbenzene-sulfonyl)indol-5-yl]oxy]-3,5-dimethylphenyl)-3,5-dioxo-4H-1,2,4-triazine-6-carbonitrile with the exception that the reaction duration was 5 h.

Subsequent tosyl group deprotection via TBAF to afford 2-(3,5-dichloro-4-[[3-(1,1,1-trifluoropropan-2-yl)-1H-indol-5-yl]oxy]phenyl)-3,5-dioxo-4H-1,2,4-triazine-6-carbonitrile as a light-yellow solid (18.9 mg, 26%) was performed similarly as described for 2-[4-[(3-isopropyl-1H-pyrrolo[3,2-b]pyridin-5-yl)methyl]-3,5-dimethyl-phenyl]-3,5-dioxo-1,2,4-triazine-6-carbonitrile. $^1$H NMR (300 MHz, DMSO-$d_6$) δ 11.20 (br, 1H), 7.81 (s, 2H), 7.34-7.42 (m, 2H), 7.04 (s, 1H), 6.69-6.72 (m, 1H), 3.92-3.97 (m, 1H), 1.46 (d, J=7.2 Hz, 3H). LCMS (ESI, m/z): 508[M−H]$^-$.

Example 40. Synthesis of Compound 46

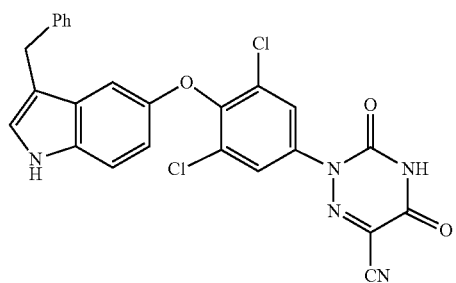

To a solution of 5-(2,6-dichloro-4-nitrophenoxy)-1H-indole (3.00 g, 9.29 mmol) in DCM (25 mL) was added diethyl aluminum chloride (15 mL, 0.9 M in toluene, 13.5 mmol) dropwise at 0° C. The mixture was stirred at 0° C. for 30 min, then benzoyl chloride (1.96 g, 13.9 mmol) was added at 0° C. The reaction mixture was stirred at 0° C. for 3 h and quenched with water (25 mL). The resulting mixture was extracted with DCM (3×20 mL). The organic layers were combined, washed with brine (3×20 mL), dried over anhyd. $Na_2SO_4$, the solids were removed by filtration and the filtrate was concentrated under reduced pressure. The residue was purified on a silica gel column with PE:EA (4:1) to afford 3-benzoyl-5-(2,6-dichloro-4-nitro-phenoxy)-1H-indole as a light brown solid (1.3 g, 26%).

To a solution of 3-benzoyl-5-(2,6-dichloro-4-nitrophenoxy)-1H-indole (1.3 g, 3.04 mmol) in THF (30 mL) was added $LiAlH_4$ (462 mg, 12.2 mmol) at 0° C. under $N_2$. The reaction mixture was stirred overnight at 60° C. and quenched with water (30 mL) at 0° C. To the resulting solution was added NaOH (1N, 30 mL) and followed by water (30 mL). The solids were removed by filtration, and the filter cake was washed with water (3×10 mL). The filtrate was concentrated under reduced pressure. The residue was purified by preparatory TLC with PE:EA (1:1) to afford 4-[(3-benzyl-1H-indol-5-yl)oxy]-3,5-dichloroaniline as a light yellow solid (250 mg, 21%).

Ethyl (2-(2-(4-((3-benzyl-1H-indol-5-yl)oxy)-3,5-dichlorophenyl)-hydrazineylidene)-2-cyanoacetyl)carbamate (300 mg, 52%) was prepared similarly as described for ethyl (2-cyano-2-(2-(3,5-dichloro-4-((1-tosyl-1H-indol-5-yl) oxy)-phenyl)-hydrazineylidene)-acetyl) carbamate.

2-[4-[(3-benzyl-1H-indol-5-yl)oxy]-3,5-dichlorophenyl]-3,5-dioxo-4H-1,2,4-triazine-6-carbonitrile, a light brown solid was prepared similarly as described for 2-(4-[[3-isopropyl-1-(4-methylbenzene-sulfonyl)indol-5-yl]oxy]-3,5-dimethyl-phenyl)-3,5-dioxo-4H-1,2,4-triazine-6-carbonitrile with the exception that the reaction duration was 5 h instead of 2 h (13.3 mg, 7%). $^1$H NMR (300 MHz, MeOH-d$_4$) δ 7.72 (s, 2H), 7.28 (d, J=9.0 Hz, 1H), 7.10-7.23 (m, 5H), 7.03 (s, 1H), 6.77-6.80 (m, 1H), 6.54 (d, J=2.4 Hz, 1H), 3.98 (s, 2H). LCMS (ESI, m z): 502 [M−H]$^-$.

Example 41. Synthesis of Compound 47

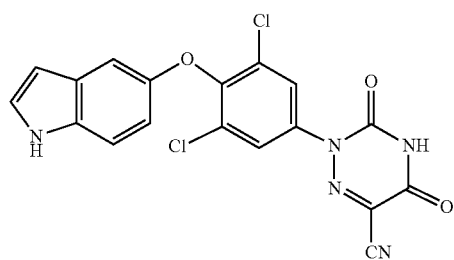

2-[3,5-dichloro-4-(1H-indol-5-yloxy)phenyl]-3,5-dioxo-4H-1,2,4-triazine-6-carbonitrile, a yellow solid (120 mg, 32%). $^1$H NMR (300 MHz, MeOH-d$_4$) δ 7.77 (s, 2 h), 7.33-7.37 (m, 1H), 7.24 (d, J=3.0 Hz, 1H), 6.80-6.84 (m, 2 h), 6.35-6.36 (m, 1H). LCMS (ESI, m/z): 412 [M−H]$^-$.

Example 42. Synthesis of Compound 48

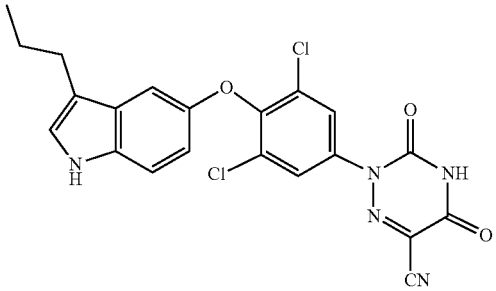

A 50 mL round-bottom was charged with 5-(2,6-dichloro-4-nitrophenoxy)-1H-indole (2.00 g, 6.19 mmol), DCM (10.0 mL). $SnCl_4$ (1.93 g, 7.42 mmol) was added at 0° C. The reaction mixture stirred at rt for 30 min. Propanoyl chloride (1.14 g, 12.3 mmol) was added, followed by $CH_3NO_2$ (15 mL). The reaction mixture was stirred overnight at rt and quenched with water (10 mL). The resulting mixture was extracted with EA (3×200 mL) and the organic layers were combined, washed with brine (100 mL), dried over anhyd. $Na_2SO_4$, filtered and concentrated under reduced pressure. The residue was purified on a silica gel column with EA:PE (9:1) to provide 1-[5-(2,6-dichloro-4-nitrophenoxy)-1H-indol-3-yl]propan-1-one as a yellow solid (1.6 g, 68.17%).

A 50 mL round-bottom flask was charged with 1-[5-(2,6-dichloro-4-nitrophenoxy)-1H-indol-3-yl]propan-1-one (1.90 g, 5.01 mmol), THF (20 mL). NaH (0.802 g, 20.0 mmol, 60% in mineral oil) was added at 0° C. 4-toluene sulfonyl chloride (1.91 g, 10.0 mmol) was added at 0° C. The resulting solution was stirred at rt for 2 h and quenched with $NaHCO_3$ (sat. aq., 30 mL). The resulting mixture was extracted with EA (3×80 mL) and the organic layers were combined, washed with brine (2×40 mL), dried over anhyd. $Na_2SO_4$, the solids were removed by filtration and the filtrate was concentrated under reduced pressure. The crude was purified on a silica gel column with EA:PE (1:5) to provide 1-[5-(2,6-dichloro-4-nitrophenoxy)-1-(4-methyl-benzene-sulfonyl)-indol-3-yl]propan-1-one as a yellow solid (1.1 g, 41%).

$NBH_4$ (0.78 g, 20.6 mmol) was added to TFA (10 mL) at 0° C. under $N_2$. Then a solution of 1-[5-(2,6-dichloro-4-nitrophenoxy)-1-(4-methylbenzene-sulfonyl)indol-3-yl]propan-1-one (1.10 g, 2.06 mmol) in DCM (30 mL) was added to the mixture. The reaction mixture stirred overnight at rt and quenched with water (50 mL), then extracted with DCM (3×150 mL) and the organic layers were combined, washed with brine (1×100 mL), dried over anhyd. $Na_2SO_4$, the solids were removed by filtration and the filtrate was concentrated under reduced pressure to provide 1-[5-(2,6-dichloro-4-nitrophenoxy)-1H-indol-3-yl]propan-1-one as a yellow solid (1.1 g, 99%).

3,5-dichloro-4-[[1-(4-methylbenzenesulfonyl)-3-propylindol-5-yl]-oxy]aniline, a yellow solid (870 mg, 74%) was prepared similarly as described for 3,5-dichloro-4-[[3-isopropyl-1-(4-methy-lbenzenesulfonyl)-indol-5-yl]oxy]aniline with the exception that the reaction stirred overnight at 50° C.

Ethyl (2-cyano-2-(2-(3,5-dichloro-4-((3-propyl-1-tosyl-1H-indol-5-yl)oxy)phenyl)hydrazineylidene)acetyl)carbamate, an orange solid (850 mg, 48%) was prepared similarly as described for ethyl (2-cyano-2-(2-(3,5-dichloro-4-((1-tosyl-1H-indol-5-yl)oxy)phenyl)-hydrazineylidene)-acetyl) carbamate.

2-(3,5-dichloro-4-[[1-(4-methylbenzenesulfonyl)-3-propylindol-5-yl]oxy]phenyl)-3,5-dioxo-4H-1,2,4-triazine-6-carbonitrile, a white solid (400 mg, 48%), was prepared similarly as described for 2-(4-[[3-isopropyl-1-(4-methyl-benzene-sulfonyl)indol-5-yl]oxy]-3,5-dimethylphenyl)-3,5-dioxo-4H-1,2,4-triazine-6-carbonitrile with the exception that the reaction duration was 5 h instead of 2 h.

Subsequent tosyl group deprotection via TBAF afford 2-[3,5-dichloro-4-[(3-propyl-1H-indol-5-yl)oxy]phenyl]-3,5-dioxo-4H-1,2,4-triazine-6-carbonitrile as an orange solid (51.7 mg, 20%) was performed similarly as described for 2-[4-[(3-isopropyl-1H-pyrrolo[3,2-b]pyridin-5-yl)methyl]-3,5-dimethyl-phenyl]-3,5-dioxo-1,2,4-triazine-6-carbonitrile. $^1$H NMR (400 MHz, DMSO-$d_6$) δ 10.79 (s, 1H), 7.80 (s, 2H), 7.30 (d, J=8.8 Hz, 1H), 7.14 (s, 1H), 6.85 (d, J=2.4 Hz, 1H), 6.65-6.68 (m, 1H), 2.52-2.57 (m, 2H), 1.54-1.64 (m, 2H), 0.90 (t, J=7.2 Hz, 3H). LCMS (ESI, m z): 454 [M–H]$^-$.

Example 43. Synthesis of Compound 49

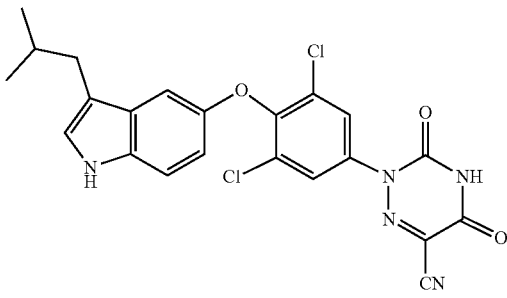

To a stirred solution of 5-(2,6-dichloro-4-nitrophenoxy)-1H-indole (2.00 g, 6.19 mmol) in 1,2-dichloroethane (80 mL) was added InBr$_3$ (0.22 g, 0.619 mmol) and isobutyryl chloride (0.99 g, 9.28 mmol) at 0° C. under N$_2$. The reaction mixture was stirred for 2 h at 85° C., then quenched with water (20 mL). The solution was extracted with EA (3×200 mL) and the organic layers were combined, dried over MgSO$_4$, filtered and concentrated under reduced pressure. The residue was purified on a silica gel column with PE:EA (3:1) to afford 1-[5-(2,6-dichloro-4-nitrophenoxy)-1H-indol-3-yl]-2-methylpropan-1-one as a light brown solid (1.5 g, 56%).

1-[5-(2,6-Dichloro-4-nitrophenoxy)-1-(4-methyl-benzenesulfonyl)-indol-3-yl]-2-methylpropan-1-one, a light yellow solid (1.3 g, 70%) was prepared similarly as described for 1-[5-(2,6-dichloro-4-nitrophenoxy)-1-(4-methyl-benzenesulfonyl)-indol-3-yl]propan-1-one.

5-(2,6-Dichloro-4-nitrophenoxy)-1-(4-methylbenzenesulfonyl)-3-(2-methylpropyl)indole, a light brown solid (1.2 g, 85%), was prepared similarly as described for 1-[5-(2,6-dichloro-4-nitrophenoxy)-1H-indol-3-yl]propan-1-one with the exception that, after quenching with water, the reaction was neutralized by the addition of NaOH solution at 0° C.

3,5-Dichloro-4-[[1-(4-methyl-benzenesulfonyl)-3-(2-methylpropyl)indol-5-yl]oxy]aniline as a light yellow solid (1.2 g, 95%) was prepared similarly as described for 3,5-dichloro-4-[[3-isopropyl-1-(4-methy-lbenzenesulfonyl)-indol-5-yl]oxy]aniline.

Ethyl (2-cyano-2-(2-(3,5-dichloro-4-((3-isobutyl-1-tosyl-1H-indol-5-yl)oxy)phenyl)hydrazineylidene)acetyl)carbamate, a red solid (860 mg, 48%), was prepared similarly as described for ethyl (2-cyano-2-(2-(3,5-dichloro-4-((1-tosyl-1H-indol-5-yl)oxy)phenyl)-hydrazineylidene)-acetyl) carbamate.

2-(3,5-Dichloro-4-[[1-(4-methylbenzenesulfonyl)-3-(2-methylpropyl)indol-5-yl]oxy]phenyl)-3,5-dioxo-4H-1,2,4-triazine-6-carbonitrile, a red solid (600 mg, 56%) was prepared similarly as described for 2-(4-[[3-isopropyl-1-(4-methylbenzene-sulfonyl)indol-5-yl]oxy]-3,5-dimethylphenyl)-3,5-dioxo-4H-1,2,4-triazine-6-carbonitrile.

Tosyl group deprotection to afford 2-(3,5-dichloro-4-[[3-(2-methylpropyl)-1H-indol-5-yl]oxy]phenyl)-3,5-dioxo-4H-1,2,4-triazine-6-carbonitrile as an orange solid (51.2 mg, 22%) was prepared similarly as described for 2-[3,5-dichloro-4-(1H-indol-5-yloxy)phenyl]-3,5-dioxo-4H-1,2,4-triazine-6-carbonitrile. $^1$H NMR (300 MHz, MeOH-$d_4$) δ 7.78 (s, 2H), 7.28 (d, J=8.7 Hz, 1H), 7.02 (s, 1H), 6.73-6.83 (m, 2H), 2.51 (d, J=7.2 Hz, 2H), 1.83-1.92 (m, 1H), 0.90-1.00 (m, 6H). LC-MS (ESI, m/z): 468 [M–H].

Example 44. Synthesis of Compound 50

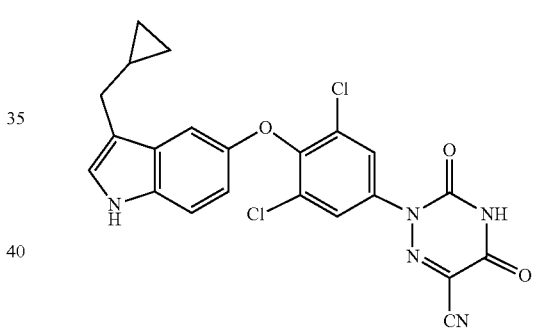

To a solution of 5-(2,6-dichloro-4-nitrophenoxy)-1H-indole (2.00 g, 6.19 mmol) in DCM (50 mL) was added SnCl$_4$ (1.93 g, 7.43 mmol) at 0° C. The solution warmed to rt and stirred for 30 min, then cyclopropanecarbonyl chloride (0.78 g, 7.43 mmol) was added in small portions to the suspension by syringe, followed by nitromethane (40 mL). The reaction mixture was stirred at rt for 2 h, after which ice water (40 mL) was slowly added. The solids were removed by filtration, and the filtrate was extracted with EA (3×50 mL), the organic layers were combined, dried over anhyd. Na$_2$SO$_4$, the solids were removed by filtration and the filtrate was concentrated under reduced pressure. The residue was purified on a silica gel column with hexane:EA (3:1) to afford 3-cyclopropanecarbonyl-5-(2,6-dichloro-4-nitrophenoxy)-1H-indole as a yellow solid (1.3 g, 48%).

3-Cyclopropanecarbonyl-5-(2,6-dichloro-4-nitrophenoxy)-1-(4-methylbenzenesulfonyl)-indole, a light brown solid (1.8 g, 70%) was prepared similarly as described for 1-[5-(2,6-dichloro-4-nitrophenoxy)-1-(4-methyl-benzenesulfonyl)-indol-3-yl]propan-1-one.

3-(Cyclopropylmethyl)-5-(2,6-dichloro-4-nitrophenoxy)-1-(4-methylbenzenesulfonyl)indole, a light brown solid (1.6 g, 77%) was prepared similarly as described for 1-[5-(2,6- dichloro-4-nitrophenoxy)-1H-indol-3-yl]propan-1-one with the exception that, after quenching with water, the reaction was neutralized by the addition of NaOH solution at 0° C.

3,5-Dichloro-4-[[3-(cyclopropylmethyl)-1-(4-methylbenzenesulfonyl)-indol-5-yl]oxy]aniline, a light yellow solid (1.3 g, 78%) was prepared similarly as described for 3,5-dichloro-4-[[3-isopropyl-1-(4-methy-lbenzenesulfonyl)-indol-5-yl]oxy]aniline.

Ethyl (2-cyano-2-(2-(3,5-dichloro-4-((3-(cyclopropylmethyl)-1-tosyl-1H-indol-5-yl)oxy)phenyl)hydrazineylidene) acetyl)carbamate, a red solid (1.18 g, 62%) was prepared similarly as described for ethyl (2-cyano-2-(2-(3,5-dichloro-4-((1-tosyl-1H-indol-5-yl)oxy)phenyl)-hydrazineylidene)-acetyl) carbamate.

2-(3,5-Dichloro-4-[[3-(cyclopropylmethyl)-1-(4-methylbenzenesulfonyl)indol-5-yl]oxy]phenyl)-3,5-dioxo-4H-1,2,4-triazine-6-carbonitrile, a light brown solid (732 mg, 62%), purified via reverse phase chromatography using a C18 column, was prepared similarly as described for 2-(4-[[3-isopropyl-1-(4-methylbenzene-sulfonyl)indol-5-yl]oxy]-3,5-dimethylphenyl)-3,5-dioxo-4H-1,2,4-triazine-6-carbonitrile.

Tosyl group deprotection to afford 2-(3,5-dichloro-4-[[3-(cyclopropylmethyl)-1H-indol-5-yl]oxy]phenyl)-3,5-dioxo-4H-1,2,4-triazine-6-carbonitrile as a orange solid (121 mg, 22%) was prepared similarly as described for 2-[3,5-dichloro-4-(1H-indol-5-yloxy)phenyl]-3,5-dioxo-4H-1,2,4-triazine-6-carbonitrile. $^1$H NMR (300 MHz, MeOH-$d_4$) δ 7.79 (s, 2H), 7.28-7.31 (m, 1H), 7.11 (s, 1H), 6.77-6.85 (m, 2H), 2.57 (d, J=6.6 Hz, 2H), 0.95-1.02 (m, 1H), 0.47-0.50 (m, 2H), 0.13-0.16 (m, 2H). LCMS (ESI, m/z): 466 [M–H].

Example 45. Synthesis of Compound 51

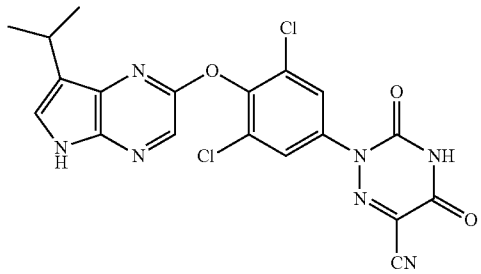

51

To a stirred solution of 2-bromo-5H-pyrrolo[2,3-b]pyrazine (14.0 g, 70.7 mmol), $Cs_2CO_3$ (34.7 g, 106 mmol) in DMF (200 mL) was added [2-(chloro-methoxy)ethyl]trimethylsilane (17.7 g, 106 mmol) dropwise at 0° C. The mixture was stirred for 2 h at rt and quenched with water (400 mL). The mixture was extracted with EA (3×500 mL) and the organic layers were combined, dried over anhyd. $Na_2SO_4$, the solids were removed by filtration and the filtrate was concentrated under reduced pressure. The residue was purified by silica gel column chromatography with PE:EA (18:1) to afford 2-bromo-5-[[2-(trimethylsilyl) ethoxy] methyl]pyrrolo[2,3-b]pyrazine as a yellow solid (21 g, 86%).

To a stirred solution of 2-bromo-5-[[2-(trimethylsilyl) ethoxy]-methyl]pyrrolo[2,3-b]pyrazine (20.0 g, 60.9 mmol) and 4-amino-2,6-dichloro-phenol (16.3 g, 91.4 mmol) in DMSO (200 mL) were added $K_2CO_3$ (25.3 g, 183 mmol) and CuI (4.64 g, 24.4 mmol) at rt. The mixture was stirred for overnight at 90° C. under $N_2$. The reaction was quenched with sat. $NH_4C_1$ (aq.) and extracted with EA (3×800 mL). The organic layers were combined, washed with brine (2×600 mL), dried over anhyd. $Na_2SO_4$, the solids were removed by filtration and the filtrate was concentrated under reduced pressure. The residue was purified by reverse phase column chromatography using a $C_{18}$ column (ACN: $H_2O$=10-60% in 50 min) to afford 3,5-dichloro-4-[(5-[[2-(trimethylsilyl)ethoxy]-methyl]pyrrolo[2,3-b]pyrazin-2-yl) oxy]aniline as a yellow solid (2.2 g, 8%).

To a stirred solution of 3,5-dichloro-4-[(5-[[2-(trimethylsilyl)ethoxy]-methyl]-pyrrolo[2,3-b]pyrazin-2-yl)oxy]aniline (2.20 g, 5.17 mmol) in $CH_3CN$ (30 mL) was added (dimethoxymethyl)dimethylamine (1.54 g, 12.9 mmol) dropwise at rt. The mixture was stirred for overnight at 80° C., quenched with water (50 mL), then was extracted with EA (3×50 mL) and the organic layers were combined, washed with brine (2×40 mL), dried over anhyd. $Na_2SO_4$, filtered and concentrated under reduced pressure. The residue was purified by silica gel column chromatography with PE:EA (1:1) to afford N-[3,5-dichloro-4-[(5-[[2-(trimethylsilyl)ethoxy]methyl]pyrrolo-[2,3-b]pyrazin-2-yl)oxy]phenyl]-N,N-dimethylmethanimid-amide as a brown oil (1.875 g, 72%).

To a stirred solution of N-[3,5-dichloro-4-[(5-[[2-(trimethylsilyl)ethoxy]-methyl]pyrrolo[2,3-b]pyrazin-2-yl)oxy] phenyl]-N,N-dimethylmethanimidamide (1.83 g, 3.81 mmol) in DCM (20 mL) was added NIS (1.11 g, 4.95 mmol) and p-toluenesulfonic acid (0.20 g, 1.16 mmol) in portions at 0° C. The reaction mixture was stirred for 4 h at rt and quenched with water (50 mL). The mixture was extracted with DCM (3×50 mL) and the organic layers were combined, washed with brine (2×40 mL), dried over anhyd. $Na_2SO_4$, the solids were removed by filtration and the filtrate was concentrated under reduced pressure. The residue was purified by silica gel column chromatography with PE:EA (4:1) to afford N-[3,5-dichloro-4-[(7-iodo-5-[[2-(trimethylsilyl)ethoxy]methyl]-pyrrolo[2,3-b]pyrazin-2-yl)oxy]phenyl]-N,N-dimethylmethanimidamide as a brown oil (1.33 g, 55%).

To a stirred mixture of N-[3,5-dichloro-4-[(7-iodo-5-[[2-(trimethylsilyl)-ethoxy]methyl]pyrrolo[2,3-b]pyrazin-2-yl) oxy]phenyl]-N,N-dimethyl-methanimidamide (980 mg, 1.62 mmol), $PdCl_2$(dppf) (106 mg, 0.162 mmol) and $K_2PO_3$ (515 mg, 2.42 mmol) in dioxane (33 mL) and water (6 mL) were added 4,4,5,5-tetramethyl-2-(prop-1-en-2-yl)-1,3,2-dioxaborolane (1.09 g, 6.47 mmol) at rt. The mixture was stirred for overnight at 55° C. under $N_2$, then quenched with water (60 mL). The mixture was extracted with EA (3×60 mL) and the organic layers were combined, washed with brine (3×50 mL), dried over anhyd. $Na_2SO_4$, filtered and concentrated under reduced pressure. The residue was purified by silica gel column chromatography with PE:EA (7:1) to afford N-(3,5-dichloro-4-[[7-(prop-1-en-2-yl)-5-[[2-(trimethylsilyl)ethoxy]methyl]-pyrrolo[2,3-b]pyra-zin-2-yl] oxy]-phenyl)-N,N-dimethylmethanimidamide as a yellow solid (688 mg, 81%).

To a stirred mixture of 2-(3,5-dichloro-4-[[3-(prop-1-en-2-yl)-1H-pyrrolo[3,2-b]pyridin-5-yl]oxy]phenyl)-3,5-dioxo-4H-1,2,4-triazine-6-carbonitrile (688 mg, 1.51 mmol) in EA (24.0 mL) was added Pd/C (90.0 mg, 0.846 mmol) at rt under $N_2$. The mixture was stirred for 1 h at rt under $H_2$, the solids were removed by filtration through celite, and the filtrate was concentrated under reduced pressure to provide 2-[3,5-dichloro-4-([3-isopropyl-1H-pyrrolo[3,2-b]pyridin-5-yl]oxy)phenyl]-3,5-dioxo-4H-1,2,4-triazine-6-carbonitrile as a yellow oil (670 mg, 93%). The crude product was used in the next step without further purification.

To a stirred solution of (E)-N-[3,5-dichloro-4-[(7-isopropyl-5-[[2-(trimethyl-silyl)ethoxy]methyl]pyrrolo[2,3-b]pyrazin-2-yl)oxy]phenyl]-N,N-dimethyl-methanimid-amide (670 mg, 1.28 mmol) in ethyl alcohol (15 mL) was added ethylenediamine (347 mg, 5.77 mmol) dropwise at rt. The mixture was stirred overnight at 80° C. then concentrated under reduced pressure. The mixture was diluted with EA (40 mL), washed with brine (2×30 mL), dried over anhyd. Na$_2$SO$_4$, the solids were removed by filtration and the filtrate was concentrated under reduced pressure to afford 3,5-dichloro-4-[(7-isopropyl-5-[[2-(trimethylsilyl)-ethoxy]methyl]-pyrrolo[2,3-b]-pyrazin-2-yl)oxy] aniline as a brown solid (700 mg, crude).

Ethyl (Z)-(2-cyano-2-(2-(3,5-dichloro-4-((7-isopropyl-5-((2-(trimethyl-silyl)ethoxy)methyl)-5H-pyrrolo[2,3-b]pyrazin-2-yl)oxy)phenyl)hydrazineylidene)-acetyl)carbamate, a red solid (800 mg, crude) was prepared similarly as described for ethyl (2-cyano-2-(2-(3,5-dichloro-4-((1-tosyl-1H-indol-5-yl)oxy)phenyl)-hydrazineyl-idene)-acetyl) carbamate.

2-[3,5-dichloro-4-[(7-isopropyl-5-[[2-(trimethylsilyl)ethoxy]methyl]-pyrrolo[2,3-b]pyrazin-2-yl)-oxy]phenyl]-3,5-dioxo-4H-1,2,4-triazine-6-carbonitrile, a brown solid (186 mg, 21%) was prepared similarly as described for 2-(4-[[3-isopropyl-1-(4-methylbenzene-sulfonyl)indol-5-yl]oxy]-3,5-dimethylphenyl)-3,5-dioxo-4H-1,2,4-triazine-6-carbonitrile.

Tosyl group deprotection to afford 2-[3,5-dichloro-4-([7-isopropyl-5H-pyrrolo[2,3-b]pyrazin-2-yl]oxy)phenyl]-3,5-dioxo-4H-1,2,4-triazine-6-carbonitrile as a white solid (25.5 mg, 17%) was prepared similarly as described for 2-[3,5-dichloro-4-(1H-indol-5-yloxy)phenyl]-3,5-dioxo-4H-1,2,4-triazine-6-carbonitrile. $^1$H NMR (300 MHz, DMSO-d$_6$) δ 12.45 (br, 1H), 12.21 (s, 1H), 8.10 (s, 2H), 7.43 (s, 1H), 3.58 (s, 3H), 3.11-2.97 (m, 1H), 1.20 (d, J=6.9 Hz, 6H). LCMS (ESI, m/z): 456 [M−H]$^+$.

Example 46. Synthesis of Compound 52

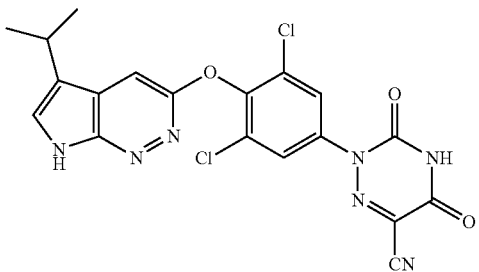

To a stirred solution of 3-chloro-7H-pyrrolo[2,3-c]pyridazine (4.00 g, 26.1 mmol) and NEt$_3$ (3.96 g, 39.2 mmol) in DCM (50 mL) was added [2-(chloromethoxy)ethyl]trimethylsilane (13.02 g, 78.4 mmol) dropwise at 0° C. The mixture was stirred for overnight at rt and quenched with water (100 mL), then was extracted with DCM (3×150 mL). The combined organic layers were washed with brine (2×100 mL), dried over anhyd. Na$_2$SO$_4$, filtrated and concentrated under reduced pressure. The residue was purified by silica gel column chromatography, eluted with PE:EA (10:1) to afford 3-chloro-7-[[2-(trimethylsilyl)ethoxy]methyl]pyrrolo[2,3-c]pyrid-azine as a yellow solid (3.50 g, 47%).

To a stirred solution of 3-chloro-7-[[2-(trimethylsilyl)ethoxy]methyl]-pyrrolo[2,3-c]pyridazine (3.20 g, 11.3 mmol) and (E)-N'-(3,5-dichloro-4-hydroxyphenyl)-N,N-dimethylformimidamide (2.63 g, 11.3 mmol) in THF (40 mL) was added Pd$_2$(dba)$_3$-chloroform adduct (1.17 g, 1.13 mmol), JosiPhos (625 mg, 1.13 mmol) and Cs$_2$CO$_3$ (7.35 g, 22.5 mmol) at rt. The mixture was stirred for 48 h at 95° C. under N$_2$ and quenched with water (50 mL). The mixture was extracted with EA (3×60 mL). The combined organic layers were washed with brine (2×50 mL), dried over anhyd. Na$_2$SO$_4$, filtrated and concentrated under reduced pressure. The residue was purified by silica gel column chromatography, eluted with PE:EA (1:2) to afford (E)-N'-(3,5-dichloro-4-((7-((2-(trimethylsilyl)ethoxy)methyl)-7H-pyrrolo[2,3-c]pyridazin-3-yl)oxy)phenyl)-N,N-dimethylformimidamide as a yellow solid (2.2 g crude).

To a stirred mixture of (E)-N-[3,5-dichloro-4-[(7-[[2-(trimethylsilyl)-ethoxy]methyl]pyrrolo[2,3-c]pyridazin-3-yl)oxy]phenyl]-N,N-dimethylmethanimidamide (1.12 g, 2.33 mmol) in DCM (12 mL) was added NIS (0.68 g, 3.02 mmol) and p-toluenesulfonic acid (0.12 g, 0.699 mmol) in portions at 0° C. The mixture was stirred for 4 h at rt and quenched with water (30 mL) at rt. The mixture was extracted with DCM (3×40 mL). The combined organic layers were washed with brine (2×30 mL), dried over anhyd. Na$_2$SO$_4$ the solids were removed by filtration and the filtrate was concentrated under reduced pressure. The residue was purified by silica gel column chromatography, eluted with PE:EA (4:1) to afford (E)-N-[3,5-dichloro-4-[(5-iodo-7-[[2-(trimethylsilyl)ethoxy]-methyl]pyrrolo[2,3-c]pyridazin-3-yl)oxy] phenyl]-N,N-dimethyl-methanimidamide as a brown solid (600 mg, crude).

To a stirred mixture of (E)-N-[3,5-dichloro-4-[(5-iodo-7-[[2-(trimethylsilyl)-ethoxy]methyl]pyrrolo[2,3-c]pyridazin-3-yl)oxy]phenyl]-N,N-dimethylmethanimidamide (650 mg, 1.07 mmol), 1,1'-Bis (di-t-butylphosphino)ferrocene palladium dichloride (69.9 mg, 0.107 mmol) and K$_2$PO$_3$ (341 mg, 1.61 mmol) in 1,4-dioxane (10 mL) and water (2 mL) was added 4,4,5,5-tetramethyl-2-(prop-1-en-2-yl)-1,3,2-dioxaborolane (721 mg, 4.29 mmol) at rt. The mixture was stirred for 4 h at 50° C. under N$_2$ and quenched with water (50 mL) at rt, then was extracted with EA (3×50 mL). The combined organic layers were washed with brine (2×40 mL), dried over anhyd. Na$_2$SO$_4$, the solids were removed by filtration and the filtrate was concentrated under reduced pressure. The residue was purified by silica gel column chromatography, eluted with PE:EA (3:1) to afford (E)-N-(3,5-dichloro-4-[[5-(prop-1-en-2-yl)-7-[[2-(trimethylsilyl)ethoxy]-methyl]pyrrolo[2,3-c]pyridazin-3-yl]oxy]phenyl)-N,N-dimethylmethanimidamide as a brown solid (675 mg, crude).

To a stirred mixture of (E)-N-(3,5-dichloro-4-[[5-(prop-1-en-2-yl)-7-[[2-(trimethylsilyl)ethoxy]methyl]pyrrolo[2,3-c]pyridazin-3-yl]oxy]phenyl)-N,N-dimethyl-methanimidamide (800 mg, 1.54 mmol) in EA (10 mL) was added Pd:C (300 mg) at rt under hydrogen. The mixture was stirred for 1 h at rt, then was filtered and the filter cake was washed with EA (3×20 mL). The combined organic layers were concentrated under reduced pressure to afford (E)-N-[3,5-dichloro-4-[(5-isopropyl-7-[[2-(trimethylsilyl)ethoxy]methyl]pyrrolo[2,3-c]pyridazin-3-yl)oxy]phenyl]-N,N-dimethyl-methanimidamide as a yellow oil (1 g, crude).

To a stirred solution of (E)-N-[3,5-dichloro-4-[(5-isopropyl-7-[[2-(trimethylsilyl)ethoxy]methyl]pyrrolo[2,3-c]

pyridazin-3-yl)oxy]phenyl]-N,N-dimethyl-methanimidamide (1.00 g, 1.92 mmol) in EtOH (9 mL) was added NaOH (9 mL, 9.00 mmol, 1 M) dropwise at rt. The mixture was stirred for 3 h at 80° C. then diluted with water (30 mL) and extracted with EA (3×40 mL). The combined organic layers were washed with brine (2×30 mL), filtrated and concentrated under reduced pressure to afford 3,5-dichloro-4-[(5-isopropyl-7-[[2-(trimethylsilyl)-ethoxy]methyl]-pyrrolo[2,3-c]pyridazin-3-yl)oxy]aniline as a brown oil (900 mg, crude).

Ethyl (2-cyano-2-(2-(3,5-dichloro-4-((5-isopropyl-7-((2-(trimethylsilyl)-ethoxy)methyl)-7H-pyrrolo[2,3-c]pyridazin-3-yl)oxy)phenyl)hydrazineylidene)-acetyl)carbamate, a red solid (920 mg) was prepared similarly as described for ethyl (2-cyano-2-(2-(3,5-dichloro-4-((1-tosyl-1H-indol-5-yl)oxy)phenyl)-hydrazineylidene)-acetyl) carbamate with the exception that the reaction stirred for 10 min at OC. The crude product was used in the next step without further purification.

2-[3,5-dichloro-4-[(5-isopropyl-7-[[2-(trimethylsilyl)-ethoxy]methyl]pyrrolo[2,3-c]pyridazin-3-yl)oxy] phenyl]-3,5-dioxo-4H-1,2,4-triazine-6-carbonitrile as a brown solid (690 mg, 69%) was prepared similarly as described for 2-(4-[[3-isopropyl-1-(4-methylbenzene-sulfonyl)indol-5-yl]oxy]-3,5-dimethylphenyl)-3,5-dioxo-4H-1,2,4-triazine-6-carbonitrile.

Tosyl group deprotection to afford 2-[3,5-dichloro-4-([5-isopropyl-7H-pyrrolo[2,3-c]pyridazin-3-yl]oxy)phenyl]-3,5-dioxo-4H-1,2,4-triazine-6-carbonitrile as a yellow solid (24.8 mg, 31%) was prepared similarly as described for 2-[3,5-dichloro-4-(1H-indol-5-yloxy)phenyl]-3,5-dioxo-4H-1,2,4-triazine-6-carbonitrile. $^1$H NMR (400 MHz, DMSO-$d_6$) 13.28 (s, 1H), 12.03-12.05 (m, 1H), 7.83 (s, 1H), 7.79 (s, 2H), 7.73-7.75 (m, 1H), 3.12-3.19 (m, 1H), 1.32 (d, J=6.8 Hz, 6H). LCMS (ESI, m/z): 458[M+H]$^+$.

Example 47. Synthesis of Compound 53

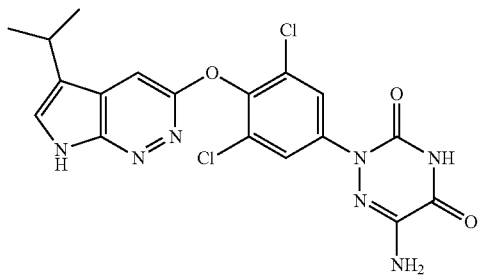

The conversion of compound 52 to 53 was analogous to the method to prepare 6-amino-2-[3,5-dichloro-4-[(5-isopropyl-6-oxo-1H-pyridazin-3-yl)oxy]-phenyl]-4H-1,2,4-triazine-3,5-dione to afford 2-[3,5-dichloro-4-([5-isopropyl-7H-pyrrolo[2,3-c]pyridazin-3-yl]oxy)phenyl]-3,5-dioxo-4H-1,2,4-triazine-6-carboxylic acid as a yellow solid (190 mg). The crude product was used in the next step without further purification.

To a stirred solution of 2-[3,5-dichloro-4-([5-isopropyl-7H-pyrrolo[2,3-c]pyridazin-3-yl]oxy)phenyl]-3,5-dioxo-4H-1,2,4-triazine-6-carboxylic acid (150 mg, 0.314 mmol) and DPPA (260 mg, 0.943 mmol) in tBuOH (3 mL) was added NEt$_3$ (127 mg, 1.26 mmol) dropwise at rt. The resulting mixture was stirred overnight at 85° C. then quenched with water (30 mL) at rt and extracted with EA (3×30 mL). The combined organic layers were washed with brine (2×20 mL), dried over anhyd. Na$_2$SO$_4$, the solids were removed by filtration and the filtrate was concentrated under reduced pressure. The residue was purified by silica gel column chromatography, eluted with PE:EA (3:1) to afford t-butyl-N-[2-[3,5-dichloro-4-([5-isopropyl-7H-pyrrolo[2,3-c]pyridazin-3-yl]-oxy)phenyl]-3,5-dioxo-4H-1,2,4-triazin-6-yl]carbamate as a yellow solid (130 mg, crude).

To a stirred solution of t-butyl-N-[2-[3,5-dichloro-4-([5-isopropyl-7H-pyrrolo[2,3-c]pyridazin-3-yl]oxy)phenyl]-3,5-dioxo-4H-1,2,4-triazin-6-yl]carbamate (120 mg) in DCM (1 mL) was added TFA (2 mL) dropwise at rt. The resulting mixture was stirred for 2 h at rt and concentrated under reduced pressure. The reaction was quenched with sat aq. Na$_2$CO$_3$ (20 mL) at rt. The resulting mixture was extracted with DCM (3×30 mL). The combined organic layers were washed with brine (2×20 mL), dried over anhyd. Na$_2$SO$_4$, filtrated and concentrated under reduced pressure. The crude product was purified by preparative HPLC to afford 6-amino-2-[3,5-dichloro-4-([5-isopropyl-7H-pyrrolo[2,3-c]pyridazin-3-yl]oxy)phenyl]-4H-1,2,4-triazine-3,5-dione as a white solid (44.8 mg). $^1$H NMR (300 MHz, DMSO-$d_6$) δ 11.41-12.07 (br, 2H), 7.85-7.92 (m, 2H), 7.68-7.79 (m, 2H), 6.41 (s, 2H), 3.10-3.20 (m, 1H), 1.36-1.21 (m, 6H).

LCMS (ESI, m/z): 448[M+H]$^+$.

Example 48. Synthesis of Compound 54

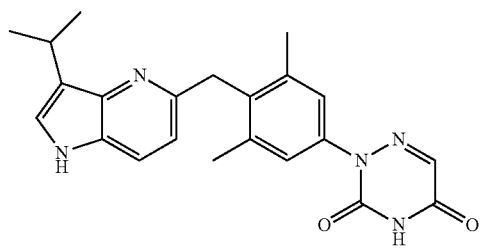

To a mixture of [4-[[3-isopropyl-1-(p-tolylsulfonyl)pyrrolo[3,2-b]pyridin-5-yl]methyl]-3,5-dimethyl-phenyl] trifluoromethanesulfonate (50 mg, 86.1 µmol), 2H-1,2,4-triazine-3,5-dione (29.2 mg, 258 µmol), di-t-butyl-[2,3,4,5-tetramethyl-6-(2,4,6-triiso-propylphenyl)phenyl]phosphane (8.28 mg, 17.2 µmol) and K$_2$CO$_3$ (35.7 mg, 258 µmol) in t-BuOH (3 mL) was added Pd$_2$(dba)$_3$ (7.89 mg, 8.61 µmol) under N$_2$ protection. The mixture was stirred at 110° C. for 90 min under microwave irradiation. The reaction was diluted with H$_2$O (5 mL) and extracted with EA (3×5 mL). The combined organic layers were washed with brine (5 mL), dried over anhyd. Na$_2$SO$_4$, the solids were removed by filtration and the filtrate was concentrated to give a residue, which was purified by silica gel chromatography (0~50% EA in PE) to give 2-[4-[[3-isopropyl-1-(p-tolylsulfonyl)-pyrrolo[3,2-b]pyridin-5-yl]methyl]-3,5-dimethyl-phenyl]-1,2,4-triazine-3,5-dione as a yellow solid (60 mg, 98%, 37% purity).

Tosyl group deprotection was performed similarly as described for 2-[3,5-dichloro-4-(1H-indol-5-yloxy)phenyl]-3,5-dioxo-4H-1,2,4-triazine-6-carbonitrile to afford 2-[4-[(3-isopropyl-1H-pyrrolo[3,2-b]pyridine-5-yl)methyl]-3,5-dimethyl-phenyl]-1,2,4-triazine-3,5-dione as a white solid (5.88 mg, 15%). $^1$H NMR (400 MHz, DMSO-$d_6$) δ 10.81 (br s, 1H), 8.23 (br s, 1H), 7.59 (s, 1H), 7.56 (d, J=8.4 Hz, 1H), 7.29 (s, 1H), 7.16 (s, 2H), 6.69 (d, J=8.4 Hz, 1H), 4.23 (s, 2H), 3.20 (td, J=6.8, 13.6 Hz, 1H), 2.38 (s, 6H), 1.33 (d, J=6.9 Hz, 6H). LCMS (ESI, m/z): 390.3[M+H]$^+$.

Example 49. Synthesis of Compound 55

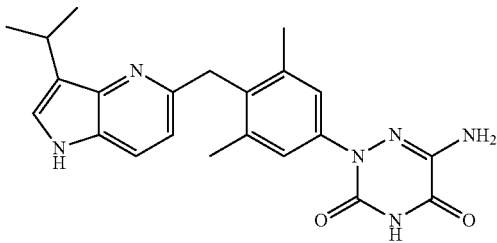

5-[(4-benzyloxy-2,6-dimethyl-phenyl)methyl]-3-isopropyl-1-(p-tolyl-sulfonyl)pyrrolo[3,2-b]pyridine, a yellow solid (1.36 g, 73%) was prepared similarly as described for 5-[(4-benzyloxy-2,6-dimethyl-phenyl)methyl]-3-isopropyl-1-(p-tolylsulfonyl)pyrrolo[3,2-b]pyridine.

4-[[3-isopropyl-1-(p-tolylsulfon-yl)pyrrolo[3,2-b]pyridin-5-yl]methyl]-3,5-dimethyl-phenol, a white solid (1 g, 88%) was prepared similarly as described for 4-[[3-isopropyl-1-(p-tolylsulfonyl)pyrrolo[3,2-b]pyridin-5-yl]methyl]-3,5-dimethyl-phenol.

A mixture of [4-[[3-isopropyl-1-(p-tolylsulfonyl)pyrrolo[3,2-b]pyridin-5-yl]methyl]-3,5-dimethyl-phenyl] trifluoromethanesulfonate (600 mg, 1.03 mmol), bis(pinacolato)diboron (525 mg, 2.07 mmol), Pd(dppf)Cl$_2$·CH$_2$Cl$_2$ (84.4 mg, 103 µmol), KOAc (304 mg, 3.10 mmol) in DMSO (10 mL) was degassed and purged with N$_2$. The mixture was stirred at 130° C. for 16 h under N$_2$. The reaction mixture was partitioned between H$_2$O (30 mL) and EA (50 mL). The organic phase was separated, washed with brine (30 mL), dried over Na$_2$SO$_4$, the solids were removed by filtration and the filtrate was concentrated under reduced pressure to give a residue. The residue was purified by silica gel chromatography (0~10% EA in PE) to give 5-[[2,6-dimethyl-4-(4,4,5,5-tetramethyl-1,3,2-dioxa-borolan-2-yl)phenyl]-methyl]-3-isopropyl-1-(p-tolylsulfonyl)pyrrolo[3,2-b]pyridine as a yellow solid (340 mg, 59%).

To a solution of 5-[[2,6-dimethyl-4-(4,4,5,5-tetramethyl-1,3,2-dioxaborolan-2-yl)phenyl]methyl]-3-isopropyl-1-(p-tolylsulfonyl)pyrrolo[3,2-b]pyridine (290 mg, 519 µmol) in acetone (12 mL) and H$_2$O (6 mL) was added NaIO$_4$ (1.11 g, 5.19 mmol, 287.71 µL) and NH$_4$OAc (400 mg, 5.19 mmol) at 25° C. After the addition, the mixture was stirred at 25° C. for 16 h. The reaction mixture was extracted with EA (3×10 mL). The organic layers were washed with brine (20 mL), dried over Na$_2$SO$_4$, the solids were removed by filtration and the filtrate was concentrated under reduced pressure, then purified by preparatory TLC (SiO$_2$, PE:EA=1:1) to give [4-[[3-isopropyl-1-(p-tolylsulfonyl)pyrrolo[3,2-b]pyridin-5-yl] methyl]-3,5-dimethyl-phenyl]-boronic acid as a white solid (190 mg, 76%).

A mixture of 6-amino-4-(benzyloxymethyl)-2H-1,2,4-triazine-3,5-dione (252 mg, 1.02 mmol), [4-[[3-isopropyl-1-(p-tolylsulfonyl)pyrrolo[3,2-b]pyridin-5-yl]methyl]-3,5-dimethyl-phenyl]boronic acid (440 mg, 923 µmol), pyridine (146 mg, 1.85 mmol, 149 µL), 4 Å molecular sieves (5 g) and Cu(OAc)$_2$ (83.9 mg, 462 µmol) in DMF (15 mL) was degassed and purged with O$_2$, then the mixture was stirred at 60° C. for 16 h under an O2 atmosphere (via balloon). The reaction mixture was cooled to 25° C. and diluted with EA (30 mL), then the solids were removed by filtration. The filtrate was washed with H$_2$O (3×10 mL), brine (20 mL), dried over Na$_2$SO$_4$, the solids were removed by filtration and the filtrate was concentrated under reduced pressure to give a residue. The residue was purified by silica gel chromatography (0~30% EA in PE) to give 6-amino-4-(benzyloxymethyl)-2-[4-[[3-isopropyl-1-(p-tolylsulfonyl)-pyrrolo[3,2-b]pyrid-ine-5-yl]methyl]-3,5-dimethyl-phenyl]-1,2,4-triazine-3,5-dione as a yellow gum (140 mg, 20%).

A solution of 6-amino-4-(benzyloxymethyl)-2-[4-[[3-isopropyl-1-(p-tolyl-sulfonyl)pyrrolo[3,2-b]pyridine-5-yl]methyl]-3,5-dimethyl-phenyl]-1,2,4-triazine-3,5-dione (140 mg, 206 µmol) in TFA (5 mL) was stirred at 80° C. for 16 hr. The reaction mixture was diluted with EA (10 mL), and the pH was adjusted to 7 by NaHCO$_3$ (sat. aq.). The organic layer was separated, and the aq. layer was extracted with EA (3×20 mL). The combined organic layers were washed with brine (20 mL), dried over Na$_2$SO$_4$, the solids were removed by filtration and the filtrate was concentrated under reduced pressure to give a residue, which was purified by preparatory TLC (SiO$_2$, PE:EA=1:2) to give 6-amino-2-[4-[[3-isopropyl-1-(p-tolylsulfonyl)-pyrrolo[3,2-b]pyridin-5-yl]methyl]-3,5-dimethyl-phenyl]-1,2,4-triazine-3,5-dione as a white solid (45 mg, 39%).

Tosyl group deprotection to afford 6-amino-2-[4-[(3-isopropyl-1H-pyrrolo[3,2-b]pyridin-5-yl)methyl]-3,5-dimethyl-phenyl]-1,2,4-triazine-3,5-dione, a white solid (11.3 mg, 35%) was prepared similarly as described for 2-[3,5-dichloro-4-(1H-indol-5-yloxy)phenyl]-3,5-dioxo-4H-1,2,4-triazine-6-carbonitrile. $^1$H NMR (400 MHz, DMSO-d$_6$) δ=12.07 (br s, 1H), 10.80 (br s, 1H), 7.55 (d, J=8.4 Hz, 1H), 7.29 (s, 1H), 7.19 (s, 2H), 6.63 (d, J=8.4 Hz, 1H), 6.29 (s, 2H), 4.21 (s, 2H), 3.25-3.19 (m, 1H), 2.34 (s, 6H), 1.34 (d, J=6.9 Hz, 6H). LCMS (ESI, m/z): 405.6 [M+H]$^+$.

Example 50. Synthesis of Compound 56

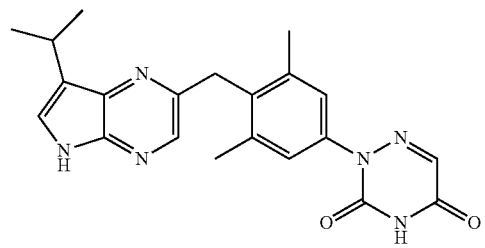

2-(2,6-Dimethyl-4-(4,4,5,5-tetramethyl-1,3,2-dioxaborolan-2-yl)benzyl)-7-isopropyl-5-tosyl-5H-pyrrolo[2,3-b]pyraz-ine, a yellow solid (520 mg, 73%), was prepared similarly as described for 5-[[2,6-dimethyl-4-(4,4,5,5-tetramethyl-1,3,2-dioxa-borolan-2-yl)phenyl]-methyl]-3-isopropyl-1-(p-tolylsulfonyl)pyrrolo[3,2-b]pyridine with the exception that the reaction was heated for 12 h.

(4-((7-Isopropyl-5-tosyl-5H-pyrrolo[2,3-b]pyrazin-2-yl)methyl)-3,5-dimethylphenyl)boronic acid, a yellow solid (670 mg, crude) was prepared similarly as described for [4-[[3-isopropyl-1-(p-tolylsulfonyl)pyrrolo[3,2-b]pyridin-5-yl]methyl]-3,5-dimethyl-phenyl]-boronic acid.

4-((Benzyloxy)methyl)-2-(4-((7-isopropyl-5-tosyl-5H-pyrrolo[2,3-b]pyrazin-2-yl)-methyl)-3,5-dimethylphenyl)-1,2,4-triazine-3,5(2H,4H)-dione, a light yellow solid (110 mg, 11%), was prepared similarly as described for 6-amino-4-(benzyloxymethyl)-2-[4-[[3-isopropyl-1-(p-tolylsulfonyl) pyrrolo[3,2-b]pyrid-ine-5-yl] methyl]-3,5-dimethyl-phenyl]-1,2,4-triazine-3,5-dione.

Tosyl group deprotection to give 2-(4-((7-isopropyl-5H-pyrrolo[2,3-b]pyrazin-2-yl)methyl)-3,5-dimethylphenyl)-1,2,4-triazine-3,5(2H,4H)-dione, a white solid (20 mg, 80%), was prepared similarly as described for 2-[3,5-dichloro-4-(1H-indol-5-yloxy)phenyl]-3,5-dioxo-4H-1,2,4-triazine-6-carbonitrile. $^1$H NMR (400 MHz, DMSO-d$_6$) δ=12.48 (brs, 1H), 11.54 (br s, 1H), 7.93 (s, 1H), 7.58 (s, 1H), 7.51 (s, 1H), 7.16 (s, 2H), 4.26 (s, 2H), 3.09-3.17 (m, 1H), 2.40 (s, 6H), 1.31 (d, J=6.8 Hz, 6H). LCMS (ESI, m/z): 391.6[M+H]$^+$.

Example 51. Synthesis of Compound 57

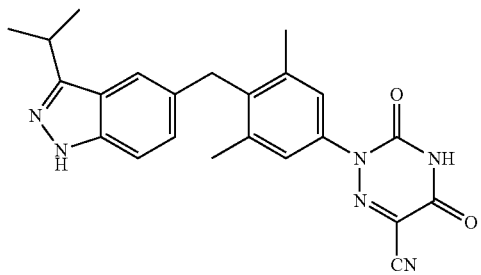

57

2,2,2-Trifluoro-N-(4-(hydroxy(3-isopropyl-1H-indazol-5-yl)methyl)-3,5-dimethylphenyl)acetamide, a white solid (294 mg, 36%), was prepared similarly as described for 2,2,2-trifluoro-N-(4-(hydroxy(3-pentyl-1H-indazol-5-yl)methyl)-3,5-dimethylphenyl)acetamide with the exception that t-butyl lithium was used (2.2 eq).

2,2,2-Trifluoro-N-(4-((3-isopropyl-1H-indazol-5-yl)methyl)-3,5-dimethylphenyl)acetamide (209 mg, 81%), a white solid, was prepared similarly as described for 2,2,2-trifluoro-N-(4-[[3-isopropyl-1-(4-methylbenzene-sulfonyl)indol-5-yl]methyl]-3,5-dimethylphenyl)acetamide.

Trifluoroacetamide deprotection to afford 4-((3-isopropyl-1H-indazol-5-yl)methyl)-3,5-dimethylaniline (141 mg, 96%) was prepared similarly as described for 3,5-dimethyl-4-((3-pentyl-1H-indazol-5-yl)methyl)aniline.

2-(4-((3-Isopropyl-1H-indazol-5-yl)methyl)-3,5-dimethylphenyl)-3,5-dioxo-2,3,4,5-tetrahydro-1,2,4-triazine-6-carbonitrile, an orange solid (10 mg, 8%) was prepared similarly as described for 2-(4-[[3-isopropyl-1-(4-methylbenzene-sulfonyl)indol-5-yl]oxy]-3,5-dimethylphenyl)-3,5-dioxo-4H-1,2,4-triazine-6-carbonitrile. $^1$H NMR (DMSO-d$_6$ 400 MHz): 1.31 (d, J=6.8 Hz, 6H); 2.28 (s, 6H); 3.22-3.27 (m, 1H); 4.15 (s, 2H); 6.96 (d, J=8.3 Hz, 1H); 7.18 (s, 2H); 7.35 (d, J=8.3 Hz, 1H); 7.38 (s, 1H); 12.47 (s, 1H); 12.99 (s, 1H).

Example 52. Synthesis of Compound 58

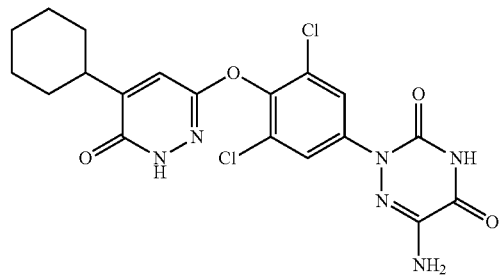

58

6-Amino-2-[3,5-dichloro-4-[(5-cyclohexyl-6-oxo-1H-pyridazin-3-yl)oxy]phenyl]-4H-1,2,4-triazine-3,5-dione was prepared similarly as described for 6-amino-2-(3,5-dichloro-4-((5-cyclobutyl-6-oxo-1,6-dihydropyridazin-3-yl)oxy)phenyl)-1,2,4-triazine-3,5(2H,4H)-dione to afford a white solid (101.1 mg, 40%). $^1$H NMR (400 MHz, DMSO-d$_6$) 12.18 (br, 2H), 7.83 (s, 2H), 7.35-7.36 (m, 1H), 6.47 (s, 2H), 2.68-2.72 (m, 1H), 1.21-1.84 (m, 10H). LCMS (ESI, m/z): 465 [M+H]$^+$.

Example 53. Synthesis of Compound 59

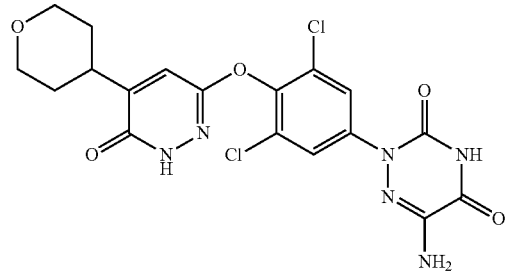

59

3,6-dichloro-4-(tetrahydro-2H-pyran-4-yl)pyridazine was prepared similarly as described for 3,6-dichloro-4-isopropylpyridazine (see also Samaritoni, J. G. Homolytic alkylation of 3,6-dichloropyridazine. Org. Prep. Proced. Int. 1988, 20, 117-121) as a white solid (5.3 g, 68%).

Ethyl (2-cyano-2-(2-(3,5-dichloro-4-hydroxyphenyl)hydrazineylidene)-acetyl)carbamate, a brown solid (42 g, crude) was prepared similarly as described for ethyl (2-cyano-2-(2-(3,5-dichloro-4-((1-tosyl-1H-indol-5-yl)oxy)phenyl)-hydrazineyl-idene)-acetyl) carbamate with the exception that the reaction was stirred for 10 min at 0° C.

To a stirred mixture of ethyl (2-cyano-2-(2-(3,5-dichloro-4-hydroxyphenyl)hydrazineylidene)acetyl)carbamate (41.0 g, 119 mmol) in DMA (400 mL) was added KOAc (46.6 g, 475 mmol) in portions at rt. The resulting mixture was stirred for 2 h at 110° C. and quenched with water (400 mL). The resulting mixture was extracted with EA (3×600 mL) and the organic layers were combined, washed with brine (3×400 mL), dried over anhyd. Na$_2$SO$_4$ the solids were removed by filtration and the filtrate was concentrated under reduced pressure. The residue was purified by silica gel column chromatography with DCM:MeOH (19:1) to afford 2-(3,5-dichloro-4-hydroxyphenyl)-3,5-dioxo-4H-1,2,4-triazine-6-carbonitrile as a yellow solid (24.3 g, 62%).

To a stirred solution of 2-(3,5-dichloro-4-hydroxyphenyl)-3,5-dioxo-4H-1,2,4-triazine-6-carbonitrile (20 g, 66.9 mmol) in AcOH (200 mL) was added HCl (100 mL) at rt. The resulting mixture was stirred for 5 h at 110° C. and concentrated under reduced pressure. The residue was adjusted to pH=9 with NaOH (1 M). The resulting mixture was extracted with EA (2×80 mL). The mixture was adjusted to pH=5 with HCl (1 M), then extracted with EA (3×100 mL) and the organic layers were combined, washed with brine (2×60 mL), dried over anhyd. Na$_2$SO$_4$ and concentrated under reduced pressure to afford 2-(3,5-dichloro-4-hydroxyphenyl)-3,5-dioxo-4H-1,2,4-triazine-6-carboxylic acid as a yellow solid (19 g, crude).

To a stirred solution of 2-(3,5-dichloro-4-hydroxyphenyl)-3,5-dioxo-4H-1,2,4-triazine-6-carboxylic acid (13.8 g, 43.4 mmol) in tBuOH (150 mL) was added DPPA (29.9 g, 108 mmol) and NEt$_3$ (17.7 g, 174 mmol) at rt. The mixture was stirred for overnight at 85° C. and concentrated under reduced pressure, diluted with water (100 mL) and extracted with EA (3×120 mL). The combined organic layers were washed with brine (2×80 mL), dried over anhyd. Na$_2$SO$_4$, filtrated and concentrated under reduced pressure. The residue was purified by silica gel column chromatography with DCM:MeOH (40:1) to afford t-butyl-N-(2-[3,5-dichloro-4-[(diphenoxyphosphoryl)-oxy]phenyl]-3,5-dioxo-4H-1,2,4-triazin-6-yl)carbam-ate as a yellow solid (16.0 g, 53%).

To a stirred mixture of t-butyl-N-(2-[3,5-dichloro-4-[(diphenoxyphosphor-yl)oxy]phenyl]-3,5-dioxo-4H-1,2,4-triazin-6-yl)carbamate (11.0 g, 17.7 mmol) in tBuOH (200 mL) was added NaOH (25 mL, 2 M) dropwise at rt. The resulting mixture was stirred for 4 h at rt and concentrated under reduced pressure. The mixture was diluted with water (50 mL), acidified to pH 6 with HCl (1 M), and extracted with EA (3×100 mL). The organic layers were combined, washed with brine (2×70 mL), dried over anhyd. Na$_2$SO$_4$, the solids were removed by filtration and the filtrate was concentrated under reduced pressure. The residue was purified by silica gel column chromatography with PE:EA (1:1) to afford t-butyl-N-[2-(3,5-dichloro-4-hydroxyphenyl)-3,5-dioxo-4H-1,2,4-triazin-6-yl]-carbam-ate as a yellow solid (6.0 g, 78%).

To a stirred mixture of 3,6-dichloro-4-(oxan-4-yl) pyridazine (300 mg, 1.29 mmol) and t-butyl-N-[2-(3,5-dichloro-4-hydroxyphenyl)-3,5-dioxo-4H-1,2,4-triazin-6-yl]carbamate (501 mg, 1.29 mmol) in DMSO (10 mL) was added K$_2$CO$_3$ (534 mg, 3.86 mmol) and CuI (123 mg, 0.644 mmol) at rt. The mixture was stirred for 16 h at 110° C. under N$_2$ and quenched with water (30 mL) at rt. The mixture was extracted with EA (3×40 mL) and the organic layers were combined, washed with brine (2×30 mL), dried over anhyd. Na$_2$SO$_4$ and concentrated under reduced pressure. The residue was purified by silica gel column chromatography DCM:MeOH (3:1) to afford 6-amino-2-(3,5-dichloro-4-[[6-chloro-5-(oxan-4-yl)pyrida-zin-3-yl]oxy] phenyl)-4H-1,2,4-triazine-3,5-dione as a brown solid (280 mg, 36%).

To a stirred mixture of 6-amino-2-(3,5-dichloro-4-[[6-chloro-5-(oxan-4-yl)-pyridazin-3-yl]oxy]phenyl)-4H-1,2,4-triazine-3,5-dione (250 mg, 0.515 mmol) in AcOH (4 mL) was added NaOAc (169 mg, 2.06 mmol) at rt. The mixture was stirred for overnight at 100° C. then quenched with water (30 mL). The mixture was extracted with EA (3×30 mL), the organic layers were combined, washed with brine (2×30 mL), dried over anhyd. Na$_2$SO$_4$, the solids were removed by filtration and the filtrate was concentrated under reduced pressure. The residue was purified by silica gel column chromatography with DCM:MeOH (20:1) to afford crude product that was purified by preparative HPLC to afford 6-amino-2-(3,5-dichloro-4-[[5-(oxan-4-yl)-6-oxo-1H-pyridazin-3-yl]oxy]phenyl)-4H-1,2,4-triazine-3,5-dione as a white solid (23.3 mg, 10%). $^1$H NMR (300 MHz, DMSO-d$_6$) 12.26-12.28 (m, 2H), 7.86 (s, 2H), 7.44-7.46 (m, 1H), 6.54 (s, 2H), 3.93-3.99 (m, 2H), 3.41-3.49 (m, 2H), 2.95-3.05 (m, 1H), 1.58-1.78 (m, 4H). LCMS (ESI, m/z): 467 [M+H]$^+$.

Example 54. Synthesis of Compounds 60 and 60-A

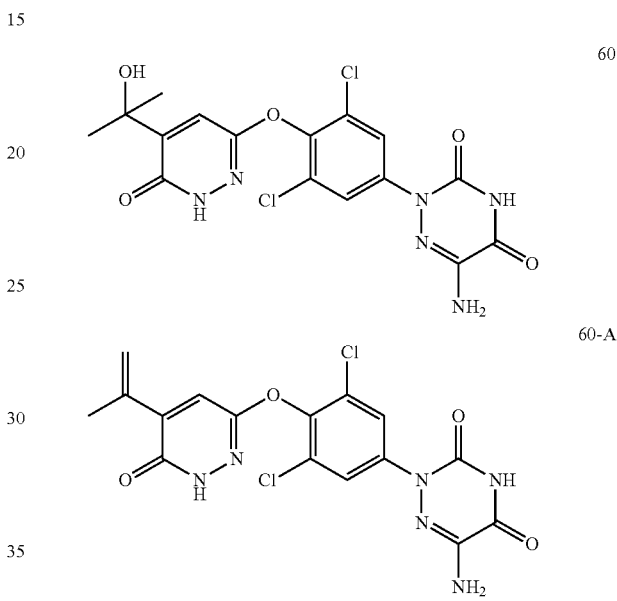

To a mixture of methyl 3,6-dichloropyridazine-4-carboxylate (10.0 g, 48.4 mmol) in THF (100 mL) was added NaOCH$_3$ (9.57 g, 53.1 mmol, 30% in MeOH) dropwise at 0° C. The mixture was stirred for 0.5 h at 0° C. then quenched with NH$_4$Cl (sat., aq., 150 mL). The mixture was extracted with EA (3×150 mL), the organic layers were combined, washed with brine (2×150 mL), dried over anhyd. Na$_2$SO$_4$, the solids were removed by filtration and the filtrate was concentrated under reduced pressure. The sample was purified by column chromatography (EA:PE=0-30% over 30 min) to afford methyl 6-chloro-3-methoxy-pyridazine-4-carboxylate as a yellow solid (7.3 g, 60%).

A mixture of methyl 6-chloro-3-methoxypyridazine-4-carboxylate (9.00 g, 44.4 mmol) in THF (100 mL) was added dropwise CH$_3$MgBr (59.2 mL, 178 mmol, 3 M in Et$_2$O) at −50° C. The mixture was stirred for 2 h at −50° C. to 0° C., then quenched with sat. aq. NH$_4$C$_1$ (150 mL) and extracted with EA (3×150 mL). The organic layers were combined, washed with brine (2×150 mL), dried over anhyd. Na$_2$SO$_4$, the solids were removed by filtration and the filtrate was concentrated under reduced pressure to afford crude product that was purified by silica column chromatography (EA:PE=0~30% over 20 min) to afford 2-(6-chloro-3-methoxypyridazin-4-yl)propan-2-ol as an off-white solid (2.35 g, 25%).

To a mixture of 2-(6-chloro-3-methoxypyridazin-4-yl) propan-2-ol (2.90 g, 14.3 mmol), (E)-N'-(3,5-dichloro-4-hydroxyphenyl)-N,N-dimethylmethan-imidamide (3.67 g, 15.7 mmol), Cs$_2$CO$_3$ (9.33 g, 28.6 mmol) and JosiPhos (0.85 g, 1.43 mmol) in THF (30 mL) was added Pd$_2$(dba)$_3$-CHCl$_3$ (1.48 g, 1.43 mmol). The mixture was stirred for 48 h at 95° C. under N$_2$ then quenched with water (50 mL). The mixture was extracted with EA (3×80 mL) and the organic layers were combined, washed with brine (2×50 mL), dried over anhyd. Na$_2$SO$_4$, the solids were removed by filtration and the filtrate was concentrated under reduced pressure. The sample was purified by column chromatography and eluted with EA:PE to afford (E)-N'-(3,5-dichloro-4-[[5-(2-hydroxypropan-2-yl)-6-methoxypyridazin-3-yl]oxy]phenyl)-N,N-dimethylmethanimidamide as a yellow solid (690 mg, 11%).

To a mixture of (E)-N'-(3,5-dichloro-4-[[5-(2-hydroxypropan-2-yl)-6-meth-oxypyridazin-3-yl]oxy]phenyl)-N,N-dimethylmethanimidamide (690 mg, 1.73 mmol) and KI (861 mg, 5.18 mmol) in DCM (10 mL) was added TMSCl (563 mg, 5.18 mmol) at 0° C. The mixture was stirred overnight at rt and quenched with water (20 mL). The mixture was extracted with DCM (3×30 mL) and the organic layers were combined, washed with brine (2×20 mL), dried over anhyd. Na$_2$SO$_4$, the solids were removed by filtration and the filtrate was concentrated under reduced pressure to provide (E)-N'-(3,5-dichloro-4-[[5-(2-hydroxypropan-2-yl)-6-oxo-1H-pyridazin-3-yl]oxy]phenyl)-N,N-dimethylmethanimidamide as a yellow solid (670 mg, crude).

A mixture of (E)-N'-(3,5-dichloro-4-[[5-(2-hydroxypropan-2-yl)-6-oxo-1H-pyridazin-3-yl]oxy]phenyl)-N,N-dimethylmethanimidamide (670 mg, 1.74 mmol) in ethanol (10 mL) and NaOH (10 mL, 1 M). The mixture was stirred overnight at 70° C. then concentrated under reduced pressure, diluted with water (50 mL) and extracted with EA (3×50 mL). The organic layers were combined, washed with brine (2×30 mL), dried over anhyd. Na$_2$SO$_4$, the solids were removed by filtration and the filtrate was concentrated under reduced pressure to provide 6-(4-amino-2,6-dichlorophenoxy)-4-(2-hydroxypropan-2-yl)-2H-pyridazin-3-one as a yellow solid (560 mg, 83%).

Ethyl (2-cyano-2-(2-(3,5-dichloro-4-((5-(2-hydroxypropan-2-yl)-6-oxo-1,6-dihydropyridazin-3-yl)oxy)phenyl)hydrazineylidene)acetyl)carbamate, a yellow solid (500 mg, 55%), was prepared similarly as described for ethyl (2-cyano-2-(2-(3,5-dichloro-4-((1-tosyl-1H-indol-5-yl)oxy)phenyl)-hydrazineylidene)-acetyl) carbamate.

2-(3,5-dichloro-4-[[5-(2-hydroxypropan-2-yl)-6-oxo-1H-pyridazin-3-yl]oxy]-phenyl)-3,5-dioxo-4H-1,2,4-triazine-6-carbonitrile as a yellow solid (380 mg, 80%) was prepared similarly as described for 2-(4-[[3-isopropyl-1-(4-methylbenzene-sulfonyl)indol-5-yl]oxy]-3,5-dimethylphenyl)-3,5-dioxo-4H-1,2,4-triazine-6-carbonitrile.

Further steps in the synthesis of compound 60, 6-amino-2-(3,5-dichloro-4-[[5-(2-hydroxypropan-2-yl)-6-oxo-1H-pyridazin-3-yl]oxy]phenyl)-4H-1,2,4-triazine-3,5-dione as a white solid (63.9 mg, 35%). $^1$H NMR (300 MHz, DMSO-d$_6$) δ ppm: 12.2-12.4 (m, 2H), 7.87 (s, 2H), 7.53 (s, 1H), 6.53 (s, 2H), 5.50 (s, 1H), 1.51 (s, 6H). LCMS (ESI, m/z): 441 [M+H]$^+$.

Compound 60-A, 6-amino-2-(3,5-dichloro-4-[[6-oxo-5-(prop-1-en-2-yl)-1H-pyridazin-3-yl]oxy]phenyl)-4H-1,2,4-triazine-3,5-dione was obtained as a white solid (13.8 mg, 8%). $^1$H NMR (300 MHz, DMSO-d$_6$) δ ppm: 12.0-12.5 (m, 2H), 7.87 (s, 2H), 7.54 (s, 1H), 6.49 (s, 3H), 5.57 (s, 1H), 2.12 (s, 3H). LCMS (ESI, m/z): 423 [M+H]$^+$.

Example 55. Synthesis of Compound 61

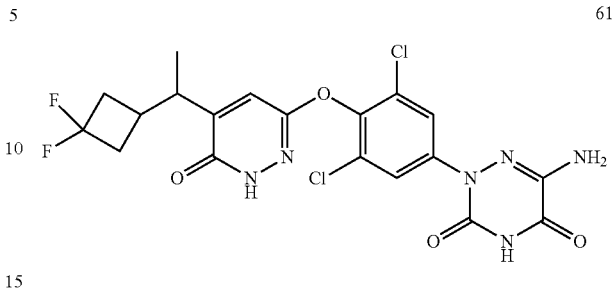

61

To a solution of diisopropylamine (5.18 g, 51.2 mmol) in THF (60 mL) was added dropwise n-buLi (19.5 mL, 2.5 M in hexane, 48.7 mmol) at −78° C. under N$_2$. The solution was stirred at −78~−50° C. for 0.5 h. Methyl 2-(3,3-difluorocyclobutyl)acetate (prepared according to procedures detailed in WO2015005901 and WO20150023913) (4 g, 24.4 mmol) in THF (10 mL) was added dropwise at −78° C. The solution was stirred at −78° C. for 0.5 h. CH$_3$I (4.50 g, 31.7 mmol) was added at −78° C. The reaction mixture was slowly warmed to rt over 3 h, then quenched with water (30 mL) and extracted with EA (3×50 mL). The organic layer was dried over anhyd. Na$_2$SO$_4$, the solids were removed by filtration and the filtrate was concentrated under reduced pressure to provide methyl 2-(3,3-difluorocyclobutyl)propanoate as a yellow oil (3.9 g, crude).

To a solution of methyl 2-(3,3-difluorocyclobutyl)propanoate (3.8 g, 21.3 mmol) in THF (40 mL) and MeOH (10 mL) was added NaOH solution (10 N, 20 mL). The solution was stirred overnight at rt. The pH was adjusted to 5 with HCl (1 N). The mixture was extracted with EA (3×50 mL). The organic phases were combined, washed with brine, dried over anhyd. Na$_2$SO$_4$, the solids were removed by filtration and the filtrate was concentrated under reduced pressure to provide 2-(3,3-difluorocyclobutyl)propanoic acid as a yellow oil (1.5 g, crude).

3,6-Dichloro-4-[1-(3,3-difluoro-cyclobutyl)ethyl]-pyridazine was prepared similarly as described for 3,6-dichloro-4-isopropylpyridazine (see also Samaritoni, J. G. Homolytic alkylation of 3,6-dichloropyridazine. Org. Prep. Proced. Int. 1988, 20, 117-121) to afford a yellow oil (390 mg, 21%).

6-Amino-2-[3,5-dichloro-4-([6-chloro-5-[1-(3,3-difluorocyclobutyl)-ethyl]pyrida-zin-3-yl]oxy)-phenyl]-4H-1,2,4-triazine-3,5-dione, a yellow oil (280 mg, 33%) was prepared similarly as described for 6-amino-2-(3,5-dichloro-4-[[6-chloro-5-(oxan-4-yl)pyrida-zin-3-yl]oxy]phenyl)-4H-1,2,4-triazine-3,5-dione.

To a solution of 6-amino-2-[3,5-dichloro-4-([6-chloro-5-[1-(3,3-difluoro-cyclobutyl)ethyl]pyridazin-3-yl]oxy)phenyl]-4H-1,2,4-triazine-3,5-dione (280 mg, 0.539 mmol) in AcOH (8 mL) was added NaOAc (221 mg, 2.69 mmol). The mixture was stirred overnight at 100° C. The mixture reaction was cooled to rt and quenched with water (50 mL). The reaction mixture was stirred for 10 min, the solid was filtered and washed with water (2×10 mL) and PE (2×5 mL), then dried under reduced pressure to afford the crude product that was purified by preparative HPLC to afford 6-amino-2-[3,5-dichloro-4-([5-[1-(3,3-difluorocyclobutyl)ethyl]-6-oxo-1H-pyridazin-3-yl]oxy)phenyl]-4H-1,2,4-tri-azine-3,5-dione as a white solid (34.2 mg, 13%). LCMS (ESI, m/z): 523 [M+Na]$^+$.

The enantiomers were separated by preparative pre-chiral-HPLC using the following gradient conditions: Column: CHIRALPAK IA, 3×25 cm, 5 μm; Mobile Phase A:Hex:DCM=3:1 (10 mM NH₃—CH3OH)-HPLC, Mobile Phase B: EtOH-HPLC; Flow rate: 40 mL/min; Gradient: 10 B to 10 B in 50 min; 220/254 nm; Injection Volume: 1 mL; Number Of Runs: 14. Purification resulted in (RT 1: 35.6 min (compound 61-A (RT 1=35.6 min, 43.9 mg) as an off-white solid, and compound 61-B (RT 2=42.1 min, 41.8 mg).

61-A: ¹H NMR (300 MHz, DMSO-d₆) δ 12.28 (br, 2H), 7.86 (s, 2H), 7.52 (s, 1H), 6.54 (br, 2H), 2.99-3.04 (m, 1H), 2.73 (br, 1H), 2.51-2.60 (m, 1H), 2.44-2.50 (m, 2H), 2.12-2.24 (m, 1H), 1.15 (d, J=6.9 Hz, 3H). LCMS (ESI, m/z): 501 [M+H]⁺. $[\alpha]^{22.1}_D$=+18° (MeOH, C=1 mg/mL).

And (RT 2: 42.1 min (compound 61-B), 41.8 mg)¹H NMR (300 MHz, DMSO-d₆) δ 12.27 (br, 2H), 7.85 (s, 2H), 7.52 (s, 1H), 6.53 (br, 2H), 2.98-3.03 (m, 1H), 2.69-2.74 (m, 1H), 2.52-2.54 (m, 1H), 2.44-2.50 (m, 2H), 2.12-2.24 (m, 1H), 1.15 (d, J=6.9 Hz, 3H). LCMS (ESI, m/z): 501 [M+H]⁺. $[\alpha]^{22.1}_D$=−14° (MeOH, C=1 mg/mL).

Example 56. Synthesis of Compound 62

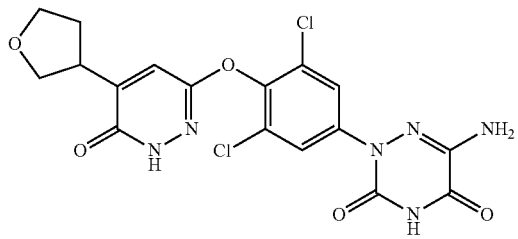

62

To a solution of 3,6-dichloropyridazine (5.00 g, 33.6 mmol) in water (100 mL) was added silver nitrate (2.85 g, 16.8 mmol) and oxolane-3-carboxylic acid (3.90 g, 33.6 mmol) in portions at rt and then stirred at 50° C. To the mixture was added sulfuric acid (9.88 g, 101 mmol) in portions at 50° C. and stirred at 80° C. Then ammonium persulfate (23 g, 101 mmol) in water (50 mL) was added and stirred for 1 h at 70° C. The mixture was neutralized to pH 9 with NaOH solution (2N). The mixture was extracted with EA (3×50 mL). The combined organic layers were washed with brine (50 mL), dried over anhyd. Na₂SO₄, filtered and concentrated under reduced pressure. The residue was purified on a silica gel column with PE:EA (10:1) to provide 3,6-dichloro-4-(oxolan-3-yl)pyridazine as a light yellow oil (2.8 g, 36%).

To a solution of 3,6-dichloro-4-(oxolan-3-yl)pyridazine (330 mg, 1.51 mmol) and t-butyl-N-[2-(3,5-dichloro-4-hydroxyphenyl)-3,5-dioxo-4H-1,2,4-triazin-6-yl]-carbamate (586 mg, 1.51 mmol) in DMSO (10 mL) was added K₂CO₃ (625 mg, 4.52 mmol) and CuI (28.7 mg, 0.15 mmol). The reaction was stirred at 110° C. for 16 h under N₂, then quenched with water (50 mL) The mixture was extracted with EA (3×50 mL), washed with brine (30 mL), dried over anhyd. Na₂SO₄, filtered and concentrated under reduced pressure. The residue was purified on a silica gel column with MeOH:DCM (1:20) to afford t-butyl-N-[2-(3,5-dichloro-4-[[6-chloro-5-(oxolan-3-yl)pyridazin-3-yl]oxy]phenyl)-3,5-dioxo-4H-1,2,4-triazin-6-yl]carbamate as a brown solid (600 mg, 49%).

To a solution of 6-amino-2-(3,5-dichloro-4-[[6-chloro-5-(oxolan-3-yl)-pyridazin-3-yl]oxy]phenyl)-4H-1,2,4-triazine-3,5-dione (420 mg, 0.89 mmol) in AcOH (10 mL) was added NaOAc (292 mg, 3.56 mmol). The reaction was stirred overnight at 100° C. The reaction solution was poured into water (100 mL) and filtered. The precipitate was purified by preparative HPLC to afford 6-amino-2-(3,5-dichloro-4-[[6-hydroxy-5-(oxolan-3-yl)pyridazin-3-yl]oxy]phenyl)-4H-1,2,4-tri-azine-3,5-dione as a white solid (72.8 mg, 18%). ¹H NMR (300 MHz, DMSO-d₆) δ 12.28-12.30 (m, 2H), 7.86 (s, 2H), 7.50 (s, 1H), 6.54 (s, 2H), 3.80-4.01 (m, 2H), 3.75-3.78 (m, 1H), 3.63-3.68 (m, 1H), 3.42-3.54 (m, 1H), 2.18-2.29 (m, 1H), 1.98-2.10 (m, 1H). LCMS (ESI, m/z): 453 [M+H]⁺.

Example 57. Synthesis of Compound 63

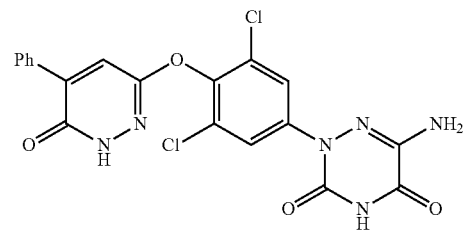

63

To a solution of 3,6-dichloro-pyridazine (5.00 g, 33.6 mmol) and phenyl boronic acid (8.18 g, 67.1 mmol) in water (180 mL) and 1,2-dichloroethane (180 mL) was added Selectfluor™ (23.8 g, 67.1 mmol) and TFA (3.83 g, 33.6 mmol). The reaction was stirred at rt for 2 min and AgNO₃ (1.14 g, 6.71 mmol) in water (20 mL) was added. Then the reaction mixture was stirred 50° C. for 16 h. The solution was extracted with DCM (2×200 mL). The organic layers were combined, dried over anhyd. Na₂SO₄, the solids were removed by filtration and the filtrate was concentrated under reduced pressure. The residue was purified on a silica gel column with PE:EA (25:1) to afford 3,6-dichloro-4-phenylpyridazine as a yellow solid (950 mg, 12%).

To a solution of 3,6-dichloro-4-phenylpyridazine (338 mg, 1.50 mmol) and t-butyl-N-[2-(3,5-dichloro-4-hydroxyphenyl)-3,5-dioxo-4H-1,2,4-triazin-6-yl]carbam-ate (585 mg, 1.50 mmol) in DMSO (15 mL) was added K₂CO₃ (623 mg, 4.50 mmol) and CuI (143 mg, 0.75 mmol). The reaction mixture was stirred at 110° C. for 16 h under N₂, then quenched with water (100 mL). The mixture was extracted with EA (3×100 mL) and the organic layers were combined, washed with brine (100 mL), dried over anhyd. Na₂SO₄, filtered and concentrated under reduced pressure. The residue was purified on a silica gel column with PE:EA (2:3) to get t-butyl-N-(2-[3,5-dichloro-4-[(6-chloro-5-phenylpyridazin-3-yl)oxy]phenyl]-3,5-dioxo-4H-1,2,4-triazin-6-yl)carbamate as a brown solid (350 mg, 32%).

To a solution of 6-amino-2-[3,5-dichloro-4-[(6-chloro-5-phenylpyridazin-3-yl)oxy]phenyl]-4H-1,2,4-triazine-3,5-dione (350 mg, 0.733 mmol) and in AcOH (10 mL) was added NaOAc (240 mg, 2.93 mmol). The reaction was stirred overnight at 100° C. and cooled to rt. The reaction solution was poured into water (100 mL) and filtered. The precipitate was purified by preparative HPLC to afford 6-amino-2-[3,5-dichloro-4-[(6-hydroxy-5-phenylpyridazin-3-yl)oxy]phenyl]-4H-1,2,4-triazine-3,5-dione as a white solid (30.4 mg, 9%). ¹H NMR (300 MHz, DMSO-d₆) δ 12.48 (s, 1H), 12.29

(s, 1H), 7.95-7.98 (m, 2H), 7.88 (s, 3H), 7.49-7.52 (m, 3H), 6.55 (s, 2H). LCMS (ESI, m/z): 459 [M+H]+.

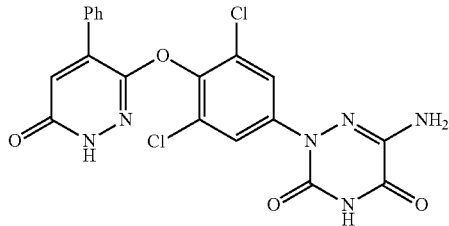

63-A

The regioisomeric product 6-amino-2-(3,5-dichloro-4-((6-oxo-4-phenyl-1,6-dihydropyridazin-3-yl)oxy)phenyl)-1,2,4-triazine-3,5(2H,4H)-dione (63-A) was isolated. $^1$H NMR (300 MHz, DMSO-$d_6$) δ 12.40 (s, 1H), 12.28 (s, 1H), 7.87 (s, 1H), 7.79-7.82 (m, 2H), 7.55-7.59 (m, 3H), 7.13 (s, 1H), 6.53 (s, 2H).

Example 58. Synthesis of Compound 64

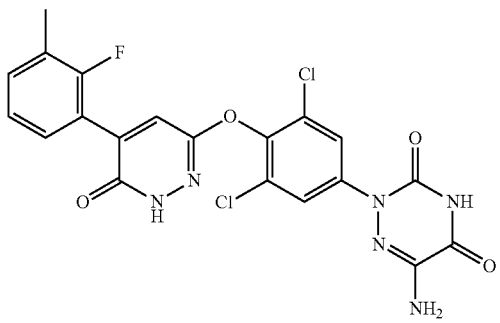

64

A 250 mL round-bottom flask was charged with Na$_2$CO$_3$ (6.00 g, 56.6 mmol), dioxane (45.0 mL), water (15 mL) under N$_2$. The mixture was stirred for 10 min at rt. 4-Bromo-6-chloropyridazin-3-amine (5.90 g, 28.3 mmol), 2-fluoro-3-methylphenylboronic acid (4.79 g, 31.1 mmol), PdCl$_2$(dppf)-DCM complex (2.31 g, 2.83 mmol) was added. The reaction was stirred overnight at 110° C. under N$_2$. The solids were removed by filtration. The organic layers were separated with 400 mL EA:brine (1:1). The organic layer was dried over anhyd. Na$_2$SO$_4$, the solids were removed by filtration and the filtrate was concentrated under reduced pressure. The residue was purified on a silica gel column with EA:PE (40:60) to provide 6-chloro-4-(2-fluoro-3-methylphenyl)pyridazin-3-amine as a brown solid (3 g, 37%).

A 100 mL round-bottom flask was charged with t-butyl nitrite (3.38 g, 32.8 mmol), cupric chloride (1.77 g, 13.1 mmol) in ACN (30.0 mL). 6-Chloro-4-(2-fluoro-3-methylphenyl)pyridazin-3-amine (2.60 g, 10.9 mmol) was added dropwise at 0° C. The reaction was stirred overnight at 60° C. and quenched with water (20 mL). The mixture was extracted with EA (3×50 mL), washed with brine (50 mL), dried over anhyd. Na$_2$SO$_4$, the solids were removed under reduced pressure and the filtrate was concentrated under reduced pressure. The residue was purified on a silica gel with EA:PE (15:85) to provide 3,6-dichloro-4-(2-fluoro-3-methylphenyl)-pyridazine as an off-white solid (1.1 g, 37%).

A 40 mL vial was charged with 3,6-dichloro-4-(2-fluoro-3-methylphenyl)-pyridazine (1.10 g, 4.28 mmol), 4-amino-2,6-dichlorophenyloxidanyl (0.98 g, 5.56 mmol), K$_2$CO$_3$ (1.77 g, 12.8 mmol), CuI (0.33 g, 1.71 mmol), DMSO (10 mL) under N$_2$. The reaction was stirred for 16 h at 90° C. and quenched with water (20 mL). The mixture was extracted with EA (3×50 mL), dried over anhyd. Na$_2$SO$_4$, the solids were removed by filtration and the filtrate was concentrated under reduced pressure. The residue was purified on a silica gel with EA:PE (1:5) to provide 3,5-dichloro-4-[[6-chloro-5-(2-fluoro-3-methylphenyl)pyridazin-3-yl]-oxy]aniline as a brown solid (1.4 g, 78%).

A 40 mL vial was charged with 3,5-dichloro-4-[[6-chloro-5-(2-fluoro-3-methylphenyl)pyridazin-3-yl]oxy]aniline (1.40 g, 3.51 mmol), NaOAc (1.73 g, 21.1 mmol), AcOH (14 mL) under N$_2$. The reaction was stirred overnight at 100° C. The reaction was quenched by water (20 mL), extracted with EA (3×50 mL) and the organic layers were washed with brine (50 mL), dried over anhyd. Na$_2$SO$_4$, filtered and concentrated under reduced pressure. NaOH (1.40 g, 35.1 mmol)), MeOH (7 mL) and water (7 mL) was added. The reaction was stirred overnight at 120° C. The reaction was extracted with EA (3×50 mL) and the organic layers were combined, washed with brine (50 mL), dried over anhyd. Na$_2$SO$_4$, the solids were removed under reduced pressure and the filtrate was concentrated under reduced pressure. The residue was purified on a silica gel column with EA:PE (3:7) to provide 6-(4-amino-2,6-dichlorophenoxy)-4-(2-fluoro-3-methylphenyl)-2H-pyridazin-3-one as a brown semi-solid (950 mg, 57%).

Ethyl (2-cyano-2-(2-(3,5-dichloro-4-((5-(2-fluoro-3-methylphenyl)-6-oxo-1,6-dihydropyridazin-3-yl)oxy)phenyl)hydrazineylidene)acetyl)carbamate, a brown solid (800 mg, 55%), was prepared similarly as described for ethyl (2-cyano-2-(2-(3,5-dichloro-4-((1-tosyl-1H-indol-5-yl)oxy)phenyl)-hydrazineylidene)-acetyl) carbamate.

2-(3,5-dichloro-4-[[5-(2-fluoro-3-methylphenyl)-6-oxo-1H-pyridazin-3-yl]oxy]phenyl)-3,5-dioxo-4H-1,2,4-triazine-6-carbonitrile, a brown solid (400 mg, 64%), was prepared similarly as described for 2-(4-[[3-isopropyl-1-(4-methylbenzene-sulfonyl)indol-5-yl]oxy]-3,5-dimethylphenyl)-3,5-dioxo-4H-1,2,4-triazine-6-carbonitrile.

A 100 mL round-bottom flask was charged with 2-(3,5-dichloro-4-[[5-(2-fluoro-3-methylphenyl)-6-oxo-1H-pyridazin-3-yl]oxy]phenyl)-3,5-dioxo-4H-1,2,4-tri-azine-6-carbonitrile (250 mg, 0.499 mmol), HCl (2 mL), AcOH (10 mL). The reaction was stirred for 2 h at 120° C. and concentrated reduced pressure. The residue was diluted with sat. NaHCO$_3$ solution (20 mL), the mixture was extracted with EA (3×30 mL) and the organic layers were discarded. The pH of the aq. layer was adjusted to 5-6 with conc. HCl. The solution was extracted with CHCl$_3$:isopropanol=3:1) (3×40 mL), the organic layers were combined, dried over anhyd. Na$_2$SO$_4$, the solids were removed by filtration and the filtrate was concentrated under reduced pressure to provide 2-(3,5-dichloro-4-[[5-(2-fluoro-3-methylphenyl)-6-oxo-1H-pyridazin-3-yl]oxy]phenyl)-3,5-dioxo-4H-1,2,4-triazine-6-carboxylic acid as an off-white solid (110 mg, 41%).

A 25 mL round-bottom flask was charged with 2-(3,5-dichloro-4-[[5-(2-fluoro-3-methylphenyl)-6-oxo-1H-pyridazin-3-yl]oxy]phenyl)-3,5-dioxo-4H-1,2,4-tri-azine-6-carboxylic acid (110 mg, 0.211 mmol), diphenylphosphoryl azide (174 mg, 0.634 mmol), NEt$_3$ (85.6 mg, 0.846 mmol), tBuOH (5 mL) under N$_2$. The reaction was stirred overnight at 85° C. and quenched with water (10 mL). The mixture was extracted with EA (3×30 mL), washed with brine (20 mL), dried over anhyd. Na$_2$SO$_4$, the solids were removed by filtration and the filtrate was concentrated under reduced pressure. The residue was purified by preparatory TLC with EA:PE (4:1) to provide t-butyl-N-[2-(3,5-dichloro-4-[[5-(2-fluoro-3-methyl-phenyl)-6-oxo-1H-pyridazin-3-yl]oxy]phenyl)-3,5-dioxo-4H-1,2,4-triazin-6-yl]carbamate as an off-white solid (80 mg, 46%).

A 50 mL round-bottom flask was charged with t-butyl-N-[2-(3,5-dichloro-4-[[5-(2-fluoro-3-methylphenyl)-6-oxo-1H-pyridazin-3-yl]oxy]phenyl)-3,5-dioxo-4H-1,2,4-triazin-6-yl]carbamate (130 mg, 0.220 mmol), DCM (5 mL), TFA (1 mL). The reaction was stirred overnight at rt and concentrated under reduced pressure. The pH of the residue was adjusted to 8 with NaHCO$_3$ (sat., aq.). The solution was extracted with EA (3×30 mL) and the organic layers were combined, washed with brine (30 mL), dried over anhyd. Na$_2$SO$_4$, the solids were removed by filtration and the filtrate was concentrated under reduced pressure. The crude product was purified by preparative HPLC to provide 6-amino-2-(3,5-dichloro-4-[[5-(2-fluoro-3-methylphenyl)-6-oxo-1H-pyridazin-3-yl]oxy]phenyl)-4H-1,2,4-triazine-3,5-dione as a white solid (10.3 mg, 9%).

$^1$H NMR (300 MHz, DMSO-d$_6$) δ 12.52 (s, 0.3H), 12.29 (s, 0.3H), 7.90 (s, 2H), 7.78 (s, 1H), 7.42-7.44 (m, 2H), 7.21 (t, J=7.8 Hz, 1H), 6.48-6.55 (m, 2H), 2.31 (s, 3H).

LCMS (ESI, m/z): 491 [M+H]$^+$.

Example 59. Synthesis of Compound 65

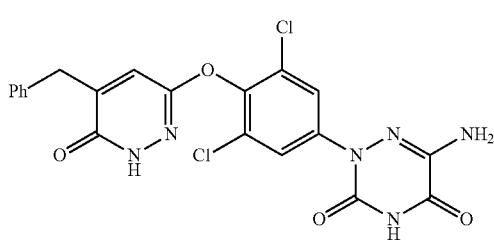

65

4-Benzyl-3,6-dichloro-pyridazine, a yellow oil (270 mg, 27%), was prepared similarly to 3,6-dichloro-4-isopropylpyridazine.

To a solution of 4-benzyl-3,6-dichloropyridazine (270 mg, 1.13 mmol) and t-butyl-N-[2-(3,5-dichloro-4-hydroxyphenyl)-3,5-dioxo-4H-1,2,4-triazin-6-yl]carbam-ate (483 mg, 1.24 mmol) in DMSO (10 mL) was added K$_2$CO$_3$ (468 mg, 3.39 mmol) and CuI (215 mg, 1.13 mmol). The reaction was stirred at 110° C. for 16 h under N$_2$ and quenched with water (100 mL). The mixture was extracted with EA (3×100 mL) and the organic layers were combined, washed with brine (100 mL), dried over anhyd. Na$_2$SO$_4$, the solids were removed by filtration and the filtrate was concentrated under reduced pressure. The residue was purified on a silica column with MeOH:DCM (4:96) to afford t-butyl-N-(2-[4-[(5-benzyl-6-chloropyridazin-3-yl)oxy]-3,5-dichlorophenyl]-3,5-dioxo-4H-1,2,4-triazin-6-yl)carbam-ate as a brown solid (400 mg, 36%).

To a solution of 6-amino-2-[4-[(5-benzyl-6-chloropyridazin-3-yl)oxy]-3,5-dichlorophenyl]-4H-1,2,4-triazine-3,5-dione (240 mg, 0.49 mmol) in AcOH (6 mL) was added NaOAc (160 mg, 1.95 mmol). The reaction was stirred overnight at 100° C. and cooled to rt. The reaction solution was poured into water (100 mL) and filtered. The precipitate was purified by preparative HPLC to afford 6-amino-2-[4-[(5-benzyl-6-hydroxypyridazin-3-yl)oxy]-3,5-dichlorophenyl]-4H-1,2,4-triazine-3,5-dione as a white solid (56.6 mg, 24%).

$^1$H NMR (300 MHz, DMSO-d$_6$) δ 12.27-12.30 (m, 2H), 7.85 (s, 2H), 7.24-7.37 (m, 6H), 6.53 (s, 2H), 3.87 (s, 2H).

LCMS (ESI, m/z): 495 [M+Na]$^+$.

Example 60. Synthesis of Compound 66

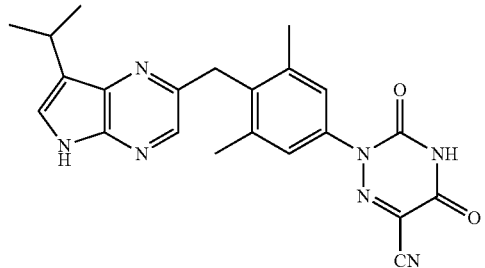

66

2-[(4-Benzyloxy-2,6-dimethyl-phenyl)methyl]-7-isopropyl-5-(p-tolylsulfonyl)pyrrolo [2,3-b]pyrazine as a yellow solid (770 mg, 70%) was prepared similarly as described for 5-[(4-benzyloxy-2,6-dimethyl-phenyl)methyl]-3-isopropyl-1-(p-tolylsulfonyl)pyrrolo[3,2-b]pyridine.

A mixture of 2-[(4-benzyloxy-2,6-dimethyl-phenyl)methyl]-7-isopropyl-5-(p-tolylsulfonyl)pyrrolo[2,3-b]pyrazine (610 mg, 1.13 mmol) in DCM (20 mL) and BBr$_3$ (1.42 g, 5.65 mmol, 544.54 µL) was added. The reaction mixture was degassed and purged with N$_2$ for 3 times, and then the mixture was stirred at 0° C. for 1 h. The reaction mixture was quenched by addition NaHCO$_3$ (15 mL) at 0° C., and then diluted with H$_2$O (25 mL) and extracted with DCM (3×45 mL). The combined organic layers were dried over MgSO$_4$, the solids were removed by filtration and the filtrate was concentrated under reduced pressure. The crude was purified by flash silica gel chromatography (EA:PE=0-10%) to afford 4-[[7-isopropyl-5-(p-tolylsulfonyl)pyrrolo-[2,3-b]pyrazin-2-yl]methyl]-3,5-dimethyl-phenol as a yellow solid (400 mg, 79%).

[4-[[7-Isopropyl-5-(p-tolylsulfonyl)pyrrolo[2,3-b]pyrazine-2-yl]methyl]-3,5-dimethyl-phenyl] trifluoromethanesulfonate, a white solid (430 mg, 83%) was prepared similarly as described for [4-[[3-isopropyl-1-(p-tolylsulfonyl)pyrrolo[3,2-b]pyridin-5-yl]methyl]-3,5-dimethyl-phenyl] trifluoromethanesulfonate.

A mixture of [4-[[7-isopropyl-5-(p-tolylsulfonyl)pyrrolo [2,3-b]pyrazin-2-yl]methyl]-3,5-dimethyl-phenyl] trifluoromethanesulfonate (280 mg, 481 µmol), t-butyl carbamate (226 mg, 1.93 mmol), XantPhos (68.9 mg, 144 µmol), Pd(OAc)$_2$ (10.8 mg, 48.1 µmol) and Cs$_2$CO$_3$ (627 mg, 1.93 mmol) in dioxane (10 mL) was degassed and purged with N$_2$, then the mixture was stirred at 100° C. for 4 h under N$_2$. The reaction mixture was concentrated under reduced pressure, then the residue was diluted with H$_2$O (20 mL) and extracted with EA (3×20 mL). The combined organic layers were washed with brine (20 mL), dried over Na$_2$SO$_4$, filtered and concentrated under reduced pressure to give crude product, which was purified by silica gel chromatography (EA:PE=0~15%) to give t-butyl-N-[4-[[7-isopropyl-5-(p-tolylsulfonyl)-pyrrolo[2,3-b]-pyrazin-2-yl]methyl]-3,5-dimethyl-phenyl]carbamate as a yellow gum (290 mg, 76%).

To a solution of t-butyl-N-[4-[[7-isopropyl-5-(p-tolylsulfonyl)-pyrrolo-[2,3-b]pyrazin-2-yl]methyl]-3,5-dimethyl-phenyl]carbamate (356 mg, 454 µmol) in DCM (3 mL) was added TFA (518 mg, 4.54 mmol, 336.27 µL). The mixture was stirred at 20° C. for 2 h. The reaction mixture was quenched with sat. aq. NaHCO₃ (5 mL) at 20° C., then diluted with H₂O (5 mL) and extracted with DCM (3×20 mL). The combined organic layers were washed with brine (20 mL), dried over MgSO₄, filtered and concentrated under reduced pressure to give a residue, which was purified by flash silica gel chromatography (EA:PE=0-30%) to give 4-[[7-isopropyl-5-(p-tolyl-sulfonyl)pyrrolo[2,3-b]pyrazin-2-yl]methyl]-3,5-dimethyl-aniline as a yellow solid (183 mg, 89%).

Ethyl N-[2-cyano-2-[[4-[[7-isopropyl-5-(p-tolylsulfonyl)pyrrolo-[2,3-b]pyrazin-2-yl]-methyl]-3,5-dimethyl-phenyl]hydrazono]acetyl]carbamate, a yellow solid (90 mg, 47%), was prepared similarly as described for ethyl (2-cyano-2-(2-(3,5-dichloro-4-((1-tosyl-1H-indol-5-yl)oxy)phenyl)-hydrazineylidene)-acetyl) carbamate.

To a solution of ethyl N-[2-cyano-2-[[4-[[7-isopropyl-5-(p-tolylsulfonyl)pyrrolo[2,3-b]pyrazine-2-yl]methyl]-3,5-dimethyl-phenyl]hydrazono]-acet-yl]carbamate (146 mg, 237 µmol) in AcOH (15 mL) was added NaOAc (97.3 mg, 1.19 mmol). The mixture was stirred at 130° C. for 3 h. The reaction mixture was concentrated under reduced pressure, adjusted to pH 7~8 by NaHCO₃ (sat., aq. 5 mL) then extracted with EA (3×20 mL). The combined organic layers were washed with brine (20 mL), dried over anhyd. Na₂SO₄, the solids were removed under reduced pressure and the filtrate was concentrated under reduced pressure to give 2-[4-[[7-isopropyl-5-(p-tolylsulfonyl)pyrrolo[2,3-b]pyrazin-2-yl]methyl]-3,5-di-methyl-phenyl]-3,5-dioxo-1,2,4-triazine-6-carbonitrile as a yellow solid (100 mg, crude).

Tosyl group deprotection to give 2-[4-[(7-isopropyl-5H-pyrrolo[2,3-b]pyrazin-2-yl)methyl]-3,5-dimethyl-phenyl]-3,5-dioxo-1,2,4-triazine-6-carbonitrile, a yellow solid (34.8 mg, 48%), was prepared similarly as described for methyl 5-[2,6-dichloro-4-(6-cyano-3,5-dioxo-4H-1,2,4-triazin-2-yl)phenoxy]-1H-indole-3-carboxylate. ¹H NMR (400 MHz, DMSO-d₆) δ=12.98 (br s, 1H), 11.57 (br s, 1H), 7.96 (s, 1H), 7.53 (s, 1H), 7.16 (s, 2H), 4.29 (s, 2H), 3.19-3.07 (m, 1H), 2.43 (s, 6H), 1.32 (d, J=6.9 Hz, 6H). LCMS (ESI, m/z): 416.3[M+H]+.

Example 61. Synthesis of Compound 67 and 67-A

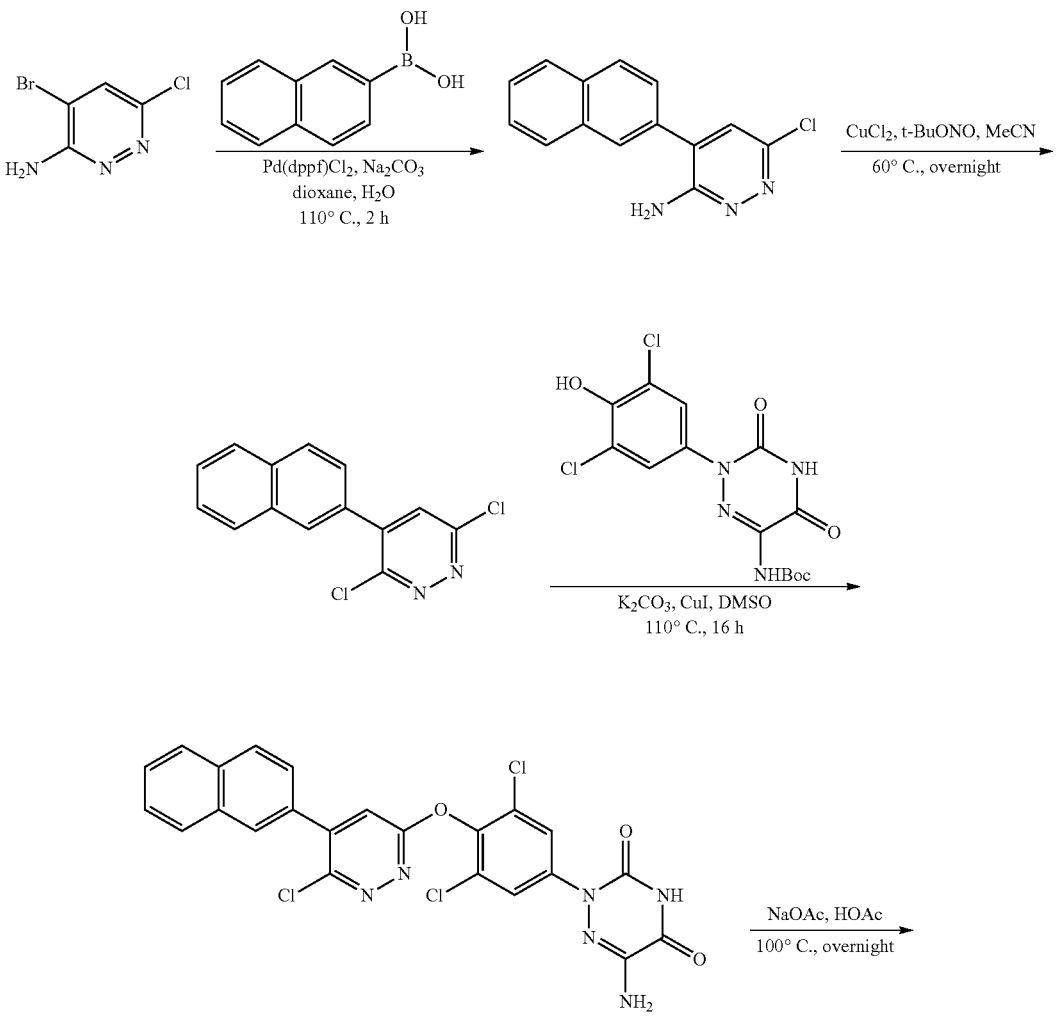

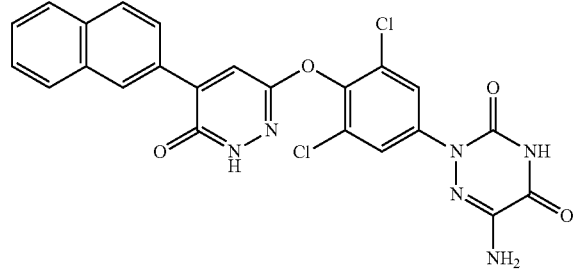

67

A 100 mL round-bottom flask was charged with sodium carbonate (2.03 g, 19.190 mmol), dioxane (20 mL) and water (4 mL). The mixture was stirred for 10 min at rt. 4-bromo-6-chloropyridazin-3-amine (2 g, 9.595 mmol), 2-naphthalene boronic acid (1.82 g, 10.555 mmol) and PdCl$_2$(dppf) (783.57 mg, 0.960 mmol) was added. The mixture was stirred for 2 h at 110° C. under N$_2$. The reaction mixture was diluted with EA (20 mL) and filtered through packed celite, the celite pad was washed with EA (2×10 mL), and the filtrate was washed with brine (20 mL). The organic layer was dried over anhydr. sodium sulfate, the solids were removed by filtration and the filtrate was concentrated under reduced pressure. The residue was chromatographed on a silica gel column (PE:EA=10:1) to provide 6-chloro-4-(naphthalen-1-yl)pyridazin-3-amine as a yellow solid (1.75 g, 68%). LCMS (ESI, m/z): 256 [M+H]$^+$.

To a solution of CuCl$_2$ (1.10 g, 8.212 mmol) in CH$_3$CN (5 mL) was added t-butyl nitrite (2.12 g, 20.531 mmol) at 0° C. was added 6-chloro-4-(naphthalen-2-yl)pyridazin-3-amine (1.75 g, 6.844 mmol) in CH$_3$CN (15 mL) dropwise. The reaction mixture was stirred 18 h at 60° C. The reaction mixture was cooled to rt and filtered through packed celite, the celite pad was washed with EA (3×10 mL), and then quenched with water (10 mL) and extracted with EA (3×20 mL). The combined organic layers were washed with brine (20 mL), dried over anhydr. sodium sulfate. After filtration, the filtrate was concentrated. The residue was purified by silica gel column chromatography (EA:PE=1:10) to afford 3,6-dichloro-4-(naphthalen-2-yl)pyridazine as a yellow solid (990 mg, 50%). LCMS (ESI, m/z): 275 [M+H]$^+$.

To a solution of 3,6-dichloro-4-(naphthalen-2-yl)pyridazine (400.00 mg, 1.454 mmol), t-butyl N-[2-(3,5-dichloro-4-hydroxyphenyl)-3,5-dioxo-4H-1,2,4-triazin-6-yl]carbamate (565.83 mg, 1.454 mmol) and K$_2$CO$_3$ (602.79 mg, 4.362 mmol) in DMSO (8 mL) was added CuI (83.07 mg, 0.436 mmol) under N$_2$. The solution was stirred overnight at 110° C. then quenched with water (10 mL). The mixture was acidified to pH ~5 with HCl (1 M, aq.), then extracted with EA (3×30 mL). The combined organic layers were washed with brine (1×20 mL), dried over anhydr. sodium sulfate, the solids were removed by filtration, and the filtrate was concentrated under reduced pressure. The residue was purified by silica gel column chromatography (EA:PE=1:1) to afford 6-amino-2-(3,5-dichloro-4-[[6-chloro-5-(naphthalen-2-yl)pyridazin-3-yl]oxy]phenyl)-4H-1,2,4-triazine-3,5-dione as a red solid (300 mg, 37%). LCMS (ESI, m/z): 527 [M+H]$^+$.

To a solution of 6-amino-2-(3,5-dichloro-4-[[6-chloro-5-(naphthalen-2-yl)pyridazin-3-yl]oxy]phenyl)-4H-1,2,4-triazine-3,5-dione (300 mg, 0.568 mmol) in acetic acid (6 mL) was added NaOAc (233.16 mg, 2.842 mmol). The mixture was stirred overnight at 100° C. The reaction mixture was cooled to rt, quenched with water (20 mL) and then stirred for 10 min. The solid was filtered and washed with water (2×10 mL) and PE (2×5 mL), then dried under reduced pressure then purified by preparative HPLC (XBridge Prep OBD C18 Column, 19×250 mm, 5 um; Mobile Phase A: Water (0.05% TFA), Mobile Phase B: ACN; Flow rate: 25 mL/min; Gradient: 49% B to 69% B in 7 min; 220 nm) to afford 6-amino-2-(3,5-dichloro-4-[[5-(naphthalen-2-yl)-6-oxo-1H-pyridazin-3-yl]oxy]phenyl)-4H-1,2,4-triazine-3,5-dione as a white solid (40.4 mg, 14%). $^1$H NMR (300 MHz, DMSO-d$_6$) δ 12.55 (s, 1H), 12.29 (s, 1H), 8.67 (s, 1H), 7.97-8.07 (m, 5H), 7.89 (s, 2H), 7.57-7.64 (m, 2H), 6.55 (br, 2H). LCMS (ESI, m/z): 509 [M+H]$^+$.

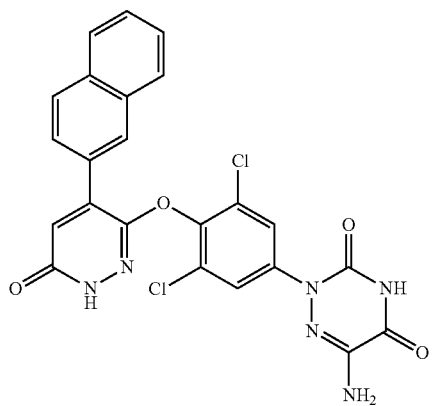

67-A 6-amino-2-(3,5-dichloro-4-((4-(naphthalen-2-yl)-6-oxo-1,6-dihydropyridazin-3-yl)oxy)phenyl)-1,2,4-triazine-3,5 (2H,4H)-dione (67-A) was isolated during the synthesis of 6-amino-2-(3,5-dichloro-4-[[5-(naphthalen-2-yl)-6-oxo-1H-pyridazin-3-yl]oxy]phenyl)-4H-1,2,4-triazine-3,5-dione. $^1$H NMR (300 MHz, DMSO-d$_6$) 12.44 (br, 1H), 12.27 (br, 1H), 8.38 (br, 1H), 8.03-8.11 (m, 3H), 7.88-7.93 (m, 3H), 7.60-7.66 (m, 2H), 7.26 (s, 1H), 6.52 (br, 2H).

Compounds 68, 69, 70, 71, 72 were prepared similarly as described in Example 61. The regioisomer products 68-A, 69-A, 70-A, 71-A, and 72-A were also isolated.

| Structure | LCMS (ESI, m/z) | ¹H NMR |
|---|---|---|

68

6-Amino-2-(3,5-dichloro-4-((5-(3-chlorophenyl)-6-oxo-1,6-dihydropyridazin-3-yl)oxy)phenyl)-1,2,4-triazine-3,5(2H,4H)-dione 493 [M + H]⁺ ¹H (300 MHz, DMSO-d₆) δ 12.55 (br, 1H), 12.28 (br, 1H), 8.09 (s, 1H), 7.99 (s, 1H), 7.88-7.94 (m, 3H), 7.53-7.57 (m, 2H), 6.53 (s, 2H).

68-A

6-amino-2-(3,5-dichloro-4-((4-(3-chlorophenyl)-6-oxo-1,6-dihydropyridazin-3-yl)oxy)phenyl)-1,2,4-triazine-3,5(2H,4H)-dione 493 [M + H]⁺ ¹H NMR (300 DMSO-d₆) δ 12.45 (s, 1H), 12.28 (s, 1H), 7.85-7.88 (m, 3H), 7.77 (d, J = 6.6 Hz, 1H), 7.60-7.62 (m, 2H), 7.21 (s, 1H), 6.55 (s, 2H).

69

6-Amino-2-(3,5-dichloro-4-((5-(3-fluorophenyl)-6-oxo-1,6-dihydropyridazin-3-yl)oxy)phenyl)-1,2,4-triazine-3,5(2H,4H)-dione 477 [M + H]⁺ ¹H NMR (300 MHz, DMSO-d₆) δ 12.46 (br, 1H), 12.28 (s, 1H), 7.88 (s, 2H), 7.61-7.68 (m, 3H), 7.34-7.42 (m, 1H), 7.21 (s, 1H), 6.54 (br, 2H).

| Structure | LCMS (ESI, m/z) | ¹H NMR |
|---|---|---|
| 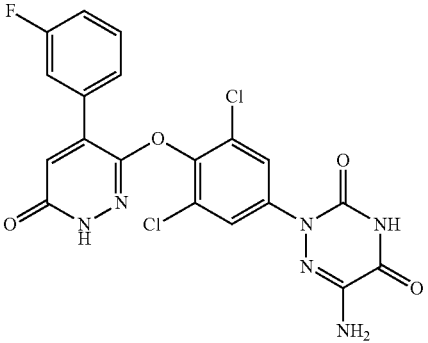<br>69-A<br>6-amino-2-(3,5-dichloro-4-((4-(3-fluorophenyl)-6-oxo-1,6-dihydropyridazin-3-yl)oxy)phenyl)-1,2,4-triazine-3,5(2H,4H)-dione | 477 [M + H]⁺ | ¹H NMR (300 MHz, DMSO-d₆) δ 12.46 (br, 1H), 12.28 (s, 1H), 7.88 (s, 2H), 7.61-7.68 (m, 3H), 7.34-7.42 (m, 1H), 7.21 (s, 1H), 6.54 (br, 2H). |
| 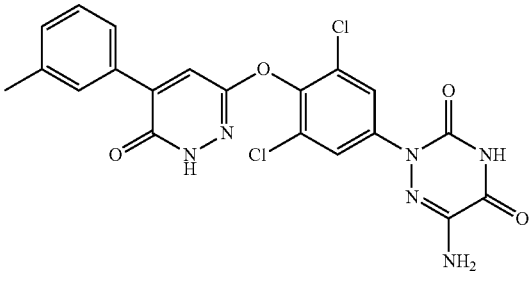<br>70<br>6-Amino-2-(3,5-dichloro-4-((6-oxo-5-(m-tolyl)-1,6-dihydropyridazin-3-yl)oxy)phenyl)-1,2,4-triazine-3,5(2H,4H)-dione | 473 [M + H]⁺ | ¹H NMR (300 MHz, DMSO-d₆) δ 12.28-12.45 (m, 2H), 7.84-7.88 (m, 3H), 7.74-7.77 (m, 2H), 7.30-7.40 (m, 2H), 6.54 (s, 2H), 2.08 (s, 3H). |
| 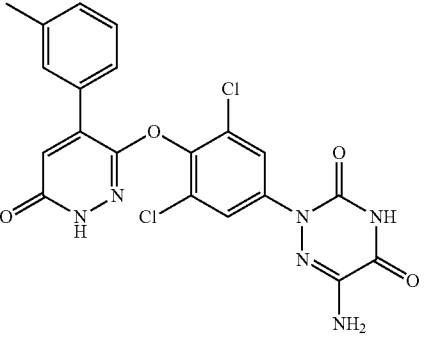<br>70-A<br>6-amino-2-(3,5-dichloro-4-((6-oxo-4-(m-tolyl)-1,6-dihydropyridazin-3-yl)oxy)phenyl)-1,2,4-triazine-3,5(2H,4H)-dione | 473 [M + H]⁺ | ¹H NMR (300 MHz, DMSO-d₆) δ 12.28-12.38 (m, 2H), 7.87 (s, 2H), 7.59-7.61 (m, 2H), 7.42-7.47 (m, 2H), 7.35-7.37 (m, 1H), 7.10 (d, J = 2.1 Hz, 1H), 6.54 (s, 2H), 2.08 (s, 3H). |

| Structure | LCMS (ESI, m/z) | ¹H NMR |
|---|---|---|
| 71<br>6-Amino-2-(3,5-dichloro-4-((5-(3-ethylphenyl)-6-oxo-1,6-dihydro-pyridazin-3-yl)oxy)phenyl)-1,2,4-triazine-3,5(2H,4H)-dione | 487 [M + H]⁺ | ¹H NMR (300 MHz, DMSO-d₆) δ 12.29-12.45 (m, 2H), 7.79-7.88 (m, 3H), 7.77-7.79 (m, 2H), 7.33-7.43 (m, 2H), 6.54 (br, 2H), 2.64-2.74 (m, 2H), 1.23 (t, J = 7.5 Hz, 3H). |
| 71-A<br>6-Amino-2-(3,5-dichloro-4-((4-(3-ethylphenyl)-6-oxo-1,6-dihydropyridazin-3-yl)oxy)phenyl)-1,2,4-triazine-3,5(2H,4H)-dione | 487 [M + H]⁺ | ¹H NMR (300 MHz, DMSO-d₆) δ 12.28-12.38 (m, 2H), 7.87 (s, 2H), 7.61-7.65 (m, 2H), 7.45-7.50 (m, 1H), 7.38-7.41 (m, 1H), 7.11 (d, J = 1.8 Hz, 1H), 6.54 (s, 2H), 2.67-2.74 (m, 2H), 1.19-1.26 (m, 3H). |
| 72<br>6-Amino-2-(3,5-dichloro-4-((6-oxo-5-(5,6,7,8-tetrahydro-naphthalen-2-yl)-1,6-dihydro-pyridazin-3-yl)oxy)phenyl)-1,2,4-triazine-3,5(2H,4H)-dione | 513 [M + H]⁺ | ¹H NMR (300 MHz, DMSO-d₆) δ 12.23-12.41 (m, 2H), 7.87 (s, 2H), 7.80 (s, 1H), 7.67-7.69 (m, 2H), 7.14-7.17 (m, 1H), 6.53 (br, 2H), 2.77 (br, 4H), 1.76 (br, 4H). |

| Structure | LCMS (ESI, m/z) | 1H NMR |
|---|---|---|
| 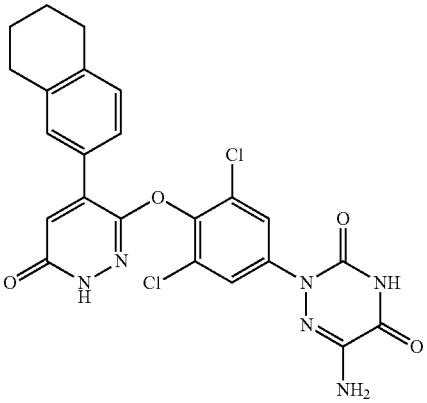

72-A 6-amino-2-(3,5-dichloro-4-[[6-oxo-4-(5,6,7,8-tetrahydronaphthalen-2-yl)-1H-pyridazin-3-yl]oxy]phenyl)-4H-1,2,4-triazine-3,5-dione | 513 [M + H]+ | 1H NMR (300 MHz, DMSO-d6) δ 12.34-12.42 (m, 2H), 7.86 (s, 2H), 7.48-7.52 (m, 2H), 7.21-7.23 (m, 1H), 7.06 (s, 1H), 6.53 (br, 2H), 2.78 (br, 4H), 1.76 (br, 4H). |

Example 62: Synthesis of Compound 73

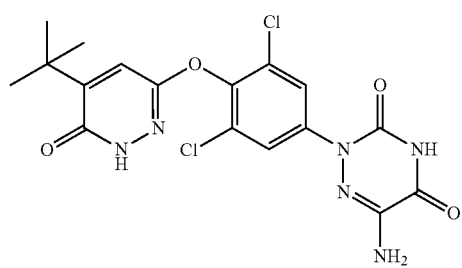

73

6-Amino-2-(4-((5-(t-butyl)-6-oxo-1,6-dihydropyridazin-3-yl)oxy)-3,5-dichlorophenyl)-1,2,4-triazine-3,5(2H, 4H)-dione was prepared similarly as described for 6-amino-2-(3,5-dichloro-4-[[5-(oxan-4-yl)-6-oxo-1H-pyridazin-3-yl]oxy]phenyl)-4H-1,2,4-triazine-3,5-dione. 1H NMR (300 MHz, DMSO-d6) δ 12.29 (s, 1H), 12.13 (s, 1H), 7.86 (s, 2H), 7.33 (s, 1H), 6.54 (s, 2H), 1.35 (s, 9H). LCMS (ESI, m/z): 439 [M+H]+.

Example 63: Synthesis of Compound 74

74

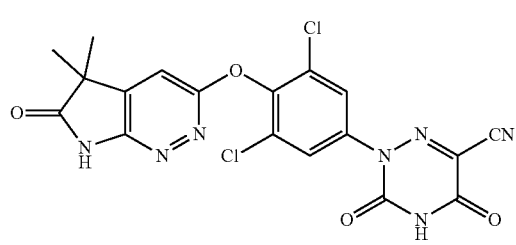

3-Chloro-7-(4-methoxybenzyl)-5,5-dimethyl-5,7-dihydro-6H-pyrrolo[2,3-c]pyridazin-6-one was prepared according to the literature procedure (Tet. Lett. 2015, 56, 772-774).

A mixture of 3-chloro-7-[(4-methoxyphenyl)methyl]-5,5-dimethyl-pyrrolo[2,3-c]pyridazin-6-one (6 g, 18.88 mmol), N-(3,5-dichloro-4-hydroxy-phenyl)-N,N-dimethyl-formamidine (4.40 g, 18.88 mmol), Pd(dbtpf)Cl2 (1.23 g, 1.89 mmol), Cs2CO3 (18.46 g, 56.64 mmol) in dioxane (100 mL) was degassed and purged with N2 for 3 times. The mixture was stirred at 100° C. for 16 h under N2. The reaction mixture was diluted with H2O (200 mL) and extracted with EA (3×150 mL). The combined organic layers were washed with brine (200 mL), dried over Na2SO4, the solids were removed by filtration and the filtrate was concentrated under reduced pressure. The crude was purified by silica gel chromatography (EA:PE=0-50%) to give N-[3,5-dichloro-4-[7-[(4-methoxyphenyl)methyl]-5,5-dimethyl-6-oxo-pyrrolo[2,3-c]pyrida-zin-3-yl]oxy-phenyl]-N,N-dimethyl-formamidine as a brown solid (6.5 g, 67%).

To a solution of N'-[3,5-dichloro-4-[7-[(4-methoxyphenyl)methyl]-5,5-dimethyl-6-oxo-pyrrolo[2,3-c]pyridazin-3-yl]oxy-phenyl]-N,N-dimethyl-formamidine (4.5 g, 8.75 mmol) in 2-propanol (80 mL) was added NH2NH2 hydrate (4.38 g, 87.48 mmol, 4.25 mL) at 20° C. After the addition, the mixture was stirred at 80° C. for 16 h. The reaction mixture was quenched by H2O (160 mL) and extracted with EA (3×100 mL). The combined organic layers were washed with brine (3×50 mL), dried over Na2SO4, the solids were removed by filtration and the filtrate was concentrated under reduced pressure. The crude product was purified by flash silica gel chromatography (EA in PE: 0~50%) to afford 3-(4-amino-2,6-dichloro-phenoxy)-7-[(4-methoxyphenyl)methyl]-5,5-dimethyl-pyrrolo[2,3-c]pyridazin-6-one as awhite solid (3.2 g, 80%).

Ethyl (2-cyano-2-(2-(3,5-dichloro-4-((7-(4-methoxybenzyl)-5,5-dimethyl-6-oxo-6,7-dihydro-5H-pyrrolo[2,3-c]pyridazin-3-yl)oxy)phenyl)hydrazine-ylidene)acetyl)carbamate (6.46 g, 5.16 mmol, 74%, 50% purity), an orange solid, was prepared similarly as described for ethyl (2-cyano-2-(2-(3,5-dichloro-4-((1-tosyl-1H-indol-5-yl)oxy)phenyl)-hydrazineylidene)-acetyl) carbamate.

To a solution of ethyl N-[2-cyano-2-[[3,5-dichloro-4-[7-[(4-methoxyphenyl)methyl]-5,5-dimethyl-6-oxo-pyrrolo[2,3-c]pyridazin-3-yl]oxy-phenyl]hydrazono]acetyl]carbamate (6.46 g, 5.16 mmol) in DMF (60 mL) was added Et₃N (2.61 g, 25.78 mmol, 3.59 mL) in one portion at 20° C. The mixture was stirred at 90° C. for 16 h. The reaction mixture was diluted with H₂O (150 mL) and extracted with EA (3×150 mL). The combined organic layers were washed with brine (3×100 mL), dried over Na₂SO₄, the solids were removed by filtration and the filtrate was concentrated under reduced pressure. The crude product was purified by flash chromatography (MeOH:DCM=0~5%) to afford 2-[3,5-dichloro-4-[7-[(4-methoxyphenyl)methyl]-5,5-dimethyl-6-oxo-pyrrolo[2,3-c]pyridazin-3-yl]oxy-phenyl]-3,5-dioxo-1,2,4-triazine-6-carbonitrile as a brown solid (4.1 g, 96%).

To a solution of 2-[3,5-dichloro-4-[7-[(4-methoxyphenyl)methyl]-5,5-dimethyl-6-oxo-pyrrolo[2,3-c]pyridazin-3-yl]oxy-phenyl]-3,5-dioxo-1,2,4-triazine-6-carbonitrile (780 mg, 1.34 mmol) in ACN (10 mL) and H₂O (10 mL) was added CAN (2.21 g, 4.03 mmol, 2.01 mL) at 0° C. The mixture was stirred at 25° C. for 2 h. The reaction mixture was diluted with H₂O (20 mL) and extracted with EA (3×30 mL). The combined organic layers were washed with brine (3×20 mL), dried over Na₂SO₄, filtered and concentrated under reduced pressure to give a residue. The residue was purified by preparative HPLC ([Column: Welch Xtimate C18 150×30 mm×5 um; Mobile phase: from 15% ACN in water (0.225% NH₃·H₂O) to 45% ACN in water (0.225% NH₃·H₂O)]) to give 2-[3,5-dichloro-4-[(5,5-dimethyl-6-oxo-7H-pyrrolo[2,3-c]pyridazin-3-yl)oxy]phenyl]3,5-dioxo-1,2,4-triazine-6-carbonitrile as a white solid (61.1 mg, 10%). ¹H NMR (400 MHz, DMSO-d₆) δ=11.55 (br s, 1H), 7.82 (s, 1H), 7.80 (s, 2H), 7.09 (br s, 3H), 1.39 (s, 6H). LCMS (ESI, m/z): 460.1[M+H]⁺.

Example 64: Synthesis of Compound 75

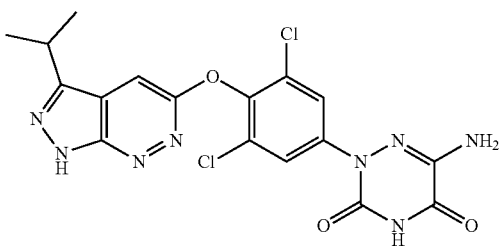

75

To a solution of 2,2,6,6-tetramethylpiperidine (4.55 g, 32.22 mmol, 5.47 mL) in THF (20 mL) at −30° C. was added dropwise n-BuLi (2.5 M, 11.28 mL) over 30 min. After addition, the mixture was stirred at −30° C. for 30 min, and then 3,6-dichloropyridazine (3 g, 20.14 mmol) and 2-methylpropanal (1.60 g, 22.15 mmol, 2.02 mL) in THF (20 mL) was added dropwise at −65° C. The mixture was stirred at −65° C. for 1 h. The reaction mixture was quenched by NH₄C₁ (sat., aq., 10 mL) at −60° C. The mixture was worked up with a previous batch and then diluted with H₂O (100 mL) and extracted with EA (100 mL×3). The combined organic layers were washed with brine (80 mL), dried over Na₂SO₄, the solids were removed by filtration and the filtrate was concentrated under reduced pressure. The crude product was purified by silica gel chromatography (EA:PE=0-15%) to afford 1-(3,6-dichloropyridazin-4-yl)-2-methylpropan-1-ol as a yellow liquid (3.34 g, 15%).

To a suspension of NaH (4.11 g, 102.68 mmol, 60% purity) in THF (40 mL) was added 1-(3,6-dichloropyridazin-4-yl)-2-methylpropan-1-ol (2.27 g, 10.27 mmol) and TBSCl (3.10 g, 20.54 mmol, 2.52 mL) in THF (10 mL) at 0° C. The mixture was stirred at 0° C. for 1 hr. The reaction mixture was quenched with H₂O (10 mL), then diluted with H₂O (50 mL) and extracted with EA (3×50 mL). The combined organic layers were washed with brine (3×50 mL), dried over anhydr. Na₂SO₄, filtered and concentrated under reduced pressure to give a residue, which was purified by flash silica gel chromatography (0~5% EA in PE) to afford 4-(1-(((t-butyldimethylsilyl)oxy)-2-methylpropyl)-3,6-dichloropyridazine as a yellow liquid (2.49 g, 72%).

To a solution of 4-amino-2,6-dichloro-phenol (3 g, 16.85 mmol) in toluene (30 mL) was added DMF-DMA (2.21 g, 18.54 mmol, 2.46 mL). After the addition, the mixture was stirred at 100° C. for 2 h. The mixture was concentrated to give a residue, which was triturated (PE:EA=6:1) to give N-(3,5-dichloro-4-hydroxyphenyl)-N,N-dimethylformimidamide as a brown solid (4.05 g).

N'-(4-((5-(1-(((t-Butyldimethylsilyl)oxy)-2-methylpropyl)-6-chloro-pyridazin-3-yl)oxy)-3,5-dichlorophenyl)-N,N-dimethylformimidamide (3.86 g, 74%), a yellow solid, was prepared similarly as described for 3,5-dichloro-4-[(6-chloro-5-isopropylpyridazin-3-yl)oxy]aniline with the exception that the reaction was heated for 16 h at 90° C.

N'-(4-((5-(1-(((t-Butyldimethylsilyl)oxy)-2-methylpropyl)-6-chloro-pyridazin-3-yl)oxy)-3,5-dichlorophenyl)-N,N-dimethylformimidamide (3.85 g, 6.84 mmol) in THF (30 mL) was added TBAF (1 M, 13.68 mL) at 25° C. and the mixture was stirred at 25° C. for 6 h. The mixture was quenched with NH₄Cl (sat., aq., 50 mL) and extracted with EA (3×50 mL). The combined organic layers were washed with brine (50 mL), dried over anhydr. Na₂SO₄, filtered and concentrated to give N'-(3,5-dichloro-4-((6-chloro-5-(1-hydroxy-2-methylpropyl)pyridazin-3-yl)oxy)phenyl)-N,N-dimethylformimidamide (3.67 g, crude) as a yellow solid.

N'-(3,5-Dichloro-4-((6-chloro-5-(1-hydroxy-2-methylpropyl)pyridazin-3-yl)oxy)phenyl)-N,N-dimethylformimidamide (3.6 g, crude) in DCM (40 mL) was added Dess-Martin reagent (6.84 g, 16.12 mmol, 4.99 mL) at 25° C. in one portion and the mixture was stirred at 25° C. for 2 h. The mixture diluted with NaHCO₃ (sat., aq., 50 mL) and extracted with DCM (2×50 mL). The combined organic layers were washed with brine (50 mL), dried over anhydr. Na₂SO₄, the solids were removed by filtration and the filtrate was concentrated under reduced pressure to give a residue, which was purified by combi flash (EA:PE=0-40%) to give N-(3,5-dichloro-4-((6-chloro-5-isobutyrylpyridazin-3-yl)oxy)phenyl)-N,N-dimethylformimidamide as a yellow oil (2.23 g, 53%).

To a solution of N'-(3,5-dichloro-4-((6-chloro-5-isobutyrylpyridazin-3-yl)oxy)phenyl)-N,N-dimethylformimidamide (1.3 g, 3.13 mmol) in 2-propanol (20 mL) was added NH₂NH₂ hydrate (5.4 g, 107.87 mmol, 5.24 mL) and the mixture was stirred at 90° C. for 72 h under N₂. The mixture was diluted with H₂O (50 mL) and extracted with EA (3×50 mL). The combined organic layers were washed with brine (50 mL), dried over anhydr. Na₂SO₄, the solids were removed by filtration and the filtrate was concentrated under reduced pressure to give a residue, which was purified by silica column chromatography (EA in PE: 0~40%) to afford 3,5-dichloro-4-[(3-isopropyl-1H-pyrazolo[3,4-c]pyridazin-5-yl)oxy]aniline as a yellow solid (435 mg, 40%). ¹H NMR (400 MHz, DMSO-d₆) δ 13.83 (s, 1H), 8.03 (s, 1H), 6.71 (s, 2H), 5.63 (s, 2H), 3.45-3.36 (m, 1H), 1.37 (d, J=6.9 Hz, 6H). LCMS (ESI, m/z): 338[M+H]⁺.

Ethyl (2-cyano-2-(2-(3,5-dichloro-4-((3-isopropyl-1H-pyrazolo[3,4-c]pyridazin-5-yl)oxy)phenyl)hydrazineylidene)acetyl)carbamate (960 mg), a yellow solid, was prepared similarly as described for ethyl (2-cyano-2-(2-(3,5-dichloro-4-((1-tosyl-1H-indol-5-yl)oxy)phenyl)-hydrazineylidene)-acetyl) carbamate, and was used in the subsequent step without further purification.

2-(3,5-Dichloro-4-((3-isopropyl-1H-pyrazolo[3,4-c]pyridazin-5-yl)oxy)phenyl)-3,5-dioxo-2,3,4,5-tetrahydro-1,2,4-triazine-6-carbonitrile (compound 75A, 910 mg, 76%), a red solid, was prepared similarly as described for 2-(4-[[3-isopropyl-1-(4-methylbenzene-sulfonyl)indol-5-yl]oxy]-3,5-dimethylphenyl)-3,5-dioxo-4H-1,2,4-triazine-6-carbonitrile with the exception that the reaction mixture was heated at 120° C. for 12 h and that NaOAc was used. $^1$H NMR (400 MHz, DMSO-d$_6$) δ=13.97 (s, 1H), 13.28 (br s, 1H), 8.31 (s, 1H), 7.82 (s, 2H), 3.46-3.39 (m, 1H), 1.40 (d, J=7.0 Hz, 6H). LCMS (ESI, m/z): 459[M+H]$^+$.

2-(3,5-Dichloro-4-((3-isopropyl-1H-pyrazolo[3,4-c]pyridazin-5-yl)oxy)phenyl)-3,5-dioxo-2,3,4,5-tetrahydro-1,2,4-triazine-6-carboxylic acid (415 mg, 37%), a yellow solid, was prepared similarly as described for 2-[3,5-dichloro-4-[(5-isopropyl-6-oxo-1H-pyridazin-3-yl)oxy]phenyl]-3,5-dioxo-4H-1,2,4-triazine-6-carboxylic acid, which used in next step without further purification. LCMS (ESI, m/z): 478[M+H]$^+$.

To a solution of 2-(3,5-dichloro-4-((3-isopropyl-1H-pyrazolo[3,4-c]pyridazin-5-yl)oxy)phenyl)-3,5-dioxo-2,3,4,5-tetrahydro-1,2,4-triazine-6-carboxylic acid (410 mg, 0.857 mmol) in DMF (8 mL) was added Et$_3$N (260 mg, 2.57 mmol, 0.357 mL) at 0° C., followed by slow addition of DPPA (472 mg, 1.71 mmol, 0.371 mL) under N$_2$. The mixture was stirred at 25° C. for 3 h. Then H$_2$O (1 mL) was added and the reaction was heated at 100° C. for additional 2 h. The mixture was diluted with H$_2$O (50 mL) and extracted with EA (3×30 mL). The combined organic layers were washed with brine (50 mL), dried over anhydr. Na$_2$SO$_4$, the solids were removed by filtration and the filtrate was concentrated under reduced pressure. The crude was purified by preparative HPLC [Phenomenex Luna C18 100×30 mm×5 um; Mobile phase: from 35% ACN in water (0.225% FA) to 65% ACN in water (0.225% FA)] to give 6-amino-2-(3,5-dichloro-4-((3-isopropyl-1H-pyrazolo[3,4-c]pyridazin-5-yl)oxy)phenyl)-1,2,4-triazine-3,5 (2H,4H)-dione as a white solid (120 mg, 31%). $^1$H NMR (400 MHz, DMSO-d$_6$) δ=13.92 (s, 1H), 12.28 (br s, 1H), 8.24 (s, 1H), 7.89 (s, 2H), 6.52 (s, 2H), 3.47-3.38 (m, 1H), 1.40 (d, J=7.0 Hz, 6H). LCMS (ESI, m z): 449.1[M+H]$^+$.

Example 65: Synthesis of Compound 76

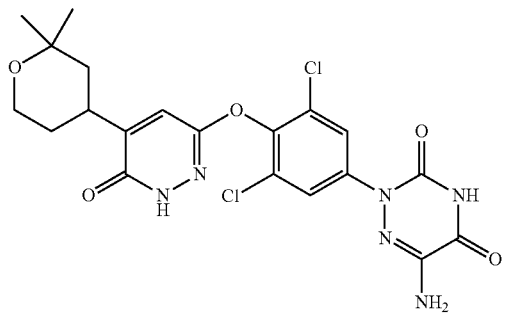

76

6-Amino-2-(3,5-dichloro-4-((5-(2,2-dimethyltetrahydro-2H-pyran-4-yl)-6-oxo-1,6-dihydropyridazin-3-yl)oxy)phenyl)-1,2,4-triazine-3,5(2H, 4H)-dione, a white solid (95.2 mg, 27%) was prepared similarly as described for 6-amino-2-(3,5-dichloro-4-[[5-(oxan-4-yl)-6-oxo-1H-pyridazin-3-yl]oxy]phenyl)-4H-1,2,4-triazine-3,5-dione. $^1$H NMR (400 MHz, DMSO-d$_6$) δ 12.25-12.27 (m, 2H), 7.85 (s, 2H), 7.42 (s, 1H), 6.52 (s, 2H), 3.68-3.71 (m, 2H), 3.13-3.20 (m, 1H), 1.68-1.74 (m, 2H), 1.50-1.58 (m, 1H), 1.40 (t, J=12.6 Hz, 1H), 1.25 (s, 3H), 1.19 (s, 3H). LCMS (ESI, m/z): 495 [M+H]$^+$.

Example 66: Synthesis of Compound 77

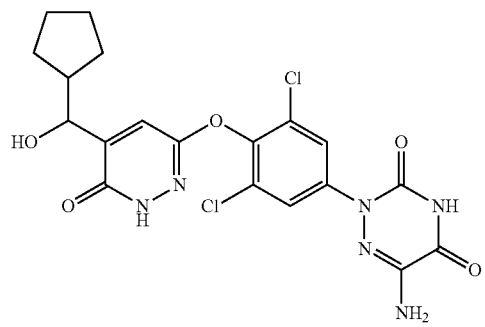

77

A 500 mL round-bottom flask was charged with 2,2,6,6-tetramethylpiperidine (6.20 g, 43.9 mmol) in THF (60 mL) under N$_2$. n-BuLi (12.1 mL, 30.2 mmol) was added dropwise at −75° C. The mixture was warmed to 0° C. and stirred for 30 min. Then the mixture was cooled to −75° C. and 3,6-dichloropyridazine (3.00 g, 20.1 mmol) in THF (60 mL) was added dropwise. The mixture was stirred for 30 min at −75° C. Cyclopentanecarboxaldehyde (5.93 g, 60.4 mmol) in THF (30 mL) was added dropwise. The reaction was stirred for 90 min at −75° C., then quenched with NH$_4$C$_1$ (sat., aq., 100 mL) and extracted with EA (3×100 mL), the combined organic layers were washed with brine (2×50 mL), dried over anhydr. Na$_2$SO$_4$, the solids were removed by filtration and the filtrate was concentrated under reduced pressure. The residue was purified by reverse phase chromatography using a C18 column (MeCN:water+0.05% TFA)=85:15) to provide (6-chloro-3-methoxypyridazin-4-yl)(cyclopentyl)methanol as a yellow oil (1.7 g, 30%). LCMS (ESI, m/z): 247 [M+H]$^+$.

A 100 mL round-bottom flask was charged with cyclopentyl(3,6-dichloropyridazin-4-yl)methanol (1.40 g, 5.66 mmol), imidazole (1.54 g, 22.7 mmol), t-butyldimethylsilyl chloride (2.56 g, 17.0 mmol), DMF (15 mL) under N$_2$. The reaction was stirred overnight at rt. The reaction was quenched with water (10 mL), then extracted with EA (3×30 mL), washed with brine (30 mL), dried over anhydr. Na$_2$SO$_4$, filtered and concentrated under reduced pressure. The residue was chromatographed on a silica gel column with (EA:PE=3:97) to provide 4-[[(t-butyldimethylsilyl)oxy]-(cyclopentyl)methyl]-3,6-dichloropyridazine as a colorless oil (1.3 g, 63%). LCMS (ESI, m/z): 361 [M+H]$^+$.

An 8 mL vial was charged with 4-[[(t-butyldimethylsilyl)oxy](cyclopentyl)methyl]-3,6-dichloropyridazine (1.30 g, 3.60 mmol), t-butyl N-[2-(3,5-dichloro-4-hydroxyphenyl)-3,5-dioxo-4H-1,2,4-triazin-6-yl]carbamate (1.40 g, 3.60 mmol), CuI (342 mg, 1.80 mmol), K$_2$CO$_3$ (1.24 g, 9 mmol), DMSO (20 mL) under N₂. The reaction was stirred overnight at 110° C. and quenched with water (80 mL). The solids were removed by filtration. The filtrate was extracted with EA (3×100 mL) and the organic layers were combined, washed with brine (2×50 mL), dried over anhydr. Na₂SO₄, the solids were removed by filtration and the filtrate was concentrated under reduced pressure. The residue was chromatographed on a silica gel column (EA:PE=15:85) to provide 6-amino-2-[4-[(5-[[(t-butyldimethylsilyl)oxy]-(cyclopentyl)methyl]-6-chloropyridazin-3-yl)oxy]-3,5-dichlorophenyl]-4H-1,2,4-triazine-3,5-dione as a brown solid (360 mg, 14%). LCMS (ESI, m/z): 613 [M+H]⁺.

A 40 mL vial was charged with 6-amino-2-[4-[(5-[[(t-butyl-dimethylsilyl)oxy](cyclopentyl)methyl]-6-chloro-pyridazin-3-yl)oxy]-3,5-dichloro-phenyl]-4H-1,2,4-triazine-3,5-dione (170 mg, 0.277 mmol), NaOAc (90.8 mg, 1.11 mmol), CH₃CO₂H (5 mL) under N₂. The reaction was stirred overnight at 110° C. The pH value of the solution was adjusted to 8.0 with NaHCO₃ (sat., aq.). The solution was extracted with DCM (3×20 mL) and the organic layers were combined, washed with brine (2×10 mL), dried over anhydr. Na₂SO₄, the solids were removed by filtration and the filtrate was concentrated under reduced pressure. The product was dissolved into CH₃OH (2 mL). NaOH (55.4 mg, 1.38 mmol) in water (2 mL) was added. The reaction was stirred for 2 h at 50° C. The reaction was quenched with H₂O (10 mL), then extracted with EA (3×20 mL). The organic layers were combined, washed with brine (2×10 mL), dried over anhydr. Na₂SO₄, the solids were removed by filtration and the filtrate was concentrated under reduced pressure to afford 6-amino-2-[4-[(5-[[(t-butyldimethylsilyl)oxy](cyclopentyl)methyl]-6-oxo-1H-pyridazin-3-yl)oxy]-3,5-dichlorophenyl]-4H-1,2,4-triazine-3,5-dione as a brown solid (150 mg, 57%). LCMS (ESI, m/z): 595 [M+H]⁺.

6-amino-2-[3,5-dichloro-4-([5-[cyclopentyl(hydroxy) methyl]-6-oxo-1H-pyridazin-3-yl]oxy)phenyl]-4H-1,2,4-triazine-3,5-dione, a white solid (3.4 mg) was prepared similarly as described for 2-[3,5-dichloro-4-[(3-isopropyl-1H-indol-5-yl)oxy]-phenyl]-3,5-dioxo-4H-1,2,4-tri-azine-6-carbonitrile except that the reaction with TBAF occurred at rt. ¹H NMR (300 MHz, DMSO-d₆) δ 12.27 (br, 1H), 7.88 (s, 2H), 7.40 (s, 1H), 6.34 (br, 2H), 5.41 (d, J=4.8 Hz, 1H), 4.63 (br, 1H), 2.22 (br, 1H), 1.44-1.57 (m, 8H). LCMS (ESI, m/z): 481 [M+H]⁺.

Example 67: Synthesis of Compounds 78 and 79

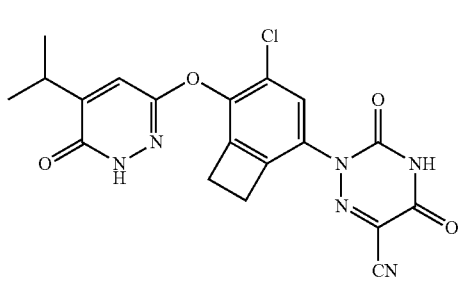

78

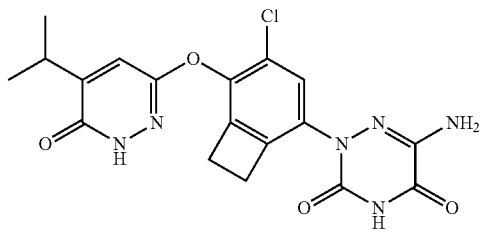

79

T
o a solution of 1-(benzyloxy)-2-bromobenzene (10 g, 38.003 mmol) and sodium amide (4.45 g, 114.010 mmol) in THF (150 mL) was added 1,1-diethoxyethene (13.24 g, 114.010 mmol) under N₂. The reaction was stirred at 70° C. for 16 h. The solution was poured into ice water (100 mL), acidified with concentrated hydrochloric acid (25 mL), and extracted with EA (2×200 mL). The organic layers were combined, dried over anhydr. Na₂SO₄, the solids were removed by filtration and the filtrate was concentrated under reduced pressure. The residue was chromatographed on a silica gel column (EA:PE=1:50) to afford 5-(benzyloxy) bicyclo[4.2.0]octa-1(6), 2,4-trien-7-one as a white solid (3.3 g, 37%). GCMS (ESI, m/z): 224 [M].

T
o a solution of 5-(benzyloxy)bicyclo[4.2.0]octa-1(6), 2,4-trien-7-one (9 g, 40.132 mmol) in CH₃OH (250 mL) was added NaBH₄ (3.036 g, 80.264 mmol). The reaction was stirred at rt for 4 h. The reaction was quenched with water and extracted with EA (2×200 mL). The organic layers were combined, dried over anhydr. Na₂SO₄, filtered and concentrated under reduced pressure. The residue was chromatographed on a silica gel column (EA:PE=1:15) to get 5-(benzyloxy)bicyclo[4.2.0]octa-1(6),2,4-trien-7-ol as a white solid. GCMS (ESI, m/z): 226 [M]. (7.4 g, 77%).

T
o a solution of iodine (11.41 g, 44.945 mmol) in toluene (90 mL) was added triphenylphosphine (10.22 g, 38.953 mmol). The reaction was stirred at rt for 5 min under N₂ and imidazole (6.12 g, 89.891 mmol) was added. The mixture was stirred at rt for 10 min and 5-(benzyloxy)bicyclo[4.2.0] octa-1(6),2,4-trien-7-ol (3.39 g, 14.982 mmol) in toluene (30 mL) was added. The solution was stirred at rt for 1 h and quenched with sodium sulfite (sat., aq., 100 mL). The mixture was extracted with EA (100 mL×3), dried over anhydr. Na₂SO₄, the solids were removed by filtration and the filtrate was concentrated under reduced pressure. The residue was chromatographed on a silica gel column (EA:PE=1:50) to get 2-(benzyloxy)-8-iodobicyclo[4.2.0]octa-1 (6),2,4-triene as a yellow oil. GCMS (ESI, m/z): 336 [M]. (4.46 g, 84%).

T
o a solution of LiAlH₄ (4.01 g, 105.601 mmol) in THF (100 mL) was added 2-(benzyloxy)-8-iodobicyclo[4.2.0] octa-1(6),2,4-triene (14.20 g, 42.240 mmol) in THF (150 mL) dropwise. The reaction mixture was stirred at rt for 30 min and quenched with ice water (200 mL) and adjusted to pH=5 with concentrated hydrochloric acid. The mixture was extracted with EA (3×200 mL) and the organic layers was combined, washed with brine (100 ml) dried over anhydr. Na₂SO₄, filtered and concentrated under reduced pressure to get 2-(benzyloxy)bicyclo[4.2.0]octa-1(6),2,4-triene as a colorless oil. GCMS (ESI, m/z): 210 [M]. (8.900 g, 90%).

A
solution of 2-(benzyloxy)bicyclo[4.2.0]octa-1(6),2,4-triene (7 g,33.290 mmol) in methanol (175 mL) was added Pd/C (3 g). The reaction was stirred for 16 h at rt under hydrogen and filtered. The filtrate was concentrated under reduced pressure. The residue was chromatographed on a silica gel column (EA:PE=1:20) to get bicyclo[4.2.0]octa-1 (6),2,4-trien-2-ol as a colorless oil. LCMS (ESI, m/z): 119 [M–H]. (1.66 g, 35%).

To a solution of bicyclo[4.2.0]octa-1(6),2,4-trien-2-ol (1 g, 8.323 mmol) and diisopropylamine (84.22 mg, 0.832 mmol) in DCM (37.50 mL) was added sulphone chloride (1123.34 mg, 8.323 mmol) in DCM (10 mL) dropwise at 0° C. The reaction was stirred at rt for 16 h and quenched with water (100 mL). The mixture was extracted with DCM (3×50 mL), washed with brine, dried over anhydr. $Na_2SO_4$, filtered and concentrated under reduced pressure. The residue was chromatographed on a silica gel column (EA:PE=1: 50) to 3-chlorobicyclo[4.2.0]octa-1(6),2,4-trien-2-ol as a yellow oil (760 mg, 51%). LCMS (ESI, m/z): 153 [M–H]⁻.

To a solution of 3-chlorobicyclo[4.2.0]octa-1(6),2,4-trien-2-ol (800 mg, 5.175 mmol) in acetic acid (22 mL) was added $HNO_3$ (326.09 mg, 5.175 mmol) in acetic acid (2 mL) at 0° C. The reaction was stirred at rt overnight and quenched with water (100 mL). The reaction mixture was extracted with EA (3×50 mL), washed with brine, dried over anhydr. $Na_2SO_4$, filtered and concentrated under reduced pressure. The residue was chromatographed on a silica gel column with (EA:PE=1:50) to get 3-chloro-5-nitrobicyclo[4.2.0] octa-1(6),2,4-trien-2-ol (500 mg, 41%) as a yellow solid. LCMS (ESI, m/z): 198 [M–H]⁻.

To a solution of 3-chloro-5-nitrobicyclo[4.2.0]octa-1(6), 2,4-trien-2-ol (500.00 mg, 2.505 mmol) in ethanol (20 mL) and $H_2O$ (10 mL) was added Fe (699.50 mg, 12.526 mmol) and $NH_4Cl$ (1.072 g, 20.041 mmol). The mixture was stirred for 5 h at 60° C. The mixture was filtered, the filter cake was washed with DCM (6×50 mL). The filtrate was extracted with dichloromethane (3×300 mL). The combined organic layers were dried over anhydr. $Na_2SO_4$. The solids were removed by filtration, the filtrate was concentrated under reduced pressure to afford 5-amino-3-chlorobicyclo[4.2.0] octa-1(6),2,4-trien-2-ol (450 mg, 95%) as a brown solid. LCMS (ESI, m/z): 170 [M+H]⁺.

4-Chloro-5-[(6-chloro-5-isopropylpyridazin-3-yl)oxy]bicyclo[4.2.0]octa-1(6),2,4-trien-2-amine (640 mg, 72%), a yellow oil, LCMS (ESI, m/z): 324 [M+H]⁺, was prepared similarly as described for 3,5-dichloro-4-[(6-chloro-5-isopropylpyridazin-3-yl)oxy]aniline.

6-([5-Amino-3-chlorobicyclo[4.2.0]octa-1(6),2,4-trien-2-yl]oxy)-4-isopropyl-2H-pyridazin-3-one (300 mg, 52%), a brown solid, LCMS (ESI, m/z): 306 [M+H]⁺, was prepared similarly as described for 6-(4-amino-2,6-dichlorophenoxy)-4-isopropyl-2H-pyridazin-3-one.

Ethyl (2-(2-(4-chloro-5-((5-isopropyl-6-oxo-1,6-dihydropyridazin-3-yl)oxy)bicyclo[4.2.0]octa-1(6),2,4-trien-2-yl) hydrazineylidene)-2-cyanoacetyl)-carbamate (250 mg, 77%), a yellow solid, was prepared similarly as described for ethyl (2-cyano-2-(2-(3,5-dichloro-4-((1-tosyl-1H-indol-5-yl)oxy)phenyl)-hydrazineylidene)-acetyl) carbamate. LCMS (ESI, m/z): 473 [M+H]⁺.

2-[4-Chloro-5-[(5-isopropyl-6-oxo-1H-pyridazin-3-yl) oxy]bicyclo[4.2.0]octa-1(6),2,4-trien-2-yl]-3,5-dioxo-4H-1, 2,4-triazine-6-carbonitrile, compound 78 was prepared similarly as described for 2-(4-[[3-isopropyl-1-(4-methylbenzene-sulfonyl)indol-5-yl]oxy]-3,5-dimethylphenyl)-3,5-dioxo-4H-1,2,4-triazine-6-carbonitrile, and was isolated as a yellow solid. ¹H NMR (300 MHz, DMSO-d₆) δ 7.56 (s, 1H), 7.37 (s, 1H), 6.90-7.20 (br, 2H), 2.96-3.13 (m, 5H), 1.18 (d, J=6.9 Hz, 6H). LCMS (ESI, m/z): 427 [M+H]*), was prepared similarly as described for 2-(4-[[3-isopropyl-1-(4-methylbenzene-sulfonyl)indol-5-yl] oxy]-3,5-dimethylphenyl)-3,5-dioxo-4H-1,2,4-triazine-6-carbonitrile.

2-[4-Chloro-5-[(5-isopropyl-6-oxo-1H-pyridazin-3-yl) oxy]bicyclo-[4.2.0]octa-1(6),2,4-trien-2-yl]-3,5-dioxo-4H-1,2,4-triazine-6-carboxylic acid (180 mg, 82%), a white solid (LCMS (ESI, m/z): 446 [M+H]⁺), was prepared similarly as described for 2-[3,5-dichloro-4-[(5-isopropyl-6-oxo-1H-pyridazin-3-yl)oxy]phenyl]-3,5-dioxo-4H-1,2,4-triazine-6-carboxylic acid.

N-(2-[4-Chloro-5-[(5-isopropyl-6-oxo-1H-pyridazin-3-yl)oxy]-bicyclo[4.2.0]octa-1(6),2,4-trien-2-yl]-3,5-dioxo-4H-1,2,4-triazin-6-yl)carbamate (200 mg, 81%), a yellow oil (LCMS (ESI, m/z): 517 [M+H]⁺) was prepared similarly as described for t-butyl N-(2-[3,5-dichloro-4-[(5-isopropyl-6-oxo-1H-pyridazin-3-yl)oxy]phenyl]-3,5-dioxo-4H-1,2,4-triazin-6-yl)-carbamate.

6-Amino-2-[4-chloro-5-[(5-isopropyl-6-oxo-1H-pyridazin-3-yl)oxy]-bicyclo[4.2.0]octa-1(6),2,4-trien-2-yl]-4H-1,2,4-triazine-3,5-dione (92.5 mg, 56%), a white solid, compound 79 (¹H NMR (300 MHz, DMSO-d₆) δ 12.20-12.27 (m, 2H), 7.58 (s, 1H), 7.31 (s, 1H), 6.46 (s, 2H), 3.16 (br, 2H), 2.99-3.08 (m, 1H), 2.95 (br, 2H), 1.18 (d, J=6.9 Hz, 6H). LCMS (ESI, m/z): 417 [M+H]⁺) was prepared similarly as described for 6-amino-2-[3,5-dichloro-4-[(3-isopropyl-1H-indol-5-yl)oxy]phenyl]-4H-1,2,4-triazine-3,5-dione.

Example 68: Synthesis of Compounds 80 and 81

The synthesis of 6-amino-2-(3-bromo-5-chloro-4-((5-isopropyl-6-oxo-1,6-dihydropyridazin-3-yl)oxy)phenyl)-1,2,4-triazine-3,5(2H,4H)-dione (white solid, 203.7 mg, 57%), and 6-amino-2-(3,5-dibromo-4-((5-isopropyl-6-oxo-1,6-dihydropyridazin-3-yl)oxy)phenyl)-1,2,4-triazine-3,5(2H, 4H)-dione were prepared similarly as described for 6-amino-2-(3,5-dichloro-4-((5-isopropyl-6-oxo-1,6-dihydropyridazin-3-yl)oxy)phenyl)-1,2,4-triazine-3,5(2H, 4H)-dione with the exception that 4-amino-2-bromo-6-chlorophenol was employed instead of 4-amino-2,6-dichlorophenol in the synthesis of compound 80, and 4-amino-2,6-dibromophenol was employed instead of 4-amino-2,6-dichlorophenol in the synthesis of compound 81.

| Structure | LCMS (ESI, m/z) | ¹H NMR |
|---|---|---|
| | 469 [M + H]⁺ | ¹H NMR (300 MHz, DMSO-d₆) δ 12.20 (br, 1H), 7.97 (s, 1H), 7.88 (s, 1H), 7.42 (s, 1H), 6.51 (br, 2H), 3.01-3.10 (m, 1H), 1.20 (d, J = 6.6 Hz, 6H). |

80

| Structure | LCMS (ESI, m/z) | ¹H NMR |
|---|---|---|
| 6-Amino-2-(3-bromo-5-chloro-4-((5-isopropyl-6-oxo-1,6-dihydropyridazin-3-yl)oxy)phenyl)-1,2,4-triazine-3,5(2H,4H)-dione<br><br>81 | 513 [M + H]⁺ | ¹H NMR (300 MHz, DMSO-d₆) δ 12.20-12.26 (m, 2H), 7.99 (s, 2H), 7.41 (s, 1H), 6.52 (br, 2H), 3.03-3.08 (m, 1H), 1.20 (d, J = 6.6 Hz, 6H). |
| 6-Amino-2-(3,5-dibromo-4-((5-isopropyl-6-oxo-1,6-dihydropyridazin-3-yl)oxy)phenyl)-1,2,4-triazine-3,5(2H,4H)-dione | | |

Example 69: Synthesis of Compound 82

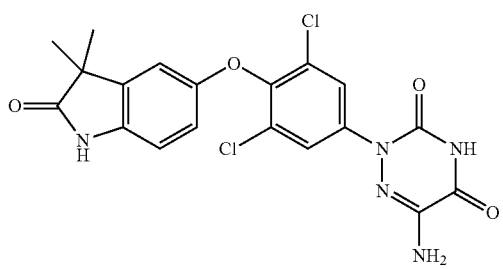

82

5-Bromo-3,3-dimethyl-1H-indol-2-one (3.7 g, 67%), a yellow solid, was prepared similarly as described in the procedures of WO2000066167 and WO2000066556. LCMS (ESI, m z): 240 [M+H]⁺.

A 50-mL round-bottom flask was charged with 5-bromo-3,3-dimethyl-1H-indol-2-one (1.50 g, 6.247 mmol), 2-(5,5-dimethyl-1,3,2-dioxaborinan-2-yl)-5,5-dimethyl-1,3,2-dioxaborinane (4.23 g, 18.742 mmol), potassium acetate (1.84 g, 18.742 mmol), DMSO (20 mL), PdCl₂(PPh₃)₂ (438.50 mg, 0.625 mmol) under N₂. The mixture was stirred for 2 h at 60° C. under N₂. The solution was purified by C₁₈ reverse phase chromatography to provide 3,3-dimethyl-2-oxo-1H-indol-5-ylboronic acid (1.2 g, 89%) as a white solid. LCMS (ESI, m/z): 206 [M+H]⁺.

A 100-mL 3-necked round-bottom flask was charged with t-butyl N-[4-[(benzyloxy)methyl]-2-(3,5-dichloro-4-hydroxyphenyl)-3,5-dioxo-1,2,4-triazin-6-yl]carbamate (1.20 g, 2.356 mmol), 3,3-dimethyl-2-oxo-1H-indol-5-ylboronic acid (2.42 g, 11.780 mmol), Cu(OAc)₂ (855.86 mg, 4.712 mmol), pyridine (372.72 mg, 4.712 mmol), dichloromethane (100 mL), 4 Å molecular sieves (500 mg) under 0₂. The reaction was stirred for 3 days at rt. The solids were filtered out. The organic layer was concentrated under reduced pressure. The residue was chromatographed on a C₁₈ column (CH₃CN:H₂O+0.05% TFA=7:3) to provide t-butyl N-[4-[(benzyloxy)-ethyl]-2-[3,5-dichloro-4-[(3,3-dimethyl-2-oxo-1H-indol-5-yl)oxy]phenyl]-3,5-dioxo-1,2,4-triazin-6-yl]carbamate as a yellow solid (830 mg, 45%). LCMS (ESI, m/z): 668 [M+H]⁺.

A 50-mL round-bottom flask was charged with t-butyl N-[4-[(benzyloxy)methyl]-2-[3,5-dichloro-4-[(3,3-dimethyl-2-oxo-1H-indol-5-yl)oxy]-phenyl]-3,5-dioxo-1,2,4-triazin-6-yl]carbamate (500 mg, 0.748 mmol), DCM (10 mL) under N₂. BBr₃ (1.499 g, 5.983 mmol) was added dropwise at 0° C. The mixture was stirred at 0° C. for 1 h. The reaction mixture was added dropwise to methanol (5 mL) at 0° C. and concentrated under reduced pressure at 0° C. The crude was dissolved in methanol (5 mL) and purified by preparative HPLC using the following gradient conditions: XBridge Prep OBD C18 Column, 19×250 mm, 5 um; Mobile Phase A: Water (10 mmol/L NH₄HCO₃₊₀.₁% NH₃·H₂O), Mobile Phase B: ACN; Flow rate: 25 mL/min; Gradient: 20 B to 40 B in 7 min; 220 nm; RT1:6.42; Injection Volume: 6 ml; Purification afforded 6-amino-2-[3,5-dichloro-4-[(3,3-dimethyl-2-oxo-1H-indol-5-yl)oxy]phenyl]-4H-1,2,4-triazine-3,5-dione as a white solid (59.4 mg, 18%). ¹H NMR (300 MHz, DMSO-d₆) δ 12.25 (br, 1H), 10.27 (s, 1H), 7.90 (s, 2H), 7.05 (d, J=2.4 Hz, 1H), 6.77 (d, J=8.4 Hz, 1H), 6.54 (br, 2H), 6.45-6.49 (m, 1H), 1.25 (s, 6H). LCMS (ESI, m/z): 448 [M+H]⁺.

Example 70: Synthesis of Compound 83

83

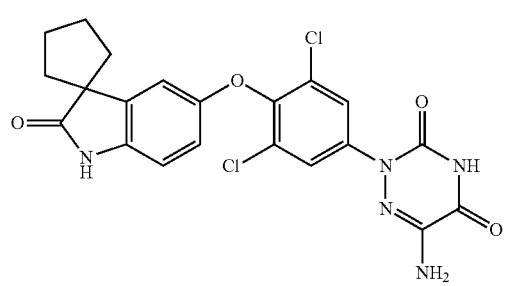

A 50-mL round-bottom flask was charged with 5'-bromo-1'H-spiro[cyclopentane-1,3'-indol]-2'-one (prepared according to the procedure in J. Med. Chem. 2008, 51, 1861-1873, 1 g, 3.757 mmol), 2-(5,5-dimethyl-1,3,2-dioxaborinan-2-yl)-5,5-dimethyl-1,3,2-dioxaborinane (2.55 g, 11.289 mmol), potassium acetate (1.11 g, 11.272 mmol), PdCl$_2$(PPh$_3$)$_2$ (263.8 mg, 0.375 mmol), dimethyl sulfoxide (25 mL) under N$_2$. The resulting solution was stirred for 3 h at 60° C. The solution was purified by reverse phase column chromatography (C18, H$_2$O:CH$_3$CN=13:87) to provide 2'-oxo-1'H-spiro[cyclopentane-1,3'-indol]-5'-ylboronic acid as a yellow solid (1.07 g, 74%). LCMS (ESI, m/z): 232 [M+H]$^+$.

The subsequent coupling reaction, deprotection, and purification were prepared similarly as described for 6-amino-2-[3,5-dichloro-4-[(3,3-dimethyl-2-oxo-1H-indol-5-yl)oxy]phenyl]-4H-1,2,4-triazine-3,5-dione to afford 6-amino-2-(3,5-dichloro-4-[1'H-spiro[cyclopentane-1,3'-indol]-2'-oneoxy]phenyl)-4H-1,2,4-triazine-3,5-dione as a white solid (11.3 mg, 13%). $^1$H NMR (300 MHz, DMSO-d$_6$) δ 10.23 (s, 1H), 7.91 (s, 2H), 6.96 (s, 1H), 6.72-6.75 (m, 1H), 6.43-6.48 (m, 3H), 1.89-2.01 (m, 6H), 1.70-1.81 (m, 2H). LCMS (ESI, m/z): 474 [M+H]$^+$.

Example 71: Synthesis of Compound 84

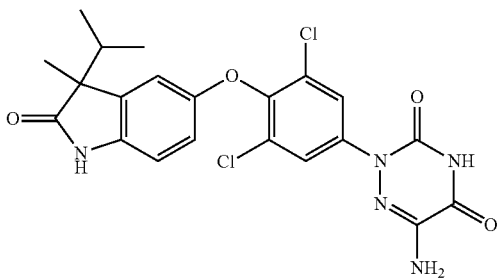

84

3-Isopropyl-3-methyl-1H-indol-2-one was obtained as a yellow solid after following the preparation outlined in Molecules 2017, 22, 1-18. LCMS (ESI, m/z): 190 [M+H]$^+$.

A 40 mL vial was charged with 3-isopropyl-3-methyl-1H-indol-2-one (2.80 g, 14.8 mmol), NaOAc (1.23 g, 14.9 mmol), acetic acid (30 mL). Br$_2$ (0.77 mL, 4.84 mmol) in acetic acid (10 mL) was added dropwise. The reaction was stirred for 50 min at rt and concentrated under reduced pressure. The residue was chromatographed on a silica gel column (EA:PE=25:75) to provide 5-bromo-3-isopropyl-3-methyl-1H-indol-2-one as a white solid (4 g, 95%). LCMS (ESI, m z): 268 [M+H]$^+$.

The subsequent formation of the boronic acid, the coupling reaction, deprotection, and purification were prepared similarly as described for 6-amino-2-[3,5-dichloro-4-[(3,3-dimethyl-2-oxo-1H-indol-5-yl)oxy]phenyl]-4H-1,2,4-triazine-3,5-dione to afford 6-amino-2-[3,5-dichloro-4-[(3-isopropyl-3-methyl-2-oxo-1H-indol-5-yl)oxy]phenyl]-4H-1,2,4-triazine-3,5-dione (52.8 mg, 29%). $^1$H NMR (400 MHz, DMSO-d$_6$) δ 12.28 (s, 1H), 10.28 (s, 1H), 7.89 (s, 2H), 6.86 (d, J=2.8 Hz, 1H), 7.77 (d, J=8.4 Hz, 1H), 6.54-6.58 (m, 3H), 1.91-2.00 (m, 1H), 1.23 (s, 3H), 0.85 (d, J=7.2 Hz, 3H), 0.70 (d, J=6.8 Hz, 3H). LCMS (ESI, m/z): 476 [M+H]$^+$.

Example 72: Synthesis of Compound 85

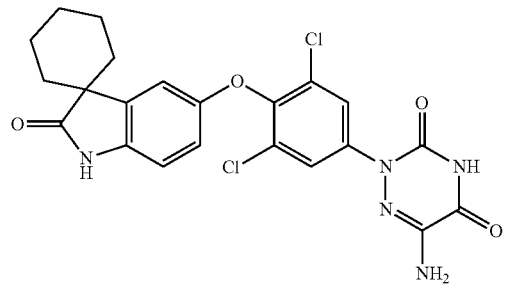

85

6-Amino-2-(3,5-dichloro-4-[1'H-spiro[cyclohexane-1,3'-indol]-2'-oneoxy]phenyl)-4H-1,2,4-triazine-3,5-dione, a white solid ($^1$H NMR (300 MHz, DMSO-d$_6$) δ 10.26 (s, 1H), 7.90 (s, 2H), 7.12 (s, 1H), 6.76 (d, J=4.8 Hz, 1H), 6.49-6.53 (m, 3H), 1.86 (br, 2H), 1.53-1.62 (m, 8H). LCMS (ESI, m/z): 488 [M+H]$^+$) was prepared similarly as described for 6-amino-2-(3,5-dichloro-4-[1'H-spiro[cyclopentane-1,3'-indol]-2'-oneoxy]phenyl)-4H-1,2,4-triazine-3,5-dione.

Example 73: Synthesis of Compounds 86 to 89

Compound 86 was prepared similarly as described for 6-amino-2-(3,5-dichloro-4-((5-cyclobutyl-6-oxo-1,6-dihydropyridazin-3-yl)oxy)phenyl)-1,2,4-triazine-3,5(2H,4H)-dione where 3-methylcyclobutane-1-carboxylic acid was employed instead of cyclobutane carboxylic acid. Compound 86 was purified by SFC-HPLC [Column: (R,R)-Whelk-01, 2.12×25 cm, 5 μm; Mobile Phase A: Hex (0.1% FA)-HPLC, Mobile Phase B: EtOH-HPLC; Flow rate: 20 mL/min; Gradient: 20 B to 20 B in 41 min; 254/220 nm] to afford compound 86-A (RT1=31.945, 10.8 mg, 98% pure, SFC analytical Column: (R,R)-Whelk, 0.46×5 cm; 3.5 μm, Hex (0.1% FA):EtOH=75:25, 1.0 mL/min, Rt: 3.788 min), and compound 86-B (RT2=37.638, 7.1 mg, 98% pure, SFC Column: (R,R)-Whelk, 0.46×5 cm; 3.5 μm, Hex (0.1% FA): EtOH=75:25, 1.0 mL/min, Rt: 4.378 min), both as a white solids.

Compounds 87-A and 87-B were prepared similarly as described for 6-amino-2-(3,5-dichloro-4-((5-cyclobutyl-6-oxo-1,6-dihydropyridazin-3-yl)oxy)phenyl)-1,2,4-triazine-3,5(2H,4H)-dione with the exception that 3-(benzyloxy)cyclobutane-1-carboxylic acid was employed instead of cyclobutane carboxylic acid. 6-amino-2-(4-((5-(3-(benzyloxy)cyclobutyl)-6-oxo-1,6-dihydro-pyridazin-3-yl)oxy)-3,5-dichlorophenyl)-1,2,4-triazine-3,5(2H,4H)-dione was isolated by preparative HPLC (Column: Xcelect CSH F-pheny OBD Column, 19×250 mm, 5 μm; Mobile Phase A: Water (10 mmol/L NH$_4$HCO$_3$), Mobile Phase B: ACN; Flow rate: 25 mL/min; Gradient: 26 B to 46 B in 9 min; 220 nm; RT:8.85 min). This was followed by chiral preparative HPLC (Column: CHIRALPAK IC, 2×25 cm, 5 μm; Mobile Phase A: Hex (0.1% FA)-HPLC, Mobile Phase B: EtOH-HPLC; Flow rate: 20 mL/min; Gradient: 40 B to 40 B in 25 min; 220/254 nm; RT:10.881 min; Injection Volume:0.6 ml; Number Of Runs: 25) to afford compound 87-A as a white solid (150 mg, 23%). An additional separation on the racemic mixture was required by SFC prep-HPLC (Column: CHIRALPAK IG, 20×250 mm, 5 μm; Mobile Phase A: CO$_2$, Mobile Phase B: IPA (2 mM NH$_3$-MEOH); Flow rate: 40 mL/min; Gradient: 50% B; 220 nm; RT 1:7.1 min; Injection Volume:2 mL; Number Of Runs: 4) to afford 87-B as an off-white solid (13.3 mg).

To compound 87-A (130 mg, 0.239 mmol) in EA (10 mL) was added Pd/C (100 mg). The mixture was stirred for 2 h at rt under $H_2$. The mixture was filtered through a celite pad and washed with EA (20 mL) and $CH_3OH$ (20 mL). The filtrate was concentrated under reduced pressure. The crude product was purified by preparative HPLC (XBridge Prep OBD C18 Column, 19×250 mm, 5 μm; Mobile Phase A: Water (10 mmol/L $NH_4HCO_3$+0.1% $NH_3·H_2O$), Mobile Phase B: ACN; Flow rate: 25 mL/min; Gradient: 10 B to 30 B in 7 min; 220 nm; RT: 6.13 min) to provide 88-A as a white solid (52.5 mg, 48%).

6-amino-2-(3,5-dichloro-4-((5-(3,3-dimethylcyclobutyl)-6-oxo-1,6-dihydropyridazin-3-yl)oxy)phenyl)-1,2,4-triazine-3,5(2H,4H)-dione was prepared similarly as described for 6-amino-2-(3,5-dichloro-4-((5-cyclobutyl-6-oxo-1,6-dihydropyridazin-3-yl)oxy)phenyl)-1,2,4-triazine-3,5(2H,4H)-dione, starting from 3,3-dimethylcyclobutane-1-carboxylic acid.

| Structure | LCMS (ESI, m/z) | $^1$H NMR |
|---|---|---|
| 86<br>6-Amino-2-(3,5-dichloro-4-[[5-(3-methylcyclobutyl)-6-oxo-1H-pyridazin-3-yl]oxy]phenyl)-4H-1,2,4-triazine-3,5-dione | 451[M + H]$^+$ | $^1$H NMR (300 MHz, DMSO-d$_6$) δ 12.36-12.03 (m, 2H), 7.84-7.85 (m, 2H), 7.40-7.50 (m, 1H), 6.52 (s, 2H), 3.60-3.65 (m, 1H), 2.24-2.46 (m, 3H), 1.84-2.00(m, 1H), 1.61-1.75 (m, 1H), 1.19-1.20 (m, 1H), 1.01-1.09 (m, 2H). |
| 86 A<br>6-Amino-2-(3,5-dichloro-4-((5-((1r,3r)-3-methylcyclobutyl)-6-oxo-1,6-dihydropyridazin-3-yl)oxy)phenyl)-1,2,4-triazine-3,5(2H,4H)-dione | 1$^{st}$ eluting isomer was labelled 86-A. 451 [M + H]$^+$ | $^1$H NMR(300 MHz, DMSO-d$_6$) δ 12.13-12.27(m, 2H), 7.84 (s, 2H), 7.40-7.41 (m, 1H), 6.52 (s, 2H), 3.15-3.25 (m, 1H), 2.29-2.45 (m, 3H), 1.60-1.78 (m, 2H), 0.98 (d, J = 6.0 Hz, 3H). |
| 86-B<br>6-Amino-2-(3,5-dichloro-4-((5-((1s,3s)-3-methylcyclobutyl)-6-oxo-1,6-dihydropyridazin-3-yl)oxy)phenyl)-1,2,4-triazine-3,5(2H,4H)-dione | 2$^{nd}$ eluting isomer was labelled 86-B. 451 [M + H]$^+$ | $^1$H NMR (300 MHz, DMSO-d$_6$) δ 12.14-12.27 (m, 2H), 7.84 (s, 2H), 7.49-7.50 (m, 1H), 6.52 (s, 2H), 3.59-3.65 (m, 1H), 2.23-2.38 (m, 3H), 1.88-1.98 (m, 2H), 1.18 (d, J = 6.0 Hz, 3H). |

| Structure | LCMS (ESI, m/z) | ¹H NMR |
|---|---|---|
| 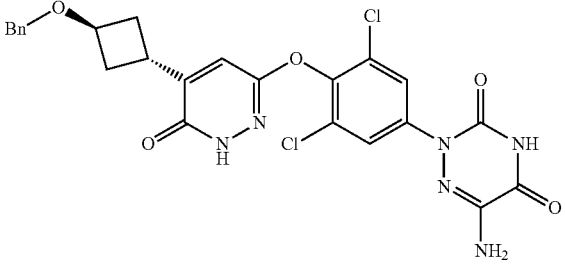<br>87-A<br><br>6-Amino-2-(4-((5-((1r,3r)-3-(benzyloxy)cyclobutyl)-6-oxo-1,6-dihydropyridazin-3-yl)oxy)-3,5-dichlorophenyl)-1,2,4-triazine-3,5(2H,4H)-dione | 543 [M + H]⁺ | ¹HNMR (400 MHz, DMSO-d₆) δ ppm: 12.28 (s, 1H), 12.19 (s, 1H), 7.84 (s, 2H), 7.44-7.47 (m, 1H), 7.24-7.37 (m, 5H), 6.53 (s, 2H), 4.42 (s, 2H), 4.03-4.11 (m, 1H), 2.99-3.06 (m, 1H), 2.53-2.63 (m, 2H), 1.93-2.05 (m, 2H). |
| 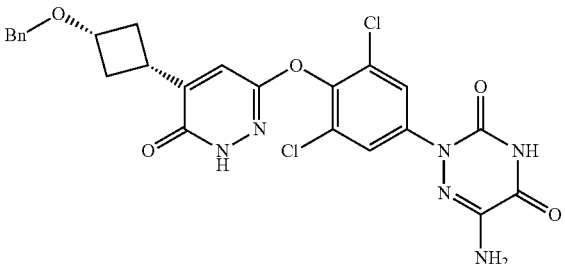<br>87-B<br><br>6-Amino-2-(4-((5-((1s,3s)-3-(benzyloxy)cyclobutyl)-6-oxo-1,6-dihydropyridazin-3-yl)oxy)-3,5-dichlorophenyl)-1,2,4-triazine-3,5(2H,4H)-dione | 543 [M + H]⁺ | ¹HNMR (400 MHz, DMSO-d₆) δ 12.10-12.40 (m, 2H), 7.85 (s, 2H), 7.58 (s, 1H), 7.24-7.38 (m, 5H), 6.50 (s, 2H), 4.41 (s, 2H), 4.13-4.22 (m, 1H), 3.47-3.57 (m, 1H), 2.28-2.45 (m, 4H). |
| 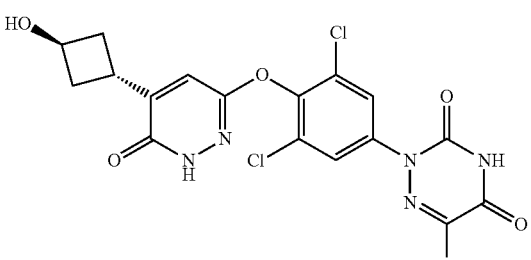<br>88-A<br><br>6-Amino-2-[3,5-dichloro-4-([6-oxo-5-[(1r,3r)-3-hydroxycyclobutyl]-1H-pyridazin-3-yl]oxy)phenyl]-4H-1,2,4-triazine-3,5-dione | 453 [M + H]⁺ | ¹HNMR (400 MHz, DMSO-d₆) δ 12.10-12.42 (m, 2H), 7.85 (s, 2H), 7.38-7.41 (m, 1H), 6.51 (s, 2H), 5.09-5.15 (m, 1H), 4.06-4.13 (m, 1H), 2.88-2.95 (m, 1H), 2.50-2.60 (m, 2H), 1.85-1.93 (m, 2H). |

| Structure | LCMS (ESI, m/z) | ¹H NMR |
|---|---|---|
| 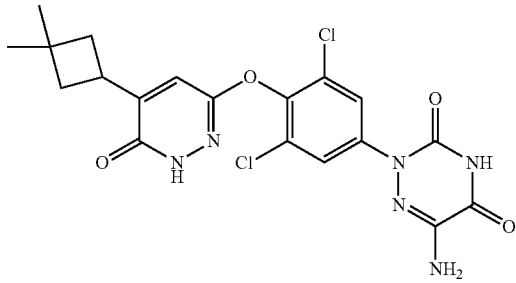<br>89<br><br>6-Amino-2-(3,5-dichloro-4-((5-(3,3-dimethylcyclobutyl)-6-oxo-1,6-dihydropyridazin-3-yl)oxy)phenyl)-1,2,4-triazine-3,5(2H,4H)-dione | 465 [M + H]⁺ | ¹HNMR (400 MHz, DMSO-d₆) δ 12.20 (s, 1H), 12.15 (s, 1H), 7.84 (s, 2H), 7.45(s, 1H), 6.54 (s, 2H), 3.34-3.32 (m, 1H), 2.08-2.06 (m, 2H), 2.06-1.93 (m, 2H), 1.24 (s, 3H), 1.10 (s, 3H) |

The following compounds were prepared similarly as described for 6-amino-2-(3,5-dichloro-4-((5-cyclobutyl-6-oxo-1,6-dihydropyridazin-3-yl)oxy)phenyl)-1,2,4-triazine-3,5(2H,4H)-dione.

| Structure | LCMS (ESI, m/z) | ¹H NMR |
|---|---|---|
| 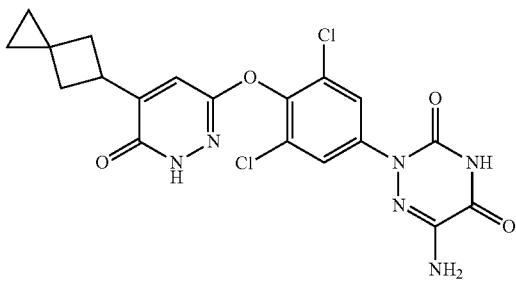<br>93<br><br>6-amino-2-(3,5-dichloro-4-((6-oxo-5-(spiro[2.3]hexan-5-yl)-1,6-dihydropyridazin-3-yl)oxy)phenyl)-1,2,4-triazine-3,5(2H,4H)-dione | 463 [M + H]⁺ | ¹HNMR (400 MHz, DMSO-d₆) δ 12.16 (s, 1H), 7.86 (s, 2H), 7.54 (s, 1H), 6.46 (s, 2H), 3.72-3.67 (m, 1H), 2.34 (d, J = 8.4 Hz, 4H), 0.54-0.41 (m, 4H). |
| 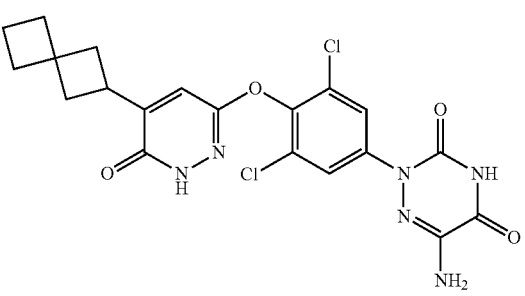<br>94<br><br>6-amino-2-(3,5-dichloro-4-((6-oxo-5-(spiro[3.3]heptan-2-yl)-1,6-dihydropyridazin-3-yl)oxy)phenyl)-1,2,4-triazine-3,5(2H,4H)-dione | 477 [M + H]⁺ | ¹H NMR (400 MHz, DMSO-d₆) δ 1.78-1.82 (m, 2H), 1.88-1.92 (m, 2H), 2.05-2.12 (m, 4H), 2.32 (td, 2H, J = 9.3 Hz, 2.8 Hz), 3.36-3.38 (m, 1H), 6.51 (br.s, 2H), 7.4 (d, 1H, J = 1.5 Hz), 7.84 (s, 2H), 12.13 (s, 1H), 12.26 (br.s, 1H) |

-continued

| Structure | LCMS (ESI, m/z) | ¹H NMR |
|---|---|---|
| 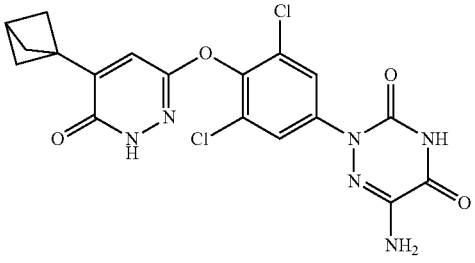<br>95<br>6-amino-2-(4-((5-(bicyclo[1.1.1]pentan-1-yl)-6-oxo-1,6-dihydropyridazin-3-yl)oxy)-3,5-dichlorophenyl)-1,2,4-triazine-3,5(2H,4H)-dione | 449 [M + H]⁺ | ¹H NMR (400 MHz, DMSO-d₆) δ 12.25 (s, 1H), 12.16 (s, 1H), 7.82 (s, 2H), 7.29 (s, 1H), 6.49 (s, 2H), 2.56 (s, 1H), 2.14 (s, 6H) |
| 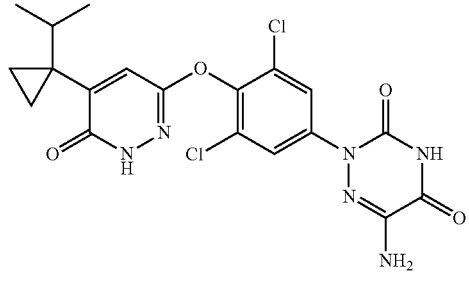<br>96<br>6-amino-2-(3,5-dichloro-4-((5-(1-isopropylcyclopropyl)-6-oxo-1,6-dihydropyridazin-3-yl)oxy)phenyl)-1,2,4-triazine-3,5(2H,4H)-dione | 463 [M + H]⁺ | ¹H NMR (400 MHz, DMSO-d₆) δ 0.64 (t, J = 5.3 Hz, 2H), 0.77 (t, J = 5.1 Hz, 2H), 0.80 (d, J = 6.9 Hz, 6H), 1.94 (p, J = 6.8 Hz, 1H), 6.51 (s, 2H), 7.38 (s, 1H), 7.84 (s, 2H), 12.14 (s, 1H), 12.27 (s, br, 1H) |
| 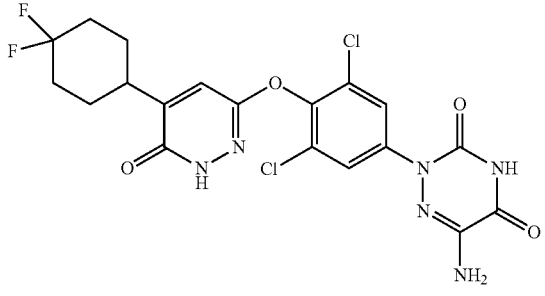<br>97<br>6-amino-2-(3,5-dichloro-4-((5-(4,4-difluorocyclohexyl)-6-oxo-1,6-dihydropyridazin-3-yl)oxy)phenyl)-1,2,4-triazine-3,5(2H,4H)-dione | 501 [M + H]⁺ | ¹H NMR (400 MHz, DMSO-d₆) δ 7.85 (s, 2H), 7.48 (s, 1H), 6.53 (s, 2H), 2.90 (t, J = 11.6 Hz, 1H), 1.89-2.11 (m, 6H), 1.62-1.68 (m, 2H) |

| Structure | LCMS (ESI, m/z) | ¹H NMR |
|---|---|---|
| 98<br>6-amino-2-(3,5-dichloro-4-((6-oxo-5-(1,2,3,4-tetrahydronaphthalen-2-yl)-1,6-dihydropyridazin-3-yl)oxy)phenyl)-1,2,4-triazine-3,5(2H,4H)-dione | 513 [M + H]⁺ | ¹H NMR (400 MHz, DMSO-$d_6$) δ 1.82-1.91 (m, 1H), 2.03-2.08 (m, 1H), 2.85-2.91 (m, 3H), 2.97-3.04 (m, 1H), 3.10-3.18 (m, 1H), 6.51 (s, 2H), 7.08-7.16 (m, 4H), 7.47 (s, 1H), 7.86 (s, 2H), 12.27 (br s, 1H), 12.29 (s, 1H) |
| 99<br>6-amino-2-(3,5-dichloro-4-((6-oxo-5-((1s,3s)-3-phenylcyclobutyl)-1,6-dihydropyridazin-3-yl)oxy)phenyl)-1,2,4-triazine-3,5(2H,4H)-dione | 513 [M + H]⁺ | ¹H NMR (400 MHz, DMSO-$d_6$) δ 12.11-12.31 (m, 2H), 7.87 (s, 2H), 7.71 (s, 1H), 7.32-7.37 (m, 4H), 7.20-7.24 (m, 1H), 6.52 (s, 2H), 3.58-3.66 (m, 2H), 3.38-3.49 (m, 2H), 2.53-2.63 (m, 2H) |
| 100<br>6-amino-2-(3,5-dichloro-4-((6-oxo-5-((1r,3r)-3-phenylcyclobutyl)-1,6-dihydropyridazin-3-yl)oxy)phenyl)-1,2,4-triazine-3,5(2H,4H)-dione | 513 [M + H]⁺ | ¹H NMR (400 MHz, DMSO-$d_6$) δ 12.14-12.34 (m, 2H), 7.85 (s, 2H), 7.53 (s, 1H), 7.29-7.33 (m, 4H), 7.17-7.23 (m, 1H), 6.54 (s, 2H), 3.46-3.58 (m, 2H), 2.63-2.70 (m, 2H), 2.20-2.29 (m, 2H). |

| Structure | LCMS (ESI, m/z) | ¹H NMR |
|---|---|---|
| 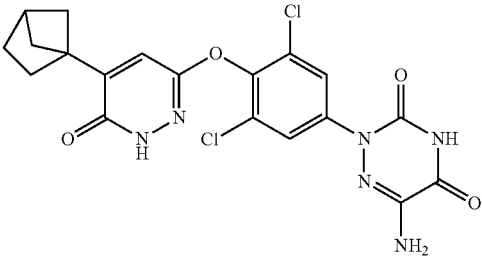<br>101<br>6-amino-2-(4-((5-(bicyclo[2.1.1]hexan-1-yl)-6-oxo-1,6-dihydropyridazin-3-yl)oxy)-3,5-dichlorophenyl)-1,2,4-triazine-3,5(2H,4H)-dione | 463 [M + H]⁺ | ¹H NMR (400 MHz, DMSO-d₆) δ ppm: 12.27 (s, 1H), 12.13 (s, 1H), 7.84 (s, 2H), 7.29 (s, 1H), 6.53 (s, 2H), 2.08 (s, 1H), 1.71-1.95 (m, 6H), 1.47-1.55 (m, 2H) |
| 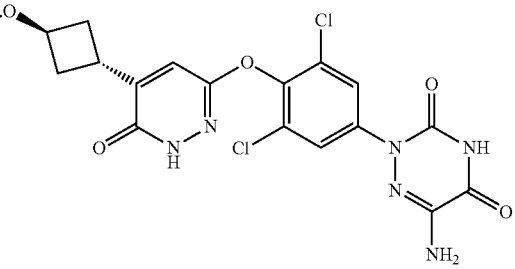<br>102<br>6-amino-2-(3,5-dichloro-4-((5-((1r,3r)-3-methoxycyclobutyl)-6-oxo-1,6-dihydropyridazin-3-yl)oxy)phenyl)-1,2,4-triazine-3,5(2H,4H)-dione | 467 [M + H]⁺ | ¹H NMR (400 MHz, DMSO-d₆) δ 12.18-12.27 (m, 2H), 7.85-7.86 (m, 2H), 7.45-7.46 (m, 1H), 6.53 (s, 2H), 3.85-3.93 (m, 1H), 3.16-3.18 (m, 3H), 2.98-3.10 (m, 1H), 2.58-2.65 (m, 2H), 1.90-1.99 (m, 2H) |
| 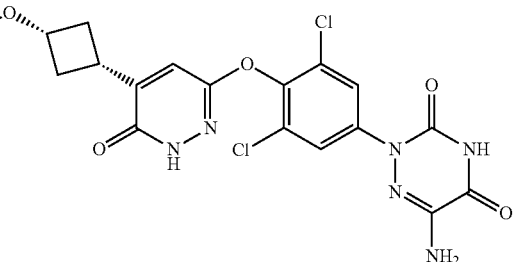<br>103<br>6-amino-2-(3,5-dichloro-4-((5-((1s,3s)-3-methoxycyclobutyl)-6-oxo-1,6-dihydropyridazin-3-yl)oxy)phenyl)-1,2,4-triazine-3,5(2H,4H)-dione | 467 [M + H]⁺ | ¹H NMR (400 MHz, DMSO-d₆) δ 12.19-12.27 (m, 2H), 7.85-7.86 (m, 2H), 7.56-7.57 (m, 1H), 6.52 (s, 2H), 3.96-4.00 (m, 1H), 3.49-3.53 (m, 1H), 3.17-3.18 (m, 3H), 2.36-2.42 (m, 2H), 2.24-2.32 (m, 2H) |

| Structure | LCMS (ESI, m/z) | ¹H NMR |
|---|---|---|
| 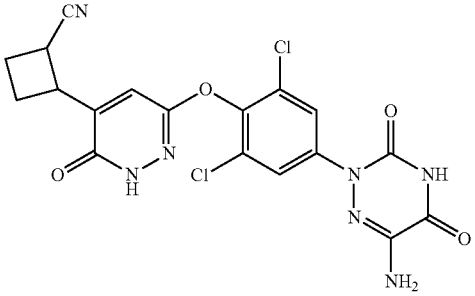<br>104<br>rac-6-amino-2-(3,5-dichloro-4-((5-(2-methylcyclobutyl)-6-oxo-1,6-dihydropyridazin-3-yl)oxy)phenyl)-1,2,4-triazine-3,5(2H,4H)-dione | 462 [M + H]⁺ | ¹H NMR (400 MHz, DMSO-$d_6$) δ 12.29-12.31 (m, 1H), 7.96 (s, 2H), 7.59-7.64 (m, 1H), 5.85 (s, 2H), 3.78-3.97 (m, 2H), 2.56-2.66 (m, 1H), 2.10-2.32 (m, 3H) |
| 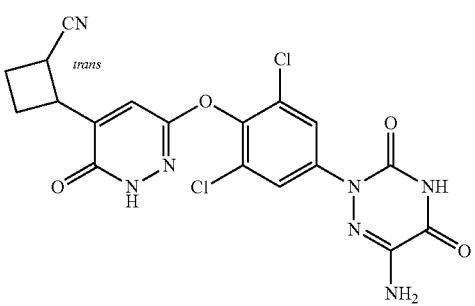<br>105<br>trans-2-(6-(4-(6-amino-3,5-dioxo-4,5-dihydro-1,2,4-triazin-2(3H)-yl)-2,6-dichlorophenoxy)-3-oxo-2,3-dihydropyridazin-4-yl)cyclobutane-1-carbonitrile | 462 [M + H]⁺ | ¹H NMR (400 MHz, DMSO-$d_6$) δ 12.27 (s, 2H), 7.85 (s, 2H), 7.59 (d, J = 1.3 Hz, 1H), 6.44 (s, 2H), 3.82-3.89 (m, 1H), 3.57-3.65 (m, 1H), 2.22-2.32 (m, 4H) |
| 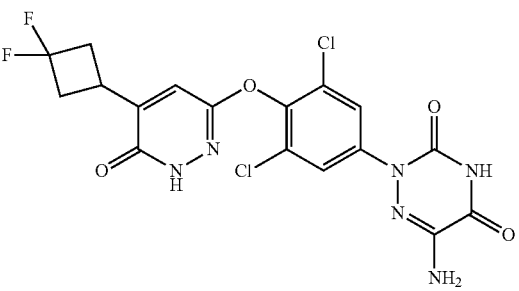<br>106<br>6-amino-2-(3,5-dichloro-4-((5-(3,3-difluorocyclobutyl)-6-oxo-1,6-dihydropyridazin-3-yl)oxy)phenyl)-1,2,4-triazine-3,5(2H,4H)-dione | 473 [M + H]⁺ | ¹H NMR (400 MHz, DMSO-$d_6$) δ 12.31-12.28 (m, 2H), 7.85 (s, 2H), 7.66 (s, 1H), 6.53 (s, 2H), 3.39-3.31 (m, 1H), 2.94-2.86 (m, 4H) |

| Structure | LCMS (ESI, m/z) | ¹H NMR |
|---|---|---|
| 107<br><br>6-amino-2-(3,5-dichloro-4-((6-oxo-5-(1-phenylcyclopropyl)-1,6-dihydropyridazin-3-yl)oxy)phenyl)-1,2,4-triazine-3,5(2H,4H)-dione | 499 [M + H]⁺ | ¹H NMR (400 MHz, DMSO-$d_6$) δ 1.21-1.25 (m, 2H), 1.37-1.43 (m, 2H), 6.50 (s, 2H), 7.17-7.27 (m, 1H), 7.26-7.34 (m, 4H), 7.58 (s, 1H), 7.84 (s, 2H), 12.17 (s, 1H), 12.26 (br s, 1H) ppm |
| 155<br><br>6-amino-2-(3,5-dichloro-4-((5-(2,3-dihydro-1H-inden-2-yl)-6-oxo-1,6-dihydropyridazin-3-yl)oxy)phenyl)-1,2,4-triazine-3,5(2H,4H)-dione | 499 [M + H]⁺ | ¹H NMR (400 MHz, DMSO-$d_6$) δ 3.1 (dd, 2H, J = 15.5 Hz, 8.2 Hz), 3.25 (dd, 2H, J = 15.5 Hz, 7.8 Hz), 3.72 (quint, 1H, J = 8.2 Hz), 6.49 (s, 2H), 7.17 (dd, 2H, J = 5.7 Hz, 3.0 Hz), 7.26 (dd, 2H, J = 5.0 Hz, 2.8 Hz), 7.45 (s, 1H), 7.84 (s, 2H), 12.26 (br s, 1H), 12.27 (s, 1H) ppm |
| 158<br><br>6-amino-2-(4-((5-(bicyclo[4.2.0]octa-1(6),2,4-trien-7-yl)-6-oxo-1,6-dihydropyridazin-3-yl)oxy)-3,5-dichlorophenyl)-1,2,4-triazine-3,5(2H,4H)-dione | 485 [M + H]⁺ | ¹H NMR (400 MHz, DMSO-$d_6$) δ 12.25-12.33 (m, 2H), 7.82 (s, 2H), 7.20-7.40 (m, 5H), 6.52 (s, 2H), 4.71 (s, 1H), 3.63-3.69 (m, 1H), 3.19-3.24 (m, 1H) |

| Structure | LCMS (ESI, m/z) | ¹H NMR |
|---|---|---|
| 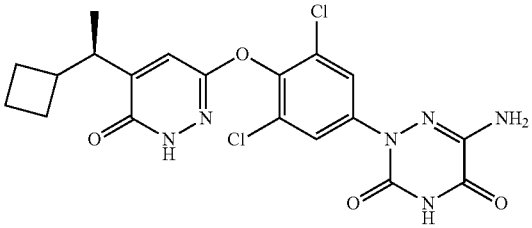<br>167<br>6-amino-2-(3,5-dichloro-4-((5-(1-cyclobutylethyl)-6-oxo-1,6-dihydropyridazin-3-yl)oxy)phenyl)-1,2,4-triazine-3,5(2H,4H)-dione | 465 [M + H]⁺ | ¹H NMR (300 MHz, DMSO-d₆) δ 12.18-12.28 (m, 2H), 7.85 (s, 2H), 7.38 (s, 1H), 6.53 (s, 2H), 3.03-2.90 (m, 1H), 2.55-2.67 (m, 1H), 2.02-2.13 (m, 1H), 1.68-1.93 (m, 4H), 1.53-1.66 (m, 1H), 1.08 (d, J = 6.9 Hz, 3H) |
| 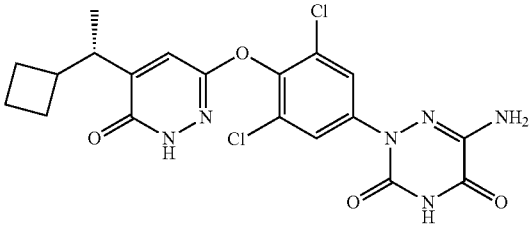<br>168<br>6-amino-2-(3,5-dichloro-4-((5-(1-cyclobutylethyl)-6-oxo-1,6-dihydropyridazin-3-yl)oxy)phenyl)-1,2,4-triazine-3,5(2H,4H)-dione | 465 [M + H]⁺ | ¹H NMR (300 MHz, DMSO-d₆) δ 12.18-12.28 (m, 2H), 7.85 (s, 2H), 7.38 (s, 1H), 6.53 (s, 2H), 3.03-2.90 (m, 1H), 2.55-2.67 (m, 1H), 2.02-2.13 (m, 1H), 1.68-1.93 (m, 4H), 1.53-1.66 (m, 1H), 1.08 (d, J = 6.9 Hz, 3H) |
| 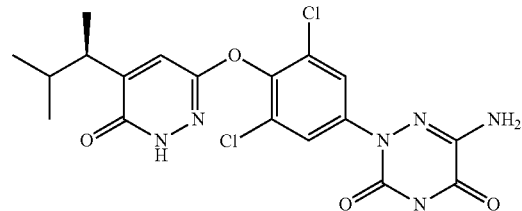<br>169<br>6-amino-2-(3,5-dichloro-4-((5-(3-methylbutan-2-yl)-6-oxo-1,6-dihydropyridazin-3-yl)oxy)phenyl)-1,2,4-triazine-3,5(2H,4H)-dione | 465 [M + H]⁺ | ¹H NMR (300 MHz, DMSO-d₆) δ 12.19 (s, 2H), 7.87 (s, 2H), 7.46 (s, 1H), 6.51 (s, 2H), 2.78-2.87 (m, 1H), 1.92-2.03 (m, 1H), 1.23 (d, J = 7.5 Hz, 3H), 0.86 (d, J = 6 Hz, 6H) |
| 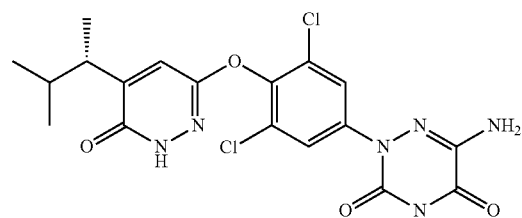<br>170<br>6-amino-2-(3,5-dichloro-4-((5-(3-methylbutan-2-yl)-6-oxo-1,6-dihydropyridazin-3-yl)oxy)phenyl)-1,2,4-triazine-3,5(2H,4H)-dione | 465 [M + H]⁺ | ¹H NMR (300 MHz, DMSO-d₆) δ 12.19 (s, 2H), 7.87 (s, 2H), 7.46 (s, 1H), 6.51 (s, 2H), 2.78-2.87 (m, 1H), 1.92-2.03 (m, 1H), 1.23 (d, J = 7.5 Hz, 3H), 0.86 (d, J = 6 Hz, 6H) |

Example 74: Synthesis of Compound 90

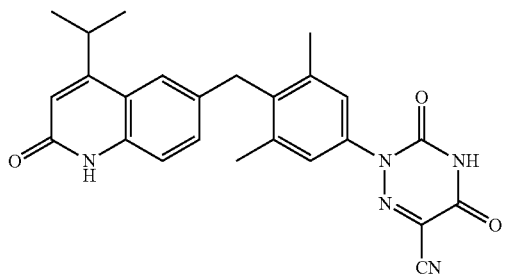

90

Anhydrous THF (5 mL) was added to a mixture of 6-bromo-4-isopropylquinolin-2(1H)-one (was prepared as in Synthesis (6), 934-942; 2011 and International Journal of Chemical Sciences, 7(3), 1784-1792; 2009) (400 mg, 1.50 mmol) and NaH 60% (90 mg) at 0° C., under $N_2$. The reaction mixture was stirred at 25° C. for 1 h. Then, the mixture was cooled to −78° C. and t-BuLi (1.94 mL) was added dropwise and the reaction mixture was stirred at −78° C. for 30 min. Then, a solution of 2,2,2-trifluoro-N-(4-formyl-3,5-dimethylphenyl)acetamide (368 mg) in anhydr. THF (5 mL) was added dropwise to the reaction mixture at −78° C. The reaction was further stirred at this temperature for 1.5 h and finally hydrolyzed with sat. aq. $NH_4Cl$ (8 mL) and poured in DCM (50 mL). The organic phase was washed with water (3×), dried over $MgSO_4$, filtered and evaporated to dryness. The crude mixture was purified by chromatography on silica gel (20 to 85% EA in cyclohexane) to give 2,2,2-trifluoro-N-(4-(hydroxy(4-isopropyl-2-oxo-1,2-dihydroquinolin-6-yl)methyl)-3,5-dimethyl-phenyl)acetamide as a white solid (162 mg, 25%). LCMS (ESI, m/z): 433 $[M+H]^+$.

$Et_3SiH$ (1.71 mL) and TMSOTf (0.039 mL) were added dropwise to a solution of 2,2,2-trifluoro-N-(4-(hydroxy(4-isopropyl-2-oxo-1,2-dihydroquinolin-6-yl)methyl)-3,5-dimethylphenyl)acetamide (255 mg, 0.59 mmol) in anhydr. DCM (29 mL) at 0° C. under $N_2$. The reaction was stirred at 0° C. for 1 h, the ice bath was removed and the reaction was stirred at 25° C. for 6 h. Additional $Et_3SiH$ (0.57 mL) and TMSOTf (0.013 mL) were added and the reaction mixture was stirred at rt. After 16 h, 36 h, and 42 h, additional $Et_3SiH$ (0.57 mL) and TMSOTf (0.013 mL) were added and the mixture was stirred for 64 h. The reaction mixture was evaporated to dryness. $NaHCO_3$ (sat., aq., 50 mL) and EA (3×50 mL) were added. The combined organic layers were washed with brine (150 mL), dried over $MgSO_4$, the solids were removed by filtration and the filtrate was evaporated to dryness to afford 2,2,2-trifluoro-N-(4-((4-isopropyl-2-oxo-1,2-dihydroquinolin-6-yl)methyl)-3,5-dimethylphenyl)acetamide (306 mg) which was used without purification in the next step. $^1H$ NMR (DMSO, 400 MHz) δ 1.19 (d, J=6.8 Hz, 6H), 2.22 (s, 6H), 3.20 (hept., J=6.8 Hz, 1H), 4.06 (s, 2H), 6.31 (s, 1H), 7.11 (d, J=8.4 Hz, 1H), 7.22 (d, J=8.4 Hz, 1H), 7.37 (s, 2H), 7.42 (s, 1H), 11.09 (br s, 1H), 11.52 (br s, 1H) ppm. LCMS: $C_{23}H_{23}F_3N_2O_2$ $[M+H]^+$: 417

NaOH (94 mg) was added to a solution of 2,2,2-trifluoro-N-(4-((4-isopropyl-2-oxo-1,2-dihydroquinolin-6-yl)methyl)-3,5-dimethylphenyl)acetamide (245 mg, 0.59 mmol) in MeOH (25 mL) and water (2.5 mL) under $N_2$. The reaction mixture was stirred at 60° C. for 37 h. Additional NaOH (23 mg) was added and heating continued for 24 h. Then, the reaction mixture was quenched with water (150 mL). The solution was extracted with EA (3×100 mL). The combined organic layers were washed with brine (100 mL), dried over $MgSO_4$, the solids were removed by filtration and the filtrate was evaporated to dryness. The crude product was purified by chromatography on silica gel (MeOH:DCM=0-10%) to give 6-(4-amino-2,6-dimethyl-benzyl)-4-isopropylquinolin-2(1H)-one as a white solid (133 mg, 71%). $^1H$-NMR (DMSO, 400 MHz): 1.19 (d, J=6.8 Hz, 6H), 2.06 (s, 6H), 3.17 (hept., J=6.8 Hz, 1H), 3.89 (s, 2H), 4.76 (s, 2H), 6.29 (s, 2H), 6.30 (s, 1H), 7.13 (d, J=8.4 Hz, 1H), 7.21 (d, J=8.4 Hz, 1H), 7.37 (s, 2H), 11.50 (br s, 1H) ppm. LCMS: $C_{21}H_{24}N_2O$ $[M+H]^+$: 321

2-(4-((4-Isopropyl-2-oxo-1,2-dihydroquinolin-6-yl)methyl)-3,5-dimethylphenyl)-3,5-dioxo-2,3,4,5-tetrahydro-1,2,4-triazine-6-carbonitrile, compound 90, was prepared similarly as described for 2-(4-[[3-isopropyl-1-(4-methyl-benzene-sulfonyl)indol-5-yl]oxy]-3,5-dimethylphenyl)-3,5-dioxo-4H-1,2,4-triazine-6-carbonitrile, starting from 6-(4-amino-2,6-dimethylbenzyl)-4-isopropylquinolin-2(1H)-one.

Example 75: Synthesis of Compound 91 and 91-A

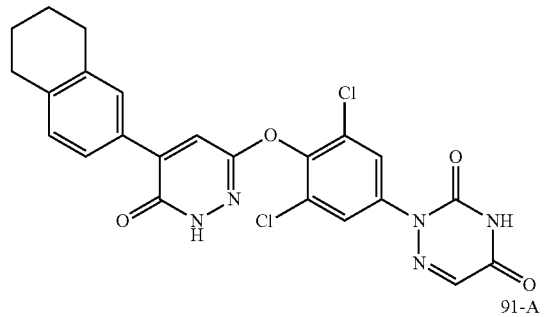

91

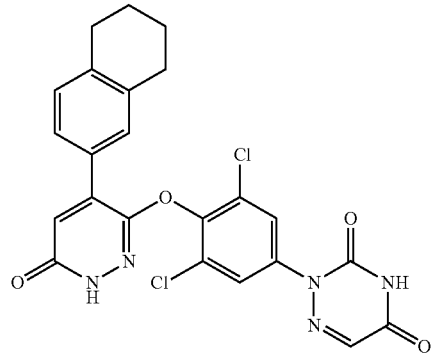

91-A

Water (17 mL) was added to a solution of (5,6,7,8-tetrahydronaphthalen-2-yl)boronic acid (1 eq., 0.95 g, 5.4 mmol), 4-bromo-6-chloropyridazin-3-amine (1.12 g, 5.4 mmol), $Na_2CO_3$ (1.14 g, 10.8 mmol) and $Pd(dppf)Cl_2$ DCM (0.37 g, 0.46 mmol) in 1,4-dioxane (51 mL). The reaction mixture was evacuated and backfilled with $N_2$ (3×) and was stirred at 110° C. for 1 h. After cooling to rt, the reaction mixture was diluted in EA and washed with brine. The aqueous phase was extracted with EA (2×). The combined organic phases were dried with $Na_2SO_4$, filtered and evaporated to dryness. The crude mixture was purified by flash chromatography on silica gel (0% to 10% $CH_3OH$ in DCM) to give 6-chloro-4-(5,6,7,8-tetrahydronaphthalen-2-yl)

pyridazin-3-amine (1.12 g, 80%) as a beige solid. $^1$H-NMR (300 MHz DMSO-d$_6$,) δ 1.75-1.76 (m, 4H), 2.76-2.77 (m, 4H), 6.32 (br s, 2H), 7.20-7.23 (m, 3H), 7.30 (s, 1H) ppm.

t-Butyl nitrite (1.05 mL, 8.78 mmol) was added to a solution of 6-chloro-4-(5,6,7,8-tetrahydronaphthalen-2-yl)pyridazin-3-amine (1.14 g, 4.39 mmol) and CuCl (0.87 g, 8.78 mmol) in anhydrous CH$_3$CN (40 mL) under N$_2$. The reaction mixture was stirred at 60° C. for 24 h. After cooling to rt, the reaction mixture was diluted in EA, washed with sat. aq. NaHCO$_3$ (2×), washed with brine, dried over MgSO$_4$, filtered and evaporated to dryness. The crude mixture was purified by flash chromatography on silica gel (0% to 3% CH$_3$OH in DCM) to give 3,6-dichloro-4-(5,6,7,8-tetrahydronaphthalen-2-yl)pyridazine (0.81 g, 66%) as a yellow solid. $^1$H-NMR (300 MHz DMSO-d$_6$,) δ 1.77 (m, 4H), 2.78 (m, 4H), 7.21-7.35 (m, 3H), 8.06 (s, 1H) ppm.

Preparation of 2-(3,5-dichloro-4-hydroxyphenyl)-1,2,4-triazine-3,5(2H,4H)-dione

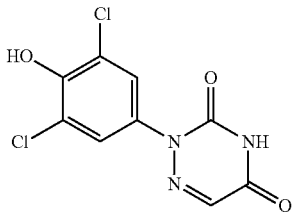 [SMILES: O=c1cnn(-c2cc(Cl)c(O)c(Cl)c2)c(=O)[nH]1]

A cooled solution of NaNO$_2$ (3.88 g, 56.2 mmol) in water (6.5 mL) was added to a solution of 4-amino-2,6-dichlorophenol (10 g, 56.2 mmol) in HCl 37% (23 mL, 281 mmol) and water (63 mL) at 0° C. under N$_2$. The reaction mixture was stirred at 0° C. for 1 h. This reaction mixture was slowly added to a mixture of ethyl N-(2-cyanoacetyl)carbamate (10.5 g, 67.4 mmol), ice (20 g), water (25 mL) and pyridine (225 mL) at 0° C. The resulting reaction mixture was stirred at 0° C. for 1 h. The precipitate was filtered and washed with water. The precipitate was dissolved in DCM and CH$_3$OH and evaporated to dryness to give ethyl (2-cyano-2-(2-(3,5-dichloro-4-hydroxyphenyl)hydrazineylidene)acetyl)carbamate (11.94 g, 62%) as a yellow solid, that was used without further purification in the next step.

NaOAc (4 eq., 11.35 g, 0.14 mol) was added to a solution of ethyl (2-cyano-2-(2-(3,5-dichloro-4-hydroxyphenyl)hydrazineylidene)acetyl)carbamate (11.94 g, 35 mmol) in acetic acid (330 mL) under N$_2$. The reaction mixture was heated to reflux for 3 h and then cooled to 0° C., water (400 mL) was added and the mixture was stirred for 2 h. Then, the precipitate was filtered, washed with water, dissolved in CH$_3$OH and evaporated to dryness to give 2-(3,5-dichloro-4-hydroxyphenyl)-3,5-dioxo-2,3,4,5-tetrahydro-1,2,4-triazine-6-carbonitrile (6.48 g, 63%) as a beige solid that was used without further purification in the next step.

A mixture of 2-(3,5-dichloro-4-hydroxyphenyl)-3,5-dioxo-2,3,4,5-tetrahydro-1,2,4-triazine-6-carbonitrile (1 eq., 6.48 g, 21.7 mmol), HCl 37% (16 mL, 195 mmol) and AcOH (33 mL, 580 mmol) under N$_2$ was stirred at 120° C. for 2.5 h. After cooling to rt, the reaction mixture was diluted in water and the precipitate was filtered and washed with water. The precipitate was dissolved in CH$_3$OH and evaporated to dryness to give 2-(3,5-dichloro-4-hydroxyphenyl)-3,5-dioxo-2,3,4,5-tetrahydro-1,2,4-triazine-6-carboxylic acid (9.2 g) as a yellow solid, that was used without further purification in the next step. $^1$H-NMR (400 MHz DMSO-d$_6$,) δ 7.57 (s, 2H), 10.66 (s, 1H), 12.57 (br s, 1H) ppm.

A solution of 2-(3,5-dichloro-4-hydroxyphenyl)-3,5-dioxo-2,3,4,5-tetrahydro-1,2,4-triazine-6-carboxylic acid (8.88 g, 27.9 mmol) in mercaptoacetic acid (14 mL) under N$_2$ was stirred at 170° C. for 3 h. After cooling to rt, the reaction mixture was diluted in water and the precipitate was filtered and washed with water. The precipitate was dissolved in CH$_3$OH and evaporated to dryness to give 2-(3,5-dichloro-4-hydroxyphenyl)-1,2,4-triazine-3,5(2H,4H)-dione (9.4 g) as a yellow solid, that was used without further purification in the next step. $^1$H-NMR (DMSO, 300 MHz): 4.37 (s, 1H), 7.54 (s, 2H), 7.61 (s, 1H) ppm.

A mixture of 3,6-dichloro-4-(5,6,7,8-tetrahydronaphthalen-2-yl)pyridazine (780 mg, 2.79 mmol), 2-(3,5-dichloro-4-hydroxyphenyl)-1,2,4-triazine-3,5(2H,4H)-dione (766 mg, 2.79 mmol), K$_2$CO$_3$ (1.16 mg, 8.38 mmol) and CuI (266 mg, 1.4 mmol) in anhydrous DMSO (13 mL) under N$_2$ was stirred at 120° C. for 16 h. After cooling to rt, the reaction mixture was diluted in EtOAc and washed with sat. aq. NH$_4$Cl (2×). The aqueous phase was extracted with EtOAc (2×) and the combined organic layers were dried over Na$_2$SO$_4$, filtered and evaporated to dryness. The crude mixture was purified by flash chromatography on silica gel (0% to 3% MeOH in DCM) to give a mixture of 2-(3,5-dichloro-4-((6-chloro-5-(5,6,7,8-tetrahydronaphthalen-2-yl)pyridazin-3-yl)oxy)phenyl)-1,2,4-triazine-3,5(2H,4H)-dione and 2-(3,5-dichloro-4-((6-chloro-4-(5,6,7,8-tetrahydronaphthalen-2-yl)pyridazin-3-yl)oxy)phenyl)-1,2,4-triazine-3,5(2H,4H)-dione (65:35, 593 mg, 41%) as a beige solid. LCMS: C$_{23}$H$_{16}$C$_{13}$N$_5$O$_3$ [M+H]$^+$: 516/518.

The regioisomeric compound mixture (560 mg, 1.08 mmol) and NaOAc (533 mg, 6.50 mmol) in AcOH (11 mL) under N$_2$ was stirred at 118° C. for 4 h. After cooling to rt, the reaction mixture was diluted in water, filtered, washed with water (3×) and n-pentane. The precipitate was dissolved in EtOAc, dried with Na$_2$SO$_4$, filtered and evaporated to dryness. The crude mixture was purified by flash chromatography on silica gel (0% to 5% MeOH in DCM) to give two fractions. The first fraction was purified by trituration with diethylether (3×) to give 2-(3,5-dichloro-4-((6-oxo-5-(5,6,7,8-tetrahydronaphthalen-2-yl)-1,6-dihydropyridazin-3-yl)oxy)phenyl)-1,2,4-triazine-3,5(2H,4H)-dione (286 mg, 53%) as a beige solid. $^1$H-NMR (400 MHz DMSO-d$_6$,) δ 1.76 (br s, 4H), 2.77 (br s, 4H), 7.15-7.17 (m, 1H), 7.68-7.71 (m, 3H), 7.82 (s, 3H), 12.41 (s, 1H), 12.49 (br s, 1H) ppm. LCMS: C$_{23}$H$_{16}$C$_{13}$N$_5$O$_3$ [M+H]$^+$: 516/518.

The second fraction was purified by trituration with Et$_2$O (3×) to give 2-(3,5-dichloro-4-((6-oxo-4-(5,6,7,8-tetrahydronaphthalen-2-yl)-1,6-dihydropyridazin-3-yl)oxy)phenyl)-1,2,4-triazine-3,5(2H,4H)-dione (64 mg, 12%) as a beige solid. $^1$H-NMR (400 MHz DMSO-d$_6$,) δ 1.77 (br s, 4H), 2.78 (br s, 4H), 7.06 (d, J=2.4 Hz, 1H), 7.22 (d, J=7.9 Hz, 1H), 7.48-7.52 (m, 2H), 7.70 (s, 1H), 7.81 (s, 2H), 12.34 (d, J=2.5 Hz, 1H), 12.49 (br s, 1H) ppm. LCMS: C$_{23}$H$_{16}$C$_{13}$N$_5$O$_3$: [M+H]$^+$: 516/518.

Example 76: Synthesis of Compounds 92 and 92-A

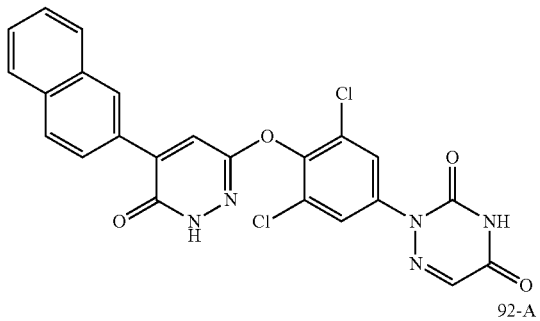

92

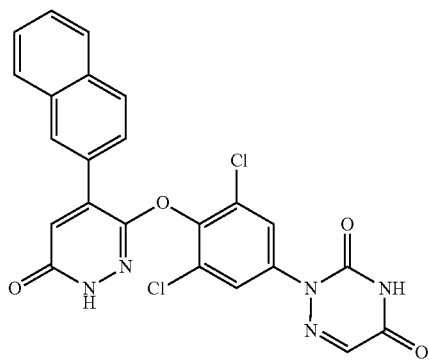

92-A

The titled compounds were prepared using a method analogous to that described for 2-(3,5-dichloro-4-((6-oxo-5-(5,6,7,8-tetrahydronaphthalen-2-yl)-1,6-dihydropyridazin-3-yl)oxy)phenyl)-1,2,4-triazine-3,5(2H,4H)-dione and 2-(3,5-dichloro-4-((6-oxo-4-(5,6,7,8-tetrahydronaphthalen-2-yl)-1,6-dihydropyridazin-3-yl)oxy)phenyl)-1,2,4-triazine-3,5(2H,4H)-dione with the exception that 2-naphthylboronic acid was employed in the aryl coupling reaction instead of (5,6,7,8-tetrahydronaphthalen-2-yl)boronic acid.

92: $^1$H-NMR (400 MHz DMSO-$d_6$,) δ 7.56-7.64 (m, 2H), 7.72 (s, 1H), 7.84 (s, 2H), 7.96-8.07 (m, 5H), 8.68 (s, 1H), 12.51 (s, 1H), 12.55 (s, 1H) ppm. LCMS: $C_{23}H_{13}Cl_2N_5O_4$ [M+H]$^+$: 494/496.

92-A: $^1$H-NMR (400 MHz DMSO-$d_6$,) δ 7.27 (d, J=2.1 Hz, 1H), 7.59-7.67 (m, 2H), 7.70 (s, 1H), 7.82 (s, 2H), 7.92 (dd, J=8.5 Hz, 1.9 Hz, 1H), 7.99-8.06 (m, 2H), 8.09 (d, J=8.7 Hz, 1H), 8.38 (d, J=1.2 Hz, 1H), 12.45 (d, J=1.9 Hz, 1H), 12.49 (s, 1H) ppm. LCMS: $C_{23}H_{13}Cl_2N_5O_4$ [M+H]$^+$: 494/496.

The following compounds were prepared similarly as described for 6-amino-2-(3,5-dichloro-4-[[5-(naphthalen-2-yl)-6-oxo-1H-pyridazin-3-yl]oxy]phenyl)-4H-1,2,4-triazine-3,5-dione (compound 67).

| Structure | LC MS (ESI, m/z) | NMR |
|---|---|---|
| 108 6-amino-2-(3,5-dichloro-4-((5-(cinnolin-6-yl)-6-oxo-1,6-dihydropyridazin-3-yl)oxy)phenyl)-1,2,4-triazine-3,5(2H,4H)-dione | [M + H]$^+$ = 511 | $^1$H NMR (400 MHz, DMSO-$d_6$) δ 12.56 (Br,2H), 9.39(d, J = 3.0 Hz, 1H), 8.71(s, 1H), 8.49-8.46(m, 1H), 8.42-8.38(m, 1H), 8.32-8.21(m, 1H), 8.07 (s,1H), 7.92(s, 2H), 5.79 (Br, 2H) |

| Structure | LC MS (ESI, m/z) | NMR |
|---|---|---|

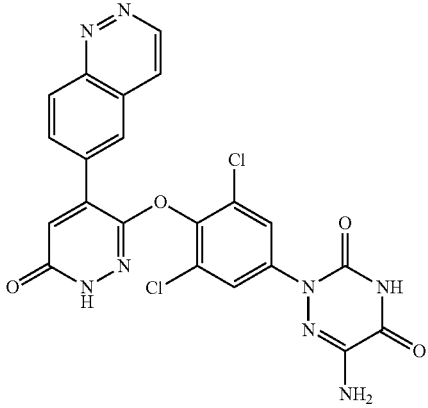

109

6-amino-2-(3,5-dichloro-4-((4-(cinnolin-6-yl)-6-oxo-1,6-dihydropyridazin-3-yl)oxy)phenyl)-1,2,4-triazine-3,5(2H,4H)-dione

[M + H]$^+$ = 511  $^1$H NMR (400 MHz, DMSO-d$_6$) δ 12.54 (Br,1H), 12.30(s, 1H), 9.49(d, J = 3.0 Hz, 1H), 8.64 (d, J = 4.4 Hz, 1H), 8.52(s,1H), 8.35-8.31(m, 2H), 7.91(s, 2H), 7.37(s, 1H), 6.33 (Br,2H)

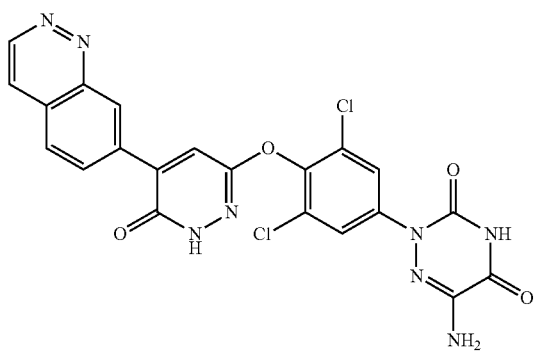

110

6-amino-2-(3,5-dichloro-4-((5-(cinnolin-7-yl)-6-oxo-1,6-dihydropyridazin-3-yl)oxy)phenyl)-1,2,4-triazine-3,5(2H,4H)-dione

[M + H]$^+$ = 511  $^1$H NMR (400 MHz, DMSO-d$_6$) δ 12.41 (Br,1H), 9.45(d, J = 3.0 Hz, 1H), 9.21(s, 1H), 8.39-8.37(m, 1H), 8.37-8.36(m, 1H), 8.28 (s,1H), 8.23-8.17(m, 1H), 7.96(s,2H), 6.10 (Br,2H)

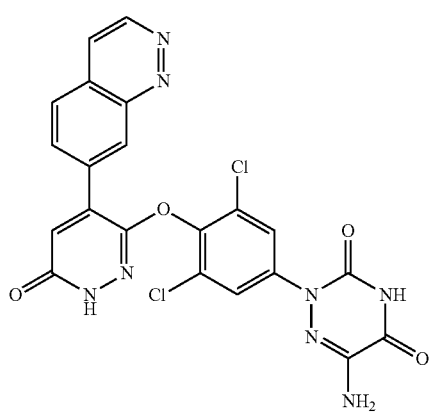

111

6-amino-2-(3,5-dichloro-4-((4-(cinnolin-7-yl)-6-oxo-1,6-dihydropyridazin-3-yl)oxy)phenyl)-1,2,4-triazine-3,5(2H,4H)-dione

[M + H]$^+$ = 511  $^1$H NMR (400 MHz, DMSO-d$_6$) δ 12.48 (Br,2H), 9.48(d, J = 3.0 Hz, 1H), 8.91(s, 1H), 8.34-8.32(m, 1H), 8.29-8.25(m, 2H), 7.94 (s,2H), 7.43(s, 1H), 6.18 (Br,2H)

| Structure | LC MS (ESI, m/z) | NMR |
|---|---|---|
| 112<br><br>6-amino-2-(3,5-dichloro-4-((5-(3,4-dimethylphenyl)-6-oxo-1,6-dihydropyridazin-3-yl)oxy)phenyl)-1,2,4-triazine-3,5(2H,4H)-dione | [M + H]⁺ = 487 | ¹H NMR (400 MHz, DMSO-d₆) δ 12.40 (s, 1H), 12.28 (s, 1H), 7.72-7.87 (m, 5H), 7.77 (d, J = 7.8 Hz, 1H), 6.53 (s, 2H), 2.29 (s, 6H) |
| 113<br><br>6-amino-2-(3,5-dichloro-4-((4-(3,4-dimethylphenyl)-6-oxo-1,6-dihydropyridazin-3-yl)oxy)phenyl)-1,2,4-triazine-3,5(2H,4H)-dione | [M + H]⁺ = 487 | ¹H NMR (400 MHz, DMSO-d₆) δ 12.38 (s, 1H), 12.27 (s, 1H), 7.86 (s, 2H), 7.51-7.57 (m, 2H), 7.31 (d, J = 7.8 Hz, 1H), 7.06 (s, 1H), 6.51 (s, 2H), 2.29 (s, 6H) |
| 114<br><br>6-amino-2-(3,5-dichloro-4-((5-(chroman-6-yl)-6-oxo-1,6-dihydropyridazin-3-yl)oxy)phenyl)-1,2,4-triazine-3,5(2H,4H)-dione | [M + H]⁺ = 515 | ¹H NMR (400 MHz, DMSO-d₆) δ 12.37 C 12.29 (m, 2H), 7.86 C 7.78 (m, 5H), 6.83 C 6.81 (m, 1H), 6.55 (s, 2H), 4.21 C 4.19 (m, 2H), 2.82 C 2.78 (m, 2H), 1.98 C 1.95 (m, 6H) |

-continued

| Structure | LC MS (ESI, m/z) | NMR |
|---|---|---|
| 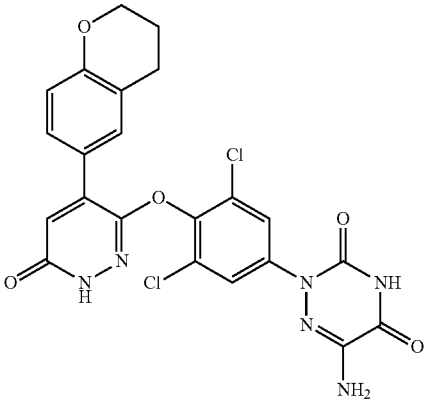 115<br><br>6-amino-2-(3,5-dichloro-4-((4-(chroman-6-yl)-6-oxo-1,6-dihydropyridazin-3-yl)oxy)phenyl)-1,2,4-triazine-3,5(2H,4H)-dione | [M + H]$^+$ = 515 | $^1$H NMR (400 MHz, DMSO-$d_6$) δ 12.92 (s, 2H), 7.86 (s, 2H), 7.56 C 7.54 (m, 2H), 7.03 (s, 1H), 6.90C 6.88 (m, 1H), 6.54 (s, 2H), 4.21 C 4.19 (m, 2H), 2.83 C 2.80 (m, 2H), 1.97C 1.94 (m, 2H) |
| 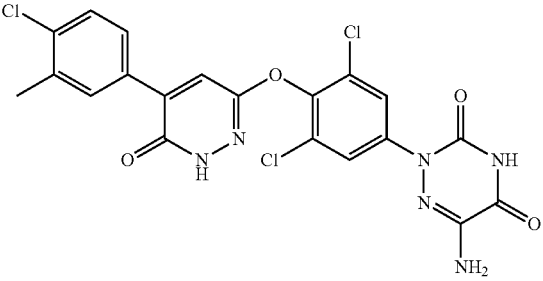 116<br><br>6-amino-2-(3,5-dichloro-4-((5-(4-chloro-3-methylphenyl)-6-oxo-1,6-dihydropyridazin-3-yl)oxy)phenyl)-1,2,4-triazine-3,5(2H,4H)-dione | [M + H]$^+$ = 507 | $^1$H NMR (400 MHz, DMSO-$d_6$) δ 12.51 (br, 1H), 12.27 (br, 1H), 7.87-8.06 (m, 5H), 7.53 (d, J = 8.1 Hz, 1H), 6.53 (s, 2H), 2.40 (s, 3H). |
| 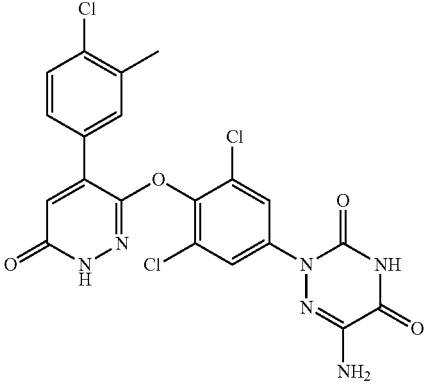 117<br><br>6-amino-2-(3,5-dichloro-4-((4-(4-chloro-3-methylphenyl)-6-oxo-1,6-dihydropyridazin-3-yl)oxy)phenyl)-1,2,4-triazine-3,5(2H,4H)-dione | [M + H]$^+$ = 507 | $^1$HNMR (400 MHz, DMSO-$d_6$) δ 12.28-12.41 (m, 2H), 7.87 (s, 2H), 7.78 (s, 1H), 7.59-7.67 (m, 2H), 7.16 (s, 1H), 6.54 (s, 2H), 2.41 (s, 3H) |

| Structure | LC MS (ESI, m/z) | NMR |
|---|---|---|
| 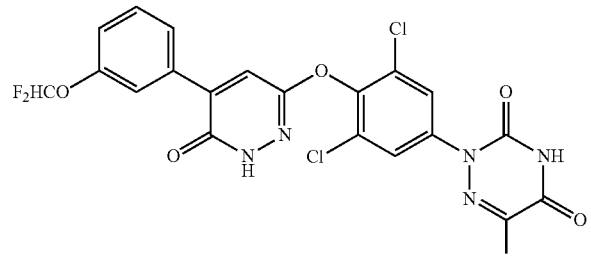 118<br>6-amino-2-(3,5-dichloro-4-((5-(3-difluoromethoxyphenyl)-6-oxo-1,6-dihydropyridazin-3-yl)oxy)phenyl)-1,2,4-triazine-3,5(2H,4H)-dione | [M + H]⁺ = 525 | $^1$HNMR (400 MHz, DMSO-$d_6$) δ 12.29-12.57 (m, 2H), 7.99 (s, 1H), 7.82-7.90 (m, 4H), 7.53-7.60 (m, 1H), 7.23-7.40 (m, 2H), 6.55 (s, 2H) |
| 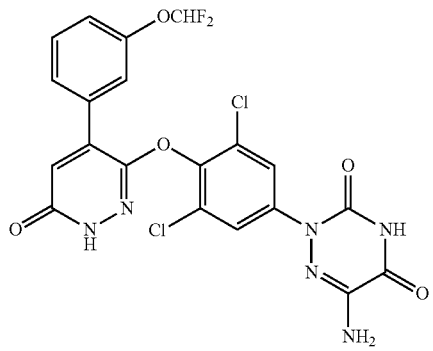 119<br>6-amino-2-(3,5-dichloro-4-((4-(3-(difluoromethoxy)phenyl)-6-oxo-1,6-dihydropyridazin-3-yl)oxy)phenyl)-1,2,4-triazine-3,5(2H,4H)-dione | [M + H]⁺ = 525 | $^1$H NMR (400 MHz, DMSO-$d_6$) δ 12.28-12.46 (m, 2H), 7.87 (s, 2H), 7.59 C 7.72 (m, 3H), 7.36-7.39 (m, 2H), 7.21-7.23 (m, 1H), 6.55 (s, 2H) |
| 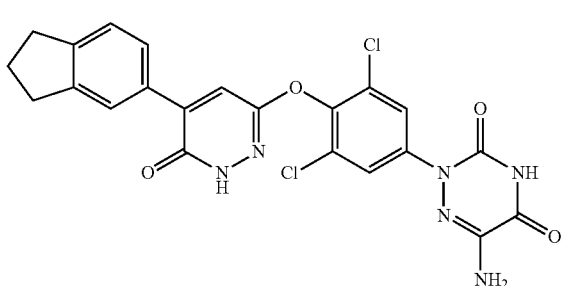 120<br>6-amino-2-(3,5-dichloro-4-((5-(2,3-dihydro-1H-inden-5-yl)-6-oxo-1,6-dihydropyridazin-3-yl)oxy)phenyl)-1,2,4-triazine-3,5(2H,4H)-dione | [M + H]⁺ = 525 | $^1$H NMR (400 MHz, DMSO-$d_6$) δ 12.27-12.40 (m, 2H), 7.72-7.87 (m, 5H), 7.33 (d, J = 8.1 Hz, 1H), 6.53 (s, 2H), 2.50 (t, J = 1.8 Hz, 4H), 2.01-2.11 (m, 2H) |

| Structure | LC MS (ESI, m/z) | NMR |
|---|---|---|
| 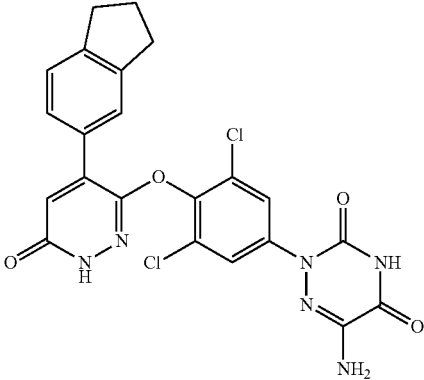<br>121<br>6-amino-2-(3,5-dichloro-4-((4-(2,3-dihydro-1H-inden-5-yl)-6-oxo-1,6-dihydropyridazin-3-yl)oxy)phenyl)-1,2,4-triazine-3,5(2H,4H)-dione | [M + H]⁺ = 525 | ¹H NMR (400 MHz, DMSO-d$_6$) δ 12.26-12.33 (m, 2H), 7.86 (s, 2H), 7.63 (s, 1H), 7.55 (d, J = 7.8 Hz, 1H), 7.39 (d, J = 7.8 Hz, 1H), 7.05 (s, 1H), 6.53 (s, 2H), 2.91-2.96 (m, 4H), 2.01-2.11 (m, 2H) |
| 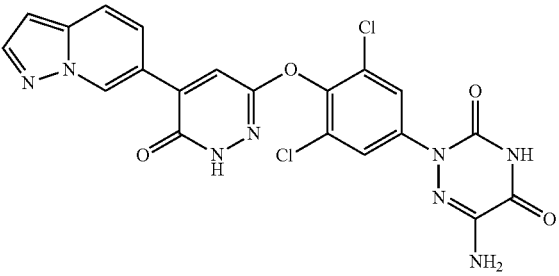<br>122<br>6-amino-2-(3,5-dichloro-4-((6-oxo-5-(pyrazolo[1,5-a]pyridin-6-yl)-1,6-dihydropyridazin-3-yl)oxy)phenyl)-1,2,4-triazine-3,5(2H,4H)-dione | [M + H]⁺ = 499 | ¹H NMR (400 MHz, DMSO-d$_6$) δ 12.64 (s, 1H), 12.29 (s, 1H), 9.84 (s, 1H), 8.09-8.18 (m, 2H), 7.76-7.89 (m, 4H), 6.66-6.71 (m, 1H), 6.53 (s, 2H) |
| 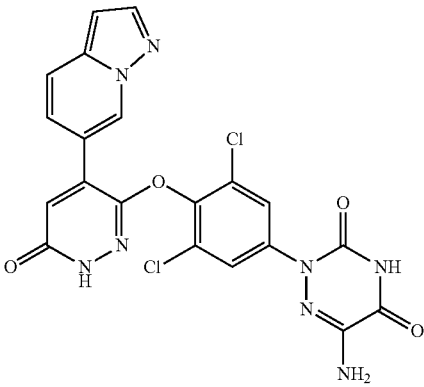<br>123<br>6-amino-2-(3,5-dichloro-4-((6-oxo-4-(pyrazolo[1,5-a]pyridin-6-yl)-1,6-dihydropyridazin-3-yl)oxy)phenyl)-1,2,4-triazine-3,5(2H,4H)-dione | [M + H]⁺ = 499 | ¹H NMR (400 MHz, DMSO-d$_6$) δ 12.44 (s, 1H), 12.28 (s, 1H), 9.17 (s, 1H), 8.11-8.15 (m, 1H), 7.82-7.89 (m, 3H), 7.57-7.62 (m, 1H), 7.35 (s, 1H), 6.70-6.74 (m, 1H), 6.54 (s, 2H) |

| Structure | LC MS (ESI, m/z) | NMR |
|---|---|---|
| 124
6-amino-2-(3,5-dichloro-4-((6-oxo-5-(pyrazolo[1,5-a]pyridin-5-yl)-1,6-dihydropyridazin-3-yl)oxy)phenyl)-1,2,4-triazine-3,5(2H,4H)-dione | [M + H]⁺ = 499 | ¹H NMR (300 MHz, DMSO-$d_6$) δ 12.60 (s, 1H), 12.28 (s, 1H), 8.70-8.77 (m, 2H), 8.08-8.11 (m, 2H), 7.88 (s, 2H), 7.46-7.49 (m, 1H), 6.82 (d, J = 1.8 Hz, 1H), 6.54 (br, 2H) |
| 125
6-amino-2-(3,5-dichloro-4-((6-oxo-4-(pyrazolo[1,5-a]pyridin-5-yl)-1,6-dihydropyridazin-3-yl)oxy)phenyl)-1,2,4-triazine-3,5(2H,4H)-dione | [M + H]⁺ = 499 | ¹H NMR (300 MHz, DMSO-$d_6$) δ 0.85 (d, J = 7.2 Hz, 1H), 8.11-8.18 (m, 2H), 7.98 (s, 2H), 8.27-7.28 (m, 2H), 6.82 (d, J = 1.5 Hz, 1H), 5.87 (br, 2H) |
| 126
6-amino-2-(3,5-dichloro-4-((5-(imidazo[1,5-a]pyridin-7-yl)-6-oxo-1,6-dihydropyridazin-3-yl)oxy)phenyl)-1,2,4-triazine-3,5(2H,4H)-dione | [M + H]⁺ = 499 | ¹H NMR (300 MHz, DMSO-$d_6$) δ 12.52 (s, 1H), 8.80 C 8.81 (m, 1H), 8.39 C 8.47 (m, 2H), 8.01 (s, 1H), 7.87 (s, 2H), 7.62 (s, 1H), 7.25 C 7.29 (m, 1H), 6.47 (s, 2H). |

| Structure | LC MS (ESI, m/z) | NMR |
|---|---|---|
| 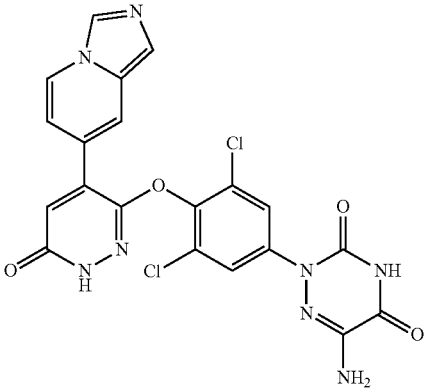 127  6-amino-2-(3,5-dichloro-4-((4-(imidazo[1,5-a]pyridin-7-yl)-6-oxo-1,6-dihydropyridazin-3-yl)oxy)phenyl)-1,2,4-triazine-3,5(2H,4H)-dione | [M + H]⁺ = 499 | $^1$H NMR (300 MHz, DMSO-d$_6$) δ 12.25 C 12.38 (m, 2H), 8.42 C 8.53 (m, 2H), 8.11 (s, 1H), 7.88 (s, 2H), 7.59 (s, 1H), 7.23 (s, 1H), 7.03 C 7.07 (m, 1H), 6.49 (s, 2H) |
| 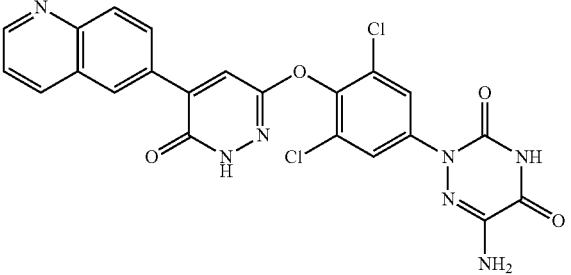 128  6-amino-2-(3,5-dichloro-4-((6-oxo-5-(quinolin-6-yl)-1,6-dihydropyridazin-3-yl)oxy)phenyl)-1,2,4-triazine-3,5(2H,4H)-dione | [M + H]⁺ = 510 | $^1$H NMR (300 MHz, DMSO-d$_6$) δ 12.52 (br, 1H), 8.97-8.94 (m, 1H), 8.72-8.71 (m, 1H), 8.51-8.47 (m, 1H), 8.28 (d, J = 1 Hz, 1H), 8.05-8.02 (m, 4H), 7.62-7.60 (m, 1H), 5.65 (s, 2H) |
| 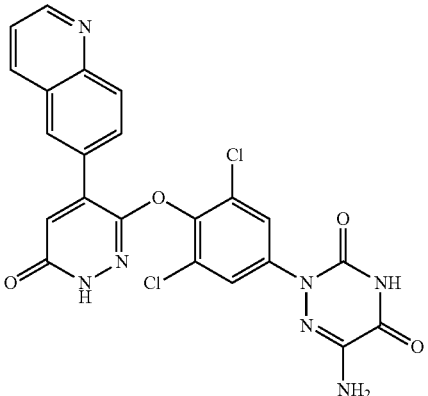 129  6-amino-2-(3,5-dichloro-4-((6-oxo-4-(quinolin-6-yl)-1,6-dihydropyridazin-3-yl)oxy)phenyl)-1,2,4-triazine-3,5(2H,4H)-dione | [M + H]⁺ = 510 | $^1$H NMR (400 MHz, DMSO-d$_6$) δ 9.01 C 8.99 (m, 1H), 8.49 (d, J = 4.0 Hz, 1H), 8.43 (s, 1H), 8.17 (s, 2H), 8.01 (s, 2H), 7.65-7.62 (m, 1H), 7.22 (s, 1H), 5.56 (s, 2H). |

| Structure | LC MS (ESI, m/z) | NMR |
|---|---|---|
| 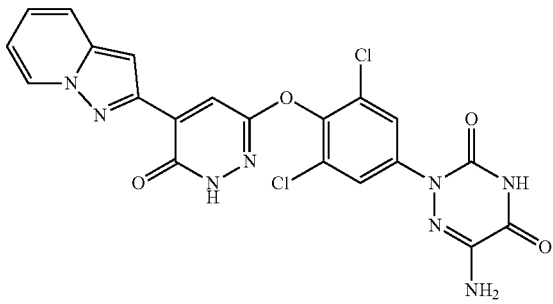 130  6-amino-2-(3,5-dichloro-4-((6-oxo-5-(pyrazolo[1,5-a]pyridin-2-yl)-1,6-dihydropyridazin-3-yl)oxy)phenyl)-1,2,4-triazine-3,5(2H,4H)-dione | [M + H]⁺ = 499 | ¹H NMR (400 MHz, DMSO-$d_6$) δ 12.78-11.75 (m, 2H), 8.79 C 8.72 (m, 1H), 8.07 (s, 1H), 7.92 C 7.74 (m, 3H), 7.62 (d, J = 0.9 Hz, 1H), 7.27-7.15(m, 1H), 7.03-6.95 (m, 1H), 6.49 (s, 2H) |
| 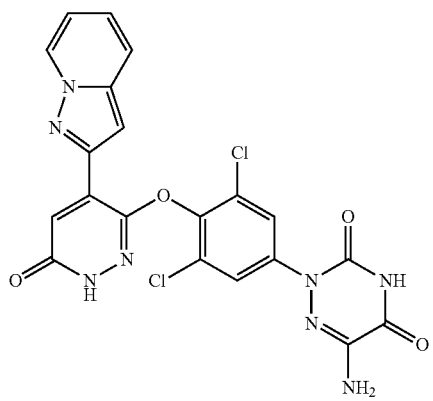 131  6-amino-2-(3,5-dichloro-4-((6-oxo-4-(pyrazolo[1,5-a]pyridin-2-yl)-1,6-dihydropyridazin-3-yl)oxy)phenyl)-1,2,4-triazine-3,5(2H,4H)-dione | [M + H]⁺ = 499 | ¹H NMR (400 MHz, DMSO-$d_6$) δ 8.84-8.82 (m, 1H), 7.89 (s, 2H), 7.83 (m, 1H), 7.52 (s, 1H), 7.35 (d, J = 0.9 Hz, 1H), 7.34-7.32 (m, 1H), 7.08-7.03 (m, 1H), 6.49 (s, 2H). |
| 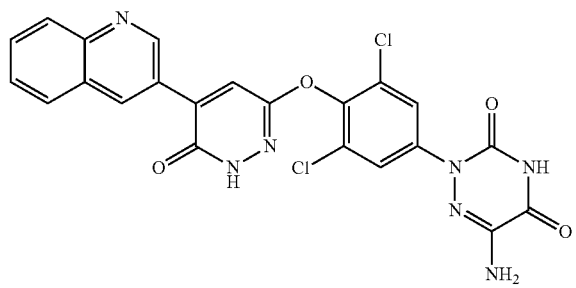 132  6-amino-2-(3,5-dichloro-4-((6-oxo-5-(quinolin-3-yl)-1,6-dihydropyridazin-3-yl)oxy)phenyl)-1,2,4-triazine-3,5(2H,4H)-dione | [M + H]⁺ = 510 | ¹H NMR (400 MHz, DMSO-$d_6$) δ 9.38 (s, 1H), 9.04 (d, J = 2.0 Hz, 1h), 8.19 (s, 1H), 8.08-8.11 (m, 2H), 7.93 (s, 2H), 7.84-7.88 (m, 1H), 7.68-7.71 (m, 1H), 6.32 (s, 2H). |

| Structure | LC MS (ESI, m/z) | NMR |
|---|---|---|
| 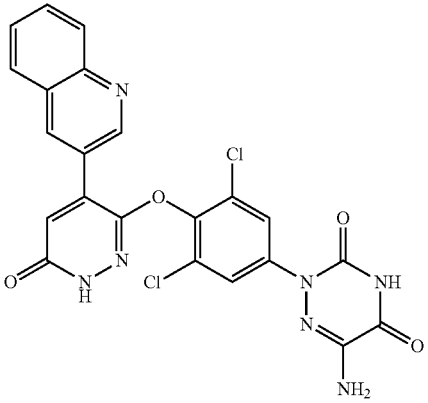 133<br>6-amino-2-(3,5-dichloro-4-((6-oxo-4-(quinolin-3-yl)-1,6-dihydropyridazin-3-yl)oxy)phenyl)-1,2,4-triazine-3,5(2H,4H)-dione | [M + H]⁺ = 510 | ¹H NMR (400 MHz, DMSO-d₆) δ 12.25 (br, 2H), 9.28 (d, J = 2.0 Hz, 1H), 8.81 (d, J = 2.0 Hz, 1H), 8.12 (d, J = 8.8 Hz, 2H), 7.89-7.92 (m, 3H), 7.71-7.75 (m, 1H), 7.43 (s, 1H), 6.51 (s, 2H). |
| 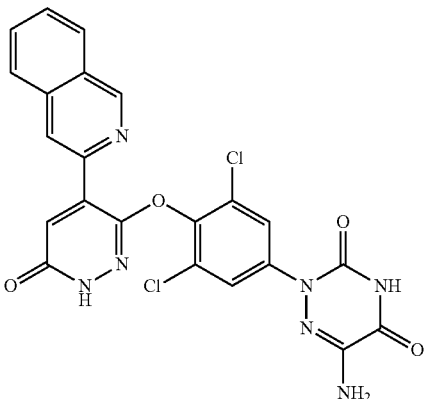 134<br>6-amino-2-(3,5-dichloro-4-((4-(isoquinolin-3-yl)-6-oxo-1,6-dihydropyridazin-3-yl)oxy)phenyl)-1,2,4-triazine-3,5(2H,4H)-dione | [M + H]⁺ = 510 | ¹H NMR (400 MHz, DMSO-d₆) δ 9.53 (s, 1H), 8.66 (s, 1H), 8.26 (d, J = 8.1 Hz, 1H), 8.15 (d, J = 8.4 Hz, 1H), 7.80-7.93 (m, 4H), 7.62 (s, 1H), 6.33 (br, 2H). |

The following compounds were prepared similarly as described for compounds 91 and 91-A.

| Structure | LCMS (ESI, m/z) | ¹HNMR |
|---|---|---|
| 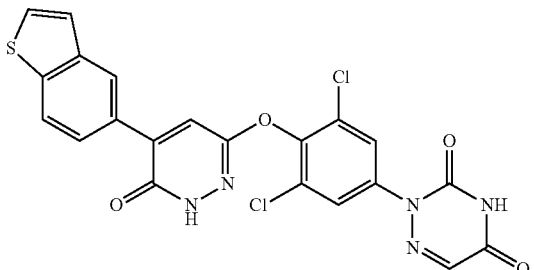 135 | [M + H]⁺ = 500 | ¹H NMR (400 MHz, DMSO-d₆) δ 7.57 (d, 1H, J = 5.4 Hz), 7.71 (s, 1H), 7.83-7.86 (m, 3H), 7.93 (dd, 1H, J = 8.6 Hz, 1.8 Hz), 7.98 (s, 1H), 8.12 (d, 1H, J = 8.5 Hz), 8.59 (d, 1H, J = 1.8 Hz), 12.50-12.52 (m, 2H) |

| Structure | LCMS (ESI, m/z) | ¹HNMR |
|---|---|---|
| 2-(4-((5-(benzo[b]thiophen-5-yl)-6-oxo-1,6-dihydropyridazin-3-yl)oxy)-3,5-dichlorophenyl)-1,2,4-triazine-3,5(2H,4H)-dione 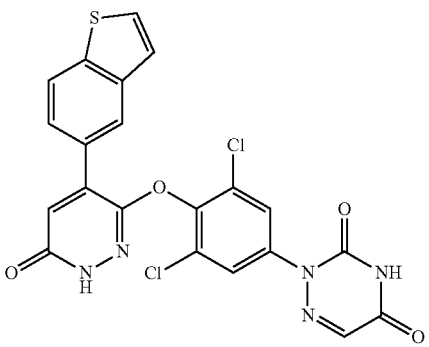 136 | [M + H]⁺ = 500 | ¹H NMR (400 MHz, DMSO-d₆) δ 7.21 (d, 1H, J = 2.1 Hz), 7.58 (d, 1H, J = 5.5 Hz), 7.70 (br.s, 1 H), 7.77 (dd, 1H, J = 8.6 Hz, 1.9 Hz), 7.82 (s, 2H), 7.9 (d, 1H, J = 5.5 Hz), 8.2 (d, 1H, J = 8.7 Hz), 8.31 (d, 1H, J = 1.6 Hz), 12.41 (br.s, 1H), 12.49 (br.s, 1H) |
| 2-(4-((4-(benzo[b]thiophen-5-yl)-6-oxo-1,6-dihydropyridazin-3-yl)oxy)-3,5-dichlorophenyl)-1,2,4-triazine-3,5(2H,4H)-dione 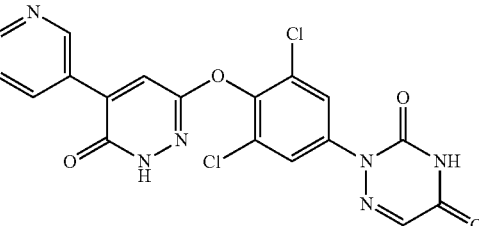 137 | [M + H]⁺ = 459 | ¹H NMR (400 MHz, DMSO-d₆) δ 2.37 (s, 3H), 7.59 (br s, 1H), 7.82 (s, 2H), 8.02 (s, 1H), 8.17-8.19 (m, 1H), 8.51 (d, J = 1.7 Hz, 1H), 8.91 (d, J = 1.9 Hz, 1H), 12.50 (br s, 1H), 12.57 (s, 1H) |
| 2-(3,5-dichloro-4-((5-(5-methylpyridin-3-yl)-6-oxo-1,6-dihydropyridazin-3-yl)oxy)phenyl)-1,2,4-triazine-3,5(2H,4H)-dione 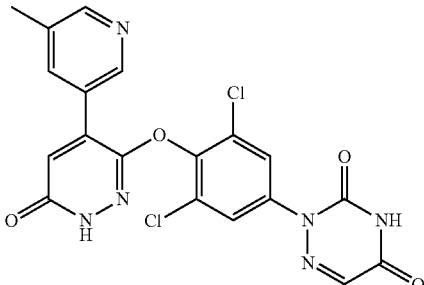 138 | [M + H]⁺ = 459 | ¹H NMR (400 MHz, DMSO-d₆) δ 2.40 (s, 3H), 7.27 (d, J = 2.0 Hz, 1H), 7.66 (s, 1H), 7.82 (s, 2H), 8.00-8.04 (m, 1H), 8.57 (d, J = 1.5 Hz, 1H), 8.79 (d, J = 1.8 Hz, 1H), 12.46 (d, J = 1.6 Hz, 1H), 12.49 (s, 1H) |
| 2-(3,5-dichloro-4-((4-(5-methylpyridin-3-yl)-6-oxo-1,6-dihydropyridazin-3-yl)oxy)phenyl)-1,2,4-triazine-3,5(2H,4H)-dione | | |

| Structure | LCMS (ESI, m/z) | ¹HNMR |
|---|---|---|
| 139<br>2-(3,5-dichloro-4-((6-oxo-5-(m-tolyl)-1,6-dihydropyridazin-3-yl)oxy)phenyl)-1,2,4-triazine-3,5(2H,4H)-dione | [M + H]⁺ = 458 | ¹H NMR (400 MHz, DMSO-$d_6$) δ 2.38 (s, 3H), 7.31 (d, 1H, J = 7.6 Hz), 7.38 (t, 1H, J = 7.6 Hz), 7.71 (s, 1 H), 7.75-7.78 (m, 2H), 7.82 (s, 2H), 7.86 (s, 1H), 12.47 (s, 1H), 12.50 (br.s, 1H) |
| 140<br>2-(3,5-dichloro-4-((6-oxo-4-(m-tolyl)-1,6-dihydropyridazin-3-yl)oxy)phenyl)-1,2,4-triazine-3,5(2H,4H)-dione | [M + H]⁺ = 458 | ¹H NMR (400 MHz, DMSO-$d_6$) δ 2.38 (s, 3H), 7.1 (d, 1H, J = 2.2 Hz), 7.36 (d, 1H, J = 7.6 Hz), 7.44 (t, 1H, J = 7.7 Hz), 7.59-7.61 (m, 2H), 7.70 (s, 1H), 7.81 (s, 2H), 12.38 (br.s, 1H), 12.49 (br.s, 1H) |
| 141<br>2-(3,5-dichloro-4-((5-(2-methylpyridin-4-yl)-6-oxo-1,6-dihydropyridazin-3-yl)oxy)phenyl)-1,2,4-triazine-3,5(2H,4H)-dione | [M + H]⁺ = 459 | ¹H NMR (400 MHz, DMSO-$d_6$) δ 2.55 (s, 3H), 7.72 (d, 1H, J = 1.8 Hz), 7.75 (dd, 1H, J = 5.0 Hz, J = 1.8 Hz), 7.82 (br.s, 1H), 7.83 (s, 2H), 8.07 (s, 1H), 8.57 (d, 1H, J = 5.3 Hz), 12.50 (br.s, 1H), 12.63 (s, 1H). |
| 142<br>2-(3,5-dichloro-4-((4-(2-methylpyridin-4-yl)-6-oxo-1,6-dihydropyridazin-3-yl)oxy)phenyl)-1,2,4-triazine-3,5(2H,4H)-dione | [M + H]⁺ = 459 | ¹H NMR (400 MHz, DMSO-$d_6$) δ 2.62 (s, 3H), 7.32 (s, 1H), 7.71 (d, 1H, J = 1.8 Hz), 7.73 (dd, 1 H, J = 5.2 Hz, J = 1.8 Hz), 7.79 (br.s, 1H), 7.82 (s, 2H), 8.72 (d, 1H, J = 5.4 Hz), 12.49 (s, 1H), 12.56 (br.s, 1H). |

Example 77: Synthesis of Compound 143

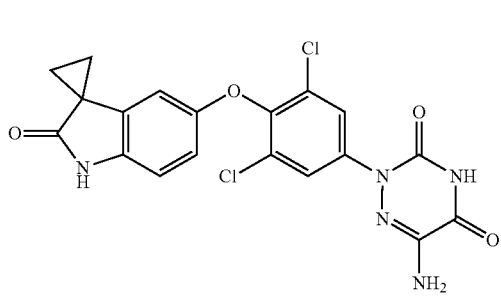

The titled compound was prepared similarly as described for compound 82 with the exception that 5'-bromospiro[cyclopropane-1,3'-indolin]-2'-one was used instead of 5-bromo-3,3-dimethylindolin-2-one. $^1$H NMR (400 MHz, DMSO-$d_6$) δ 1.44-1.48 (m, 2H), 1.55-1.60 (m, 2H), 6.43 (dd, J=8.4 Hz, 2.6 Hz, 1H), 6.49 (brs, 2H), 6.75 (d, J=2.6 Hz, 1H), 6.80 (d, J=8.4 Hz, 1H), 7.89 (s, 2H), 10.47 (s, 1H), 12.26 (brs, 1H).

Example 78: Synthesis of Compound 144

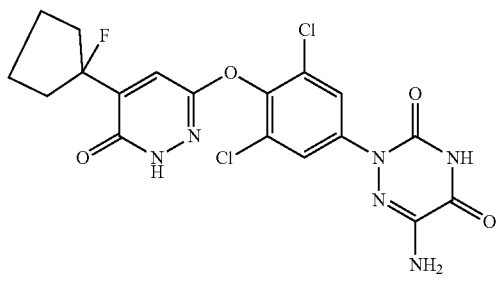 [SMILES: Nc1nn(-c2cc(Cl)c(Oc3cc(C4(F)CCCC4)c(=O)[nH]n3)c(Cl)c2)c(=O)[nH]c1=O]

A 500 mL round-bottom flask was charged with 2,2,6,6-tetramethylpiperidine (26 mL) in THF (100 mL) under $N_2$. n-Butyllithium (60.00 mL, 636.953 mmol) was added dropwise at −78° C. The mixture was warm to −45° C. and stirred for 30 min. Then the mixture was cooled to −78° C. and 3,6-dichloropyridazine (10.00 g, 67.128 mmol) in THF (100 mL) was added dropwise. The mixture was stirred for 30 min at −78° C. Cyclopentanone (60 mL) in THF (50 mL) was added dropwise. The reaction was stirred for 60 min at −75° C. The reaction was quenched by saturated ammonium chloride (100 mL) and extracted with EA (3×100 mL), the combined organic layers were washed with brine (2×100 mL), dried over anhydrous sodium sulfate, filtered and concentrated under reduced pressure. The residue was purified by silica gel column chromatography with EA/PE (2/5) to afford 1-(3,6-dichloropyridazin-4-yl)cyclopentan-1-ol (5 g, 28.76%) as yellow oil. LCMS (ESI, m/z): 233 [M+H]$^+$.

A 100 mL round-bottom flask was charged with 1-(3,6-dichloropyridazin-4-yl)cyclopentan-1-ol (4.50 g, 19.306 mmol) in $CH_2Cl_2$ (50 mL) under $N_2$. Bis(2-methoxyethyl)aminosulfur trifluoride (BAST) (12.81 g, 57.918 mmol, 3.00 equiv) was added dropwise at 0° C. The reaction was stirred for 16 h at rt. The reaction mixture was diluted with water (50 mL) and filtered through celite, the celite pad was washed with dichloromethane (2×50 mL), the filtrate was washed with brine (2×50 mL). The organic layer was dried over anhydrous sodium sulfate, filtered and concentrated under reduced pressure. The residue was chromatographed on a silica gel column with PE/EA=5/2 to provide the 3,6-dichloro-4-(1-fluorocyclopentyl)pyridazine (2.5 g, 44%) as a yellow oil. LCMS (ESI, m/z): 235 [M+H]$^+$.

To a solution of 3,6-dichloro-4-(1-fluorocyclopentyl)pyridazine (500.00 mg, 2.127 mmol), t-butyl N-[2-(3,5-dichloro-4-hydroxyphenyl)-3,5-dioxo-4H-1,2,4-triazin-6-yl]carbamate (827.78 mg, 2.127 mmol) and $K_2CO_3$ (881.86 mg, 6.381 mmol, 3.00 equiv) in DMSO (10 mL) was added CuI (81.01 mg, 0.425 mmol) under nitrogen. The mixture was stirred for 16 h at 110° C. and then quenched with water (20 mL). The mixture was acidified to pH ~5 with HCl (1M, aq.). The resulting mixture was extracted with ethyl acetate (3×30 mL). The combined organic layers were washed with brine (2×20 mL), dried over anhydrous sodium sulfate. After filtration, the filtrate was concentrated. The residue was purified by silica gel column chromatography, eluted with EA/PE (1:1) to afford 6-amino-2-(3,5-dichloro-4-[[6-chloro-5-(1-fluorocyclopentyl)pyridazin-3-yl]oxy]phenyl)-4H-1,2,4-triazine-3,5-dione (250 mg, 24%) as a yellow solid. LCMS (ESI, m/z): 487 [M+H]$^+$.

To a solution of 6-amino-2-(3,5-dichloro-4-[[6-chloro-5-(1-fluorocyclopentyl)pyridazin-3-yl]oxy]phenyl)-4H-1,2,4-triazine-3,5-dione (200.00 mg, 0.410 mmol) in acetic acid (5 mL) was added sodium acetate (168.21 mg, 2.050 mmol). The mixture was stirred overnight at 100° C. The mixture reaction was cooled to rt and then quenched with water (10 ml) and then stirred for 10 min, the resulting solid was filtered and washed with water (2×10 ml) and petroleum ether (2×5 mL), then dried under high vacuum to afford the crude product. The crude product (100 mg) was purified by preparative HPLC using the following gradient conditions: Column: XBridge Prep OBD C18 Column, 19×250 mm, 5um; mobile Phase A: Water (10 MMOL/L $NH_4HCO_3$+ 0.1% $NH_3·H_2O$), Mobile Phase B: $CH_3CN$; Flow rate: 25 mL/min; Gradient: 29 B to 49 B in 7 min; 220 nm; RT1:6.98; Purification resulted in 6-amino-2-(3,5-dichloro-4-[[5-(1-fluorocyclopentyl)-6-oxo-1H-pyridazin-3-yl]oxy]phenyl)-4H-1,2,4-triazine-3,5-dione (4 mg, 2.06%) as a white solid. $^1$H NMR (400 MHz, DMSO-$d_6$) δ 12.47 (s, 1H), 12.27 (s, 1H), 7.87 (s, 2H), 7.53 (s, 1H), 6.50 (s, 2H), 2.50-2.49 (m, 2H), 1.87-1.85 (m, 6H).

Example 79: Synthesis of Compound 145

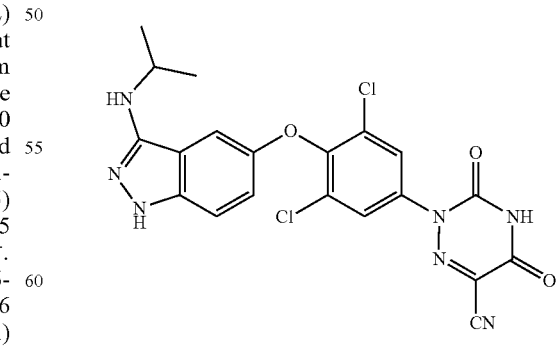

A mixture of 2-bromo-5-hydroxybenzonitrile (5 g, 25.25 mmol), 1,2,3-trichloro-5-nitrobenzene (5.72 g, 25.25 mmol) and $K_2CO_3$ (5.23 g, 37.88 mmol) in DMF (185 mL) under $N_2$ was stirred at 60° C. for 1 h. After cooling to rt, the reaction mixture was diluted in water and filtered. The precipitate was washed with water and dissolved in DCM. The solution was dried with MgSO$_4$, filtered and evaporated to dryness providing 2-bromo-5-(2,6-dichloro-4-nitrophenoxy)benzonitrile (9.65 g, 98%) as a yellow solid which was used without further purification. $^1$H NMR (400 MHz, DMSO-d$_6$) δ 7.36 (dd, J=8.9 Hz, 3.1 Hz, 1H), 7.71 (d, J=3.2 Hz, 1H), 7.88 (d, J=9.0 Hz, 1H), 8.58 (s, 2H) ppm.

A solution of benzophenone hydrazone (1.89 g, 9.64 mmol), Pd(OAc)$_2$ (98 mg, 0.44 mmol) and BINAP (300.1 mg, 0.48 mmol) in toluene (17 mL) was evacuated and backfilled with N$_2$ (3×) and the reaction mixture was heated at 100° C. for 3 min. After cooling to rt, 2-bromo-5-(2,6-dichloro-4-nitrophenoxy)benzonitrile (3.4 g, 8.76 mmol), Cs$_2$CO$_3$ (4 g, 12.27 mmol) and toluene (5.1 mL) were added. The reaction vessel was again evacuated and backfilled with N$_2$ (3×) and the reaction mixture was heated at 100° C. for 5 h. After cooling to rt, the mixture was filtrated through a pad of Celite, the Celite was washed with DCM, and the solution was evaporated to dryness providing 5-(2,6-dichloro-4-nitrophenoxy)-2-(2-(diphenylmethylene)hydrazinyl) benzonitrile as a dark red solid (4.41 g, quant.) which was used without further purification. $^1$H NMR (400 MHz, DMSO-d$_6$) δ 6.76 (d, J=2.9 Hz, 1H), 7.15 (dd, J=9.3 Hz, 2.9 Hz, 1H), 7.32-7.37 (m, 6H), 7.59-7.63 (m, 4H), 7.73 (d, J=9.3 Hz, 1H), 8.08 (s, 1H), 8.31 (s, 2H) ppm.

p-Toluenesulfonic acid monohydrate (3.33 g, 17.5 mmol) was added to a solution of 5-(2,6-dichloro-4-nitrophenoxy)-2-(2-(diphenylmethylene)hydrazineyl)benzonitrile (4.4 g, 8.74 mmol) in MeOH (61 mL) under N$_2$. The reaction mixture was refluxed for 21 h. After cooling to rt, the reaction mixture was diluted with a sat. aq. Na$_2$CO$_3$ and extracted with EA (3×). The combined organic layers were washed with brine (3×) and water, dried over MgSO$_4$, filtered and evaporated to dryness. The crude was purified by chromatography on silica gel (20% to 70% EA in DCM) providing 5-(2,6-dichloro-4-nitrophenoxy)-1H-indazol-3-amine (1.45 g, 49%) as a yellow solid. $^1$H NMR (400 MHz, DMSO-d$_6$) δ 5.20 (s, 2H), 6.99 (d, J=2.4 Hz, 1H), 7.08 (dd, J=9.0 Hz, 2.4 Hz, 1H), 7.26 (d, J=9.0 Hz, 1H), 8.57 (s, 2H), 11.40 (s, 1H) ppm.

Trifluoroacetic anhydride (0.36 mL, 2.57 mmol) was added to a solution of 5-(2,6-dichloro-4-nitrophenoxy)-1H-indazol-3-amine (435 mg, 1.28 mmol) in anhydrous DCM (10 mL) at 0° C. under N$_2$. The reaction mixture was stirred at rt for 1 h. Afterward, the reaction mixture was diluted in water and extracted with DCM (3×). The combined organic layers were dried over MgSO$_4$, the solids were removed by filtration and the solvent of the filtrate was evaporated to dryness. The crude mixture was purified by flash chromatography on silica gel (20% to 60% EA in cyclohexane) to give N-(5-(2,6-dichloro-4-nitrophenoxy)-1H-indazol-3-yl)-2,2,2-trifluoroacetamide (558 mg, quant.) as a yellow solid. $^1$H NMR (400 MHz, DMSO-d$_6$) δ 7.05 (d, J=2.1 Hz, 1H), 7.17 (dd, J=9.1 Hz, 2.2 Hz, 1H), 7.57 (d, J=9.0 Hz, 1H), 8.56 (s, 2H), 11.82 (s, 1H), 13.18 (s, 1H) ppm.

A solution of NH$_4$Cl (685.9 mg, 12.82 mmol) in water (6.4 mL) was added to a solution of N-(5-(2,6-dichloro-4-nitrophenoxy)-1H-indazol-3-yl)-2,2,2-trifluoroacetamide (558 mg, 1.28 mmol) in ethanol (13 mL) under N$_2$. Fe (358.1 mg, 6.41 mmol) was added and the reaction mixture was stirred at 70° C. for 3 h. After cooling to rt, HCl 37% (1 mL) was added and the reaction mixture was diluted in water. K$_2$CO$_3$ was slowly added until basic pH and the resulting solution was extracted with EA (3×). The combined organic layers were dried with Na$_2$SO$_4$, filtered and evaporated to dryness providing N-(5-(4-amino-2,6-dichlorophenoxy)-1H-indazol-3-yl)-2,2,2-trifluoroacetamide (365 mg, 70%) as a green solid which was used without further purification. $^1$H NMR (400 MHz, DMSO-d$_6$) δ 5.60 (s, 2H), 6.73 (s, 2H), 6.85 (s, 1H), 7.08 (d, J=9.1 Hz, 1H), 7.50 (d, J=9.0 Hz, 1H), 11.74 (s, 1H), 13.01 (s, 1H) ppm.

A solution of NaNO$_2$ (94.8 mg, 1.37 mmol) in water (13.7 mL) was added to a solution of N-(5-(4-amino-2,6-dichlorophenoxy)-1H-indazol-3-yl)-2,2,2-trifluoroacetamide (265 mg, 0.65 mmol) in HCl 37% (5.7 mL, 69.1 mmol), acetic acid (17.5 mL) and water (13.7 mL) at 0° C. under N$_2$. The reaction mixture was stirred at 0° C. for 1 h. In parallel, a solution of ethyl N-(2-cyanoacetyl)carbamate (153.2 mg, 0.98 mmol) in water (16.5 mL) and pyridine (5.7 mL) was stirred at 0° C. for 15 min. The first reaction mixture was quickly added to the second one. The resulting reaction mixture was stirred at 0° C. for 1.5 h. Afterwards, the reaction mixture was diluted in water and filtered. The precipitate was washed with water providing ethyl (2-cyano-2-(2-(3,5-dichloro-4-((3-(2,2,2-trifluoroacetamido)-1H-indazol-5-yl)oxy)phenyl)hydrazineylidene)acetyl)carbamate (170 mg, 45%) as a beige solid which was used without further purification.

Sodium acetate (97.5 mg, 1.19 mmol) was added to a solution of ethyl (2-cyano-2-(2-(3,5-dichloro-4-((3-(2,2,2-trifluoroacetamido)-1H-indazol-5-yl)oxy)phenyl)hydrazineylidene)acetyl)carbamate (170 mg, 0.3 mmol) in acetic acid (10 mL) under N$_2$. The reaction mixture was stirred at 120° C. for 3 h. After cooling to 0° C., the reaction mixture was diluted in water, stirred for 30 min at 0° C. and filtered. The precipitate was washed with water and pentane. The crude mixture was purified by flash chromatography on silica gel (0% to 10% MeOH in DCM) to give N-(5-(2,6-dichloro-4-(6-cyano-3,5-dioxo-4,5-dihydro-1,2,4-triazin-2(3H)-yl)phenoxy)-1H-indazol-3-yl)-2,2,2-trifluoroacetamide (45 mg, 29%) as an orange solid. LCMS: C$_{19}$H$_8$Cl$_2$F$_3$N$_7$O$_4$ [M+H]$^+$: 525.

A solution of N-(5-(2,6-dichloro-4-(6-cyano-3,5-dioxo-4,5-dihydro-1,2,4-triazin-2(3H)-yl)phenoxy)-1H-indazol-3-yl)-2,2,2-trifluoroacetamide (158 mg, 0.3 mmol) in ammonia (15 mL, 7 N in MeOH) under N$_2$ was stirred at 60° C. for 3 h. The reaction mixture was evaporated to dryness to give 2-(4-((3-amino-1H-indazol-5-yl)oxy)-3,5-dichlorophenyl)-3,5-dioxo-2,3,4,5-tetrahydro-1,2,4-triazine-6-carbonitrile (127 mg, 98%) as an orange solid which was used without further purification. $^1$H NMR (400 MHz, DMSO-d$_6$) δ 5.25 (br s, 2H), 6.96 (d, J=2.6 Hz, 1H), 7.05 (dd, J=9.2 Hz, 2.6 Hz, 1H), 7.09 (br s, 1H), 7.24 (d, J=8.9 Hz, 1H), 7.81 (s, 2H), 11.34 (br s, 1H) ppm.

Acetone (0.109 mL, 1.48 mmol) was added to a solution of 2-(4-((3-amino-1H-indazol-5-yl)oxy)-3,5-dichlorophenyl)-3,5-dioxo-2,3,4,5-tetrahydro-1,2,4-triazine-6-carbonitrile (127 mg, 0.3 mmol) in ethanol (1.5 mL), THF (1.5 mL) and acetic acid (0.3 mL) under N$_2$. After cooling to 0° C., NaCNBH$_3$ (2 eq., 37.1 mg, 0.59 mmol) was added and the mixture was stirred at 0° C. for 1.5 h. Then, the reaction mixture was diluted in water and filtered. The precipitate was washed with water. The crude mixture was purified by flash chromatography on silica gel (0% to 10% MeOH in DCM) and the resulting product was dissolved in MTBE and filtered. The solution was evaporated to dryness to give 2-(3,5-dichloro-4-((3-(isopropylamino)-1H-indazol-5-yl)oxy)phenyl)-3,5-dioxo-2,3,4,5-tetrahydro-1,2,4-triazine-6-carbonitrile (12 mg, 9%) as a red solid. $^1$H NMR (400 MHz, DMSO-d$_6$) δ 1.17 (d, J=6.4 Hz, 6H), 3.76 (br s, 1H), 5.67 (s, 1H), 6.98 (d, J=2.5 Hz, 1H), 7.09 (dd, J=2.5 Hz, 8.9 Hz, 1H), 7.26 (d, J=8.9 Hz, 1H), 7.81 (s, 2H), 11.34 (s, 1H), 13.28 (br s, 1H).

Example 80: Synthesis of Compound 146 and 147

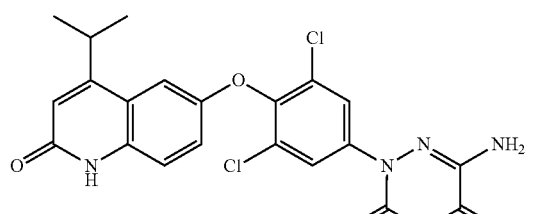
146

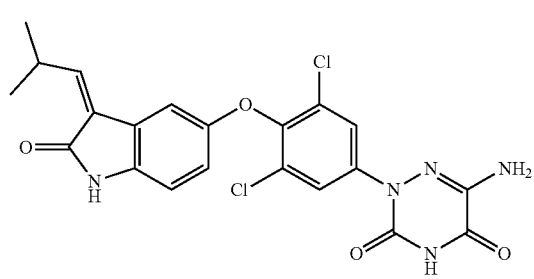
147

The mixture of 4-amino-2,6-dichloro-phenol (30 g, 168.52 mmol) and Boc₂O (91.95 g, 421.31 mmol, 96.79 mL) in THF (400 mL) was heated to 80° C. for 2 h. The mixture was concentrated to afford crude. The residue was purified by silica gel chromatography (eluent of 0-15% EA/PE) to afford t-butyl N-(3,5-dichloro-4-hydroxy-phenyl) carbamate (35 g, 125.84 mmol, 75% yield) was obtained as light yellow solid. ¹H NMR (400 MHz, CDCl₃) δ 7.19 (s, 1H), 6.27 (br s, 1H), 5.55 (s, 1H), 1.44 (s, 10H).

The mixture of t-butyl N-(3,5-dichloro-4-hydroxy-phenyl)carbamate (33.14 g, 119.15 mmol) and 2-bromo-4-fluoro-1-nitro-benzene (31.46 g, 142.98 mmol) and Cs₂CO₃ (54.35 g, 166.81 mmol) in CH₃CN (500 mL) was heated to 65° C. for 18 h. The mixture was concentrated to remove CH₃CN and diluted with EA (500 mL) and the organic layer was washed with H₂O (200 mL×2). The organic layer was dried over MgSO₄ and concentrated to afford crude, purified by silica gel chromatography (eluent of 0~15% EA/PE) to afford t-butyl N-[4-(3-bromo-4-nitro-phenoxy)-3,5-dichloro-phenyl] carbamate (20 g, 41.83 mmol, 35% yield) obtained as white solid. H NMR (400 MHz, CDCl₃) δ 7.97 (d, J=9.0 Hz, 1H), 7.55 (s, 2H), 7.18 (d, J=2.6 Hz, 1H), 6.88 (dd, J=2.6, 9.0 Hz, 1H), 6.60 (s, 1H), 1.56 (s, 9H).

The mixture of t-butyl N-[4-(3-bromo-4-nitro-phenoxy)-3,5-dichloro-phenyl]carbamate (21.5 g, 44.97 mmol) and TFA (51.27 g, 449.68 mmol, 33.29 mL) in DCM (200 mL) was stirred at 20° C. for 4 h. The mixture was concentrated. NaHCO₃ (sat., aq., 500 mL) was added to mixture. The mixture was stirred at 20° C. for 4 h. The precipitated solid was filtered and dried. 4-(3-bromo-4-nitro-phenoxy)-3,5-dichloro-aniline (16.1 g, 39.18 mmol, 87% yield, 92% purity) was obtained as yellow solid.

To a solution of 4-(3-bromo-4-nitro-phenoxy)-3,5-dichloro-aniline (5 g, 13.23 mmol) in AcOH (60 mL) was added HCl (12 M, 11.02 mL). The mixture was cooled to 5° C. in an ice bath. A solution of NaNO₂ (2.74 g, 39.68 mmol) in H₂O (30 mL) was added to above suspended solution, while maintaining the temperature between 5-10° C. The mixture was stirred at 5° C. for 30 min. A solution of ethyl N-(2-cyanoacetyl)carbamate (2.48 g, 15.87 mmol) in pyridine (25 mL) was added to above light yellow clear solution slowly. The mixture was stirred at 5° C. for 1 hr and then 20° C. for 1 h. The mixture was filtered and the filtered solid was diluted with ethyl acetate (500 mL) and washed with H₂O (200 mL×2). The organic layer was dried over MgSO₄ and concentrated to afford crude product. The crude product was used for the next step without further purification. ethyl N-[2-[[4-(3-bromo-4-nitro-phenoxy)-3,5-dichloro-phenyl] hydrazono]-2-cyano-acetyl]carbamate (6.7 g, 12.29 mmol, 93% yield) was obtained as red solid. ¹H NMR (400 MHz, DMSO-d₆) δ 10.94 (s, 1H), 8.13-8.06 (m, 3H), 7.51 (d, J=2.6 Hz, 1H), 7.09 (dd, J=2.7, 9.1 Hz, 1H), 4.21 (q, J=7.1 Hz, 2H), 1.28 (t, J=7.1 Hz, 3H).

The mixture of ethyl N-[2-[[4-(3-bromo-4-nitro-phenoxy)-3,5-dichloro-phenyl]hydrazono]-2-cyano-acetyl]carbamate (2 g, 3.67 mmol) and Et3N (1.86 g, 18.34 mmol, 2.55 mL) in DMF (30 mL) was heated to 100° C. and stirred for 18 h under N₂. The mixture was diluted with EA (200 mL) and washed with H₂O (100 mL×3) and brine (100 mL×3). The organic layer was dried over MgSO₄, the solids were removed by filtration and the filtrate was concentrated under reduced pressure. The crude was purified by silica gel chromatography (eluent of 0~100% EA/PE then 0~10% MeOH/EA). 2-[4-(3-bromo-4-nitro-phenoxy)-3,5-dichloro-phenyl]-3,5-dioxo-1,2,4-triazine-6-carbonitrile (1.3 g, 2.60 mmol, 61.74% yield) was obtained as yellow solid. ¹H NMR (400 MHz, DMSO-d₆) δ 8.10 (d, J=9.0 Hz, 1H), 7.89 (s, 2H), 7.61 (d, J=2.8 Hz, 1H), 7.10 (dd, J=2.8, 9.1 Hz, 1H).

To a solution of 2-[4-(3-bromo-4-nitro-phenoxy)-3,5-dichloro-phenyl]-3,5-dioxo-1,2,4-triazine-6-carbonitrile (12.1 g, 24.25 mmol) in AcOH (20 mL) was added HCl (70 mL) and the mixture was stirred at 120° C. for 16 h. The mixture was concentrated to remove HCl and AcOH. H₂O (80 mL) was added and the mixture was cooled to 0° C. The precipitated solid was isolated by filtration and dried to afford 2-[4-(3-bromo-4-nitro-phenoxy)-3,5-dichloro-phenyl]-3,5-dioxo-1,2,4-triazine-6-carboxylic acid (10.06 g, 19.42 mmol, 80% yield) as yellow solid. ¹H NMR (400 MHz, DMSO-d₆) δ 13.19-12.22 (m, 1H), 8.09 (d, J=9.0 Hz, 1H), 7.91 (s, 2H), 7.63 (d, J=2.6 Hz, 1H), 7.10 (dd, J=2.7, 9.1 Hz, 1H).

The mixture of 2-[4-(3-bromo-4-nitro-phenoxy)-3,5-dichloro-phenyl]-3,5-dioxo-1,2,4-triazine-6-carboxylic acid (9.06 g, 17.49 mmol) and DPPA (7.22 g, 26.23 mmol) and Et₃N (7.08 g, 69.95 mmol) in t-BuOH (15 mL) was heated to 85° C. for 16 h under nitrogen atmosphere. The mixture was diluted with EA (30 mL) and washed with H₂O (10 mL×2). The organic layer was dried over MgSO₄ and concentrated to afford crude. The residue was purified by silica gel chromatography (eluent of 0-50% EA/PE). t-Butyl N-[2-[4-(3-bromo-4-nitro-phenoxy)-3,5-dichloro-phenyl]-3,5-dioxo-1,2,4-triazin-6-yl] carbamate (5.2 g, 8.83 mmol, 45.47% yield) was obtained as yellow solid. ¹H NMR (400 MHz, DMSO-d₆) δ 12.66 (br s, 1H), 9.18 (s, 1H), 8.10 (d, J=9.1 Hz, 1H), 7.98 (s, 2H), 7.61-7.55 (m, 1H), 7.08 (dd, J=2.7, 9.1 Hz, 1H), 1.46 (s, 9H).

To a solution of t-butyl N-[2-[4-(3-bromo-4-nitro-phenoxy)-3,5-dichloro-phenyl]-3,5-dioxo-1,2,4-tria-zin-6-yl] carbamate (1 g, 1.70 mmol) in THF (20 mL), MeOH (10 mL) and H₂O (5 mL) was added Fe (473.92 mg, 8.49 mmol) and NH₄Cl (453.95 mg, 8.49 mmol). The mixture was stirred at 80° C. for 2 h. The reaction mixture was diluted with EA (50 mL), filtered and the filtrate was concentrated under reduced pressure to give t-butyl N-[2-[4-(4-amino-3-bromo-phenoxy)-3,5-dichloro-phenyl]-3,5-dioxo-1,2,4-tri-azin-6-yl]carbamate (700 mg, 1.25 mmol, 74% yield) as a yellow solid. $^1$H NMR (400 MHz, DMSO-d$_6$) δ 12.30 (br s, 1H), 9.15 (s, 1H), 7.88 (s, 2H), 6.87 (d, J=2.8 Hz, 1H), 6.79 (d, J=8.8 Hz, 1H), 6.71-6.64 (m, 1H), 5.10 (br s, 2H), 1.45 (s, 9H).

To a solution of t-butyl N-[2-[4-(4-amino-3-bromo-phenoxy)-3,5-dichloro-phenyl]-3,5-dioxo-1,2,4-triazin-6-yl]carbamate (700 mg, 1.25 mmol) in THF (20 mL) was added DIEA (485.35 mg, 3.76 mmol), and 4-methylpent-2-enoyl chloride (199.17 mg, 1.50 mmol, 11.69 uL) at 25° C. The mixture was stirred at 25° C. for 3 hr. The reaction mixture was diluted with H$_2$O (50 mL) and extracted with EA (50 mL×3). The combined organic layers were washed with brine (60 mL), dried over Na$_2$SO$_4$, filtered and concentrated under reduced pressure to give a residue. The residue was purified by flash silica gel chromatography (eluent 0~35% THF/PE) to give t-butyl N-[2-[4-[3-bromo-4-[[4-methylpent-2-enoyl]amino]phenoxy]-3,5-dichloro-phenyl]-3,5-dioxo-1,2,4-triazin-6-yl]carbamate (370 mg, 564.61 umol, 45.10% yield) as a yellow solid. $^1$H NMR (400 MHz, DMSO-d$_6$) δ 12.65 (br s, 1H), 9.52 (s, 1H), 9.09 (br s, 1H), 7.97-7.94 (m, 2H), 7.53 (d, J=8.9 Hz, 1H), 7.23 (d, J=2.9 Hz, 1H), 6.87 (s, 1H), 6.80 (dd, J=6.3, 15.4 Hz, 1H), 6.67 (s, 1H), 6.58 (s, 1H), 6.18 (br d, J=15.1 Hz, 1H), 1.46 (s, 9H), 1.05 (d, J=6.8 Hz, 6H).

To a solution of t-butyl N-[2-[4-[3-bromo-4-[[4-methylpent-2-enoyl]amino]phenoxy]-3,5-dichloro-phenyl]-3,5-dioxo-1,2,4-triazin-6-yl]carbamate (320 mg, 488.31 umol) in dioxane (2 mL) was added TEA (148.24 mg, 1.46 mmol, 203.90 uL), and palladium tri-t-butylphosphane (24.96 mg, 48.83 umol) at 25° C. Then the mixture was stirred at 130° C. for 1.5 h. LCMS showed the starting material was consumed completely and desired mass was detected. The reaction mixture was diluted with H$_2$O (10 mL) and extracted with EA (10 mL×3). The combined organic layers were washed with brine (20 mL), dried over Na$_2$SO$_4$, filtered and concentrated under reduced pressure to give a residue. The residue was purified by prep-HPLC [Column: Welch Xtimate C18 150×30 mm×5 um; Mobile phase: from 50% CH$_3$CN in water (0.225% FA) to 80% CH$_3$CN in water (0.225% FA)] to give t-butyl-[2-[3,5-dichloro-4-[(4-isopropyl-2-oxo-1H-quinolin-6-yl)oxy]phenyl]-3,5-dioxo-1,2,4-triazin-6-yl]carbamate (20 mg, 34.82 umol, $^1$H NMR (400 MHz, DMSO-d$_6$) δ (br s, 1H), 11.66 (s, 1H), 9.15 (br s, 1H), 7.94 (s, 2H), 7.35 (d, J=9.0 Hz, 1H), 7.23 (d, J=2.9 Hz, 1H), 7.11 (dd, J=2.6, 9.0 Hz, 1H), 6.39 (s, 1H), 3.20 (br d, J=6.4 Hz, 1H), 1.46 (s, 9H), 1.21 (d, J=6.8 Hz, 6H)) as a yellow solid and t-butyl N-[2-[3,5-dichloro-4-[(3Z)-3-(2-methylpropylidene)-2-oxo-indolin-5-yl]oxy-phenyl]-3,5-dioxo-1,2,4-triazin-6-yl]carbamate (26 mg, 45.26 umol, $^1$H NMR (400 MHz, DMSO-d$_6$) δ 12.63 (s, 1H), 10.45 (s, 1H), 9.17 (s, 1H), 7.90 (s, 2H), 7.25 (d, J=2.3 Hz, 1H), 6.79 (d, J=8.5 Hz, 1H), 6.68 (d, J=10.0 Hz, 1H), 6.55 (dd, J=2.5, 8.5 Hz, 1H), 3.14 (qd, J=6.7, 16.5 Hz, 1H), 1.45 (s, 9H), 1.14 (d, J=6.5 Hz, 6H) as a yellow solid.

To a solution of t-butyl N-[2-[3,5-dichloro-4-[(4-isopropyl-2-oxo-1H-quinolin-6-yl)oxy]phenyl]-3,5-dioxo-1,2,4-triazin-6-yl]carbamate (20 mg, 34.40 umol) in MeOH (1 mL) was added HCl/dioxane (4 M, 43.00 uL) at 15° C. The mixture was stirred at 15° C. for 6 hr. The reaction mixture was concentrated in vacuo. The residue was purified by prep-HPLC [Column: Welch Xtimate C18 150×30 mm×5 um; mobile phase: from 30% CH$_3$CN in water (0.04% NH$_3$H$_2$O+10 mM NH$_4$HCO$_3$) to 60% CH$_3$CN in water (0.04% NH$_3$H$_2$O+10 mM NH$_4$HCO$_3$)] to give 6-amino-2-[3,5-dichloro-4-[(4-isopropyl-2-oxo-1H-quinolin-6-yl)oxy]phenyl]-1,2,4-triazine-3,5-dione (1.95 mg, 4.07 umol, 11.82% yield, 99% purity) as a white solid. $^1$H NMR (400 MHz, DMSO-d$_6$) δ 12.30 (br s, 1H), 11.65 (s, 1H), 7.95 (s, 2H), 7.34 (d, J=8.9 Hz, 1H), 7.19 (d, J=2.6 Hz, 1H), 7.11 (dd, J=2.7, 8.9 Hz, 1H), 6.56 (br s, 2H), 6.39 (s, 1H), 3.23-3.14 (m, 1H), 1.20 (d, J=6.8 Hz, 6H).

To a solution of t-butyl N-[2-[3,5-dichloro-4-[(3Z)-3-(2-methylpropylidene)-2-oxo-indolin-5-yl]oxy-phenyl]-3,5-dioxo-1,2,4-triazin-6-yl]carbamate (26 mg, 45.26 umol) in MeOH (1 mL) was added HCl/dioxane (4 M, 0.057 mL) at 15° C. The mixture was stirred at 15° C. for 16 hr. The reaction mixture was concentrated in vacuo to give crude product, that was purified by prep-HPLC [Column: Welch Xtimate C18 150×30 mm×5 um; mobile phase: from 10% CH$_3$CN in water (0.2% FA) to 50% CH$_3$CN in water (0.2% FA) to give 6-amino-2-[3,5-dichloro-4-[(3Z)-3-(2-methylpropylidene)-2-oxo-indolin-5-yl]oxy-phenyl]-1,2,4-triazine-3,5-dione (4.64 mg, 9.73 umol, 99.44% purity) as a yellow solid. $^1$H NMR (400 MHz, DMSO-d$_6$) δ 12.30 (br s, 1H), 10.44 (s, 1H), 7.91 (s, 2H), 7.24 (d, J=2.5 Hz, 1H), 6.78 (d, J=8.5 Hz, 1H), 6.68 (d, J=9.9 Hz, 1H), 6.54 (d, J=2.6 Hz, 1H), 6.53-6.50 (m, 2H), 3.14 (td, J=6.5, 9.8 Hz, 1H), 1.14 (d, J=6.5 Hz, 6H).

Example 81: Synthesis of Compound 148

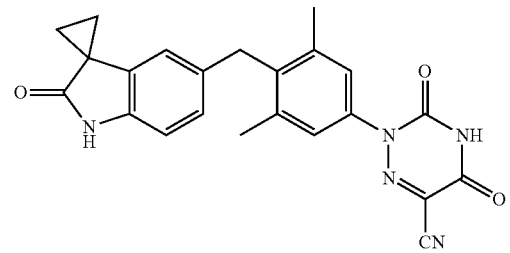

148

Anhydrous THF (20 mL) was added to a mixture of 5'-bromospiro[cyclopropane-1,3'-indolin]-2'-one (400 mg, 1.68 mmol) and NaH 60% (1.5 eq., 101 mg) at 0° C., under N$_2$. The resulting reaction mixture was stirred at 25° C. for 1 h. Then, the mixture was cooled to −78° C. and t-BuLi (2.2 eq., 2.17 mL) was added dropwise and the reaction mixture was stirred at −78° C. for 30 min. Then, a solution of 2,2,2-trifluoro-N-(4-formyl-3,5-dimethylphenyl)acetamide (1 eq., 412 mg) in anhydrous THF (5 mL) was added dropwise to the reaction mixture at −78° C. The reaction mixture was then allowed to warm to rt for 2 h and finally quenched with NH$_4$Cl (sat., aq., 4 mL) and poured in CH$_2$Cl$_2$ (100 mL). The organic phase was washed with water (3×), dried over MgSO$_4$, filtered and evaporated to dryness. The crude mixture was purified by flash chromatography on silica gel (0 to 50% EA in cyclohexane) to give 2,2,2-trifluoro-N-(4-(hydroxy(2'-oxospiro[cyclopropane-1, 3'-indolin]-5'-yl)methyl)-3,5-dimethylphenyl)acetamide (269 mg, 40%) as a white solid. $^1$H NMR (400 MHz, DMSO-d$_6$) δ 1.38-1.52 (m, 4H), 2.20 (s, 6H), 5.75 (d, J=4.0 Hz, 1H), 6.06 (d, J=4.0 Hz, 1H), 6.78 (s, 2H), 6.92 (s, 1H), 7.28 (s, 2H), 10.46 (s, 1H), 11.06 (br s, 1H) ppm.

Et$_3$SiH (0.64 mL) and TMSOTf (0.027 mL) were added dropwise to a solution of 2,2,2-trifluoro-N-(4-(hydroxy(2'-oxospiro[cyclopropane-1,3'-indolin]-5'-yl)methyl)-3,5-dimethylphenyl)acetamide (268 mg, 0.66 mmol) in anhydrous CH$_2$Cl$_2$ (30 mL) at 0° C. under N$_2$. The reaction was stirred at 0° C. for 1 h, at which point the ice bath was removed and the reaction was stirred at 25° C. for 16 h. The reaction mixture was quenched with sat. aq. NaHCO$_3$ (20 mL) and extracted with CH$_2$Cl$_2$ (3×40 mL). The combined organic layers were washed with brine (100 mL), dried over MgSO$_4$, filtered and evaporated to dryness to afford N-(3,5-dimethyl-4-((2'-oxospiro[cyclopropane-1,3'-indolin]-5'-yl)methyl)phenyl)-2,2,2-trifluoroacetamide (229 mg, 89%) as a white solid which was used without further purification. $^1$H NMR (400 MHz, DMSO-d$_6$) δ 1.41-1.48 (m, 4H), 2.18 (s, 6H), 3.91 (s, 2H), 6.58 (d, J=8.0 Hz, 1H), 6.72 (s, 1H), 6.75 (d, J=8.0 Hz, 1H), 7.35 (s, 2H), 10.43 (s, 1H), 11.06 (br s, 1H) ppm.

NaOH (6 eq., 141 mg) was added to a solution of N-(3,5-dimethyl-4-((2'-oxospiro[cyclopropane-1,3'-indolin]-5'-yl)methyl)phenyl)-2,2,2-trifluoroacetamide (229 mg, 0.59 mmol) in CH$_3$OH (25 mL) and water (2.5 mL) under N$_2$. The mixture was stirred at 60° C. for 23 h. Then, the mixture was quenched with water (100 mL). The resulting solution was extracted with CH$_2$Cl$_2$ (3×100 mL). The combined organic layers were washed with brine (300 mL), dried over MgSO$_4$, filtered and evaporated to dryness to give 5'-(4-amino-2,6-dimethylbenzyl)spiro[cyclopropane-1,3'-indolin]-2'-one (147 mg, 85%) as a white solid which was used without further purification. $^1$H NMR (400 MHz, DMSO-d$_6$) δ 1.40-1.46 (m, 4H), 2.02 (s, 6H), 3.76 (s, 2H), 4.71 (s, 2H), 6.26 (s, 2H), 6.61 (d, J=8.0 Hz, 1H), 6.68 (s, 1H), 6.73 (d, J=8.0 Hz, 1H), 10.39 (s, 1H) ppm.

t-Butyl nitrite (0.090 mL) and pyridine (0.12 mL) were added to a solution of 5'-(4-amino-2,6-dimethylbenzyl)spiro[cyclopropane-1,3'-indolin]-2'-one (1 eq., 147 mg, 0.503 mmol) and ethyl N-(2-cyanoacetyl)carbamate (118 mg) in anhydrous CH$_3$CN (15.5 mL) under N$_2$. The reaction mixture was stirred at 60° C. for 1.5 h. After cooling to rt, NaOAc (6 eq., 248 mg) was added and the reaction mixture was heated at 80° C. for 3 h. Additional NaOAc (82 mg) was added and heating was pursued for 64 h. The reaction mixture was cooled to 0° C. and water (50 mL) was added. The mixture was stirred for 30 min at 0° C. and the resulting solution was extracted with EA (3×20 mL). The combined organic layers were dried over MgSO$_4$, filtered and evaporated to dryness. The crude mixture was purified by flash chromatography on silica gel (0 to 7.5% CH$_3$OH in CH$_2$Cl$_2$) to give 2-(3,5-dimethyl-4-((2'-oxospiro[cyclopropane-1,3'-indolin]-5'-yl)methyl)phenyl)-3,5-dioxo-2,3,4,5-tetrahydro-1,2,4-triazine-6-carbonitrile (143 mg, 69%) as a white solid. $^1$H NMR (400 MHz, DMSO-d$_6$) δ 1.42-1.50 (m, 4H), 2.24 (s, 6H), 3.98 (s, 2H), 6.59 (d, J=8.0 Hz, 1H), 6.76 (d, J=8.0 Hz, 1H), 6.78 (s, 1H), 7.16 (s, 2H), 10.45 (s, 1H), 12.98 (br s, 1H).

Example 82: Synthesis of Compound 149

149

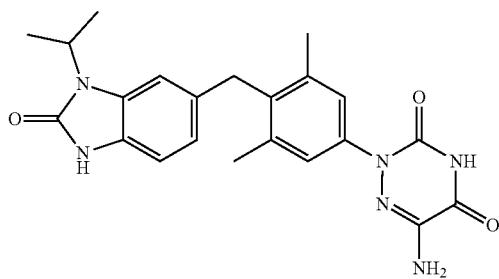

Anhydrous THF (6 mL) was added to a mixture of 6-bromo-1-isopropyl-1,3-dihydro-2H-benzo[d]imidazol-2-one (prepared according to Bioorganic & Medicinal Chemistry Letters 2005, 15(15), pages 3600-3603, 300 mg, 1.18 mmol) and NaH 60% (70.6 mg, 1.76 mmol) at 0° C., under N$_2$. The resulting reaction mixture was stirred at rt for 1 h. Then, the mixture was cooled to −78° C. and t-BuLi (1.5 mL, 2.59 mmol, 1.7 M in pentane) was added dropwise and the reaction mixture was stirred at −78° C. for 1 h. Then, a solution of 4-bromo-2,6-dimethylbenzaldehyde (250.6 mg, 1.18 mmol) in anhydrous THF (3.8 mL) was added dropwise to the reaction mixture at −78° C. The reaction mixture warmed to rt for 1 h and then quenched with sat. aq. NH$_4$Cl and extracted with CH$_2$Cl$_2$ (3×). The combined organic phases were washed with water (3×), dried over Na$_2$SO$_4$, filtered and evaporated to dryness. The crude mixture was purified by flash chromatography on silica gel (0 to 60% AcOEt in cyclohexane) to give 6-((4-bromo-2,6-dimethylphenyl)(hydroxy)methyl)-1-isopropyl-1,3-dihydro-2H-benzo[d]imidazol-2-one (277 mg, 61%) as a white solid. $^1$H NMR (400 MHz, DMSO-d$_6$) δ 1.36-1.43 (m, 6H), 2.22 (s, 6H), 4.53 (p, J=6.9 Hz, 1H), 5.85 (d, J=3.3 Hz, 1H), 6.12 (d, J=3.0 Hz, 1H), 6.56 (d, J=8.0 Hz, 1H), 6.84 (d, J=8.3 Hz, 1H), 7.19 (s, 1H), 7.21 (s, 2H), 10.66 (s, 1H) ppm.

Et$_3$SiH (0.69 mL, 4.27 mmol) and TMSOTf (28.8 μL, 0.16 mmol) were added dropwise to a solution of 6-((4-bromo-2,6-dimethylphenyl)(hydroxy)methyl)-1-isopropyl-1,3-dihydro-2H-benzo[d]imidazol-2-one (277 mg, 0.71 mmol) in anhydrous CH$_2$Cl$_2$ (32.2 mL) at 0° C. under N$_2$. The reaction was stirred at 0° C. for 30 min, at which point the ice bath was removed and the reaction was stirred at rt for 2 h. The reaction mixture was quenched with sat. aq. NaHCO$_3$ and extracted with CH$_2$Cl$_2$ (3×). The combined organic layers were washed with brine, dried over Na$_2$SO$_4$, filtered and evaporated to dryness providing 6-(4-bromo-2,6-dimethylbenzyl)-1-isopropyl-1,3-dihydro-2H-benzo[d]imidazol-2-one (242 mg, 91%) as a white solid which was used in the next step without further purification.

A solution of 6-(4-bromo-2,6-dimethylbenzyl)-1-isopropyl-1,3-dihydro-2H-benzo[d]imidazol-2-one (195 mg, 0.52 mmol), 6-amino-4-[(benzyloxy)methyl]-2,3,4,5-tetrahydro-1,2,4-triazine-3,5-dione (142.6 mg, 0.57 mmol), K$_2$CO$_3$ (288.8 mg, 2.09 mmol), CuBr (74.9 mg, 0.52 mmol) and trans-N,N-dimethylcyclohexane-1,2-diamine (74.3 mg, 0.52 mmol) in anhydrous DMSO (3.9 mL) under N$_2$ was stirred at 120° C. for 4 h. After cooling to rt, the reaction mixture was diluted in water and was filtered. The precipitate was washed with water and was dissolved in CH$_2$Cl$_2$. The solution was dried with Na$_2$SO$_4$, filtered and evaporated to dryness. The crude mixture was purified by flash chromatography on silica gel (0% to 5% CH$_3$OH in CH$_2$Cl$_2$) to give 6-amino-4-((benzyloxy)methyl)-2-(4-((3-isopropyl-2-oxo-2,3-dihydro-1H-benzo[d]imidazol-5-yl)methyl)-3,5-dimethylphenyl)-1,2,4-triazine-3,5(2H,4H)-dione (81 mg, 29%) as a white solid. $^1$H NMR (400 MHz, DMSO-d$_6$) δ 1.39 (d, J=6.9 Hz, 6H), 2.25 (s, 6H), 4.06 (s, 2H), 4.51 (p, J=6.9 Hz, 1H), 4.66 (s, 2H), 5.41 (s, 2H), 6.38 (s, 2H), 6.46 (d, J=7.8 Hz, 1H), 6.83 (d, J=7.9 Hz, 1H), 7.00 (s, 1H), 7.19 (s, 2H), 7.26-7.35 (m, 5H), 10.63 (s, 1H) ppm.

BBr$_3$ (1.2 mL, 1.2 mmol, 1 M in CH$_2$Cl$_2$) was added dropwise to a solution of give 6-amino-4-((benzyloxy)methyl)-2-(4-((3-isopropyl-2-oxo-2,3-dihydro-1H-benzo[d]imidazol-5-yl)methyl)-3,5-dimethylphenyl)-1,2,4-triazine-3,5(2H,4H)-dione (81 mg, 0.15 mmol) in CH$_2$Cl$_2$ (50 mL) at 0° C. under N$_2$. The reaction mixture was stirred at 0° C. for 2 h. Afterwards, cold CH$_3$OH was added dropwise at 0° C. and the reaction mixture slowly warmed to rt, then was evaporated to dryness and the crude mixture was purified by chromatography on silica gel (0% to 10% CH₃OH in CH₂Cl₂). The resulting product was purified by reverse phase flash chromatography (5 to 100% CH₃CN in water (0.1% TFA)) to give 6-amino-2-(4-((3-isopropyl-2-oxo-2,3-dihydro-1H-benzo[d]imidazol-5-yl)methyl)-3,5-dimethylphenyl)-1,2,4-triazine-3,5(2H,4H)-dione (26 mg, 41%) as a white solid. ¹H NMR (400 MHz, DMSO-d₆) δ 1.39 (d, J=6.9 Hz, 6H), 2.23 (s, 6H), 4.04 (s, 2H), 4.51 (hept, J=7.0 Hz, 1H), 6.30 (s, 2H), 6.44 (d, J=8.0 Hz, 1H), 6.83 (d, J=7.9 Hz, 1H), 7.01 (s, 1H), 7.20 (s, 2H), 10.67 (s, 1H), 12.07 (s, 1H) ppm.

Example 83: Synthesis of Compound 150

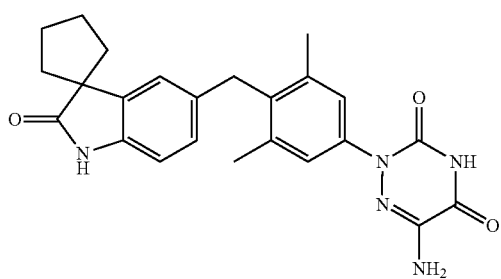 [SMILES: Cc1cc(-n2nc(N)c(=O)[nH]c2=O)cc(C)c1Cc1ccc2c(c1)C1(CCCC1)C(=O)N2]

6-Amino-2-(3,5-dimethyl-4-((2'-oxospiro[cyclopentane-1,3'-indolin]-5'-yl)methyl)phenyl)-1,2,4-triazine-3,5(2H,4H)-dione was prepared using a method analogous to that described for compound 149 where 5'-bromospiro[cyclopentane-1,3'-indolin]-2'-one was employed in the first step instead of 6-bromo-1-isopropyl-1,3-dihydro-2H-benzo[d]imidazol-2-one. ¹H NMR (400 MHz, DMSO-d₆) δ 1.65-1.73 (m, 2H), 1.84-1.98 (m, 6H), 2.21 (s, 6H), 3.96 (s, 2H), 6.29 (s, 2H), 6.59 (dd J=7.9 Hz, 1H); 6.69 (d, J=8.0 Hz, 1H), 7.03 (s, 1H), 7.19 (s, 2H), 10.17 (s, 1H), 12.07 (s, 1H).

Example 84: Synthesis of Compound 151

151

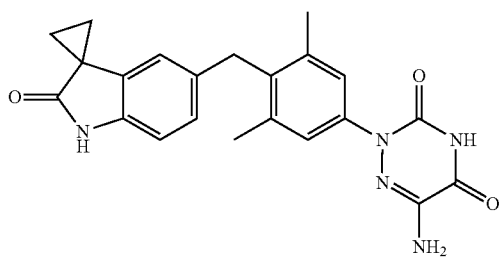

6-Amino-2-(3,5-dimethyl-4-((2'-oxospiro[cyclopropane-1,3'-indolin]-5'-yl)methyl)phenyl)-1,2,4-triazine-3,5(2H,4H)-dione was prepared using a method analogous to that described for compound 149 where 5'-bromospiro[cyclopropane-1,3'-indolin]-2'-one was employed in the first step instead of 6-bromo-1-isopropyl-1,3-dihydro-2H-benzo[d]imidazol-2-one. ¹H NMR (400 MHz, DMSO-d₆) δ 1.42-1.49 (m, 4H), 2.20 (s, 6H), 3.94 (s, 2H), 6.30 (s, 2H), 6.58 (dd, J=8.0 Hz, 1.9 Hz, 1H), 6.76 (dd, J=5.2 Hz, 3.3 Hz, 2H), 7.19 (s, 2H), 10.44 (s, 1H), 12.08 (br s, 1H) ppm.

Example 85: Synthesis of Compound 152

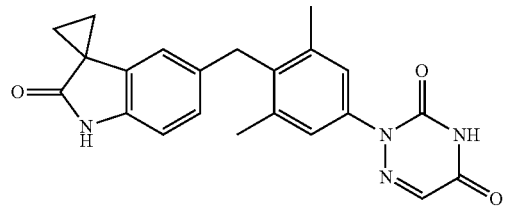 [SMILES: Cc1cc(-n2ncc(=O)[nH]c2=O)cc(C)c1Cc1ccc2c(c1)C1(CC1)C(=O)N2]

KOH (10 eq., 140 mg, 2.49 mmol) was added to a solution of 2-(3,5-dimethyl-4-((2'-oxospiro[cyclopropane-1,3'-indolin]-5'-yl)methyl)phenyl)-3,5-dioxo-2,3,4,5-tetrahydro-1,2,4-triazine-6-carbonitrile (103 mg, 0.25 mmol) in water (1.3 mL) and EtOH (1.3 mL) under N₂. The reaction mixture was stirred at 80° C. for 2 h. The reaction mixture was evaporated to dryness, water was added and aqueous 1N HCl solution was added until acidic pH. Then, the aqueous layer was extracted with EtOAc (3×). The combined organic layers were dried with Na₂SO₄, filtered and evaporated to dryness providing 2-(3,5-dimethyl-4-((2'-oxospiro[cyclopropane-1,3'-indolin]-5'-yl)methyl)phenyl)-3,5-dioxo-2,3,4,5-tetrahydro-1,2,4-triazine-6-carboxylic acid (102 mg, 95%) as a brown oil which was used without further purification.

A solution of 2-(3,5-dimethyl-4-((2'-oxospiro[cyclopropane-1,3'-indolin]-5'-yl)methyl)phenyl)-3,5-dioxo-2,3,4,5-tetrahydro-1,2,4-triazine-6-carboxylic acid (1 eq., 69 mg, 0.16 mmol) in mercaptoacetic acid (25 eq., 276 µL, 4 mmol) was stirred rapidly and heated to 100° C. for 3 h. After cooling to rt, the reaction mixture was diluted in water, filtered and washed with water. The precipitate was dissolved in MeOH and evaporated to dryness. The crude mixture was purified by flash chromatography on silica gel (0% to 5% MeOH in DCM), triturated with MeCN (2×) and co-evaporated with EtOH (2×) to give 2-(3,5-dimethyl-4-((2'-oxospiro[cyclopropane-1,3'-indolin]-5'-yl)methyl)phenyl)-1,2,4-triazine-3,5(2H,4H)-dione (11 mg, 18%) as a yellow solid. ¹H-NMR (DMSO-d₆, 400 MHz) δ 1.43-1.48 (m, 4H), 2.23 (s, 6H), 3.96 (s, 2H), 6.59 (d, J=7.7 Hz, 1H), 6.77 (d, J=8.0 Hz, 2H), 7.17 (s, 2H), 7.61 (s, 1H), 10.44 (s, 1H), 12.30 (br s, 1H) ppm.

Example 86: Synthesis of Compound 153

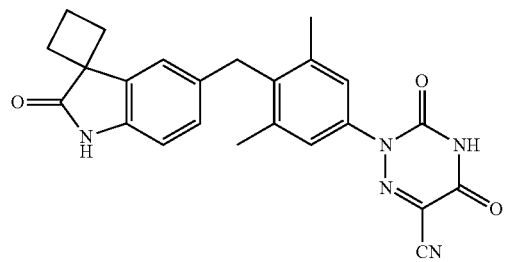 [SMILES: Cc1cc(-n2nc(C#N)c(=O)[nH]c2=O)cc(C)c1Cc1ccc2c(c1)C1(CCC1)C(=O)N2]

2-(3,5-Dimethyl-4-((2'-oxospiro[cyclobutane-1,3'-indolin]-5'-yl)methyl)phenyl)-3,5-dioxo-2,3,4,5-tetrahydro-1,2,4-triazine-6-carbonitrile was prepared using a method analogous to that described for the preparation of 2-(3,5-dimethyl-4-((2'-oxospiro[cyclopropane-1,3'-indolin]-5'-yl)methyl)phenyl)-3,5-dioxo-2,3,4,5-tetrahydro-1,2,4-triazine-6-carbonitrile, where 5'-bromospiro[cyclobutane-1,3'- indolin]-2'-one was used instead of 5'-bromospiro[cyclopropane-1,3'-indolin]-2'-one. ¹H-NMR (DMSO-d₆, 400 MHz) δ 2.11-2.27 (m, 10H), 2.37-2.43 (m, 2H), 4.04 (s, 2H), 6.60 (dd, J=8.0 Hz, 2.0 Hz, 1H), 6.66 (d, J=7.9 Hz, 1H), 7.18 (s, 2H), 7.37 (s, 1H), 10.13 (s, 1H), 12.99 (br s, 1H) ppm.

Example 87: Preparation of Compound 154

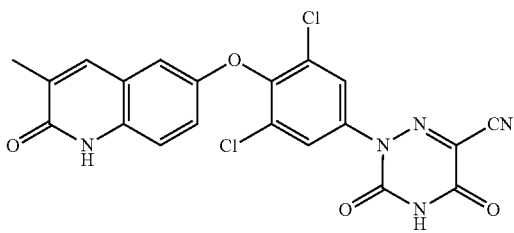 [SMILES: Cc1cc2cc(Oc3c(Cl)cc(-n4nc(C#N)c(=O)[nH]c4=O)cc3Cl)ccc2[nH]c1=O]

To a solution of 6-bromo-3-methyl-1H-quinolin-2-one (3 g, 12.60 mmol) in THF (50 mL) was added NaH (2.02 g, 50.40 mmol, 60% purity) at 20° C. The mixture was stirred at 40° C. for 0.5 hr. Then SEM-Cl (4.20 g, 25.20 mmol, 4.46 mL) was added. The mixture was stirred at 40° C. for 16 h. The reaction mixture was quenched by addition of NH₄Cl (sat., aq., 20 mL) at 10° C., and then diluted with H₂O (60 mL) and extracted with EA (60 mL×3). The combined organic layers were washed with brine (100 mL), dried over Na₂SO₄, filtered and concentrated under reduced pressure to give a residue, which was purified by flash silica gel chromatography (EA/PE=0~10%) to give 6-bromo-3-methyl-1-(2-trimethylsilylethoxymethyl)quinolin-2-one (3.25 g, 8.82 mmol, 70% yield) as a yellow oil. ¹H NMR (400 MHz, CDCl₃) δ 7.64 (d, J=2.1 Hz, 1H), 7.61-7.55 (m, 1H), 7.52-7.44 (m, 2H), 5.79 (s, 2H), 3.77-3.65 (m, 2H), 2.29 (d, J=0.9 Hz, 3H), 1.03-0.89 (m, 2H), 0.04-0.05 (m, 9H).

A mixture of 6-bromo-3-methyl-1-(2-trimethylsilylethoxymethyl)quinolin-2-one (3.25 g, 8.82 mmol, 1 eq), Pin₂B₂ (3.36 g, 13.24 mmol, 1.5 eq), KOAc (2.60 g, 26.47 mmol), PdCl₂(dppf) (720.55 mg, 882.34 umol) in dioxane (60 mL) was degassed and purged with N₂ for 3 times, and then the mixture was stirred at 100° C. for 16 hr under N₂ atmosphere. The reaction mixture was diluted with H₂O (100 mL) and extracted with EA (100 mL×3). The combined organic layers were washed with brine (100 mL×2), dried over Na₂SO₄, the solids were removed by filtration and the filtrate was concentrated under reduced pressure to give a residue. The residue was purified by silica gel chromatography (EA/PE=0~10%) to give 3-methyl-6-(4,4,5,5-tetramethyl-1,3,2-dioxaborolan-2-yl)-1-(2-trimethylsilylethoxymethyl)quinolin-2-one (4.1 g, crude) as a white solid. ¹H NMR (400 MHz, CDCl₃) δ 7.99 (s, 1H), 7.93 (dd, J=1.1, 8.4 Hz, 1H), 7.64-7.54 (m, 2H), 5.83 (s, 2H), 3.79-3.66 (m, 2H), 2.29 (s, 3H), 1.41 (s, 12H), 1.02-0.89 (m, 2H), 0.00 (s, 9H).

To a solution of 3-methyl-6-(4,4,5,5-tetramethyl-1,3,2-dioxaborolan-2-yl)-1-(2-trimethylsilylethoxymethyl)quinolin-2-one (4.1 g, 9.87 mmol) in acetone (60 mL) and H₂O (30 mL) was added NaIO₄ (21.11 g, 98.70 mmol, 5.47 mL) and NH₄OAc (7.61 g, 98.70 mmol) at 20° C. The mixture was stirred at 20° C. for 16 hr. The reaction mixture was diluted with H₂O (60 mL) and extracted with EA (60 mL×3). The combined organic layers were washed with brine (100 mL), dried over anhydrous Na₂SO₄, the solids were removed under reduced pressure and the filtrate was concentrated under reduced pressure to give [3-methyl-2-oxo-1-(2-trimethylsilylethoxymethyl)-6-quinolyl]boronic acid (2.7 g, 7.38 mmol, 75% yield, 91% purity) as a pink solid. ¹H NMR (400 MHz, DMSO-d₆) δ 8.20 (s, 2H), 8.09 (s, 1H), 8.03-7.95 (m, 1H), 7.90-7.81 (m, 1H), 7.55 (d, J=8.5 Hz, 1H), 5.79 (s, 2H), 3.68 (t, J=7.9 Hz, 2H), 2.26-2.16 (m, 3H), 0.94 (t, J=7.9 Hz, 2H), 0.05-0.05 (m, 9H).

To a solution of [3-methyl-2-oxo-1-(2-trimethylsilylethoxymethyl)-6-quinolyl]boronic acid (500 mg, 1.50 mmol) in DMF (20 mL) was added 4 Å MS (5 g, 1.50 mmol), N-(3,5-dichloro-4-hydroxy-phenyl)-N,N-dimethylformamidine (384.69 mg, 1.65 mmol), bis(trifluoromethylsulfonyloxy)copper (542.64 mg, 1.50 mmol) and triethylamine (759.08 mg, 7.50 mmol) at 15° C. The mixture was stirred at 15° C. for 16 hr under O₂. The reaction mixture was diluted with H₂O (50 mL) and extracted with EA (50 mL×2). The combined organic layers were washed with brine (50 mL×2), dried over Na₂SO₄, the solids were removed by filtration and the filtrate was concentrated under reduced pressure to give a residue. The residue was purified by flash silica gel chromatography (0~35% EA/PE=0~35%) to give N-[3,5-dichloro-4-[[3-methyl-2-oxo-1-(2-trimethylsilylethoxymethyl)-6-quinolyl]oxy]phenyl]-N,N-dimethylformamidine (250 mg, 480.29 umol, 32% yield) as a green solid. ¹H NMR (400 MHz, CDCl₃) δ 7.56 (s, 1H), 7.53 (d, J=9.1 Hz, 1H), 7.43 (s, 1H), 7.11 (dd, J=2.8, 9.2 Hz, 1H), 7.01 (s, 2H), 6.81 (d, J=2.9 Hz, 1H), 5.77 (s, 2H), 3.73-3.66 (m, 2H), 3.07 (br d, J=11.0 Hz, 6H), 2.23 (d, J=0.9 Hz, 3H), 0.98-0.92 (m, 2H), −0.01-0.04 (m, 8H), −0.01-0.04 (m, 1H).

To a solution of N-[3,5-dichloro-4-[[3-methyl-2-oxo-1-(2-trimethylsilylethoxymethyl)-6-quinolyl]oxy] phenyl]-N,N-dimethyl-formamidine (658 mg, 1.26 mmol) in isopropanol (20 mL) was added NH₂NH₂.H₂O (630.76 mg, 12.60 mmol) at 20° C. The mixture was stirred at 80° C. for 12 hr under N₂. The reaction mixture was diluted with H₂O (50 mL) and extracted with EA (30 mL×2). The aqueous phase was adjusted to pH=7 with 1M aq. HCl. The combined organic layers were washed with brine (20 mL), dried over Na₂SO₄, filtered and concentrated under reduced pressure to give a residue. The residue was purified by silica gel chromatography (EA/PE=0~30%) to give 6-(4-amino-2,6-dichloro-phenoxy)-3-methyl-1-(2-trimethylsilylethoxymethyl) quinolin-2-one (387 mg, 831.46 umol, 66% yield) as a white solid. ¹H NMR (400 MHz, DMSO-d₆) δ 7.77 (s, 1H), 7.48 (d, J=9.3 Hz, 1H), 7.10 (dd, J=2.9, 9.3 Hz, 1H), 6.94 (d, J=2.9 Hz, 1H), 6.73 (s, 2H), 5.67 (s, 4H), 3.60-3.54 (m, 2H), 2.08 (d, J=0.6 Hz, 3H), 0.89-0.81 (m, 2H), −0.04−0.15 (m, 9H).

To a mixture of 6-(4-amino-2,6-dichloro-phenoxy)-3-methyl-1-(2-trimethylsilylethoxymethyl) quinolin-2-one (387 mg, 665.17 umol, 80% purity) in AcOH (5 mL) was added HCl (12 M, 0.554 mL). Then dropwise a solution of NaNO₂ (137.69 mg, 2.00 mmol) in H₂O (5 mL) while maintaining the temperature below 0° C. After the addition was complete, the reaction mixture was stirred for 0.5 h. A mixture of ethyl N-(2-cyanoacetyl)carbamate (207.72 mg, 1.33 mmol) in pyridine (2.5 mL) was added drop-wise to the resulting diazonium salt solution below 0° C. and stirred for an additional 2 h. The reaction mixture was diluted with H₂O (50 mL), then extracted with EA (50 mL×3). The combined organic layers were washed with brine (60 mL), dried over anhydrous Na₂SO₄, the solids were removed by filtration and the filtrate was concentrated under reduced pressure. The residue was purified by silica gel chromatography (EA in PE=0~40%) to give ethyl N-[2-cyano-2-[[3,5-dichloro-4-[[3-methyl-2-oxo-1-(2-trimethylsilylethoxymethyl)-6-quinolyl]oxy]phenyl]hydrazono]acetyl]carbamate (315 mg, 497.97 umol, 74.8% yield) as a yellow solid. $^1$H NMR (400 MHz, DMSO-d$_6$) δ 10.93 (br s, 1H), 10.89 (s, 1H), 8.07 (s, 2H), 7.77 (s, 1H), 7.51 (d, J=9.3 Hz, 1H), 7.17 (dd, J=3.0, 9.3 Hz, 1H), 7.02 (d, J=3.0 Hz, 1H), 5.69 (s, 2H), 4.24-4.18 (m, 2H), 3.58 (t, J=7.9 Hz, 2H), 2.08 (d, J=0.8 Hz, 3H), 1.25-1.19 (m, 3H), 0.86 (t, J=7.9 Hz, 2H), −0.05-−0.12 (m, 9H).

N-[2-cyano-2-[[3,5-dichloro-4-[[3-methyl-2-oxo-1-(2-trimethylsilylethoxymethyl)-6-quinolyl]oxy]phenyl]hydrazono]acetyl]carbamate (315 mg, 497.97 umol) in AcOH (10 mL) was added NaOAc (204.25 mg, 2.49 mmol). The reaction mixture was concentrated in vacuo, then quenched by addition of sat. aq. NaHCO$_3$ (15 mL), then diluted with H$_2$O (25 mL) and extracted with EA (25 mL×3). The combined organic layers were washed with brine (50 mL), dried over Na$_2$SO$_4$, filtered and concentrated under reduced pressure to give 2-[3,5-dichloro-4-[[3-methyl-2-oxo-1-(2-trimethylsilylethoxymethyl)-6-quinolyl]oxy]phenyl]-3,5-dioxo-1,2,4-triazine-6-carbonitrile (300 mg, 406.48 umol, 81.6% yield, 79% purity) as an orange solid.

A mixture of 2-[3,5-dichloro-4-[[3-methyl-2-oxo-1-(2-trimethylsilylethoxymethyl)-6-quinolyl]oxy]phenyl]-3,5-dioxo-1,2,4-triazine-6-carbonitrile (265 mg, 359.06 umol, 79.5% purity), TBAF (1 M, 10.77 mL) in THF (10 mL) was degassed and purged with N$_2$ three times, then the mixture was stirred at 90° C. for 16 h under N$_2$. The reaction mixture was quenched by NH$_4$C$_1$ (sat., aq., 20 mL) at 15° C., and then diluted with H$_2$O (10 mL) and extracted with EA (20 mL×3). The combined organic layers were washed with sat. NH$_4$Cl (30 mL), dried over Na$_2$SO$_4$, the solids were removed by filtration and the filtrate was concentrated under reduced pressure. The residue was purified by prep-HPLC [Column: Welch Xtimate C18 150×30 mm×5 um; mobile phase: from 48% CH$_3$CN in water (0.225% FA) to 78% CH$_3$CN in water (0.225% FA)] to give 2-[3,5-dichloro-4-[(3-methyl-2-oxo-1H-quinolin-6-yl)oxy]phenyl]-3,5-dioxo-1,2,4-triazine-6-carbonitrile (60.05 mg, 128.59 umol, 35.8% yield, 98% purity) as a light yellow solid. $^1$H NMR (400 MHz, DMSO-d$_6$) δ 13.28 (br s, 1H), 11.75 (s, 1H), 7.82 (s, 2H), 7.76 (s, 1H), 7.31 (d, J=9.0 Hz, 1H), 7.17 (dd, J=2.8, 8.9 Hz, 1H), 7.00 (d, J=2.8 Hz, 1H), 2.05 (s, 3H).

Example 88: Synthesis of Compound 156

156

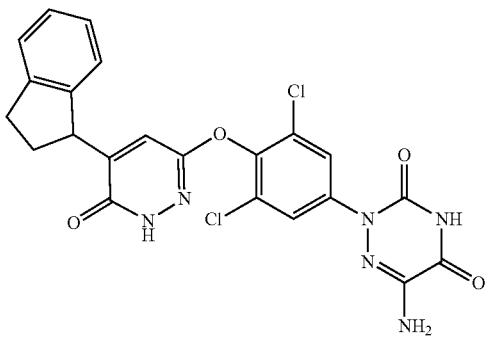

A 40 mL vial was charged with 2,2,6,6-tetramethylpiperidine (10.3 g, 73.2 mmol) in THF (100 mL) under nitrogen. n-butyllithium (26.8 mL, 67.1 mmol) was added dropwise at −75° C. The reaction was warmed to 0° C. and stirred for 30 min. 3,6-dichloropyridazine (5 g, 33.6 mmol) in THF (100 mL) was added dropwise at −75° C. The reaction was stirred for 30 min. 2,3-dihydro-1H-inden-1-one (5.32 g, 40.3 mmol) in THF (50 mL) was added dropwise at −75° C. The reaction was stirred for 90 min at −75° C. The reaction was stirred for 90 min at −75° C. The resulting solution was quenched with NH$_4$C$_1$ (sat., aq., 100 mL). The resulting solution was extracted with EA (3×100 mL) and the organic layers were combined, washed with brine (2×100 mL), dried over anhydrous sodium sulfate, the solids were removed by filtration and the filtrate was concentrated under reduced pressure. The residue was chromatographed on a silica gel column with EA/PE (1/4) to provide 2.28 g (yield 12%) of 1-(3,6-dichloropyridazin-4-yl)-2,3-dihydroinden-1-ol as a yellow solid. $^1$H NMR (400 MHz, DMSO-d$_6$) δ 8.17 (s, 1H), 7.28-7.37 (m, 2H), 7.14-7.19 (m, 1H), 6.41 (m, 1H), 3.21-3.32 (m, 1H), 3.02-3.11 (m, 1H), 2.70-2.81 (m, 1H), 2.19-2.27 (m, 1H). LCMS (ESI, m/z): 281 [M+H]$^+$.

A 40 mL vial was charged with 1-(3,6-dichloropyridazin-4-yl)-2,3-dihydroinden-1-ol (800 mg, 2.85 mmol), 4-methylbenzenesulfonic acid (245 mg, 1.42 mmol), toluene (10 mL). The reaction was stirred overnight at 60° C. The resulting solution was quenched with water (20 mL). The resulting solution was extracted with EA (3×20 mL) and the organic layers were combined, washed with brine (2×20 mL), dried over anhydrous sodium sulfate, filtered and concentrated under reduced pressure. The residue was chromatographed on a silica gel column with EA/PE (1/9) to provide 520 mg (yield 50%) of 3,6-dichloro-4-(3H-inden-1-yl)pyridazine as a yellow solid. $^1$H NMR (300 MHz, CDCl$_3$) δ 7.59-7.62 (m, 2H), 733-7.40 (m, 2H), 723-7.26 (m, 1H), 6.92 (t, J=2.1 Hz, 1H), 3.68 (br, 2H). LCMS (ESI, m/z): 263 [M+H]$^+$.

A 100 mL round-bottom flask was charged with 3,6-dichloro-4-(3H-inden-1-yl)pyridazine (800 mg, 0.380 mmol), platinumoxidehydrate (400 mg), EA (5 mL), ethanol (5 mL). The content of the flask was placed under an atmosphere of hydrogen. The reaction was stirred overnight at rt. The solids were filtered out. The filtrate was concentrated under reduced pressure. The residue was chromatographed on a silica gel column with EA/PE (12/88) to provide 165 mg (yield 19%) of 3,6-dichloro-4-(2,3-dihydro-1H-inden-1-yl)pyridazine as a white solid. $^1$H NMR (300 MHz, CDCl$_3$) δ 7.31-7.40 (m, 3H), 7.08 (d, J=7.5 Hz, 1H), 7.01 (s, 1H), 4.74 (t, J=7.5 Hz, 1H), 3.05 (t, J=7.5 Hz, 2H), 2.74-2.86 (m, 1H), 1.94-2.06 (m, 1H). LCMS (ESI, m/z): 265 [M+H]$^+$.

A 40 mL vial was charged with 3,6-dichloro-4-(2,3-dihydro-1H-inden-1-yl)pyridazine (200 mg, 0.754 mmol), t-butyl N-[2-(3,5-dichloro-4-hydroxyphenyl)-3,5-dioxo-4H-1,2,4-triazin-6-yl]carbamate (382 mg, 0.981 mmol), potassium carbonate (313 mg, 2.26 mmol), CuI (57.5 mg, 0.302 mmol), DMSO (10 mL) under nitrogen. The reaction was stirred for 16 h at 110° C. The reaction was quenched by water (10 mL). The resulting solution was extracted with ethyl acetate (3×20 mL) and the organic layers were combined, washed with brine (2×10 mL), dried over anhydrous sodium sulfate, filtered and concentrated under reduced pressure. The residue was chromatographed on a silica gel column with ethyl acetate/petroleum ether (1/1) to provide 120 mg (yield 21%) of 6-amino-2-(3,5-dichloro-4-[[6-chloro-5-(2,3-dihydro-1H-inden-1-yl)pyridazin-3-yl]oxy]phenyl)-4H-1,2,4-triazine-3,5-dione as a brown solid. LCMS (ESI, m/z): 517 [M+H]$^+$.

A 40 mL vial was charged with 6-amino-2-(3,5-dichloro-4-[[6-chloro-5-(2,3-dihydro-1H-inden-1-yl)pyridazin-3-yl] oxy]phenyl)-4H-1,2,4-triazine-3,5-dione (120 mg, 0.232 mmol, 1.00 equiv), sodium acetate (114 mg, 1.39 mmol), acetic acid (5 mL) under nitrogen. The reaction was stirred overnight at 100° C. The reaction was poured into water (5 mL). The solids were collected by filtration to provide the crude product. The crude product was purified by preparative HPLC using the following gradient conditions: Column: XBridge Prep OBD C18, 19×250 mm, 5um; mobile phase A: Water (0.05% TFA), mobile phase B: CH$_3$CN; Flow rate: 25 mL/min; Gradient: 48 B to 68 B in 7 min; 220 nm; RT1:5.38; Purification resulted in 26.6 mg (yield 31%) of 6-amino-2-(3,5-dichloro-4-[[5-(2,3-dihydro-1H-inden-1-yl)-6-oxo-1H-pyridazin-3-yl]oxy]phenyl)-4H-1,2,4-triazine-3,5-dione as a light yellow solid. $^1$H NMR (300 MHz, DMSO-d$_6$) δ 12.27-12.36 (m, 2H), 7.84 (s, 2H), 7.33 (d, J=6.3 Hz, 1H), 7.16-7.26 (m, 3H), 7.03 (s, 1H), 6.53 (s, 2H), 4.55 (t, J=7.2 Hz, 1H), 2.88-3.09 (m, 2H), 2.42-2.45 (m, 1H), 2.08-2.18 (m, 1H). LCMS (ESI, m/z): 499 [M+H]$^+$.

Example 89: Synthesis of Compound 157

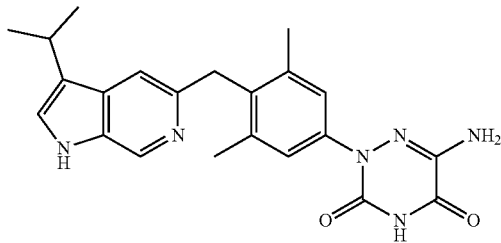 [SMILES: Cc1cc(-n2nc(N)c(=O)[nH]c2=O)cc(C)c1Cc1cc2c(C(C)C)c[nH]c2cn1]

To a solution of 5-bromo-3-isopropyl-1-(p-tolylsulfonyl)pyrrolo[2,3-c]pyridine (1.9 g, 4.83 mmol) in MeOH (20 mL) and THF (5 mL) was added Et$_3$N (1.47 g, 14.49 mmol, 2.02 mL, 3 eq) and Pd(dppf)Cl$_2$ (706.97 mg, 0.966 mmol), and the mixture was stirred at 80° C. for 12 h under CO (50 psi), then diluted with H$_2$O (100 mL) and extracted with EA (100 mL×3). The combined organic layers were washed with brine (100 mL), dried over anhydrous Na$_2$SO$_4$, the solids were removed by filtration and the filtrate was concentrated under reduced pressure. The crude was purified by silica gel chromatography (EA in PE 0~30%) to give methyl 3-isopropyl-1-(p-tolylsulfonyl)pyrrolo[2,3-c] pyridine-5-carboxylate (1.61 g, 4.29 mmol, 88.77% yield, 99.2% purity) as a white solid. $^1$H NMR (400 MHz, CDCl$_3$) δ 9.34 (d, J=0.6 Hz, 1H), 8.38 (d, J=0.6 Hz, 1H), 7.80 (d, J=8.4 Hz, 2H), 7.49 (d, J=0.8 Hz, 1H), 7.28-7.23 (m, 3H), 4.02 (s, 3H), 3.14 (spt, J=6.8 Hz, 1H), 2.37 (s, 3H), 1.35 (d, J=6.9 Hz, 6H).

To a solution of methyl 3-isopropyl-1-(p-tolylsulfonyl)pyrrolo[2,3-c]pyridine-5-carboxyl-ate (1.0 g, 2.66 mmol) in THF (30 mL) was added DIBAL-H (1 M, 7.99 mL) dropwise at −65° C. After the addition, the resulting mixture was stirred at −65° C. for 0.5 hr under N$_2$. The reaction mixture was quenched with methanol (10 mL) and citric acid (sat., aq., 10 mL). The mixture was diluted with H$_2$O (100 mL) and extracted with EA (50 mL×3). The combined organic layers were washed with brine (100 mL), dried over anhydrous Na$_2$SO$_4$, filtered and concentrated under reduced pressure to give a residue, which was purified by silica gel chromatography (eluent of 0-15% EA/PE) to give 3-isopropyl-1-(p-tolylsulfonyl)pyrrolo[2,3-c]pyridine-5-carbaldehyde (807 mg, 2.28 mmol, 85.61% yield, 96.694% purity) as a white solid. $^1$H NMR (400 MHz, CDCl$_3$) δ 10.18 (s, 1H), 9.42 (d, J=0.8 Hz, 1H), 8.23 (d, J=0.9 Hz, 1H), 7.85 (d, J=8.4 Hz, 2H), 7.53 (d, J=0.8 Hz, 1H), 7.31 (d, J=8.3 Hz, 2H), 3.16 (td, J=6.8, 13.4 Hz, 1H), 2.40 (s, 3H), 1.37 (d, J=6.9 Hz, 6H).

To a solution of 5-bromo-2-iodo-1,3-dimethyl-benzene (544.88 mg, 1.75 mmol) in THF (20 mL) was added dropwise n-BuLi (2.5 M, 0.701 mL) at −70° C. over 30 min. After addition, the mixture was stirred at −70° C. for 1 h, then 3-isopropyl-1-(p-tolylsulfonyl)pyrrolo[2,3-c]pyridine-5-carbaldehyde (200 mg, 584.09 umol) in THF (2 mL) was added dropwise at −70° C. The resulting mixture was stirred at −70° C. for 1 h. Then the mixture was stirred for 12 hr at 20° C. The reaction mixture was quenched by addition of NH$_4$Cl (sat., aq., 80 mL) at 15° C., extracted with EA (40 mL×3). The combined organic layers were combined with those of previous batches, washed with H$_2$O (60 mL), dried over Na$_2$SO$_4$, the solids were removed by filtration and the filtrate was concentrated under reduced pressure to give a residue. The residue was purified by flash silica gel chromatography (eluent of 0~15% EA/PE) to give (4-bromo-2,6-dimethyl-phenyl)-[3-isopropyl-1-(p-tolylsulfonyl)pyrrolo[2,3-c]pyridin-5-yl]methanol (341 mg, 646.48 umol) as a white solid. $^1$H NMR (400 MHz, CDCl$_3$) δ 9.15 (d, J=1.0 Hz, 1H), 7.73 (d, J=8.4 Hz, 2H), 7.33 (d, J=1.0 Hz, 1H), 7.21 (s, 2H), 7.09 (s, 2H), 6.87 (s, 1H), 6.13 (s, 1H), 5.25 (s, 1H), 2.85 (dd, J=6.0, 6.9 Hz, 1H), 2.31 (s, 3H), 2.10 (s, 6H), 1.13 (dd, J=1.9, 6.9 Hz, 6H).

(4-Bromo-2,6-dimethyl-phenyl)-[3-isopropyl-1-(p-tolylsulfonyl)pyrrolo[2,3-c]pyridin-5-yl]methanol (1.11 g, 2.10 mmol), and HI (1.47 g, 6.31 mmol, 0.864 mL, 55% pure) were taken up into a microwave tube in AcOH (24 mL). The sealed tube was heated at 140° C. for 1 h in the microwave. The reaction mixture was quenched by addition of NaHCO$_3$ (sat., aq., 50 mL) at 25° C., then diluted with H$_2$O (20 mL) and extracted with EA (40 mL×2). The combined organic layers were washed with brine (30 mL), dried over Na$_2$SO$_4$, filtered and concentrated under reduced pressure to give a residue. The residue was purified by silica gel chromatography (eluent of 0~15% EA/PE) to give 5-[(4-bromo-2,6-dimethyl-phenyl)methyl]-3-isopropyl-1-(p-tolylsulfonyl)pyrrolo[2,3-c]pyridine (920 mg, 1.80 mmol, 85% yield) as a brown solid. $^1$H NMR (400 MHz, CDCl$_3$) δ 9.12 (s, 1H), 7.72 (d, J=8.4 Hz, 2H), 7.28 (d, J=0.9 Hz, 1H), 7.20 (s, 1H), 7.18 (s, 1H), 7.15 (s, 2H), 6.75 (s, 1H), 4.16 (s, 2H), 2.84 (spt, J=6.8 Hz, 1H), 2.33-2.26 (m, 3H), 2.15 (s, 6H), 1.13 (d, J=6.9 Hz, 6H).

A mixture of 5-[(4-bromo-2,6-dimethyl-phenyl)methyl]-3-isopropyl-1-(p-tolylsulfonyl)pyrrolo[2,3-c]pyridine (340 mg, 398.25 umol), Pin$_2$B$_2$ (202.26 mg, 796.50 umol), Pd(dppf)Cl$_2$·CH$_2$Cl$_2$ (32.52 mg, 39.82 umol), KOAc (97.71 mg, 995.62 umol) in DMSO (5 mL) was degassed and purged with N$_2$ for 3 times, and then the mixture was stirred at 130° C. for 16 hr under N$_2$ atmosphere. The reaction mixture was diluted with H$_2$O (20 mL) and extracted with EA (20 mL×3). The combined organic layers were washed with brine (30 mL), dried over Na$_2$SO$_4$, filtered and concentrated under reduced pressure to give a residue. The crude product was combined with a previous batch, then purified by chromatography on a silica gel eluted with PE:EA (from 1/0 to 6/1) to afford 5-[[2,6-dimethyl-4-(4,4,5,5-tetramethyl-1,3,2-dioxaborolan-2-yl)phenyl]methyl]-3-isopropyl-1-(p-tolylsulfonyl)pyrrolo[2,3-c]pyridine (350 mg, crude) as a white solid. $^1$H NMR (400 MHz, CDCl$_3$) δ 9.12 (d, J=0.8 Hz, 1H), 7.71 (d, J=8.4 Hz, 2H), 7.45 (s, 2H), 7.24 (d, J=1.0 Hz, 1H), 7.17 (s, 2H), 6.71 (s, 1H), 4.23 (s, 2H), 2.79 (td, J=6.5, 13.4 Hz, 1H), 2.29 (s, 3H), 2.17 (s, 6H), 1.29 (s, 12H), 1.10 (d, J=6.8 Hz, 6H).

A mixture of 5-[[2,6-dimethyl-4-(4,4,5,5-tetramethyl-1,3,2-dioxaborolan-2-yl)phenyl]methyl]-3-isopropyl-1-(p-tolylsulfonyl)pyrrolo[2,3-c]pyridine (680 mg, 1.22 mmol), NaIO$_4$ (781.21 mg, 3.65 mmol, 202.39 uL), NH$_4$OAc (281.53 mg, 3.65 mmol) in acetone (20 mL) and H₂O (10 mL) was stirred at 25° C. for 42 hr. The reaction mixture was diluted with H₂O (30 mL) and extracted with EA (30 mL×3). The combined organic layers were washed with brine (20 mL×3), dried over Na₂SO₄, the solids were removed by filtration and the filtrate was concentrated under reduced pressure. The crude was purified by prep-TLC (SiO₂, PE:EA=1:2) to afford 4-[[3-isopropyl-1-(p-tolylsulfonyl)pyrrolo[2,3-c]pyridin-5-yl]methyl]-3,5-dimethyl-phenyl]boronic acid (380 mg, 785.31 umol, 64.5% yield, 98% purity) as a white solid.

A mixture of 6-amino-4-(benzyloxymethyl)-2H-1,2,4-triazine-3,5-dione (186.22 mg, 750.18 umol), [4-[[3-isopropyl-1-(p-tolylsulfonyl)pyrrolo[2,3-c]pyridin-5-yl]methyl]-3,5-dimethyl-phenyl]boronic acid (330 mg, 681.98 umol), pyridine (107.89 mg, 1.36 mmol), 4A MS (5 g, 681.98 umol) and Cu(OAc)₂ (61.93 mg, 340.99 umol) in DMF (10 mL) was degassed and purged with O2 for 3 times, and then the mixture was stirred at 60° C. for 16 hr under O2 atmosphere. EA (60 mL) was added and stirred at 25° C. for 10 min. Then filtered and filtrate was washed with H₂O (20 mL×3), brine (20 mL), dried over Na₂SO₄, filtered and concentrated under reduced pressure. The crude was purified by prep-TLC (SiO₂, PE:EA=1:2) to give 6-amino-4-(benzyloxymethyl)-2-[4-[[3-isopropyl-1-(p-tolylsulfonyl)pyrrolo[2,3-c]pyridine-5-yl]methyl]-3,5-dimethyl-phenyl]-1,2,4-triazine-3,5-dione (120 mg, 138.10 umol, 20% yield, 78% purity) as a yellow gum. ¹H NMR (400 MHz, CDCl₃) δ 9.12 (s, 1H), 7.72 (d, J=8.3 Hz, 3H), 7.35-7.23 (m, 7H), 7.18-7.13 (m, 4H), 6.83 (s, 1H), 5.52 (s, 2H), 4.69 (s, 2H), 4.22 (s, 2H), 2.90-2.81 (m, 2H), 2.30 (s, 4H), 2.22 (s, 6H), 1.13 (d, J=6.9 Hz, 6H).

To a solution of 6-amino-4-(benzyloxymethyl)-2-[4-[[3-isopropyl-1-(p-tolylsulfonyl)pyrrolo[2,3-c]pyridine-5-yl]methyl]-3,5-dimethyl-phenyl]-1,2,4-triazine-3,5-dione (120 mg, 138.10 umol) in DCM (5 mL) was added BBr₃ (276.79 mg, 1.10 mmol, 0.106 mL) at 0° C. The mixture was stirred at 0° C. for 2 h. The reaction mixture was added dropwise to methanol (5 mL) at 0° C. and concentrated under reduced pressure to give 6-amino-2-[4-[[3-isopropyl-1-(p-tolylsulfonyl)pyrrolo[2,3-c]pyridin-5-yl]methyl]-3,5-dimethyl-phenyl]-1,2,4-triazine-3,5-dione (160 mg, crude) as a yellow solid.

To a solution of 6-amino-2-[4-[[3-isopropyl-1-(p-tolylsulfonyl)pyrrolo[2,3-c]pyridin-5-yl]methyl]-3,5-dimethyl-phenyl]-1,2,4-triazine-3,5-dione (160 mg, 286.40 umol) in THF (6 mL) was added TBAF (1 M, 5.73 mL) under N₂. The mixture was stirred at 65° C. for 16 hr. The reaction mixture was quenched by addition of sat. aq. NH₄Cl (10 mL) at 25° C., then diluted with H₂O (10 mL) and extracted with EA (20 mL×3). The combined organic layers were washed with brine (20 mL), dried over anhydrous Na₂SO₄, filtered and concentrated under reduced pressure. The residue was purified by prep-HPLC [Column: Welch Xtimate C18 150×30 mm×5 um; mobile phase: from 15% CH₃CN in water (0.225% FA) to 45% CH₃CN in water (0.225% FA)] to give 6-amino-2-[4-[(3-isopropyl-1H-pyrrolo[2,3-c]pyridin-5-yl)methyl]-3,5-dimethyl-phenyl]-1,2,4-triazine-3,5-dione (12.34 mg, 30.30 umol, 10.6% yield, 99% purity) as a white solid. ¹H NMR (400 MHz, DMSO-d₆) δ 11.15 (br s, 1H), 8.58 (s, 1H), 8.16 (s, 1H), 7.27 (d, J=2.0 Hz, 1H), 7.18 (s, 2H), 7.13 (s, 1H), 6.31 (s, 2H), 4.18 (s, 2H), 3.01 (td, J=7.0, 13.7 Hz, 1H), 2.31 (s, 6H), 1.23 (d, J=6.9 Hz, 6H).

Example 90: Synthesis of Compound 159

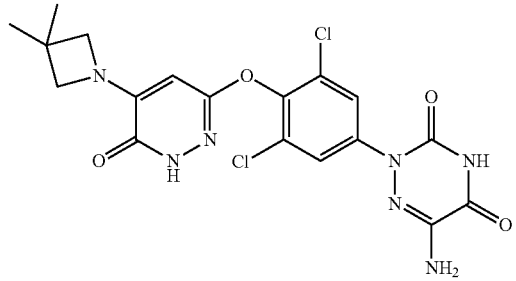 [SMILES: CC1(C)CN(c2cc(Oc3c(Cl)cc(-n4nc(N)c(=O)[nH]c4=O)cc3Cl)n[nH]c2=O)C1]

To a stirred mixture of 3,4,6-trichloropyridazine (4.00 g, 21.808 mmol) and 3,3-dimethylazetidine (2.93 g, 23.989 mmol) in DMF (50 mL) was added K₂CO₃ (9.04 g, 65.424 mmol) in portions at rt. The resulting mixture was stirred for 3 h at 40° C. and quenched with water (150 mL) at rt. The resulting mixture was filtered, the filter cake was washed with water (2×50 mL) and dried under IR lamp to afford 3,6-dichloro-4-(3,3-dimethylazetidin-1-yl)pyridazine (4.6 g, 88.15%) as a white solid. ¹H NMR (300 MHz, CDCl₃) δ 6.21 (s, 1H), 4.00 (s, 4H), 1.38 (s, 6H). LCMS (ESI, m/z): 232 [M+H]⁺.

To a stirred mixture of 3,6-dichloro-4-(3,3-dimethylazetidin-1-yl)pyridazine (4.60 g, 19.818 mmol) in methanol (30 mL) was added NaOCH₃ (1.28 g, 23.693 mmol) dropwise at rt. The resulting mixture was stirred overnight at 60° C. and concentrated under reduced pressure. Then water (60 mL) was added. The resulting mixture was filtered, the filter cake was washed with water (2×40 mL) and dried under IR lamp to afford 6-chloro-4-(3,3-dimethylazetidin-1-yl)-3-methoxypyridazine (4.22 g, 87%) as a white solid. ¹H NMR (300 MHz, CDCl₃) δ 6.02 (s, 1H), 4.03 (s, 3H), 3.86-3.91 (m, 4H), 1.35 (s, 6H). LCMS (ESI, m/z): 228 [M+H]⁺.

To a stirred mixture of 6-chloro-4-(3,3-dimethylazetidin-1-yl)-3-methoxypyridazine (4.00 g, 17.568 mmol), N-(3,5-dichloro-4-hydroxyphenyl)-N,N-dimethylmethanimidamide (4.09 g, 17.568 mmol), Pd₂(dba)₃ (2.73 g, 2.635 mmol) and (R)-1-[(S)-2-(dicyclohexylphosphino)ferrocenyl]ethyldi-t-butylphosphine (1.46 g, 2.631 mmol) in dioxane (80 mL) was added Cs₂CO₃ (11.45 g, 35.135 mmol) in portions at rt. The resulting mixture was stirred overnight at 110° C. under nitrogen. The resulting mixture was concentrated under reduced pressure and diluted with water (60 mL). The resulting mixture was extracted with ethyl acetate (3×120 mL) and the organic layers were combined, washed with brine (2×80 mL), dried over anhydrous sodium sulfate, filtered and concentrated under reduced pressure. The residue was purified by silica gel column chromatography with CH₂Cl₂/methanol (40/1) to afford N-(3,5-dichloro-4-[[5-(3,3-dimethylazetidin-1-yl)-6-methoxypyridazin-3-yl]oxy]phenyl)-N,N-dimethylmethanimidamide (6 g, 74.05%) as a brown solid. ¹H NMR (400 MHz, DMSO-d₆) δ 7.90 (s, 1H), 7.07 (s, 2H), 6.11 (s, 1H), 3.81-3.91 (m, 7H), 2.90-3.05 (m, 6H), 1.26-1.30 (m, 6H). LCMS (ESI, m/z): 424 [M+H]⁺.

To a stirred mixture of N-(3,5-dichloro-4-[[5-(3,3-dimethylazetidin-1-yl)-6-methoxypyridazin-3-yl]oxy]phenyl)-N,N-dimethylmethanimidamide (2.00 g, 4.713 mmol) in CH₃CN (20 mL) was added TMSI (1.89 g, 9.446 mmol) dropwise at rt. The resulting mixture was stirred overnight at 70° C. and quenched by water (50 mL). The resulting solution was extracted with EA (3×60 mL) and the organic layers were combined, washed with brine (2×50 mL), dried over anhydrous sodium sulfate, the solids were removed by filtration and the filtrate was concentrated under reduced pressure. The residue was purified by silica gel column chromatography with $CH_2Cl_2$/methanol (16:1) to afford N-(3,5-dichloro-4-[[5-(3,3-dimethylazetidin-1-yl)-6-oxo-1H-pyridazin-3-yl]oxy]phenyl)-N,N-dimethylmethanimidamide (950 mg, 44.70%) as a yellow solid. $^1$H NMR (400 MHz, DMSO-$d_6$) δ 11.62 (s, 1H), 7.85 (s, 1H), 7.02 (s, 2H), 5.80 (s, 1H), 3.59-4.13 (m, 4H), 3.01 (s, 3H), 2.89 (s, 3H), 1.24 (s, 6H). LCMS (ESI, m z): 410 [M+H]$^+$.

To a stirred solution of N-(3,5-dichloro-4-[[5-(3,3-dimethylazetidin-1-yl)-6-oxo-1H-pyridazin-3-yl]oxy]phenyl)-N,N-dimethylmethanimidamide (950.00 mg, 2.315 mmol) in ethanol (10 mL) was added ethylenediamine (626.19 mg, 10.419 mmol) dropwise at rt. The resulting mixture was stirred overnight at 70° C. and concentrated under reduced pressure. The residue was purified by silica gel column chromatography with $CH_2Cl_2$/methanol (49/1) to afford 6-(4-amino-2,6-dichlorophenoxy)-4-(3,3-dimethylazetidin-1-yl)-2H-pyridazin-3-one (420 mg, 49.53%) as a yellow solid. $^1$H NMR (400 MHz, DMSO-$d_6$) δ 11.59 (s, 1H), 6.60 (s, 2H), 5.74 (s, 1H), 5.53 (s, 2H), 3.86 (br, 4H), 1.24 (s, 6H). LCMS (ESI, m/z): 355 [M+H]$^+$.

To a stirred solution of 6-(4-amino-2,6-dichlorophenoxy)-4-(3,3-dimethylazetidin-1-yl)-2H-pyridazin-3-one (250.00 mg, 0.706 mmol) in HCl (8.0 mL), acetic acid (22 mL) and water (16 mL) was added sodium nitrite (102.0 mg, 1.483 mmol) in water (2 mL), dropwise at 0° C. The resulting mixture was stirred for 45 min at 0° C. Ethyl N-(2-cyanoacetyl)carbamate (165.0 mg, 1.059 mmol) in water (52 mL) and pyridine (8 mL) was stirred for 10 min at 0° C. Put the above solution to this mixture and the resulting mixture was stirred for 1 h at 0° C. The resulting mixture was filtered, the filter cake was washed with water (2×10 mL) and dried under IR lamp to afford ethyl (2-cyano-2-(2-(3,5-dichloro-4-((5-(3,3-dimethylazetidin-1-yl)-6-oxo-1,6-dihydropyridazin-3-yl)oxy)phenyl)hydrazineylidene)acetyl)carbamate (300 mg, crude) as a yellow solid. $^1$H NMR (400 MHz, DMSO-$d_6$) δ 12.07-12.10 (m, 1H), 11.66 (s, 1H), 10.90 (s, 1H), 7.93 (s, 2H), 5.83 (s, 1H), 4.15-4.22 (m, 2H), 3.61-4.01 (m, 4H), 1.26 (s, 9H). LCMS (ESI, m z): 522 [M+H]$^+$.

To a stirred mixture of ethyl (2-cyano-2-(2-(3,5-dichloro-4-((5-(3,3-dimethylazetidin-1-yl)-6-oxo-1,6-dihydropyridazin-3-yl)oxy)phenyl)hydrazineylidene)acetyl)carbamate (300 mg, 0.574 mmol) in DMA (8 mL) was added KOAc (225.47 mg, 2.297 mmol) in portions at rt. The resulting mixture was stirred for 6 h at 110° C. and quenched by water (15 mL) at rt. The mixture was extracted with ethyl acetate (3×40 mL) and the organic layers were combined, washed with brine (2×40 mL), dried over anhydrous sodium sulfate, filtered and concentrated under reduced pressure to afford 2-(3,5-dichloro-4-[[5-(3,3-dimethylazetidin-1-yl)-6-oxo-1H-pyridazin-3-yl]oxy]phenyl)-3,5-dioxo-4H-1,2,4-triazine-6-carbonitrile (300 mg, crude) as a yellow solid. $^1$H NMR (400 MHz, DMSO-$d_6$) δ 13.27 (s, 1H), 11.70 (s, 1H), 7.73 (s, 2H), 5.91 (s, 1H), 3.92 (br, 4H), 1.27 (s, 6H). LCMS (ESI, m z): 476 [M+H]$^+$.

To a stirred mixture of 2-(3,5-dichloro-4-[[5-(3,3-dimethylazetidin-1-yl)-6-oxo-1H-pyridazin-3-yl]oxy]phenyl)-3,5-dioxo-4H-1,2,4-triazine-6-carbonitrile (180.00 mg, 0.378 mmol) in methanol (4 mL) was added NaOH (8 mL, 2M) dropwise at rt. The resulting mixture was stirred for 30 min at 55° C. and diluted with water (30 mL) at rt. The resulting mixture was extracted with EA (3×50 mL) and the organic layers were combined, were washed with brine (2×40 mL), dried over anhydrous sodium sulfate, filtered and concentrated under reduced pressure to afford 2-(3,5-dichloro-4-[[5-(3,3-dimethylazetidin-1-yl)-6-oxo-1H-pyridazin-3-yl]oxy]phenyl)-3,5-dioxo-4H-1,2,4-triazine-6-carboxylic acid (180 mg, crude) as a yellow solid. LCMS (ESI, m/z): 495 [M+H]$^+$.

To a stirred mixture of 2-(3,5-dichloro-4-[[5-(3,3-dimethylazetidin-1-yl)-6-oxo-1H-pyridazin-3-yl]oxy]phenyl)-3,5-dioxo-4H-1,2,4-triazine-6-carboxylic acid (180.00 mg, 0.363 mmol) and triethylamine (147.11 mg, 1.454 mmol) in t-butanol (5 mL) was added diphenylphosphoryl azide (300.05 mg, 1.090 mmol) dropwise at rt. The resulting mixture was stirred for overnight at 85° C. The resulting mixture was concentrated under reduced pressure. The residue was extracted with EA (3×40 mL) and the organic layers were combined, washed with brine (2×30 mL), dried over anhydrous sodium sulfate, the solids were removed by filtration and the filtrate was concentrated under reduced pressure. The residue was purified by silica gel column chromatography, eluted with dichloromethane/methanol (24/1) to afford t-butyl N-[2-(3,5-dichloro-4-[[5-(3,3-dimethylazetidin-1-yl)-6-oxo-1H-pyridazin-3-yl]oxy]phenyl)-3,5-dioxo-4H-1,2,4-triazin-6-yl]carbamate (48 mg, 18%) as a yellow solid. $^1$H NMR (400 MHz, CDCl$_3$) δ 12.79 (s, 1H), 11.13 (s, 1H), 7.59 (s, 1H), 7.55 (s, 2H), 5.72 (s, 1H), 4.02 (s, 4H), 1.51 (s, 9H), 1.25 (s, 6H). LCMS (ESI, m/z): 566 [M+H]$^+$.

To a stirred solution of t-butyl N-[2-(3,5-dichloro-4-[[5-(3,3-dimethylazetidin-1-yl)-6-oxo-1H-pyridazin-3-yl]oxy]phenyl)-3,5-dioxo-4H-1,2,4-triazin-6-yl]carbamate (38.00 mg, 0.067 mmol) in $CH_2Cl2$ (5 mL) was added TFA (1 mL) dropwise at rt. The resulting mixture was stirred for 2 h at rt and concentrated under reduced pressure. The residue was purified by prep-HPLC with the following conditions (Column: XBridge Prep Phenyl OBD, 19×150 mm Sum 13 nm; Mobile Phase A: water (10 MMOL/L NH$_4$CO$_3$+0.1% NH$_4$OH), Mobile Phase B: Acetonitrile; Flow rate: 25 mL/min; Gradient: 20 B to 39 B in 8 min; 254 nm; RT1:6.52) to afford 6-amino-2-(3,5-dichloro-4-[[5-(3,3-dimethylazetidin-1-yl)-6-oxo-1H-pyridazin-3-yl]oxy]phenyl)-4H-1,2,4-triazine-3,5-dione (8.1 mg, 26%) as a white solid. $^1$H NMR (300 MHz, DMSO-$d_6$) δ 11.67 (br, 2H), 7.79 (s, 2H), 6.44 (s, 2H), 5.87 (s, 1H), 3.77 (br, 4H), 1.27 (s, 6H). LCMS (ESI, m/z): 466 [M+H]$^+$.

Example 91: Synthesis of Compound 160

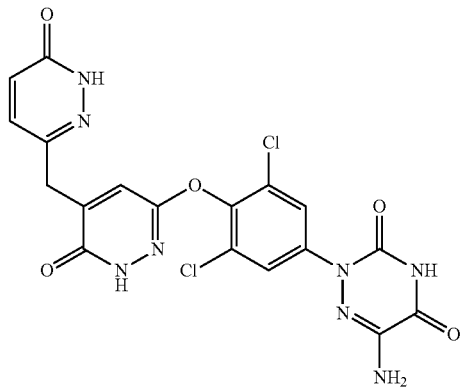 [SMILES: Nc1nn(-c2cc(Cl)c(Oc3cc(Cc4ccc(=O)[nH]n4)c(=O)[nH]n3)c(Cl)c2)c(=O)[nH]c1=O]

A 500 mL autoclave was charged with 3-chloro-6-methoxypyridazine (50.00 g, 345.877 mmol), Pd(dppf)Cl$_2$ (15.18 g, 20.753 mmol), triethylamine (12.25 g, 121.057 mmol) and methanol (150 mL), and CO (30 atm). The reaction was stirred at 60° C. for 3 days. The resulting solution was concentrated under reduced pressure to get the residue. The residue was chromatographed on a silica gel column with PE/EA (3/1) to get methyl 6-methoxy-pyridazine-3-carboxylate (16.4 g, 27%) as a white solid. $^1$H NMR (300 MHz, CDCl$_3$) δ 8.10 (d, J=9.0 Hz, 1H), 7.07 (d, J=9.0 Hz, 1H), 4.25 (s, 3H), 4.06 (s, 3H). LCMS (ESI, m/z): 169 [M+H]$^+$.

To a solution of methyl 6-methoxypyridazine-3-carboxylate (16.40 g, 97.531 mmol) in methanol (55 mL) and THF (275 mL) was added NaBH$_4$ (11.07 g, 292.592 mmol) and CaCl$_2$ (10.82 g, 97.531 mmol) in portions. The reaction was stirred at rt for 1 h and quenched with water and concentrated under reduced pressure. The residue was chromatographed on a silica gel column with methanol/CH$_2$Cl$_2$ (1/17) to get (6-methoxypyridazin-3-yl)methanol (10.5 g, 73%) as a brown oil. $^1$H NMR (300 MHz, methanol-d$_4$) δ 7.24 (d, J=9.0 Hz, 1H), 7.22 (d, J=9.0 Hz, 1H), 4.79 (s, 2H), 4.10 (s, 3H). LCMS (ESI, m/z): 141 [M+H]$^+$.

To a solution of (6-methoxypyridazin-3-yl)methanol (10.20 g, 72.783 mmol) in dichloromethane (500 mL) was added Dess-Martin periodinane (43.22 g, 101.897 mmol). The reaction was stirred at rt for 16 h and quenched with water (200 mL). The resulting solution was extracted with CH$_2$Cl$_2$ (3×200 mL) and the organic layers were combined, washed with brine (2×100 mL), dried over anhydrous sodium sulfate, the solids were removed by filtration and the filtrate was concentrated under reduced pressure. The residue was chromatographed on a silica gel column with EA/PE (1/3) to provide 6-methoxypyridazine-3-carbaldehyde (7.5 g, 67%) as a yellow solid. $^1$H NMR (300 MHz, CDCl$_3$) δ 10.27 (s, 1H), 7.97 (d, J=9.0 Hz, 1H), 7.12 (d, J=9.0 Hz, 1H), 4.29 (s, 3H). LCMS (ESI, m/z): 139 [M+H]$^+$.

To a solution of 2,2,6,6-tetramethylpiperidine (6.83 g, 48.332 mmol) in THF (100 mL) was added n-butyllithium (17.7 mL, 2.5M in hexane, 44.304 mmol) at −85° C. under nitrogen and then the solution was allowed to warm to 0° C. and stirred for 30 min. Then the solution was cooled to −85° C. and a solution of 3,6-dichloropyridazine (6 g, 40.277 mmol) in THF (25 mL) was added. The reaction was stirred at −85° C. for 30 min and a solution of 6-methoxy-pyridazine-3-carbaldehyde (6.12 g, 44.304 mmol) in THF (25 mL) was added. The resulting solution was stirred at −85° C. for 1 h and quenched with NH$_4$Cl (aq., 100 mL). The resulting solution was extracted with EA (3×100 mL) and the organic layers were combined, washed with brine (1×100 mL), dried over anhydrous sodium sulfate, filtered and concentrated under reduced pressure. The residue was chromatographed on a silica gel column with EA/PE (2/3) to get the crude product. The crude product was purified by C18 column (CH$_3$CN/water=1/3) to provide (3,6-dichloro-pyridazin-4-yl)(6-methoxypyridazin-3-yl)methanol (2.38 g, 18.52%) as a brown solid. $^1$H NMR (300 MHz, CDCl$_3$) δ 7.94 (s, 1H), 7.52 (d, J=9.0 Hz, 1H), 7.13 (d, J=9.0 Hz, 1H), 6.27 (s, 1H), 4.76 (b, 1H), 4.29 (s, 3H). LCMS (ESI, m/z): 287 [M+H]$^+$.

To a solution of (3,6-dichloropyridazin-4-yl)(6-methoxypyridazin-3-yl)methanol (4 g, 13.93 mmol) in CH$_2$Cl2 (160 mL) was added 2,6-lutidine (5.9718 g, 55.73 mmol) and sulfurous dichloride (3.3151 g, 27.86 mmol). The reaction was stirred at rt for 16 h and quenched with water (100 mL). The resulting solution was extracted with CH$_2$Cl$_2$ (3×100 mL) and the organic layers were combined, washed with brine (2×100 mL), dried over anhydrous sodium sulfate, the solids were removed by filtration and the filtrate was concentrated under reduced pressure. The residue was chromatographed on a silica gel column with EA/PE (1/3) to get 3,6-dichloro-4-[chloro(6-methoxypyridazin-3-yl)methyl]pyridazine (2.6 g, 61.2%) as a yellow oil. $^1$H NMR (300 MHz, CDCl$_3$) δ 8.07 (s, 1H), 7.65 (d, J=9.0 Hz, 1H), 7.12 (d, J=9.0 Hz, 1H), 6.43 (s, 1H), 4.16 (s, 3H). LCMS (ESI, m/z): 305 [M+H]$^+$.

To a solution of 3,6-dichloro-4-[chloro(6-methoxy-pyridazin-3-yl)methyl]pyridazine (2.600 g, 8.510 mmol) in toluene (104 mL) was added tributyltin hydride (4954 mg, 17.019 mmol) and 2,2'-azobis(2-methylpropionitrile) (279.47 mg, 1.702 mmol). The reaction was stirred at 100° C. for 16 h and quenched with water (100 mL). The mixture was extracted with ethyl acetate (3×100 mL) and the organic layers were combined, washed with brine (100 mL), dried over anhydrous sodium sulfate, the solids were removed by filtration and the filtrate was concentrated under reduced pressure. The residue was chromatographed on a silica gel column with EA/PE (1/2) to get 3,6-dichloro-4-[(6-methoxypyridazin-3-yl)methyl]pyridazine (1.9 g, 76%) as a yellow oil. $^1$H NMR (300 MHz, CDCl$_3$) δ 7.55 (s, 1H), 7.41 (d, J=6.0 Hz, 1H), 7.05 (d, J=6.0 Hz, 1H), 4.35 (s, 2H), 4.16 (s, 3H). LCMS (ESI, m/z): 271 [M+H]$^+$.

To a solution of 3,6-dichloro-4-[(6-methoxypyridazin-3-yl)methyl]pyridazine (1.100 g, 4.058 mmol) and 4-amino-2,6-dichlorophenol (866.74 mg, 4.869 mmol) in DMSO (22 mL) was added K$_2$CO$_3$ (1401.94 mg, 10.144 mmol). The reaction was stirred at 90° C. for 8 h and quenched with water (100 mL). The mixture was extracted with EA (3×100 mL) and the organic layers were combined, washed with brine (1×50 mL), dried over anhydrous sodium sulfate, the solids were removed by filtration and the filtrate was concentrated under reduced pressure. The residue was chromatographed on a silica gel column with EA/PE (1/2) to afford 3,5-dichloro-4-([6-chloro-5-[(6-methoxypyridazin-3-yl)methyl]pyridazin-3-yl]oxy)aniline (430 mg, 25%) as brown solid. $^1$H NMR (300 MHz, DMSO-d$_6$) δ 7.68-7.71 (m, 2H), 7.26 (d, J=9.0 Hz, 1H), 6.72 (s, 2H), 4.97 (b, 2H), 4.40 (s, 2H), 3.99 (s, 3H). LCMS (ESI, m/z): 412 [M+H]$^+$.

To a solution of 3,5-dichloro-4-([6-chloro-5-[(6-methoxy-pyridazin-3-yl)methyl]pyridazin-3-yl]oxy)aniline (435.00 mg, 1.054 mmol) in water (32 mL), conc. HCl (12 mL) and acetic acid (36 mL) was added sodium nitrite (152.73 mg, 2.214 mmol) in water (5 mL) dropwise at 0° C. After the addition, the reaction was stirred at 0° C. for 45 min. Then the reaction mixture was added to a solution of ethyl N-(2-cyanoacetyl)carbamate (246.89 mg, 1.581 mmol) in water (32 mL) and pyridine (14 mL) at 0° C. quickly. The resulting mixture was stirred at 0° C. for 1 h and filtered. The filter cake was dried under IR lamp to get ethyl (2-cyano-2-(2-(3,5-dichloro-4-((6-chloro-5-((6-methoxypyridazin-3-yl)methyl)pyridazin-3-yl)oxy)phenyl)hydrazineylidene)acetyl)carbamate (410 mg, 62.01%) as a brown yellow solid. LCMS (ESI, m/z): 579 [M+H]$^+$.

To a solution of ethyl (2-cyano-2-(2-(3,5-dichloro-4-((6-chloro-5-((6-methoxypyridazin-3-yl)methyl)pyridazin-3-yl)oxy)phenyl)hydrazineylidene)acetyl)carbamate (410.00 mg, 0.707 mmol) in acetic acid (10 mL) was added sodium acetate (290.3 mg, 3.54 mmol). The reaction was stirred at 105° C. for 4 h and cooled to rt. The reaction was poured into water (100 mL) and filtered. The filter cake was dissolved in DMF and purified by C18 column (CH$_3$CN/water=2/3) to get 2-[3,5-dichloro-4-([5-[(6-methoxypyridazin-3-yl)methyl]-6-oxo-1H-pyridazin-3-yl]oxy)phenyl]-3,5-dioxo-4H-1,2,4-triazine-6-carbonitrile (270 mg, 67%) as a brown solid. $^1$H NMR (300 MHz, methanol-d$_4$) δ 7.83-7.87 (m, 2H), 7.78 (s, 2H), 7.56 (s, 1H), 4.15 (s, 3H), 2.05 (s, 2H). LCMS (ESI, m/z): 515 [M+H]$^+$.

A solution of 2-[3,5-dichloro-4-([5-[(6-methoxy-pyridazin-3-yl)methyl]-6-oxo-1H-pyridazin-3-yl]oxy)phenyl]-3,5-dioxo-4H-1,2,4-triazine-6-carbonitrile (160.00 mg, 0.311 mmol) in acetic acid (5 mL) and conc. HCl (aq. 2.5 mL) was stirred at 105° C. for 3 h. The pH value of the reaction mixture was adjusted to 10 with NaHCO$_3$ (sat., aq.) and extracted with EA (2×20 mL) and the organic layers were discarded. The pH value of the aqueous layers was adjusted to 4 with conc. HCl and extracted with isopropanol/CHCl$_3$ (1/3) (2×50 ml). The organic layers were combined, dried over anhydrous sodium sulfate, filtered and concentrated under reduced pressure to get 2-[3,5-dichloro-4-([5-[(6-hydroxypyridazin-3-yl)methyl]-6-oxo-1H-pyridazin-3-yl]oxy)phenyl]-3,5-dioxo-4H-1,2,4-triazine-6-carboxylic acid (120 mg, 66.8%) as a brown solid. LCMS (ESI, m/z): 520 [M+H]$^+$.

To a solution of 2-[3,5-dichloro-4-([6-oxo-5-[(6-oxo-1H-pyridazin-3-yl)methyl]-1H-pyridazin-3-yl]oxy)phenyl]-3,5-dioxo-4H-1,2,4-triazine-6-carboxylic acid (110 mg, 0.211 mmol) in t-butanol (4 mL) was added DPPA (174.57 mg, 0.634 mmol) and triethylamine (85.58 mg, 0.846 mmol). The reaction was stirred at 80° C. for 16 h and concentrated under reduced pressure. The residue was dissolved in EA (50 mL). The resulting mixture was washed with sodium bicarbonate solution (3×30 mL) and brine. The combined organic layers were dried over anhydrous sodium sulfate. After filtration, the filtrate was concentrated under reduced pressure to afford t-butyl N-[2-[3,5-dichloro-4-([6-oxo-5-[(6-oxo-1H-pyridazin-3-yl)methyl]-1H-pyridazin-3-yl]oxy)phenyl]-3,5-dioxo-4H-1,2,4-triazin-6-yl]carbamate (60 mg, 38%) as a white solid. LCMS (ESI, m/z): 591 [M+H]$^+$.

To a solution of t-butyl N-[2-[3,5-dichloro-4-([6-oxo-5-[(6-oxo-1H-pyridazin-3-yl)methyl]-1H-pyridazin-3-yl]oxy)phenyl]-3,5-dioxo-4H-1,2,4-triazin-6-yl]carbamate (60 mg, 0.101 mmol) in CH$_2$Cl$_2$ (5 mL) was added TFA (2 mL). The reaction was stirred at rt for 2 h and concentrated under reduced pressure. The residue was purified by Pre-HPLC (Column: XBridge Shield RP18 OBD Column, 19×250 mm, 10 μm; Mobile Phase A: Water (10 MMOL/L NH$_4$HCO$_3$+ 0.1% NH$_3$·H$_2$O), Mobile Phase B: CH$_3$CN; Flow rate: 25 mL/min; Gradient: 10 B to 35 B in 7 min; 220 nm; RT1:6.35) to get 6-amino-2-[3,5-dichloro-4-([6-oxo-5-[(6-oxo-1H-pyridazin-3-yl)methyl]-1H-pyridazin-3-yl]oxy)phenyl]-4H-1,2,4-triazine-3,5-dione (5.7 mg, 11.32%) as a white solid. $^1$H NMR (300 MHz, DMSO-d$_6$) δ 7.86 (s, 2H), 7.56 (s, 1H), 7.47 (d, J=9.6 Hz, 1H), 6.88 (d, J=9.6 Hz, 1H), 6.48 (s, 2H), 3.83 (s, 2H). LCMS (ESI, m/z): 491 [M+H]$^+$.

Example 92: Synthesis of Compound 161

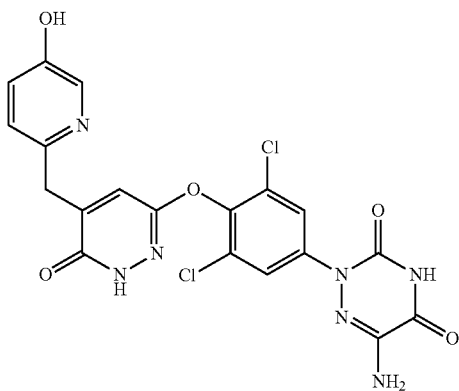 [SMILES: Nc1nn(-c2cc(Cl)c(Oc3cc(Cc4ccc(O)cn4)c(=O)[nH]n3)c(Cl)c2)c(=O)[nH]c1=O]

Potassium t-butoxide (43.19 g, 384.869 mmol) was added to 6-methylpyridin-3-ol (40.00 g, 366.542 mmol) in THF (1.6 L) at 0° C. The mixture was stirred at rt for 30 min. CH$_3$I (54.63 g, 384.869 mmol) was added dropwise at 0° C., and stirring was continued at rt for overnight. Water (500 mL) was added and the mixture was evaporated to half its volume and extracted with ethyl acetate (3×500 mL). The combined organic layers were washed with brine, dried over anhydrous sodium sulfate, and filtered. The filtrate was concentrated under reduced pressure. The residue was chromatographed on a silica gel column with EA/PE (1/3) to give 5-methoxy-2-methylpyridine (17.5 g, 36.8%). $^1$H NMR (300 MHz, Methanol-d$_4$) δ 8.09 (d, J=3.0 Hz, 1H), 7.33 (dd, J=8.6, 3.0 Hz, 1H), 7.22 (d, J=8.6 Hz, 1H), 3.86 (s, 3H), 2.46 (s, 3H). LCMS (ESI, m z): 124 [M+H]$^+$.

To a solution of 2,2,6,6-tetramethylpiperidine (13.76 g, 97.438 mmol) in THF (75 mL) was added n-butyllithium (39 mL, 2.5M in hexane, 97.438 mmol) at −75° C. under nitrogen and then the solution was allowed to warm to 0° C. and stirred for 30 min. Then the solution was cooled to −75° C. and a solution of 5-methoxy-2-methylpyridine (10.00 g, 81.198 mmol) in THF (75 mL) was added. The reaction was stirred at −75° C. for 30 min and a solution of 3,4,6-trichloropyridazine (17.87 g, 97.438 mmol) in THF (50 mL) was added. The resulting solution was stirred at −75° C. for 1 h. The reaction was quenched with NH$_4$C$_1$ (aq., 100 mL). The resulting solution was extracted with EA (3×300 mL) and the organic layers were combined, washed with brine (1×100 mL), dried over anhydrous sodium sulfate, filtered and concentrated under reduced pressure. The residue was chromatographed on a silica gel column with EA/PE (1/3) to get 3,6-dichloro-4-[(5-methoxypyridin-2-yl)methyl]pyridazine (3.2 g, 13.8%) as a light brown solid. $^1$H NMR (300 MHz, methanol-d$_4$) δ 8.19-8.20 (m, 1H), 7.67 (s, 1H), 7.33-7.48 (m, 2H), 4.26 (s, 2H), 3.89 (s, 3H). LCMS (ESI, m/z): 270 [M+H]$^+$.

To a solution of 3,6-dichloro-4-[(5-methoxypyridin-2-yl)methyl]pyridazine (3.20 g, 11.847 mmol) in DMSO (90 mL) was added 4-amino-2,6-dichlorophenol (2.53 g, 14.216 mmol) and potassium carbonate (4.91 g, 35.541 mmol). The mixture was stirred at 90° C. for 2 h and quenched with water (100 mL). The resulting solution was extracted with EA (3×200 mL) and the organic layers were combined, washed with brine, dired over anhyrous sodium sulfate, filtered and concentrated under reduced pressure. The residue was chromatographed on a C$_{18}$ column with acetonitrile/water (2/3) to get 3,5-dichloro-4-([6-chloro-5-[(5-methoxypyridin-2-yl)methyl]pyridazin-3-yl]oxy)aniline (1.51 g, 165.13%) as a brown solid. $^1$H NMR (300 MHz, DMSO-d$_6$) δ 8.27 (s, 1H), 7.55 (s, 1H), 7.39-7.52 (m, 2H), 6.70 (s, 2H), 4.80 (br, 2H), 4.26 (s, 2H), 3.83 (s, 3H). LCMS (ESI, m/z): 411 [M+H]$^+$.

To a solution of 3,5-dichloro-4-([6-chloro-5-[(5-methoxypyridin-2-yl)methyl]pyridazin-3-yl]oxy)aniline (1.50 g, 3.635 mmol) in acetic acid (130 mL), concentrated HCl (45 mL) and water (100 mL) was added sodium nitrite solution (0.53 g, 7.633 mmol) in water (10 mL) dropwise at 0° C. Then the reaction was stirred at 0° C. for 45 min. Then the reaction mixture was added to the mixture of ethyl N-(2-cyanoacetyl)carbamate (0.85 g, 5.452 mmol) in pyridine (50 mL) and water (100 mL) at 0° C. quickly. The resulting mixture was stirred for 30 min at 0° C. The precipitated solids were collected by filtration and washed with water and PE (50 mL) to afford ethyl (2-cyano-2-(2-(3,5-dichloro-4-((6-chloro-5-((5-methoxypyridin-2-yl)methyl)pyridazin-3-yl)oxy)phenyl)hydrazineylidene)acetyl)carbamate (1.03 g, 45.5%) as a yellow solid. LCMS (ESI, m/z): 578 [M+H]$^+$.

To a solution of ethyl (2-cyano-2-(2-(3,5-dichloro-4-((6-chloro-5-((5-methoxypyridin-2-yl)methyl)pyridazin-3-yl)oxy)phenyl)hydrazineylidene)acetyl)carbamate (1.00 g, 1.785 mmol) in acetic acid (30 mL) was added sodium acetate (0.73 g, 8.923 mmol). The mixture was stirred at 105° C. for 3 h and quenched with water (100 mL). The precipitated solids were collected by filtration and washed with water and PE (20 mL). The residue was chromatographed on a $C_{18}$ column with $CH_3CN$/water (2/3) to get 2-[3,5-dichloro-4-([5-[(5-methoxypyridin-2-yl)methyl]-6-oxo-1H-pyridazin-3-yl]oxy)phenyl]-3,5-dioxo-4H-1,2,4-triazine-6-carbonitrile (200 mg, 20.27%) as a brown solid. LCMS (ESI, m/z): 514 [M+H]$^+$.

To a solution of 2-[3,5-dichloro-4-([5-[(5-methoxypyridin-2-yl)methyl]-6-oxo-1H-pyridazin-3-yl]oxy)phenyl]-3,5-dioxo-4H-1,2,4-triazine-6-carbonitrile (200.00 mg, 0.390 mmol) in acetic acid (4 mL) was added concentrated hydrochloric acid (2 mL). The mixture was stirred at 105° C. for 3 h. The pH of the reaction mixture was adjusted to 10 with $NaHCO_3$ (sat., aq.) and extracted with EA (2×20 mL) and the organic layers were discarded. The pH value of the aqueous layers was adjusted to 4 with concentrated hydrochloride acid and extracted with isopropanol/chloroform (1/3) (2×50 ml). The organic layers were combined, dried over anhydrous sodium sulfate, the solids were removed by filtration and the filtrate was concentrated under reduced pressure to afford 2-[3,5-dichloro-4-([5-[(5-methoxypyridin-2-yl)methyl]-6-oxo-1H-pyridazin-3-yl]oxy)phenyl]-3,5-dioxo-4H-1,2,4-triazine-6-carboxylic acid (200 mg, 77.15%) as a yellow solid. LCMS (ESI, m/z): 533 [M+H]$^+$.

To a solution of 2-[3,5-dichloro-4-([5-[(5-methoxypyridin-2-yl)methyl]-6-oxo-1H-pyridazin-3-yl]oxy)phenyl]-3,5-dioxo-4H-1,2,4-triazine-6-carboxylic acid (200 mg, 0.375 mmol) in t-butyl alcohol (8 mL) was added DPPA (309.63 mg, 1.125 mmol), triethylamine (151.80 mg, 1.500 mmol). The mixture was stirred at 85° C. overnight and concentrated under reduced pressure. The residue was dissolved in EA (50 mL). The resulting mixture was washed with sodium bicarbonate solution (3×30 mL) and brine. The combined organic layers were dried over anhydrous sodium sulfate. The solids were removed by filtration, and the filtrate was concentrated under reduced pressure. The residue was chromatographed on a C18 column with $CH_3CN$/water (1/2) to afford t-butyl N-[2-[3,5-dichloro-4-([5-[(5-methoxypyridin-2-yl)methyl]-6-oxo-1H-pyridazin-3-yl]oxy)phenyl]-3,5-dioxo-4H-1,2,4-triazin-6-yl]carbamate (112 mg, 47.38%) as a brown solid. LCMS (ESI, m/z): 604 [M+H]$^+$.

To a solution of t-butyl N-[2-[3,5-dichloro-4-([5-[(5-methoxypyridin-2-yl)methyl]-6-oxo-1H-pyridazin-3-yl]oxy)phenyl]-3,5-dioxo-4H-1,2,4-triazin-6-yl]carbamate (50.00 mg, 0.083 mmol) in $CH_2Cl_2$ (3 mL) was added BBr3 (414.50 mg, 1.655 mmol) at 0° C. The mixture was stirred at rt for 2 days. The reaction mixture was quenched with methanol and concentrated under reduced pressure. The residue was purified by preparatory HPLC (Column: XSelect CSH Prep C18 OBD, 19×250 mm, 5 μm; Mobile Phase A: Water (10 MMOL/L $NH_4CO_3$+0.1% $NH_4OH$), Mobile Phase B: $CH_3CN$; Flow rate: 25 mL/min; Gradient: 10 B to 30 B in 8 min; 254 nm; RT1:6.65) to get 6-amino-2-[3,5-dichloro-4-([5-[(5-hydroxypyridin-2-yl)methyl]-6-oxo-1H-pyridazin-3-yl]oxy)phenyl]-4H-1,2,4-triazine-3,5-dione (8 mg, 19.41%) as awhite solid. $^1$H NMR (400 MHz, DMSO-$d_6$) δ 12.26 (br, 2H), 9.82 (br, 1H), 8.07 (d, J=2.8 Hz, 1H), 7.85 (s, 2H), 7.13-7.28 (m, 3H), 6.49 (br, 2H), 3.89 (s, 2H). LCMS (ESI, m/z): 490 [M+H]$^+$.

Example 93: Synthesis of Compound 162

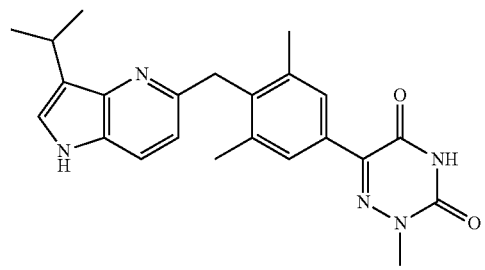

A mixture of 5-[[2,6-dimethyl-4-(4,4,5,5-tetramethyl-1,3,2-dioxaborolan-2-yl)phenyl]methyl]-3-isopropyl-1-(p-tolylsulfonyl)pyrrolo[3,2-b]pyridine (200 mg, 322.27 umol, 90% purity), 6-bromo-2-methyl-1,2,4-triazine-3,5-dione (69.71 mg, 338.38 umol), $K_2CO_3$ (89.08 mg, 644.54 umol) and palladium; triphenylphosphane (74.48 mg, 64.45 umol) in dioxane (8 mL) and $H_2O$ (1.6 mL) was stirred at 110° C. for 12 hr under $N_2$. The reaction mixture was cooled down, diluted with $H_2O$ (30 mL) and extracted with EA (30 mL×2). The combined organic layers were washed with brine (30 mL), dried over anhydrous $Na_2SO_4$, filtered and concentrated under reduced pressure to give a residue. The residue was purified by silica gel chromatography (Eluent of 0-50% EA/PE) to give 6-[4-[[3-isopropyl-1-(p-tolylsulfonyl)pyrrolo[3,2-b]pyridin-5-yl]methyl]-3,5-dimethyl-phenyl]-2-methyl-1,2,4-triazine-3,5-dione (96 mg, 106.73 umol, 33.12% yield, 62% purity) as a yellow solid.

To a solution of 6-[4-[[3-isopropyl-1-(p-tolylsulfonyl)pyrrolo[3,2-b]pyridin-5-yl]methyl]-3,5-dimethyl-phenyl]-2-methyl-1,2,4-triazine-3,5-dione (96 mg, 172.15 umol) in THF (8 mL) was added TBAF (1 M, 1.38 mL) at 20° C. After the addition, the mixture was stirred at 65° C. for 12 h. LCMS showed the starting material was consumed completely and 29% desired mass was detected. The reaction mixture was diluted with sat. aq. $NH_4C_1$ (120 mL) and extracted with EA (30 mL×2). The combined organic layers were washed with brine (30 mL), dried over anhydrous $Na_2SO_4$, filtered and concentrated under reduced pressure to give a residue. The residue was purified by prep-HPLC [Column: Phenomenex luna C18 80×40 mm×3 um; mobile phase: from 15% $CH_3CN$ in water (0.05% HCl) to 45% $CH_3CN$ in water (0.05% HCl)] to give 6-[4-[(3-isopropyl-1H-pyrrolo[3,2-b] pyridin-5-yl)methyl]-3,5-dimethyl-phenyl]-2-methyl-1,2,4-triazine-3,5-dione]0.6-[4-[(3-isopropyl-1H-pyrrolo[3,2-b]pyridin-5-yl)methyl]-3,5-dimethyl-phenyl]-2-methyl-1,2,4-triazine-3,5-dione (14.07 mg, 33.87 umol, 19.68% yield, 97.13% purity) as a white solid.

Example 94: Synthesis of Compounds 163 and 164

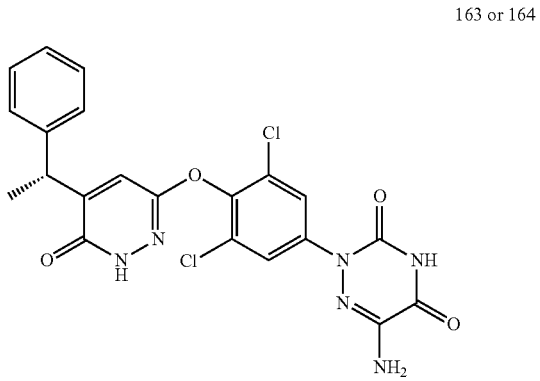

163 or 164

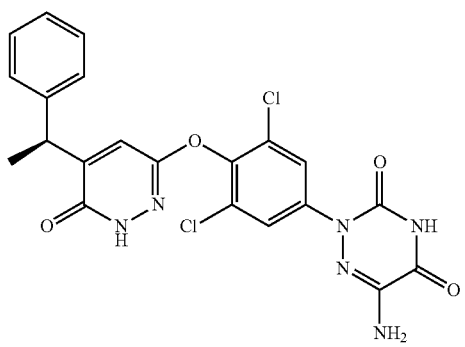

163 or 164

6-Amino-2-(3,5-dichloro-4-((6-oxo-5-(1-phenylethyl)-1,6-dihydropyridazin-3-yl)oxy)phenyl)-1,2,4-triazine-3,5(2H,4H)-dioneSynthesis of 6-bromo-4-isopropyl-1,5-naphthyridin-2(1H)-one was synthesized using a method analogous to that described for the synthesis of 6-amino-2-(3,5-dichloro-4-((5-(2-fluoro-3-methylphenyl)-6-oxo-1,6-dihydropyridazin-3-yl)oxy)phenyl)-1,2,4-triazine-3,5(2H,4H)-dione where (1-phenylvinyl)boronic acid was employed instead of (2-fluoro-3-methylphenyl)boronic acid.

The crude product (200 mg) was purified by preparative HPLC (Column: CHIRALPAK IE-3, 4.6×50 mm, 3 μm, Hexane (0.1% TFA): EtOH=55:45, flow rate: 1 mL/min) to provide the first eluting enantiomer (Rt: 2.340 min), compound 163 (37.9 mg, 19.69%), as a white solid. And the second eluting isomer (Rt: 2.903 min), compound 164 (41.5 mg, 21.65%) as a white solid. $^1$H NMR (400 MHz, DMSO-$d_6$) δ 12.24-12.27 (m, 2H), 7.85 (s, 2H), 7.51 (s, 1H), 7.31-7.35 (m, 4H), 7.21-7.26 (m, 1H), 6.52 (s, 2H), 4.27-4.33 (m, 1H), 1.55 (d, J=7.2 Hz, 3H). LCMS (ESI, m/z): 487 [M+H]$^+$.

Example 95: Synthesis of Compounds 165 and 166

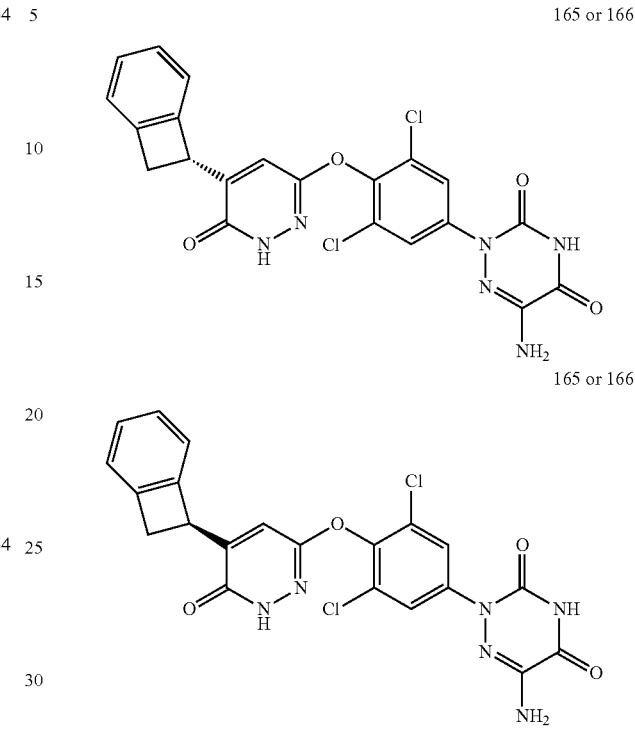

165 or 166

165 or 166

A chiral separation was performed on 6-amino-2-(4-((5-(bicyclo[4.2.0]octa-1(6),2,4-trien-7-yl)-6-oxo-1,6-dihydropyridazin-3-yl)oxy)-3,5-dichlorophenyl)-1,2,4-triazine-3,5(2H,4H)-dione to afford compounds 165 (Rt: 2.845 min on chiral HPLC) and 166 (Rt: 3.697 min on chiral HPLC) (Chiral HPLC conditions: column name: (R,R)-WHELK-01 4.6×50 mm 3.5 um, mobile phase: Hex (0.1% DEA): ethanol=70:30, temperature: 25° C., flow 1.000 mL/min, instrument: Agilent 1260). $^1$H NMR (400 MHz, DMSO-$d_6$) δ 12.33 (br, 2H), 7.84 (s, 2H), 7.19-7.39 (m, 5H), 6.50 (s, 2H), 4.71 (s, 1H), 3.63-3.69 (m, 1H), 3.19-3.24 (m, 1H).

Example 96: Synthesis of Compound 171

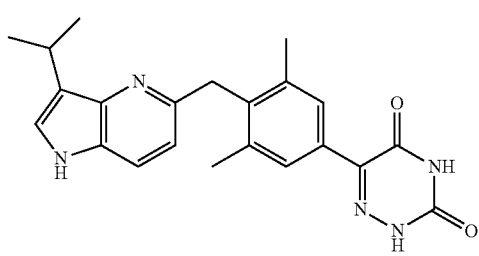 [SMILES: Cc1cc(-c2n[nH]c(=O)[nH]c2=O)cc(C)c1Cc1ccc2[nH]cc(C(C)C)c2n1]

A mixture of 5-[[2,6-dimethyl-4-(4,4,5,5-tetramethyl-1,3,2-dioxaborolan-2-yl)phenyl]methyl]-3-isopropyl-1-(p-tolylsulfonyl)pyrrolo[3,2-b]pyridine (320 mg, 0.516 mmol, 90% purity), 6-bromo-2H-1,2,4-triazine-3,5-dione (148.48 mg, 0.773 mmol), K$_2$CO$_3$ (142.53 mg, 1.03 mmol) and palladium; triphenylphosphane (119.17 mg, 0.103 mmol) in dioxane (10 mL) and H$_2$O (1 mL) was stirred at 100° C. for 12 h under N$_2$. The reaction mixture was diluted with H$_2$O (20 mL) and extracted with EA (20 mL×2). The combined organic layers were washed with brine (20 mL), dried over anhydrous Na$_2$SO$_4$, filtered and concentrated to give crude product, which was purified by flash silica gel chromatography (Eluent of 0~50% EA/PE) to give 6-[4-[[3-isopropyl-1-(p-tolylsulfonyl)pyrrolo[3,2-b]pyridin-5-yl]methyl]-3,5-dimethyl-phenyl]-2H-1,2,4-triazine-3,5-dione (246 mg, 0.453 mmol, 88% yield) as a colorless oil. LCMS (ESI, m/z): 544 [M+H]$^+$.

To a solution of 6-[4-[[3-isopropyl-1-(p-tolylsulfonyl)pyrrolo[3,2-b]pyridin-5-yl]methyl]-3,5-dimethyl-phenyl]-2H-1,2,4-triazine-3,5-dione (200 mg, 0.368 mmol) in THF (8 mL) was added TBAF (1 M, 1.84 mL) at 20° C. The mixture was stirred at 65° C. for 12 h. The reaction mixture was diluted with H$_2$O (50 mL), extracted with EA (100 mL). The organic layer was washed with brine (50 mL), dried over anhydrous Na$_2$SO$_4$, filtered and concentrated to give a residue. The residue was purified by prep-HPLC [Column: Phenomenex luna C18 80×40 mm×3 um; mobile phase: from 10% CH$_3$CN in water (0.05% HCl) to 40% CH$_3$CN in water (0.05% HCl)] then dissolved in EA (20 mL), washed with NH$_4$C$_1$ (sat., aq., 20 mL), brine (20 mL) and concentrated to afford 6-[4-[(3-isopropyl-1H-pyrrolo[3,2-b]pyridin-5-yl)methyl]-3,5-dimethyl-phenyl]-2-methyl-1,2,4-triazine-3,5-dione (5 mg, 12.84 umol, 3.5% yield, 100% purity) as a white solid. $^1$H NMR (400 MHz, DMSO-d$_6$) δ 12.43 (d, J=1.8 Hz, 1H), 12.04 (s, 1H), 10.80 (br s, 1H), 7.58-7.52 (m, 3H), 7.29 (d, J=1.6 Hz, 1H), 6.65 (d, J=8.4 Hz, 1H), 4.23 (s, 2H), 3.24-3.16 (m, 1H), 2.37 (s, 6H), 1.33 (d, J=6.9 Hz, 6H).

Example 97: Synthesis of 6-bromo-4-isopropyl-1,5-naphthyridin-2(1H)-one

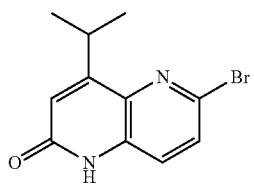

To a solution of 2,6-dibromopyridin-3-amine (30 g, 119.09 mmol) in DCM (500 mL) was added Et$_3$N (36.15 g, 357.27 mmol, 49.73 mL) and 2,2-dimethylpropanoyl chloride (28.72 g, 238.18 mmol, 29.31 mL) at 0° C., and the mixture was stirred at 15° C. for 12 h. The mixture was quenched by sat. aq. NH$_4$C$_1$ (sat., aq., 100 mL), extracted with DCM (200 mL×3). The combined organic layers were washed with brine (100 mL×2), dried over MgSO$_4$, filtered and concentrated to give a residue, which was purified by silica gel chromatography (Eluent of 0~20% EA/PE) to give N-(2,6-dibromopyridin-3-yl)pivalamide (41.4 g, crude) as a yellow solid. $^1$H NMR (400 MHz, DMSO-d$_6$) δ 9.18 (s, 1H), 7.83 (d, J=8.3 Hz, 1H), 7.71 (d, J=8.3 Hz, 1H), 1.24 (s, 9H).

To a solution of N-(2,6-dibromopyridin-3-yl)pivalamide (21 g, 62.50 mmol) in toluene (300 mL) was added dropwise n-BuLi (2.5 M, 62.50 mL) at −70° C. under N$_2$, the mixture was stirred at −70° C. for 2 h. Then to the mixture was added 2-methylpropanal (9.01 g, 124.99 mmol, 11.41 mL), the resulting mixture was stirred at −70° C. for 2 h. The mixture was quenched by sat. aq. NH$_4$Cl (60 mL) at −70° C., then warmed to 10° C., diluted with H$_2$O (200 mL) and extracted with EA (200 mL×3). The combined organic layers were washed with brine (300 mL), dried over anhydrous Na$_2$SO$_4$, filtered and concentrated to give a residue, which was purified by flash silica gel chromatography (0~10% EA in PE) to afford N-(6-bromo-2-(1-hydroxy-2-methylpropyl)pyridin-3-yl)pivalamide (13 g, 37.71 mmol, 30.17% yield, 95.5% purity) as a yellow solid. $^1$H NMR (400 MHz, DMSO-d$_6$) δ 10.27 (s, 1H), 8.50 (d, J=8.6 Hz, 1H), 7.49 (d, J=8.8 Hz, 1H), 6.77 (d, J=4.5 Hz, 1H), 4.45 (dd, J=4.6, 6.8 Hz, 1H), 2.06-1.93 (m, 1H), 1.21 (s, 9H), 0.93 (d, J=6.6 Hz, 3H), 0.77 (d, J=6.8 Hz, 3H).

To a solution of N-(6-bromo-2-(1-hydroxy-2-methylpropyl)pyridin-3-yl)pivalamide (13 g, 39.49 mmol) in DCM (350 mL) was added Dess-Martin (50.24 g, 118.46 mmol, 36.67 mL) in portions at 20° C. After the addition, the mixture was stirred at 20° C. for 3 h. LCMS showed the starting material was consumed completely and 47.3% of desired product formed under 220 nm. The mixture was quenched by addition of sat. aq. Na$_2$SO$_3$ (100 mL) and sat. aq. NaHCO$_3$ (200 mL), extracted with DCM (100 mL×3). The combined organic layers were washed with brine (200 mL), dried over anhydrous MgSO$_4$, filtered and concentrated to give a residue, which was purified by flash silica gel chromatography (EA in PE=0-10%) to give N-(6-bromo-2-isobutyrylpyridin-3-yl)pivalamide (11 g, 33.48 mmol, 84.80% yield, 99.6% purity) as a colorless oil. $^1$H NMR (400 MHz, DMSO-d$_6$) δ 11.59 (s, 1H), 8.94 (d, J=9.0 Hz, 1H), 7.89 (d, J=9.0 Hz, 1H), 4.02 (spt, J=6.9 Hz, 1H), 1.26 (s, 9H), 1.13 (d, J=6.9 Hz, 6H).

To a solution of LDA (2 M, 35.30 mL) in THF (250 mL) was added t-butyl acetate (8.20 g, 70.60 mmol, 9.47 mL) at −70° C., the mixture was stirred at −70° C. for 30 min. Then to the mixture was added N-(6-bromo-2-isobutyrylpyridin-3-yl)pivalamide (11 g, 33.62 mmol) in THF (50 mL) at −70° C., the resulting mixture was stirred at −70° C. for 1 h. The mixture was quenched with sat. aq. NH$_4$Cl (100 mL) at −70° C. Then warmed to 20° C., diluted with H$_2$O (100 mL) and extracted with EA (100 mL×3). The combined organic layers were washed with brine (200 mL), dried over anhydrous MgSO$_4$, filtered and concentrated to give a residue, which was purified by flash silica gel chromatography (0~10% EA in PE) to afford t-butyl 3-(6-bromo-3-pivalamidopyridin-2-yl)-3-hydroxy-4-methylpentanoate (14.92 g, 26.55 mmol, 78.98% yield, 78.9% purity) as a yellow oil.

The reaction was set up in 4 batches. t-Butyl 3-(6-bromo-3-pivalamidopyridin-2-yl)-3-hydroxy-4-methylpentanoate (2 g, 3.56 mmol, 78.9% pure) and HBr (18.42 mmol, 5 mL, 20%) were taken up into a microwave tube in dioxane (1 mL). The sealed tube was heated at 160° C. for 25 min under microwave irradiation. The combined reaction mixture was diluted with H$_2$O (100 mL) and EA (100 mL). The suspension was filtered, and the filtrate was extracted with EA (100 mL×3). The combined organic layers were washed with brine (100 mL), dried over anhydrous MgSO$_4$, filtered and concentrated to give a residue, which was purified by flash silica gel chromatography (0~70% EA in PE) to give 6-bromo-4-isopropyl-1,5-naphthyridin-2(1H)-one (4.36 g, 15.64 mmol, 60.60% yield, 95.8% purity) as a yellow solid. $^1$H NMR (400 MHz, DMSO-d$_6$) δ 11.89 (br s, 1H), 7.75-7.66 (m, 1H), 7.60 (d, J=8.6 Hz, 1H), 6.60 (s, 1H), 3.70-3.56 (m, 1H), 1.23 (d, J=7.0 Hz, 6H).

Example 98: Methodology for LCMS

1. Description of LCMS Conditions

Several different conditions were used to assess the purity, retention time and [M+H]$^+$ or [M−H]$^−$ of the compounds disclosed herein using LCMS methods. The conditions are listed in Table 1, below. All data were obtained using a Shimadzu LCMS-2020 instrument except when noted differently. For all conditions, column temperature was 40° C. and run time was 3 m, except when noted differently. Flow is reported in units of mL/min. "C" is the number indicator for the listed LCMS condition, which is then referenced in Table 2, below.

TABLE 1

| C | Column | Mobile phase | Gradient | Flow |
|---|---|---|---|---|
| 1 | Ascentis Express C18 (2.7 μm, 3.0 × 50 mm) column temp: 40° C. | A: $H_2O$ + 0.05% TFA B: $CH_3CN$ + 0.05% TFA | From 95% A to 5% A in 1.99 min, held for 0.6 min, to 95% A in 0.15 min, held for 0.25 min | 1.5 |
| 2 | ACE Excel 3 Super (3.0 μm, 3.0x50 mm) column temp: 40° C. | A: $H_2O$ + 5 mM $NH_4HCO_3$ B: $CH_3CN$ | From 90% A to 5% A in 2.09 min, held for 0.6 min, to 90% A in 0.05 min, held for 0.25 min | 1.2 |
| 3 | YMC-Triart C18 (3.0 μm, 3.0 × 50 mm) column temp: 40° C. | A: $H_2O$ + 0.04% $NH_4OH$ B: $CH_3CN$ | From 90% A to 5% A in 1.89 min, held for 0.8 min, to 90% A in 0.05 min, held for 0.25 min | 1.5 |
| 4 | Poroshell HPH-C18 (2.7 μm, 3.0 × 50 mm) column temp: 40° C. | A: 6.5 mM $NH_4HCO_3$ +$NH_3H_2O$ B: $CH_3CN$ | From 90% A to 5% A in 1.99 min, held for 0.6 min, to 90% A in 0.15 min, held for 0.25 min | 1.2 |
| 5 | HALO C18 (2.0 μm, 3.0 × 30 mm) column temp: 40° C. | A: $H_2O$ + 0.05% TFA B: $CH_3CN$ + 0.05% TFA | From 95% A to 50% A in 1.79 min, to 5% A in 0.7 min, held for 0.3 min, to 95% A in 0.01 min, held for 0.19 min. Runtime 3 min | 1.5 |
| 5A | HALO C18 (2.7 μm, 3.0 × 50 mm), column temp.: 40° C. | | From 95% A to 0% A in 1.99 min, held for 0.7 min, to 95% A in 0.05 min, held for 0.15 min. Runtime 2.9 min | |
| 5B | (2.7 μm, 3.0 × 50 mm), column temp.: 45° C. | | From 70% A to 5% A in 3.99 min, held for 0.8 min, to 95% A in 0.2 min, held for 0.2 min. Runtime 5.2 min | |
| 5C | | | From 95% A to 45% A in 2.99 min, to 0% A in 1 min, held for 0.6 min, to 95% A in 0.1 min, held for 0.5 min. Runtime 5.2 min | 1.5 |
| 6 | Shim-pack XR-ODS (2.2 μm, 3.0 × 50 mm) column temp.: 40° C. | | From 95% A to 0% A in 1.99 min, held for 0.7 min, to 95% A in 0.05 min, held for 0.25 min | 1.2 |
| 7 | Xselect CSH C18 (2.5 μm, 3.0 × 50 mm) column temp.: 40° C. | A: $H_2O$/0.1% FA B: $CH_3CN$/0.1% FA | From 95% A to 5% A in 2.09 min, held for 0.6 min, to 95% A in 0.05 min, held for 0.25 min | 1.2 |
| 8 | CORTECS C18 (2.7 μm, 2.1 × 50 mm) column temp.: 40° C. | A: $H_2O$ + 0.05% TFA B: $CH_3CN$ + 0.05% TFA | From 95% A to 0% A in 1.99 min, held for 0.8 min, to 95% A in 0.1 min, held for 0.1 min | 1.0 |
| 9 | Ascentis Express C18 (2.7 μm, 3.0 × 50 mm) column temp.: 40° C. | A: $H_2O$ + 0.05% TFA B: $CH_3CN$ + 0.05% TFA | From 95% A to 0% A in 1.99 min, held for 0.8 min, to 95% A in 0.1 min, held for 0.1 min | 1.5 |
| 10 | | | From 95% A to 5% A in 1.99 min, held for 0.7 min, to 95% A in 0.1 min, held for 0.2 min | 1.0 |
| 11 | Ascentis Express C18 (2.7 μm, 3.0 × 50 mm), column temp.: 45° C. | A: $H_2O$ + 0.05% TFA B: $CH_3C$ + 0.05% TFA | From 95% A to 60% A in 3.19 min, to 0% A in 0.8 min, held for 0.6 min, to 95% A in 0.1 min, held for 0.5 min. Runtime: 5.2 min | 1.5 |
| 12 | Kinetex 2.6 μm EVO C18 100A (2.6 μm, 3.0 × 50 mm), column temp.: 40° C. | A: $H_2O$ + 5 mM $NH_4HCO_3$ B: $CH_3CN$ | From 90% A to 5% A in 1.99 min, held for 0.6 min, to 90% A in 0.15 min, held for 0.10 min. Runtime: 2.85 min | 1.2 |
| 12A | | | From 90% A to 5% A in 1.99 min, held for 0.7 min, to 90% A in 0.05 min, held for 0.10 min. Runtime: 2.85 min | |
| 13 | Ascentis Express C18 (2.7 μm, 3.0 × 50 mm), column temp.: 40° C. | A: $H_2O$ + 0.05% TFA B: $CH_3CN$ + 0.05% TFA | From 95% A to 40% A in 3.19 min, to 5% A in 0.9 min, held for 0.9 min, to 95% A in 0.1 min, held for 0.2 min. Runtime: 5.3 min | 1.5 |
| 13B | | | From 95% A to 30% A in 3.59 min, to 5% A in 0.6 min, held for 0.8 min, to 95% A in 0.1 min, held for 0.2 min | |

TABLE 1-continued

| C | Column | Mobile phase | Gradient | Flow |
|---|---|---|---|---|
| 14A/ B/F | Xtimate C18 2.1 × 30 mm, 3 μm column temp.: 50° C. | A: H$_2$O (4L) + TFA (1.5 mL) B: CH$_3$CN (4L) + TFA (0.75 mL) | From 90% A to 20% A in 3 minutes and holding at 20% for 0.5 minutes to 90% A in 0.01 min held for 0.49 min. Runtime: A/B/F: 4 min | 14A: 0.8 14B: 1.2 14F: 1.0 |
| 14C | | | From 95% A to 5% A in 0.9 minutes and holding at 5% for 0.2 minutes, to 95% A in 0.01 min held for 0.49 min. Runtime 2 min | 1.2 |
| 14D | | | From 95% A to 5% A in 0.9 minutes and holding at 5% for 0.2 minutes, to 95% A in 0.01 min held for 0.49 min. Runtime 2 min | |
| 14E | | | From 10% B to 80% B in 0.9 minutes and holding at 80% for 0.6 minutes, to 10% B in 0.01 min held for 0.49 min. Runtime 2 min | |
| 15 | Agilent Poroshell 120, EC-C18, 4.6 × 100 mm-4 μm column temp.: 30° C. Agilent 1260 Infinity II | A: 0.1% FA in H$_2$O B: 0.05% FA in CH$_3$CN | 2.0 min 98% A, from 98% A to 0% A in 10 min, hold for 3.4 min. Runtime: 15.4 min | 1 |
| 16A | HALO 90A C18 (2.0 μm, 2.1 × 30 mm) column temp.: 40° C. | A: H$_2$O + 0.05% TFA B: CH$_3$CN + 0.05% TFA | From 95% A to 0% A in 2.19 min, held for 0.5 min, to 95% A in 0.05 min, held for 0.25 min. Runtime: 3 min | 1 |
| 16B | | | From 95% A to 50% A in 2.79 min, to 0% A in 1 min, held for 0.6 min, to 95% A in 0.1 min, held for 0.5 min. Runtime: 5 min | 1 |
| 16C | | | From 95% A to 40% A in 2.79 min, to 0% A in 1 min, held for 0.6 min, to 95% A in 0.1 min, held for 0.5 min. Runtime: 5 min | 1 |
| 17 | Ascentis Express C18 (2.7 μm, 3.0 × 50 mm) Column temp.: 45° C. | A: H$_2$O /0.05% TFA B: CH$_3$CN/0.05% TFA | From 95% A to 50% A in 2.99 min, to 0% A in 1.0 min, held for 0.6 min, to 95% A in Runtime: 5.2 min 0.1 min, held for 0.5 min | 1.5 |
| 18 | Kinetex EVO C18100A (2.6 μm, 3.0 × 50 mm) column temp.: 40° C. | A: H$_2$O/5 mM NH$_4$HCO$_3$ B: CH$_3$CN | From 90% A to 5% A in 2.99 min, held for 0.6 min, to 90% A in 0.10 min, held for 0.30 min. Runtime: 4 min | 1.2 |
| 18B | | | From 90% A to 60% A in 3.19 min, to 5% in 0.8 min, held for 0.9 min, to 90% A in 0.2 min, held for 0.20 min. Runtime: 5.3 min | |
| 19 | Ascentis Express C18 (2.7 μm, 3.0 × 50 mm), column temp.: 40° C. | A: H$_2$O/0.05% TFA B: CH$_3$CN/0.05% TFA | From 95% A to 5% A in 1.99 min, held for 0.7 min, to 95% A in 0.05 min, held for 0.25 min | 1.5 |
| 19A | | | From 95% A to 0% A in 1.99 min, held for 0.7 min, to 95% A in 0.05 min, held for 0.25 min. Runtime 3 min | |
| 19B | | | From 95% A to 0% A in 1.09 min, held for 0.6 min, to 95% A in 0.05 min, held for 0.1 min. Runtime 1.85 min | |
| 20 | HALO 90A C18 (2.0 μm, 3.0 × 30 mm), column temp.: 40° C. | A: H$_2$O/0.05% TFA B: CH$_3$CN/0.05% TFA | From 95% A to 50% A in 3.09 min, to 5% A in 1.0 min, held for 0.9 min, to 95% A in 0.1 min, held for 0.2 min. Runtime: 5.3 min | 1.5 |
| 20A | | | From 95% A to 0% A in 1.99 min, held for 0.7 min, to 95% A in 0.05 min, held for 0.25mi. n Runtime: 3 min | |

TABLE 1-continued

| C | Column | Mobile phase | Gradient | Flow |
|---|---|---|---|---|
| 20B | | | From 95% A to 0% A in 1.99 min, held for 0.7 min, to 95% A in 0.05 min, held for 0.45 min. Runtime 3.2 min | |
| 20C | | | From 95% A to 60% A in 3.09 min, to 10% A in 1.0 min, held for 0.9 min, to 95% A in 0.1 min, held for 0.2 min. Runtime: 5.3 min | |
| 21 | | | From 90% A to 5% A in 1.99 min, held for 0.7 min, to 90% A in 0.05 min, held for 0.25 min | |
| 21A | Poroshell HPH-C18 (2.7 μm, 3.0 × 50 mm), Column temp: 40° C. | A: 6.5 mM NH$_4$HCO$_3$ + NH$_3$H$_2$O B: CH$_3$CN | From 90% A to 55% A in 2.99 min, to 5% in 1 min, held for 0.7 min, to 90% A in 0.2 min, held for 0.1 min (Run time 5 min) | 1.2 |
| 21B | | | From 90% A to 60% A in 2.99 min, to 5% in 1 min, held for 0.7 min, to 90% A in 0.2 min, held for 0.1 min. Runtime 5 min | |
| 22 | Ascentis Express C18 (2.7 μm, 4.6 × 100 mm) Column temp: 40° C. | A: Water/0.05% TFA B: CH$_3$CN/0.05% TFA | From 90% A to 5% A in 7.99 min, held for 2.0 min, to 90% A in 0.5 min, held for 1.5 min. Runtime: 12 min | 1.5 |
| 23 | HALO C18 (2.7 μm, 3.0 × 50 mm) Column temp: 40° C. | | From 95% A to 0% A in 1.99 min, held for 0.7 min, to 95% A in 0.05 min, held for 0.25 min. Runtime: 3 min | 1.5 |
| 24 | HPH-C18 (2.7 μm, 3.0*50 mm) Column temp: 35° C. | A: 6.5 mM NH$_4$HCO$_3$ + NH$_3$H$_2$O B: CH$_3$CN | From 90% A to 50% A in 2.99 min, to 5% A in 0.3 min held for 0.45 min, to 90% A in 0.05 min, held for 0.2 min. Runtime 4 min | 1.2 |

2. LCMS Results

The results of LCMS characterizations and the particular set of conditions used for the compounds disclosed here are presented in Table 2.

TABLE 2

| Cmp'd No. | Rt (min) | [M + H]$^+$ or [M − H]$^−$ | LCMS method |
|---|---|---|---|
| 1 | 1.660 | [M − H]$^−$ = 454 | 2 |
| 2 | 1.035 | [M − H]$^−$ = 414 | 3 |
| 3 | 1.394 | [M + H]$^+$ = 414 | 4 |
| 4 | 1.217 | [M − H]$^−$ = 470 | 4 |
| 5 | 1.461 | [M − H]$^−$ = 480 | 4 |
| 6 | 1.428 | [M − H]$^−$ = 516 | 4 |
| 7 | 1.429 | [M − H]$^−$ = 488 | 4 |
| 8 | 1.375 | [M + H]$^+$ = 454 | 5 |
| 9 | 0.734 | [M + H]$^+$ = 453 | 3 |
| 10 | 1.392 | [M + H]$^+$ = 425 | 6 |
| 11 | 1.379 | [M + H]$^+$ = 434 | 1 |
| 12 | 1.304 | [M + H]$^+$ = 449 | 8 |
| 13 | 0.808 | [M + H]$^+$ = 468 | 4 |
| 14 | 1.310 | [M + H]$^+$ = 439 | 1 |
| 15 | 1.489 | [M + H]$^+$ = 453 | 1 |
| 16 | 1.363 | [M + H]$^+$ = 424 | 8 |
| 17 | 1.131 | [M − H]$^−$ = 437 | 4 |
| 18 | 1.592 | [M + H]$^+$ = 457 | 1 |
| 19 | 1.572 | [M + H]$^+$ = 457 | 1 |
| 20 | 2.692 | [M + H]$^+$ = 499 | 13 |
| 21 | 1.331 | [M + H]$^+$ = 485 | 1 |
| 22 | 1.536 | [M + H]$^+$ = 573 | 1 |
| 23 | 1.504 | [M + H]$^+$ = 438 | 1 |
| 24 | 2.246 | [M + H]$^+$ = 453 | 11 |
| 25 | 1.141 | [M + H]$^+$ = 440 | 9 |
| 26 | 1.234 | [M + H]$^+$ = 467 | 10 |
| 27 | 1.004 | [M + H]$^+$ = 490 | 9 |
| 28 | 1.133 | [M + H]$^+$ = 460 | 12 |
| 29 | 1.293 | [M + H]$^+$ = 454 | 9 |
| 30 | 0.950 | [M + H]$^+$ = 439 | 9 |
| 31 | 1.862 | [M + H]$^+$ = 415 | 14A |
| 32 | 10.91 | [M + H]$^+$ = 443 | 15 |
| 33 | 1.427 | [M + H]$^+$ = 470 | 9 |
| 34 | 1.036 | [M + H]$^+$ = 502 | 4 |
| 35 | 1.237 | [M + H]$^+$ = 439 | 1 |
| 36 | 1.107 | [M + H]$^+$ = 423 | 16A |
| 37 | 1.099 | [M + H]$^+$ = 405 | 16A |
| 38 | 1.075 | [M + Na]$^+$ = 385 | 9 |
| 39-A | 2.295 | [M + H]$^+$ = 439 | 16B |
| 39-B | 2.298 | [M + H]$^+$ = 439 | 16B |
| 40-A | 2.614 | [M + H]$^+$ = 447 | 16B |
| 40 | 1.229 | [M + H]$^+$ = 459 | 9 |
| 41 | 1.441 | [M + H]$^+$ = 446 | 16A |
| 42 | 1.323 | [M + H]$^+$ = 451 | 9 |
| 43 | 0.865 | [M + H]$^+$ = 416 | 4 |
| 44 | 1.193 | [M + H]$^+$ = 471 | 16A |
| 45 | 1.348 | [M − H]$^−$ = 508 | 12 |
| 46 | 1.348 | [M − H]$^−$ = 502 | 4 |
| 47 | 1.199 | [M − H]$^−$ = 412 | 4 |
| 48 | 1.361 | [M − H]$^−$ = 454 | 4 |
| 49 | 1.394 | [M − H]$^−$ = 468 | 4 |
| 50 | 1.324 | [M − H]$^−$ = 466 | 4 |
| 51 | 1.182 | [M − H]$^−$ = 456 | 4 |
| 52 | 2.541 | [M + H]$^+$ = 458 | 16C |
| 53 | 1.338 | [M + H]$^+$ = 448 | 9 |
| 54 | 0.992 | [M + H]$^+$ = 390 | 14C |
| 55 | 1.144 | [M + H]$^+$ = 405 | 14C |
| 56 | 2.557 | [M + H]$^+$ = 391 | 14B |
| 57 | 10.149 | [M + H]$^+$ = 415 | 15 |
| 58 | 1.576 | [M + H]$^+$ = 465 | 18 |

TABLE 2-continued

| Cmp'd No. | Rt (min) | [M + H]⁺or [M − H]⁻ | LCMS method |
|---|---|---|---|
| 59 | 0.796 | [M + H]⁺ = 467 | 4 |
| 60 | 1.020 | [M + H]⁺ = 441 | 1 |
| 60-A | 0.933 | [M + H]⁺ = 423 | 4 |
| 61 | 1.191 | [M + Na]⁺ = 523 | 9 |
| 62 | 1.042 | [M + H]⁺ = 453 | 1 |
| 63 | 1.013 | [M + H]⁺ = 459 | 4 |
| 63-A | 2.290 | [M + H]⁺ = 459 | 11 |
| 64 | 1.410 | [M + H]⁺ = 491 | 1 |
| 65 | 2.657 | [M + Na]⁺ = 495 | 17 |
| 66 | 1.195 | [M + H]⁺ = 416 | 14C |
| 67 | 1.525 | [M + H]⁺ = 509 | 19 |
| 67-A | 1.105 | [M + H]⁺ = 509 | 21 |
| 68 | 1.452 | [M + H]⁺ = 493 | 19 |
| 68-A | 1.340 | [M + H]⁺ = 493 | 19 |
| 69 | 1.084 | [M + H]⁺ = 477 | 21 |
| 69-A | 0.988 | [M + H]⁺ = 477 | 21 |
| 70 | 1.428 | [M + H]⁺ = 473 | 19 |
| 70-A | 1.313 | [M + H]⁺ = 473 | 19 |
| 71 | 1.518 | [M + H]⁺ = 487 | 19 |
| 71-A | 1.392 | [M + H]⁺ = 487 | 19 |
| 72 | 1.286 | [M + H]⁺ = 513 | 21 |
| 72-A | 2.349 | [M + H]⁺ = 513 | 21 |
| 73 | 1.393 | [M + H]⁺ = 439 | 1 |
| 74 | 0.849 | [M + H]⁺ = 460 | 14D |
| 75 | 2.167 | [M + H]⁺ = 449 | 14B |
| 75A | 0.928 | [M + H]⁺ = 459 | 14D |
| 76 | 1.209 | [M + H]⁺ = 495 | 19 |
| 77 | 2.348 | [M + H]⁺ = 481 | 17 |
| 78 | 1.238 | [M + H]⁺ = 427 | 9 |
| 79 | 0.977 | [M + H]⁺ = 417 | 21 |
| 80 | 1.019 | [M + H]⁺ = 469 | 21 |
| 81 | 1.017 | [M + H]⁺ = 513 | 21 |
| 82 | 1.223 | [M + H]⁺ = 448 | 19 |
| 83 | 1.079 | [M + H]⁺ = 474 | 21 |
| 84 | 2.612 | [M + H]⁺ = 476 | 17 |
| 85 | 2.864 | [M + H]⁺ = 488 | 20 |
| 86 | 1.270 | [M + H]⁺ = 451 | 19 |
| 86-A | 1.268 | [M + H]⁺ = 451 | 19 |
| 86-B | 1.219 | [M + H]⁺ = 451 | 19 |
| 87-A | 1.462 | [M + H]⁺ = 543 | 20 |
| 87-B | 1.453 | [M + H]⁺ = 543 | 20 |
| 88-A | 0.910 | [M + H]⁺ = 453 | 20 |
| 89 | 2.872 | [M + H]⁺ = 465 | 13 |
| 90 | 9.502 | [M + H]⁺ = 442 | 15 |
| 91 | 11.305 | [M + H]⁺ = 498 | 15 |
| 92 | 10.622 | [M + H]⁺ = 494 | 15 |
| 93 | 2.276 | [M + H]⁺ = 463 | 21A |
| 94 | 10.309 | [M + H]⁺ = 477 | 15 |
| 95 | 1.231 | [M + H]⁺ = 449 | 12A |
| 96 | 9.653 | [M + H]⁺ = 463 | 15 |
| 97 | 1.352 | [M + H]⁺ = 501 | 19 |
| 98 | 10.265 | [M + H]⁺ = 513 | 15 |
| 99 | 1.195 | [M + H]⁺ = 513 | 21 |
| 100 | 1.188 | [M + H]⁺ = 513 | 21 |
| 101 | 1.448 | [M + H]⁺ = 463 | 19 |
| 102 | 0.973 | [M + H]⁺ = 467 | 20B |
| 103 | 2.502 | [M + H]⁺ = 467 | 20C |
| 104 | 1.647 | [M + H]⁺ = 462 | 24 |
| 105 | 1.712 | [M + H]⁺ = 462 | 24 |
| 106 | 1.416 | [M + H]⁺ = 473 | 19A |
| 107 | 9.809 | [M + H]⁺ = 499 | 15 |
| 108 | 0.842 | [M + H]⁺ = 511 | 21 |
| 109 | 0.727 | [M + H]⁺ = 511 | 21 |
| 110 | 0.86 | [M + H]⁺ = 511 | 21 |
| 111 | 0.751 | [M + H]⁺ = 511 | 21 |
| 112 | 1.341 | [M + H]⁺ = 487 | 5A |
| 113 | 1.34 | [M + H]⁺ = 487 | 19A |
| 114 | 1.146 | [M + H]⁺ = 515 | 5B |
| 115 | 1.023 | [M + H]⁺ = 515 | 21 |
| 116 | 2.964 | [M + H]⁺ = 507 | 13B |
| 117 | 2.709 | [M + H]⁺ = 507 | 5C |
| 118 | 2.733 | [M + H]⁺ = 525 | 13 |
| 119 | 1.257 | [M + H]⁺ = 525 | 19A |
| 120 | 2.733 | [M + H]⁺ = 525 | 13 |
| 121 | 1.257 | [M + H]⁺ = 525 | 19A |
| 122 | 1.208 | [M + H]⁺ = 499 | 19 |
| 123 | 1.098 | [M + H]⁺ = 499 | 19 |
| 124 | 0.94 | [M + H]⁺ = 499 | 21 |
| 125 | 1.941 | [M + H]⁺ = 499 | 18B |
| 126 | 2.381 | [M + H]⁺ = 499 | 22 |
| 127 | 0.731 | [M + H]⁺ = 499 | 21 |
| 128 | 0.941 | [M + H]⁺ = 510 | 21 |
| 129 | 0.844 | [M + H]⁺ = 510 | 21 |
| 130 | 2.283 | [M + H]⁺ = 499 | 21B |
| 131 | 1.842 | [M + H]⁺ = 499 | 21B |
| 132 | 1.003 | [M + H]⁺ = 510 | 21 |
| 133 | 0.906 | [M + H]⁺ = 510 | 21 |
| 134 | 1.196 | [M + H]⁺ = 510 | 19A |
| 135 | 10.362 | [M + H]⁺ = 500 | 15 |
| 136 | 9.674 | [M + H]⁺ = 500 | 15 |
| 137 | 7.539 | [M + H]⁺ = 459 | 15 |
| 138 | 7.52 | [M + H]⁺ = 459 | 15 |
| 139 | 10.135 | [M + H]⁺ = 458 | 15 |
| 140 | 9.48 | [M + H]⁺ = 458 | 15 |
| 141 | 6.874 | [M + H]⁺ = 459 | 15 |
| 142 | 6.669 | [M + H]⁺ = 459 | 15 |
| 143 | 8.458 | [M + H]⁺ = 446 | 15 |
| 144 | 1.124 | [M + H]⁺ = 469 | 21 |
| 145 | 9.305 | [M + H]⁺ = 472 | 15 |
| 146 | 0.831 | [M + H]⁺ = 474 | 14D |
| 147 | 0.870 | [M + H]⁺ = 474 | 14A |
| 148 | 9.338 | [M + H]⁺ = 414 | 15 |
| 149 | 8.28 | [M + H]⁺ = 421 | 15 |
| 150 | 8.915 | [M + H]⁺ = 432 | 15 |
| 151 | 8.195 | [M + H]⁺ = 404 | 15 |
| 152 | 8.695 | [M + H]⁺ = 389 | 15 |
| 153 | 9.801 | [M + H]⁺ = 428 | 15 |
| 154 | 1.963 | [M + H]⁺ = 456 | 14A |
| 155 | 9.865 | [M + H]⁺ = 499 | 15 |
| 156 | 1.418 | [M + H]⁺ = 499 | 19A |
| 157 | 0.740 | [M + H]⁺ = 405 | 14D |
| 158 | 1.239 | [M + H]⁺ = 485 | 23 |
| 159 | 1.533 | [M + H]⁺ = 466 | 19A |
| 160 | 0.696 | [M + H]⁺ = 491 | 21 |
| 161 | 0.705 | [M + H]⁺ = 490 | 20A |
| 162 | 0.681 | [M + H]⁺ = 404 | 14E |
| 163 | 1.125 | [M + H]⁺ = 487 | 21 |
| 164 | 1.122 | [M + H]⁺ = 487 | 21 |
| 165 | 0.945 | [M + H]⁺ = 485 | 19B |
| 166 | 1.373 | [M + H]⁺ = 485 | 19A |
| 167 | 2.345 | [M + H]⁺ = 465 | 21A |
| 168 | 1.092 | [M + H]⁺ = 465 | 21 |
| 169 | 1.041 | [M + H]⁺ = 453 | 21 |
| 170 | 1.046 | [M + H]⁺ = 453 | 21 |
| 171 | 1.036 | [M + H]⁺ = 390 | 14F |

Example 99: Biological Assays

THR Biochemical Assay

The TR-FRET thyroid receptor beta coactivator assay was used with slight, optimized modifications of the manufacturer's protocol (Invitrogen). The assay uses a terbium-labeled anti-GST antibody, a glutathione-S-transferase (GST) tagged human thyroid receptor, beta or alpha, ligand-binding domain (LBD), and a fluorescein labeled SRC2-2 coactivator peptide. The antibody interacts with the LBD, where the agonist also binds, resulting in increased affinity for the SRC2-2 coactivator peptide causing energy transfer of the acceptor fluorophore and a FRET emission shift from 495 to 520 nm. The energy transfer is detected as an increase in the fluorescence emission of the fluorescein acceptor, and a decrease in the fluorescence emission of the terbium donor. The assay is performed in a 384-well black plate in a final volume of 20 µL. Serial dilution of various test agonists was performed in DMSO (1% final DMSO concentration) and added to the test plate. Thyroid receptor beta LBD is added to the plate at a final concentration of 1 nM, followed by the mixture of the fluorescein labeled SRC2-2 coactivator peptide, and the terbium-labeled anti-GST antibody at final concentrations of 200 nM and 2 nM respectively. The assay is incubated for 1 hr at rt protected from light. The TR-FRET is then measured on a Victor multilabel reader (Perkin Elmer) using an excitation wavelength of 340 nm with emission filters of 495 nm and 520 nm. The assay is quantified by expressing a ratio (520:495) of the intensities, and the resulting activation curves; $EC_{50}$ values were generated using a sigmoidal dose response (variable slope) equation in GraphPad™ Prism 8.0.

HEK293T Reporter THRalpha/Beta/RXR Reporter Assay (Assay 2)

The purpose of this assay is to evaluate the effect of compounds on the thyroid hormone nuclear receptor pathway in HEK293T cells. To this end, HEK293T cells are transiently transfected with a luciferase reporter under the control of the thyroid response element (TRE), an RXR expression plasmid and either a THR alpha or THR beta expression plasmid. Transfected cells are stimulated with test compounds for 18-24 hours before activation of the thyroid hormone pathway is measured via a luciferase read-out.

Procedure. 24 hours prior to transfection, approximately $7 \times 10^5$ HEK293 T (ATCC, catalog #CRL-3216) are plated in one well of a 6-well-plate using DMEM (Hyclone, catalog #SH30022) supplemented with 10% FBS (Gibco, catalog #16000-044) and incubated overnight. Transfection complexes are prepared by mixing 12 μL of Lipofectamine 2000 (Invitrogen catalog #11668019) with 4 μg of a plasmid mixture at a ratio of 1:1:4 (TRalpha or TRbeta: RXR: TRE-Luc) in 200 μL OptiMem (Invitrogen catalog #11058-021) and added to the cells. After overnight incubation, transfected cells are re-seeded at ($1 \times 10^4$ cells/well, 30 L/well) in a 384 microplate and incubated for an additional 5-6 hours. Ten five-fold dilutions of test compounds are prepared in DMSO and 30 nL are dispensed to the cells. Pure DMSO serves as negative control while T3 (MCE catalog #HY-A0070) and GC-1 (MCE catalog #HY-14823) are used as positive controls. Approximately 18-24 h after compound addition, 384 well plates are allowed to adjust to rt, 30 μL One-Glo (Promega catalog #E6120) is added to each well and luminescence is measured on a Perkin Elmer Enspire plate reader. Percent agonism is calculated using the following equation: 100× (sample-negative control)/(positive control-negative control).

Huh-7 Differential Gene Expression (Assay 3)
Serum Stripping

AG® 1-X8 Anion Exchange Resin (analytical grade, 200-400 mesh, chloride form; 1401451, Bio-Rad) was prewashed with distilled water three times; water was separated from resin via centrifugation. Fetal bovine serum (FBS) was incubated with washed resin (50 mg resin/mL FBS; resin weight is dry weight of resin prior to washing) for 5 hr at room temperature on a rotor. The FBS was separated from the resin via centrifugation and incubated with new, washed resin for 18 h at room temperature on a rotor. The resin-treated FBS (rFBS) was separated via centrifugation and then sterilized via filtration (0.22 μM PES membrane).

Cell Culture and Drug Treatment

Huh-7 cells were cultured in DMEM (10-013-CM, Corning) supplemented with 10% FBS and 1% Pen-Strep at 37° C. under 5% $C_{O2}$. When 70-80% confluence was reached, the cells were removed by trypsinization. The medium was aspirated from the cell culture dish, the cell monolayer was washed with 1×PBS, and 0.05% trypsin, 0.53 mM EDTA (25-052-CV, Corning) solution was added to the dish. After 3 min incubation, the cells were detached completely by repeatedly pipetting solution onto the monolayer. Equal volume of DMEM supplemented with 10% rFBS and 1% Pen-Strep (TH-depleted DMEM) was added to the dish to inactivate the trypsin. The cell suspension was centrifuged at 350×g at room temperature for 3 min. The supernatant was aspirated out and the cell pellet was resuspended in TH-depleted DMEM. Cell density was quantified with a Vi-CELL XR Cell Viability Analyzer (Beckman Coulter) and cells were seeded onto Collagen I 96-well plates (356407, Corning) at 50,000 cells/well in 150 μL TH-depleted DMEM; the outer, perimeter wells were not used to avoid edge effect. After 24 hr incubation, the media was replaced with treatment media. All compounds were serially diluted in DMSO and final concentrations were reached by dilution in TH-depleted DMEM (0.1% DMSO). The cells were incubated in treatment media for 24 hr. Treatments were performed in biological duplicates.

Cell Lysis and RT-qPCR

After 24 hr in treatment media, the cells were lysed directly on the culture plates and cDNA was produced using the TaqMan™ Fast Advanced Cells-to-CT™ Kit (A35374, Invitrogen) and following the manufacturer's protocol. RT-qPCR for CPT1A (Hs00912671_m1) and two housekeeping genes, ACTB (Hs01060665_g1) and TFG (Hs02832013_g1), was performed using TaqMan™ Fast Advanced Master Mix. RT-qPCR reactions were run on the qTOWER³ 84 G (Analytik Jena) in technical duplicates.

Data Analysis

ΔRn values were obtained from the qPCRsoft384 1.0 software and CPT1A gene expression was quantified via the 2-ΔΔCt method. Dose-response curves were generated using GraphPad Prism 8 using four parameter logistic equation without top constraint to derive $EC_{50}$ and $E_{max}$.

Compounds of Formula (I) are active as THR-beta agonists as shown in Table 3, where: for Assay 1: 'A' indicates an $EC_{50}$<50 nM, 'B' indicates an $EC_{50}$ of ≥50 nM and 250 nM, 'C' indicates an $EC_{50}$≥250 nM and <1000 nM, 'D' indicates an $EC_{50}$≥1000 nM and <25000 nM, and 'E' indicates an $EC_{50}$>25000 nM. For Assay 2, 'A' indicates an $EC_{50}$<50 nM, 'B' indicates an $EC_{50}$ of ≥50 nM and <250 nM, 'C' indicates an $EC_{50}$≥250 nM and <1000 nM, 'D' indicates an $EC_{50}$≥1000 nM and <10000 nM, and 'E' indicates an $EC_{50}$>10000 nM.

TABLE 3

| Compound number | Activity category | |
|---|---|---|
| | Assay 1 | Assay 2 |
| 1 | A | B |
| 2 | A | B |
| 3 | A | B |
| 4 | A | D |
| 5 | A | C |
| 6 | E | |
| 7 | E | |
| 8 | E | |
| 9 | D | |
| 10 | B | B |
| 11 | A | B |
| 12 | C | D |
| 13 | E | E |
| 14 | E | |
| 15 | E | E |
| 16 | B | B |
| 17 | A | D |
| 18 | A | D |
| 19 | A | D |
| 20 | E | E |
| 21 | B | E |

TABLE 3-continued

| Compound number | Activity category | |
|---|---|---|
| | Assay 1 | Assay 2 |
| 22 | E | |
| 23 | D | |
| 24 | E | |
| 25 | D | |
| 26 | E | |
| 27 | E | |
| 28 | B | C |
| 29 | C | C |
| 30 | E | |
| 31 | A | C |
| 32 | A | B |
| 33 | C | |
| 34 | D | |
| 35 | D | D |
| 35-A | B | E |
| 36 | A | A |
| 37 | B | B |
| 38 | C | C |
| 39-A | A | B |
| 39-B | A | A |
| 40-A | C | D |
| 40 | A | B |
| 41 | A | A |
| 42 | A | B |
| 43 | A | |
| 44 | B | E |
| 45 | A | B |
| 46 | A | D |
| 47 | A | D |
| 48 | A | B |
| 49 | A | C |
| 50 | A | B |
| 51 | D | E |
| 52 | B | E |
| 53 | A | C |
| 54 | A | A |
| 55 | A | A |
| 56 | A | B |
| 57 | A | B |
| 58 | A | B |
| 59 | D | D |
| 60 | C | D |
| 60-A | A | C |
| 61 | A | B |
| 61-A | A | A |
| 61-B | B | C |
| 62 | D | E |
| 63 | B | B |
| 63-A | E | E |
| 64 | A | B |
| 65 | A | B |
| 66 | B | D |
| 67 | B | B |
| 67-A | A | |
| 68 | A | A |
| 68-A | E | |
| 69 | B | B |
| 69-A | E | |
| 70 | A | A |
| 70-A | E | |
| 71 | A | A |
| 71-A | E | |
| 72 | B | B |
| 72-A | A | B |
| 73 | B | B |
| 74 | D | E |
| 75 | A | A |
| 75A | A | |
| 76 | D | C |
| 77 | B | B |
| 78 | C | |
| 79 | D | E |
| 80 | A | A |
| 81 | A | A |
| 82 | A | A |
| 83 | A | A |
| 84 | A | B |
| 85 | A | |
| 86-A | B | B |
| 86-B | B | C |
| 87-A | C | E |
| 87-B | E | |
| 88-A | D | E |
| 89 | A | |
| 90 | A | E |
| 91 | A | B |
| 91-A | A | B |
| 92 | B | B |
| 92-A | A | C |
| 93 | B | C |
| 94 | B | B |
| 95 | B | B |
| 96 | A | A |
| 97 | C | D |
| 98 | B | B |
| 99 | B | E |
| 100 | B | B |
| 101 | B | B |
| 102 | D | D |
| 103 | D | D |
| 104 | C | D |
| 105 | D | |
| 106 | C | D |
| 107 | A | B |
| 108 | E | |
| 109 | E | |
| 110 | E | |
| 111 | E | |
| 112 | B | B |
| 113 | B | C |
| 114 | B | C |
| 115 | B | C |
| 116 | B | B |
| 117 | B | E |
| 118 | A | A |
| 119 | D | E |
| 120 | A | B |
| 121 | B | B |
| 122 | D | |
| 123 | E | |
| 124 | D | E |
| 125 | D | |
| 126 | E | |
| 127 | E | |
| 128 | E | E |
| 129 | C | E |
| 130 | E | |
| 131 | D | |
| 132 | E | |
| 133 | C | |
| 134 | A | C |
| 135 | E | |
| 136 | D | |
| 137 | D | |
| 138 | E | |
| 139 | B | A |
| 140 | E | |
| 141 | D | |
| 142 | E | |
| 143 | A | A |
| 144 | B | C |
| 145 | A | D |
| 146 | A | A |
| 147 | A | A |
| 148 | A | D |
| 149 | A | A |
| 150 | A | A |
| 151 | A | A |
| 152 | A | A |
| 153 | A | |
| 154 | B | E |
| 155 | B | C |

TABLE 3-continued

| Compound number | Activity category Assay 1 | Activity category Assay 2 |
|---|---|---|
| 156 | A | B |
| 157 | A | A |
| 158 | A | B |
| 159 | B | B |
| 160 | D | E |
| 161 | C | D |
| 162 | A | |
| 163 | E | |
| 164 | A | |
| 165 | A | |
| 166 | B | |
| 167 | B | |
| 168 | A | |
| 169 | A | |
| 170 | B | |

Compounds of Formula (I) may have activity as TER-alpha agonists as shown in Table 4, where: for Assay 1: 'A' indicates an $EC_{50}$<50 nM, 6B' indicates an $EC_{50}$ of ≥50 nM and <250 nM, 'C' indicates an $EC_{50}$≥250 nM and <1000 nM, 'D' indicates an $EC_{50}$≥1000 nM and <25000 nM, and 'E' indicates an $EC_{50}$≥25000 nM. For Assay 2, 'A' indicates an $EC_{50}$<50 nM, 'B' indicates an $EC_{50}$ of ≥50 nM and <250 nM, 'C' indicates an $EC_{50}$≥250 nM and <1000 nM, 'D' indicates an $EC_{50}$≥1000 nM and <10000 nM, and 'E' indicates an $EC_{50}$>10000 nM.

TABLE 4

| Compound number | Activity category Assay 1 | Activity category Assay 2 |
|---|---|---|
| 1 | A | C |
| 2 | A | C |
| 3 | E | C |
| 4 | E | E |
| 5 | E | D |
| 6 | E | |
| 7 | E | |
| 8 | D | |
| 9 | E | |
| 10 | C | B |
| 11 | B | C |
| 12 | D | D |
| 13 | C | D |
| 14 | E | |
| 15 | E | E |
| 16 | C | C |
| 17 | E | E |
| 18 | E | D |
| 19 | E | D |
| 20 | E | E |
| 21 | E | E |
| 22 | E | |
| 23 | D | |
| 24 | E | |
| 25 | D | |
| 26 | E | |
| 27 | E | |
| 28 | C | D |
| 29 | D | C |
| 30 | E | |
| 31 | A | D |
| 32 | A | B |
| 33 | C | |
| 34 | E | |
| 35 | D | D |
| 35-A | C | B |
| 36 | B | A |
| 37 | C | B |
| 38 | D | E |

TABLE 4-continued

| Compound number | Activity category Assay 1 | Activity category Assay 2 |
|---|---|---|
| 39-A | C | B |
| 39-B | B | A |
| 40-A | C | D |
| 40 | B | C |
| 41 | A | A |
| 42 | C | C |
| 43 | A | A |
| 44 | E | E |
| 45 | A | C |
| 46 | E | E |
| 47 | A | D |
| 48 | A | C |
| 49 | A | C |
| 50 | A | C |
| 51 | E | E |
| 52 | D | E |
| 53 | C | D |
| 54 | A | A |
| 55 | A | B |
| 56 | C | B |
| 57 | A | C |
| 58 | C | C |
| 59 | D | E |
| 60 | D | D |
| 60-A | B | C |
| 61 | C | C |
| 61-A | B | B |
| 61-B | D | C |
| 62 | D | E |
| 63 | C | C |
| 63-A | E | E |
| 64 | C | C |
| 65 | C | D |
| 66 | C | D |
| 67 | D | E |
| 67-A | E | D |
| 68 | B | B |
| 68-A | E | |
| 69 | C | B |
| 69-A | E | |
| 70 | B | B |
| 70-A | E | |
| 71 | B | B |
| 71-A | E | |
| 72 | E | E |
| 72-A | B | E |
| 73 | C | C |
| 74 | D | E |
| 75 | B | C |
| 75-A | B | E |
| 76 | E | E |
| 77 | C | C |
| 78 | D | |
| 79 | D | D |
| 80 | B | B |
| 81 | A | A |
| 82 | A | A |
| 83 | A | A |
| 84 | A | B |
| 85 | A | A |
| 86-A | C | C |
| 86-B | D | D |
| 87-A | C | E |
| 87-B | E | |
| 88-A | E | E |
| 89 | C | D |
| 90 | B | E |
| 91 | D | E |
| 91-A | D | E |
| 92 | D | E |
| 92-A | D | E |
| 93 | C | D |
| 94 | C | D |
| 95 | C | C |
| 96 | B | B |
| 97 | D | E |

TABLE 4-continued

| Compound number | Activity category | |
|---|---|---|
| | Assay 1 | Assay 2 |
| 98 | E | E |
| 99 | E | E |
| 100 | E | E |
| 101 | C | B |
| 102 | D | E |
| 103 | E | E |
| 104 | D | E |
| 105 | D | |
| 106 | D | D |
| 107 | D | C |
| 108 | E | |
| 109 | E | |
| 110 | E | |
| 111 | E | |
| 112 | C | D |
| 113 | C | E |
| 114 | E | E |
| 115 | E | E |
| 116 | E | E |
| 117 | E | E |
| 118 | B | B |
| 119 | E | E |
| 120 | E | E |
| 121 | C | E |
| 122 | D | |
| 123 | E | |
| 124 | D | E |
| 125 | E | |
| 126 | E | |
| 127 | E | |
| 128 | E | E |
| 129 | E | E |
| 130 | D | |
| 131 | D | |
| 132 | E | |
| 133 | E | |
| 134 | C | E |
| 135 | E | |
| 136 | D | |
| 137 | E | |
| 138 | E | |
| 139 | B | B |
| 140 | E | |
| 141 | E | |
| 142 | E | |
| 143 | A | A |
| 144 | C | D |
| 145 | A | D |
| 146 | B | B |
| 147 | A | A |
| 148 | A | D |
| 149 | A | A |
| 150 | A | A |
| 151 | A | A |
| 152 | A | A |
| 153 | A | |
| 154 | E | |
| 155 | E | E |
| 156 | B | D |
| 157 | C | B |
| 158 | C | D |
| 159 | C | D |
| 160 | D | E |
| 161 | C | E |
| 162 | B | |
| 163 | E | |
| 164 | B | C |
| 165 | C | |
| 166 | E | |
| 167 | D | |
| 168 | B | |
| 169 | C | |
| 170 | E | |

Compounds of Formula (I) have activity as THR-alpha/beta agonists as shown in Table 5, where: for Assays 1 and 2: 'C' indicates an $E_{max}<50\%$, 'B' indicates an $E_{max}\geq 50\%$, and $<75\%$, 'A' indicates an $E_{max}\geq 75\%$.

TABLE 5

| Compound number | Activity category | | | |
|---|---|---|---|---|
| | Assay 1 | | Assay 2 | |
| | THRα | THRβ | THRα | THRβ |
| 1 | C | B | A | A |
| 2 | C | A | A | A |
| 3 | C | B | A | A |
| 4 | C | C | B | A |
| 5 | C | C | B | A |
| 6 | C | C | | |
| 7 | C | C | | |
| 8 | C | C | | |
| 9 | C | C | | |
| 10 | B | B | A | A |
| 11 | C | C | A | A |
| 12 | B | A | A | A |
| 13 | C | C | A | A |
| 14 | C | C | | |
| 15 | C | C | C | C |
| 16 | C | B | A | A |
| 17 | C | C | C | A |
| 18 | C | C | B | A |
| 19 | C | C | C | A |
| 20 | C | C | C | C |
| 21 | C | C | C | C |
| 22 | C | C | | |
| 23 | C | C | | |
| 24 | C | C | | |
| 25 | B | B | | |
| 26 | C | C | | |
| 27 | C | C | | |
| 28 | B | C | B | A |
| 29 | B | B | A | A |
| 30 | A | B | | |
| 31 | C | B | A | A |
| 32 | B | A | A | A |
| 33 | C | A | | |
| 34 | C | C | | |
| 35 | B | B | C | B |
| 35-A | B | C | C | A |
| 36 | B | B | C | B |
| 37 | B | B | B | A |
| 38 | A | B | C | A |
| 39-A | B | C | A | A |
| 39-B | B | B | A | A |
| 40-A | C | C | C | A |
| 40 | B | B | A | A |
| 41 | B | B | B | A |
| 42 | C | B | A | A |
| 43 | A | A | A | A |
| 44 | C | C | C | C |
| 45 | C | C | A | A |
| 46 | C | C | C | B |
| 47 | C | C | A | A |
| 48 | B | B | A | A |
| 49 | C | C | C | A |
| 50 | B | B | A | A |
| 51 | A | C | C | C |
| 52 | C | C | B | A |
| 53 | C | B | A | A |
| 54 | C | B | B | A |
| 55 | B | B | A | A |
| 56 | C | C | B | A |
| 57 | C | C | A | A |
| 58 | C | C | B | A |
| 59 | C | C | B | A |
| 60 | C | C | A | A |
| 60-A | C | C | C | B |
| 61 | B | C | A | A |
| 61-A | B | B | B | A |
| 61-B | C | C | C | A |
| 62 | C | C | B | A |
| 63 | C | C | B | A |
| 63-A | C | C | C | C |

TABLE 5-continued

| Compound number | Assay 1 THRα | Assay 1 THRβ | Assay 2 THRα | Assay 2 THRβ |
| --- | --- | --- | --- | --- |
| 64 | C | C | C | B |
| 65 | C | C | C | A |
| 66 | C | B | B | A |
| 67 | C | C | C | B |
| 67-A | C | C | C | C |
| 68 | C | B | B | A |
| 68-A | C | C | | |
| 69 | C | C | B | B |
| 69-A | C | C | | |
| 70 | C | C | B | A |
| 70-A | C | C | | |
| 71 | C | C | B | A |
| 71-A | C | C | | |
| 72 | C | C | C | B |
| 72-A | C | C | C | B |
| 73 | B | C | A | A |
| 74 | C | B | C | C |
| 75 | A | A | A | A |
| 75-A | C | B | C | B |
| 76 | C | C | C | B |
| 77 | B | C | A | A |
| 78 | C | C | | |
| 79 | C | B | B | A |
| 80 | B | B | A | A |
| 81 | B | B | A | A |
| 82 | A | A | A | A |
| 83 | B | B | A | B |
| 84 | B | C | A | A |
| 85 | C | C | B | A |
| 86-A | C | C | B | A |
| 86-B | C | C | C | A |
| 87-A | C | C | C | C |
| 87-B | C | C | | |
| 88-A | C | C | A | C |
| 89 | C | C | C | B |
| 90 | C | C | C | B |
| 91 | B | C | C | B |
| 91-A | C | C | C | B |
| 92 | C | C | C | C |
| 92-A | B | C | C | C |
| 93 | C | C | C | B |
| 94 | C | C | C | B |
| 95 | C | C | C | A |
| 96 | C | C | B | A |
| 97 | C | C | C | C |
| 98 | C | C | C | C |
| 99 | A | C | C | C |
| 100 | C | C | C | C |
| 101 | C | C | C | B |
| 102 | C | C | C | C |
| 103 | C | C | C | C |
| 104 | B | C | C | B |
| 105 | C | C | | |
| 106 | C | C | C | B |
| 107 | C | C | C | B |
| 108 | C | C | | |
| 109 | C | C | | |
| 110 | C | C | | |
| 111 | C | C | | |
| 112 | C | C | C | C |
| 113 | C | C | C | C |
| 114 | C | C | C | C |
| 115 | C | C | C | C |
| 116 | C | C | C | C |
| 117 | C | C | C | C |
| 118 | C | B | B | B |
| 119 | C | C | C | C |
| 120 | C | C | C | B |
| 121 | C | C | C | B |
| 122 | C | C | | |
| 123 | C | C | | |
| 124 | C | C | C | C |
| 125 | C | C | | |
| 126 | C | C | | |
| 127 | C | C | | |
| 128 | C | C | C | C |
| 129 | C | C | C | C |
| 130 | C | C | | |
| 131 | C | C | | |
| 132 | C | C | | |
| 133 | C | C | | |
| 134 | C | C | C | B |
| 135 | C | C | | |
| 136 | C | C | | |
| 137 | C | C | | |
| 138 | C | C | | |
| 139 | C | C | C | B |
| 140 | C | C | | |
| 141 | C | C | | |
| 142 | C | C | | |
| 143 | A | B | A | A |
| 144 | C | C | B | B |
| 145 | B | C | B | B |
| 146 | C | C | C | B |
| 147 | C | B | A | A |
| 148 | B | C | C | B |
| 149 | C | C | A | A |
| 150 | C | C | B | B |
| 151 | A | B | B | B |
| 152 | B | C | B | B |
| 153 | C | C | | |
| 154 | C | C | C | |
| 155 | C | C | C | C |
| 156 | C | C | C | B |
| 157 | B | A | B | A |
| 158 | C | C | C | B |
| 159 | C | C | C | B |
| 160 | C | C | C | C |
| 161 | C | C | C | C |
| 162 | C | B | | |
| 163 | C | C | | |
| 164 | C | C | B | A |
| 165 | C | C | | |
| 166 | C | C | | |
| 167 | C | C | | |
| 168 | B | C | | |
| 169 | C | C | | |
| 170 | C | C | | |

Compounds of Formula (I) have activity as THR agonists as shown in Table 6, where: for Assay 3 in the $EC_{50}$ column: 'A' indicates an $EC_{50}$<100 nM, 'B' indicates an $EC_{50}$ of ≥100 nM and <1000 nM, 'C' indicates an $EC_{50}$≥100 nM. In the $E_{max}$ column, 'C' indicates an $E_{max}$<50%, 'B' indicates an $E_{max}$≥50%, and <75%, 'A' indicates an $E_{max}$≥75%.

TABLE 6

| Compound | Activity category Assay 3 | |
| --- | --- | --- |
| | $EC_{50}$ | $E_{max}$ |
| Reference (T3) | A | A |
| 1 | B | A |
| 10 | A | B |
| 11 | A | A |
| 13 | C | A |
| 16 | B | C |
| 18 | C | A |
| 31 | B | A |
| 39-A | A | B |
| 39-B | A | A |
| 40 | A | A |

TABLE 6-continued

| Compound Reference (T3) | Activity category Assay 3 | |
|---|---|---|
| | $EC_{50}$ A | $E_{max}$ A |
| 42 | A | B |
| 43 | A | A |
| 52 | C | A |
| 54 | A | A |
| 55 | A | A |
| 61-A | A | B |
| 61-B | C | A |
| 67 | C | A |
| 67-A | B | C |
| 70 | A | B |
| 72 | B | A |
| 72-A | B | A |
| 75-A | C | A |
| 83 | A | A |
| 86-A | A | B |
| 89 | B | A |
| 90 | C | B |
| 93 | A | B |
| 94 | B | B |
| 101 | A | C |
| 112 | B | A |
| 114 | B | B |
| 115 | C | A |
| 120 | B | A |
| 121 | B | B |
| 145 | B | A |
| 146 | B | A |
| 148 | B | A |
| 151 | A | A |
| 157 | A | A |
| 158 | C | C |
| 164 | A | B |

Example 100: X-Ray Diffraction Data

The chemical structures of compounds 67 and 67-A were confirmed by x-ray crystallography as described below.

Experimental. Single colorless chunk crystals of compound 67 recrystallized from a mixture of THF and acetonitrile by slow evaporation. A suitable crystal with dimensions 0.39×0.20×0.10 mm3 was selected and mounted on a nylon loop with paratone oil on a Bruker APEX-II CCD diffractometer. The crystal was kept at a steady T=173(2) K during data collection. The structure was solved with the XT (Sheldrick, 2015) solution program using dual methods and by using OLEX2 as the graphical interface. The model was refined with ShelXL 2018/3 (Sheldrick, 2015) using full matrix least squares minimization on F2.

Crystal Data. $C_{29}H_{25}Cl_2N_7O_5$, Mr=622.46, triclinic, P-1 (No. 2), a=8.91530(10) Å, b=10.93240(10) Å, c=16.2174(2) Å, α=75.7870(10)°, β=83.5020(10)°, γ=67.6090(10)°, V=1416.39(3) Å$^3$, T=173(2) K, Z=2, Z'=1, μ(CuK$_α$)=2.518, 22070 reflections measured, 5231 unique (Rint=0.0434) which were used in all calculations. The final wR2 was 0.1228 (all data) and R1 was 0.0445 (I>2(I)).

Experimental. Single colorless block crystals of compound 67-A recrystallized from THF by slow evaporation. A suitable crystal with dimensions 0.14×0.07×0.04 mm3 was selected and mounted on a nylon loop with paratone oil on a Bruker APEX-II CCD diffractometer. The crystal was kept at a steady T=173(1) K during data collection. The structure was solved with the ShelXT (Sheldrick, G. M. (2015). Acta Cryst. A71, 3-8) solution program using dual methods and by using OLEX2 as the graphical interface. The model was refined with ShelXL (Sheldrick, Acta Cryst. A64 2008, 112-122) using full matrix least squares minimization on F2.

Crystal Data. $C_{27}H_{22}Cl_2N_6O_5$, $M_r$=581.40, monoclinic, C2/c (No. 15), a=38.956(17) Å, b=8.001(3) Å, c=23.093(13) Å, R=125.580(12)°, α=γ=90°, V=5854(5) Å$^3$, T=173(1) K, Z=8, Z'=1, μ(CuK$_α$)=2.389, 44732 reflections measured, 5360 unique (Rint=0.1596) which were used in all calculations. The final wR2 was 0.3362 (all data) and R1 was 0.1018 (I>2(I)).

Example 101: Comparison of Compounds 42, 40, and 10 with —CN Counterparts

Compounds 42, 40, and 10 have $R_9$=$NH_2$. These compounds were compared to direct analogs wherein $R_9$=CN, in the HEK293T reporter THRalpha/beta/RXR reporter assay.

TABLE 7

| HEK293T reporter THRalpha/beta/RXR reporter assay data | | | | | | |
|---|---|---|---|---|---|---|
| | Compd 42 | CN analog 1 | Compd 40 | CN analog 2 | Compd 10 | CN analog 3 |
| $EC_{50}$ α (μM) | 0.834 (87%) | >10 | 0.564 (95%) | 9.65 (35%) | 0.191 (79%) | 16.9 (62%) |
| $EC_{50}$ β (μM) | 0.077 (94%) | >10 | 0.058 (92%) | 3.78 (81%) | 0.050 (91%) | 2.37 (93%) |
| Ratio (α/β) | 11 (n = 5) | — | 10 (n = 3) | 2.5 (n = 1) | 4 (n = 7) | >4 (n = 4) |

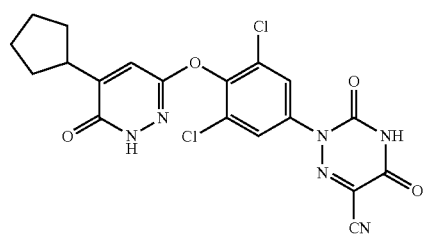

CN analog 1

TABLE 7-continued

HEK293T reporter THRalpha/beta/RXR reporter assay data

Compd 42  CN analog 1  Compd 40  CN analog 2  Compd 10  CN analog 3

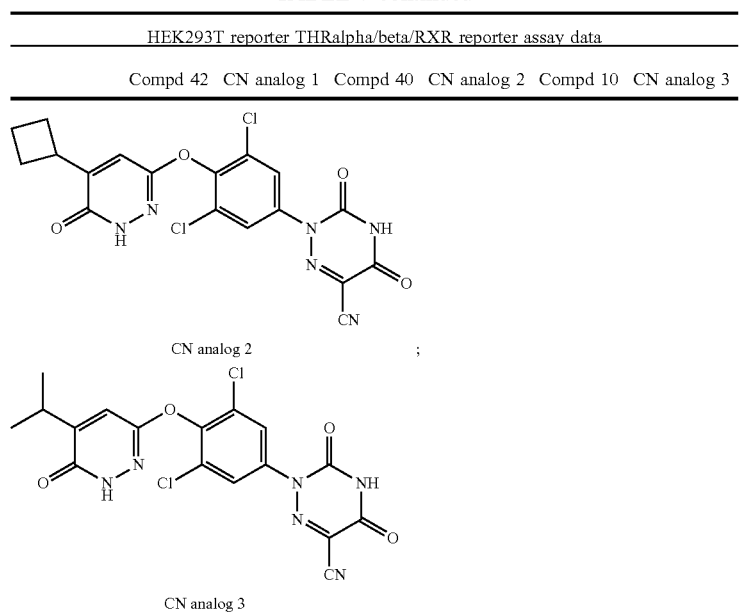

CN analog 2 ;

CN analog 3

REFERENCES

1. Younossi, Z. M., Koenig, A. B., Abdelatif, D., Fazel, Y., Henry, L., Wymer, M., 2016. Global epidemiology of nonalcoholic fatty liver disease-Meta-analytic assessment of prevalence, incidence, and outcomes. Hepatology 64(1): 73e84.
2. Gastroenterology. 2012 June; 142(7): 1592-609. doi: 10.1053/j.gastro.2012.04.001. Epub 2012 May 15.
3. Serfaty, L., Lemoine, M., 2008. Definition and natural history of metabolic steatosis: clinical aspects of NAFLD, NASH and cirrhosis. Diabetes and Metabolism 34 (6 Pt 2): 634e637.
4. Hepatology. 2012 October; 56(4): 1580-1584. doi: 10.1002/hep.26031
5. Dulai, P. S., Singh, S., Patel, J., Soni, M., Prokop, L. J., Younossi, Z., et al., 2017. Increased risk of mortality by fibrosis stage in nonalcoholic fatty liver disease: systematic review and meta-analysis. Hepatology 65(5): 1557e1565.
6. Younossi, Z. M., Loomba, R., Rinella, M. E., Bugianesi, E., Marchesini, G., Neuschwander-Tetri, B. A., et al., 2018. Current and future therapeutic regimens for non-alcoholic fatty liver disease (NAFLD) and non-alcoholic steatohepatitis (NASH). Hepatology 68(1): 349e360.
7. Thyroid. 2002 June; 12(6): 441-6. Mechanism of thyroid hormone action. Harvey C B, Williams G R.
8. A. L. Bookout, Y. Jeong, M. Downes, R. T. Yu, R. M. Evans, D. J. Mangelsdorf Anatomical profiling of nuclear receptor expression reveals a hierarchical transcriptional network. Cell, 126 (2006), pp. 789-799
9. F. Flamant, J. D. Baxter, D. Forrest, S. Refetoff, H. H. Samuels, T. S. Scanlan, B. Vennstrom, J. Samarut International union of pharmacology. LIX. The pharmacology and classification of the nuclear receptor superfamily: thyroid hormone receptors. Pharmacol. Rev., 58 (2006), pp. 705-711
10. Bioorg Med Chem Lett. 2005 Apr. 1; 15(7): 1835-40. Novel heterocyclic thyromimetics. Haning H1, Woltering M, Mueller U, Schmidt G, Schmeck C, Voehringer V, Kretschmer A, Pernerstorfer J.
11. Expert Opin Ther Pat. 2010 February; 20(2): 213-28. doi: 10.1517/13543770903567069. Thyromimetics: a review of recent reports and patents (2004-2009). Hirano T1, Kagechika H.
12. Front Endocrinol (Lausanne). 2018 Jul. 10; 9: 382. doi: 10.3389/fendo.2018.00382. eCollection 2018. Thyroid Hormones, Thyromimetics and Their Metabolites in the Treatment of Liver Disease. Kowalik M A, Columbano A, Perra A
13. Proc Natl Acad Sci USA. 2007 Sep. 25; 104(39): 15490-5. Epub 2007 Sep. 18. Targeting thyroid hormone receptor-beta agonists to the liver reduces cholesterol and triglycerides and improves the therapeutic index. Erion MD1, Cable E E, Ito B R, Jiang H, Fujitaki J M, Finn P D, Zhang B H, Hou J, Boyer S H, van Poelje P D, Linemeyer D L.

Embodiment 1. A compound of Formula I:

$$TL-L_a-CE-HD \quad (I)$$

or a pharmaceutically acceptable salt, prodrug, amide or ester thereof, wherein:

i) TL is a moiety of Formula IIa, IIb, IIIa, IIIb, IIIc, or IIId:

(IIa)

(IIb)

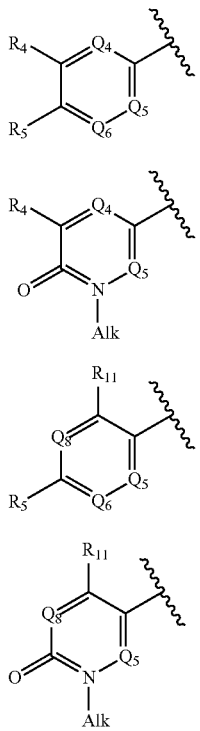

(IIIa)

(IIIb)

(IIIc)

(IIId)

wherein:
each of $Q_1$, $Q_2$, $Q_3$, $Q_4$, $Q_5$, $Q_6$, and $Q_8$, is independently nitrogen or —$CR_b$—, wherein each $R_b$ is independently hydrogen, halogen, or lower alkyl;

$R_1$ is hydrogen, an optionally substituted alkyl, an optionally substituted carbocyclic group, an optionally substituted aryl group, an optionally substituted heterocyclic group, an optionally substituted heteroaryl group, an optionally substituted carbocyclic alkyl group, an optionally substituted aralkyl group, an optionally substituted heterocyclicalkyl group, an optionally substituted heteroarylalkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;

$R_2$ is hydrogen, halogen, optionally substituted alkyl, optionally substituted cycloalkyl, or —CN;

$R_3$ is hydrogen or lower alkyl;

$R_4$ is an optionally substituted alkyl, an optionally substituted carbocyclic group, an optionally substituted aryl group, an optionally substituted heterocyclic group, an optionally substituted heteroaryl group, an optionally substituted carbocyclic alkyl group, an optionally substituted aralkyl group, an optionally substituted heterocyclicalkyl group, an optionally substituted heteroarylalkyl group, an optionally substituted amino group, an optionally substituted sulfamoyl group, an optionally substituted carbamoyl group, or an optionally substituted carbamoyl alkyl group, where the nitrogen of the carbamoyl or carbamoyl alkyl group is optionally a heteroatom in a ring structure; and $R_5$ is hydroxy, $NH_2$, alkylamino, alkanoylamino, or alkylsulfonylamino;

or $R_4$ and $R_5$ taken together along with the carbon atoms to which they are attached form a five- or six-membered optionally substituted carbocyclic group, optionally substituted aryl group, optionally substituted heterocyclic group, or optionally substituted heteroaryl group;

or $R_4$ and $R_5$ taken together along with the carbon atoms to which they are attached form a seven to eleven membered, optionally substituted spirocyclic ring or a seven to eleven membered, optionally substituted spiro-heterocyclic ring;

or when $Q_6$ is nitrogen and $R_5$ is hydroxy, then the tautomer of the moiety of Formula III; and Alk is hydrogen or an optionally substituted alkyl;

ii) CE is a moiety of Formula IV

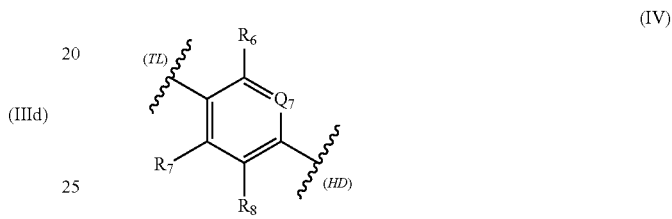

(IV)

wherein:
each of $R_6$ and $R_7$ is independently selected from halogen, —CN, optionally substituted lower alkyl, optionally substituted lower alkoxy, optionally substituted lower alkenyl, or cyclopropyl;

$R_8$ is selected from hydrogen, optionally substituted lower alkyl, optionally substituted lower alkoxy, cyano, or halogen;

optionally $R_7$ and $R_8$ taken together, along with the carbon atoms to which they are attached, form a 4, 5- or 6-membered carbocyclic, heterocyclic, aryl, or heteroaryl ring $Q_7$ is nitrogen or —$CR_c$—, wherein $R_c$ is hydrogen, halogen, or lower alkyl;

(TL) denotes the point where the moiety of Formula IV connects to TL-$L_a$-; and (HD) denotes the point where the moiety of Formula IV connects to —HD;

iii) HD is a moiety of Formula V or VI:

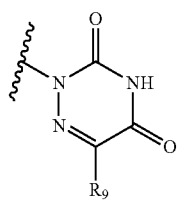

(V)

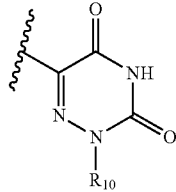

(VI)

wherein:
 R$_9$ is selected from hydrogen, —(C(R$_d$)$_2$)$_n$—C(R$_a$)$_3$, —(C(R$_d$)$_2$)$_n$—OR$_d$, —(C(R$_a$)$_2$)$_n$—N(R$_a$)$_2$, —(C(R$_a$)$_2$)$_n$—S(=O)$_q$R$_d$, —(C(R$_a$)$_2$)$_n$—CN, —(C(R$_a$)$_2$)$_n$—C≡C—R$_d$, —(C(R$_d$)$_2$)$_n$—C(=O)—OR$_d$, —(C(R$_a$)$_2$)$_n$—HeAr, or —(C(R$_a$)$_2$)$_n$—C(=O)—N(R$_a$)$_2$; wherein
 each R$_d$ is independently hydrogen or optionally substituted lower alkyl;
 each q is independently selected from 0, 1, or 2; and
 each n is independently selected from 0, 1, 2, 3, 4, or 5;
 R$_{10}$ is hydrogen, —C(R$_e$)$_3$, wherein each R$_e$ is independently hydrogen, halogen, or optionally substituted lower alkyl; and
 R$_{11}$ is an aryl group, preferably substituted with lower alkyl, halogen, cycloalkyl; or a bicyclic ring system containing either aromatic or saturated rings; or a bicyclic heterocyclic containing either aromatic or saturated ring systems
 iv) L$_a$ is independently a bond; —(C(R$_a$)$_2$)$_n$—; oxygen; sulfur; —NR$_a$—; wherein:
 each R$_a$ is independently a hydrogen or lower alkyl; and n is 0, 1, 2, 3, 4 or 5.

Embodiment 2. The compound of Embodiment 1, wherein R$_1$ is hydrogen, an optionally substituted alkyl, an optionally substituted carbocyclic group, an optionally substituted aryl group, and an optionally substituted C-carboxy group.

Embodiment 3. The compound of Embodiment 2, wherein the alkyl is selected from the group consisting of methyl, ethyl, n-propyl, i-propyl, n-butyl, i-butyl, and t-butyl.

Embodiment 4. The compound of Embodiment 3, wherein at least one carbon atom of the listed alkyl moieties is perfluorinated.

Embodiment 5. The compound of Embodiment 3, wherein the alkyl is substituted with cycloalkyl or aryl.

Embodiment 6. The compound of Embodiment 5, wherein the cycloalkyl is selected from the group consisting of cyclopropyl, cyclopentyl, and cyclohexyl.

Embodiment 7. The compound of Embodiment 5, wherein the aryl is optionally substituted phenyl.

Embodiment 8. The compound of Embodiment 2, wherein the carbocyclic group is cyclohexane or cyclopentane.

Embodiment 9. The compound of Embodiment 2, wherein the aryl group is phenyl.

Embodiment 10. The compound of Embodiment 2, wherein the C-carboxy group is a moiety of formula —C(=O)—O—R, where R is selected from the group consisting of methyl, ethyl, n-propyl, i-propyl, n-butyl, i-butyl, and t-butyl.

Embodiment 11. The compound of Embodiment 1, wherein R$_2$ is selected from the group consisting of hydrogen, methyl, ethyl, n-propyl, i-propyl, n-butyl, i-butyl, and t-butyl.

Embodiment 12. The compound of Embodiment 1, wherein Q$_1$, Q$_2$, Q$_3$, and Q$_4$ are —CR$_b$—, where each R$_b$ is independently selected from the group consisting of hydrogen, methyl, ethyl, n-propyl, i-propyl, n-butyl, i-butyl, and t-butyl.

Embodiment 13. The compound of Embodiment 1, wherein each of Q$_5$ and Q$_6$ is independently nitrogen or —NH.

Embodiment 14. The compound of Embodiment 13, wherein Q$_5$ is nitrogen and Q$_6$ is —NH.

Embodiment 15. The compound of Embodiment 1, wherein R$_4$ is selected from the group consisting of methyl, ethyl, n-propyl, i-propyl, n-butyl, i-butyl, and t-butyl.

Embodiment 16. The compound of Embodiment 1, wherein R$_5$ is hydroxy.

Embodiment 17. The compound of Embodiment 1, wherein each of R$_6$ and R$_7$ is independently chlorine, bromine, and iodine.

Embodiment 18. The compound of Embodiment 17, wherein each of R$_6$ and R$_7$ is independently —CN, an optionally substituted lower alkyl or an optionally substituted lower alkoxy, where the lower alkyl and the alkyl group of the lower alkoxy is each independently selected from methyl, ethyl, n-propyl, i-propyl, n-butyl, s-butyl, and t-butyl.

Embodiment 19. The compound of Embodiment 1, wherein R$_6$ and R$_7$ are the same.

Embodiment 20. The compound of Embodiment 1, wherein each of R$_6$ and R$_7$ is independently chlorine or methyl.

Embodiment 21. The compound of Embodiment 1, wherein R$_8$ is hydrogen.

Embodiment 22. The compound of Embodiment 1, wherein R$_e$ is hydrogen or methyl.

Embodiment 23. The compound of Embodiment 1, wherein:
 TL is a moiety of Formula IIa, IIb, IIIa, IIIb, IIIc, or IIId;

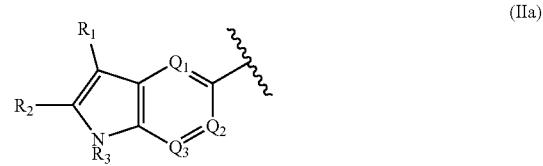

(IIa)

(IIb)

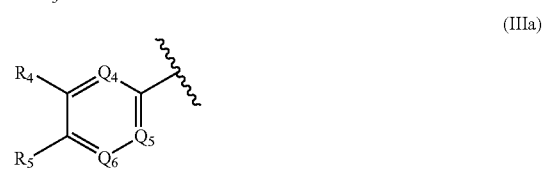

(IIIa)

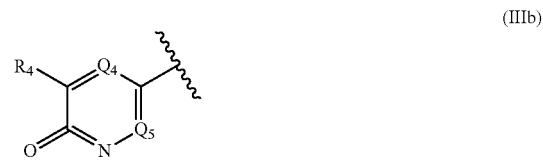

(IIIb)

(IIIc)

-continued

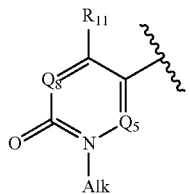

(IIId)

CE is a moiety of Formula IV

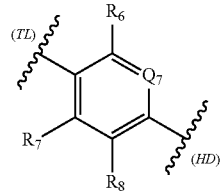

(IV)

wherein:
each of $Q_1$, $Q_2$, $Q_3$, $Q_4$, $Q_5$, $Q_6$ and Qs, is independently nitrogen or —$CR_b$—, wherein each $R_b$ is independently hydrogen, halogen, or lower alkyl;

$R_1$ is an optionally substituted alkyl, an optionally substituted carbocyclic group, an optionally substituted aryl group, an optionally substituted heterocyclic group, an optionally substituted heteroaryl group, an optionally substituted carbocyclic alkyl group, an optionally substituted aralkyl group, an optionally substituted heterocyclicalkyl group, an optionally substituted heteroarylalkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;

$R_2$ is halogen, optionally substituted alkyl, optionally substituted cycloalkyl, or —CN;

$R_3$ is hydrogen;

$R_4$ is an optionally substituted alkyl, an optionally substituted carbocyclic group, an optionally substituted aryl group, an optionally substituted heterocyclic group, an optionally substituted heteroaryl group, an optionally substituted carbocyclic alkyl group, an optionally substituted aralkyl group, an optionally substituted heterocyclicalkyl group, an optionally substituted heteroarylalkyl group, an optionally substituted amino group, an optionally substituted sulfamoyl group, an optionally substituted carbamoyl group, or an optionally substituted carbamoyl alkyl group, where the nitrogen of the carbamoyl or carbamoyl alkyl group is optionally a heteroatom in a ring structure; and $R_5$ is hydroxy, $NH_2$, alkylamino, alkanoylamino, or alkylsulfonylamino;

or $R_4$ and $R_5$ taken together along with the carbon atoms to which they are attached form a five- or six-membered optionally substituted carbocyclic group, optionally substituted aryl group, optionally substituted heterocyclic group, or optionally substituted heteroaryl group;

or $R_4$ and $R_5$ taken together along with the carbon atoms to which they are attached form a seven to eleven membered, optionally substituted spirocyclic ring or a seven to eleven membered, optionally substituted spiro-heterocyclic ring;

or when $Q_6$ is nitrogen and $R_5$ is hydroxy, then the tautomer of the moiety of Formula III; and Alk is hydrogen or an optionally substituted alkyl;

wherein:
each of $R_6$ and $R_7$ is independently selected from halogen, —CN, optionally substituted lower alkyl, optionally substituted lower alkoxy, optionally substituted lower alkenyl, or cyclopropyl;
$R_8$ is selected from hydrogen, optionally substituted lower alkyl, optionally substituted lower alkoxy, cyano, or halogen;
$Q_7$ is nitrogen or —$CR_c$—, wherein $R_c$ is hydrogen, halogen, or lower alkyl;
(TL) denotes the point where the moiety of Formula IV connects to TL-$L_a$-; and
(HD) denotes the point where the moiety of Formula IV connects to —HD;
HD is a moiety of Formula V or VI:

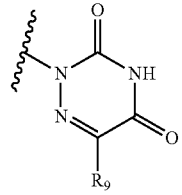

(V)

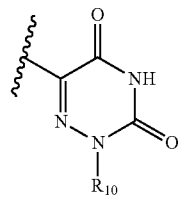

(VI)

wherein:
$R_9$ is selected from —$NH_2$, —CN, —$CH_2$—S—$CH_3$, or —$CH_2$—S(=O)$_2$—$CH_3$;
$R_{10}$ is —$CH_3$; and
$L_a$ is oxygen or —$CH_2$—.

Embodiment 24. The compound of Embodiment 1, wherein:
TL is a moiety of Formula II

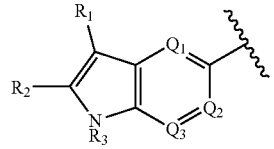

(II)

wherein:
each of $Q_1$, $Q_2$, and $Q_3$ is independently nitrogen or —$CR_b$—, wherein each $R_b$ is independently hydrogen, halogen, or lower alkyl;

R₁ is an optionally substituted alkyl, an optionally substituted carbocyclic group, an optionally substituted aryl group, an optionally substituted heterocyclic group, an optionally substituted heteroaryl group, an optionally substituted carbocyclic alkyl group, an optionally substituted aralkyl group, an optionally substituted heterocyclicalkyl group, an optionally substituted heteroarylalkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;

R₂ is halogen, optionally substituted alkyl, optionally substituted cycloalkyl, or —CN;

R₃ is hydrogen;

CE is a moiety of Formula IV

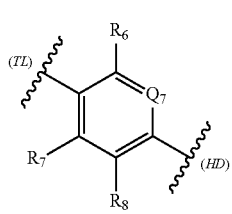

(IV)

wherein:

each of R₆ and R₇ is independently selected from halogen, —CN, optionally substituted lower alkyl, optionally substituted lower alkoxy, optionally substituted lower alkenyl, or cyclopropyl;

R₈ is selected from hydrogen, optionally substituted lower alkyl, optionally substituted lower alkoxy, cyano, or halogen;

Q₇ is nitrogen or —CR_c—, wherein R_c is hydrogen, halogen, or lower alkyl;

(TL) denotes the point where the moiety of Formula IV connects to TL-L_a-; and (HD) denotes the point where the moiety of Formula IV connects to —HD;

HD is a moiety of Formula V:

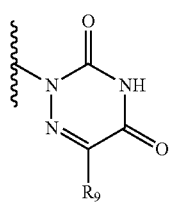

(V)

wherein R₉ is hydrogen, —CN, —C(R_d)₂—S—R_d, —C(R_d)₂—S(=O)₂R_d, or —C≡C—R_d, wherein each R_d is independently hydrogen or lower alkyl; and L_a is oxygen or —CH₂—.

Embodiment 25. A compound selected from the group consisting of:

1

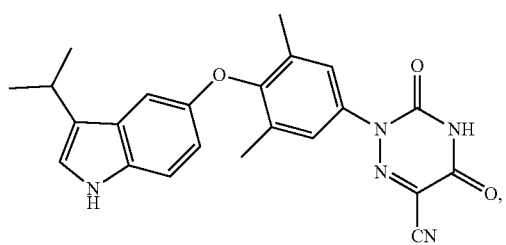

2

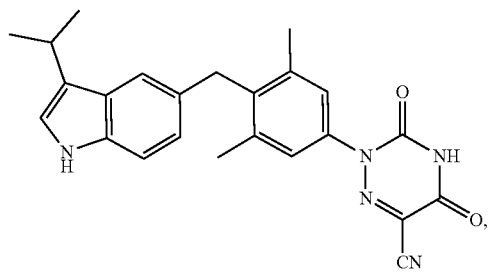

3

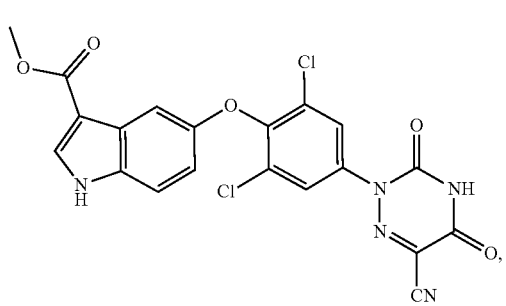

4

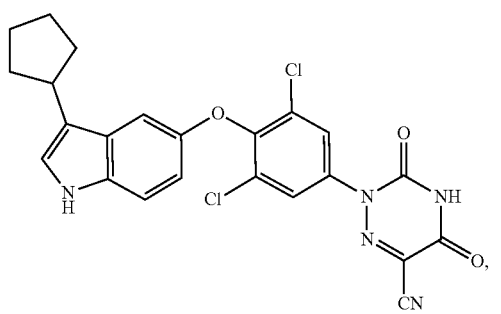

5

353
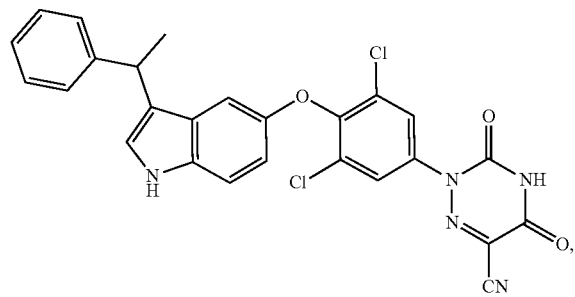
6
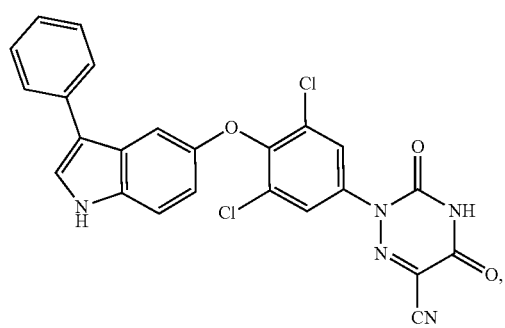
7
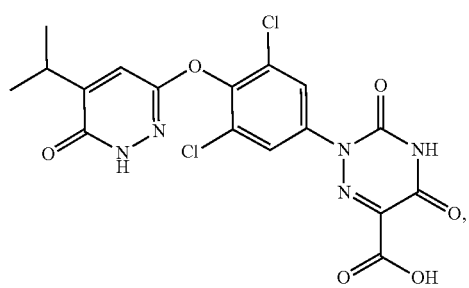
8
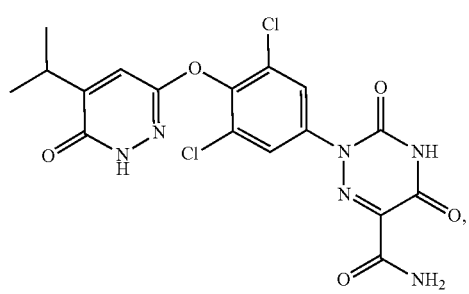
9
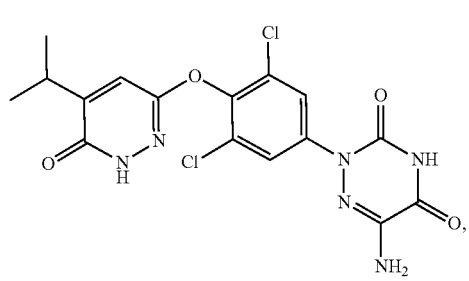
10
354
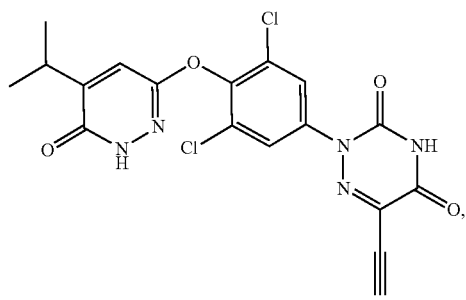
11
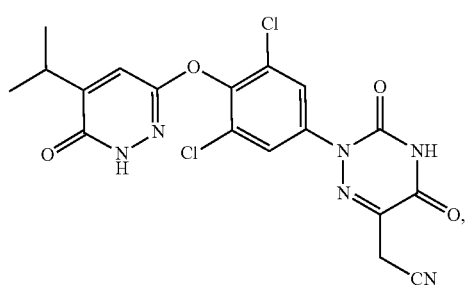
12
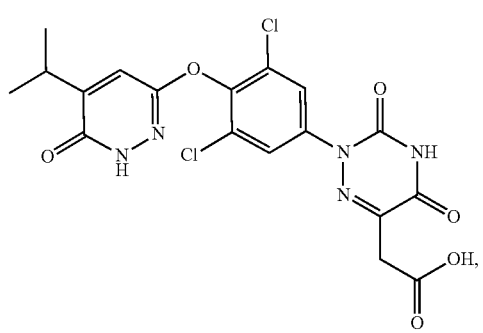
13
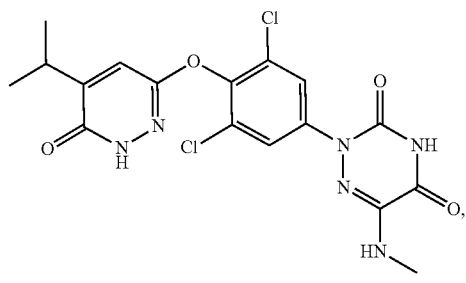
14
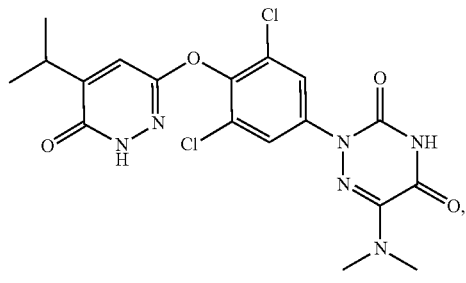
15

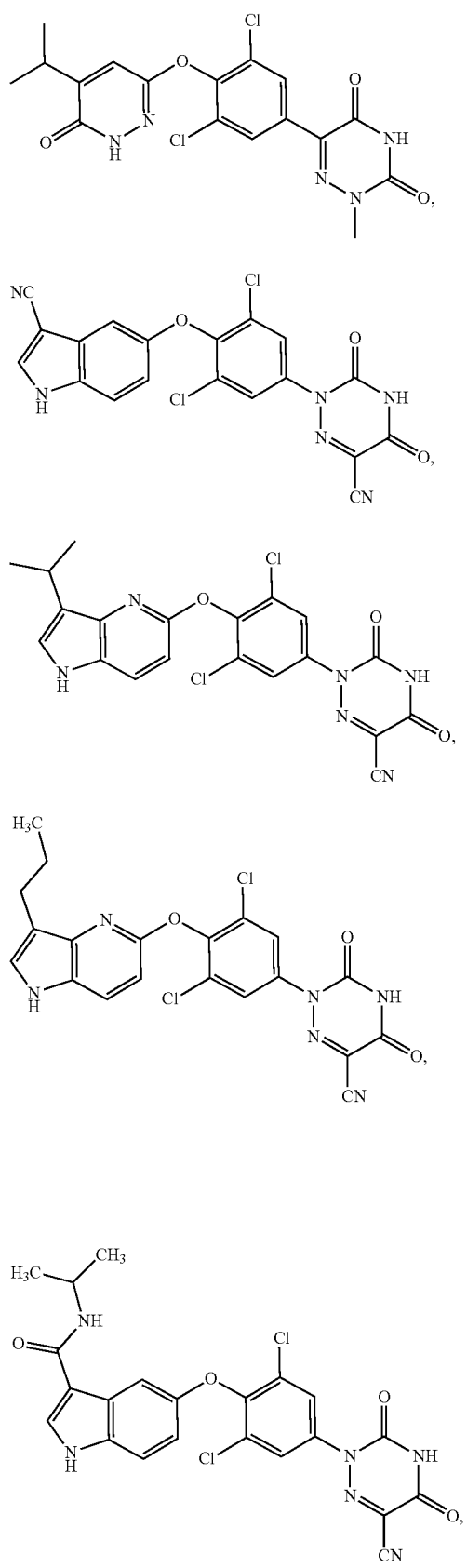
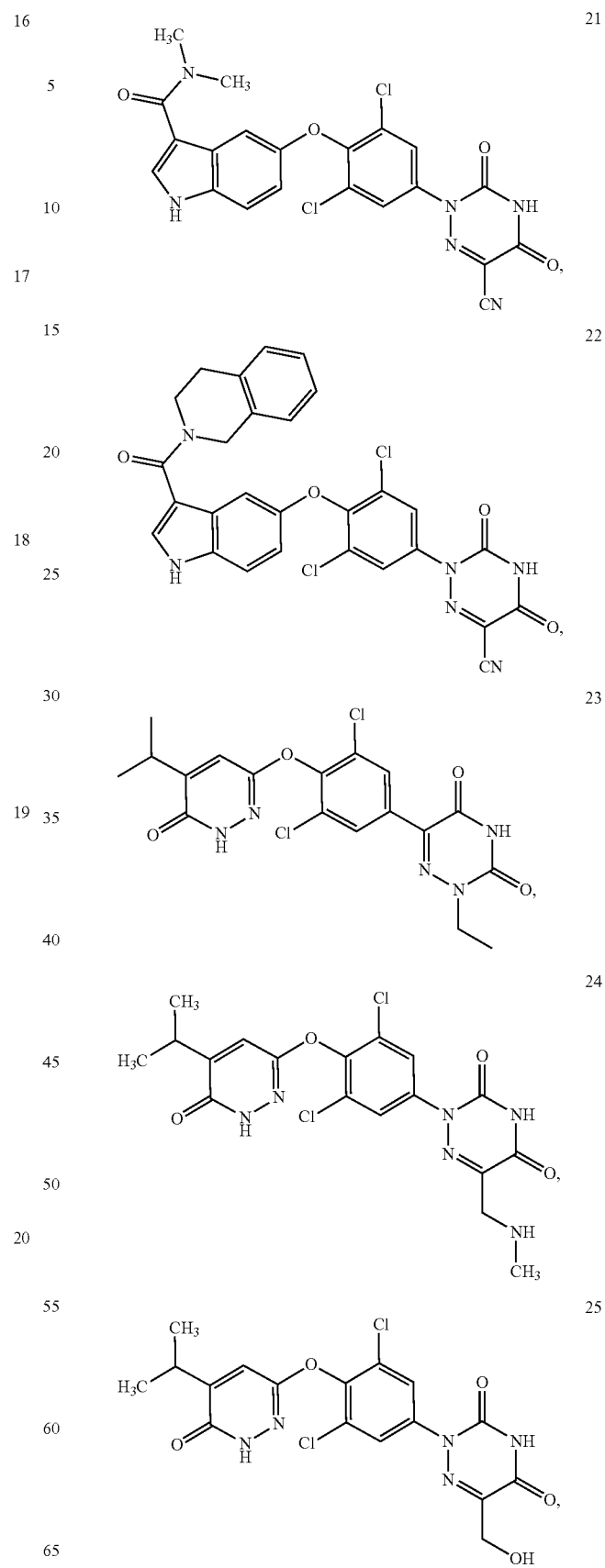

26
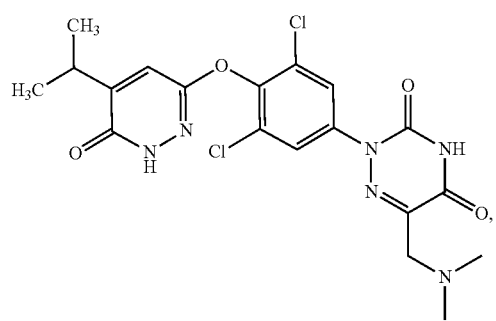
27
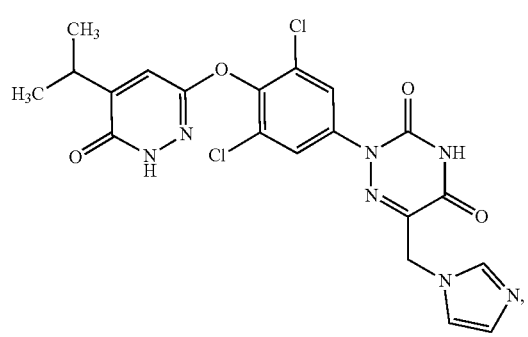
28
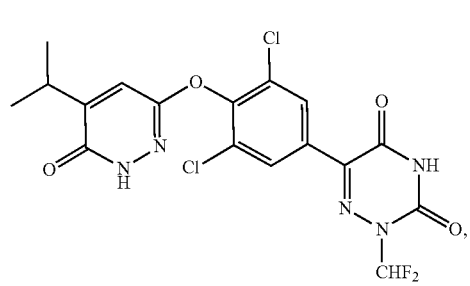
29
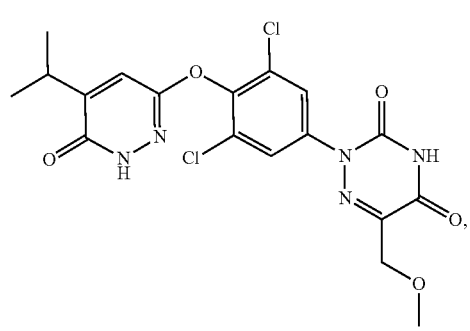
30
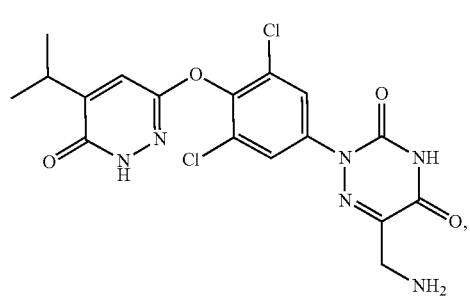
31
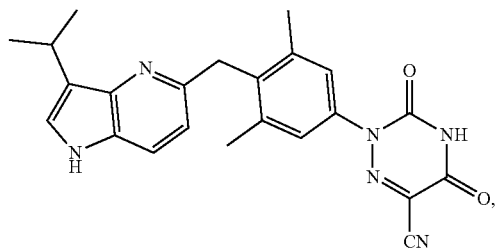
32
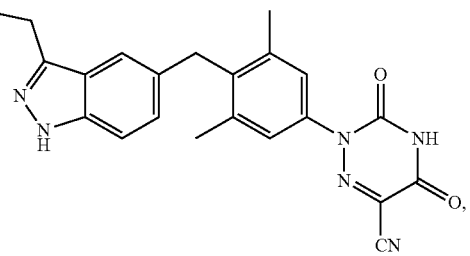
33
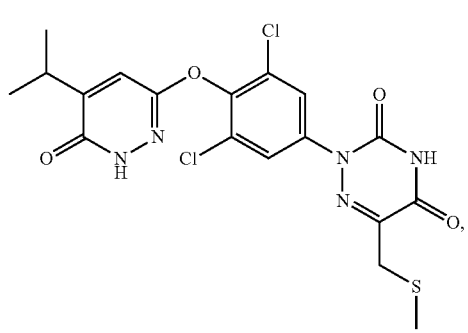
34
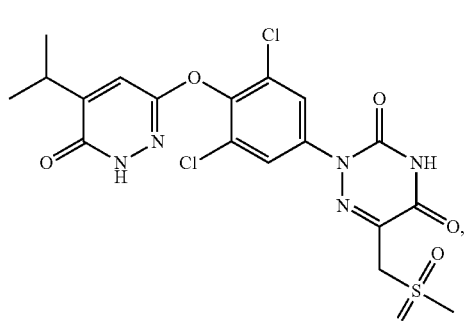
35
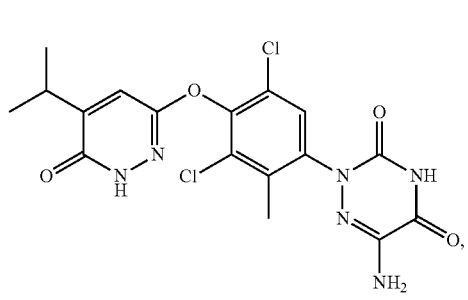

-continued

35-A

36

37

38

39

-continued

39-A or 39-B

39-A or 39-B

40

41

42

43
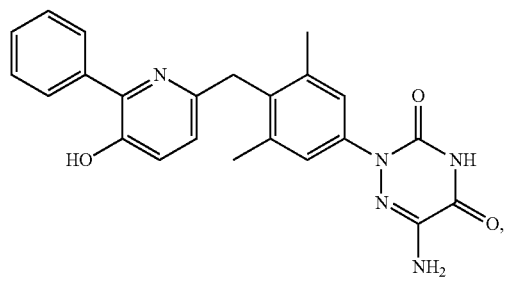
44
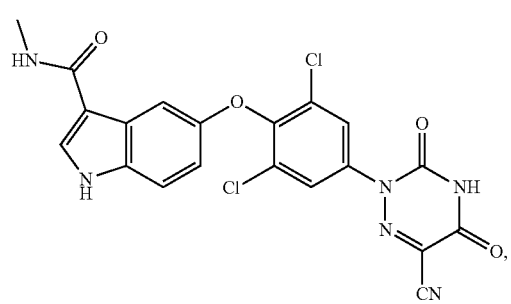
45
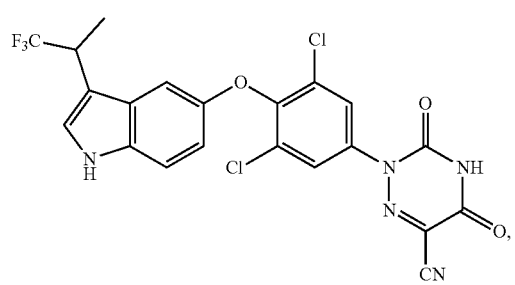
46
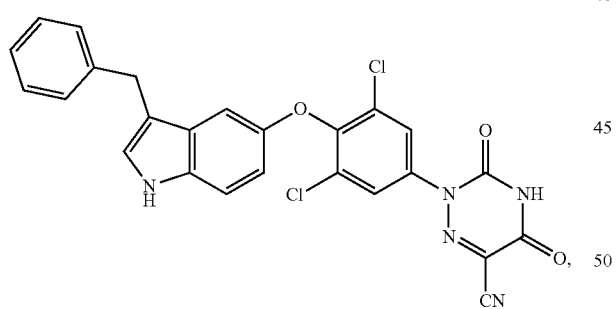
47
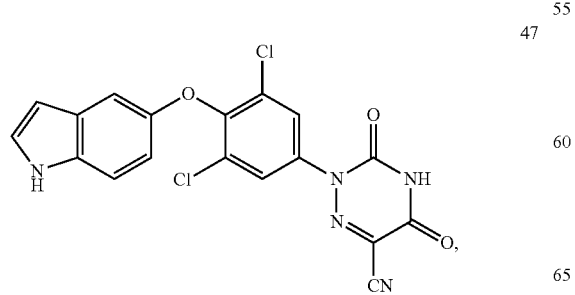
48
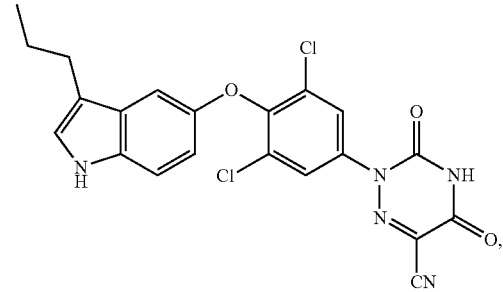
49
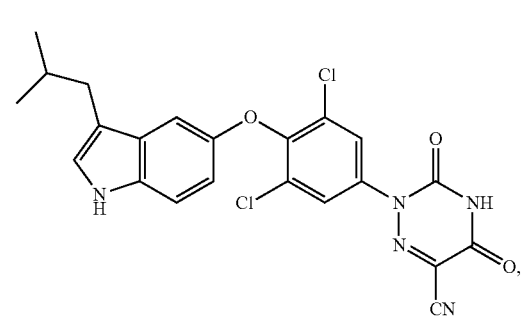
50
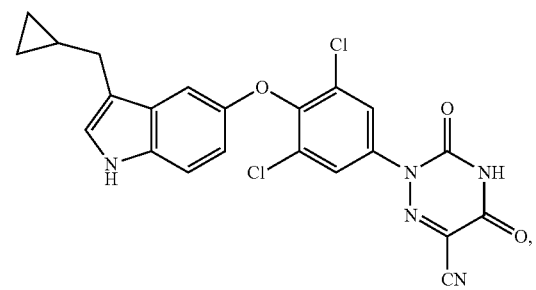
51
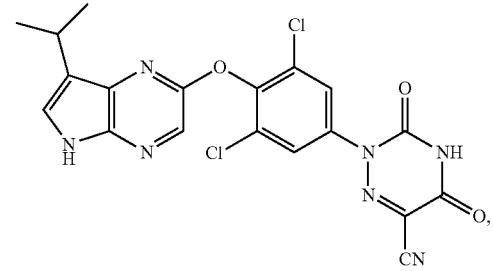
52
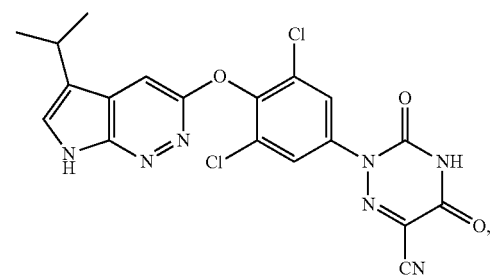

53
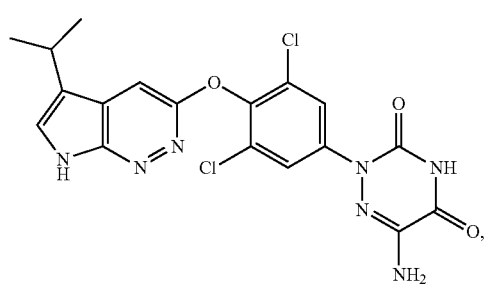
54
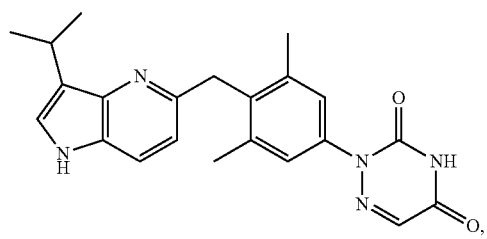
55
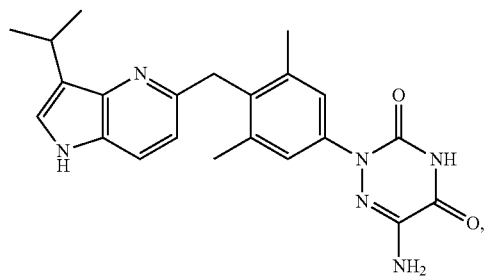
56
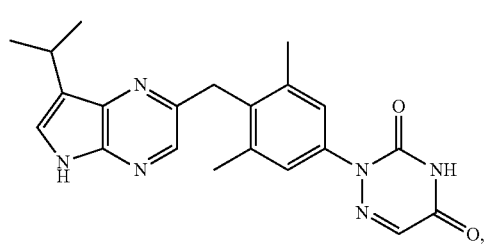
57
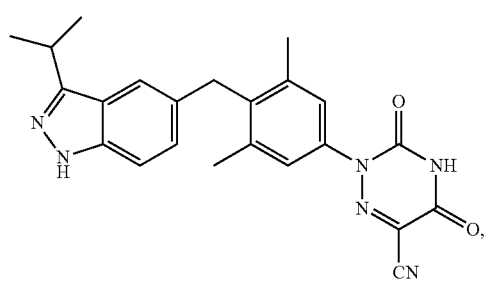
58
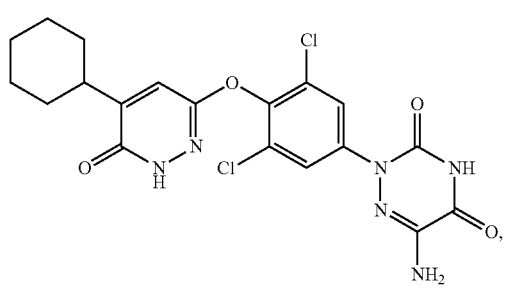
59
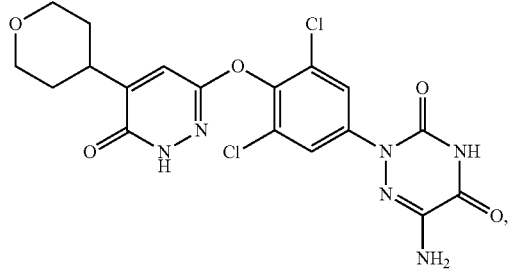
60
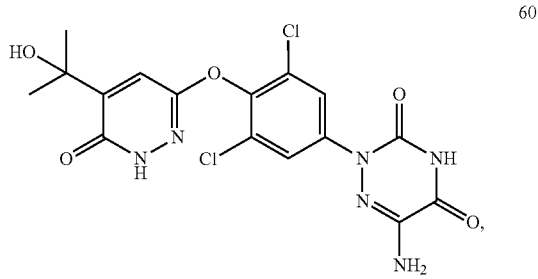
60A
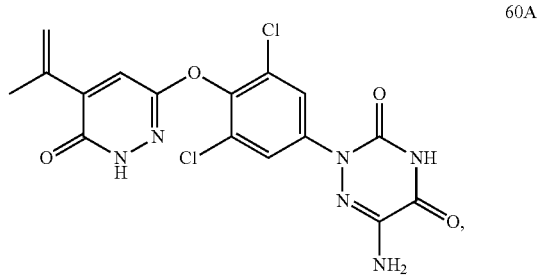
61
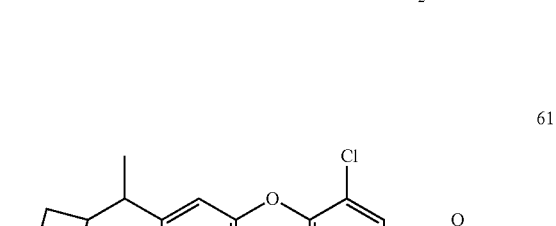
61A or 61-B
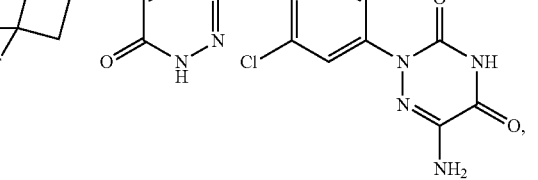
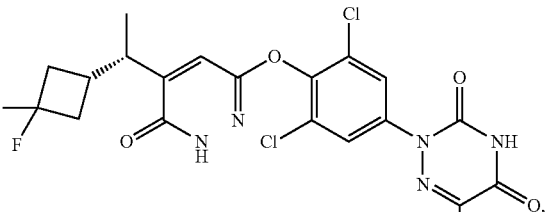

-continued
61-A or 61-B
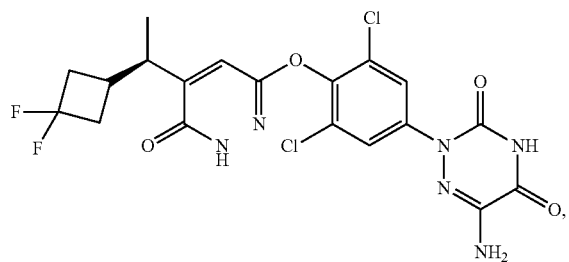
62
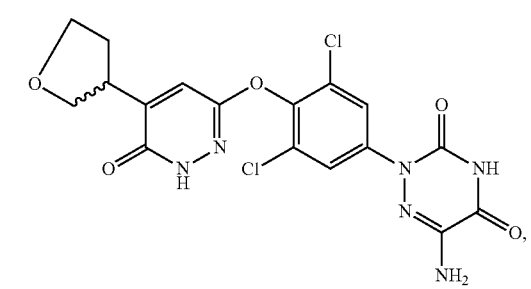
63
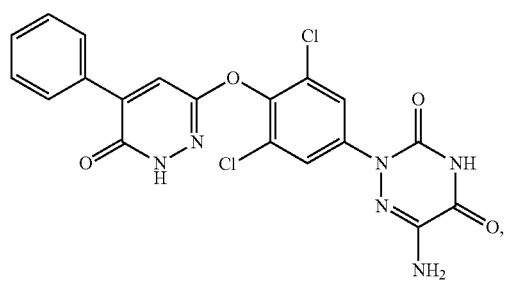
63-A
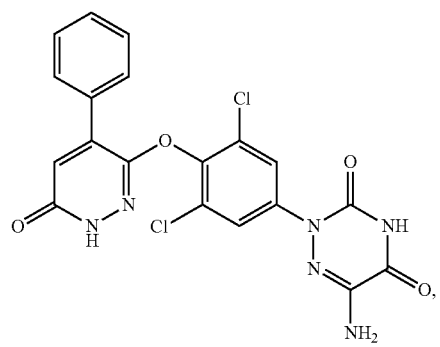
64
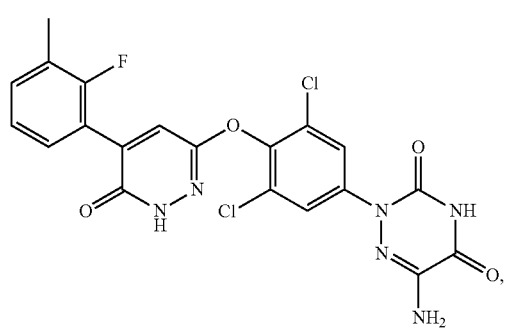
-continued
65
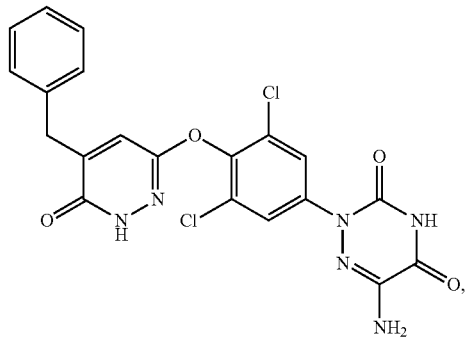
66
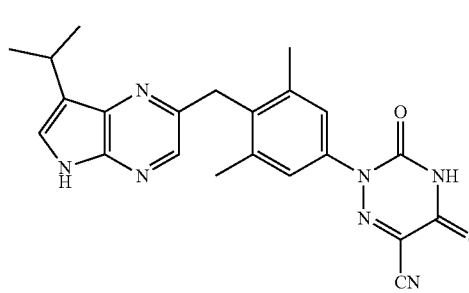
67
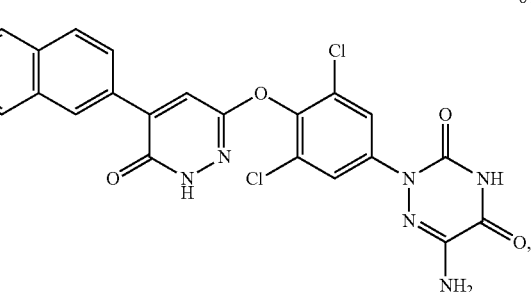
67-A
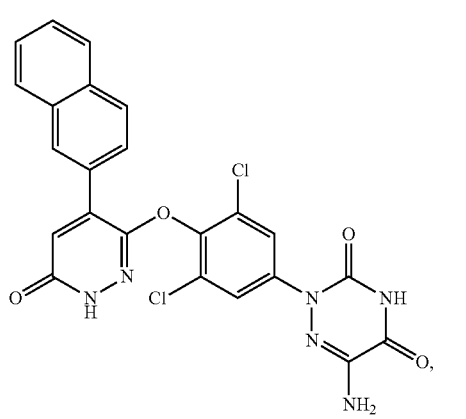
68
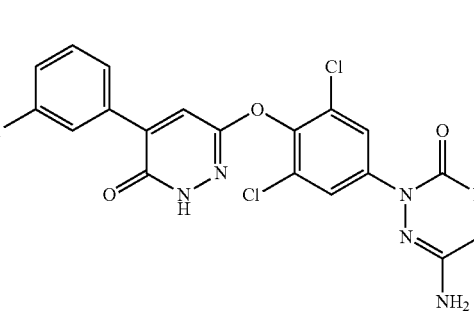

68-A
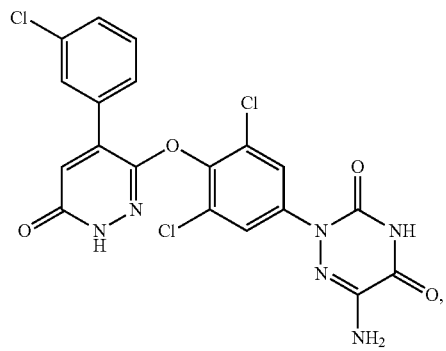
69
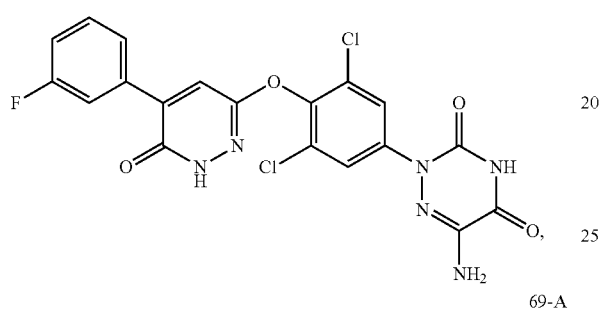
69-A
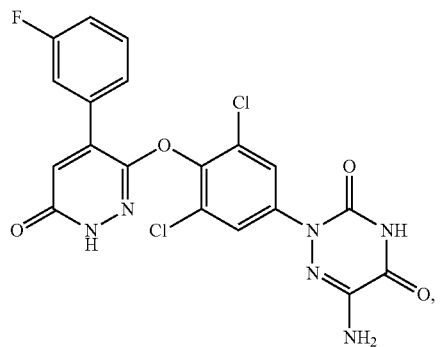
70
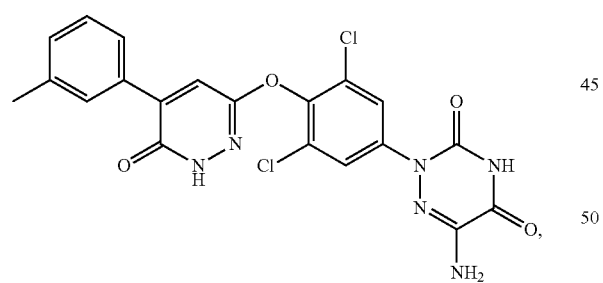
70-A
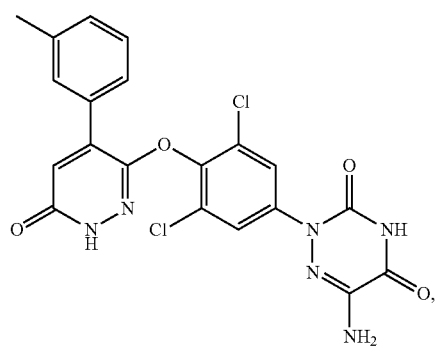
71
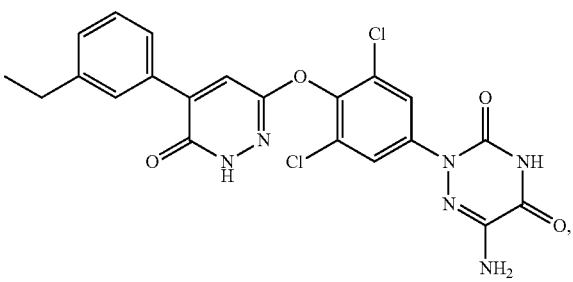
71-A
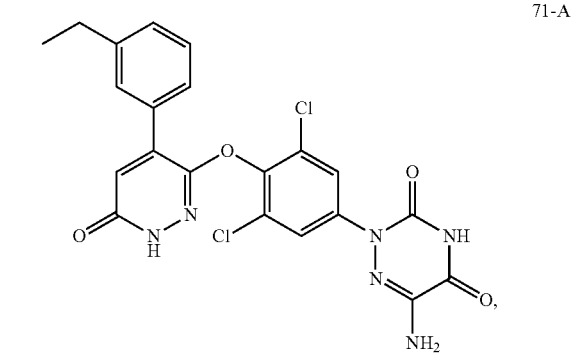
72
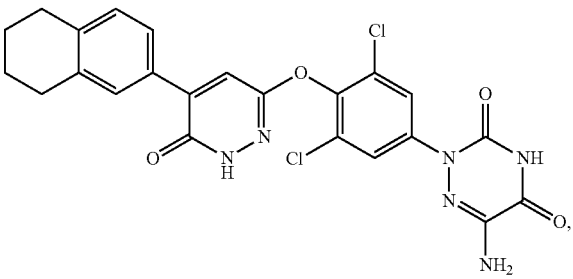
72-A
73
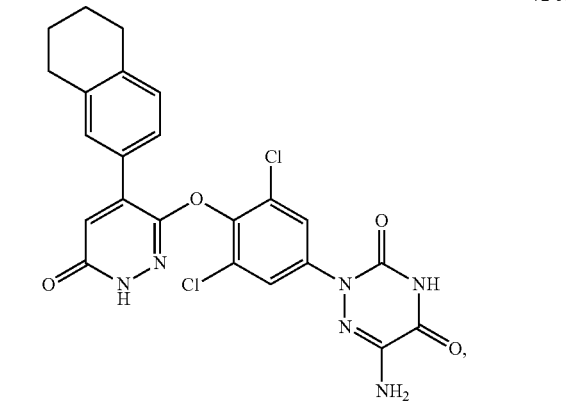

74
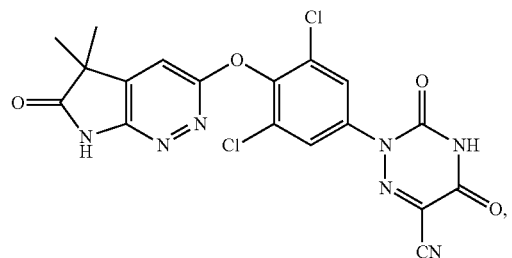
75
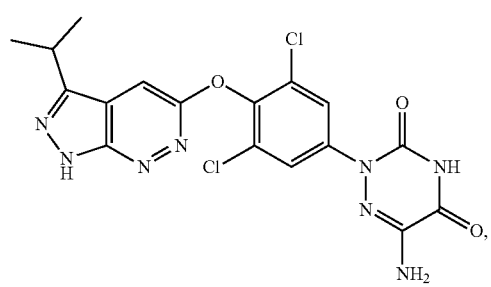
75-A
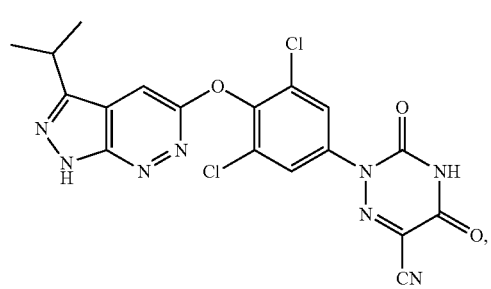
76
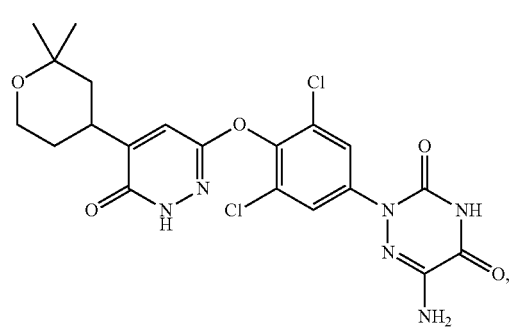
77
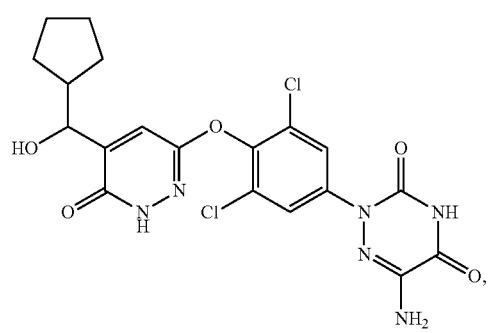
78
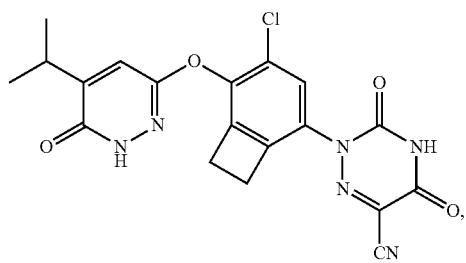
79
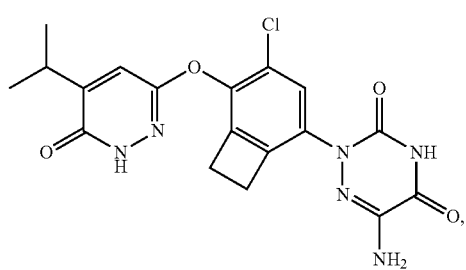
80
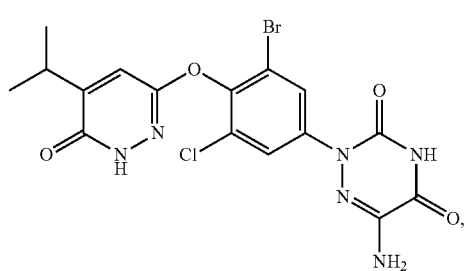
81
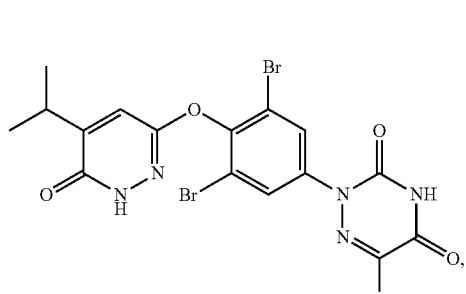
82
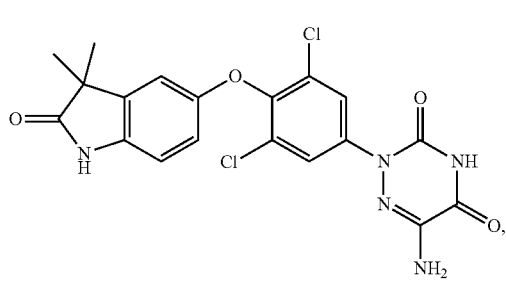

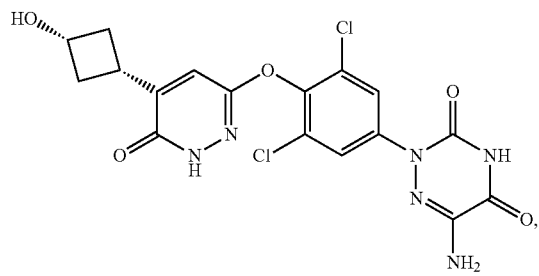

88-B

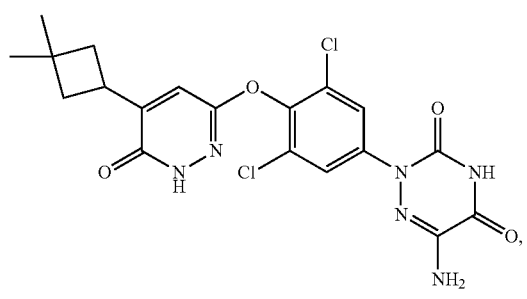

89

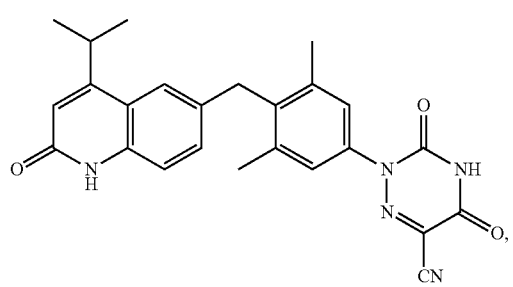

90

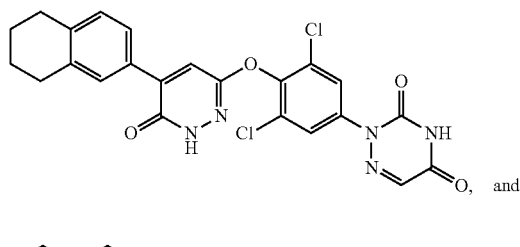

91

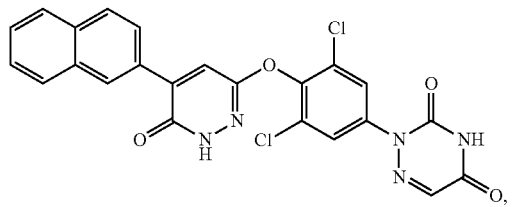

92

Embodiment 26. A method of treating a thyroid hormone receptor related disorder in a patient, the method comprising the steps of:

identifying a patient in need of treatment for the thyroid hormone receptor related disorder, and administering to the patient, or contacting the patient with, a compound of Embodiment 1.

Embodiment 27. The method of Embodiment 26, wherein the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 28. A method of selectively modulating the activity of a thyroid hormone receptor beta (THR-β) comprising contacting a compound of Embodiment 1 with a thyroid hormone receptor.

Embodiment 29. The method of Embodiment 28, wherein the contacting is in vitro or ex vivo.

Embodiment 30. The method of Embodiment 28, wherein the contacting is in vivo.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least,"

"greater than," "less than," and the like, include the number recited and refer to ranges which can be subsequently broken down into subranges as discussed above. Finally, as will be understood by one skilled in the art, a range includes each individual member.

What is claimed is:

1. A compound of Formula I':

TL-L$_a$-CE-HD    (I')

or a stereoisomer or a tautomer thereof, or a pharmaceutically acceptable salt thereof, wherein:
i) TL is a moiety of Formula IIa, IIb, IIIa, IIIb, IIIc, or IIId:

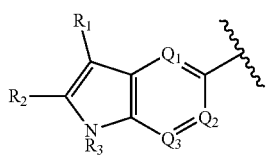
(IIa)

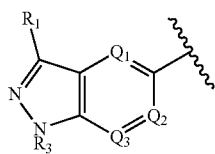
(IIb)

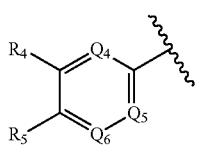
(IIIa)

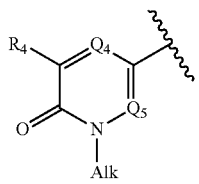
(IIIb)

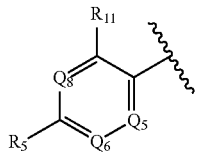
(IIIc)

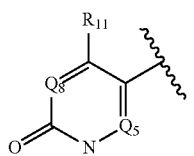
(IIId)

wherein:
each of $Q_1$, $Q_2$, $Q_3$, $Q_4$, $Q_5$, $Q_6$, and $Q_8$, is independently nitrogen or —$CR_b$—, wherein each $R_b$ is independently hydrogen, halogen, or lower alkyl;
$R_1$ is hydrogen, an optionally substituted alkyl, an optionally substituted non-aromatic carbocyclic group, an optionally substituted aryl group, an optionally substituted heterocycloalkyl group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted C-carboxy or O-carboxy group, —CN, an optionally substituted carbamoyl group, or an optionally substituted carbamoyl alkyl group, where the nitrogen of the carbamoyl or carbamoyl alkyl group is optionally a heteroatom in a ring structure;
$R_2$ is hydrogen, halogen, optionally substituted alkyl, optionally substituted cycloalkyl, or —CN;
$R_3$ is hydrogen or lower alkyl;
$R_4$ is an optionally substituted alkyl, an optionally substituted alkenyl, an optionally substituted non-aromatic carbocyclic group, an optionally substituted aryl group, an optionally substituted heterocyclic group, an optionally substituted heteroaryl group, an optionally substituted (carbocyclic)alkyl group, an optionally substituted aralkyl group, an optionally substituted (heterocycloalkyl)alkyl group, an optionally substituted (heteroaryl)alkyl group, an optionally substituted amino group, an optionally substituted sulfamoyl group, an optionally substituted carbamoyl group, or an optionally substituted carbamoyl alkyl group, where the nitrogen of the carbamoyl or carbamoyl alkyl group is optionally a heteroatom in a ring structure; and
$R_5$ is hydroxy, NH$_2$, alkylamino, alkanoylamino, or alkylsulfonylamino;
or $R_4$ and $R_5$ taken together along with the carbon atoms to which they are attached form a five- or six-membered optionally substituted non-aromatic carbocyclic group, optionally substituted aryl group, optionally substituted heterocyclic group, or optionally substituted heteroaryl group;
or $R_4$ and $R_5$ taken together along with the carbon atoms to which they are attached form a seven to eleven membered, optionally substituted spirocyclic ring or a seven to eleven membered, optionally substituted spiro-heterocyclic ring;
Alk is hydrogen or an optionally substituted alkyl; and
$R_{11}$ is an aryl group optionally substituted with one to five substituents independently selected from lower alkyl, alkoxy, haloalkoxy, halogen, and cycloalkyl; or a heteroaryl group optionally substituted with one to five substituents independently selected from lower alkyl, alkoxy, haloalkoxy, halogen, and cycloalkyl; or a bicyclic ring system; or a bicyclic heterocyclic ring system;
ii) CE is a moiety of Formula IV

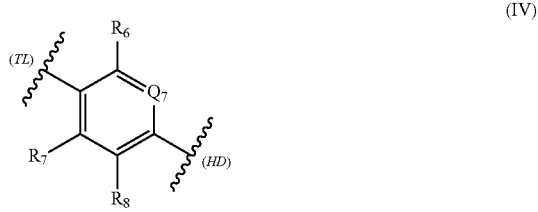
(IV)

wherein:
each of $R_6$ and $R_7$ is independently selected from halogen or lower alkyl;
$R_8$ is selected from hydrogen or lower alkyl;

or $R_6$ is selected from halogen and lower alkyl, and $R_7$ and $R_8$ taken together, along with the carbon atoms to which they are attached, form a 4-, 5- or 6-membered non-aromatic carbocyclic ring;

$Q_7$ is —$CR_c$—, wherein $R_c$ is hydrogen;

(TL) denotes the point where the moiety of Formula IV connects to TL-$L_a$-; and (HD) denotes the point where the moiety of Formula IV connects to —HD;

iii) HD is a moiety of Formula V:

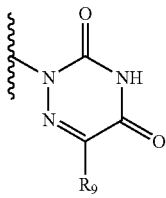

(V)

wherein:

$R_9$ is —$(C(R_d)_2)_n$–$N(R_d)_2$; wherein each $R_d$ is independently hydrogen or optionally substituted lower alkyl; and each n is 0; and $L_a$ is —$(C(R_a)_2)_z$—; oxygen; or sulfur; wherein each $R_a$ is a hydrogen; and z is 1.

2. The compound of claim 1, or a stereoisomer or a tautomer thereof, or a pharmaceutically acceptable salt thereof, wherein:

TL is a moiety of Formula IIIb:

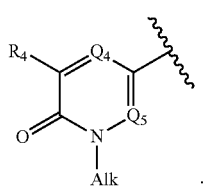

(IIIb)

3. The compound of claim 2, or a stereoisomer or a tautomer thereof, or a pharmaceutically acceptable salt thereof, wherein $R_4$ is $C_1$-$C_6$ alkyl; $C_2$-$C_{10}$ alkenyl; a non-aromatic $C_3$-$C_{12}$ carbocyclic ring; a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic) alkyl group; an aralkyl group; or a (heterocycloalkyl)alkyl group; and $R_4$ is optionally substituted with one to five $R_g$ independently selected from the group consisting of hydroxy, halogen, CN, $C_1$-$C_6$ alkyl, $C_6$-$C_{10}$ aryl, $C_1$-$C_6$ alkoxy, $C_1$-$C_6$ haloalkoxy, and $C_6$-$C_{10}$ aralkoxy, or two $R_g$ together with the atoms to which they are attached form an aromatic or non-aromatic 3- to 6-membered ring, optionally containing one or two ring heteroatoms independently selected from oxygen, sulfur, or nitrogen.

4. The compound of claim 1, or a stereoisomer or a tautomer thereof, or a pharmaceutically acceptable salt thereof, wherein:

TL is a moiety of Formula IIIa:

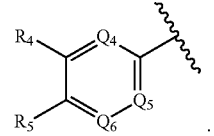

(IIIa)

5. The compound of claim 4, or a stereoisomer or a tautomer thereof, or a pharmaceutically acceptable salt thereof, wherein TL is a moiety of Formula IIIaa:

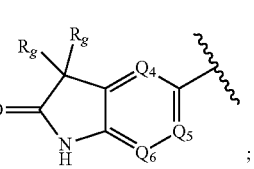

(IIIaa)

wherein each $R_g$ is independently $C_1$-$C_6$ alkyl or the two $R_g$ together with the atom(s) to which they are attached form a 3- to 6-membered non-aromatic carbocyclic group.

6. The compound of claim 4, or a stereoisomer or a tautomer thereof, or a pharmaceutically acceptable salt thereof, wherein TL is a moiety of Formula IIIab:

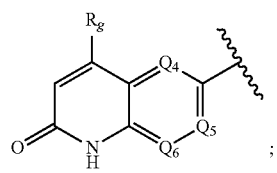

(IIIab)

wherein $R_g$ is $C_1$-$C_6$ alkyl.

7. The compound of claim 4, or a stereoisomer or a tautomer thereof, or a pharmaceutically acceptable salt thereof, wherein TL is a moiety of Formula IIIac:

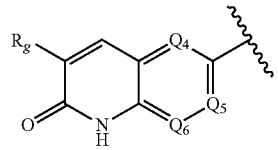

(IIIac)

wherein $R_g$ is $C_1$-$C_6$ alkyl.

8. The compound of claim 4, or a stereoisomer or a tautomer thereof, or a pharmaceutically acceptable salt thereof, wherein TL is a moiety of Formula IIIad:

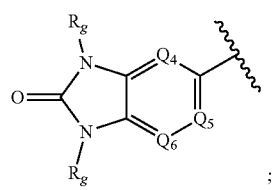

(IIIad)

wherein each $R_g$ is independently hydrogen or $C_1$-$C_6$ alkyl.

9. The compound of claim 4, or a stereoisomer or a tautomer thereof, or a pharmaceutically acceptable salt wherein:
   $R_4$ is $C_1$-$C_6$ alkyl; $C_2$-$C_{10}$ alkenyl; a non-aromatic $C_3$-$C_{12}$ carbocyclic ring, a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic)alkyl group; an aralkyl group; a (heterocycloalkyl)alkyl group; a (heteroaryl)alkyl group; or —C(O)NR$_m$R$_n$;
   $R_m$ and $R_n$ are independently selected from the group consisting of hydrogen, $C_1$-$C_6$ alkyl, $C_1$-$C_6$ haloalkyl, $C_2$-$C_6$ alkoxy, a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic)alkyl group; an aralkyl group; a (heterocycloalkyl)alkyl group; or a (heteroaryl)alkyl group;
   and $R_4$ is optionally substituted with one to five $R_g$ independently selected from the group consisting of hydroxy, halogen, $C_1$-$C_6$ alkyl, $C_1$-$C_6$ haloalkyl, $C_6$-$C_{10}$ aryl, $C_1$-$C_6$ alkoxy, and $C_6$-$C_{10}$ aralkoxy; and
   $R_5$ is hydroxy, $NH_2$, alkylamino, alkanoylamino, or alkylsulfonylamino.

10. The compound of claim 1, or a stereoisomer or a tautomer thereof, or a pharmaceutically acceptable salt thereof, wherein:
    TL is a moiety of Formula IIId:

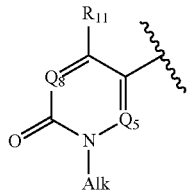

(IIId)

11. The compound of claim 1, or a stereoisomer or a tautomer thereof, or a pharmaceutically acceptable salt thereof, wherein:
    TL is a moiety of Formula IIa:

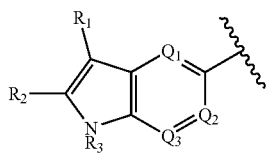

(IIa)

12. The compound of claim 11, or a stereoisomer or a tautomer thereof, or a pharmaceutically acceptable salt thereof, wherein:
    $R_1$ is hydrogen, —CN, $C_1$-$C_6$ alkyl; a non-aromatic $C_3$-$C_{12}$ carbocyclic ring; a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic)alkyl group; an aralkyl group; a (heterocycloalkyl)alkyl group; or —C(O)—R$_j$; wherein R$_j$ is —NR$_m$R$_n$ or —OR$_m$; R$_m$ is hydrogen or $C_1$-$C_6$ alkyl; R$_n$ is $C_1$-$C_6$ alkyl; or R$_m$ and R$_n$, together with the nitrogen to which they are attached, form a ring structure; and
    $R_1$ is optionally substituted with one to three $R_k$ independently selected from phenyl and haloalkyl.

13. The compound of claim 11, or a stereoisomer or a tautomer thereof, or a pharmaceutically acceptable salt thereof, wherein $R_2$ is hydrogen; halogen; $C_1$-$C_6$ alkyl optionally substituted with one to five substituents independently selected from the group consisting of hydroxy, halogen, and $C_1$-$C_6$ alkoxy; $C_3$-$C_9$ cycloalkyl optionally substituted with one to ten substituents independently selected from the group consisting of hydroxy, halogen, and $C_1$-$C_6$ alkoxy; or —CN.

14. The compound of claim 1, or a stereoisomer or a tautomer thereof, or a pharmaceutically acceptable salt wherein:
    TL is a moiety of Formula IIb:

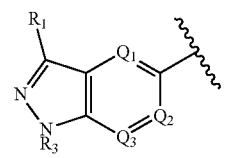

(IIb)

15. The compound of claim 1, or a stereoisomer or a tautomer thereof, or a pharmaceutically acceptable salt thereof, wherein:
    $R_1$ is hydrogen; —CN; $C_1$-$C_6$ alkyl; a non-aromatic $C_3$-$C_{12}$ carbocyclic ring; a $C_6$-$C_{10}$ aryl group; a 3- to 6-membered heterocycloalkyl ring containing one to four ring heteroatoms independently selected from oxygen, sulfur, or nitrogen; a five- to ten-membered heteroaryl ring containing one to four ring heteroatoms independently selected from oxygen, sulfur, or nitrogen; a (carbocyclic)alkyl group; an aralkyl group; a (heterocycloalkyl)alkyl group; or —C(O)—R$_j$; wherein R$_j$ is —NR$_m$R$_n$ or —OR$_m$; R$_m$ is hydrogen or $C_1$-$C_6$ alkyl; R$_n$ is $C_1$-$C_6$ alkyl; or R$_m$ and R$_n$, together with the nitrogen to which they are attached, form a ring structure; and
    $R_1$ is optionally substituted with one to five $R_k$ independently selected from hydroxy, halogen, $C_1$-$C_6$ alkyl, $C_1$-$C_6$ haloalkyl, $C_1$-$C_6$ alkoxy, and $C_6$-$C_{10}$ aralkoxy.

16. The compound of claim 1, or a stereoisomer or a tautomer thereof, or a pharmaceutically acceptable salt wherein:
    TL is a moiety of Formula IIIc:

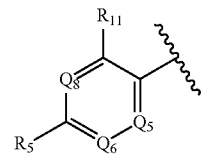

(IIIc)

17. The compound of claim 16, or a stereoisomer or a tautomer thereof, or a pharmaceutically acceptable salt thereof, wherein $R_{11}$ is a benzene optionally substituted with $C_1$-$C_5$ alkyl, halogen, or $C_3$-$C_9$ cycloalkyl; or naphthalene.

18. The compound of claim 16, or a stereoisomer or a tautomer thereof, or a pharmaceutically acceptable salt thereof, wherein $R_5$ is hydroxy, $NH_2$, $C_1$-$C_6$ alkylamino, $C_1$-$C_6$ alkanoylamino, or $C_1$-$C_6$ alkylsulfonylamino.

19. The compound of claim 1 selected from the group consisting of:

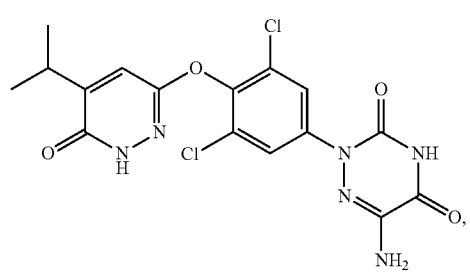
10

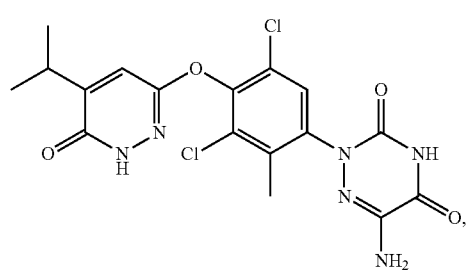
35

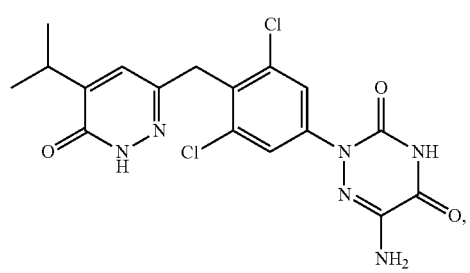
36

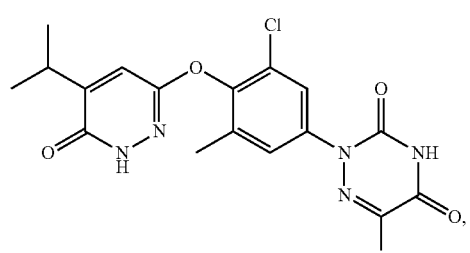
37

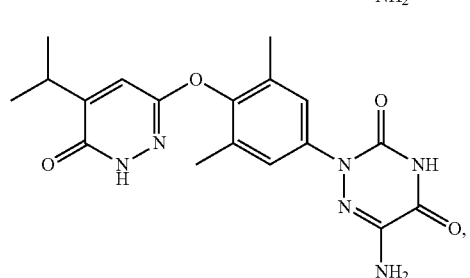
38

-continued

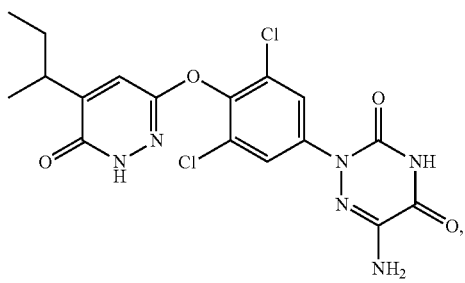
39

39-A or 39-B

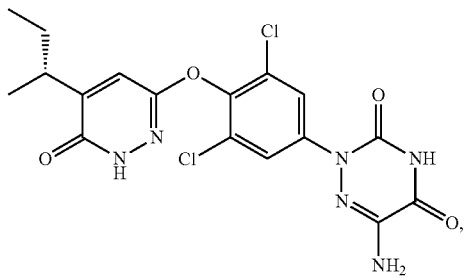

39-A or 39-B

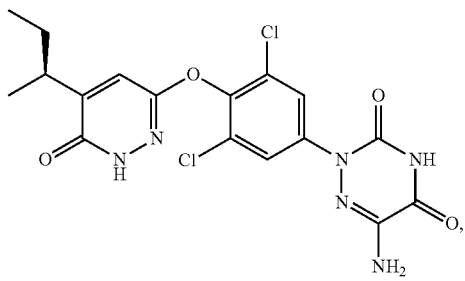

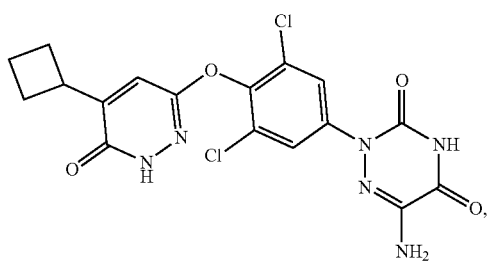
40

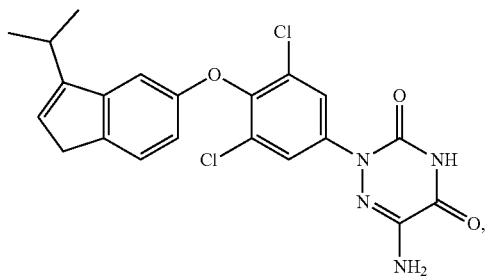
41

383
42
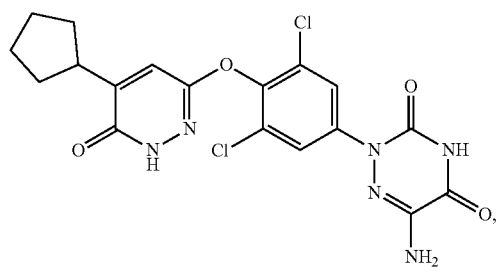
43
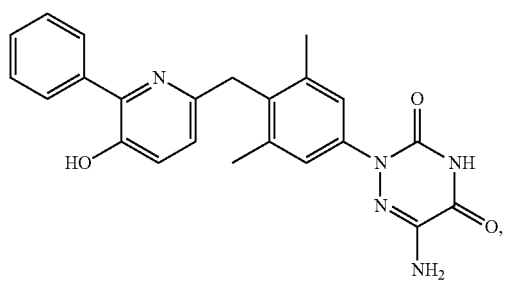
53
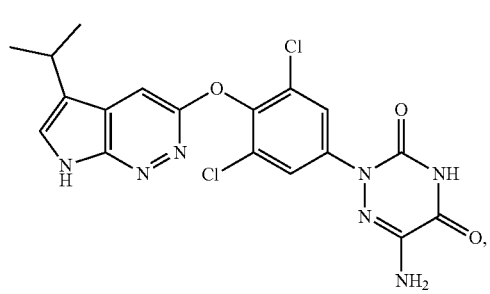
55
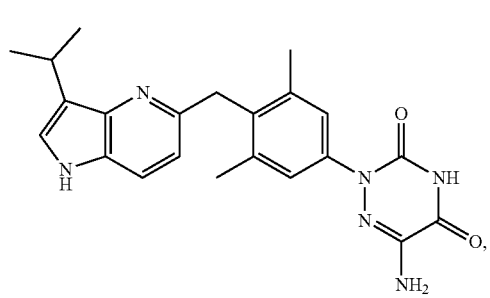
58
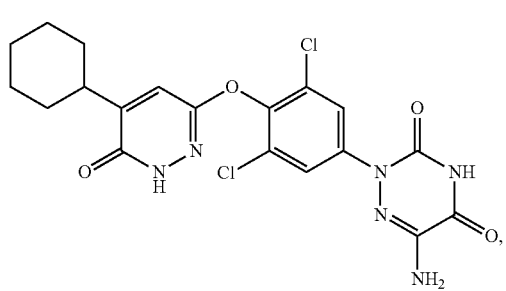
384
59
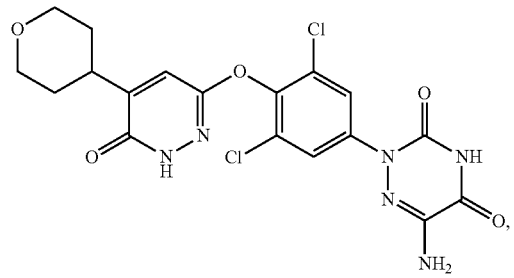
60
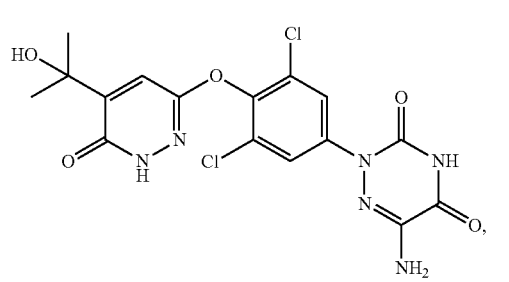
60A
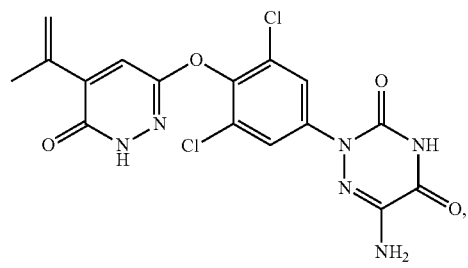
61
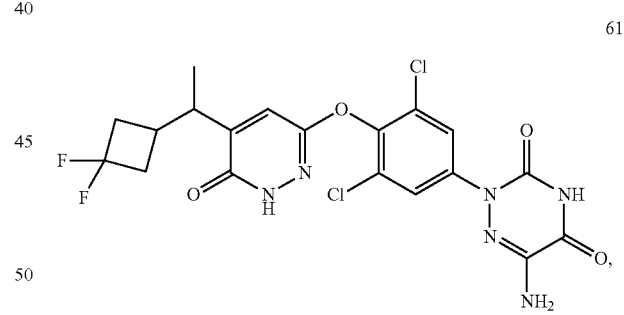
61-A or 61-B
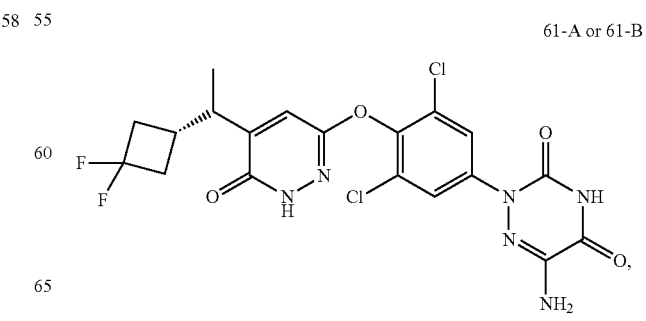

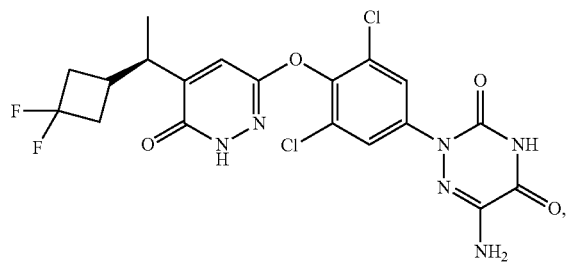
61-A or 61-B
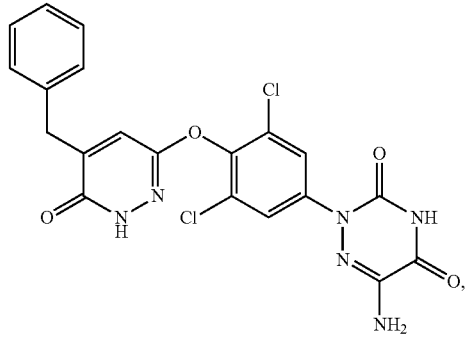
65
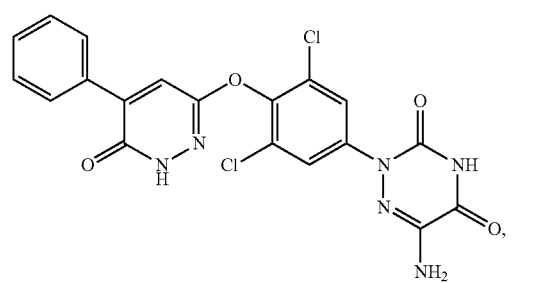
62
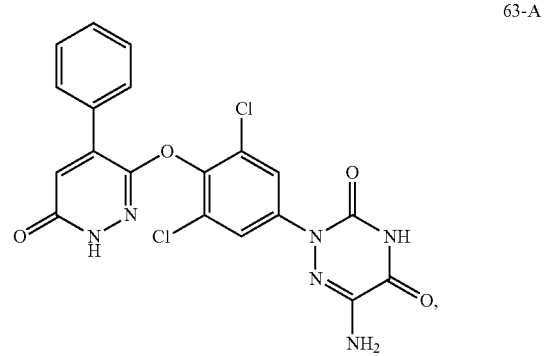
63
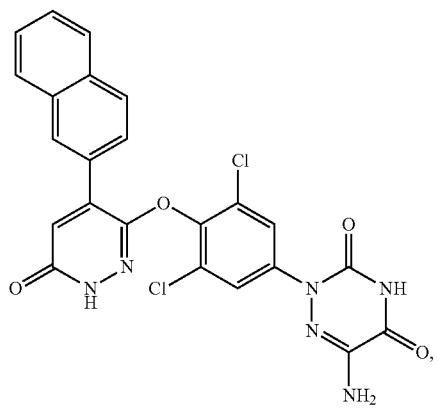
67
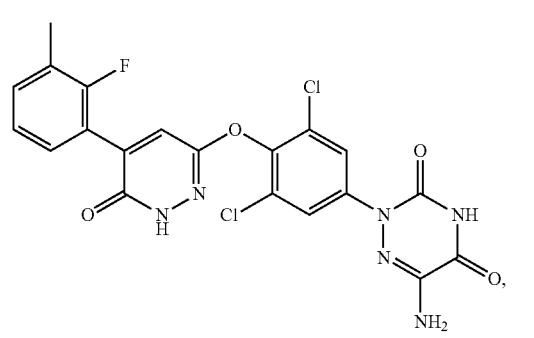
63-A
64
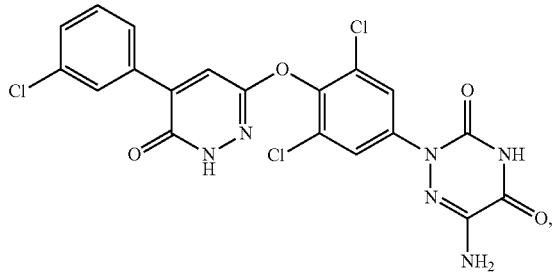
67-A
68

68-A
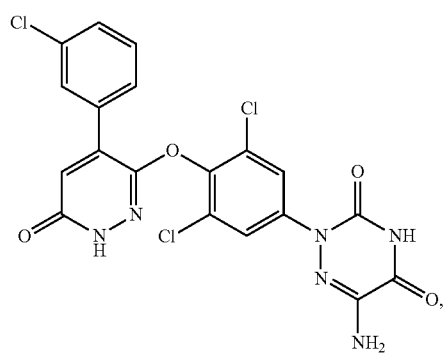
69
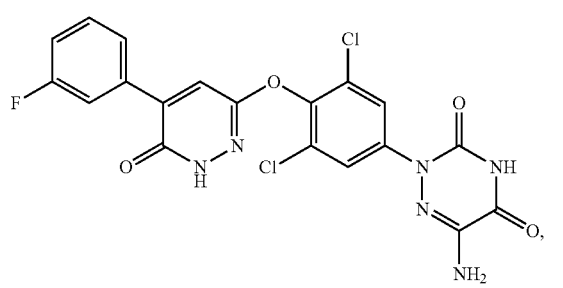
69-A
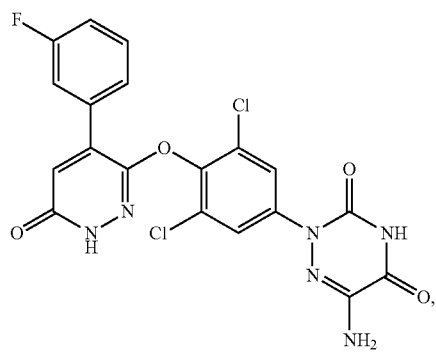
70
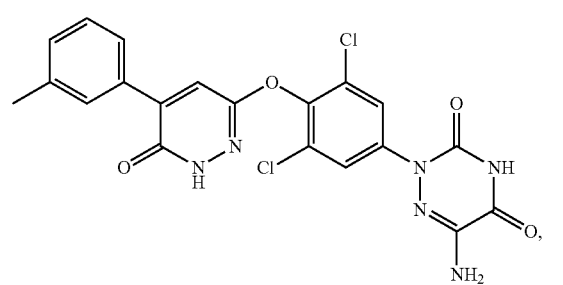
70-A
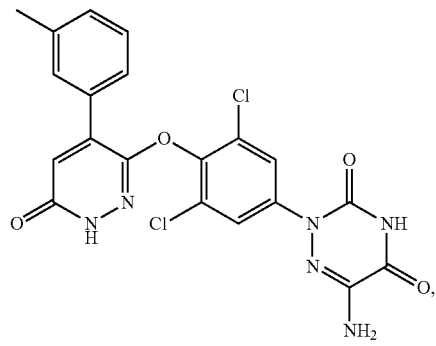
71
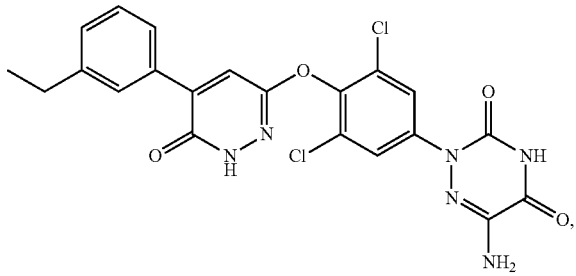
71-A
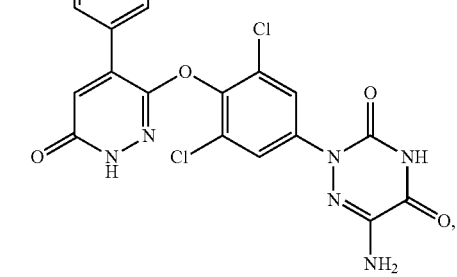
72
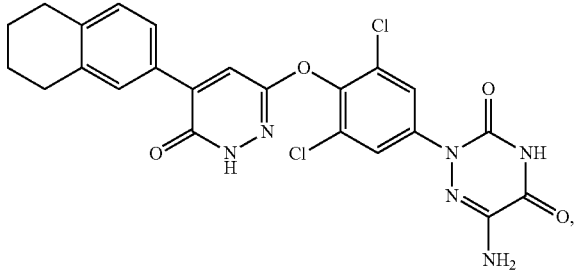
72-A
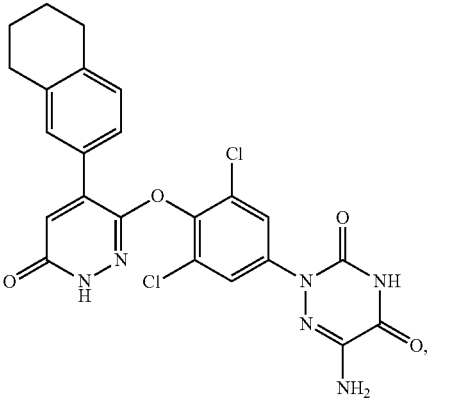
73

75
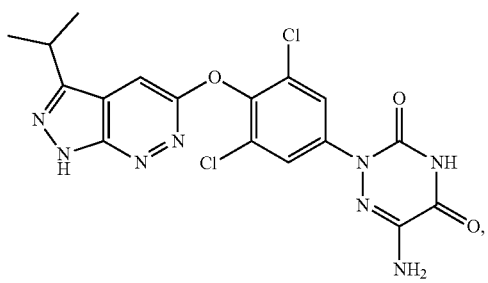
76
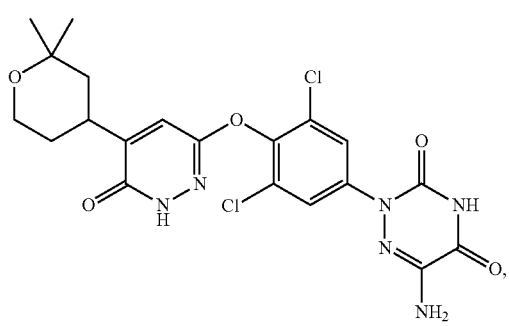
77
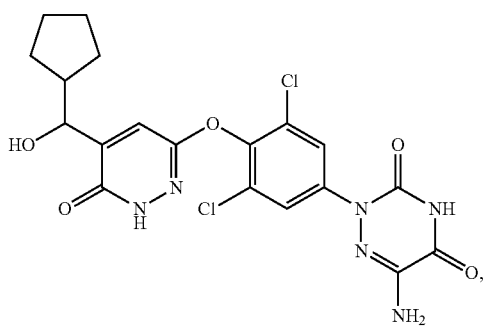
79
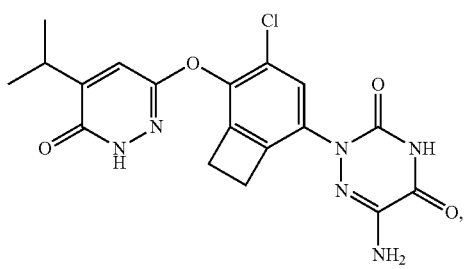
80
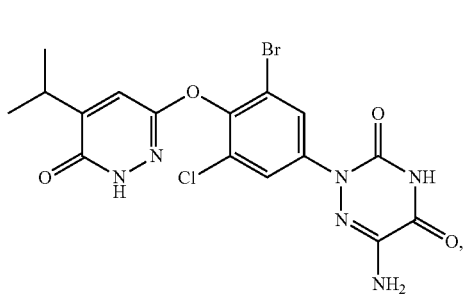
81
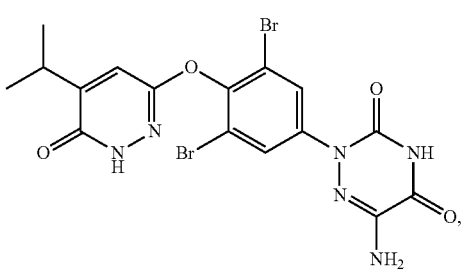
82
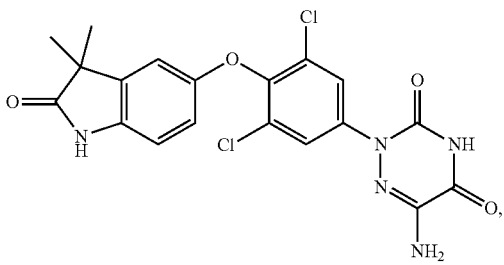
83
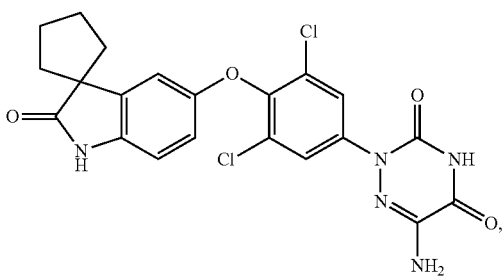
84
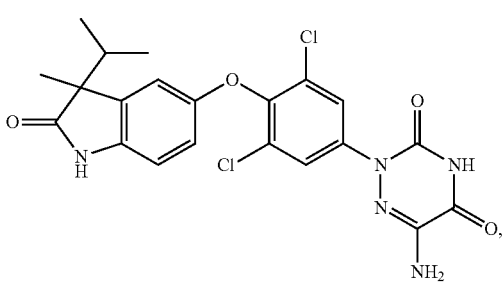
85
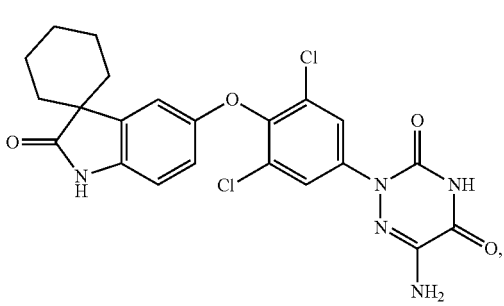

86
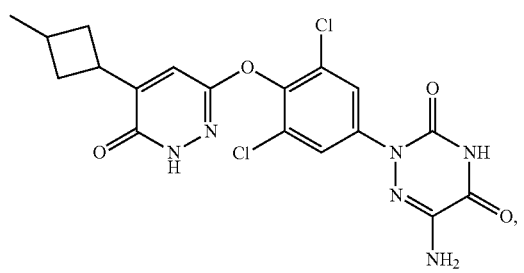
86-A
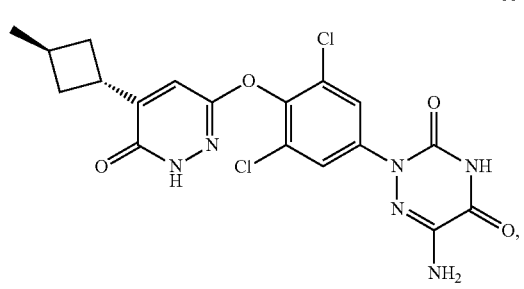
86-B
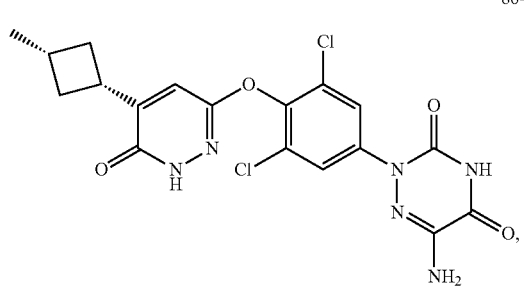
87-A
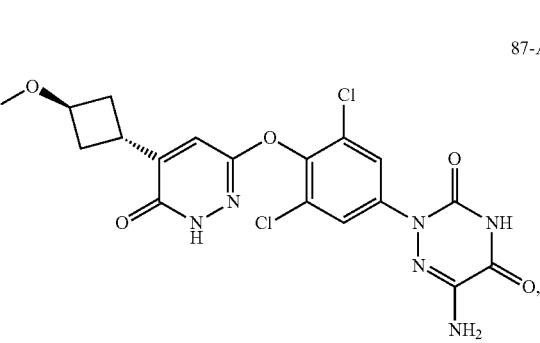
87-B
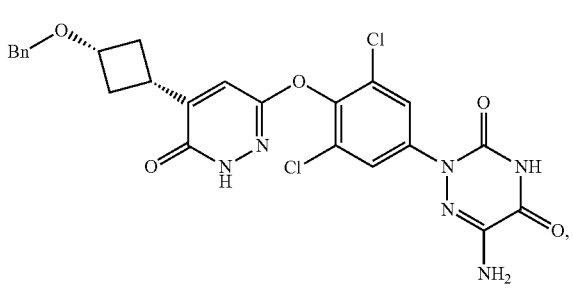
88
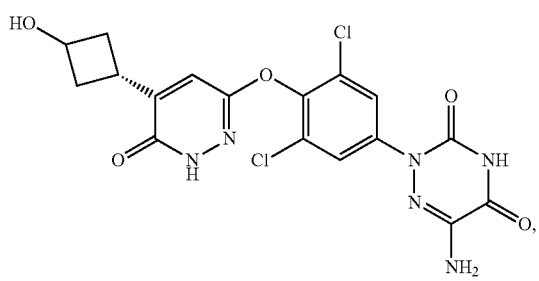
88-A
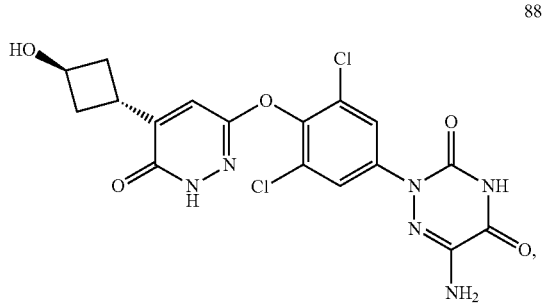
88-B
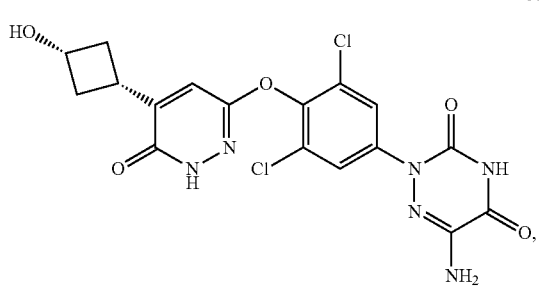
89
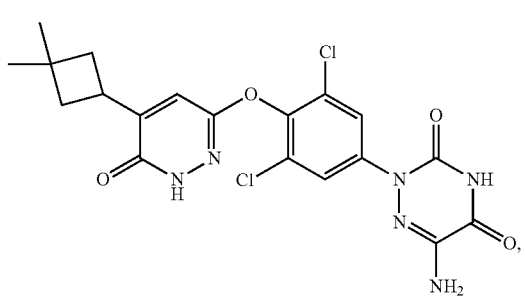
93
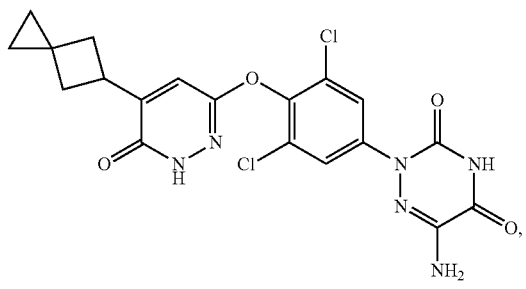

94
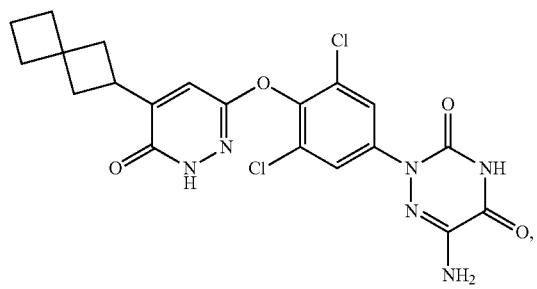
95
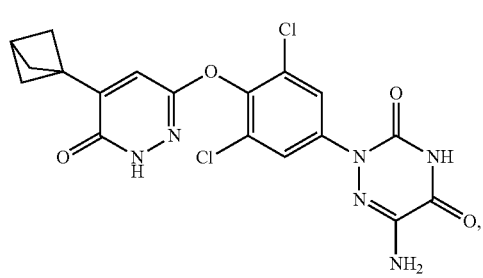
96
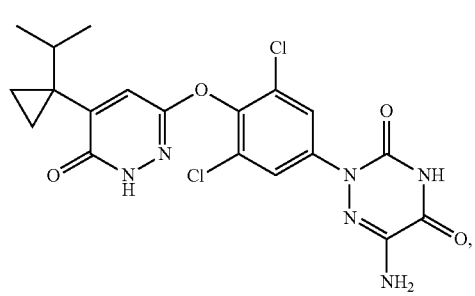
97
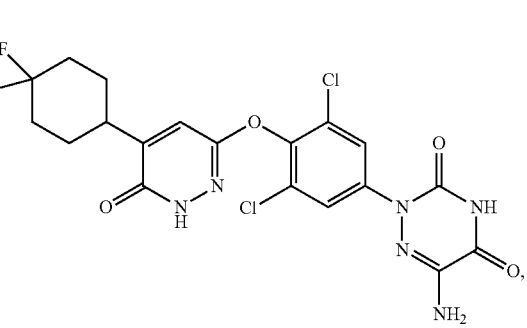
99
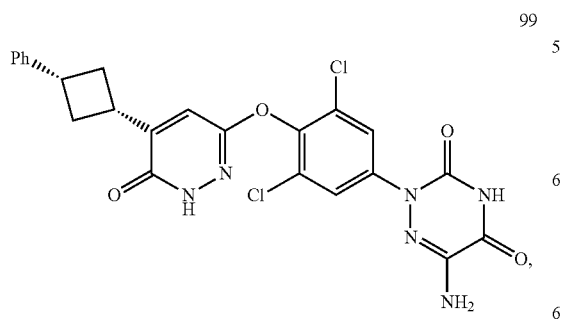
100
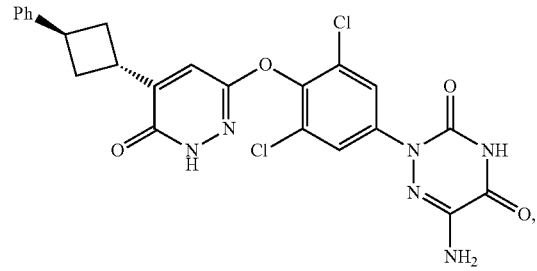
101
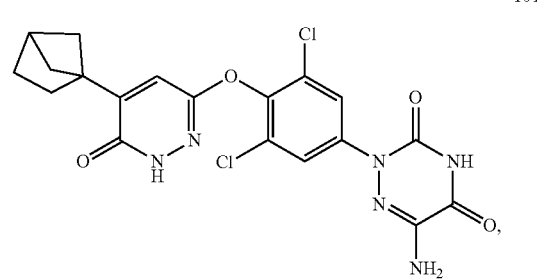
102
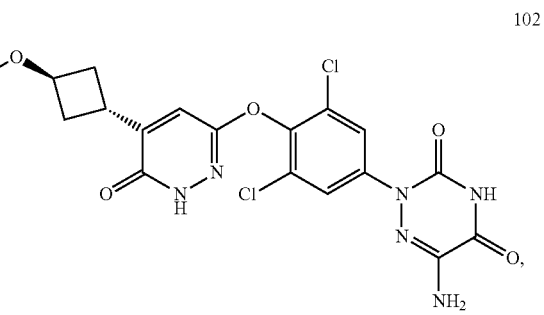
103
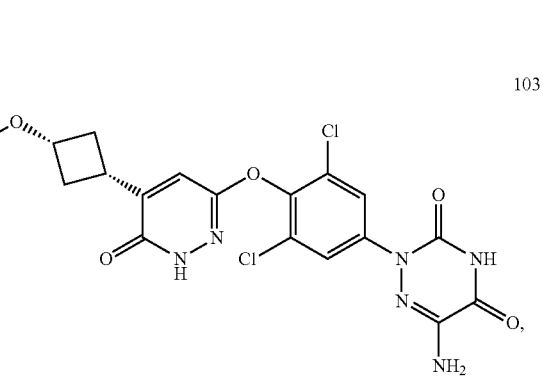
104
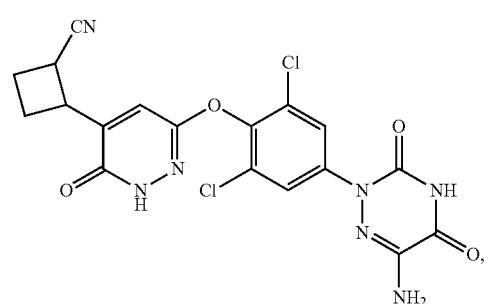

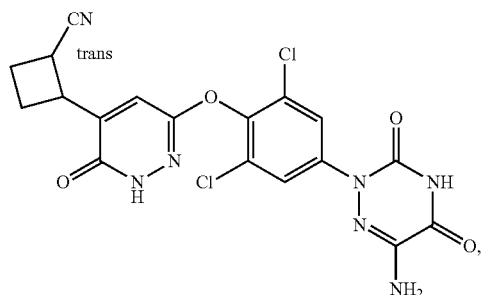
105
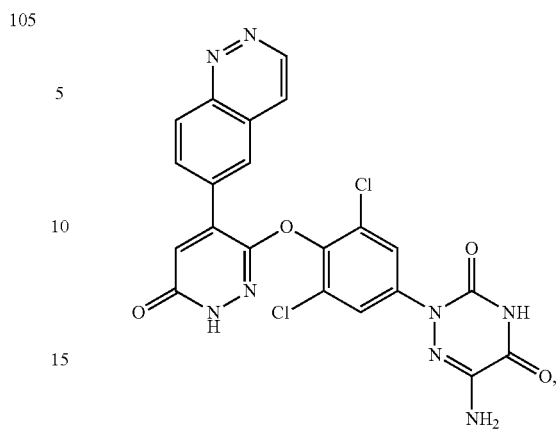
109
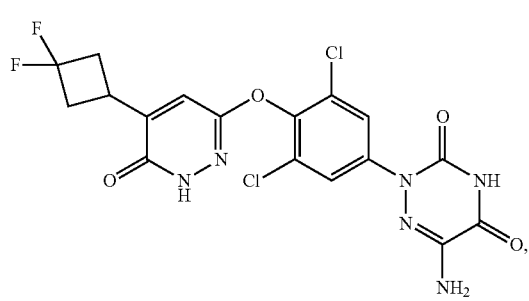
106
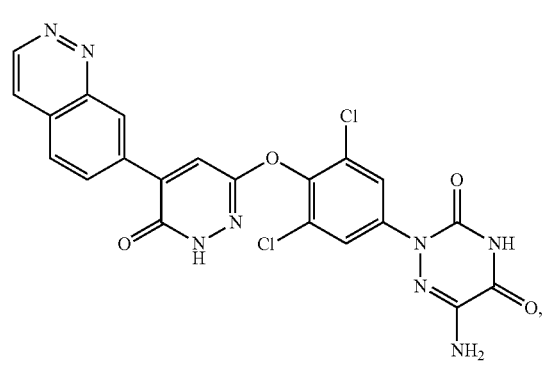
110
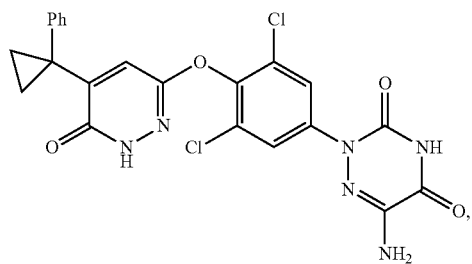
107
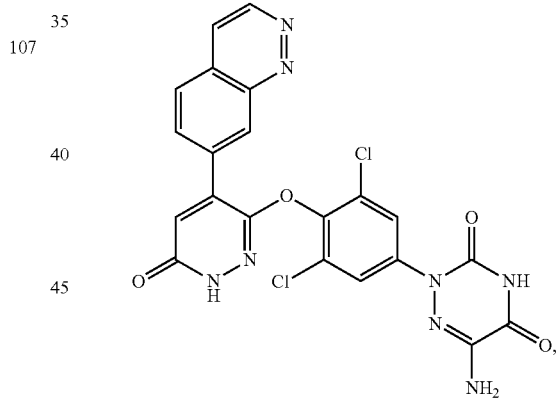
111
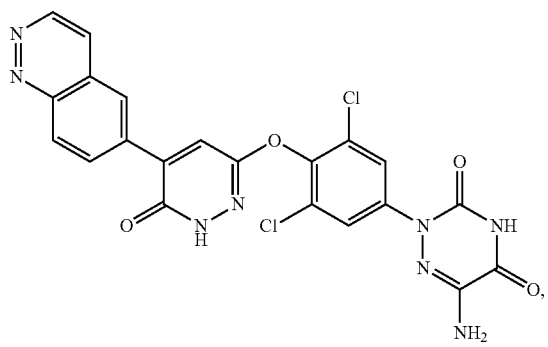
108
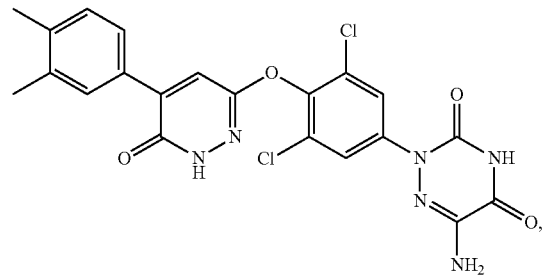
112

113
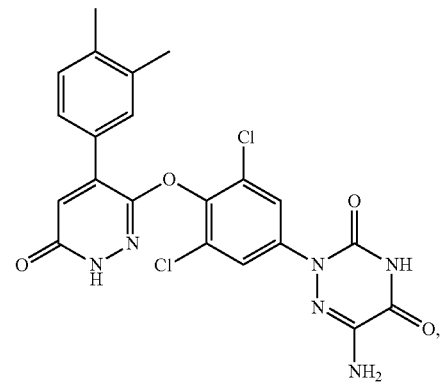
114
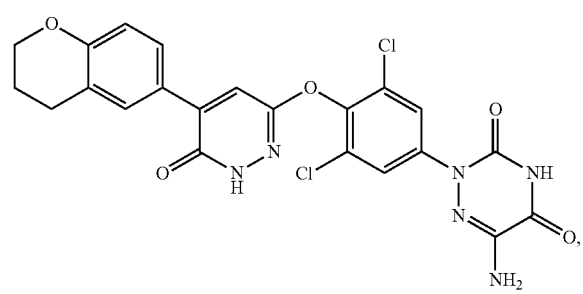
115
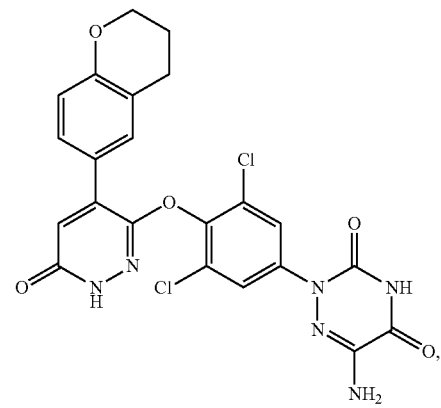
116
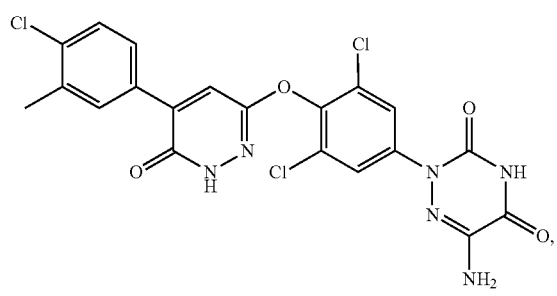
117
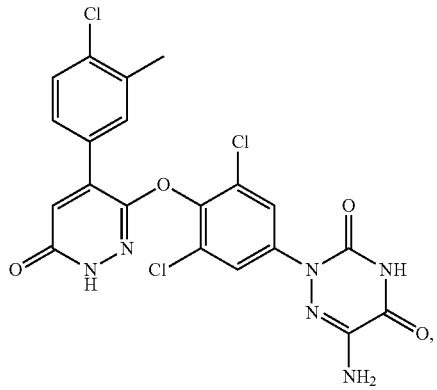
118
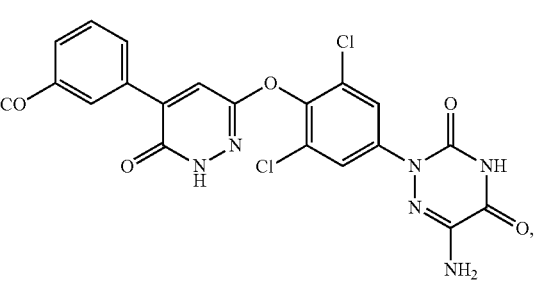
119
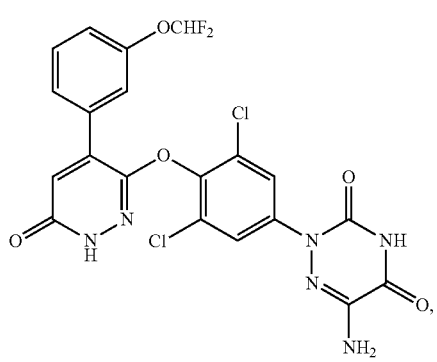
120
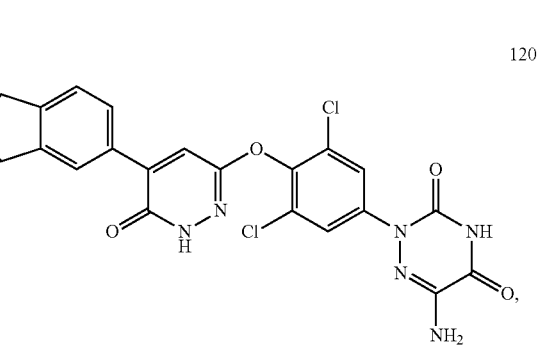

121
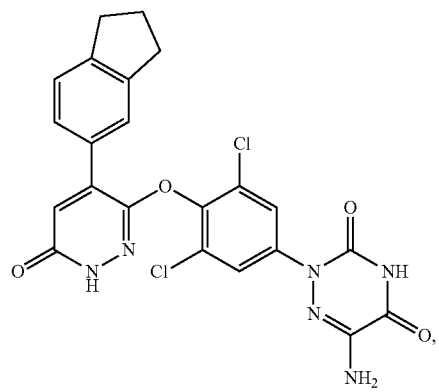
122
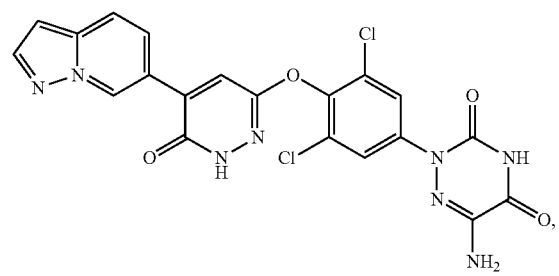
123
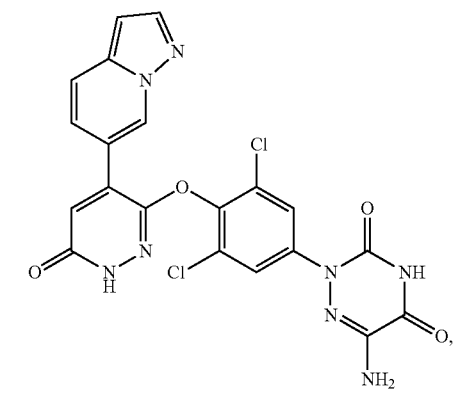
124
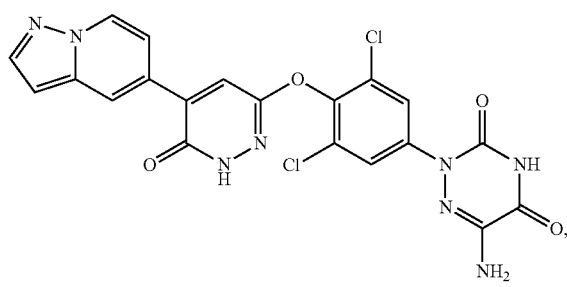
125
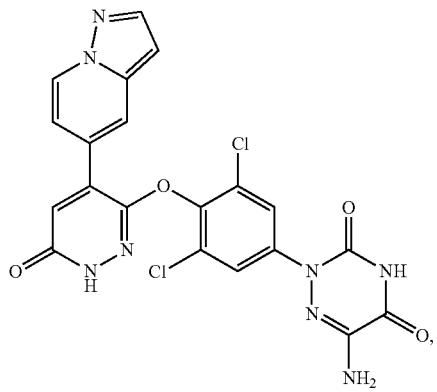
126
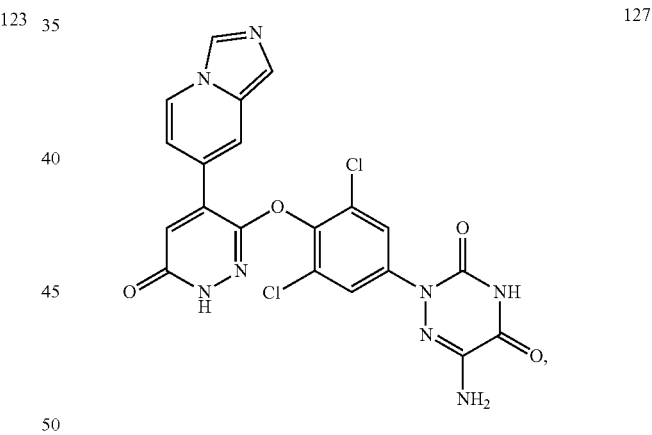
127
128
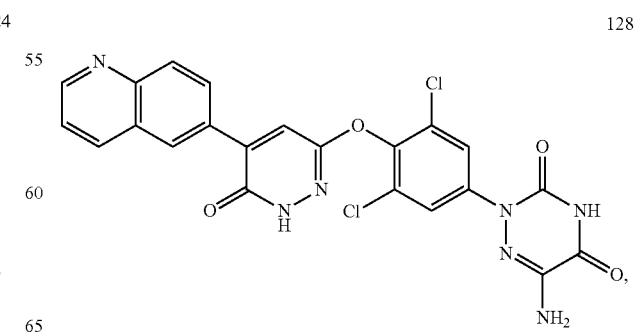

129
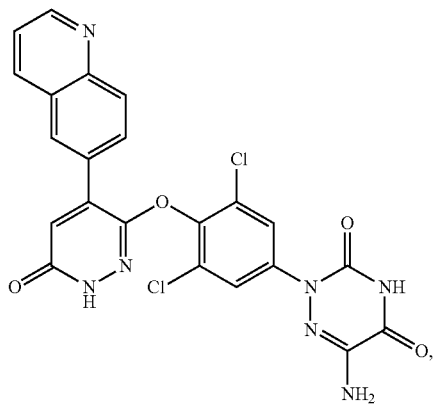
130
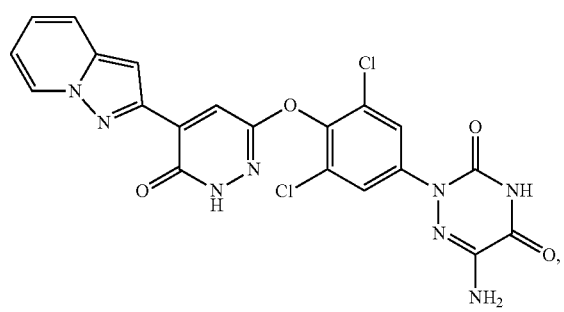
131
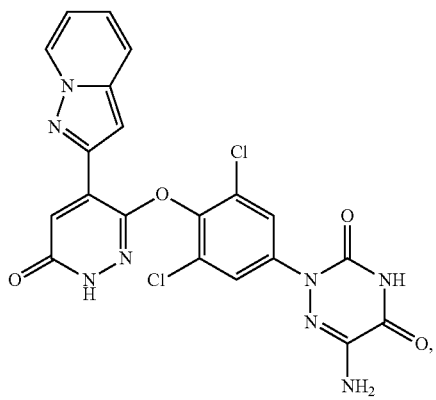
132
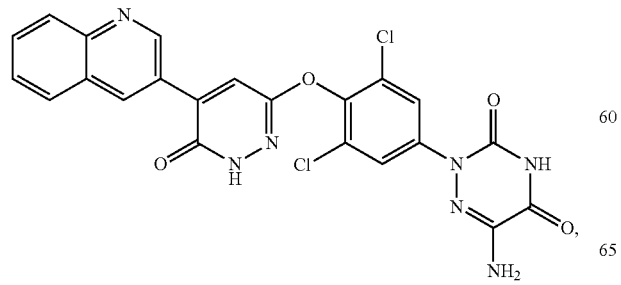
133
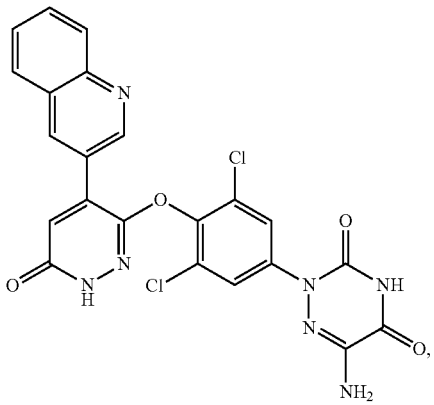
134
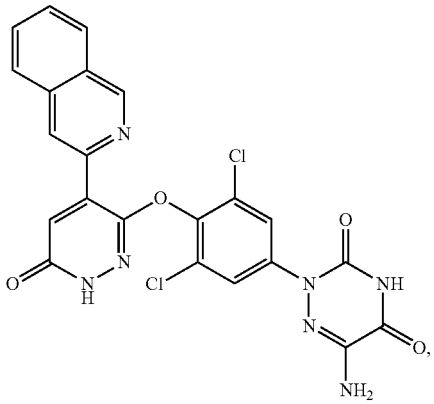
143
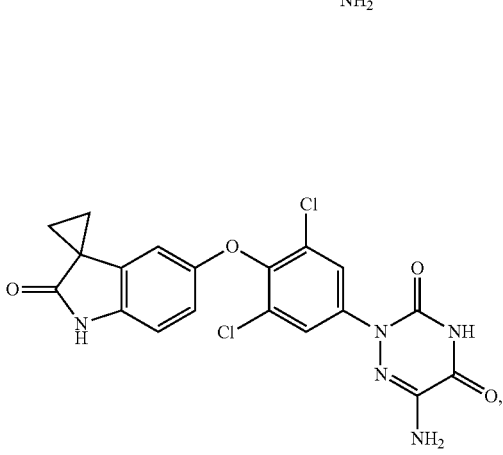
144
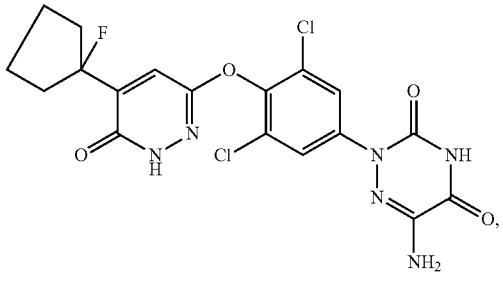

146
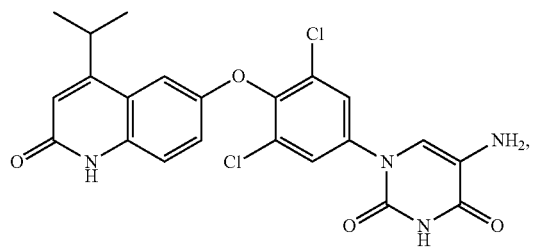
147
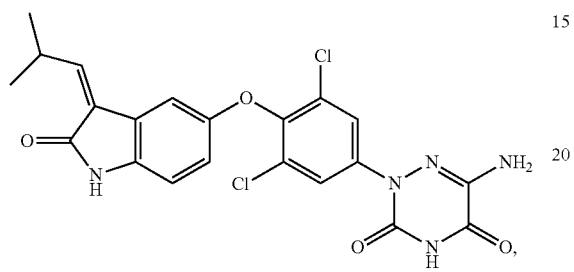
149
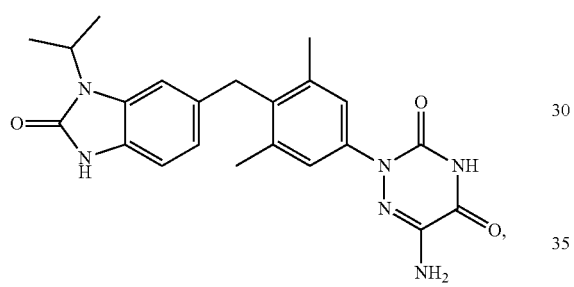
150
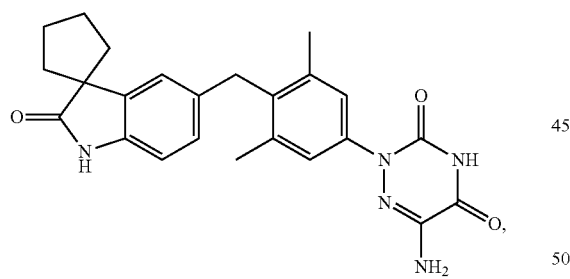
151
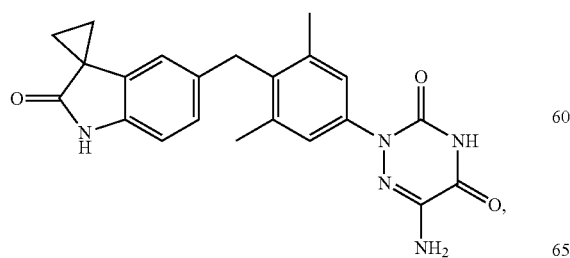
155
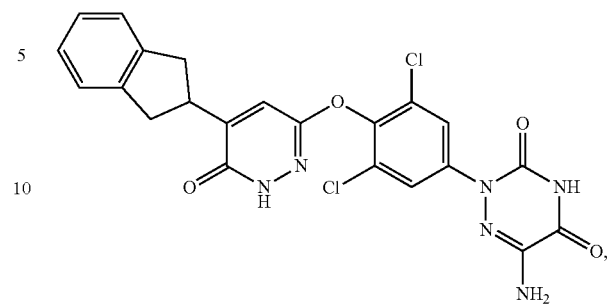
156
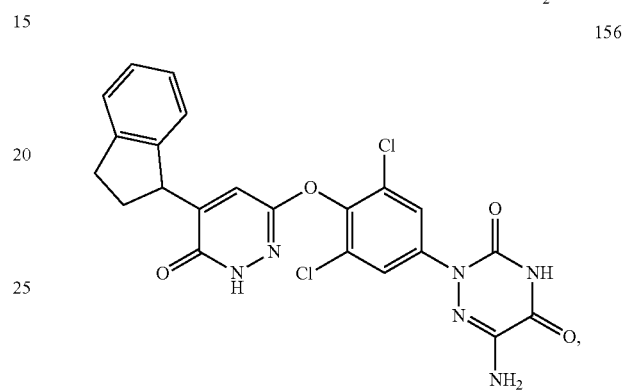
157
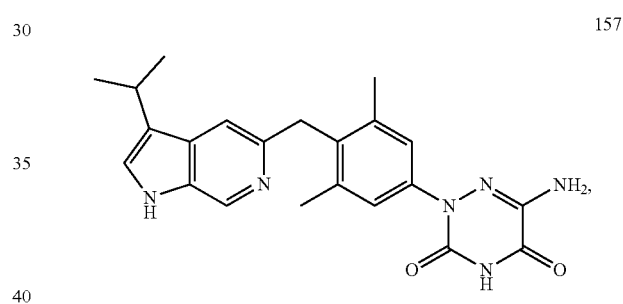
158
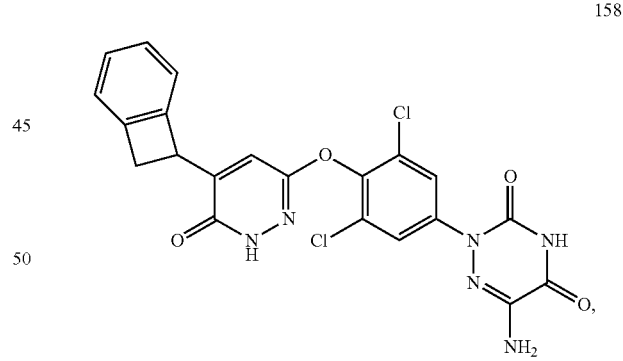
159
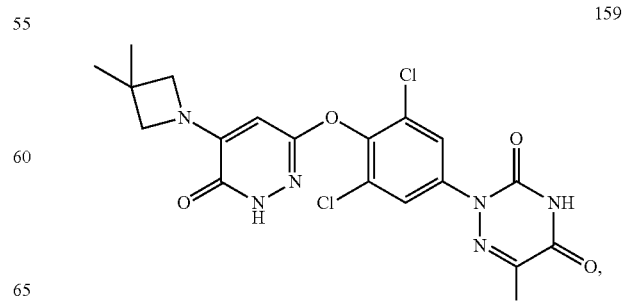

405
-continued
160
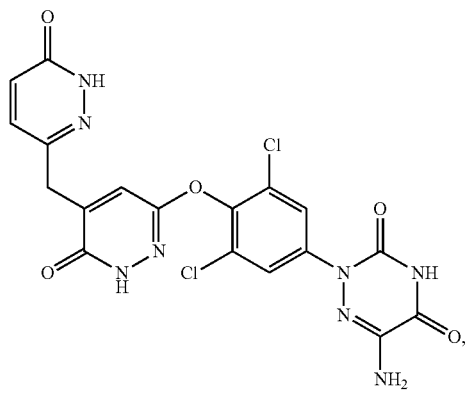
161
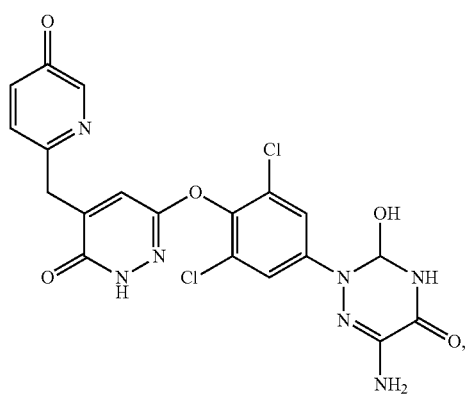
163 or 164
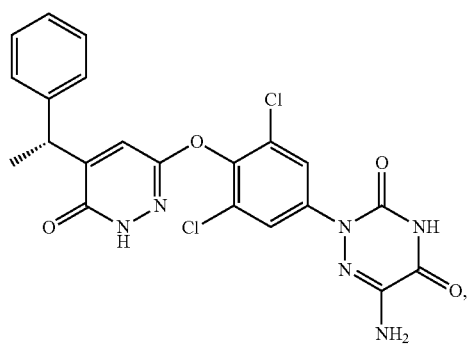
163 or 164
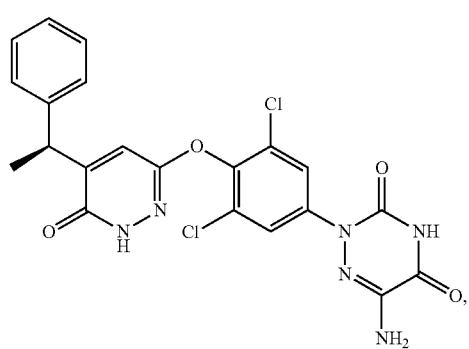
406
-continued
165 or 166
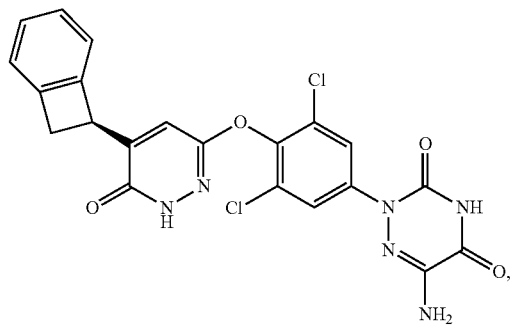
165 or 166
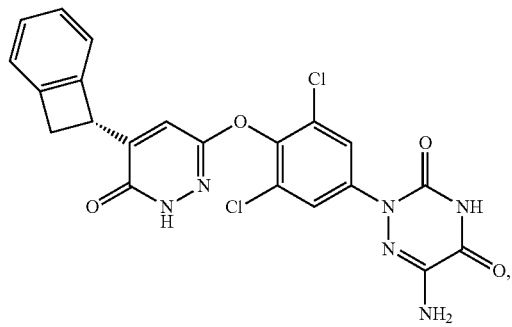
167 or 168
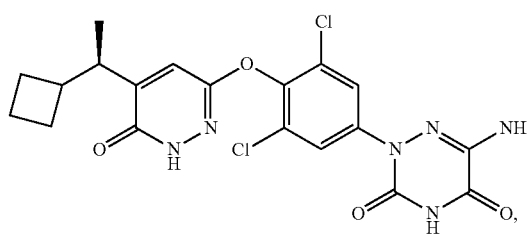
167 or 168
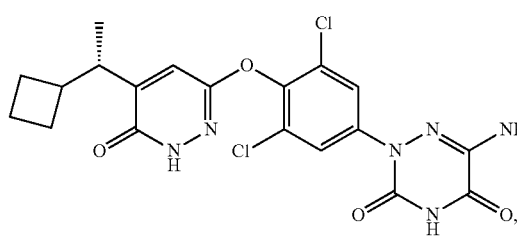
169 or 170
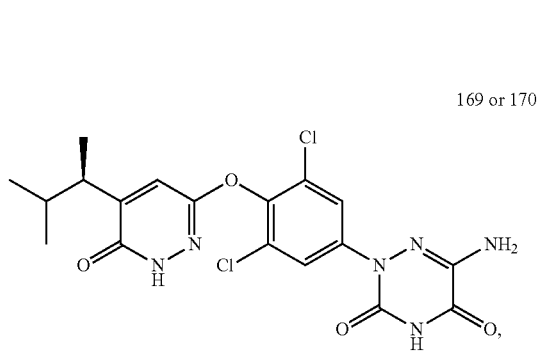

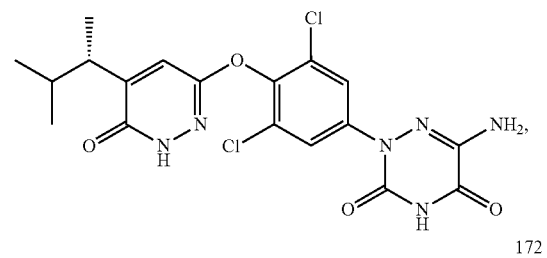

169 or 170

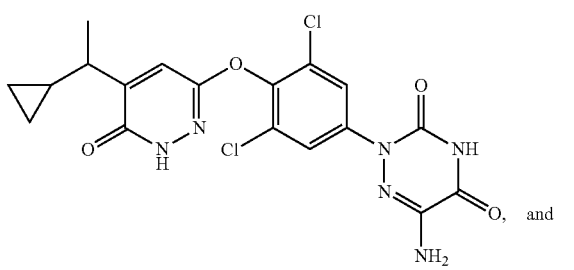

172

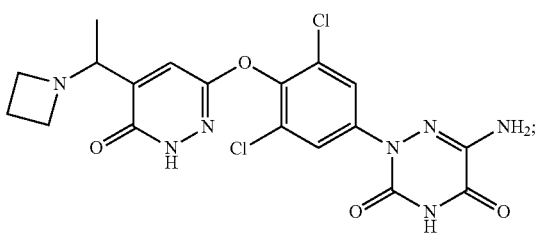

173 or a stereoisomer or a tautomer thereof, or a pharmaceutically acceptable salt thereof.

20. A pharmaceutical composition comprising the compound of claim 1, or the stereoisomer or the tautomer thereof, or the pharmaceutically acceptable salt thereof, and at least one pharmaceutically acceptable excipient.

21. A method of treating a disorder or disease in a subject in need thereof, the method comprising administering to the subject a therapeutically effective amount of the compound of claim 1, or the stereoisomer or the tautomer thereof, or the pharmaceutically acceptable salt thereof, wherein the disorder or disease is selected from non-alcoholic steatohepatitis (NASH), obesity, hyperlipidemia, hypercholesterolemia, diabetes, liver steatosis, atherosclerosis, hypothyroidism, and thyroid cancer.

22. A method of treating a thyroid hormone receptor related disorder in a patient, the method comprising the steps of:
identifying a patient in need of treatment for the thyroid hormone receptor related disorder, and administering to the patient, or contacting the patient with, the compound of claim 1, or the stereoisomer or the tautomer thereof, or the pharmaceutically acceptable salt thereof;
wherein the thyroid hormone receptor related disorder is selected from non-alcoholic steatohepatitis (NASH), obesity, hyperlipidemia, hypercholesterolemia, diabetes, liver steatosis, atherosclerosis, hypothyroidism, and thyroid cancer.

23. A method of selectively modulating the activity of a thyroid hormone receptor beta (THR-β) comprising contacting the compound of claim 1, or the stereoisomer or the tautomer thereof, or the pharmaceutically acceptable salt thereof, with the thyroid hormone receptor.

* * * * *